US010793600B2

(12) United States Patent
Baumann et al.

(10) Patent No.: US 10,793,600 B2
(45) Date of Patent: *Oct. 6, 2020

(54) CYSTOBACTAMIDES

(71) Applicant: HELMHOLTZ-ZENTRUM FÜR INFEKTIONSFORSCHUNG GMBH, Braunschweig (DE)

(72) Inventors: Sascha Baumann, Saarbrücken (DE); Jennifer Herrmann, Saarbrücken (DE); Kathrin Mohr, Braunschweig (DE); Heinrich Steinmetz, Hildesheim (DE); Klaus Gerth, Braunschweig (DE); Ritesh Raju, Sydney (AU); Rolf Müller, Blieskastel (DE); Rolf W. Hartmann, Saarbrucken (DE); Mostafa Hamed, Saarbrücken (DE); Walid A. M. Elgaher, Saarbrücken (DE); Maria Moreno, Hannover (DE); Franziska Gille, Langenhagen (DE); Liang Liang Wang, Hannover (DE); Andreas Kirschning, Clausthal-Zellerfeld (DE); Stephan Hüttel, Braunschweig (DE)

(73) Assignee: HELMHOLTZ-ZENTRUM FÜR INFEKTIONSFORSCHUNG GMBH, Braunschweig (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/042,753

(22) Filed: Jul. 23, 2018

(65) Prior Publication Data

US 2019/0185514 A1 Jun. 20, 2019

Related U.S. Application Data

(63) Continuation of application No. 14/904,654, filed as application No. PCT/EP2014/001925 on Jul. 14, 2014, now abandoned.

(30) Foreign Application Priority Data

Jul. 12, 2013 (EP) .................................... 13003539

(51) Int. Cl.
```
A61K 38/00      (2006.01)
C07K 7/06       (2006.01)
C07C 237/44     (2006.01)
C12P 13/02      (2006.01)
C07C 237/42     (2006.01)
C07K 5/065      (2006.01)
C12N 15/52      (2006.01)
```

(52) U.S. Cl.
CPC ............. C07K 7/06 (2013.01); C07C 237/42 (2013.01); C07C 237/44 (2013.01); C07K 5/06078 (2013.01); C12N 15/52 (2013.01); C12P 13/02 (2013.01); A61K 38/00 (2013.01)

(58) Field of Classification Search
None
See application file for complete search history.

(56) References Cited

U.S. PATENT DOCUMENTS

| 4,525,354 A   | * | 6/1985 | Birch ........................ C12R 1/64 424/115 |
| 7,056,942 B2  | * | 6/2006 | Hildesheim .......... C07D 209/88 514/411 |
| 7,758,972 B2  |   | 7/2010 | Egawa et al. |
| 2008/0145700 A1 | | 6/2008 | Egawa et al. |
| 2010/0178324 A1 | | 7/2010 | Ahn |
| 2017/0204052 A1 | | 7/2017 | Kim et al. |

FOREIGN PATENT DOCUMENTS

| EP | 1867331 A1     | 12/2007 |
| JP | H11279163 A    | 10/1999 |
| JP | 2004-501191 A  | 1/2004  |
| JP | 2008-106044 A  | 5/2008  |
| WO | 02/00216 A1    | 1/2002  |
| WO | 2004035760 A2  | 4/2004  |
| WO | 2013078277 A1  | 5/2013  |
| WO | 2014125075 A1  | 8/2014  |
| WO | 2015/003816 A2 | 1/2015  |
| WO | 2016-082934 A1 | 6/2016  |

OTHER PUBLICATIONS

Pubchem entry for albicidin (retrieved from https://pubchem.ncbi.nlm.nih.gov/compound/Albicidin on Sep. 3, 2019, 11 pages). (Year: 2019).*
Plante et al., "Oligobenzamide proteomimetic inhibitors of the p53-hDM2 proten-protein interaction," Chemical Communications. 34: 5091-5093 (2009).
"List of new names and new combinations previously effectively, but not validly, published," International Journal of Systematic and Evolutionary Microbiology. 57:893-897 (2007).
Mensa et al., "Antibacterial Mechanism of Action of Arylamide Foldamers," Antimicrobial Agents and Chemotherapy. 55(11): 5043-5053 (2011).
Kulikov et al., "Design and synthesis of oligamide-based double alfa-helix mimetics," European Journal of Organic Chemistry. 3433-3445 (2013).
Yap et al., "Relaxation of the rigid backbone of an oligamide-foldamer-based alfa-helix mimetic: identification of potent Bcl-xL inhibitors," Organic and Biomolecular Chemistry. 10: 2928-2933 (2012).
Seyler et al., "Tuning the solubility of hepta(p-benzamide)s via the monomer sequence," Tetrahedron Letters. 54(8): 753-756 (2013).
Beyer et al., "Metabolic diversity in myxobacteria: identification of the myxalamid and the stigmatellin biosynthetic gene cluster of Stigmatella aurantiaca Sg a15 and a combined polyketide-(poly)peptide gene cluster from the epothilone producing strain *Sorangium cellulosum* So ce90," Biochim et Biophysica Acta. 1445(2): 189-195 (1999).

(Continued)

*Primary Examiner* — Ronald T Niebauer
(74) *Attorney, Agent, or Firm* — Mintz Levin Cohn Ferris Glovsky and Popeo, P.C.; Peter F. Corless

(57) ABSTRACT

The present invention provides cystobactamides of formula (I) and the use thereof for the treatment or prophylaxis of bacterial infections.

Figure 1:
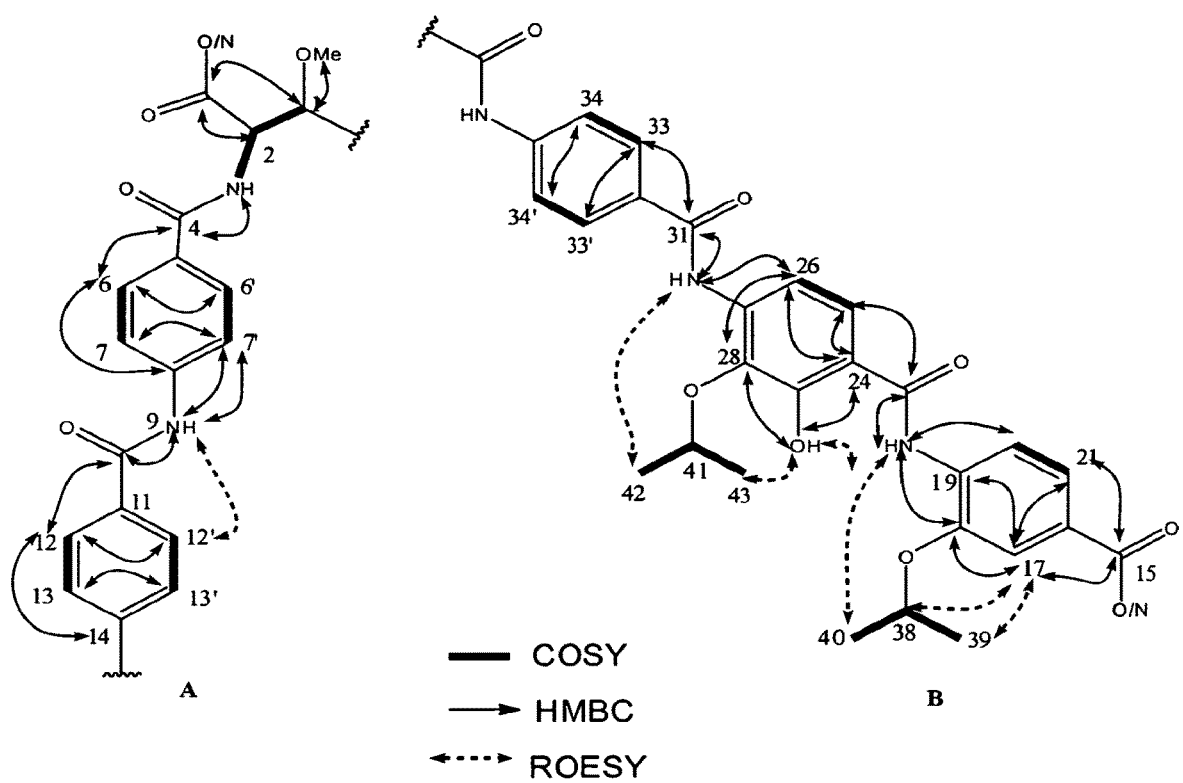

$$R^1\text{—}Ar^1\text{-}L^1\text{-}Ar^2\text{-}L^2\text{-}Ar^3\text{-}L^3\text{-}Ar^4\text{-}L^4\text{-}Ar^5\text{—}R^2 \quad \quad (I):$$

7 Claims, 15 Drawing Sheets

Specification includes a Sequence Listing.

(56) References Cited

OTHER PUBLICATIONS

Database UniProt [Online] Jul. 5, 2004, "SubName: Full=Non-ribosomal peptide synthase;" XP002730995, retrieved from EBI accession No. UNIPROT:Q70C52, Database accession No. Q70C52 sequence.
International Search Report issued in corresponding International Application No. PCT/EP2014/001925, dated Jan. 20, 2015, 8 pages.
Sambrook, ed., Molecular Cloning: A Laboratory Manual (2nd Ed.) vols. 1-3, Cold Spring Harbor Laboratory, (1989).
Current Protocols in Molecular Biology, Ausubel, ed. John Wiley & Sons, Inc., New York (1997).
Laboratory Techniques in Biochemistry and Molecular Biology: Hybridization With Nucleic Acid Probes, Part I. Theory and Nucleic Acid Preparation, Tijssen, ed. Elsevier, N.Y. (1993).
Adams (1983) J. Am. Chem. Soc. 105:661.
Belousov (1997) Nucleic Acids Res. 25:3440-3444.
Frenkel (1995) Free Radic. Biol. Med. 19:373-380.
Blommers (1994) Biochemistry 33:7886-7896.
Narang (1979) Meth. Enzymol. 68:90.
Brown (1979) Meth. Enzymol. 68:109.
Beaucage (1981) Tetra. Lett. 22: 1859.
Goeddel, Gene Expression Technology: Methods in Enzymology 185, Academic Press, San Diego, CA (1990).
Kozak, 1991, J. Biol. Chem. 266:19867-19870.
Davis, L. et al., Basic Methods in Molecular Biology (1986).
Gruger, T., et al., Antimicrob. Agents Chemother. 48, 2004, 4495-4504.
Schedletzky, H. et al., J. Antimicrob. Chemother. 43, 1999, 31-37.
Khodursky, A.B. et al., Proc. Natl. Acad. Sci. USA 92, 1995, 11801-11805.
Schulte, A. et al., J. Antimicrob. Chemother. 46, 2000, 1037-1046.
Keeney, D., et al., Antimicrob. Chemother. 61, 2008, 46-53.
Heisig, P. et al., Antimicrob. Agents Chemother. 37, 1993, 669-701.
Mosmann, T. et al., J. Immunol. Meth. 65, 1983, 55-63.
Pommier, Y. et al., Chemistry & Biology 2010, 17, 421.
Gould et al., Journal of Magnetic Resonance, Academic Press, London, GB, vol. 34, No. 1, Apr. 1, 1979, pp. 37-55.
International Search Report and Written Opion—International Application No. PCT/EP2015/002382.
Azzarito et al., "2-O-Alkylated para-benzamide a-helix mimetics: the role of scaffold curvature", Organic & Biomolecular Chemistry, 2012, 10, 6469-6472.
Fomovska et al., "Salicylanilide Inhibitors of Toxoplasma gondii", Journal of Medicinal Chemistry, 2012, 55, 8375-8391.
Vippagunta, S.R., "Crystalline solids", Advanced Drug Delivery Reviews, Elsevier, 48 (2001) 3-26.
Bohle, A. et al, Hydrogen-Bonded Aggregates of Oligoaramide-Poly(ethylene glycol) Block Copolymers, Macromolecules (2010) 43, 4978-4985.
Baumann, S. et al., "Cystobactamids: Myxobacterial Topoisomerase Inhibitors Exhibiting Potent Antibacterial Activity", Angew. Chem. Int. Ed. (2014) 53, 14605-14609.
International Search Report for International Patent Application No. PCT/EP2018/072817, dated Jan. 10, 2019, 7 pages.
Kretz, J. et al., "Total Synthesis of Albicidin: A Lead Structure form Xanthomonas albilineans for Potent Antibacterial Gyrase Inhibitors", Angew. Chem. Int. Ed. (2015) 54, 1969-1973.
Grätz, S. et al., "Synthesis and Antimicrobial Activity of Albicidin Derivatives with Variations of the Central Cyanoalanine Building Block", ChemMedChem (2016) 11, 1499-1502.
Kerwat, D. et al., "Synthesis of Albicidin Derivatives: Assessing the Role of N-terminal Acylation on the Antibacterial Activity", ChemMedChem (2016) 11, 1899-1903.
Kim, Y.J. et al., "Isolation of Coralmycins A and B, Potent Anti-Gram Negative Compounds from the Myxobacteria Corallococcus coralloides M23", Journal of Natural Products (2016) 79, 2223-2228.
Petras, D. et al., "The O-Carbamoyl-Transferase Alb15 Is Responsible for the Modification of Albicidin", ACS Chem. Biol. (2016) 11, 1198-1204.
von Eckardstein, L. et al., "Total Synthesis and Biological Assessment of Novel Albicidins Discovered by Mass Spectrometric Networking" Chem. Eur. J. (2017) 23, 15316-15321.
Lakemeyer, M. et al., "Thinking Outside the Box—Novel Antibacterials to Tackle the Resistance Crisis", Angew. Chem. Int. Ed. (2018) 57, 2-39.
Bhattacharya, M. et al., "Second order nonlinearity in oligoamides", Synthetic Metals, 155 (2005) 389-392.
Japanese Office Action for Japanese Patent Application No. 2017-528464, dated Aug. 21, 2019, 7 pages, English translation.

* cited by examiner

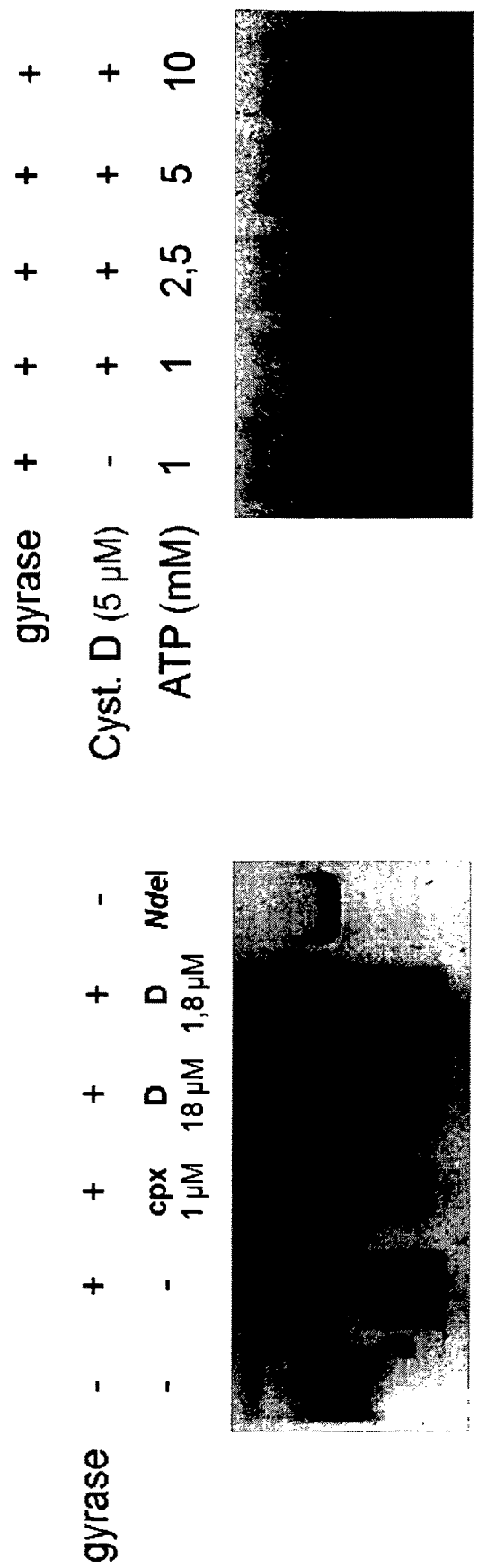
Figure 10 a and b

SEQUENCE LISTING

```
<160> NUMBER OF SEQ ID NOS: 73

<210> SEQ ID NO 1
<211> LENGTH: 58456
<212> TYPE: DNA
<213> ORGANISM: Cystobacter velatus
<220> FEATURE:
<221> NAME/KEY: misc_feature
<222> LOCATION: (1)..(58456)
<223> OTHER INFORMATION: Cystobactamide biosynthetic gene cluster

<400> SEQUENCE: 1
gtagacgccg cggctcagag ggcggtgccg cagtgcttgc agtggtgcgc gtccaggtcg      60
tggccctgca ggccgcagcc gggacaggcg cgcgggtcga tggcgtgctg ccgggtcgcc     120
tgggcgagct ccacggacac gatgcccgtg ggcaccgcga ggatgccgta gcccatgatc     180
atcaacaccg aggcgatgaa ctgtccgggc accgtcttgg gcgagaggtc tccgtagccc     240
accgtggtca tcgtcacgat ggcccaatac atcccccgcg ggatgctgtc gaagccgttg     300
gcgcgcccct ccaccatgta catcaccgcg cccatgatga cgaccgtgct cagcaccgcc     360
ccgaggaaga cgatgatctt ccgccgactg gcccggagcg cggtgagcag cacgtccgcc     420
tccccgagga agctggcgag cttgagtacg cggaagacgc gcagcaggcg gaacacccgc     480
accaccagca gggactgcat gccgggcagc atcaagctca gcaccgaggg caggatggcc     540
agcagatcca ccagcccgaa gaagctcagc gcatagcgca gcggccgttt caccgacagc     600
agccgcagca cgtactccag tgtgaagagc ccggtgaaac accactcgag gacgcggatg     660
gtctgcccat gctggacgct gatggactcc acgctctcga gcatcaccgc gaggacgctg     720
agcacgatgg cccacagcaa tgccacatcg aaggcgcggc ccgccgggt gtccgactcg     780 aagatgattt cgtgcagccg cgcccggagt cccgacggag cgctctgctc ggatggatgt     840
```

```
ggcacgaggg cagtctagcc ctccacggcg cggcggggc ggaatgcggt ccgcccaccg      900
tgacgcgccg gctactggga gcccgccttg gagctgccgg gggcatgcag ttgccgccgg      960
tcttccttgc cgcccttgtt ggggcctccg tgggtgccga actcgcccgc gttgcgctgc     1020
ttggggtatt cctcgtcggg ccgccgctcg cggcccggc ccgagacgtc acccgagtcg     1080
accttcgggt gcagcctctc cttgtccgcg tcggaatgca gcttctccct gtcctggtcc     1140
tgtgccatcg gcacctccg tttcctggag gaaacatggg gacggaagac gggagcggct     1200
caggagtgcc gccgcttcgc ggggagggcg ggccgccggg cgtctggagg aaagccgct     1260
gtcgccagtt gggcgttccc tcccgccgca cggaccagcc gcgggaccgg gctcgcggcc     1320
ggcccccgcc aggcgcactc agcgcttctt cgcggacttg cgcgcggcgg cggtcttcac     1380
ggcgcgcgcc acggtcttct tcgccgcgac cgcggcccga gtcaccacct tgcgcccgat     1440
gctacccacg agccccgtgg cgctcagctt cttgcgcgcg ggggccttcg gctcggtctc     1500
ctcccgcgct tgacgggtag gggccttggc ggtggcctct tgcgtcgcca ccttccgggt     1560
gggcttcgcc ttggggcgg ccttcttcgc ccgggtagcg ggggtcttgg gctccgtgcg     1620
cttcttctcc gcgcgggcgc ggtagcgctt caccggtctcg gcgtgggcct gtccatagcc     1680
ggtgggcgtg tcaggcaggg ccgccttctc ctcttccttg gtgagggcga tcttgtgttc     1740
ttcattgccg agccggggac ccgagcccct gtaggtctgc gcgggttgct gcgacaagaa     1800
gggttcgaaa ctgtaggttc ttcccatggc tgtctcctgc ctgcgtgact gggatgtctt     1860
gaagaaataa gtaaggagtg gtccctgatt ttggaatggg cccctctcaa ggcgcctcgc     1920
ggtccccgta ccaggactct tcctcttccc cgtccaggta gcgcaccacg aggcccgcgg     1980
gcttgtgctg gcgagccagc ctgcgcccgc cgtggatggc ctgggtcacg ttggaatacc     2040
ggccgagctg acggttgccc tcgaatcgga cgtaccaacc ccggccatcc gtcgccacga     2100
tcacccgccg tgcgtgtgtg gcggagccca cttcgtgctg cttgctctcc ttgcgtcttg     2160
ccgggctcat gaaagcaaac tgtcaacccg gagcggaggt cgcattgtcc cagggatcag     2220
ggtgcgcgga ttcaggtcgc ccaggagcat gagacggccc cggggacttc aacggccccc     2280
ggagccctcc tgctgcccgg cgcacgggtc ctgccagcga ccatcgtgc gccagggagc     2340
gcggcgtcag cggctggtgt cgtcttcgga gcccgtgccg ctcatgttgc cgctggagtc     2400
cgtgctgccg gagccgtcca cgtcactgcc ggtgccggag ccgccaggt cgctgtccac     2460
gcccgaggcg tcgggctga aaccgcccgg ttcactggac acgcccgagc cgccggagcc     2520
gcccacgtcg ctaccggagc ccgtgctgcc actgctcgaa ccgtcgatgt cgccagcacc     2580
tgttccgccg gtgcctccgc ccgtggtgtc accaccttcc gtggtgcctc cggtcgttcc     2640
ggttccggtc gtctcacttc cggtcatggt gccgccctga gacgtatcgc tcccgcccgt     2700
tccttgattc ccagcaccgc ccgtcgtctg acatcccacg ccgaagagca gagccgcgga     2760
caacgcaccc accaccaccg ccttgatgtg tttcatgcgc tttcctctcc tccagttgga     2820
cacctgtgga ggctaggaat ggctccacac gggtgcattg gacgtgaaga cagctccccc     2880
gctcggtgtc ccactgatgg tggctcggat tcttccttgc cctccgagcg atgaggcacc     2940
ccgtcgtggt gcgatgggtt cgacccgcgt ggggtcctca gggcgaggcc tggcgcgagg     3000
agccgggtgg cttcgcgcgc cagacccggt ccggctactt ccaggtgtcg ttagggtcg     3060
cggtccccga ggcggggatc gtggtcgagc ggttggcgcc gctctcccag gtgacgttcc     3120
cggagccgtc cttcttgatg tacttgtatt cgagggccgt cgagccgggc aggctgagcg     3180
tcacgctcca cttcgggtag ctggccggag acaggaggat ggcggcgccg gtgttccagt     3240
```

```
tgccgagcgc ggcatggtta cccacgaggt agacgttctg tcccacgacg gtgctggccg    3300
tcacgttgaa ggtgacggag gtggccgagg aggtgctcgt ggtgacgctc agggcggtgc    3360
tctgggcgga ggcattgccc gcggtgtcgc gcgcgcgcac ggtgtagcgg taggtcgtgc    3420
cggcactcag gtcgctgtcg gtgtagctgg tggagacggg tgagcccacc agcgagccat    3480
cgcggtacac gtcatatccg gcgatgccgc tggcatccgt ggaggcgctc aggagagcg    3540 acacggagga ggacgtcttg gacgccgccg tgaggcccga gggacggag ggtgcggtgg    3600 tgtcgagcgc gggcgctccg ctggagacga cgccgtcctt caccgtggag gtgcccgcgg    3660
gcaggaggta gttgttgccc ttgttgttgt cccaggtgcc cttgccatcg ttgaagacac    3720
actcgagctg ggtggccgct cccagattga cggtgtattt ggcgtagccc ggcacctcgg    3780
aggtggccat gacgttgccg ggcacggtcg tccacgtgcc accgccgatg cggaagtgga    3840
tgtatttgag ggcgaagttg ttgttgaaat agtagacggt ggcgctgttg cccgtctggg    3900
tggtgacgga cagggccgtg ctgggcgagg agacattgcc cgccgcgtcc gggcgcgca    3960 cggtgtagct gtaggtggtg ctcggcgaga ggccggtatc cgagtaggtc gtcccccgtga    4020 cggacgcgac ctgggtgccg tttcggagca cctcgtagtt cgcgacgccg tagttgtcgg    4080
tggaggccgt ccaggcgagg gccaccgagg agctcgtcgt gcccgacgcc gtcaggcccg    4140
agggaacgga gggtggggtg gtgtccggcg tcagggtggc gacgctcagg gcggtgctct    4200
gggcggacgc gttgcccgcc gcgtcccggg cgcgcacggt gtagctgtat tgagtgctcg    4260
gggagaggcc gctgtcggta taggccgtgc tggtgctcga gcccacctgc gtgccatcgc    4320
ggaagacgtc atagccgctc accgccacgt tgtccgaggc cgcgctccag ctcagggtca    4380
ccgagcggtc cgtcttcgcc ttcgcggtca gtcccgaggg gaccgagggc gcggtggtgt    4440
ccaccacgag gaagggatgc gttccctgta ccgtgccgtt ggggtcctcg atgtacttgc    4500 cgccaccag gttgtaccgg cccgagccca cgtagacgga ctggatctct ccccgggtga    4560
tgttgccccg gctgtcggtg gcctcgatgt agtagtcgag gagctggtcg cggtagttgc    4620
ccaggtagac gtagtagagg tcgccgatct cctgcgcggg caccttggcc atgacgggca    4680
ggtaggcggg ctgccaggaa acaccattca tgacaggctt caggtcgcgc cgggtgagcg    4740
ggtagtccac ccaggcgccc acgcgggccg gatcgatgtt gggaacaccc gcggccttgc    4800
gcgccgccgg atcatagacc ttgtgggtgt tgtcgagcgg gtcgatgctc ttgtgggtgt    4860
gcacccggac gcgggccttg atggaggaga tgccgctcgc gtcgtaggcg taggtgtaga    4920
gggcgaagtg gttgttgaag aagtggacg tccagccctc ggacttgtcg gtgttggcgc    4980 tgccgggggtt gtagggccag cgctgggccc accagacgga ggggcccgtc ttgtcctggg    5040
cgatgcgctg ctgcacgtag ggcttggaga agtagaggga ttgattgaag acagcgtgg    5100 gcttgacgtt gtcgtcctgg ttctcgtcgt agtagccgaa gcccgagtcc atggcgggca    5160
gcaggaagta ccaggcgagt tccgcggggt tggcccgcc cgcccagtcg ttgttcacgt    5220
cgcccttgac gggaaaggac atcatccacg ggttgagctg gttgcccgtg tgggtgatct    5280
gcttgtcgat cgcggtggtg ggcgaccagt gattggggtg cgcgtcgagc cagatctgct    5340
cggcggtctt cgcgtagttg agggcggcct ggagcagggc gaagttgcgc tcgaggtagt    5400
gccagccgtg ctcgagggag accgtcatgc cctcctgcac gccgctgagg ttcgtcttgg    5460
gagagagatt gaggccggtg gcggcgttga aggcggggaa ctgacccttc cagatgccga    5520
agggcagctt ccagtggtgc cactggggat ccgaggagga gtcgcgcgtg tccacccacg    5580
```

```
agccgtcctg gacgtgcacc acgtcggtgg aggcggggt  gtggtggacg aggtactcgg   5640
agatgcccac gcactgcacg ccattggcgc aggtgacgga gcggccgttg taccaggtgg   5700
agtcggagcc ggcgcgtccg ctcgagttgt cgccatcatg cgcgatgacg aagaactgcc   5760
gctggggaac gaggccctcg aagctcttga ggttgacgac gtcgacggtg gcctcgcctt   5820
cccagccctc gagccaggag ccgttctggt tgacggggat gccgacgacg cgcgactcgg   5880
cgcccgtggc ggggtccacg tagcgcaccc agtgggagt  ggaggcgaag gggtacttgt   5940
tcttgatgac ctgctgctcg tgggccatct gggcgctcac ccaggagccc acggagctgg   6000
tgttctggag atcggcgcgg ttgggcgggg agacgagcgt gtcggagccc ggatcgttga   6060
ggtaggggta gtccttgagg gtgcgggaga agtggttgtc gccgatgacg gcccactgca   6120
cgccgagctt ggagagggtg gggatgaggc gctcggagaa gccgagctcg gtggggaaga   6180
agcccttgga ggactggaag gagccgccga ggaagtaggg ctgggcgagc gtggcgctct   6240
ggtagatgag atccttgagg aagtagtcgg gaccgaccag gggccccatg gagtggtggc   6300
cggtgaagtg gatgagatcc agggtgcggt tgcccgcggg ggtgagcagg gcgctgtagc   6360
ggtccttcca ggaggcgccc cagttcggat tgtcgtagcc ggggacgttc ttcagggtga   6420
cgagatcctg gacattgttc accacggcgc cggacatggt gacgtgcacc tggccggtgg   6480
gggcattggt tttcatgtcc gaggcgacgc ttggaggcca gtacaggtag gcacccgtct   6540
tcgcgttgtg cgagtaatag gtgacgaggt catcgtgcgg catgggcgcg cccgatggca   6600
ggtagtatgt gtaattggac gggggattct tcttcaggtt gatgacctgc gcgtcataca   6660
tgtaccggat ggggccgccg gtgggcgtgg acgcgtattg gcccaggtcg tagtaggccc   6720
agaagttggg catgtggttg tggtagacgt gggccgcggc gatctgcgcc ctggcgggca   6780
gggcacacag caacagcgcc gacaggacgg gccctatcaa cggcttcact cgatgcatgg   6840
gggttcctct ggggtaagga ggagcgcacc ctagtggagc cgtccggact ttcctcgttt   6900
tctgatgaaa aaggatttgc cgcatcgcgg caatcgtttg gcagcagact ggaacgtcag   6960
cgaggagcaa caacagccac tggcggcacg cgcggctctt ctccagagag aagagccgcg   7020 cgtggggag  cgaaagcctg gaggcctgtc agcccgcgac ggccacttgt ggccgccgga   7080
ccggtgtgcg cgaagggacg gccgactccc agaccggaag tatgcttccc atcttgtgga   7140
gcttcgcctc gcagtaggag aggttgtcct cgtacggctt gttcgccatg aacggcattt   7200
gagtcccgcg gtacttcacg cgcaggctcg tgctgggagc gccctcgagc ccgagtagct   7260
cagacgtgag ctgcgcgtac ttttcgggaa cgcgcaggac aatggcatcc ttctccttcg   7320
agacgaccgt cacgtgtttc agcaacccct cgccattatt gatgggcgtg ttgctgtaca   7380
cgtgcggacg gttgaggaga tccatctcga acaggaactc cagcagctca tcgttcatca   7440
tgcccagggt ttgaatgaac ccgaagagca gttggtcgaa ctctctgcgg aactcgtgaa   7500
gtgtgacgtg gaagatgccg ccgttggcgc tgaacttcga ctggctggtc ccgtcgatca   7560
cgctggtgat gtactgcgtg tagggtggt  cagggttccg cttgcagtac tccgagaacg   7620
aggagatcaa gtccttgaag gccagccgcc cctgcttgtc gaggtacctc ccgacgaagc   7680
ggagtgcgcg caggctgtac aggctcgtga atgataccc  gaaccgcaca ccctccttgt   7740
attcctcgcg ggtaacgtcc ttcgtcgcga cgacgacctg cgcctcgctg ttcgggtctt   7800
catcattcga cacctccagc ttgaactcct cgcgctggct gttcatcggc acgttgttga   7860
tgagcaggag gtggtggatg aggatcgcgt cggcgtcgta gctgcagagc ttcccgatgc   7920
cctccctgaa ggtctccagc gtctcgccgg gaagcggcca gatcatctcc acgaacgagg   7980
```

```
agagcttgct gcggtgcagt tcttcctgga ggctcaggta ggcgctctcc ttgatgttgc    8040
cgcgcttcac gctcttcagc gtgttcgcgt ccatcgtctg gagcgagacc ggctgggtgg    8100
agatcaaacc ctcctggctc aggatccgcg tgatctgcgt gacccggtca ggcgagttct    8160
tcgccgcgct cagccaaatg gtgagcggat agccatactt ccgcttgcac tcggcgatgt    8220
gctgggcgat ctcaatgtcg cgggtcagca tgccgaaatt cgcgtcggtg atgaagatgt    8280
agaacgcccg gtgctggctg agccaggtga tctccgcctt gacccggtcc atgtcggact    8340
tgaacacgcg cgagttggtc gccgcccccc agaagcagta ggtgcactgg taggggcatc    8400
cccggttcgt ctcaaggggc gcccacacgt acttctcgct gtcgaagtag ccttccaggt    8460
agggagatgg gaccgtgttc agatcctgga tgcgcgcttg gggctcggtc gtgatcagct    8520
ctccgttccg gtagaaggag aggcccttga ccttgccaag gtcgggctgg ggggagcaga    8580
gttcggccag gtagttcgcg aaggtatact caccctcacc gttgcagagc accacccgct    8640
cgttgcccgg atccaggtac tgcgcccgt ggttcatcac ctgcggaccg ccaaggatga    8700
tgtgcgcgtt gggcttgcgg gcggtgaggg tggggagcca ccgcttcacg aagcccatgt    8760
tccagacata gcaagagatc gcgtagacat cggcatcgat cttgttgagc ttgtcttcga    8820
atcggtcgtc gttgatgcag atcgagtgga tttcgaagct gcacgactcc ctgatcaagg    8880
ggttctgctc ggccacgcca cgcatgtagc cagaggccaa gggataaacg ccagagaaga    8940
ccgtcaactc aatgaatgcg acccgctggt tggccatgac acacgctccc cgttacctac    9000
aaattggtat attgccaaca tgatggcggg caggctagct gaaaaattta ctctccggca    9060
ctctcatgtt cctgggtctc cgggctcagt gggcgagcag cttgaatcgg cggaacgcct    9120
cgcgcgtcgg cgcgtgcgac aggacgtcgc actgcatcag cacgtagacc aggtacccgg    9180 agagggata tcgcgcgcgg aaatcctcca gcggcggctc cgagtacgtc tcggagagga    9240
tccgctcgat gtgctcggcc gctagaccga gctgctccag cacgacgcgc tcgtactccg    9300
ccatcatctt cgggctgagg tactcgcgga tgaactctgg cagcagctga ccgatggcga    9360
gccgggcgct ctcctccatc tcactccaca ccagcttgag cacgttcatg aagaggaccg    9420
cgtggcggcc ctcgtcgcga acatggtcct ccatcacctg atggagcact tcgttgaagg    9480
acttctcacc cgtcaggttc agcagatcct tggtgagtgt gttttccccg atgcagacgg    9540
cgatgatttc ccagagcccg tgcagcgtct cgggcagccg gtgcttgccg aaagccatgg    9600
ccctggacag gtccgtttcc gttcccaggg gcagcggctt gacgcccgtg cgctgctcga    9660
tctgccgcat gaagtcgcgt gccacgtagg cgtgataggc ctcatcgatg atgacggtga    9720
gcgcgtcgtg gcggatgtcg tccgggaacg tgatgggcgt gtgaccgttg gcgatcttca    9780
tcgccacctc gttgacggtc tccgtctcga agatggcgat gtccccatg aacttgtagg    9840 cggagtggat gaagaacagc cgcagcgtct cgggcggaag gttcttcatg agcgggtggg    9900
tgagcagggc cgccttggcc ggcgggtaca ggtgcccgac cacgtccccc tccggcagta    9960
cgcgccgggg cttgctgcgt gtggcggcaa gcgaatccca caccaactcc ttggacttgt   10020
agtccctcgg ggaaatcgcg cccgacccttt ctgctaccaa ccctgtcttc cctgtcgtcc   10080
cattcactct ggcttctccg acggcaccgt attgctgcat tgaaagggga gcgagcgcct   10140
gcgggcgctg gtcgcgcgcg ctcagcgctt gactccgtgc accaggtatc cctggggcac   10200 accggggtg ccgcgtggcg ccacggggaa gggccagcgc ccgagctgct tcccgatggc   10260
cgcggtggtg tagacgtggg ggtcccagcc aatcggcctg agaatcacct cgggctcgtc   10320
```

```
ggtgccgaac tggcgggcga ggtcgtgcat caacttgacg cgcgaggagt ccaaaatcga   10380
acggccaacg acgtcgatga ggacgatgct ctcgggaacg ctcagggcgt tgacacgggc   10440
catgagcagc gtgacctgcg cctcggtgag gtagacgagc aatccctcga tgagccacag   10500
ggtgggcacg ccgggatcga atccgctttt cttcagcgcc gccggccagt catcggccag   10560
atcgaccgac acggcatgtc gctcacattt cggcgcgacg ccggtcagct tcgcctcctt   10620
gtcctggagc acggcgtcgt ggtcgagctc gaacagccgc gtgtctcccg gccaggccaa   10680
acggtaggcg cgggcatcca ttcccgcggc gaggatgacg atctggcgga tgccgcggcc   10740 caacccagc gtgatctgat catcgagcca gcgcgtgcga acctcgatgg cgggaggcat   10800
ggcgccctca ccggcattgc ggcgccgcag ctcctcgacg agcgtgtcac cggcgagtcg   10860
acgggcaaag ggatcccgga acagtgggtt ggaacgctcg gtctcaagcg cgcgcattcc   10920
cgccacccaa agtgccgtct ggccgatctc ttgcatatgt tttatgaccg ccgcctcgtg   10980
agatgggtta agggttcggc aacacgtcaa ctcgcaacga cggagcgctc agcgtccgtg   11040
gctggattcg cgaagcgcga acgccgcccg ttgcggatcc tcgcacacgg cgatgcgatc   11100
gccattcgga agttccatgg ggccgatgac gacgcctccg gccttgcgga cgacctccat   11160
cgcgggatcg agcgcggcga cgcggaaatg gaacagccag tgtgaatgga ccccccttgag  11220 ccccgccacg tccacgaccg agccggcgct cggctcgtcc gagcgccagg tgaactcctg   11280
gtgaaccccc agcgcaccaa ggtcgcggcg atccgagagc cgccatccga acaggtcgca   11340
atacgaggcg gccgtctgtt gcacgttcgc ggcatagagc tgctgccaga ccacctccgg   11400
ctggagcgct ctcgtcgttg ccggtgccgt cgccacggcg aaggtcgccc tccaggatc    11460 gcggaggatc gcgacgcgcc cgccgtcgtt cgtcgggtgg gtcgggccga gctgggtcgc   11520
cccgcgcccc acgaacgagc gcaccgcttc atcgacgtcc tcgacgccga cgtaacccag   11580
ccaatgggcg ggtgcgccgc gggcaatcgc ctgctcgggc agcggcacga tgtctgcgtt   11640
ggcggcgccc tcaccgaaca gagccgtgta gaacgcccgt gccgcgggga cgttggtggt   11700
gcgcaactgg agcttgaaga accgtttcat accacgtgac ctcgttaccg ccgggggggcc   11760 ggctcagggt gtctgatagc cgtcgaccac cattcccaac gcctgggcga gggcgacggc   11820
ggtctccacg ccaacacgcg tcccctttgac ctggttcgcc ttcgggtcga agatgaaatt   11880
ggtcgatcga gcaaaattgg tcttggtgag gacgcagccc tgcatggtgc atcctggcat   11940
atcggtgccg gtgaagtccg actcggcgag gtccacgtca atgaagttgg cttcgcgcgc   12000
ggagcagcca acgaaccgcg tcttgcgtag attcaacttc aagaaggagc tgtagcgcag   12060
atcgcactgt tcgaactgga cgtccggcat ggttccgagt ccactccagt ccacgcccat   12120
gaggcgggtg tctttgaagg tcacgcttcg cagcgcgagc ttctccggta ccatccgcag   12180
gagatcgcat ccctcgaata cacaatcctc caggcggctc cggacccagc ggctttcggg   12240
caacttgcac cgccggaacg tgcagcgctc gaattccttg ccggagagat cagccgactc   12300
gatcgagaga tcagaaaacg tgacgtcggc gaaaaagtcg ccactttcca gagagggagt   12360
ggagcgggcg gcatatgtc ctcatggctg acacgacgag cggcccctaa taccagtgcg   12420
tgcgctaggg atccagcaca gtcagtccta tgtcctccaa ccgacatatc gtctagatga   12480
gtcaaactta agttgactcc acaacacgta tgtgccttga atcgagcata actgaactcg   12540
tggcgtgcgc gggccgaatg ccgagtgcgt cggcctgtcc ggaaacgcct gcctcgtccg   12600 gagacgccc caactgggcg cgacgcgccc tggtggctcg gtgacgcag ggcaggaagc    12660 gtatttggcc gaaccgcaag ttgccgggcc gcgaggctcg gcagggggaac gacgatgagc   12720
```

```
atgaacgggg acgaagccga gtacgttgtc ttgatcaacg gcgaagagca gtactcgctc    12780
tggcccgtgc accgcgaaat tccgggcggt tggaagaccg ttgggcccaa gggaagcaag    12840
gaaacgtgtc agtcctacat ccaggaggtc tggacggaca tgaggccgaa atcgctacgg    12900
gaagccctga cgcgcagcaa ctgctgatcc cgctgcctcg ggggctcctg taccgccgtc    12960
gtctccagat gaggattgca gcgaggccac aaccaatgag tacgccagca gcaggagcga    13020
agccgtccta tctcgcgggt attgaaacgg tgatggtcga acctgagctt gaggaggttc    13080
gctacctgac cgtggagagc ggcgacggac ggcagagtac cctctatgag ttcggtccga    13140
aggacgcgga gaaggtcgtg gtcttgccgc cctacggagt caccttcttg ctggtggcgc    13200
gactcgcccg gctcctctcc cagcgattcc atgtcttgat ttgggagtca agggggtgtc    13260
cggactccgc catcccggtg tatgacacgg accttgggct cgccgaccag tcaaggcatt    13320
tctccgaggt cctcaagcag cagggcttcg aggcgtttca cttcgtcggc tggtgtcagg    13380
cggcgcagct ggccgtgcat gccaccgcca gcggccaggt caagccgcgg acgatgtctt    13440
ggattgcccc ggcggggctg ggttactcgc tggtcaagtc cgagttcgat cgatgtgcac    13500
tgcccatcta cctggagatc gagaagcatg gcctgttgca cgccgagaag ctcggcaggc    13560
ttctgaacaa atacaatggc gttcccgcga cggcgcagaa cgcggcggaa aagctgacga    13620
tgcgccattt ggccgacccg cggatgacat acgtcttctc caggtacatg aaggcgtatg    13680
aagacaacag gctcctcgcc aagcaatttg tctcgaccgc gctcgactcg gtgccgacgc    13740
tggccattca ctgccgggac gacacgtaca gccacttctc ggagtccgtt cagctctcga    13800
agctgcatcc atccctcgag cttcgcctac tcggtaaggg cggccatctg cagatcttca    13860
acgaccccgc cacactggcg gagtacgttc tcggtttcat cgacaccagg gcgtcgcagg    13920
ctgccgctcc tgcggtggcg ggagcgtagg gagacaacat gatacttccc aacaacatcg    13980
gcctcgacga gcggacgcag ctcgcacggc agatctcctc gtaccagaag aagttccacg    14040
tgtggtggcg cgagcggggg cccaccgagt tcctcgatcg gcagatgcgc cttcgcacgc    14100
cgaccggggc ggtcagcggc gtggactggg ccgagtacaa gacgatgcgt cccgacgagt    14160
atcgctgggg cctcttcatg gtgccgatgg accaggacga gatcgccttc ggcgaccacc    14220
gtggcaagaa ggcgtgggag gaggttccga gcgaataccg cacgctgctg ctgcagcaca    14280
tctgcgtgca ggccgacgtg gagaacgccg ccgtcgagca gagccggctg ctgacgcaga    14340
tggcgccgag caacccggac ctggagaacg tgttccagtt cttcctcgag gaggggcgcc    14400
acacctgggc catggttcac ctcctgctcg cccacttcgg tgaggacggg gtcgtcgagg    14460
ccgaagcgct cctggagcgg ctgagcggtg acccgaggaa ccccgcttg ctggaggcgt    14520 tcaactatcc gaccgaggac tggctgtccc acttcatgtg gtgcttgctg gccgaccggg    14580
ttggcaagta ccagatacat gcagtgaccg aggcttcgtt cgccccgttg gcccgggcgg    14640
cgaagttcat gatgttcgag gaaccgctcc acatcgccat gggcgccgtg gtctggaac    14700 gagtgctggc caggaccgcc gaggtcaccc tgcgtgaggg gacgttcgat acgttccacg    14760
cgggggcgat tccgttcccg gttgtccaga agtatctcaa ttattgggcg ccgaaggtct    14820
acgacctctt cggaaacgac ggctccgaac gctcgaacga actcttccgg gctgggctcc    14880
ggaggccgcg gaatttcgtg ggaagcgaat cgcagatcgt tcgcatcgat gagcgcatgg    14940
gcgacggact gaccgtcgtg gaagtggaag gggagtgggc gatcaacgcc atcatgcgac    15000
gacagttcat cgccgaagtg caaacgctca ttgatcgctg gaacgccagc ctgcgagcgc    15060
```

```
tgggcgtcga cttccagttg tacctccctc acgagcgctt cagcaggacc tatggcccct   15120
gcgccggtct gcccttcgac gtggacggaa aactgctccc ccgcggcacg gaggcgaagc   15180
tcgccgagta cttccccaca cctcgcgaac tcgcgaacgt ccgctcgctg atgcagcggg   15240
agctggctcc cgggcagtac tcctcgtgga tcgccccgtc cgcgacgcgg ctgagcgcgc   15300
tggtccaggg caggaacacg cccaaggagc acgaatgaaa cgaagccgtc ggatcgttga   15360
cgggagaaga gcgagcagtt cgtgggaacg ggagaggggc tcgccatgag cggcaagctg   15420
cctcctcgta tgtgtccgac accccggaaa gagcactcat cacatgcgtt gcctcatcat   15480
cgacaactac gattcgttca cctggaatct ggcgcagcta cgttgcgcaga cgttcgggag   15540
cgagccgttg gtcgtccgca acgaccagca tacctggcaa gaaatcaagg ccttgggctc   15600
cttcggatgc atcctggttt ctccgggtcc gggctcggtg accaatccga aggatttcaa   15660
tgtctcgcga gacgcgctcg agcaggatga gttcccggtg tttggggtct gcctgggcca   15720
tcaagggctg gcgtacatct acggggggcga gatcactcac gctccggttc cgttccacgg   15780
caggacgtcg accatctacc atgacggcac gggcgtgttt cagggactcc cgccgagctt   15840
cgacgcggtg agatatcact cgctggtcgt gcggccggag tcgcttcccg cgaacctggt   15900
cgtcaccgct cggacggaat gcggcctgat catgggggttg cggcacgtga gtcgcccgaa   15960
gtggggcgtc cagttccatc ccgagtcgat tctgactgcg cacggcttgc agctcatctc   16020
caatttccgt gacgaggcgt accgatacgc ggggaaagag gttccgtcgc gccgtcccca   16080
ttcgactgcc ggcaacggtg tcggcgcagg tgctgccagg cgtgacccga gcgcccgccg   16140
cacaccggag cggagaaggg aacttcagac gttcaccagg cggctggcga cgtctctcga   16200
ggccgagacc gttttcctgg gcctgtatgc gggccgcgag cactgcttct ggctcgacag   16260
ccagtccgtg agagaaggga tatcccggtt ctccttcatg ggctgcgtgc cggagggctc   16320
gctgctgacg tacggcgctg cggaagcggc gtcagagggg ggcgccgagc ggtacctggc   16380
ggcgctggag cgggcgctcg aaagccgtat cgttgttcgc cccgtggatg ggctgccatt   16440
cgagtttcat ggcggctaca tcggcttcat gacctacgaa atgaaggagg cgtttgggc   16500
cgcgacgacg cacaagaaca ctattcccga cgccttgtgg atgcacgtga agcggttcct   16560
ggcgttcgac cactcgacgc gagaagtgtg gctggtcgcc atcgcggagc tcgaggagag   16620
cgcgagcgtc ctcgcctgga tggacgagac cgccgacgct ctgaagtcgc ttccgcgcgg   16680
caccgttcg ccccagtccc tggggttgaa atccatctcg gtatcaatgg attgtggacg   16740
ggatgactac ttcgccgcca tcgagcgctg caaggagaag atcgtcgatg gggagtccta   16800
cgaggtctgc ttgacgaacg gtttctcgtt cgatctgaag ctggatcccg tcgagctgta   16860
cgtgacgatg cggagaggca atcccgcccc gttcggcgct ttcatcaaga caggcaagac   16920
ctgcgtcctc agtacctccc cggagcgctt cctgaaggtg gatgaggatg gggacggtcca   16980
ggccaagccc atcaagggga cctgcgcgcg ctctgacgac cccgccaccg acagcacgaa   17040
tgccgcgcgg ctgccgcct cggagaagga ccggcggag aacctgatga tcgtggacct   17100
gatgcggaac gacctcggac gggtgtccgt gccgggcagc gtccatgtct ccaatctaat   17160
ggacatcgag agcttcaaga cggtccatca gatggtcagc accgtcgaat cgaccttgac   17220
gccggagtgc agcctcgttg acctcctgcg cgcggtcttc ccggggggat ccatcaccgg   17280
ggctcccaag atccgcacga tggagatcat cgatcggctc gagaagagcc ctcgggggcat   17340
ctactgcggg acgatcggct acctcgggta caaccggatc gccgacctga acatcgccat   17400
ccgcaccttg tcctacgacg gcaccctcgt gaagttcggt gccggcggag ccatcaccta   17460
```

```
cttgtcacag ccggaggggg agtttcagga gatcctgctc aaggcggaat ccatcctccg    17520
gccgatttgg cagtacatca atggcgcggg tgctcccttc gaaccccagt tgcgcgaccg    17580
ggttctgtgc ctggaggaga agccgcgaag ggtcattcgt ggccacgggt cggcaattga    17640
tgcagtggag cctagcgcgt gaagcctacg tcgagtcgag acctgcccat cgcgcgtca     17700 agcccccagg gaccatccga accgcgtgcg cgtccccggg ccagtggat gattgcgttc     17760 aacccgcagg cgcggcccag gctgcggctc ttctgctttc cgtacgccgg tggcgacgcg    17820
aacatcttcc gggactgggc cgcggcgatg cccgaggggg tcgaggtcct cggcgttcag    17880
taccccgggc gcggtaccaa cctggcgttg ccgccgatca gcgactgtga cgagatggcg    17940
tcacaactgc tggcggtgat gacgccgttg cttggcatca acttcgcttt tttcggccac    18000
agcaatggcg ccttgatcag cttcgaggtg gcgcgaaggc tccacgacga actgaagggc    18060
cgcatgcggc atcacttcct gtcggccaag tccgcccctc actacccgaa caacaggagt    18120
aagatcagcg gcctcaacga cgaggacttt ctccggggcga tccggaagat gggcggtacg    18180
ccccaggaag tgctcgacga cgcccggctg atgcagattc tgctgccaag actgcgcgcg    18240
gacttcgcgc tcggcgagac gtatgtgttt cgccccggac ccaccctgac gtgcgacgtc    18300
agcatcctgc gaggcgagag cgaccacctg gtcgacggcg agttcgtcca gcggtggtcc    18360
gagctgacga cgggcggcgc gagccagtac gcaatagatg gtggccattt cttcctgaat    18420
tcccacaagt cgcaggtcgt ggcgctcgtg cgagcggcac tgcttgagtg tgtgttgtag    18480
cgagaaaacg gattcccaaa taatgaccgc tcagaaccaa gcctccgcgt tttctttcga    18540
tctcttctac acgacggtca atgcgtacta ccggaccgcc gccgtcaagg cggccatcga    18600
gctcggcgtg ttcgacgtcg ttggcgagaa gggcaagacc ctggccgaga tcgcgaaggc    18660
ctgcaacgcg tcgccgcgtg gcatccgcat tctctgccgg ttcctcgtgt cgatcgggtt    18720
cctcaagaat gcgggtgagt tgttcttcct cacgcgagag atgggccctgt ttctggacaa    18780 gaagtcgccc ggctatctgg gcggcagcat tgatttcctt ctgtcgccgt acatcatgga    18840
cggcttcaag gacctcgcgt cggtggtgcg gacgggcgag ttgacgctgc cggaaaaagg    18900
ggtggtggcg ccagatcatc cgcagtgggt gacgttcgcg cgcgcgatgg cgccgatgat    18960
gtccctgcca tccctcctgc tcgcggaact ggcggaccgc caggcgaacc agccgctcaa    19020
ggtgctcgat gtcgccgccg gccacggcct cttcggcctg gccatcgccc agcggaatcc    19080
gaaggcgcat gtgacgttcc tcgactggga aaacgtgcta caggtggcgc gcgagaacgc    19140
gacgaaggcg ggagttctcg acagggtcga gttccgcccg ggagatgcct ctccgtgga    19200 cttcggcaag gagctggacg tcatcctcct gacgaacttc ttgcatcact tcgacgaggc    19260
gggctgcgag aagatcctca agaagcccca cgctgccctg aaggagggcg gccgtgtgct    19320
gacgttcgag ttcatcgcga acgaggaccg gacgtcgcct ccgcttgccg ccacgttcag    19380
catgatgatg ctcggcacga cgcccggcgg tgagacctac gcctactccg atctggagcg    19440
gatgttcaag aacacggggtt acgatcaagt cgagctcaag gccattcctc ccgcgatgga    19500
gaaggtcgtc gtttcgatca agggcaaagc gcagctctga gcaacattca gcacaatagg    19560
acctcctggg agatttcgaa tggccaccaa attgtcgac ttcgcgctcc tcgactccga     19620
agacgccaac gtcatctccc gctcgaacga gacggggata tcgctggatc tgtccaagag    19680
cgtggttgac ttgttcaacc tccaggtcga gagggcgcct gacgccacgg cgtgtctcgg    19740
ccgccagggg cgcttgactt acggagaact caaccggcgg acgaaccagc tcgcgcatca    19800
```

```
cctgatcgcg cgaggcgtcg ggccggatgt tcccgtgggc gtcctgttcg agcgctccgc   19860
cgagcagctc atcgccatcc tgggcgtcct caaggcgggc gggtgttatg tcccgttgga   19920
tccgcagtac cccgccgatt acatgcagca ggtcctgacg gacgcccggc cgcggatggt   19980
ggtgtcgagc cgggcgctcg gcgagcgcct ccgctcgggc gaggagcaga tcgtctacct   20040
cgatgacgaa cagctcctgg cgcgcgagac ccgcgacccg cctgtgaagg tgttgccgga   20100
gcagctcgcg tacgtgatgt acacgtcggg ctcgtccgga gtgccgaagg gcgtcatggt   20160
gccccatcgc cagatcctca actggctgca tgcactcctg gcgcgggtgc cgttcggcga   20220
gaacgaagtg gtggcccaga agacgtccac gtcattcgcc atctcagtga aggaactctt   20280
cgcgggattg gtcgcgggtg tcccgcaggt cttcatcgac gatgcgactg tccgcgacgt   20340
tgccagcttc gttcgtgagc tggagcagtg gcgcgtcacg cggctctata cttttccctc   20400
ccagctggcg gcgattctct cgagcgtgaa tggcgcgtac gagcgcctcc gctcgctgcg   20460
ccacctgtac atctcgatcg agccctgccc aacagagctg ctggcgaagc tccgggcggc   20520
gatgccgtgg gtcacccct ggtacatcta tggctgcacc gagatcaacg acgtcaccta   20580
ctgcgaccca ggggaccagg ctggcaacac gggcttcgtg ccgatcgggc ggcccatccg   20640
caacacgcgg gtgttcgtcc tcgacgaaga gctccggatg gtgcccgtcg gcgcgatggg   20700
tgagatgtac gtggagagcc tgagcacggc gcggggctac tggggccttc ccgagttgac   20760
ggcggagcgg ttcatcgcca accctcacgc ggaggacggt tcgcgcctgt acaagacagg   20820
cgacctcgcc cgctacctgc cggatggttc cctggagttc ctcgggcgcc gggactacga   20880
ggtgaagatc cgcgggtatc gcgtggacgt ccggcaggtc gagaaggtcc tcggggcgca   20940
tcccgacatc ctcgaggtgg cggtggtggg ctggccgctc ggcggggcga atccacaact   21000
ggtcgcctac gtcgtgccga gggcgaaggg ggctgctccc atccaggaga tccgggacta   21060
cctgtcggcg tccctgccgg cctacatggt gccgacgatc ttccaggtgc tggcggcgct   21120
gccacgtctt cccaatgaca aggtggatcg gttgagcctg cccgaccca aggtggagga   21180
gcagaccgag gggtacgtgg cgcctcgcac ggaaaccgag aaggtactgg ccgaaatctg   21240
gagcgacgtc ctcagccagg ccgggcccc cctgaccgtc ggcgcgacgc acaactttt   21300
cgaactggga ggccattcgc ttctcgccgc ccagatgttc tcgcggatcc ggcagaagtt   21360
cgatctcgaa ctgcccatca acccctgtt cgagacccc gtgctggagg ctttgcgag   21420
cgccgtcgac gcggctcttg ccgagcggaa cggtccggcg cagaggctga tcagcatgac   21480
ggaccgcggc caggcgcttc cgctgtcgca cgtccaggag cggctctggt tcgtgcacga   21540
gcacatggtc gagcagcgga gcagctacaa cgttgccttc gcctgccaca tgcgtggcaa   21600
ggggctgtcg atgccggcgc tgcgcgccgc catcaacggg ctggtggctc gccacgagac   21660
cttgcggacg acgttcgtcg tctccgaggg cggaggagat cccgtccagc ggatcgccga   21720
ctccctgtgg atcgaggttc cgctatatga ggtcgatgcg tcggaagtcc cggcccgcat   21780
ggcggcccac gcgggccacg tgttcgacct tgcgaagggc cccctgctga agacctcggt   21840
cctgcgggtg acgcccgatc accacgtgtt cttgatgaac atgcatcaca tcatctgtga   21900
tgggtggtcg atcgacatcc tgctgcggga cctctacgag ttctacaagg cggccgagac   21960
gggctcgcag ccgaacctgc cggtcctgcc aatccagtat gccgactact ccgtgtggca   22020
gcgtcagcag gacctcagca gtcacctcga ctactggaag aagacgctcg agggctacca   22080
ggaagggttg tcgcttccgt acgacttcgc ccgcccgtcc aacaggacct ggcgtgccgc   22140
gagtgtccgg caccagtacc cggcggaact cgccacccgt ctgtcggagg tgagcaagag   22200
```

```
ccatcaggcg acggtgttca tgacgttgat ggccagcacg gcaatcgtgc tgaaccggta  22260
cacgggtcgg gatgatctgt gcgtgggtgc cacggtggcg ggccgtgacc acttcgagct  22320
cgagaacctg attggcttct tcgtcaacat cctcgccatc aggctcgacc tcagcgggaa  22380
tcccacggcc gagacggtgc tgcagcgggc gcgagcgcag gtgctggaag gcatgaagca  22440
tcgcgacctg ccgttcgagc acatcctggc ggcgctgcag aagcagcgcg acagcagcca  22500
gattcccctg gtgccggtga tggtccgcca ccagaacttc ccgacagtga cctcgcagga  22560 gcagggctc gacctgggta tcggggagat cgagtttggt gagcggacga cgcccaacga  22620
gctcgacatc cagttcatcg gcgagggaag cacgctggag gtggtggtcg agtacgcgaa  22680
ggatctgttc tccgagcgca cgatccagcg gctcatcacg cacttgcagc aggtgctgca  22740
gactctcgtg gacaagccgg actgccggct gacggatttt ccgctggtgg ccggggacgc  22800
gctgcagggc ggtgtgtcgg gctccggggg cgcgacgaag accggcaagc tcgacgtgtc  22860
gaagagcccg gtcgagttgt tcaacgagcg ggtagaggcc tcgccggacg cggtcgcctg  22920
catgggcgcg gacggaagcc tgacctaccg ggagctggac cgaagggcca atcaggtcgc  22980
ccgccacctg atggggcgag gggtggggcg ggagacgcgg gtggggttgt ggttcgagcg  23040
ctcgccggac ctgctggtcg cactcctggg catactcaag gcgggggggct gcttcgttcc  23100 gctcgatccg agctatccgc aggagtacat caacaacatc gtcgccgatg cgcagccgct  23160
tctggtgatg tcgagcccggg cgctgggctc acgcctgtca ctggaggcag ggcggctggt  23220
gtacctcgat gacgcgctgg cggcgtccac cgatgcgagc gatccccagg tgcgcatcga  23280
cccggagcag ctcatctacg tcatgtacac ctccggttcc accggtctgc cgaagggggt  23340
gctcgttccc catcggcaga tcctgaactg gctgtaccg ctgtgggcga tggtgccctt  23400
cgggcaggac gaggtggtgg cgcagaagac atccacggcc ttcgcggtct cgatgaagga  23460
gctcttcacg gggctgctgg cgggcgtgcc ccaggtattc atcgacggca ccgtggtcaa  23520
ggacgcggcg gccttcgtgc tccacctgga gcgatggcgg gtcacccggc tgtacacgct  23580
cccgtcgcac ctcgatgcca tcctgtccca cgtcgacggg gcggcggagc gcctgcggtc  23640
cctgcggcat gtcatcctcg cgggggagcc gtgccccgtt gagctgatgg agaagctgcg  23700
cgagaccctg ccgtcgtgca cggcgtggtt caactacggc tgtaccgagg tcaacgacat  23760
ctcctactgc gtcccgaacg agcagttcca cagctcgggg ttcgtgccga tcggccggcc  23820
catccagtac acccgggcgc tggtgctcga cgacgagctg cggacggtgc cggtgggcat  23880
catgggggag atttacgtcg agagcccggg gacggcgcgg ggctactgga ggcagccgga  23940
tttgacggcc gagcggttca tccccaaccc gttcggcgag ccgggtagcc gtctctaccg  24000
tacgggcgat atgcgcgat gccttgagga tggctcgctg gagttcttgg ggcgccggga  24060
ctacgaggtc aagatccgtg gccatcgcgt ggacgtccgc caggtcgaga agatcctcgc  24120
gagccacccg gaagtcctcg agtcggcggt gttgggctgg ccacgggggg cgaagaaccc  24180
tcagttgctt gcctacgccg ccacgaagcc gggccgtccc ctgtcgactg aaaacgtgcg  24240
ggagtacctg tcggcccgct tgccgacgta catggtgcca acgctctacc agttcctgcc  24300
agcgctgccg cgcctgccca atggcaagct cgaccgcttc gggctgcccg atcacaagaa  24360
agtcgaggtg ggcggcgtct acgtcgcccc gcagacgccg acggagaagg tcttggcggg  24420
actgtgggcc gagtgcctca agcagggcga catgcccgcg ccgcaggttg gccgcttgca  24480
caacttcttc gacctcggtg ggcactcgct gctcgccaat cgcgtactga tgcaggtgca  24540
```

```
gcggcatttc ggggtcagcc tgggcatcag tgcgttgttc ggttctccgg tgctgaatga   24600
cttcgcggcg gccatcgaca aggcgctcgg gaccgaggag ccaggcgagg aaggttcgag   24660
cgacgcacga gaggtcgctg cgaaggacac ctccgtgctc gtgccgctct ccacccacgg   24720
gacgctgccg agcctgttct gcgtccatcc ggtgggcggg caggtccatg cctaccgcga   24780
gctcgcccag gcgatggaga agcacgccag catgtacgcg ctccagtcgg agggcgcccg   24840
tgagttcgac acaatcgaga ccttggcgcg cttctacgcc gatgcgatcc gcggggctca   24900
gcccgacggg agctaccgtc tcctcggatg gtcttctggt gggctcatca ccctggcgat   24960
tgctcgcgag ctggagcacc agggctgcgc cgtggagtac gtgggcctcg tggattcaaa   25020
gccaatcccg cggttggcgg gtgagcgcgg ctgggcgtcg ctgatcgcgg cgacgaacat   25080
cctgggcgcg atgcgggggc gcggcttctc ggtcgccgag gtcgatgctg ccgggaagat   25140
cctcgagtcg cgcggatgga cggaggagtc cttcgactcg gaggggcatg cggcgttgga   25200
ggagttggct cggcacttcg gcatcaccgt cgcgcaagag tcatcggagt acctcctggc   25260
ccggttcaag accacgaagt actacttgtc gctgttcgct ggcttcaagc cggcggcgct   25320
cgggccggag acgtacctct atgaggcttc agagcgggtc ggagccacct cgaacgacga   25380
cacgggcgag tgggggacg cgctggatcg caaggcctg cgggcgaaca tcgtgcaggt   25440
gccaggcaat cactatactg tcctgcaggg agagaacgtg ctgcaactgg cggggcggat   25500
cgccgaagcc ttgtctgcga tcgacaactc ggtggtaacg aggacgcgag cttcgtgacc   25560
cttcgcccct cgggttcgcc aagaggcaac aaacgctgat tcaccggcaa gggaattccg   25620
tgcagatgga caatcgagag atcgcaccca cccaatcggc gcgcacgcgt gatgcgtaca   25680
cggcggtacc accagccaag gccgagtatc cgtcggacgt ctgtgtgcac caactgttcg   25740
agttgcaggc ggacaggatt cccgacgccg ttgcggcgag ggcggggaac gagtccctga   25800
cctaccggga gctgaacttc cgggcgaatc agctcgcccg gtaccttgtt gcgaaaggcg   25860
tggtcccgcg aggctcggtg gccgtgctga tgaaccggac ccctgcgtgt ctggtctcac   25920
tgctcgccat catcaaggcg ggcgcggcgt acgttccggt ggacgccgga ttgcccgcca   25980
aacgggtgga ctacattctg acggacagcg gcgcgacctg cgtcctgacc gacagggaga   26040
cgcggtcact cctcgacgag ccgcggtcgg cttcgacgct cgtcatcgac gtggatgatc   26100
catccatcta ttcgggcgag accagcaacc tcgggctcgc tgtcgatccc gagcagcagg   26160
tctactgcat ctacacctcg ggttcgacgg gccttcccaa aggcgtgatg gtccagcacc   26220
gcgcgctgat gaactacgtc tggtgggcga agaagcagta cgtcaccgac gcggtcgaga   26280
gttttgccct gtactcctcg ttgtcgttcg acctcacggt cacctccatc ttcgttccgc   26340
tgatctccgg acgctgcatc gatgtgtacc cggacctggg cgaggacgtc cccgtcatca   26400
accgggtact ggaggacaat aaggtcgatg tcgtgaagct cacgccggcc caccttgccc   26460
tgctcaggaa cacggaccta tcgcaaagcc ggctgaaagt gctcatcctg ggaggagagg   26520
acctccgagc ggagacggcg ggggacgtcc acaagcggct ggacgccgg gcggtgatct   26580 acaacgagta cggccccacg gagaccgtcg tgggtgcat gattcaccgc tacgaccccg   26640
cggtggatct gcacgggtcg gtgccgattg gagtgggcat cgacaacatg cggatctact   26700
tgctcgacga ccgtcggcgt cccgtcaagc caggagaggt tggcgagatt tacatcggag   26760
gcgacggtgt gaccctgggg tacaaggaca agcctcaagt cacggcggac cacttcatct   26820
ccaatccgtt cgtggaaggg gagcggttgt acgccagtgg cgacctcggc cgggtgaatg   26880
agcgcggcgc gctcgtcttc ctcggccgga aggatttgca gatcaagctg cgggggtacc   26940
```

```
ggatcgagct gggcgagatc gagagcgccc ttctctccta tccggggatc aaggaatgca   27000
tcgtcgattc gaccaagacc gcgcagagcc aggccgccgc tcagctcacc tactgcacca   27060
agtgtggtct ggcgtcgagc ttcccgaata cgacgtactc cgccgagggg gtctgcaacc   27120
actgcgaggc cttcgacaag taccgcagcg tcgtcgacga ctacttcagc acgatggatg   27180
agctgcagtc gatcgtcacc gagatgaaga gcatccacaa ctcgaagtac gactgcatcg   27240
tggcgctcag cggcggaaaa gacagcacgt atgcactctg ccggatgatc gaaaccggtg   27300
cccgtgtatt ggccttcacg ttggataacg gctacatctc ggaggaggcg aagcagaaca   27360
tcaaccgggt cgttgcccgg ctgggagtgg atcaccgcta tctctcgacc ggccacatga   27420
aggagatctt cgtcgacagc ctgaagcgac acagcaatgt gtgcaacggc tgcttcaaga   27480
ccatctacac gtttgcgatc aacctggcgc aggaggtcgg cgtcaagcac gtggtcatgg   27540
ggttgtcaaa gggccaactg ttcgaaacgc gcctctcggc cttgttccgc acgtcgacct   27600
tcgacaacgc cgccttcgag aagagcctcg tcgacgcgcg aaagatctac catcgcatcg   27660
atgatgccgt gagccgcctg ctcgacacta cttgcgtcaa gaacgacaag gtcatcgaga   27720
acatcaggtt cgtggacttc tatcgttatt gccacgccag ccgtcaggag atgtacgact   27780
acatccagga gagagtcggg tgggccaggc cgattgacac cgggcggtcg acgaactgtc   27840
tcctcaatga tgttggcatc tacgttcaca caaggagcg caggtaccac aactactccc   27900
tgccctacag ctgggacgtc cggatgggcc acatcagcag ggaagaggcg atgagagagc   27960
tcgacgactc ggccgacatc gacgtcgaga gggtcgaggg catcatcaag gaccttggct   28020
acgagctgaa cgaccaggtg gtgggctcgg cggaagccca gctggtcgcc tactatgtct   28080
ccgcggagga gttccccgcg tccgacctgc ggcagttcct gtcggagatt ctgccggagt   28140
acatggtacc caggtcgttc gtccagctgg acagcatccc gctgacgccc aatggcaagg   28200
tcaatcgtca ggccctgccg aagcctgacc tgcttcggaa ggccggcacc gacggacaag   28260
ccgcaccccg aacaccggtg gagaagcagt tggcggagct gtggaaggag gtgctgcagg   28320
tcgacagtgt cgggatccac gacaacttct tcgagatggg cgggcactcg cttccggcgc   28380
tcatgctgct ctacaagatc gacagtcagt tccataagac gatcagcatc caggagttct   28440
cgaaggtccc caccatcagc gcgctcgcgg cgcatctcgg cagtgacacc gaagcggtgc   28500
cgccagggct gggcgaggtc gtcgatcaga gcgcgcctgc atacagggga taacgtgcgc   28560
ttcgtcactg tcaatggtga ggactcggca gtttgctcgg tgctggatcg cggactccag   28620
ttcggagatg gcctgttcga gacgatgctg tgtgttggcg gtgcgccggt cgacttcccg   28680
gaacactggg cgcggcttga tgagggctgc cgccggctgg gaatcgaatg cccggacatc   28740
cggcgcgaag tgaccgctgc gatcgccagg tggggtgctc ccaggcggt cgccaagctc   28800 gtcgtcactc ggggaagcac ggagcgggga taccggtgcg cccttccgt ccggccgaac   28860 tggatcctca ccatcacgga tgccccgaag tatccgctgg cccacgagga cagaggcgtg   28920
gccgtcaaac tctgccgaac gctcgtctcg ctcgatgacc cacagctggc cggggttgaag   28980 cacctcaacc ggttgcccca ggtgctcgcg aggaggagt gggacgacga gtaccacgat   29040
ggcctgctga ccgaccacgg tggtcacctc gtcgagggtt gcacgagcaa cctgttcctc   29100
gttgccgacg gagccttgag gacgcccgat ctgactgcgt gcggtgtgcg cggtatcgtg   29160
cggcagaagg tcctcgacca ctcgaaggca atcgggatcc gctgcgaggt aaccaccctg   29220
aagctacgag atctcgaaca cgcggacgag gtcttcctga cgaactctgt ctacgggatt   29280
```

```
gtgccggttg gtagcgtcga tggtatgagg taccggatag gtccgacgac ggcgcgtttg    29340
ctgaaagacc tttgccaggg tgtgtacttt tgaggctccg tggaggacgg tatgaccggt    29400
aatttggata gcgcggcatg gcccgtaatc atcacgcctg gccagcagcc agcggcgctg    29460
gaggattggg tctcagcgaa ccgtgacgga ctcgagcggc agttgaccga gtgtaaggcc    29520
attctctttc gaggcttccg tagcaggaat ggcttcgaga gcattgccaa cagcttcttc    29580
gaccggcgcc tcaactatac ctatcggtcg acgccccgta cggacctggg gcagaacctc    29640
tacacggcga cggagtaccc gaagcagctg tcgattccgc agcattgcga gaacgcctac    29700
cagcgcgact ggccgatgaa gctgctgttc cactgcgtgg agccggcgag caaaggcggc    29760
cggacgccct tggccgacat gacgaaggta acggcgatga tccccgccga aatcaaggag    29820
gagttcgcgc ggaagaaggt cgggtacgtg cggaactacc gtgctggagt ggatctgcct    29880
tgggaagagg tgtttggaac gagcaacaag gcagaggttg agaagttctg cgtcgagaat    29940
ggcatagagt accactggac cgagggtggc ttgaagacca tccaggtctg ccaggcgttc    30000
gcttcgcatc cactcaccgg tgagacgatc tggttcaatc aggcccacct gtttcacctt    30060
tccgcattgg acccggcttc acagaagatg atgctttcct tcttcggtga gggcggcctc    30120
ccgcgcaact cgtacttcgg agacgggtcg gccatcggga gcgacgtcct cgaccagatc    30180
cgctccgctt acgaacgcaa caaggtctcg ttcgagtggc agaaggacga cgtgttgctg    30240
atcgacaaca tgctggtttc tcacggacga gatccgttcg aaggcagccg gcgggtgctg    30300
gtctgcatgg cggagccgta ttcggaagtc cagcggcggg gattcgccgg ggcaacgaac    30360
tcagggcgct cgtaagggcc gggctcgatg gtggtgtcgc tttcgccgtt gcgcaaaaca    30420
gtcggaggag tttcttgtcc cgaatttcga tgctgctgga gggagagctg gaggggtacg    30480
aggacgggtt ggaactgccg tacgacttcc cgcggacgtc gaatagggcg tggagagcgg    30540
cgacgttcca gcatagctac ccgcccgagc tggcgaggaa ggtggcggag ctcagccggg    30600
agcagcagtc cacgctgttc atgagcctgg tggcgagcct ggcggtggtg ttgaaccggt    30660
acacgggccg cgaggacgtg tgcatcggga cgacggtggc gggccgagcg caggtggggg    30720
cgttggggga tctgagcggg tccaccgtcg acatcctccc gctgaggctg gacctgtcgg    30780
gcgctccgag ccttcacgag gtgctgcgga ggacgaaggc ggtggtgctg gagggattcg    30840
agcacgaggc gttgccgtgc cagattccct tggtgccggt ggtggtgagg caccagaact    30900
tcccgatggc gcgtctggag ggctggagtg aggggtggga gctgaagaag ttcgagctgg    30960
cgggggaaag gacgacggcg agcgagcagg actggcagtt cttcggggac gggtcctcgc    31020
tggagctgag cctggagtac gcggcggagc tgttcagcga gaagacggtg aagaggatgg    31080
tggagcacca ccagcgagtg ctggaggcgc tggtggaggg gctggaggag gtgcggctgc    31140
acgaggtgcg gctgctgacg gaggaggagg aggggctgca cgggaggttg aacgacacgg    31200
cgcgagagct ggaggagcgc tggagcctgg cggagacgtt cgagcgtcag gtgagggaga    31260
caccggaggc ggtggcttgc gttggcgtgg aggtggcgac gggagggcac tcgcggccga    31320
cataccggca gctgacatac cggcagctga atgcgcgagc caaccaggtg gcacggaggc    31380
tgagggcact gggagtgggc gcggagacac gggtcgcggt cttgagcgac cgctcgccgg    31440
agctgctggt ggcgatgctg gcgatattca aggccggggg ctgctacgtg ccggtggacc    31500
cacagtaccc gggaagctac atcgagcaga tactggagga tgcggcaccg caggtggtgt    31560
tgggcaagag gggaagagcg gacggggtgc gggtggatgt gtggctggag ctggatggag    31620
cgcaacggct gacggacgag gcgctggcgg cacaggaaga gggagagctg gagggggcgg    31680
```

```
agaggccgga gagccagcag ttggcgtgtt tgatgtacac gtcgggctcc acgggcagac   31740
cgaagggggt gatggtgccg tacagccagt tgcacaactg gctggaggcg gggaaggagc   31800
gctcgccgct cgagcgtggg gaagtaatgt tgcagaagac ggcaatcgcg ttcgcggtgt   31860
cggtgaagga gctgctgagc ggattgctgg cgggagtggc gcaggtgatg gtgccggaga   31920
cgctggtgaa ggacagcgtg gcgctggcgc aggagataga gcggtggcgg gtgacgagaa   31980
tccacctggt gccatcgcac ctgggagcac tgctggaggg ggcggggggaa gaggcgaagg   32040 ggctgaggtc gctgaagtac gtcataacgg cggggaggc actggcgcag ggggtgaggg     32100
aggaggcgag gaggaagctg ccggggggcgc agttgtggaa caactacggg tgcacggagc   32160
tgaatgacgt gacgtaccac cccgcgagcg aggggggagg ggacacggta ttcgtgccaa   32220
tcgggcggcc catcgcgaac acgcgggtgt acgtgttgga cgagcagttg aggcgggtgc   32280
cggtgggggt gatgggggag ttgtatgtgg acagcgtggg gatggcgagg gggtattggg   32340
gccagccagc gctgacggcg gagcgcttca tcgcgaaccc gtacgcgagc cagcccggag   32400
cgaggttgta ccggacggga gacatggtga gggtgctggc ggacggctcg ctggagtacc   32460
tggggaggcg agactacgag ataaaggtga gagggcaccg ggtggacgtg cgccaggtgg   32520
agaaggtggc gaacgcgcat ccagccatcc gccaggcggt ggtgtcggga tggccgttgg   32580
gctcgagcaa cgcgcagttg gtggcctacc tggtgccgca ggcgggcgcg acggtggggc   32640
cgcggcaggt gagggattac ctggcggagt cgctgccggc gtacatggtg ccaacgctat   32700
acacggtgtt ggaggagttg ccgcggctgc cgaacgggaa gctggaccgg ttgtcgctgc   32760
cggagccgga cctgtcgagc agccgagagg agtacgtcgc gccccacggc gaggtcgagc   32820
ggaagctggc ggaaatcttc ggcaacctcc tggggctcga acatgtcggc gtccacgaca   32880
acttcttcag cctcggcggg cactccctcc tggctgccca gctgatttcg cgcatacggg   32940
cgaccttccg cgtggaagtg gcgatggcca cggtgttcga gtcccccacg gtggagccgc   33000
tcgcccgcca catcgaggag aagctcaagg acgagtctcg ggtccagctc tccaacgttg   33060
tgccggtcga gcggacgcag gagattccgc tctcctacct gcaggagcgg ctgtggttcg   33120
tgcacgagca catgaaggag cagcggacca gctataacat cacctggacg ttgcacttcg   33180
ccggcaaggg tttctcggtg gaggcgttgc ggacggcctt cgatgagctg gtggccagac   33240
acgagacact gcgcacgtgg ttccaggtgg gggagggac agagcaggcc gtacaggtca   33300
tcggggagcc ctggtcgatg gagctgccgc tgagagaggt ggcggggacg gaggtgacgg   33360
cggcaatcaa tgagatgtcc cgacaggtct tcgacttgag agcgggacgg ttgctgacgg   33420
cggcggtcct gagggtggcg gaggatgagc acatcctcgt cagcaacatc caccacatca   33480
tcacggacgg ctggtcgttc gggtgatgc tgcgggagct gagggagttg tacgaggcag   33540
cggtgcgggg gaagagagcg gagctgccgc cgctgacggt gcagtacggc gactatgcgg   33600
tgtggcagag gaagcaggac ctgagcgagc acctggcgta ctggaagggg aaggtggagg   33660
agtacgagga cggggttggag ctgccgtacg acttcccgcg gacgtcgaat agggcgtgga   33720
gagcggcgac gttccagtat agctacccac ccgagctggc gaggaaggtg gcggagctca   33780
gccgggagca gcagtccacg ctgttcatga gcctggtggc gagcctggcg gtggtgttga   33840
accggtacac gggccgccag gacgtgtgca tcgggacgac ggtggcgggc cgagcgcagg   33900
tggagctgga gagcctcatc gggttcttca tcaacatcct cccgctgagg ctggacctgt   33960
cgggcgctcc gagccttcac gaggtgctgc ggaggacgaa ggcggtggtg ctggagggat   34020
```

```
tcgagcacca ggagttgccg ttcgagcacc tgctgaaggc gctgaggcgg cagcgggaca   34080
gcagccagat tcccttggtg ccagtggtgg tgaggcacca gaacttcccg atggcgcgtc   34140
tggagggctg gagtgagggg gtggagctga agaagttcga gctggcgggg gaaaggacga   34200
cggcgagcga gcaggactgg cagttcttcg ggacgggtc ctcgctggag ctgagcctgg    34260
agtacgcggc ggagctgttc agcgagaaga cggtgaggag gatggtggag caccaccagc   34320
gagtgctgga ggcgctggtg gagggctgg aggaggggct gcacgaggtg cggctgctga    34380
cggaggagga ggagggctg cacgggaggt tgaacgacac ggcgcgagag ctggaggagc    34440
gctggagcct ggcggagacg ttcgagcgtc aggtgaggga gacaccggag gcggtggctt   34500
gcgttggcgt ggaggtggcg acgggagggc actcgcggcc gacataccgg cagctgacat   34560
accggcagct gaatgcgcga gccaaccagg tggcacggag gctgagggca ctgggagtgg   34620
gcgcggagac acgggtcgcg gtcttgagcg accgctcgcc ggagctgctg gtggcgatgc   34680
tggcgatatt caaggccggg ggctgctacg tgccggtgga cccacagtac ccgggacact   34740
acatcgagca gatattggag gatgcggcac cgcaggtggt gttgggcaag aggggaagag   34800 cggacgggt gcgggtggat gtgtggttgg agctggatgg agcgcaacgg ctgacggacg    34860
aggcgctggc ggcacaggaa gagggggagc tggagggggc ggagaggccg gagagccagc   34920
agttggcgtg tttgatgtac acgtcgggct ccacgggcag gccgaagggg gtgatggtgc   34980
cgtacagcca gttgcacaac tggctggagg cggggaagga gcgctcgccg ctcgagcgtg   35040
gggaagtaat gttgcagaag acggcaatcg cgttcgcggt gtcggtgaag gagctgctga   35100
gcggattgct ggcgggagtg gcgcaggtga tggtgccgga cgctggtg aaggacagcg     35160 tggcgctggc gcaggagata gagcggtggc gggtgacgag aatccacctg gtgccatcgc   35220
acctgggagc actgctggag ggggcggggg aagaggcgaa ggggctgagg tcgctgaagt   35280
acgtcataac ggcggggag gcactggcgc agggggtgag ggaggaggcg aggaggaagc    35340
tgccgggggc gcagttgtgg aacaactacg ggtgcacgga gctgaatgac gtgacgtacc   35400
accccgcgag cgagggggga ggggacacgg tattcgtgcc aatcgggcgg cccatcgcga   35460
acacgcgggt gtacgtgttg gacgagcagt tgaggcgggt gccggtgggg gtgatggggc   35520
agttgtatgt ggacagcgtg gggatggcga gggggtattg gggccagcca gcgctgacgg   35580
cggagcgctt catcgcgaac ccgtacgcga gccagcccgg agcgaggttg taccggacgg   35640
gagacatggt gagggtgctg gcggacggct cgctggagta cctggggagg cgagactacg   35700
agataaaggt gagagggcac cgggtggacg tgcgccaggt ggagaaggtg gcgaacgcgc   35760
atccagccat ccgccaggcg gtggtgtcgg gatggccgtt gggctcgagc aacgcgcagt   35820
tggtggccta cctggtgccg caggcggcg cgacggtggg gccgcggcag gtgagggatt    35880
acctggcgga gtcgctgcca gcgtacatgg tgccaacgct atacacggtg ttggaggagt   35940
tgccgcggtt gccgaacggg aagctggacc ggctgtcgtt gccggagccg gacctgtcga   36000
gcagccgaga ggagtacgtc gcgccccacg gcgaggtcga gcggaagctg gcggaaatct   36060
tcggcaacct cctggggctc gaacatgtcg gcgtccacga caacttcttc agcctcggcg   36120
ggcactccct cctggctgcc caggtggtct caaggattgg caaggagctt ggcactcaga   36180
tctcgatcgc cgatctgttt caaaggccca cgattgaaca gctctgtgag ctgattggag   36240
gactggacga tcagacccag agggagctcg ccctcgctcc gtcggggaac accgaggcgg   36300
tgctctcgtt cgcgcaagag cgcatgtggt tcctgcacaa cttcgtcaag gcatgccct    36360 acaacacgcc agggctcgac cacctgacgg gtgagctcga tgtcgcggcg ctagaaaagg   36420
```

```
ccatccgcgc ggtcatccgt cgccacgagc ccctgcggac gaatttcgtc gagaaggacg    36480
gggtgctgtc ccagttggtg gggacggaag aacgcttccg cctgaccgtg actcccatcc    36540
gcgacgagag cgaggtcgcg cggctcatgg aagccgtgat ccaaacgcca gtcgatctgg    36600
agcgggagtt gatgatccgg gcttatctct accgggtcga cccgcggaat cactacctgt    36660
tcaccaccat ccatcacatc gccttcgatg gctggtcgac atcgatcttc taccgtgagc    36720
tggctgcgta ctacgccgcg tttctccggc gcgaagacag tccgctgccc gcgctggaaa    36780
tctcctatca ggactatgcc cgctgggagc gggcccattt ccaggacgag gtgttggcgg    36840
aaaaactgag gtactggcgg cagcggctgt cgggcgctcg gccccctcgta cttccgacca    36900 cctaccatcg gccgcccatc cagagtttcg ctggcgccgt cgtgaacttc gagatcgatc    36960
gctccatcac cgagcggttg aagacgctgt tcgccgagtc gggcaccacg atgtacatgg    37020
tgttgctcgg cgcgttctcc gtggtgctgc agcgctactc cggtcaggac gacatctgca    37080
tcggctcccc cgtggcgaac cggggtcaca tccagacaga agggctgatc ggcttgttcg    37140
tcaacaccct ggtgatgagg gtggatgccg ccgggaatcc ccgtttcatc gacctgctgg    37200
cgcgcattca acggacagcc atcgatgctt acgcgaacca agaagtgccc ttcgagaaga    37260
tcgtggacga cctgcaggtc gcgagagaca cggcccgatc tccgctcgtg caggtcattc    37320
tcaacttcca caacacgcct cctcaatccg agctggaact gcaggggtg accctcacgc    37380 ggatgccggt gcacaacggc acggccaagt tcgagctctc catcgacgtc gcggagacga    37440
gcgccggtct aacgggattc gtggagtacg cgacggatct gttcagcgag aacttcatcc    37500
ggcggatgat cggccaccct gaggtggtgc tggacgcggt cggtcgcgat ccgcgggcgc    37560
ctatccatga gttgccactg ctcacccggc aggatcagtt ggacctactg tcgcggagcg    37620
gccacacagc ccccgcggtg gaacacgtcg agttgatccc tcatacgttc gagcggcgcg    37680
tccaggagag ccctcaagcg attgccctgg tctgcggtga cgagcgcgtc acctactccg    37740
cgctcaaccg ccgggccagc cagattgccc gccgcctgcg cgccgcaggg atcggaccgg    37800
acaccctcgt cgggctttgc gcggggcgct ccatcgagct ggtctgcggc gtccttggca    37860
tcttgaaggc gggcggtgcg tacgtgccaa tcgaccccac ctcctcgccc gaggtgatct    37920
acgacgtcct gtatgagtcg aaggtgcggc atctgttgac cgagtcgcgc ctggtcgggg    37980
gactgccggt cgatgaccag gaaatcctgc tcctggatac ccccgcggac ggtgaagggg    38040
acaaggctgt tgctgaccgg gaggagccac ctgaccttgg cgaggtcagc ctcactcccg    38100
agtgcttggc gtacgtcaac ttcacctccg actccggtgg ggcgccgagg ggcatcgccg    38160
tccgccatgg ggcgctggct cgccggatgg ccgccggcca cgcacagtac ctggccaatt    38220
ccgccgtacg tttcctgctg aaggcgccgc tcacgttcga cctggcggtc gcggagctgt    38280
tccagtggat cgtcagcggc ggcagcctga gcatcctcga ccccaatgcc gaccgcgacg    38340
cctctgcctt cctcgcgcag gtgcgcaggg actcgattgg cgtcctctac tgcgtcccct    38400
ccgaactctc gacgctggtg agccacctgg agcgcgagcg tgaaagggtg catgagctga    38460
acaccctccg gttcatcttc tgcggcgggg ataccctggc ggttaccgtc gtcgagcgtc    38520
tcggggtact ggtgcgggcc ggccagctcc cgctgcggct ggtcaacgtc tatggacga    38580 aggagacggg aatcggcgcg ggttgcttcg agtgcgcgct ggacgcgaac gaccccagcg    38640
ccgaactccc gccgggacgg ctctcgcatg agcggatgcc catcggcggg cccgcccaga    38700
acctgtggtt ctatgtggtg caacccaacg gtggcctggc tccgttgggc atcccggggg    38760
```

```
aactgtacgt cggcggcgcg caactcgccg acgcccgttt cggcgacgag cccacggcga    38820
cccaccccgg cttcgtcccg aaccccttcc ggagcggagc ggagaaggac tggctgtaca    38880
agacggggga cctcgtccgc tggctgcctc aggggccgct cgagctggtc agcgcggctc    38940
gggagcgcga cggaggcggg gaccaccggc tcgatcgcgg cttcatcgag gcgcgcatgc    39000
gtcgtgtggc cattgtccgc gacgccgtgg tggcctacgt cccggatcgc caggacaggg    39060
cccggttggt ggcctacgtc gttctgaagg agtcgcccgc ggcggacgtg gagccgcgcg    39120
aagggcggga aacgctgaag gctcggatca gcgccgaact tgggagcacg ttgccggagt    39180
acatgcttcc ggccgcctac gtgttcatgg acagcctgcc gttgacggct tacgggagga    39240
tcgaccggaa agccctgccc gagccggagg atgaccgcca cggtggtagt gcgatcgcct    39300
acgtggcccc gcgcgggccc acggagaagg cactggcgca catttggcag caagtgctga    39360
aacgccccca ggtcggactg cgagacaact tctttgagct gggcgggcac tcagtggcgg    39420
ccatccaact ggtgtccgtg agccggaagc acctggaggt cgaagtcccc ctcagcctga    39480
tcttcgaatc gccggtcctg gaggcgatgg cgcgcggcat cgaagcgctg caacagcagg    39540
gccgcagcgg cgcggtgtcg tcgatccatc gggtggagcg gaccggaccg ctgcctctgg    39600
cgtacgtgca ggagaggctg tggttcgtgc acgagcacat gaaggagcag cggaccagct    39660
ataacatcac ctggacgttg cacttcgccg gcaagggttt ctcggtggag gcgttgcgga    39720
cggccttcga tgagctggtg gccagacacg agacactgcg cacgtggttc caggtggggg    39780
aggggacaga gcaggccgta caggtcatcg gggagccctg gtcgatggag ctgccgctga    39840
gagaggtggc ggggacggag gtgacggcgg caatcaatga gatgtcccgg caggtcttcg    39900
acttgagagc gggacggttg ctgacggcgg cggtcctgag ggtggcggag gatgagcaca    39960
tcctcgtcag caacatccac cacatcatca cggacggctg gtcgttcggg gtgatgctgc    40020
gggagctgag ggagttgtac gaggccgcgg tgcgggggga gcgagcggag ctgccgccgc    40080
tgacggtgca gtacgcgac tatgcggtat ggcagaggaa gcaggacctg agcgagcacc    40140
tggcgtactg gaaggggaag gtggaggggg acgaggacgg gttggagctg ccgtacgact    40200
tcccgcggac gtcgaatagg gcgtggagag cggcgacgtt ccagtatagc taccaccccg    40260
agctggcgag gaaggtggcg gagctcagcc gggagcagca gtccacgctg ttcatgagcc    40320
tggtggcgag cctggcggtg gtgttgaacc ggtacacggg ccgcgaggac ctgtgcatcg    40380
ggacgacggt ggcgggccga cgcgcaggtgg aactggagag cctcatcggg ttcttcatca    40440
acatcctccc gctgaggctg gacctgtcgg gcgctccgag ccttcacgag gtgctgcgga    40500
ggacgaaggt ggtggtgctg gagggattcg agcaccagga gttgccgttc gagcacctgc    40560
tgaaggcgct gaggcggcag cgggacagca gccagattcc cttggtgcca gtggtggtga    40620
ggcaccagaa cttcccgatg gcgcgtctgg agggctggag tgagggggtg gagctgaaga    40680
agttcgagct ggcgggggaa aggacgacgg cgagcgagca ggactggcag ttcttcgggg    40740
acgggtcctc gctggagctg agcctggagt acgcggcgga gctgttcagc gagaagacgg    40800
tgaggaggat ggtggagcac caccaacgag tgctggaggc gctggtggag gggctggagg    40860
aggggctgca cgaagtgcgg ctgctgacgg aggaggagga gggctgcac gggaggttga    40920
acgacacggc gcgagagctg gaggagcgct ggagcctggc ggagacgttc gagcgtcagg    40980
tgagggagac accggaggcg gtggcttgcg ttggcgtgga ggtggcgacg gaagggcact    41040
cgcggccgac ataccggcag ctgacatacc ggcagctgaa tgcgcgagcc aaccaggtgg    41100
cacggaggct gagggcactg ggagtgggcg cggagacacg ggtcgcggtc ttgagcgacc    41160
```

```
gctcgccgga gctgctggtg gcgatgctgg cgatattcaa ggccgggggc tgctacgtgc   41220
cggtggaccc acagtacccg ggaagctaca tcgagcagat actggaggat gcggcaccgc   41280
aggtggtgtt gggcaagagg ggaagagcgg acggggtgcg ggtggatgtg tggctggagc   41340
tggatggagc gcaacggctg acggacgagg cgctggcggc acaggaagag ggagagctgg   41400 aggggggcgga gaggccggag agccagcagt tggcgtgttt gatgtacacg tcgggctcca   41460
cgggcagacc gaaggggggtg atggtgccgt acagccagtt gcacaactgg ctggaggcgg   41520
ggaaggagcg ctcgccgctc gagcgtgggg aagtaatgtt gcagaagacg gcaatcgcgt   41580
tcgcggtgtc ggtgaaggag ctgctgagcg gattgctggc gggagtggcg caggtgatgg   41640
tgccggagac gctggtgaag gacagcgtgg cgctggcgca ggagatagag cggtggcggg   41700
tgacgagaat ccacctggtg ccatcgcacc tgggagcact gctggagggg gcgggggaag   41760
aggcgaaggg gctgaggtcg ctgaagtacg tcataacggc gggggaggca ctggcgcagg   41820
gggtgaggga ggaggcgagg aggaagctgc cgggggcgca gttgtggaac aactacgggt   41880
gcacggagct gaatgacgtg acgtaccacc ccgcgagcga gggggagggg gacacggtat   41940
tcgtgccaat cgggcggccc atcgcgaaca cgcgggtgta cgtgttggac gagcagttga   42000
ggcgggtgcc ggtgggggtg atgggggagt tgtatgtgga cagcgtgggg atggcgaggg   42060
ggtattgggg ccagccagcg ctgacggcgg agcgcttcat cgcgaacccg tacgcgagcc   42120
agcccggagc gaggttgtac cggacgggag acatggtgag ggtgctggcg gacggctcgc   42180
tggagtacct ggggaggcga gactacgaga taaaggtgag agggcaccgg gtggacgtgc   42240
gccaggtgga gaaggtggcg aacgcgcatc cagccatccg ccaggcggtg gtgtcgggat   42300
ggccgttggg ctcgagcaac gcgcagttgg tggcctacct ggtgccgcag gcgggcgcga   42360
cggtggggcc gcggcaggtg agggattacc tggcggagtc gctgccagcg tacatggtgc   42420
caacgctata cacggtgttg gaggagttgc cgcggttgcc gaacgggaag ctggaccggc   42480
tgtcgttgcc ggagccggac ctgtcgagca gccgagagga gtacgtcgcg ccccacggcg   42540
aggtcgagcg gaagctggcg gaaatcttcg gcaacctcct ggggctcgaa catgtcggcg   42600
tccacgacaa cttcttcaac ctcggcgggc actccctcct ggcttcccag ctgatttcgc   42660
gcatacgggc gaccttccgc gtggaagtgg cgatggccac ggtgttcgag tcccccacgg   42720
tggagccgct cgcccgccac atcgaggaga agctcaagga cgagtctcgg gtccagctct   42780
ccaacgttgt gccggtcgag cggacgcagg agcttccgct ctcctacctg caggagaggc   42840
tgtggttcgt gcacgagcac atgaaggagc agcggaccag ctataacgga acgatcgggc   42900
tccggcttcg gggtcctctg tcaatccccg cgctcagggc caccttccac gatctggtcg   42960
cccgtcacga gagcctgcgc accgtcttcc gggtccccga aggccgcacc acgccggtgc   43020
aggtgattct tgattcgatg gatctggaca tcccggtccg cgatgcaacc gaggccgaca   43080
tcatcccggg catggatgag ctggcgggtc acatctacga catggagaag ggtccgctgt   43140
tcatggttcg cctcttgcgg ctggccgagg actcccacgt tctcctgatg gggatgcatc   43200
acatcgtcta cgacgcatgg tcacagttca atgtgatgag tcgcgatatc aacctgctct   43260
actcggcgca cgtgacggga atcgaggcac ggcttcccgc gcttcccatc cagtacgcca   43320
acttctcggt gtggcagcgc cagcaggact tccgtcacca cctggactac tggaagtcca   43380
cactgggcga ctaccgggat gatctcgagc tgccgtatga ctaccgcggg ccgcccagcc   43440
ggacatggca cgcgacccga ttcaccttcc ggtatccgga tgcactggcg cgcgcgttcg   43500
```

```
ccaggttcaa tcagtcccat cagtcgacgc tgttcatggg gctgctgacc agcttcgcga   43560
tcgtgctcag gcactacacc ggccggaacg acatctgcat cggaacgaca acggcggggc   43620
gcgcccagtt ggagttggag aacctcgttg gcttcttcat caacatcctg ccgttgcgca   43680
tcaatctggc gggtgacccc gacatcagcg agctcatgaa tcgagcgaag aagagcgtct   43740
tgggcgcctt cgagcatcaa gctctgccgt tcgagcgtct cctcagtgcc ctcaacaaac   43800
agcgtgacag cagccatatc ccgctggttc ccgtcatgtt gcgccaccag aacttcccga   43860
cggcgatgac cggcaagtgg gccgatggtg tggacatgga ggtcatcgag cgcgacgagc   43920
gcacgacgcc caacgagctg gacctccagt tctttggcga cgacacctac ttgcatgctg   43980
tcgtcgagtt ccccgcgcag ctcttctccg aggtgaccgt ccggcgtctg atgcagcgtc   44040
accagaaggt catagagttc atgtgcgcga cgctgggggc tcggtgaacg tgctcgctag   44100
gcattccacc ggctcccacg acgagccggt ggccggcgac gtcgaactcc gcgtcggtgg   44160
ccccggtgtg ccggacgctc attccagcga gagcgttgaa gtgctggcgc ggtggctgcg   44220
gaccgccgag gagaagtacc cgggcgtcat gggcccgatc cgccaggagg gcccctggtt   44280
cgccatcccg ttgacctgcc cgcgcggtgc ccggtcggcg cgattcggcc tctggctcgg   44340
ggaactagac cgtcagggac agctcctcca catggtcgcc tcgtatctgg cggccgtgca   44400
ccacgtgctg gtcagcgttc gcgagcccag cgccaacgtg ctggaggtgc tggtctctga   44460
ctcaacaacg ccatctgggc tcaaccggtt cctgaacggc ctggactccg tcctggagat   44520
cctggctcac gggcgcagcg acctcctcct gcagcatctc acgggccggc tgcccccga   44580 cgagatgccc ttcgtggagg accgtgagga gcgcgaggag cacccggcca ccgatgtcga   44640
ggccgatgcg gttgtctccg tcctgttcca accagttgac ttcccgagcc tggcgaggct   44700
ggacgcgagc ctcctcgcgt atgacgacga ggatgccggc gcgtgggcc gggtcctggg   44760 ggagctcctc cagccgttcc tgctcgactc cgccaggatg accgtggggc gaaaggcggt   44820
gagggtcgat cacatctgcc tgcctggctt gttgcgagcc gacagcagag cggcggagga   44880
gtcggttctc gcgcccgcct tgcgcttggc gacgaagccc ggtcggcatt tcgtcgcgtt   44940
gtgccggaac accgccctgc ggctgggaga caggctgccc cacttgctcg cgcagggcc   45000 gctctgcgat ggcgcgtcaa cggcgctcct tctgttgcaa cgggtgctgg acacgcttat   45060
cgggagcggg ggactgaagg accatcgcct cacgctcgag ctggttggcg ccgatccacg   45120
gaccgaggcc gcgtttcggg cccggactcc gtggctggtg gcggaacggg ccgcttcggc   45180
tgcatcaacg gatgcaccgc gcgtcgacgt cgtcgtcctg ttcccggcgg cacggccgag   45240
cgcgctcgag ctgcggccag acagcgtcgt catcgacctt tttggcacct ggagcctgag   45300
accgcgaccc gaggttctgg cgaagaacat cgtctacgtg cgaggggcct cggtccgtct   45360
cgccggagag gccgtcgtct cgactccctc cttcgcgccg gatcgagtgg agccggcgct   45420
cctcgaggcg cttctccggg aactcgacgc ggaggccagt agtgacgggc tcgcccacga   45480
gcaccgcctt gagattggcg gcattccgcg gttctggggt gagatccgcc gggcggagtg   45540
ggacgccttt cattcgcgcc gccgggggga gctggcgagg tttcaggtgt cggggcaggt   45600
gaccgccgcc aatccggggc tcgccagcct gcccgatggg gcgacgaaca tctgcgaata   45660
catcttccgg gaagcgcacc ttcgctccgg ctcgtgcctc gtcgatcccc agagcggcca   45720
gtccgcgacc tacgccgagc tgcggcgact ggcggcagcg tacgcgcggc ggtttcgggc   45780 attgggcgctc cgccagggag acgtcgtggc gctcgcggcg ccggatggga tttcgtccgt   45840
cgcggtgatg ctgggttgct tcctgggcgg gtgggtcttc gcgccgctca accacaccgc   45900
```

```
ctcggccgtg aacttcgagg cgatgttgag ttccgccagt ccccgcctgg tgctccatgc    45960
cgcgtcgacg gtcgcccgcc atctgccggt cctgagcacg cggcgatgcg cggaactcgc    46020
gtccttcctg ccgccggacg cgctggacgg cgtggagggg gacgtcaccc ccctgccagt    46080
gtcaccggaa gcccccgccg tcatgctgtt cacctcgggc tccacggggg ggccgaaggc    46140
agtgacgcac acccacgccg acttcatcac ctgcagtcgc aactacgcac cctatgtcgt    46200
cgaactcaga ccggacgatc gtgtctatac gccgtccccg accttcttcg cctatggatt    46260
gaacaacttg ctgctgtccc tcagcgcggg ggccacgcac gtgatctcgg tccctcgcaa    46320
cggcgggatg ggtgtcgcgg agatcctcgc gcggaacgaa gtaaccgtgc tcttcgcggt    46380
tcccgccgtc tataagctga tcatctcgaa gaacgaccgg ggcctgcggt tgccgaagtt    46440
gagattgtgc atctctgctg gcgagaagct gccattgaag ctgtatcggg aggcgcgaag    46500
cttcttcagc gtgaacgtac tggacgggat cgggtgcacc gaagccatct cgacgttcat    46560
ctcgaaccgg gagagttatg tcgcgcccgg gtgcacgggc gtggtggtcc cggggttcga    46620
ggtcaagctg gtgaacccgc gtggcgagct ctgccgggtg ggagaggtgg gcgtcctctg    46680
ggttcggggt ggggcgctga cccgggggcta cgtgaacgcc cccgatctga cagagaagca    46740
cttcgtggac ggctggttca acacccagga catgttcttc atggatgccg agtaccggct    46800
ctacaacgtg ggcagggctg gttcggtcat caagatcaat tcctgctggt tctcaccgga    46860
gatgatggag tcggtcctgc aatcccatcc agcggtgaag gagtgtgccg tctgcgtcgt    46920
cattgacgac tacgggttgc caaggccgaa ggcattcatc gtcaccggcg agcatgagcg    46980
ctccgagccg gagctcgagc acttgtgggc cgagttgcgc gttctgtcga aagagaagct    47040
tgggaaggac cactacccgc atctgttcgc gaccatcaaa acgcttcccc ggacctccag    47100
cgggaagctg atgcggtccg aactcgcgaa gctgctcacc agcgggcccc catgaatcca    47160
aagttcctcg gaggcctggg ggcaggggtg tgcatcgcct ctttgttcca gacggtcatg    47220
cggaccgtgc cgctcaagga cgccggctcc ggcgacaggg cttgttagac ttgctgccaa    47280
tgtcgactcg caccaagaac ttcaatgtca tgggaatcga ctggatgcct tcctccgcgg    47340
agttcaagcg acgcgtcccg cggacccagc gggcggcaga ggccgtgctc gccggacgga    47400
gatgcttgat ggatatcctg gaccgcgggg atcctcgcct cttcgtcatc gtggggccct    47460
gctccattca cgatccggtg gcggggctgg actatgcgaa gcggctgcgg aaactcgctg    47520
atgaggttcg cgagaccctg ttcgtggtga tgcgcgtgta cttcgaaaag ccgcgcacca    47580 ccacggggttg gaaaggcttc atcaatgacc cgcgcatgga tggctctttc cacatcgagg    47640
agggcatgga gcggggacgt cgcttcctgc tcgacgtggc cgaggagggt ctacccgctg    47700
ccaccgaggc gctggacccc atcgcgtcgc agtactacgg cgacctcatt tcctggacgg    47760
ccattggcgc gcgcaccgcc gagtcgcaga cgcaccgcga gatggcgtcc ggcctttcca    47820
ccccagtagg cttcaagaac ggcacggacg gctcgctgga tgcggccgtc aatggcatca    47880
tctccgcttc acacccgcac agcttcctgg gggtgagcga aaatggcgcg tgcgccatca    47940
tccgcacgcg cggcaacacc tacgccacc tggtgctgcg cggcggtggt gggcggccca    48000
actacgacgc cgtgtcggtg gcgcttgcgg agaaggcgct tgccaaggcc aggctaccca    48060
ccaacatcgt ggtggactgc tctcacgcca actcctggaa gaatcccgag ctccagccgc    48120
tggtgatgcg ggacgtggtg caccagattc gcgagggcaa ccgctcggtg gtgggcctga    48180
tgatcgagag cttcatcgag gcaggcaacc agcccatccc ggcggacctg tcgcaactgc    48240
```

```
gctacggctg ctcggtcact gatgcatgtg tggactggaa gaccaccgag aagatgctgt   48300
acagcgcgca cgaggagctg ctccacattc tgccccgtag caaggtggct tgacgcccga   48360
gggttgaggt gtggttgctt cccagcaggg gttccccggc caggtggcgg cggcgcacgg   48420
cctggtacac gcagcggcgt tgagctttac ggagagctcg ggcgccggac tgggctgctg   48480
gcgcctgatt caaaggtcga tgcgcagacc caccccggcc tggatggtag gtggagcgac   48540
ggcgatggga ggcgtcacct gctcgcccat gcgcagggcc ggcaggttga gcgcaagcg    48600 gaactcgcca ccccgctggc catagttggc ggcgatgaag gcctcgatgc tgagatagcg   48660
cagggcccgg tgcgtcacgt ccaaccgtgt gatgaaagaa cggtcagaga ggttgcccag   48720
gttggacagg atgaagttgg tgttgtccca ggatcccgga ccggacagga acgcgtagac   48780
ggcggcgtag tgccggccga ggtagaaggg ctgatactgg ccctggagga tgaggtaggg   48840
gtaggccagc gagccgggat agcccatcga attgtagaag tactcgacgc ccacggtggc   48900
ggtgtcgctc tccgagtagg cgaacgtcca ggtcgcgccg ccgctcacct gcggcgtgta   48960
accctcgggg tagtacgcct ctatgggag cgcgcccagg tcgggaggca tgccgccatt    49020
gccctggaac tgaccgagca ggtctccgag ggagacacct tggggcatgc ggaacatggg   49080
cgcatccgag cccttcttga gggcgagttc gccgtagatg tcgatggggc cgagcccgga   49140
ggagaggtcg agcccgaagc ggggcttgcg gccgtgttgg agcacggcat cgacgccgag   49200
ttccgtatgg ccgagcacca cctcggcgcg agcagcgccc ccgacgcggc cgagcgtatt   49260
ggccgggccg gcgttgtcga gcaggccgag gacgtagaag ttccagccgt tcgcctccca   49320
gggcatgtgc atcttgagca tggtcgcgcc ggtgcgcgtg tccaagaggg cgagcggatc   49380
cctgcgctgg ggcgagagga agtcggtggg gttccagaag cgcgaggtgc cccacttcac   49440
gtgctgcttg ccgacggtga tgaagagctt gtggtccagg tcgaagcgca gccaggcctg   49500
atccaacagc acgaccggat ccgcagcgac gttggaggtg gacgtgctcg tggggacgat   49560
gccgagggag cccgccttgc gggtcggatc gaaggtgagc cgtccgagca cgaagccgcg   49620
cagccgctcg gtggggcggg catcgaagta gccgtccacc agcatggggg cggagaaggt   49680
ggtgttgctg aaggacaccc cttcgttggc ctgtgagtag gcgcgcaggt agaagcggcc   49740
gccgatcttc agcggatcct cgacggcctc ctcggtgtcg aaggcgttgg tggccgacgg   49800
gccaccgagc gcctgcgcat cccggtcctg gggcgtggcg gagggcttgt cggggccgc    49860 ggtggccgcc gcgctctgtg cggccggggt ggacgcgggg gtgtcaccga agagggaact   49920
ctcgtcgggg cggggcgcat cggccggagc gggcttcgtc tctggagtgt cgccgccgaa   49980
gaggtcgccc tcgctgggac gctcctgggc gagcgcgggc agcgcggcga gggacgcggc   50040
cagggccagg gaggtgcgcg tgctcatcgg ctttttgctct cgaaccaggc cttggtgaag   50100
atgttctcct cgagcgagcg caggtccacg ctcttcacga cgatgacggt ggagttggtc   50160
ttctccacct cgtcatagaa gcgcatctcc tgcgggtacc agacgtcggc cttcttggac   50220
tcgctgaaga gcttcatcca cttggggaag taggaggtgc gcatcaggcg gccggaaagg   50280
gcgaactcct ggcgcttgag gatgttgttc gtgtccttct ccacccacag gtgtaccacg   50340
gggtaggcga cgtccacgtt cggcttggcg gtgaggacga gcttccaggt ggtgaacttg   50400
ccgagtttct cctcgccctc gaacttgcca tcgagctcct cggccaggcg cgactcgtcg   50460 aagtcgcgc ggcggctgtc ggtgccggc atacgctcac gctcggtgcg ccggtcccac    50520
ttgccggtgt tcgggtcgta gctccagagg ttcttgtcca gccgcaggta gcccttgccg   50580
gcctcgccct tgggcttggt catgaggatc atcagctgat ccttctcgtc gcgccggtag   50640
```

```
acgacggcct cgcgcacgac gtctgttttg tccttctcct tctgctcgat atacaccagc   50700
gacttgtagt cgccgccgtt gcgctggcgg ttgtcgagcg tctccaggag cttcttgatc   50760
tcggcggggt cggtgaggtc cgcgcgagcg gtcggagcgg ccagcagcag cgcggcgaac   50820
agggcgccga ggaggttgcg cagggtcatg gtcgtcaccc gatgtggtgc atcgccgtga   50880
tgggcttcat ccgcgcggcg aggaaagagg gaatgagcga gatgaaggtg gtgcacagcg   50940
tgatgaacgc gatggctctc atcaccgatc cgggcttcac gatgaggtgg agcttgtcgg   51000
agaggatgaa gagctggacg ggcacgggca cggaggggtc cacggcgttg atgagcaggc   51060
acacgcccat gccacgagg cgcccaccg tggtgccgag cagtccgagc acgagcgcct    51120
ccaggaggaa catcaccagc acgtaccagc gctgcatgcc gatggcgcgc agggtgccga   51180
tttcccgggt gcgctcgcgg atggcgatcc acagggtgtt catgatgccc accgcgatga   51240
tgatgagcag cacgaagatg aggacgccgg tgagggcgtc catcgccgac acggtccact   51300
tgatgaagga gatctcgtcc tcccagttgg tgatgtccag cttctgcccc gtccaggcct   51360
cgcggttgac ggtctggaac ttcatgaaga aggcccgggg gtcatgctcc agcacctgat   51420
aacccaactc gggcagacgc ttgtagaggc gcgcctgcac gctggggatg gcgctcatgt   51480
ccttgaggtg gagcatgagg gcgccggtgg agtcctcgcg cagctggtag agggcgcgca   51540
gggtggcgtt gggcaccaag acgttgaagg aactcagcat gcccacgttg gcggcgatgg   51600
ccaccacacg tacgtccacg gtgttgctga tcccgcgcat ggtggacgcg gagagggtga   51660
cgctgtcacc caccttgacc tcgagccgct tcgcctgctc gtcgaagagg aggagggtat   51720
tgggttgcgc caggtcttcc aaccgaccct cccgcaactg cagcaccttg cggatgccag   51780
tctcggccgc tacgtcgatg ccgccgattc ccgtctgcac ggagccagac tcgctcacca   51840
acttgaccca gccgcgcgtg cgctggacgg agaagtccag ctcggggact tccttgcgca   51900
gctgctcgag cagcttgggg taggaggtca ccacgggcgc agactggccg gccgtcacct   51960
tgtagaagcc agccacgttg acgtgcccgg tcaccagcgt ggtggcggac cggagcatcg   52020
tgtccttcat gccgttggac aggcccatga ggatgacgag cagggccgtg acaccggcga   52080
tggcgccgcc cagcagaagc gtacggcgct tgtgggtgcc caggttgcgc actgcgatga   52140
ggaggagctg ttgcatggct tcactcgtcc gtctgcatcg cctggagagg cgagacccgg   52200
gtcgcgaggt acgcggggta gaaggtggag agggcggaca ccacgagcac gatgacgaag   52260
gccgccacga ggtttgacag gtggagactg gggaagaggc ggggtcccga gaagaagaag   52320
tagagcgcct cgttgccggc ggggatgccc acgtggccga gcatgttcat gatggcacct   52380
cccatggcgg ctcccagcac gccgaagacg agcccagca ccaccgtttc caccagcacc    52440
atgctcagca cgaacgagcg ctgcgcgccg atggcccgca gggtgcccac ctcgcgcacc   52500
cgctgcagcg tggccatcat catcgcgttg ttgatgatga cgagcgccac cacgaagatg   52560
atgaagacgg cgaagtagag caccagcttg gcgaccagga cgaactggcc gatcgtgccg   52620
gaggccttct gccaggagat gatccgcaag ggtagtttcg cgtcgtccgc cgatttccgc   52680
agctcggcca gggtctgctc cagcttctcc ggatgcttca gcagaaccgc ggtgctgagc   52740
accacgccgc tttcgatttc ctgctgcgtg tacacccggg aggcgagctc ctcgcggtgc   52800
agcttctggg cgagcccgtc gagttgcttg tcctcgtcga tctggccggc ggtcccctcg   52860
gccaccagcg aggcgctgcc ctgctcgcca aagagcgccg tctcggcgtc ctcgcgcttc   52920
acctgctgca ccccgctggc cttctgcagg cccgcgagct cggccttctt ctcagcggtg   52980
```

```
agatagccgt acagctcgcg gaaggacatc aggtccagca ggttgagggc tccggcgacc    53040
gcggacttct ccagcccgtc gaactggtag gtgccgtaga tcttcacgtt cacgctctgc    53100
acatagccgg tgcgcgagaa tgcggtgatg gtgaggtcgt ccccgatgcg gatgcggtac    53160
aggtcgagca gcgtcgccag ctcggagtag aactgctggt agcgcgtgtc gaagttggcg    53220
tcatccatgg tgaagaaggc gggcagtagc ttgcccaggt ccgtctcctg gctgcccagc    53280
acgcgctgga gccgctccac ggcctgcttc gtcttgaggt cgtcgagctg gaagaggatc    53340
tcccgcgtct gggtctggtt ctccttcacc cagcgctgga gttgcggatc catcgcgatg    53400
gtcttgtggt tggtatcacg cgcctccttg atgagatcca accggtgcgc cgtcttcagc    53460
ttgaagtcgt tctcgtaggt gaacttggag agcatcatgc cgcggtgccc cggggggcacc    53520
ggcgtgccct ccacgatgcg catgcggtcg aaggtcttct ggaagttgac caggtcggtg    53580
cctacatagc gcagggacaa catgtccccg tccgtcatat acgggcgat gcggttctcc    53640
aggaactcga gcgagtcgaa tggcttctcg tcgaagtccg cccagaaggc ctcggaacgg    53700
gcgcgggcca tggcctccgc gtccgcgggg tccgtggtct tgtcgtcgat gatttccctg    53760
cgccgcttca tatcctcctc gagcaaggtg atgatgtgac gcacatgcgc ctggaggctg    53820
tggatctgcc cgcggagttc gggtgtgtcg ccctgtgctg ctttcttgta gaggtcgcgc    53880
aggcgcgcca aggtcaggtc gatggtgttt cccgagttga tgaacgtggc gccggtgccc    53940
atgggcacca ccgtcttcac gttggggtgc tgctgtacca gttgcttgat gcgcgagaag    54000
tcatccagcg cgctcaggtc cggttcgcgg cccatctgcc cgaagagcga gagctcgtcc    54060
ttggagtggg ccgagtacac ctggaggtgg ccggcgacgc tgccgataat gctgcggctc    54120
atcgcctcgt ccacgctgtc gacgagggag ccgcccacca ccaccagcac ggtgccgaag    54180
aagatgatgc ctccgatgag gaggttgatc ctgctcacga acaagttgcg cagggccact    54240
tggagcagga gcttgagttg gcccattagt ggcccccctc gctcacggcc atgaccttct    54300
gggcctcggc cggcgtgatg cggtcgagga tcttcccgtc cgccaggcgc accacgcgt    54360
tggcgtgggt catcaccttg gcgtcgtggg tggagaagat gaaggtggtg ccctccttgc    54420
ggttgagctc cttcatcagg tcgatgatgt tctggccggt gacggagtcg aggttggcgg    54480
tgggctcgtc ggcgagcacc agcttgggcc gggtgacgag agcgcgcgcc acggccacgc    54540
gctggcgctg gcctccagac agctcattgg ggcggtgttt ggcgtgcttc tccaggccca    54600
cctgctccag cagcgtcatc acgcgcgtgc ggcgctcgga ggcgttgagc ttgcgctgca    54660
gcagcagggg gaactctacg ttctggaaga cgctgagcac cgagacgagg ttgaagctct    54720
ggaagatgaa gccgatggtg tgcagccgca agtgggtgag ctgccgctcg gtgagcttct    54780
tggtgtcctg gccatccacg ctcaccacgc ccgaggaggc cgtgtccacg cagccgatga    54840
gattgagcgc cgtcgtcttg ccactgcccg atgggccggc gatggagatg aactctcccg    54900
ggtacacctc tagcgtcacg cctcggagtg cgggcacctg caccttaccc agggagtacg    54960
tcttggtaac ctcggtgagg gagacgatcg gctgggtgct gccggggagg gcagtgacct    55020
ggctcatgat tgtttggatc ctttccgcga acggaggga tggggtgggg gacgcctggg    55080
aggggggcgc ctcggcgtgg gcgtgcgcgg gacgagggtg atggcactgg gtattgaatt    55140
cgcagatgcg cggctccccc tggtattccc ccaccggggc aaaagttgcg cgcttgtctg    55200
actactggcg tcaagacatt gagtcaacgc cgaaggagag cgcattccaa aagaggcagc    55260
gtccatggag cgaaggcagc ggcgcagtgg gcatgcgctc agaggggaaa acagggtcgg    55320
taggacagag gaatcgaacc tcccggggac atgtctccat gccccccacc ggttttgaag    55380
```

```
gctggtgtgg tcagtggggt tctccctcgg agattgcatc tggttccact cggctgtatc   55440
ccagggacgt aatagggacg taatcccgaa tccgatgggt gcagcatgcc gcagaagttc   55500
gtggggaagt ggaagggcgg gcgggtcaag ctcgtcgatg gtcggaaggt gtggctcctc   55560
gagaagatgg tctccggggc ccggttctcg gtctccttgg cggtctccaa cgaggaggac   55620
gcgctggccg agctggccct gttccggcgc gaccgggacg cctacctggc caaggtgaag   55680
gccgacaggt cggaggaagt ccaggcatcc actgtagccg gggcagttcc tctgtcgggg   55740
gatgtggggc ctcggctcga tgccgattct gtccgggagt tcctccgaca cttgacccag   55800
cgggggcgaa cggagggtta ccggcgggac gcccgaacct acctgtcgca atgggccgag   55860
gttctggccg aagggacct gagtaccgtc agcctcctcg agttgcgccg cgccctgagc   55920
caatggccca cggccaggaa gatgcggatc atcacgctca agagcttctt ctcgtggctg   55980
agggaagagg atcgcctcaa ggctgctgaa gaccccacgt tgtccctcaa ggtgccgccc   56040
gcggtcgcgg agaaggggag acgggccaag gggtattcga tggcccaagt ggagaagctc   56100
tacgcggcca tcggctccca gacggtgagg gacgtgctgt gtctgcgggc caagaccggc   56160
atgcacgact cggagatcgc ccgcctggca tcgggcaagg gggaactgcg cgtcgtcaat   56220 gaccctccg gcatcgccgg tactgcgcgg tttctgcaca agaacggccg cgttcacatc   56280
ctcagtctgg atgcccaggc ccttgctgcc gcgcagcggc tccaggttcg ggcagggcg   56340 cccatcagga acaccgtccg ggagtccatc gggtatgcgt cggcgcgcat tgggcagtcg   56400
cccatccatc ccagcgagct ccgccacagc ttcaccacct gggccacgaa tgagggccag   56460
gtcgtgaggg caacccgggg cggagtgcca ctcgatgtcg ttgcctcggt tcttggccat   56520
cagtccacac gggcgaccaa gaagttctat gacgggaccg aaattccccc gatgatcacc   56580
gtcccgctca agctgcatca tccacaggac ccagcggtga tgcagctgag gcgtaactgc   56640
tcgccggacc ccgtcgtgac gagagaggca gaggcgtgag acgtccaggc catcaacctg   56700
gaggtacacg tggagacgtc cggggctcct ccccgcacct ccttcgaggt tgatttcctg   56760
tgctcctcgc attcccctcc ggcctcctgt cgctggcgct cctgtccact accaccgaaa   56820
tctctgcggc tcttcccgtg gacgagtgcg agtcggcgag cctgcgcatc gagctgcccg   56880
ctacgccagg gggaaagcca cccgtggtgt gtctcggtcc aggtctgccc attcatttcc   56940
gcttcgactc cgcgctccaa cagaagtccc tgaggattca ggatcggggc tggttcgagg   57000
attgggcttt gggccagcag acgctcgtac tgactcctca cgacaacctg gtggctggga   57060
agcgatctga agtggaggtg tgcttcgcgg atggtgccgc ccggcgtgc gcttccttcg   57120 tgctccggcg ctgaggcgag tgcaccgcac tgattcagtt cctcttcaac cccggtaccg   57180
ctcggccacg cggtagagct gggtgaggga gtagtccagc aacgattcgc acgagcgcat   57240
gtagtggtga gcccgcgcaa acggcaacca cacacggttg ccgacgagca cctgggcctc   57300
gtcgagtttc tggcgaggta tccacttgcc gcccaggtta cgcaccagca cctcgcccaa   57360
gtacgcgcca atggcgggca ccgcgtgcgc gtcgatgtgc tgccgctcga cacccctcgg   57420
gaagtcctca tgccagaact ggtagtccac gtcactgaga gactcgggcg ttgcctcgaa   57480 gacgagggc accttcgtgt gcatcagcgc cacgaggtgc tcagccagag ttctgtaatg   57540
ctcgttagcg cgctccaggt tttccacatc cggatggcga cgctatccac cacgtgagag   57600
aggagtggcg ctacatccgg gtggaagcag ggctcaacgg gagcgagcgc ggcgctacgc   57660
tcgtgcaggg ttcgcagcac cgtgtcgaag cggaggtccg gccggaggtg aacgtgcgcg   57720
```

```
cgcgcctgtg cgtgccgtgc ctcggcgccc gcgaagtccg cagcggtggg ccacgtcacc    57780
aggaggatgg agccattggg cagttcctcc acccggtgag ctggcgtgga cagcatgcgc    57840
tcgcggccca cggcttccac caacttgggg ccgaagacgt tgagccagaa gatctcgtag    57900
attctgtcga acccgtctct ccgtgcggtc cgcgcatcgc gtccaaaatc gggcgcacct    57960
gccaacgccc tgtcagccac gctgtgggct gcggcgtgag tgaccgggta gcaagaggcc    58020
caggtgcgta ccatttctac gaattggcgg cagcgctcct tctccgcgaa gcgggtgagc    58080
ggttgcaccg tagtcattac gtccaaagcg ggcggaagcg gcggaaacca gagatgcagc    58140
gacatctcca gtgtcggccg ctgtgtgcgg tagagccagg tgtctgtgct tcgttcatcg    58200
cgccgctcct ccagagcctt ccagatattg gctcgggagt atttgagtcg ccgcctgcca    58260
ctgacgactt ccggcatcca atcgcctgca tattcctcca gcgcctggaa aaatggctcg    58320
agaactttct caagcgcagc ctgcggatca agcgcaccct caaaagtgag ccggagactg    58380
tcctccgact tcacgtcacc aagccccagc accttcattg aaacaggacc tccactcccg    58440
gaactgcctt ctcagt                                                   58456

<210> SEQ ID NO 2
<211> LENGTH: 213
<212> TYPE: DNA
<213> ORGANISM: Cystobacter velatus
<220> FEATURE:
<221> NAME/KEY: misc_feature
<222> LOCATION: (1)..(213)
<223> OTHER INFORMATION: CysA

<400> SEQUENCE: 2
atgagcatga acggggacga agccgagtac gttgtcttga tcaacggcga agagcagtac     60
tcgctctggc ccgtgcaccg cgaaattccg ggcggttgga agaccgttgg gcccaaggga    120
agcaaggaaa cgtgtcagtc ctacatccag gaggtctgga cggacatgag gccgaaatcg    180
ctacgggaag ccctgacgcg cagcaactgc tga                                 213

<210> SEQ ID NO 3
<211> LENGTH: 954
<212> TYPE: DNA
<213> ORGANISM: Cystobacter velatus
<220> FEATURE:
<221> NAME/KEY: misc_feature
<222> LOCATION: (1)..(954)
<223> OTHER INFORMATION: CysB

<400> SEQUENCE: 3
atgagtacgc cagcagcagg agcgaagccg tcctatctcg cgggtattga acggtgatg      60 gtcgaacctg agcttgagga ggttcgctac ctgaccgtgg agagcggcga cggacggcag    120
agtaccctct atgagttcgg tccgaaggac gcggagaagg tcgtggtctt gccgccctac    180
ggagtcacct tcttgctggt ggcgcgactc gccggctcc tctcccagcg attccatgtc     240
ttgatttggg agtcaagggg gtgtccggac tccgccatcc cggtgtatga cacggacctt    300
gggctcgccg accagtcaag gcatttctcc gaggtcctca gcagcaggg cttcgaggcg    360 tttcacttcg tcggctggtg tcaggcgcg cagctggccg tgcatgccac cgccagcggc    420
caggtcaagc gcggacgat gtcttggatt gccccggcgg ggctgggtta ctcgctggtc    480
aagtccgagt tcgatcgatg tgcactgccc atctacctgg agatcgagaa gcatggcctg    540
ttgcacgccg agaagctcgg caggcttctg aacaaataca atggcgttcc cgcgacggcg    600
cagaacgcgg cggaaaagct gacgatgcgc catttggccg acccgcggat gacatacgtc    660
```

| | | | | |
|---|---|---|---|---|
| ttctccaggt | acatgaaggc | gtatgaagac | aacaggctcc | tcgccaagca atttgtctcg | 720 |
| accgcgctcg | actcggtgcc | gacgctggcc | attcactgcc | gggacgacac gtacagccac | 780 |
| ttctcggagt | ccgttcagct | ctcgaagctg | catccatccc | tcgagcttcg cctactcggt | 840 |
| aagggcggcc | atctgcagat | cttcaacgac | cccgccacac | tggcggagta cgttctcggt | 900 |
| ttcatcgaca | ccagggcgtc | gcaggctgcc | gctcctgcgg | tggcgggagc gtag | 954 |

<210> SEQ ID NO 4
<211> LENGTH: 1380
<212> TYPE: DNA
<213> ORGANISM: Cystobacter velatus
<220> FEATURE:
<221> NAME/KEY: misc_feature
<222> LOCATION: (1)..(1380)
<223> OTHER INFORMATION: CysC
<400> SEQUENCE: 4

| | | | | |
|---|---|---|---|---|
| atgatacttc | caacaacat | cggcctcgac | gagcggacgc | agctcgcacg gcagatctcc | 60 |
| tcgtaccaga | agaagttcca | cgtgtggtgg | cgcgagcggg | ggccaccga gttcctcgat | 120 |
| cggcagatgc | gccttcgcac | gccgaccggg | gcggtcagcg | cgtggactg gccgagtac | 180 |
| aagacgatgc | gtcccgacga | gtatcgctgg | ggcctcttca | tggtgccgat ggaccaggac | 240 |
| gagatcgcct | tcggcgacca | ccgtggcaag | aaggcgtggg | aggaggttcc gagcgaatac | 300 |
| cgcacgctgc | tgctgcagca | catctgcgtg | caggccgacg | tggagaacgc cgccgtcgag | 360 |
| cagagccggc | tgctgacgca | gatggcgccg | agcaacccgg | acctggagaa cgtgttccag | 420 |
| ttcttcctcg | aggaggggcg | ccacacctgg | gccatggttc | acctcctgct cgcccacttc | 480 |
| ggtgaggacg | gggtcgtcga | ggccgaagcg | ctcctggagc | ggctgagcgg tgacccgagg | 540 |
| aacccccgct | tgctggaggc | gttcaactat | ccgaccgagg | actggctgtc ccacttcatg | 600 |
| tggtgcttgc | tggccgaccg | ggttggcaag | taccagatac | atgcagtgac cgaggcttcg | 660 |
| ttcgccccgt | tggcccgggc | ggcgaagttc | atgatgttcg | aggaaccgct ccacatcgcc | 720 |
| atgggcgccg | tgggtctgga | acgagtgctg | gccaggaccg | ccgaggtcac cctgcgtgag | 780 |
| gggacgttcg | atacgttcca | cgcggggcg | attccgttcc | cggttgtcca gaagtatctc | 840 |
| aattattggg | cgccgaaggt | ctacgacctc | ttcggaaacg | acggctccga acgctcgaac | 900 |
| gaactcttcc | gggctgggct | ccggaggccg | cggaatttcg | tgggaagcga atcgcagatc | 960 |
| gttcgcatcg | atgagcgcat | gggcgacgga | ctgaccgtcg | tggaagtgga aggggagtgg | 1020 |
| gcgatcaacg | ccatcatgcg | acgacagttc | atcgccgaag | tgcaaacgct cattgatcgc | 1080 |
| tggaacgcca | gcctgcgagc | gctgggcgtc | gacttccagt | tgtacctccc tcacgagcgc | 1140 |
| ttcagcagga | cctatggccc | ctgcgccggt | ctgcccttcg | acgtggacgg aaaactgctc | 1200 |
| ccccgcggca | cggaggcgaa | gctcgccgag | tacttcccca | cacctcgcga actcgcgaac | 1260 |
| gtccgctcgc | tgatgcagcg | ggagctggct | cccgggcagt | actcctcgtg gatcgccccg | 1320 |
| tccgcgacgc | ggctgagcgc | gctggtccag | ggcaggaaca | cgcccaagga gcacgaatga | 1380 |

<210> SEQ ID NO 5
<211> LENGTH: 2199
<212> TYPE: DNA
<213> ORGANISM: Cystobacter velatus
<220> FEATURE:
<221> NAME/KEY: misc_feature
<222> LOCATION: (1)..(2199)
<223> OTHER INFORMATION: CysD

<400> SEQUENCE: 5

```
atgcgttgcc tcatcatcga caactacgat tcgttcacct ggaatctggc ggactacgtt        60
gcgcagacgt tcgggagcga gccgttggtc gtccgcaacg accagcatac ctggcaagaa       120
atcaaggcct tgggctcctt cggatgcatc ctggtttctc cgggtccggg ctcggtgacc       180
aatccgaagg atttcaatgt ctcgcgagac gcgctcgagc aggatgagtt cccggtgttt       240
ggggtctgcc tgggccatca agggctggcg tacatctacg ggggcgagat cactcacgct       300
ccggttccgt tccacggcag gacgtcgacc atctaccatg acggcacggg cgtgtttcag       360
ggactcccgc cgagcttcga cgcggtgaga tatcactcgc tggtcgtgcg gccggagtcg       420
cttcccgcga acctggtcgt caccgctcgg acggaatgcg gcctgatcat ggggttgcgg       480
cacgtgagtc gcccgaagtg gggcgtccag ttccatcccg agtcgattct gactgcgcac       540
ggcttgcagc tcatctccaa tttccgtgac gaggcgtacc gatacgcggg gaaagaggtt       600
ccgtcgcgcc gtccccattc gactgccggc aacggtgtcg gcgcaggtgc tgccaggcgt       660
gacccgagcg cccgccgcac accggagcgg agaagggaac ttcagacgtt caccaggcgg       720
ctggcgacgt ctctcgaggc cgagaccgtt ttcctgggcc tgtatgcggg ccgcgagcac       780
tgcttctggc tcgacagcca gtccgtgaga aagggatat cccggttctc cttcatgggc       840
tgcgtgccgg agggctcgct gctgacgtac ggcgctgcgg aagcggcgtc agaggggggc       900
gccgagcggt acctggcggc gctggagcgg gcgctcgaaa gccgtatcgt tgttcgcccc       960
gtggatgggc tgccattcga gtttcatggc ggctacatcg gcttcatgac ctacgaaatg      1020
aaggaggcgt ttggggccgc gacgacgcac aagaacacta ttcccgacgc cttgtggatg      1080
cacgtgaagc ggttcctggc gttcgaccac tcgacgcgag aagtgtggct ggtcgccatc      1140
gcggagctcg aggagagcgc gagcgtcctc gcctggatgg acgagaccgc cgacgctctg      1200
aagtcgcttc cgcgcggcac ccgttcgccc cagtccctgg ggttgaaatc catctcggta      1260
tcaatggatt gtggacggga tgactacttc gccgccatcg agcgctgcaa ggagaagatc      1320
gtcgatgggg agtcctacga ggtctgcttg acgaacggtt tctcgttcga tctgaagctg      1380
gatcccgtcg agctgtacgt gacgatgcgg agaggcaatc ccgccccgtt cggcgctttc      1440
atcaagacag gcaagacctg cgtcctcagt acctccccgg agcgcttcct gaaggtggat      1500
gaggatggga cggtccaggc caagcccatc aaggggacct gcgcgcgctc tgacgacccc      1560
gccaccgaca gcacgaatgc cgcgcggctg ccgcctcgg agaaggaccg ggcggagaac      1620
ctgatgatcg tggacctgat gcggaacgac ctcggacggg tgtccgtgcc gggcagcgtc      1680
catgtctcca atctaatgga catcgagagc ttcaagacgg tccatcagat ggtcagcacc      1740
gtcgaatcga ccttgacgcc ggagtgcagc ctcgttgacc tcctgcgcgc ggtcttcccg      1800
gggggatcca tcaccggggc tcccaagatc cgcacgatgg agatcatcga tcggctcgag      1860
aagagccctc ggggcatcta ctgcggcacg atcggctacc tcgggtacaa ccggatcgcc      1920
gacctgaaca tcgccatccg caccttgtcc tacgacggca ccctcgtgaa gttcggtgcc      1980
ggcggagcca tcacctactt gtcacagccg gaggggagt ttcaggagat cctgctcaag      2040
gcggaatcca tcctccggcc gatttggcag tacatcaatg gcgcgggtgc tcccttcgaa      2100
ccccagttgc gcgaccgggt tctgtgcctg gaggagaagc gcgaagggt cattcgtggc      2160
cacgggtcgg caattgatgc agtggagcct agcgcgtga                            2199
```

<210> SEQ ID NO 6
<211> LENGTH: 732

```
<212> TYPE: DNA
<213> ORGANISM: Cystobacter velatus
<220> FEATURE:
<221> NAME/KEY: misc_feature
<222> LOCATION: (1)..(732)
<223> OTHER INFORMATION: CysE

<400> SEQUENCE: 6
atgattgcgt tcaacccgca ggcgcggccc aggctgcggc tcttctgctt tccgtacgcc      60
ggtggcgacg cgaacatctt ccgggactgg gccgcggcga tgcccgaggg ggtcgaggtc     120
ctcggcgttc agtaccccgg gcgcggtacc aacctggcgt tgccgccgat cagcgactgt     180
gacgagatgg cgtcacaact gctggcggtg atgacgccgt gcttggcat caacttcgct     240
tttttcggcc acagcaatgg cgccttgatc agcttcgagg tggcgcgaag gctccacgac     300
gaactgaagg gccgcatgcg gcatcacttc ctgtcggcca gtccgcccc tcactacccg      360
aacaacagga gtaagatcag cggcctcaac gacgaggact ttctccgggc gatccggaag     420
atgggcggta cgccccagga agtgctcgac gacgcccggc tgatgcagat tctgctgcca     480
agactgcgcg cggacttcgc gctcggcgag acgtatgtgt tcgccccgg acccaccctg      540
acgtgcgacg tcagcatcct gcgaggcgag agcgaccacc tggtcgacgg cgagttcgtc     600
cagcggtggt ccgagctgac gacgggcggc gcgagccagt acgcaataga tggtggccat     660
ttcttcctga attcccacaa gtcgcaggtc gtggcgctcg tgcgagcggc actgcttgag     720
tgtgtgttgt ag                                                        732

<210> SEQ ID NO 7
<211> LENGTH: 1038
<212> TYPE: DNA
<213> ORGANISM: Cystobacter velatus
<220> FEATURE:
<221> NAME/KEY: misc_feature
<222> LOCATION: (1)..(1038)
<223> OTHER INFORMATION: CysF

<400> SEQUENCE: 7
atgaccgctc agaaccaagc ctccgcgttt tctttcgatc tcttctacac gacggtcaat      60
gcgtactacc ggaccgccgc cgtcaaggcg gccatcgagc tcggcgtgtt cgacgtcgtt     120
ggcgagaagg gcaagaccct ggccgagatc gcgaaggcct gcaacgcgtc gccgcgtggc     180
atccgcattc tctgccggtt cctcgtgtcg atcgggttcc tcaagaatgc gggtgagttg     240
ttcttcctca cgcgagagat ggccctgttt ctggacaaga agtcgcccgg ctatctgggc     300
ggcagcattg atttccttct gtcgccgtac atcatggacg gcttcaagga cctcgcgtcg     360
gtggtgcgga cgggcgagtt gacgctgccg gaaaaagggg tggtggcgcc agatcatccg     420
cagtgggtga cgttcgcgcg cgcgatggcg ccgatgatgt ccctgccatc cctcctgctc     480
gcggaactgg cggaccgcca ggcgaaccag ccgctcaagg tgctcgatgt cgccgccggc     540
cacgccctct tcggcctggc catcgcccag cggaatccga aggcgcatgt gacgttcctc     600
gactgggaaa acgtgctaca ggtggcgcgc gagaacgcga cgaaggcggg agttctcgac     660
agggtcgagt tccgcccggg agatgccttc tccgtggact tcggcaagga gctggacgtc     720
atcctcctga cgaacttctt gcatcacttc gacgaggcgg gctgcgagaa gatcctcaag     780
aaggcccacg ctgccctgaa ggagggcggc cgtgtgctga cgttcgagtt catcgcgaac     840
gaggaccgga cgtcgcctcc gcttgccgcc acgttcagca tgatgatgct cggcacgacg     900
cccggcggtg agacctacgc ctactccgat ctggagcgga tgttcaagaa cacgggttac     960
```
gatcaagtcg agctcaaggc cattcctccc gcgatggaga aggtcgtcgt ttcgatcaag    1020
ggcaaagcgc agctctga                                                  1038

<210> SEQ ID NO 8
<211> LENGTH: 5979
<212> TYPE: DNA
<213> ORGANISM: Cystobacter velatus
<220> FEATURE:
<221> NAME/KEY: misc_feature
<222> LOCATION: (1)..(5979)
<223> OTHER INFORMATION: CysG

<400> SEQUENCE: 8
atggccacca aattgtctga cttcgcgctc ctcgactccg aagacgccaa cgtcatctcc      60
cgctcgaacg agacggggat atcgctggat ctgtccaaga gcgtggttga cttgttcaac     120
ctccaggtcg agagggcgcc tgacgccacg gcgtgtctcg gccgccaggg gcgcttgact     180 tacgagaac tcaaccggcg gacgaaccag ctcgcgcatc acctgatcgc gcgaggcgtc      240
gggccggatg ttcccgtggg cgtcctgttc gagcgctccg ccgagcagct catcgccatc     300
ctgggcgtcc tcaaggcggg cgggtgttat gtcccgttgg atccgcagta ccccgccgat     360
tacatgcagc aggtcctgac ggacgcccgg ccgcggatgg tggtgtcgag ccgggcgctc     420
ggcgagcgcc tccgctcggg cgaggagcag atcgtctacc tcgatgacga acagctcctg     480
gcgcgcgaga cccgcgaccc gcctgtgaag gtgttgccgg agcagctcgc gtacgtgatg     540
tacacgtcgg gctcgtccgg agtgccgaag ggcgtcatgg tgccccatcg ccagatcctc     600
aactggctgc atgcactcct ggcgcgggtg ccgttcggcg agaacgaagt ggtggcccag     660
aagacgtcca cgtcattcgc catctcagtg aaggaactct tcgcgggatt ggtcgcgggt     720
gtcccgcagg tcttcatcga cgatgcgact gtccgcgacg ttgccagctt cgttcgtgag     780
ctggagcagt ggcgcgtcac gcggctctat acttttccct cccagctggc ggcgattctc     840
tcgagcgtga atggcgcgta cgagcgcctc cgctcgctgc gccacctgta catctcgatc     900
gagccctgcc aacagagctg ctggcgaag ctccgggcgg cgatgccgtg ggtcacccccc    960 tggtacatct atggctgcac cgagatcaac gacgtcacct actgcgaccc aggggaccag    1020
gctggcaaca cgggcttcgt gccgatcggg cggcccatcc gcaacacgcg ggtgttcgtc    1080
ctcgacgaag agctccggat ggtgcccgtc ggcgcgatgg tgagatgta cgtggagagc     1140 ctgagcacgg cgcggggcta ctggggcctt ccgagttga cggcggagcg gttcatcgcc     1200
aaccctcacg cggaggacgg ttcgcgcctg tacaagacag cgacctcgc ccgctacctg     1260 ccggatggtt ccctggagtt cctcgggcgc cgggactacg aggtgaagat ccgcgggtat    1320
cgcgtggacg tccggcaggt cgagaaggtc ctcggggcgc atcccgacat cctcgaggtg    1380
gcggtggtgg gctggccgct cggcggggcg aatccacaac tggtcgccta cgtcgtgccg    1440
agggcgaagg gggctgctcc catccaggag atccgggact acctgtcggc gtccctgccg    1500
gcctacatgg tgccgacgat cttccaggtg ctggcggcgc tgccacgtct tcccaatgac    1560
aaggtggatc ggttgagcct gcccgacccc aaggtggagg agcagaccga ggggtacgtg    1620
gcgcctcgca cggaaaccga gaaggtactg ccgaaatct ggagcgacgt cctcagccag    1680
ggccgggccc ccctgaccgt cggcgcgacg cacaactttt tcgaactggg aggccattcg    1740
cttctcgccg cccagatgtt ctcgcggatc cggcagaagt tcgatctcga actgcccatc     1800
aacaccctgt tcgagacccc cgtgctggag ggctttgcga gcgccgtcga cgcggctctt    1860
gccgagcgga acgttccggc gcagaggctg atcagcatga cggaccgcgg ccaggcgctt     1920

-continued

| | | | |
|---|---|---|---|
| ccgctgtcgc acgtccagga gcggctctgg ttcgtgcacg agcacatggt cgagcagcgg | 1980 |
| agcagctaca acgttgcctt cgcctgccac atgcgtggca aggggctgtc gatgccggcg | 2040 |
| ctgcgcgccg ccatcaacgg gctggtggct cgccacgaga ccttgcggac gacgttcgtc | 2100 |
| gtctccgagg gcgaggaga tcccgtccag cggatcgccg actccctgtg gatcgaggtt | 2160 |
| ccgctatatg aggtcgatgc gtcggaagtc ccggcccgca tggcggccca cgcgggccac | 2220 |
| gtgttcgacc ttgcgaaggg ccccctgctg aagacctcgg tcctgcgggt gacgcccgat | 2280 |
| caccacgtgt tcttgatgaa catgcatcac atcatctgtg atgggtggtc gatcgacatc | 2340 |
| ctgctgcggg acctctacga gttctacaag gcggccgaga cgggctcgca gccgaacctg | 2400 |
| ccggtcctgc caatccagta tgccgactac tccgtgtggc agcgtcagca ggacctcagc | 2460 |
| agtcacctcg actactggaa gaagacgctc gagggctacc aggaagggtt gtcgcttccg | 2520 |
| tacgacttcg cccgcccgtc caacaggacc tggcgtgccg cgagtgtccg gcaccagtac | 2580 |
| ccggcggaac tcgccacccg tctgtcgag gtgagcaaga gccatcaggc gacggtgttc | 2640 |
| atgacgttga tggccagcac ggcaatcgtg ctgaaccggt acacgggtcg ggatgatctg | 2700 |
| tgcgtggggtg ccacggtggc gggccgtgac cacttcgagc tcgagaacct gattggcttc | 2760 |
| ttcgtcaaca tcctcgccat caggctcgac ctcagcggga atcccacggc cgagacggtg | 2820 |
| ctgcagcggg cgcgagcgca ggtgctggaa ggcatgaagc atcgcgacct gccgttcgag | 2880 |
| cacatcctgg cggcgctgca gaagcagcgc gacagcagcc agattcccct ggtgccggtg | 2940 |
| atggtccgcc accagaactt cccgacagtg acctcgcagg agcagggct cgacctgggt | 3000 |
| atcggggaga tcgagtttgg tgagcggacg acgcccaacg agctcgacat ccagttcatc | 3060 |
| ggcgagggaa gcacgctgga ggtggtggtc gagtacgcga aggatctgtt ctccgagcgc | 3120 |
| acgatccagc ggctcatcac gcacttgcag caggtgctgc agactctcgt ggacaagccg | 3180 |
| gactgccggc tgacggattt ccgctggtg gccggggacg cgctgcaggg cggtgtgtcg | 3240 |
| ggctccgggg gcgcgacgaa gaccggcaag ctcgacgtgt cgaagagccc ggtcgagttg | 3300 |
| ttcaacgagc gggtagaggc ctcgccggac gcggtcgcct gcatgggcgc ggacggaagc | 3360 |
| ctgacctacc gggagctgga ccgaagggcc aatcaggtcg cccgccacct gatggggcga | 3420 |
| ggggtggggc gggagacgcg ggtggggttg tggttcgagc gctcgccgga cctgctggtc | 3480 |
| gcactcctgg gcatactcaa ggcgggggc tgcttcgttc cgctcgatcc gagctatccg | 3540 |
| caggagtaca tcaacaacat cgtcgccgat gcgcagccgc ttctggtgat gtcgagccgg | 3600 |
| gcgctgggct cacgcctgtc actggaggca gggcggctgg tgtacctcga tgacgcgctg | 3660 |
| gcggcgtcca ccgatgcgag cgatccccag gtgcgcatcg acccggagca gctcatctac | 3720 |
| gtcatgtaca cctccggttc caccggtctg ccgaagggg tgctcgttcc ccatcggcag | 3780 |
| atcctgaact ggctgtaccc gctgtgggcg atggtgccct cgggcagga cgaggtggtg | 3840 |
| gcgcagaaga catccacggc cttcgcgtc tcgatgaagg agctcttcac ggggctgctg | 3900 |
| gcgggcgtgc cccaggtatt catcgacggc accgtggtca aggacgcggc ggccttcgtg | 3960 |
| ctccacctgg agcgatggcg ggtcacccgg ctgtacacgc tcccgtcgca cctcgatgcc | 4020 |
| atcctgtccc acgtcgacgg ggcggcgag cgcctgcggt ccctgcggca tgtcatcctc | 4080 |
| gcggggagc cgtgcccgt tgagctgatg agaagctgc gcgagaccct gccgtcgtgc | 4140 |
| acggcgtggt tcaactacgg ctgtaccgag gtcaacgaca tctcctactg cgtcccgaac | 4200 |
| gagcagttcc acagctcggg gttcgtgccg atcggccggc ccatccagta cacccgggcg | 4260 |

```
ctggtgctcg acgacgagct gcggacggtg ccggtgggca tcatgggggga gatttacgtc    4320
gagagcccgg ggacggcgcg gggctactgg aggcagccgg atttgacggc cgagcggttc    4380
atccccaacc cgttcggcga gccgggtagc cgtctctacc gtacgggcga tatggcgcga    4440
tgccttgagg atggctcgct ggagttcttg gggcgccggg actacgaggt caagatccgt    4500
ggccatcgcg tggacgtccg ccaggtcgag aagatcctcg cgagccaccc ggaagtcctc    4560
gagtcggcgg tgttgggctg gccacggggg gcgaagaacc ctcagttgct tgcctacgcc    4620
gccacgaagc cgggccgtcc cctgtcgact gaaaacgtgc gggagtacct gtcggcccgc    4680
ttgccgacgt acatggtgcc aacgctctac cagttcctgc cagcgctgcc gcgcctgccc    4740
aatggcaagc tcgaccgctt cgggctgccc gatcacaaga aagtcgaggt gggcggcgtc    4800
tacgtcgccc cgcagacgcc gacggagaag gtcttggcgg gactgtgggc cgagtgcctc    4860
aagcagggcg acatgcccgc gccgcaggtt ggccgcttgc acaacttctt cgacctcggt    4920
gggcactcgc tgctcgccaa tcgcgtactg atgcaggtgc agcggcattt cggggtcagc    4980
ctgggcatca gtgcgttgtt cggttctccg gtgctgaatg acttcgcggc ggccatcgac    5040
aaggcgctcg ggaccgagga gccaggcgag gaaggttcga gcgacgcacg agaggtcgct    5100
gcgaaggaca cctccgtgct cgtgccgctc tccacccacg ggacgctgcc gagcctgttc    5160
tgcgtccatc cggtgggcgg gcaggtccat gcctaccgcg agctcgccca ggcgatggag    5220
aagcacgcca gcatgtacgc gctccagtcg gagggcgccc gtgagttcga cacaatcgag    5280
accttggcgc gcttctacgc cgatgcgatc cgcggggctc agcccgacgg gagctaccgt    5340
ctcctcggat ggtcttctgg tgggctcatc accctggcga ttgctcgcga gctggagcac    5400
cagggctgcg ccgtggagta cgtgggcctc gtggattcaa agccaatccc gcggttggcg    5460
ggtgagcgcg gctgggcgtc gctgatcgcg gcgacgaaca tcctgggcgc gatgcggggg    5520
cgcggcttct cggtcgccga ggtcgatgct gccgggaaga tcctcgagtc gcgcggatgg    5580
acggaggagt ccttcgactc ggaggggcat gcggcgttgg aggagttggc tcggcacttc    5640
ggcatcaccg tcgcgcaaga gtcatcggag tacctcctgg cccggttcaa gaccacgaag    5700
tactacttgt cgctgttcgc tggcttcaag ccggcggcgc tcgggccgga gacgtacctc    5760
tatgaggctt cagagcgggt cggagccacc tcgaacgacg acacgggcga gtgggggggac    5820
gcgctggatc gcaaggccct gcgggcgaac atcgtgcagg tgccaggcaa tcactatact    5880
gtcctgcagg gagagaacgt gctgcaactg gcggggcgga tcgccgaagc cttgtctgcg    5940
atcgacaact cggtggtaac gaggacgcga gcttcgtga                          5979
```

<210> SEQ ID NO 9
<211> LENGTH: 2928
<212> TYPE: DNA
<213> ORGANISM: Cystobacter velatus
<220> FEATURE:
<221> NAME/KEY: misc_feature
<222> LOCATION: (1)..(2928)
<223> OTHER INFORMATION: CysH

<400> SEQUENCE: 9

```
atggacaatc gagagatcgc acccacccaa tcggcgcgca cgcgtgatgc gtacacggcg     60
gtaccaccag ccaaggccga gtatccgtcg gacgtctgtg tgcaccaact gttcgagttg    120
caggcggaca ggattcccga cgccgttgcg gcgagggcgg ggaacgagtc cctgacctac    180
cgggagctga acttccgggc gaatcagctc gcccggtacc ttgttgcgaa aggcgtggtc    240
ccgcgaggct cggtggccgt gctgatgaac cggaccccctg cgtgtctggt ctcactgctc    300
```

| | |
|---|---|
| gccatcatca aggcgggcgc ggcgtacgtt ccggtggacg ccggattgcc cgccaaacgg | 360 |
| gtggactaca ttctgacgga cagcggcgcg acctgcgtcc tgaccgacag ggagacgcgg | 420 |
| tcactcctcg acgagccgcg gtcggcttcg acgctcgtca tcgacgtgga tgatccatcc | 480 |
| atctattcgg gcgagaccag caacctcggg ctcgctgtcg atcccgagca gcaggtctac | 540 |
| tgcatctaca cctcgggttc gacgggcctt cccaaaggcg tgatggtcca gcaccgcgcg | 600 |
| ctgatgaact acgtctggtg ggcgaagaag cagtacgtca ccgacgcggt cgagagtttt | 660 |
| gccctgtact cctcgttgtc gttcgacctc acggtcacct ccatcttcgt tccgctgatc | 720 |
| tccgacgct gcatcgatgt gtaccccgac ctgggcgagg acgtccccgt catcaaccgg | 780 |
| gtactggagg acaataaggt cgatgtcgtg aagctcacgc cggcccacct tgccctgctc | 840 |
| aggaacacgg acctatcgca aagccggctg aaagtgctca tcctgggagg agaggacctc | 900 |
| cgagcggaga cggcggggga cgtccacaag cggctggacg gccgggcggt gatctacaac | 960 |
| gagtacggcc ccacgagac cgtcgtgggg tgcatgattc accgctacga ccccgcggtg | 1020 |
| gatctgcacg ggtcggtgcc gattggagtg ggcatcgaca catgcggat ctacttgctc | 1080 |
| gacgaccgtc ggcgtcccgt caagccagga gaggttggcg agatttacat cggaggcgac | 1140 |
| ggtgtgaccc tggggtacaa ggacaagcct caagtcacgg cggaccactt catctccaat | 1200 |
| ccgttcgtgg aaggggagcg gttgtacgcc agtggcgacc tcggccgggt gaatgagcgc | 1260 |
| ggcgcgctcg tcttcctcgg ccggaaggat ttgcagatca agctgcgggg gtaccggatc | 1320 |
| gagctgggcg agatcgagag cgcccttctc tcctatccgg ggatcaagga atgcatcgtc | 1380 |
| gattcgacca agaccgcgca gagccaggcc gccgctcagc tcacctactg caccaagtgt | 1440 |
| ggtctggcgt cgagcttccc gaatacgacg tactccgccg aggggtctg caaccactgc | 1500 |
| gaggccttcg acaagtaccg cagcgtcgtc gacgactact tcagcacgat ggatgagctg | 1560 |
| cagtcgatcg tcaccgagat gaagagcatc acaactcga agtacgactg catcgtggcg | 1620 |
| ctcagcggcg gaaaagacag cacgtatgca ctctgccgga tgatcgaaac cggtgcccgt | 1680 |
| gtattggcct tcacgttgga taacggctac atctcggagg aggcgaagca gaacatcaac | 1740 |
| cgggtcgttg cccggctggg agtggatcac cgctatctct cgaccggcca catgaaggag | 1800 |
| atcttcgtcg acagcctgaa gcgacacagc aatgtgtgca acggctgctt caagaccatc | 1860 |
| tacacgtttg cgatcaacct ggcgcaggag gtcggcgtca gcacgtggt catggggttg | 1920 |
| tcaaagggcc aactgttcga aacgcgcctc tcggccttgt tccgcacgtc gaccttcgac | 1980 |
| aacgccgcct tcgagaagag cctcgtcgac gcgcgaaaga tctaccatcg catcgatgat | 2040 |
| gccgtgagcc gcctgctcga cactacttgc gtcaagaacg acaaggtcat cgagaacatc | 2100 |
| aggttcgtgg acttctatcg ttattgccac gccagccgtc aggagatgta cgactacatc | 2160 |
| caggagagag tcgggtgggc caggccgatt gacaccgggc ggtcgacgaa ctgtctcctc | 2220 |
| aatgatgttg gcatctacgt tcacaacaag gagcgcaggt accacaacta ctccctgccc | 2280 |
| tacagctggg acgtccggat gggccacatc agcaggaag aggcgatgag agagctcgac | 2340 |
| gactcggccg acatcgacgt cgagagggtc gagggcatca tcaaggacct tggctacgag | 2400 |
| ctgaacgacc aggtggtggg ctcggcggaa gcccagctgg tcgcctacta tgtctccgcg | 2460 |
| gaggagttcc ccgcgtccga cctgcggcag ttcctgtcgg agattctgcc ggagtacatg | 2520 |
| gtacccaggt cgttcgtcca gctggacagc atcccgctga cgcccaatgg caaggtcaat | 2580 |
| cgtcaggccc tgccgaagcc tgacctgctt cggaaggccg gcaccgacgg acaagccgca | 2640 |

```
cccgaacac cggtggagaa gcagttggcg gagctgtgga aggaggtgct gcaggtcgac    2700
agtgtcggga tccacgacaa cttcttcgag atgggcgggc actcgcttcc ggcgctcatg    2760
ctgctctaca agatcgacag tcagttccat aagacgatca gcatccagga gttctcgaag    2820
gtccccacca tcagcgcgct cgcggcgcat ctcggcagtg acaccgaagc ggtgccgcca    2880
gggctgggcg aggtcgtcga tcagagcgcg cctgcataca ggggataa                 2928
```

```
<210> SEQ ID NO 10
<211> LENGTH: 819
<212> TYPE: DNA
<213> ORGANISM: Cystobacter velatus
<220> FEATURE:
<221> NAME/KEY: misc_feature
<222> LOCATION: (1)..(819)
<223> OTHER INFORMATION: CysI

<400> SEQUENCE: 10
gtgcgcttcg tcactgtcaa tggtgaggac tcggcagttt gctcggtgct ggatcgcgga     60
ctccagttcg gagatggcct gttcgagacg atgctgtgtg ttggcggtgc gccggtcgac    120
ttcccggaac actgggcgcg gcttgatgag ggctgccgcc ggctgggaat cgaatgcccg    180
gacatccggc gcgaagtgac cgctgcgatc gccaggtggg gtgctcccag ggcggtcgcc    240
aagctcgtcg tcactcgggg aagcacggag cggggatacc ggtgcgcccc ttccgtccgg    300
ccgaactgga tcctcaccat cacggatgcc ccgaagtatc cgctggccca cgaggacaga    360
ggcgtggccg tcaaactctg ccgaacgctc gtctcgctcg atgacccaca gctggccggg    420
ttgaagcacc tcaaccggtt gccccaggtg ctcgcgagga gggagtggga cgacgagtac    480
cacgatggcc tgctgaccga ccacggtggt cacctcgtcg agggttgcac gagcaacctg    540
ttcctcgttg ccgacggagc cttgaggacg cccgatctga ctgcgtgcgg tgtgcgcggt    600
atcgtgcggc agaaggtcct cgaccactcg aaggcaatcg ggatccgctg cgaggtaacc    660
accctgaagc tacgagatct cgaacacgcg gacgaggtct tcctgacgaa ctctgtctac    720
gggattgtgc cggttggtag cgtcgatggt atgaggtacc ggataggtcc gacgacggcg    780
cgtttgctga agacctttg ccagggtgtg tactttga                             819
```

```
<210> SEQ ID NO 11
<211> LENGTH: 984
<212> TYPE: DNA
<213> ORGANISM: Cystobacter velatus
<220> FEATURE:
<221> NAME/KEY: misc_feature
<222> LOCATION: (1)..(984)
<223> OTHER INFORMATION: CysJ

<400> SEQUENCE: 11
atgaccggta atttggatag cgcggcatgg cccgtaatca tcacgcctgg ccagcagcca     60
gcggcgctgg aggattgggt ctcagcgaac cgtgacggac tcgagcggca gttgaccgag    120
tgtaaggcca ttctctttcg aggcttccgt agcaggaatg gcttcgagag cattgccaac    180
agcttcttcg accggcgcct caactatacc tatcggtcga cgccccgtac ggacctgggg    240
cagaacctct acacggcgac ggagtacccg aagcagctgt cgattccgca gcattgcgag    300
aacgcctacc agcgcgactg gccgatgaag ctgctgttcc actgcgtgga gccggcgagc    360
aaaggcggcc ggacgccctt ggccgacatg acgaaggtaa cggcgatgat ccccgccgaa    420
atcaaggagg agttcgcgcg gaagaaggtc gggtacgtgc ggaactaccg tgctggagtg    480
gatctgcctt gggaagaggt gtttggaacg agcaacaagg cagaggttga aagttctgc    540
```

```
gtcgagaatg gcatagagta ccactggacc gagggtggct tgaagaccat ccaggtctgc      600
caggcgttcg cttcgcatcc actcaccggt gagacgatct ggttcaatca ggcccacctg      660
tttcaccttt ccgcattgga cccggcttca cagaagatga tgctttcctt cttcggtgag      720
ggcggcctcc cgcgcaactc gtacttcgga cgcgggtcgg ccatcgggag cgacgtcctc      780
gaccagatcc gctccgctta cgaacgcaac aaggtctcgt tcgagtggca gaaggacgac      840
gtgttgctga tcgacaacat gctggtttct cacggacgag atccgttcga aggcagccgg      900
cgggtgctgg tctgcatggc ggagccgtat tcggaagtcc agcggcgggg attcgccggg      960
gcaacgaact cagggcgctc gtaa                                             984
```

<210> SEQ ID NO 12
<211> LENGTH: 13638
<212> TYPE: DNA
<213> ORGANISM: Cystobacter velatus
<220> FEATURE:
<221> NAME/KEY: misc_feature
<222> LOCATION: (1)..(13638)
<223> OTHER INFORMATION: CysK

<400> SEQUENCE: 12

```
atgctgctgg agggagagct ggaggggtac gaggacgggt tggaactgcc gtacgacttc       60
ccgcggacgt cgaatagggc gtggagagcg gcgacgttcc agcatagcta cccgcccgag      120
ctggcgagga aggtggcgga gctcagccgg gagcagcagt ccacgctgtt catgagcctg      180
gtggcgagcc tggcggtggt gttgaaccgg tacacgggcc gcgaggacgt gtgcatcggg      240
acgacggtgg cgggccgagc gcaggtgggg gcgttggggg atctgagcgg gtccaccgtc      300
gacatcctcc cgctgaggct ggacctgtcg ggcgctccga gccttcacga ggtgctgcgg      360
aggacgaagg cggtggtgct ggagggattc gagcacgagg cgttgccgtg ccagattccc      420
ttggtgccgg tggtggtgag gcaccagaac ttcccgatgg cgcgtctgga gggctggagt      480
gagggggtgg agctgaagaa gttcgagctg gcggggaaa ggacgacggc gagcgagcag      540
gactggcagt tcttcgggga cgggtcctcg ctggagctga gcctggagta cgcggcggag      600
ctgttcagcg agaagacggt gaagaggatg gtggagcacc accagcgagt gctggaggcg      660
ctggtggagg ggctggagga ggtgcggctg cacgaggtgc ggctgctgac ggaggaggag      720
gaggggctgc acgggaggtt gaacgacacg gcgcagagc tggaggagcg ctggagcctg      780
gcggagacgt tcgagcgtca ggtgagggag acaccggagg cggtggcttg cgttggcgtg      840
gaggtggcga cggagggca ctcgcggccg acataccggc agctgacata ccggcagctg      900
aatgcgcgag ccaaccaggt ggcacggagg ctgagggcac tgggagtggg cgcggagaca      960
cgggtcgcgc tcttgagcga ccgctcgccg gagctgctgg tggcgatgct ggcgatattc     1020
aaggccgggg gctgctacgt gccggtggac ccacagtacc cgggaagcta catcgagcag     1080
atactggagg atgcggcacc gcaggtggtg ttgggcaaga ggggaagagc ggacggggtg     1140
cgggtggatg tgtggctgga gctggatgga gcgcaacggc tgacggacga ggcgctggcg     1200
gcacaggaag agggagagct ggagggggcg gagaggccgg agagccagca gttggcgtgt     1260 tgatgtaca cgtcgggctc cacgggcaga ccgaagggg tgatggtgcc gtacagccag     1320
ttgcacaact ggctggaggc ggggaaggag cgctcgccgc tcgagcgtgg ggaagtaatg     1380
ttgcagaaga cggcaatcgc gttcgcggtg tcggtgaagg agctgctgag cggattgctg     1440
gcgggagtgg cgcaggtgat ggtgccggag acgctggtga aggacagcgt ggcgctggcg     1500
```

```
caggagatag agcggtggcg ggtgacgaga atccacctgg tgccatcgca cctgggagca    1560
ctgctggagg gggcggggga agaggcgaag gggctgaggt cgctgaagta cgtcataacg    1620
gcgggggagg cactggcgca gggggtgagg gaggaggcga ggaggaagct gccggggggcg   1680
cagttgtgga acaactacgg gtgcacgagc tgaatgacg tgacgtacca ccccgcgagc    1740
gagggggag gggacacggt attcgtgcca atcggcggc ccatcgcgaa cacgcgggtg    1800
tacgtgttgg acgagcagtt gaggcgggtg ccggtggggg tgatggggga gttgtatgtg    1860
gacagcgtgg ggatggcgag ggggtattgg ggccagccag cgctgacggc ggagcgcttc    1920
atcgcgaacc cgtacgcgag ccagcccgga gcgaggttgt accggacggg agacatggtg    1980
agggtgctgg cggacggctc gctggagtac ctggggaggc gagactacga gataaaggtg    2040
agagggcacc gggtggacgt cgccaggtg gagaaggtgg cgaacgcgca tccagccatc    2100
cgccaggcgg tggtgtcggg atggccgttg ggctcgagca acgcgcagtt ggtggcctac    2160
ctggtgccgc aggcgggcgc gacggtgggg ccgcggcagg tgagggatta cctggcggag    2220
tcgctgccgg cgtacatggt gccaacgcta tacacggtgt tggaggagtt gccgcggctg    2280
ccgaacggga agctggaccg gttgtcgctg ccggagccgg acctgtcgag cagccgagag    2340
gagtacgtcg cgccccacgg cgaggtcgag cggaagctgg cggaaatctt cggcaacctc    2400
ctggggctcg aacatgtcgg cgtccacgac aacttcttca gcctcggcgg gcactccctc    2460
ctggctgccc agctgatttc gcgcatacgg gcgaccttcc gcgtggaagt ggcgatggcc    2520
acggtgttcg agtcccccac ggtggagccg ctcgcccgcc acatcgagga gaagctcaag    2580
gacgagtctc gggtccagct ctccaacgtt gtgccggtcg agcggacgca ggagattccg    2640
ctctcctacc tgcaggagcg gctgtggttc gtgcacgagc acatgaagga gcagcggacc    2700
agctataaca tcacctggac gttgcacttc gccggcaagg gttttctcggt ggaggcgttg    2760
cggacggcct tcgatgagct ggtggccaga cacgagacac tgcgcacgtg gttccaggtg    2820
ggggagggga cagagcaggc cgtacaggtc atcggggagc cctggtcgat ggagctgccg    2880
ctgagagagg tggcggggac ggaggtgacg gcggcaatca atgagatgtc ccgacaggtc    2940
ttcgacttga gagcgggacg gttgctgacg gcggcggtcc tgagggtggc ggaggatgag    3000
cacatcctcg tcagcaacat ccaccacatc atcacggacg gctggtcgtt cggggtgatg    3060
ctgcgggagc tgagggagtt gtacgaggca gcggtgcggg ggaagagagc ggagctgccg    3120
ccgctgacgg tgcagtacgg cgactatgcg gtgtggcaga ggaagcagga cctgagcgag    3180
cacctggcgt actggaaggg gaaggtggag gagtacgagg acggggttgga gctgccgtac    3240
gacttcccgc ggacgtcgaa tagggcgtgg agagcggcga cgttccagta tagctaccca    3300
cccgagctgg cgaggaaggt ggcggagctc agccgggagc agcagtccac gctgttcatg    3360
agcctggtgg cgagcctggc ggtggtgttg aaccggtaca cgggccgcca ggacgtgtgc    3420
atcgggacga cggtggcggg ccgagcgcag gtggagctgg agagcctcat cgggttcttc    3480
atcaacatcc tcccgctgag gctggacctg tcgggcgctc cgagccttca cgaggtgctg    3540
cggaggacga aggcggtggt gctggaggga ttcgagcacc aggagttgcc gttcgagcac    3600
ctgctgaagg cgctgaggcg gcagcgggac agcagccaga ttcccttggt gccagtggtg    3660
gtgaggcacc agaacttccc gatggcgcgt ctggagggct ggagtgaggg ggtggagctg    3720
aagaagttcg agctggcggg ggaaaggacg acgcgagcg agcaggactg gcagttcttc    3780
ggggacgggt cctcgctgga gctgagcctg gagtacgcgg cggagctgtt cagcgagaag    3840
acggtgagga ggatggtgga gcaccaccag cgagtgctgg aggcgctggt ggaggggctg    3900
```

```
gaggagggc  tgcacgaggt  gcggctgctg  acggaggagg  aggaggggct  gcacgggagg   3960
ttgaacgaca  cggcgcgaga  gctggaggag  cgctggagcc  tggcggagac  gttcgagcgt   4020
caggtgaggg  agacaccgga  ggcggtggct  tgcgttggcg  tggaggtggc  gacgggaggg   4080
cactcgcggc  cgacataccg  gcagctgaca  taccggcagc  tgaatgcgcg  agccaaccag   4140
gtggcacgga  ggctgagggc  actgggagtg  ggcgcggaga  cacgggtcgc  ggtcttgagc   4200
gaccgctcgc  cggagctgct  ggtggcgatg  ctggcgatat  tcaaggccgg  gggctgctac   4260
gtgccggtgg  acccacagta  cccgggacac  tacatcgagc  agatattgga  ggatgcggca   4320
ccgcaggtgg  tgttgggcaa  gaggggaaga  gcggacgggg  tgcgggtgga  tgtgtggttg   4380
gagctggatg  gagcgcaacg  gctgacggac  gaggcgctgg  cggcacagga  agaggggag   4440 ctggagggg  cggagaggcc  ggagagccag  cagttggcgt  gtttgatgta  cacgtcgggc   4500
tccacgggca  ggccgaaggg  ggtgatggtg  ccgtacagcc  agttgcacaa  ctggctggag   4560
gcggggaagg  agcgctcgcc  gctcgagcgt  ggggaagtaa  tgttgcagaa  gacggcaatc   4620
gcgttcgcgg  tgtcggtgaa  ggagctgctg  agcggattgc  tggcgggagt  ggcgcaggtg   4680
atggtgccgg  agacgctggt  gaaggacagc  gtggcgctgg  cgcaggagat  agagcggtgg   4740
cgggtgacga  gaatccacct  ggtgccatcg  cacctgggag  cactgctgga  ggggcgggg   4800 gaagaggcga  aggggctgag  gtcgctgaag  tacgtcataa  cggcggggga  ggcactggcg   4860 caggggtga  gggaggaggc  gaggaggaag  ctgccggggg  cgcagttgtg  gaacaactac   4920
gggtgcacgg  agctgaatga  cgtgacgtac  caccccgcga  gcgagggggg  aggggacacg   4980
gtattcgtgc  caatcgggcg  gcccatcgcg  aacacgcggg  tgtacgtgtt  ggacgagcag   5040
ttgaggcggg  tgccggtggg  ggtgatgggg  gagttgtatg  tggacagcgt  ggggatggcg   5100
agggggtatt  ggggccagcc  agcgctgacg  gcggagcgct  tcatcgcgaa  cccgtacgcg   5160
agccagcccg  gagcgaggtt  gtaccggacg  ggagacatgg  tgagggtgct  ggcggacggc   5220
tcgctggagt  acctggggag  gcgagactac  gagataaagg  tgagagggca  ccgggtggac   5280
gtgcgccagg  tggagaaggt  ggcgaacgcg  catccagcca  tccgccaggc  ggtggtgtcg   5340
ggatggccgt  tgggctcgag  caacgcgcag  ttggtggcct  acctggtgcc  gcaggcgggc   5400
gcgacggtgg  ggccgcggca  ggtgagggat  tacctggcgg  agtcgctgcc  agcgtacatg   5460
gtgccaacgc  tatacacggt  gttggaggag  ttgccgcggt  tgccgaacgg  gaagctggac   5520
cggctgtcgt  tgccggagcc  ggacctgtcg  agcagccgag  aggagtacgt  cgcgccccac   5580
ggcgaggtcg  agcggaagct  ggcggaaatc  ttcggcaacc  tcctgggct  cgaacatgtc   5640 ggcgtccacg  acaacttctt  cagcctcggc  gggcactccc  tcctggctgc  ccaggtggtc   5700
tcaaggattg  gcaaggagct  tggcactcag  atctcgatcg  ccgatctgtt  tcaaaggccc   5760
acgattgaac  agctctgtga  gctgattgga  ggactggacg  atcagaccca  gagggagctc   5820
gccctcgctc  cgtcgggaa  caccgaggcg  gtgctctcgt  tcgcgcaaga  gcgcatgtgg   5880
ttcctgcaca  acttcgtcaa  gggcatgccc  tacaacacgc  cagggctcga  ccacctgacg   5940
ggtgagctcg  atgtcgcggc  gctagaaaag  gccatccgcg  cggtcatccg  tcgccacgag   6000 ccctgcgga  cgaatttcgt  cgagaaggac  ggggtgctgt  cccagttggt  ggggacggaa   6060
gaacgcttcc  gcctgaccgt  gactcccatc  cgcgacgaga  gcgaggtcgc  gcggctcatg   6120
gaagccgtga  tccaaacgcc  agtcgatctg  gagcgggagt  tgatgatccg  ggcttatctc   6180
taccgggtcg  acccgcggaa  tcactacctg  ttcaccacca  tccatcacat  cgccttcgat   6240
```

```
ggctggtcga catcgatctt ctaccgtgag ctggctgcgt actacgccgc gtttctccgg   6300
cgcgaagaca gtccgctgcc cgcgctggaa atctcctatc aggactatgc ccgctgggag   6360
cgggcccatt tccaggacga ggtgttggcg gaaaaactga ggtactggcg gcagcggctg   6420
tcgggcgctc ggcccctcgt acttccgacc acctaccatc ggccgcccat ccagagtttc   6480
gctggcgccg tcgtgaactt cgagatcgat cgctccatca ccgagcggtt gaagacgctg   6540
ttcgccgagt cgggcaccac gatgtacatg gtgttgctcg gcgcgttctc cgtggtgctg   6600
cagcgctact ccggtcagga cgacatctgc atcggctccc ccgtggcgaa ccggggtcac   6660
atccagacag aagggctgat cggcttgttc gtcaacaccc tggtgatgag ggtggatgcc   6720
gccgggaatc cccgtttcat cgacctgctg gcgcgcattc aacggacagc catcgatgct   6780
tacgcgaacc aagaagtgcc cttcgagaag atcgtggacg acctgcaggt cgcgagagac   6840
acggcccgat ctccgctcgt gcaggtcatt ctcaacttcc acaacacgcc tcctcaatcc   6900
gagctggaac tgcagggggt gaccctcacg cggatgccgg tgcacaacgg cacggccaag   6960
ttcgagctct ccatcgacgt cgcggagacg agcgccggtc taacgggatt cgtggagtac   7020
gcgacggatc tgttcagcga gaacttcatc cggcggatga tcggccacct cgaggtggtg   7080
ctggacgcgt tcggtcgcga tccgcggggcg cctatccatg agttgccact gctcacccgg   7140
caggatcagt tggacctact gtcgcggagc ggccacacag cccccgcggt ggaacacgtc   7200
gagttgatcc ctcatacgtt cgagcggcgc gtccaggaga cccctcaagc gattgccctg   7260
gtctgcggtg acgagcgcgt cacctactcc gcgctcaacc gccgggccag ccagattgcc   7320
cgccgcctgc gcgccgcagg gatcggaccg gacaccctcg tcgggctttg cgcggggcgc   7380
tccatcgagc tggtctgcgg cgtccttggc atcttgaagg cgggcggtgc gtacgtgcca   7440
atcgacccca cctcctcgcc cgaggtgatc tacgacgtcc tgtatgagtc gaaggtgcgg   7500
catctgttga ccgagtcgcg cctggtcggg ggactgccgg tcgatgacca ggaaatcctg   7560
ctcctggata ccccccgcgga cggtgaaggg gacaaggctg ttgctgaccg ggaggagcca   7620
cctgaccttg gcgaggtcag cctcactccc gagtgcttgg cgtacgtcaa cttcacctcc   7680
gactccggtg gggcgccgag gggcatcgcc gtccgccatg gggcgctggc tcgccggatg   7740
gccgccggcc acgcacagta cctggccaat tccgccgtac gtttcctgct gaaggcgccg   7800
ctcacgttcg acctggcggt cgcggagctg ttccagtgga tcgtcagcgg cggcagcctg   7860
agcatcctcg accccaatgc cgaccgcgac gcctctgcct tcctcgcgca ggtgcgcagg   7920
gactcgattg gcgtcctcta ctgcgtcccc tccgaactct cgacgctggt gagccacctg   7980
gagcgcgagc gtgaaagggt gcatgagctg aacaccctcc ggttcatctt ctgcggcggg   8040
gataccctgg cggttaccgt cgtcgagcgt ctcggggtac tggtgcgggc cggcagctc   8100
ccgctgcggc tggtcaacgt ctatgggacg aaggagacgg gaatcggcgc gggttgcttc   8160
gagtgcgcgc tggacgcgaa cgaccccagc gccgaactcc cgccgggacg gctctcgcat   8220
gagcggatgc ccatcggcgg gccgcccag aacctgtggt tctatgtggt gcaacccaac   8280
ggtggcctgg ctccgttggg catcccgggg gaactgtacg tcggcggcgc gcaactcgcc   8340
gacgcccgtt tcgcgacgga gcccacgcg acccaccccg gcttcgtccc gaaccccttc   8400
cggagcggag cggagaagga ctggctgtac aagacggggg acctcgtccg ctggctgcct   8460
caggggccgc tcgagctggt cagcgcggct cgggagcgcg acggaggcgg ggaccaccgg   8520
ctcgatcgcg gcttcatcga ggcgcgcatg cgtcgtgtgg ccattgtccg cgacgccgtg   8580
gtggcctacg tcccggatcg ccaggacagg gcccggttgg tggcctacgt cgttctgaag   8640
```

```
gagtcgcccg cggcggacgt ggagccgcgc gaagggcggg aaacgctgaa ggctcggatc   8700
agcgccgaac ttgggagcac gttgccggag tacatgcttc cggccgccta cgtgttcatg   8760
gacagcctgc cgttgacggc ttacgggagg atcgaccgga aagccctgcc cgagccggag   8820
gatgaccgcc acggtggtag tgcgatcgcc tacgtggccc cgcgcgggcc cacggagaag   8880
gcactggcgc acatttggca gcaagtgctg aaacgccccc aggtcggact gcgagacaac   8940
ttctttgagc tgggcgggca ctcagtgcg gccatccaac tggtgtccgt gagccggaag    9000
cacctggagg tcgaagtccc cctcagcctg atcttcgaat cgccggtcct ggaggcgatg   9060
gcgcgcggca tcgaagcgct gcaacagcag ggccgcagcg gcgcggtgtc gtcgatccat   9120
cgggtggagc ggaccggacc gctgcctctg gcgtacgtgc aggagaggct gtggttcgtg   9180
cacgagcaca tgaaggagca gcggaccagc tataacatca cctggacgtt gcacttcgcc   9240
ggcaagggtt tctcggtgga ggcgttgcgg acggccttcg atgagctggt ggccagacac   9300
gagacactgc gcacgtggtt ccaggtgggg gaggggacag agcaggccgt acaggtcatc   9360
ggggagccct ggtcgatgga gctgccgctg agagaggtgg cggggacgga ggtgacggcg   9420
gcaatcaatg agatgtcccg gcaggtcttc gacttgagag cggacggtt gctgacggcg    9480 gcggtcctga gggtggcgga ggatgagcac atcctcgtca gcaacatcca ccacatcatc   9540
acggacggct ggtcgttcgg ggtgatgctg cgggagctga gggagttgta cgaggccgcg   9600
gtgcgggggg agcgagcgga gctgccgccg ctgacggtgc agtacggcga ctatgcggta   9660
tggcagagga agcaggacct gagcgagcac ctggcgtact ggaaggggaa ggtggagggg   9720
gacgaggacg ggttggagct gccgtacgac ttcccgcgga cgtcgaatag ggcgtggaga   9780
gcggcgacgt tccagtatag ctaccacccc gagctggcga ggaaggtggc ggagctcagc   9840
cgggagcagc agtccacgct gttcatgagc ctggtgccga gcctggcggt ggtgttgaac   9900
cggtacacgg gccgcgagga cctgtgcatc gggacgacgg tggcgggccg agcgcaggtg   9960
gaactggaga gcctcatcgg gttcttcatc aacatcctcc cgctgaggct ggacctgtcg   10020
ggcgctccga gccttcacga ggtgctgcgg aggacgaagg tggtggtgct ggagggattc   10080
gagcaccagg agttgccgtt cgagcacctg ctgaaggcgc tgaggcggca gcgggacagc   10140
agccagattc ccttggtgcc agtggtggtg aggcaccaga acttcccgat ggcgcgtctg   10200
gagggctgga gtgaggggt ggagctgaag aagttcgagc tggcggggga aaggacgacg    10260
gcgagcgagc aggactggca gttcttcggg gacgggtcct cgctggagct gagcctggag   10320
tacgcggcgg agctgttcag cgagaagacg gtgaggagga tggtggagca ccaccaacga   10380
gtgctggagg cgctggtgga ggggctggag gaggggctgc acgaagtgcg gctgctgacg   10440
gaggaggagg aggggctgca cgggaggttg aacgacacgg cgcgagagct ggaggagcgc   10500
tggagcctgg cggagacgtt cgagcgtcag gtgagggaga caccggaggc ggtggcttgc   10560
gttggcgtgg aggtggcgac gggagggcac tcgcggccga cataccggca gctgacatac   10620
cggcagctga atgcgcgagc caaccaggtg gcacggaggc tgagggcact gggagtgggc   10680
gcggagacac gggtcgcggt cttgagcgac cgctcgccgg agctgctggt ggcgatgctg   10740
gcgatattca aggccggggg ctgctacgtg ccggtgacc cacagtaccc gggaagctac     10800
atcgagcaga tactggagga tgcggcaccg caggtggtgt tgggcaagag gggaagagcg   10860
gacggggtgc gggtggatgt gtggctggag ctggatggag cgcaacgcgct gacgacgag    10920 gcgctggcgg cacaggaaga gggagagctg gaggggcgg agaggccgga gagccagcag   10980
```

```
ttggcgtgtt tgatgtacac gtcgggctcc acgggcagac cgaaggggggt gatggtgccg    11040 tacagccagt tgcacaactg gctggaggcg gggaaggagc gctcgccgct cgagcgtggg    11100
gaagtaatgt tgcagaagac ggcaatcgcg ttcgcggtgt cggtgaagga gctgctgagc    11160
ggattgctgg cgggagtggc gcaggtgatg gtgccggaga cgctggtgaa ggacagcgtg    11220
gcgctggcgc aggagataga gcggtggcgg gtgacgagaa tccacctggt gccatcgcac    11280
ctgggagcac tgctggaggg ggcgggggaa gaggcgaagg ggctgaggtc gctgaagtac    11340
gtcataacgg cggggggaggc actggcgcag ggggtgaggg aggaggcgag gaggaagctg    11400
ccggggggcg agttgtggaa caactacggg tgcacggagc tgaatgacgt gacgtaccac    11460
cccgcgagcg agggggggagg ggacacggta ttcgtgccaa tcgggcggcc catcgcgaac    11520
acgcgggtgt acgtgttgga cgagcagttg aggcgggtgc cggtgggggt gatggggggag    11580 ttgtatgtgg acagcgtggg gatggcgagg gggtattggg gccagccagc gctgacggcg    11640
gagcgcttca tcgcgaaccc gtacgcgagc cagcccggag cgaggttgta ccggacggga    11700
gacatggtga gggtgctggc ggacggctcg ctggagtacc tggggaggcg agactacgag    11760
ataaaggtga gagggcaccg ggtggacgtg cgccaggtgg agaaggtggc gaacgcgcat    11820
ccagccatcc gccaggcggt ggtgtcggga tggccgttgg gctcgagcaa cgcgcagttg    11880
gtggcctacc tggtgccgca ggcgggcgcg acggtggggc cgcggcaggt gagggattac    11940
ctggcggagt cgctgccagc gtacatggtg ccaacgctat acacggtgtt ggaggagttg    12000
ccgcggttgc cgaacgggaa gctggaccgg ctgtcgttgc cggagccgga cctgtcgagc    12060
agccgagagg agtacgtcgc gccccacggc gaggtcgagc ggaagctggc ggaaatcttc    12120
ggcaacctcc tggggctcga acatgtcggc gtccacgaca acttcttcaa cctcggcggg    12180
cactccctcc tggcttccca gctgatttcg cgcatacggg cgaccttccg cgtggaagtg    12240
gcgatggcca cggtgttcga gtcccccacg gtggagccgc tcgcccgcca catcgaggag    12300
aagctcaagg acgagtctcg ggtccagctc tccaacgttg tgccggtcga gcggacgcag    12360
gagcttccgc tctcctacct gcaggagagg ctgtggttcg tgcacgagca catgaaggag    12420
cagcggacca gctataacgg aacgatcggg ctccggcttc gggtcctct gtcaatcccc    12480 gcgctcaggg ccaccttcca cgatctggtc gcccgtcacg agagcctgcg caccgtcttc    12540
cgggtccccg aaggccgcac cacgccggtg caggtgattc ttgattcgat ggatctggac    12600
atcccggtcc gcgatgcaac cgaggccgac atcatcccgg gcatggatga gctggcgggt    12660
cacatctacg acatggagaa gggtccgctg ttcatggttc gcctcttgcg gctggccgag    12720
gactcccacg ttctcctgat ggggatgcat cacatcgtct acgacgcatg gtcacagttc    12780
aatgtgatga gtcgcgatat caacctgctc tactcggcgc acgtgacggg aatcgaggca    12840
cggcttcccg cgcttcccat ccagtacgcc gacttctcgg tgtggcagcg ccagcaggac    12900
ttccgtcacc acctggacta ctggaagtcc acactgggcg actaccggga tgatctcgag    12960
ctgccgtatg actacccgcg gccgcccagc cggacatggc acgcgacccg attccacttc    13020
cggtatccgg atgcactggc gcgcgcgttc gccaggttca atcagtccca tcagtcgacg    13080
ctgttcatgg ggctgctgac cagcttcgcg atcgtgctca ggcactacac cggcggaaac    13140
gacatctgca tcggaacgac aacggcgggg cgcgcccagt tggagttgga gaacctcgtt    13200
ggcttcttca tcaacatcct gccgttgcgc atcaatctgg cgggtgaccc cgacatcagc    13260
gagctcatga atcgagcgaa gaagagcgtc ttggcgcct tcgagcatca agctctgccg    13320
ttcgagcgtc tcctcagtgc cctcaacaaa cagcgtgaca gcagccatat cccgctggtt    13380
```

```
cccgtcatgt tgcgccacca gaacttcccg acggcgatga ccggcaagtg ggccgatggt      13440
gtggacatgg aggtcatcga gcgcgacgag cgcacgacgc ccaacgagct ggacctccag      13500
ttctttggcg acgacaccta cttgcatgct gtcgtcgagt tccccgcgca gctcttctcc      13560
gaggtgaccg tccggcgtct gatgcagcgt caccagaagg tcatagagtt catgtgcgcg      13620
acgctggggg ctcggtga                                                   13638

<210> SEQ ID NO 13
<211> LENGTH: 3072
<212> TYPE: DNA
<213> ORGANISM: Cystobacter velatus
<220> FEATURE:
<221> NAME/KEY: misc_feature
<222> LOCATION: (1)..(3072)
<223> OTHER INFORMATION: CysL

<400> SEQUENCE: 13
gtgaacgtgc tcgctaggca ttccaccggc tcccacgacg agccggtggc cggcgacgtc        60
gaactccgcg tcggtggccc cggtgtgccg gacgctcatt ccagcgagag cgttgaagtg       120
ctggcgcggt ggctgcggac cgccgaggag aagtacccgg cgtcatgggc ccgatccgc        180 caggagggcc cctggttcgc catcccgttg acctgcccgc gcggtgcccg gtcggcgcga       240
ttcggcctct ggctcgggga actagaccgt caggacagc tcctccacat ggtcgcctcg        300
tatctggcgg ccgtgcacca cgtgctggtc agcgttcgcg agcccagcgc caacgtgctg       360
gaggtgctgg tctctgactc aacaacgcca tctgggctca accggttcct gaacggcctg       420
gactccgtcc tggagatcct ggctcacggg cgcagcgacc tcctcctgca gcatctcacg       480
ggccggctgc cccccgacga gatgcccttc gtggaggacc gtgaggagcg cgaggagcac       540
ccggccaccg atgtcgaggc cgatgcggtt gtctccgtcc tgttccaacc agttgacttc       600
ccgagcctgg cgaggctgga cgcgagcctc ctcgcgtatg acgacgagga tgccggcgcg       660
gtgggccggg tcctggggga gctcctccag ccgttcctgc tcgactccgc caggatgacc       720
gtggggcgaa aggcggtgag ggtcgatcac atctgcctgc ctggcttgtt gcgagccgac       780
agcagagcgg cggaggagtc ggttctcgcg cccgccttgc gcttggcgac gaagcccggt       840
cggcatttcg tcgcgttgtg ccggaacacc gccctgcggc tgggagacag gctgccccac       900
ttgctcgcgc agggccgct ctgcgatggc gcgtcaacgg cgctccttct gttgcaacgg        960
gtgctggaca cgcttatcgg gagcggggga ctgaaggacc atcgcctcac gctcgagctg      1020
gttggcgccg atccacggac cgaggccgcg tttcgggccc ggactccgtg gctggtggcg      1080
gaacgggccg cttcggctgc atcaacggat gcaccgcgcg tcgacgtcgt cgtcctgttc      1140
ccggcggcac ggccgagcgc gctcgagctg cggccagaca cgtcgtcat cgaccttttt      1200 ggcacctgga gcctgagacc gcgacccgag gttctggcga agaacatcgt ctacgtgcga      1260
ggggcctcgg tccgtctcgc cggagaggcc gtcgtctcga ctccctcctt cgcgccggat      1320
cgagtggagc cggcgctcct cgaggcgctt ctccgggaac tcgacgcgga ggccagtagt      1380
gacgggctcg cccacgagca ccgccttgag attggcggca ttcgcgggtt ctggggtgag      1440
atccgccggg cggagtggga cgcctttcat tcgcgccgcc gggggagct ggcgaggttt        1500 caggtgtcgg ggcaggtgac cgccgccaat ccggggctcg ccagcctgcc cgatggggcg      1560
acgaacatct gcgaatacat cttcggggaa gcgcaccttc gctccggctc gtgcctcgtc      1620
gatccccaga gcggccagtc cgcgacctac gccgagctgg gcgactggc ggcagcgtac       1680
```

```
gcgcggcggt tcgggcatt ggggctccgc cagggagacg tcgtggcgct cgcggcgccg    1740
gatgggattt cgtccgtcgc ggtgatgctg ggttgcttcc tgggcgggtg ggtcttcgcg    1800
ccgctcaacc acaccgcctc ggccgtgaac ttcgaggcga tgttgagttc cgccagtccc    1860
cgcctggtgc tccatgccgc gtcgacggtc gcccgccatc tgccggtcct gagcacgcgg    1920
cgatgcgcgg aactcgcgtc cttcctgccg ccggacgcgc tggacggcgt ggagggggac    1980 gtcaccccc tgccagtgtc accggaagcc ccgccgtca tgctgttcac ctcgggctcc    2040
acgggggggc cgaaggcagt gacgcacacc cacgccgact tcatcacctg cagtcgcaac    2100
tacgcaccct atgtcgtcga actcagaccg gacgatcgtg tctatacgcc gtccccgacc    2160
ttcttcgcct atggattgaa caacttgctg ctgtccctca gcgcgggggc cacgcacgtg    2220
atctcggtcc ctcgcaacgg cgggatgggt gtcgcggaga tcctcgcgcg gaacgaagta    2280
accgtgctct tcgcggttcc cgccgtctat aagctgatca tctcgaagaa cgaccggggc    2340
ctgcggttgc cgaagttgag attgtgcatc tctgctggcg agaagctgcc attgaagctg    2400
tatcgggagg cgcgaagctt cttcagcgtg aacgtactgg acgggatcgg gtgcaccgaa    2460
gccatctcga cgttcatctc gaaccgggag agttatgtcg cgcccgggtg cacgggcgtg    2520
gtggtcccgg ggttcgaggt caagctggtg aacccgcgtg gcgagctctg ccgggtggga    2580
gaggtgggcg tcctctgggt tcggggtggg gcgctgaccc ggggctacgt gaacgccccc    2640
gatctgacag agaagcactt cgtggacggc tggttcaaca cccaggacat gttcttcatg    2700
gatgccgagt accggctcta caacgtgggc agggctggtt cggtcatcaa gatcaattcc    2760
tgctggttct caccggagat gatggagtcg gtcctgcaat cccatccagc ggtgaaggag    2820
tgtgccgtct gcgtcgtcat tgacgactac ggggttgccaa ggccgaaggc attcatcgtc    2880
accggcgagc atgagcgctc cgagccgag ctcgagcact gtgggccga ttgcgcgtt    2940 ctgtcgaaag agaagcttgg gaaggaccac tacccgcatc tgttcgcgac catcaaaacg    3000
cttccccgga cctccagcgg gaagctgatg cggtccgaac tcgcgaagct gctcaccagc    3060
gggcccccat ga                                                        3072
```

```
<210> SEQ ID NO 14
<211> LENGTH: 117
<212> TYPE: DNA
<213> ORGANISM: Cystobacter velatus
<220> FEATURE:
<221> NAME/KEY: misc_feature
<222> LOCATION: (1)..(117)
<223> OTHER INFORMATION: CysM

<400> SEQUENCE: 14
atgaatccaa agttcctcgg aggcctgggg gcagggtgt gcatcgcctc tttgttccag     60
acggtcatgc ggaccgtgcc gctcaaggac gccggctccg gcgacagggc ttgttag      117

<210> SEQ ID NO 15
<211> LENGTH: 1074
<212> TYPE: DNA
<213> ORGANISM: Cystobacter velatus
<220> FEATURE:
<221> NAME/KEY: misc_feature
<222> LOCATION: (1)..(1074)
<223> OTHER INFORMATION: CysN

<400> SEQUENCE: 15
atgtcgactc gcaccaagaa cttcaatgtc atgggaatcg actggatgcc ttcctccgcg     60
gagttcaagc gacgcgtccc gcggacccag cgggcggcag aggccgtgct cgccggacgg    120
```

-continued

```
agatgcttga tggatatcct ggaccgcggg gatcctcgcc tcttcgtcat cgtgggcccc      180
tgctccattc acgatccggt ggcggggctg gactatgcga agcggctgcg gaaactcgct      240
gatgaggttc gcgagaccct gttcgtggtg atgcgcgtgt acttcgaaaa gccgcgcacc      300
accacgggtt ggaaaggctt catcaatgac ccgcgcatgg atggctcttt ccacatcgag      360
gagggcatgg agcggggacg tcgcttcctg ctcgacgtgg ccgaggaggg tctacccgct      420
gccaccgagg cgctggaccc catcgcgtcg cagtactacg cgacctcat ttcctggacg       480 gccattggcg cgcgcaccgc cgagtcgcag acgcaccgcg agatggcgtc cggccttttcc    540 accccagtag gcttcaagaa cggcacggac ggctcgctgg atgcggccgt caatggcatc      600
atctccgctt cacacccgca cagcttcctg ggggtgagcg aaaatggcgc gtgcgccatc      660
atccgcacgc gcggcaacac ctacggccac ctggtgctgc gcggcggtgg tgggcggccc      720
aactacgacg ccgtgtcggt ggcgcttgcg gagaaggcgc ttgccaaggc caggctaccc      780
accaacatcg tggtggactg ctctcacgcc aactcctgga agaatcccga gctccagccg      840
ctggtgatgc gggacgtggt gcaccagatt cgcgagggca accgctcggt ggtgggcctg      900
atgatcgaga gcttcatcga ggcaggcaac cagcccatcc cggcggacct gtcgcaactg      960
cgctacggct gctcggtcac tgatgcatgt gtggactgga agaccaccga aagatgctg      1020 tacagcgcgc acgaggagct gctccacatt ctgccccgta gcaaggtggc ttga            1074
```

<210> SEQ ID NO 16
<211> LENGTH: 612
<212> TYPE: DNA
<213> ORGANISM: Cystobacter velatus
<220> FEATURE:
<221> NAME/KEY: misc_feature
<222> LOCATION: (1)..(612)
<223> OTHER INFORMATION: CysO

<400> SEQUENCE: 16

```
atgcccgccc gctccactcc ctctctggaa agtggcgact ttttcgccga cgtcacgttt       60
tctgatctct cgatcgagtc ggctgatctc tccggcaagg aattcgagcg ctgcacgttc      120
cggcggtgca agttgcccga aagccgctgg gtccggagcc gctgaagga ttgtgtattc       180 gagggatgcg atctcctgcg gatggtaccg gagaagctcg cgctgcgaag cgtgaccttc      240
aaagacaccc gcctcatggg cgtggactgg agtggactcg gaaccatgcc ggacgtccag      300
ttcgaacagt gcgatctgcg ctacagctcc ttcttgaagt tgaatctacg caagacgcgg      360
ttcgttggct gctccgcgcg cgaagccaac ttcattgacg tggacctcgc cgagtcggac      420
ttcaccggca ccgatatgcc aggatgcacc atgcagggct gcgtcctcac caagaccaat      480
tttgctcgat cgaccaattt catcttcgac ccgaaggcga accaggtcaa agggacgcgt      540
gttggcgtgg agaccgccgt cgccctcgcc caggcgttgg aatggtggt cgacggctat      600 cagacaccct ga                                                          612
```

<210> SEQ ID NO 17
<211> LENGTH: 702
<212> TYPE: DNA
<213> ORGANISM: Cystobacter velatus
<220> FEATURE:
<221> NAME/KEY: misc_feature
<222> LOCATION: (1)..(702)
<223> OTHER INFORMATION: CysP

<400> SEQUENCE: 17

```
atgaaacggt tcttcaagct ccagttgcgc accaccaacg tccccgcggc acgggcgttc    60
tacacggctc tgttcggtga gggcgccgcc aacgcagaca tcgtgccgct gcccgagcag   120
gcgattgccc gcggcgcacc cgcccattgg ctgggttacg tcggcgtcga ggacgtcgat   180
gaagcggtgc gctcgttcgt ggggcgcggg gcgacccagc tcggcccgac ccacccgacg   240
aacgacggcg ggcgcgtcgc gatcctccgc gatcctggag gggcgacctt cgccgtggcg   300
acggcaccgg caacgacgag agcgctccag ccggaggtgg tctggcagca gctctatgcc   360
gcgaacgtgc aacagacggc cgcctcgtat tgcgacctgt tcggatggcg gctctcggat   420
cgccgcgacc ttggtgcgct gggggttcac caggagttca cctggcgctc ggacgagccg   480
agcgccggct cggtcgtgga cgtggcgggg ctcaagggg tccattcaca ctggctgttc   540
catttccgcg tcgccgcgct cgatcccgcg atggaggtcg tccgcaaggc cggaggcgtc   600
gtcatcggcc ccatggaact tccgaatggc gatcgcatcg ccgtgtgcga ggatccgcaa   660
cgggcggcgt tcgcgcttcg cgaatccagc cacggacgct ga                      702
```

<210> SEQ ID NO 18
<211> LENGTH: 795
<212> TYPE: DNA
<213> ORGANISM: Cystobacter velatus
<220> FEATURE:
<221> NAME/KEY: misc_feature
<222> LOCATION: (1)..(795)
<223> OTHER INFORMATION: CysQ

<400> SEQUENCE: 18

```
atgcaagaga tcggccagac ggcactttgg gtggcgggaa tgcgcgcgct tgagaccgag    60
cgttccaacc cactgttccg ggatcccttt gcccgtcgac tcgccggtga cacgctcgtc   120
gaggagctgc ggcgccgcaa tgccggtgag ggcgccatgc ctcccgccat cgaggttcgc   180
acgcgctggc tcgatgatca gatcacgctg gggttgggcc gcggcatccg ccagatcgtc   240
atcctcgccg cgggaatgga tgcccgcgcc taccgtttgg cctggccggg agacacgcgg   300
ctgttcgagc tcgaccacga cgccgtgctc caggacaagg aggcgaagct gaccggcgtc   360
gcgccgaaat gtgagcgaca tgccgtgtcg gtcgatctgg ccgatgactg gccggcggcg   420
ctgaagaaaa gcggattcga tccggcgtg cccaccctgt ggctcatcga gggattgctc   480
gtctacctca ccgaggcgca ggtcacgctg ctcatggccc gtgtcaacgc cctgagcgtt   540
cccgagagca tcgtcctcat cgacgtcgtt ggccgttcga ttttggactc ctcgcgcgtc   600
aagttgatgc acgacctcgc ccgccagttc ggcaccgacg agcccgaggt gattctaagg   660
ccgattggct gggaccccca cgtctacacc accgcggcca tcgggaagca gctcgggcgc   720
tggcccttcc ccgtggcgcc acgcggcacc cccggtgtgc cccagggata cctggtgcac   780
ggagtcaagc gctga                                                    795
```

<210> SEQ ID NO 19
<211> LENGTH: 1002
<212> TYPE: DNA
<213> ORGANISM: Cystobacter velatus
<220> FEATURE:
<221> NAME/KEY: misc_feature
<222> LOCATION: (1)..(1002)
<223> OTHER INFORMATION: CysR

<400> SEQUENCE: 19

```
gtgaatggga cgacagggaa gacagggttg gtagcagaaa ggtcgggcgc gatttccccg    60
agggactaca agtccaagga gttggtgtgg gattcgcttg ccgccacacg cagcaagccc   120
```

```
cggcgcgtac tgccggaggg ggacgtggtc gggcacctgt acccgccggc caaggcggcc    180
ctgctcaccc acccgctcat gaagaacctt ccgcccgaga cgctgcggct gttcttcatc    240
cactccgcct acaagttcat gggggacatc gccatcttcg agacggagac cgtcaacgag    300
gtggcgatga agatcgccaa cggtcacacg cccatcacgt tcccggacga catccgccac    360
gacgcgctca ccgtcatcat cgatgaggcc tatcacgcct acgtggcacg cgacttcatg    420
cggcagatcg agcagcgcac gggcgtcaag ccgctgcccc tgggaacgga aacgacctg     480 tccagggcca tggctttcgg caagcaccgg ctgcccgaga cgctgcacgg gctctgggaa    540
atcatcgccc tctgcatcgg ggaaaacaca ctcaccaagg atctgctgaa cctgacgggt    600
gagaagtcct tcaacgaagt gctccatcag gtgatggagg accatgttcg cgacgagggc    660
cgccacgcgg tcctcttcat gaacgtgctc aagctggtgt ggagtgagat ggaggagagc    720
gcccggctcg ccatcggtca gctgctgcca gagttcatcc gcgagtacct cagcccgaag    780
atgatggcgg agtacgagcg cgtcgtgctg agcagctcg gtctagcggc cgagcacatc     840
gagcggatcc tctccgagac gtactcggag ccgccgctgg aggatttccg cgcgcgatat    900
cccctctccg ggtacctggt ctacgtgctg atgcagtgcg acgtcctgtc gcacgcgccg    960
acgcgcgagg cgttccgccg attcaagctg ctcgcccact ga                      1002
```

<210> SEQ ID NO 20
<211> LENGTH: 1929
<212> TYPE: DNA
<213> ORGANISM: Cystobacter velatus
<220> FEATURE:
<221> NAME/KEY: misc_feature
<222> LOCATION: (1)..(1929)
<223> OTHER INFORMATION: CysS

<400> SEQUENCE: 20

```
atggccaacc agcgggtcgc attcattgag ttgacggtct tctctggcgt ttatcccttg     60
gcctctggct acatgcgtgg cgtggccgag cagaacccct tgatcaggga gtcgtgcagc    120
ttcgaaatcc actcgatctg catcaacgac gaccgattcg aagacaagct caacaagatc    180
gatgccgatg tctacgcgat ctcttgctat gtctggaaca tgggcttcgt gaagcggtgg    240
ctccccaccc tcaccgcccg caagcccaac gcgcacatca tccttggcgg tccgcaggtg    300
atgaaccacg gggcgcagta cctggatccg ggcaacgagc gggtggtgct ctgcaacggt    360
gagggtgagt ataccttcgc gaactacctg gccgaactct gctcccccca gcccgacctt    420
ggcaaggtca agggcctctc cttctaccgg aacggagagc tgatcacgac cgagccccaa    480
gcgcgcatcc aggatctgaa cacggtccca tctccctacc tggaaggcta cttcgacagc    540
gagaagtacg tgtgggcgcc ccttgagacg aaccggggat gccctacca gtgcacctac      600 tgcttctggg gggcggcgac caactcgcgc gtgttcaagt ccgacatgga ccgggtcaag    660
gcggagatca cctggctcag ccagcaccgg gcgttctaca tcttcatcac cgacgcgaat    720
ttcggcatgc tgacccgcga cattgagatc gcccagcaca tcgccgagtg caagcggaag    780
tatggctatc cgctcaccat ttggctgagc gcggcgaaga actcgcctga ccgggtcacg    840
cagatcacgc ggatcctgag ccaggagggt ttgatctcca cccagccggt ctcgctccag    900
acgatggacg cgaacacgct gaagagcgtg aagcgcggca acatcaagga gagcgcctac    960
ctgagcctcc aggaagaact gcaccgcagc aagctctcct cgttcgtgga gatgatctgg    1020
ccgcttcccg gcgagacgct ggagaccttc agggagggca tcgggaagct ctgcagctac    1080
```

```
gacgccgacg cgatcctcat ccaccacctc ctgctcatca caacgtgcc gatgaacagc    1140 cagcgcgagg agttcaagct ggaggtgtcg aatgatgaag acccgaacag cgaggcgcag    1200
gtcgtcgtcg cgacgaagga cgttacccgc gaggaataca aggagggtgt gcggttcggg    1260
tatcatctca cgagcctgta cagcctgcgc gcactccgct tcgtcgggag gtacctcgac    1320 aagcagggc ggctggcctt caaggacttg atctcctcgt tctcggagta ctgcaagcgg    1380
aaccctgacc cccctacac gcagtacatc ccagcgtga tcgacgggac cagccagtcg    1440
aagttcagcg ccaacggcgg catcttccac gtcacacttc acgagttccg cagagagttc    1500
gaccaactgc tcttcgggtt cattcaaacc ctgggcatga tgaacgatga gctgctggag    1560
ttcctgttcg agatggatct cctcaaccgt ccgcacgtgt acagcaacac gcccatcaat    1620
aatggcgaag ggttgctgaa acacgtgacg gtcgtctcga aggagaagga tgccattgtc    1680
ctgcgcgttc ccgaaaagta cgcgcagctc acgtctgagc tactcgggct cgagggcgct    1740
cccagcacga gcctgcgcgt gaagtaccgc gggactcaaa tgccgttcat ggcgaacaag    1800
ccgtacgagg acaacctctc ctactgcgag gcgaagctcc acaagatggg aagcatactt    1860
ccggtctggg agtcggccgt cccttcgcgc acaccggtcc ggcggccaca agtggccgtc    1920
gcgggctga                                                            1929

<210> SEQ ID NO 21
<211> LENGTH: 3804
<212> TYPE: DNA
<213> ORGANISM: Cystobacter velatus
<220> FEATURE:
<221> NAME/KEY: misc_feature
<222> LOCATION: (1)..(3804)
<223> OTHER INFORMATION: CysT

<400> SEQUENCE: 21
atgcatcgag tgaagccgtt gatagggccc gtcctgtcgg cgctgttgct gtgtgcc ctg       60 cccgccaggg cgcagatcgc cgcggcccac gtctaccaca accacatgcc caacttctgg    120
gcctactacg acctgggcca atacgcgtcc acgcccaccg gcggccccat ccggtacatg    180
tatgacgcgc aggtcatcaa cctgaagaag aatccccgt ccaattacac atactacctg    240
ccatcgggcg cgcccatgcc gcacgatgac ctcgtcacct attactcgca caacgcgaag    300
acgggtgcct acctgtactg gcctccaagc gtcgcctcgg acatgaaaac caatgccccc    360
accggccagg tgcacgtcac catgtccggc gccgtggtga caatgtcca ggatctcgtc    420 accctgaaga acgtccccgg ctacgacaat ccgaactggg gcgcctcctg gaaggaccgc    480
tacagcgccc tgctcacccc gcgggcaac cgcaccctgg atctcatcca cttcaccggc    540
caccactcca tgggcccct ggtcggtccc gactacttcc tcaaggatct catctaccag    600
agcgccacgc tcgcccagcc ctacttcctc ggcggctcct ccagtcctc caagggcttc    660 ttcccaccg agctcggctt ctccgagcgc ctcatcccca ccctctccaa gctcggcgtg    720
cagtgggccg tcatcggcga caaccacttc tcccgcaccc tcaaggacta ccctaccctc    780
aacgatccgg gctccgacac gctcgtctcc ccgcccaacc gcgccgatct ccagaacacc    840
agctccgtgg gctcctgggt gagcgcccag atgcccacg agcagcaggt catcaagaac    900
aagtacccct tcgcctccac tccccactgg gtgcgctacg tggaccccgc cacgggcgcc    960
gagtcgcgcg tcgtcggcat cccgtcaac cagaacggct cctggctcga gggctgggaa    1020
ggcgaggcca ccgtcgacgt cgtcaacctc aagagcttcg agggcctcgt tccccagcgg    1080
cagttcttcg tcatcgcgca tgatggcgac aactcgagcg gacgcgccgg ctccgactcc    1140
```

```
acctggtaca acggccgctc cgtcacctgc gccaatggcg tgcagtgcgt gggcatctcc      1200
gagtacctcg tccaccacac ccccgcctcc accgacgtgg tgcacgtcca ggacggctcg      1260
tgggtggaca cgcgcgactc ctcctcggat ccccagtggc accactggaa gctgcccttc      1320
ggcatctgga agggtcagtt ccccgccttc aacgccgcca ccggcctcaa tctctctccc      1380
aagacgaacc tcagcggcgt gcaggagggc atgacggtct ccctcgagca cggctggcac      1440
tacctcgagc gcaacttcgc cctgctccag gccgccctca actacgcgaa gaccgccgag      1500
cagatctggc tcgacgcgca ccccaatcac tggtcgccca ccaccgcgat cgacaagcag      1560
atcacccaca cgggcaacca gctcaacccg tggatgatgt cctttcccgt caagggcgac      1620
gtgaacaacg actgggcggg cggcgccaac cccgcggaac tcgcctggta cttcctgctg      1680
cccgccatgg actcgggctt cggctactac gacgagaacc aggacgacaa cgtcaagccc      1740
acgctgtcct tcaatcaatc cctctacttc tccaagccct acgtgcagca gcgcatcgcc      1800
caggacaaga cgggcccctc cgtctggtgg gcccagcgct ggccctacaa ccccggcagc      1860
gccaacaccg acaagtccga gggctggacg ctccacttct tcaacaacca cttcgccctc      1920
tacacctacg cctacgacgc gagcggcatc tcctccatca aggcccgcgt ccgggtgcac      1980
acccacaaga gcatcgaccc gctcgacaac acccacaagg tctatgatcc ggcggcgcgc      2040
aaggccgcgg tgttcccaa catcgatccg gcccgcgtgg gcgcctgggt ggactacccg      2100
ctcacccggc gcgacctgaa gcctgtcatg aatggtgttt cctggcagcc cgcctacctg      2160
cccgtcatgg ccaaggtgcc cgcgcaggag atcggcgacc tctactacgt ctacctgggc      2220
aactaccgcg accagctcct cgactactac atcgaggcca ccgacagccg gggcaacatc      2280 accccggggag agatccagtc cgtctacgtg ggctcgggcc ggtacaacct ggtgggcggc      2340
aagtacatcg aggaccccaa cggcacggta cagggaacgc atcccttcct cgtggtggac      2400
accaccgcgc cctcggtccc ctcgggactg accgcgaagg cgaagacgga ccgctcggtg      2460
accctgagct ggagcgcggc ctcggacaac gtggcggtga gcggctatga cgtcttccgc      2520
gatggcacgc aggtgggctc gagcaccagc acgccctata ccgacagcgg cctcccccg      2580 agcactcaat acagctacac cgtgcgcgcc cgggacgcgg cgggcaacgc gtccgcccag      2640
agcaccgccc tgagcgtcgc caccctgacg ccggacacca ccccaccctc cgttccctcg      2700
ggcctgacgg cgtcgggcac gacgagctcc tcggtggccc tcgcctggac ggcctccacc      2760
gacaactacg gcgtcgcgaa ctacgaggtg ctccgaaacg gcacccaggt cgcgtccgtc      2820
acggggacga cctactcgga taccggcctc tcgccgagca ccacctacag ctacaccgtg      2880
cgcgcccggg acgcggcggg caatgtctcc tcgcccagca cggccctgtc cgtcaccacc      2940
cagacgggca cagcgccac cgtctactat ttcaacaaca acttcgccct caaatacatc      3000
cacttccgca tcggcggtgg cacgtggacg accgtgcccg caacgtcat ggccacctcc      3060 gaggtgccgg gctacgccaa atacaccgtc aatctgggag cggccaccca gctcgagtgt      3120
gtcttcaacg atggcaaggg cacctggac aacaacaagg gcaacaacta cctcctgccc      3180
gcgggcacct ccacggtgaa ggacggcgtc gtctccagcg gagcgcccgc gctcgacacc      3240
accgcaccct ccgtccctc gggcctcacg gcggcgtcca gacgtcctc ctccgtgtcg      3300 ctctcctgga gcgcctccac ggatgccagc ggcatcgccg gatatgacgt gtaccgcgat      3360
ggctcgctgg tgggctcacc cgtctccacc agctacaccg cagcgacct gagtgccggc      3420 acgacctacc gctacaccgt gcgcgcgcgc gacaccgcgg gcaatgcctc cgcccagagc      3480
```

```
accgccctga gcgtcaccac gagcacctcc tcggccacct ccgtcacctt caacgtgacg    3540
gccagcaccg tcgtgggaca gaacgtctac ctcgtgggta accatgccgc gctcggcaac    3600
tggaacaccg cgccgccat cctcctgtct ccggccagct acccgaagtg gagcgtgacg     3660
ctcagcctgc ccggctcgac ggccctcgaa tacaagtaca tcaagaagga cggctccggg    3720
aacgtcacct gggagagcgg cgccaaccgc tcgaccacga tccccgcctc ggggaccgcg    3780
accctcaacg acacctggaa gtag                                           3804
```

<210> SEQ ID NO 22
<211> LENGTH: 831
<212> TYPE: DNA
<213> ORGANISM: Cystobacter velatus
<220> FEATURE:
<221> NAME/KEY: misc_feature
<222> LOCATION: (1)..(831)
<223> OTHER INFORMATION: ORF1

<400> SEQUENCE: 22

```
gtgccacatc catccgagca gagcgctccg tcgggactcc gggcgcggct gcacgaaatc     60
atcttcgagt cggacacccc ggcgggccgc gccttcgatg tggcattgct gtgggccatc    120
gtgctcagcg tcctcgcggt gatgctcgag agcgtggagt ccatcagcgt ccagcatggg    180
cagaccatcc gcgtcctcga gtggtgtttc accgggctct tcacactgga gtacgtgctg    240
cggctgctgt cggtgaaacg gccgctgcgc tatgcgctga gcttcttcgg gctggtggat    300
ctgctggcca tcctgccctc ggtgctgagc ttgatgctgc ccggcatgca gtccctgctg    360
gtggtgcggg tgttccgcct gctgcgcgtc ttccgcgtac tcaagctcgc cagcttcctc    420
ggggaggcgg acgtgctgct caccgcgctc cgggccagtc ggcggaagat catcgtcttc    480
ctcggggcgg tgctgagcac ggtcgtcatc atgggcgcgg tgatgtacat ggtggagggg    540
cgcgccaacg gcttcgacag catcccgcgg gggatgtatt gggccatcgt gacgatgacc    600
acggtgggct acggagacct ctcgcccaag acggtgcccg acagttcat cgcctcggtg     660 ttgatgatca tgggctacgg catcctcgcg gtgcccacgg gcatcgtgtc cgtggagctc    720
gcccaggcga cccggcagca cgccatcgac ccgcgcgcct gtcccggctg cggcctgcag    780
ggccacgacc tggacgcgca ccactgcaag cactgcggca ccgccctctg a             831
```

<210> SEQ ID NO 23
<211> LENGTH: 237
<212> TYPE: DNA
<213> ORGANISM: Cystobacter velatus
<220> FEATURE:
<221> NAME/KEY: misc_feature
<222> LOCATION: (1)..(237)
<223> OTHER INFORMATION: ORF2

<400> SEQUENCE: 23

```
atggcacagg accaggacag ggagaagctg cattccgacg cggacaagga gaggctgcac     60
ccgaaggtcg actcgggtga cgtctcgggc cggggccgcg agcggcggcc cgacgaggaa    120
taccccaagc agcgcaacgc gggcgagttc ggcacccacg gaggccccaa caagggcggc    180
aaggaagacc ggcggcaact gcatgccccc ggcagctcca aggcgggctc ccagtag       237
```

<210> SEQ ID NO 24
<211> LENGTH: 489
<212> TYPE: DNA
<213> ORGANISM: Cystobacter velatus
<220> FEATURE:
<221> NAME/KEY: misc_feature

<222> LOCATION: (1)..(489)
<223> OTHER INFORMATION: ORF3

<400> SEQUENCE: 24

```
atgggaagaa cctacagttt cgaacccttc ttgtcgcagc aacccgcgca gacctacaag    60
ggctcgggtc cccggctcgg caatgaagaa cacaagatcg ccctcaccaa ggaagaggag   120
aaggcggccc tgcctgacac gcccaccggc tatggacagg cccacgccga gaccgtgaag   180
cgctaccgcg cccgcgcgga gaagaagcgc acggagccca gaccccgcc tacccgggcg   240
aagaaggccg ccccaaggc gaagcccacc cggaaggtgg cgacgcaaga ggccaccgcc   300
aaggccccta cccgtcaagc gcgggaggag accgagccga aggcccccgc gcgcaagaag   360
ctgagcgcca cggggctcgt gggtagcatc gggcgcaagg tggtgactcg ggccgcggtc   420
gcggcgaaga agaccgtggc gcgcgccgtg aagaccgccg ccgcgcgcaa gtccgcgaag   480
aagcgctga                                                           489
```

<210> SEQ ID NO 25
<211> LENGTH: 264
<212> TYPE: DNA
<213> ORGANISM: Cystobacter velatus
<220> FEATURE:
<221> NAME/KEY: misc_feature
<222> LOCATION: (1)..(264)
<223> OTHER INFORMATION: ORF4

<400> SEQUENCE: 25

```
atgagcccgg caagacgcaa ggagagcaag cagcacgaag tgggctccgc cacacacgca    60
cggcgggtga tcgtggcgac ggatggccgg ggttggtacg tccgattcga gggcaaccgt   120
cagctcggcc ggtattccaa cgtgacccag gccatccacg gcgggcgcag gctggctcgc   180
cagcacaagc ccgcgggcct cgtggtgcgc tacctggacg gggaagagga agagtcctgg   240
tacggggacc gcgaggcgcc ttga                                           264
```

<210> SEQ ID NO 26
<211> LENGTH: 450
<212> TYPE: DNA
<213> ORGANISM: Cystobacter velatus
<220> FEATURE:
<221> NAME/KEY: misc_feature
<222> LOCATION: (1)..(450)
<223> OTHER INFORMATION: ORF5

<400> SEQUENCE: 26

```
atgaaacaca tcaaggcggt ggtggtgggt gcgttgtccg cggctctgct cttcggcgtg    60
ggatgtcaga cgacgggcgg tgctgggaat caaggaacgg gcgggagcga tacgtctcag   120
ggcggcacca tgaccggaag tgagacgacc ggaaccggaa cgaccggagg cacccacggaa   180
ggtggtgaca ccacgggcgg aggcaccggc ggaacaggtg ctggcgacat cgacggttcg   240
agcagtggca gcacgggctc cggtagcgac gtggcggct ccggcggctc gggcgtgtcc   300
agtgaaccgg gcggtttcag ccccgacgcc tcgggcgtgg acagcgacct gggcggctcc   360
ggcaccggca gtgacgtgga cggctccggc agcacggact ccagcggcaa catgagcggc   420
acgggctccg aagacgacac cagccgctga                                    450
```

<210> SEQ ID NO 27
<211> LENGTH: 1578
<212> TYPE: DNA
<213> ORGANISM: Cystobacter velatus
<220> FEATURE:

```
<221> NAME/KEY: misc_feature
<222> LOCATION: (1)..(1578)
<223> OTHER INFORMATION: ORF6

<400> SEQUENCE: 27
atgagcacgc gcacctccct ggccctggcc gcgtccctcg ccgcgctgcc cgcgctcgcc      60
caggagcgtc ccagcgaggg cgacctcttc ggcggcgaca ctccagagac gaagcccgct     120
ccggccgatg cgccccgccc cgacgagagt tccctcttcg gtgacacccc cgcgtccacc     180
ccggccgcac agagcgcggc ggccaccgcg gccccgaca agccctccgc cacgccccag      240
gaccgggatg cgcaggcgct cggtggcccg tcggccacca acgccttcga caccgaggag     300
gccgtcgagg atccgctgaa gatcggcggc cgcttctacc tgcgcgccta ctcacaggcc     360
aacgaagggg tgtccttcag caacaccacc ttctccgccc ccatgctggt ggacggctac     420
ttcgatgccc gccccaccga gcggctgcgc ggcttcgtgc tcggacggct caccttcgat     480
ccgacccgca aggcgggctc cctcggcatc gtccccacga gcacgtccac ctccaacgtc     540
gctgcggatc cggtcgtgct gttggatcag gcctggctgc gcttcgacct ggaccacaag     600
ctcttcatca ccgtcggcaa gcagcacgtg aagtggggca cctcgcgctt ctggaacccc     660
accgacttcc tctcgcccca gcgcaggat ccgctcgccc tcttggacac gcgcaccggc      720
gcgaccatgc tcaagatgca catgccctgg gaggcgaaag gctggaactt ctacgtcctc     780
ggcctgctcg acaacgccgg cccggccaat acgctcggcc gcgtcggggg cgctgctcgc     840
gccgaggtgg tgctcggcca tacggaactc ggcgtcgatg ccgtgctcca acacggccgc     900
aagcccgct tcgggctcga cctctcctcc gggctcggcc catcgacat ctacggcgaa       960
ctcgcccctca agaagggctc ggatgcgccc atgttccgca tgccccaagg tgtctccctc    1020
ggagacctgc tcggtcagtt ccagggcaat ggcggcatgc ctcccgacct gggcgcgctc    1080
cccatagagg cgtactaccc cgagggttac acgccgcagg tgagcggcgg cgcgacctgg    1140
acgttcgcct actcggagag cgacaccgcc ccgtgggcg tcgagtactt ctacaattcg     1200
atgggctatc ccggctcgct ggcctacccc tacctcatcc tccagggcca gtatcagccc    1260
ttctacctcg gccggcacta cgccgccgtc tacgcgttcc tgtccggtcc gggatcctgg    1320
gacaacacca acttcatcct gtccaacctg gcaacctct ctgaccgttc tttcatcaca     1380
cggttggacg tgacgcaccg ggccctgcgc tatctcagca tcgaggcctt catcgccgcc    1440
aactatggcc agcggggtgg cgagttccgc ttcgcgctca acctgccggc cctgcgcatg    1500
ggcgagcagg tgacgcctcc catcgccgtc gctccaccta ccatccaggc cggggtgggt    1560
ctgcgcatcg acctttga                                                  1578

<210> SEQ ID NO 28
<211> LENGTH: 786
<212> TYPE: DNA
<213> ORGANISM: Cystobacter velatus
<220> FEATURE:
<221> NAME/KEY: misc_feature
<222> LOCATION: (1)..(786)
<223> OTHER INFORMATION: ORF7

<400> SEQUENCE: 28
atgaccctgc gcaacctcct cggcgccctg ttcgccgcgc tgctgctggc cgctccgacc      60
gctcgcgcgg acctcaccga ccccgccgag atcaagaagc tcctggagac gctcgacaac     120
cgccagcgca acggcggcga ctacaagtcg ctggtgtata tcgagcagaa ggagaaggac     180
aaaacagacg tcgtgcgcga ggccgtcgtc taccggcgcg acgagaagga tcagctgatg     240
```

```
atcctcatga ccaagcccaa gggcgaggcc ggcaagggct acctgcggct ggacaagaac    300
ctctggagct acgacccgaa caccggcaag tgggaccggc gcaccgagcg tgagcgtatc    360
gccggcaccg acagccgccg cgccgacttc gacgagtcgc gcctggccga ggagctcgat    420
ggcaagttcg agggcgagga gaaactcggc aagttcacca cctggaagct cgtcctcacc    480
gccaagccga acgtggacgt cgcctacccc gtggtacacc tgtgggtgga aaggacacg     540 aacaacatcc tcaagcgcca ggagttcgcc ctttccggcc gcctgatgcg cacctcctac    600
ttccccaagt ggatgaagct cttcagcgag tccaagaagg ccgacgtctg gtacccgcag    660
gagatgcgct ctatgacga ggtggagaag accaactcca ccgtcatcgt cgtgaagagc     720
gtggacctgc gctcgctcga ggagaacatc ttcaccaagg cctggttcga gagcaaaagc    780
cgatga                                                               786

<210> SEQ ID NO 29
<211> LENGTH: 1302
<212> TYPE: DNA
<213> ORGANISM: Cystobacter velatus
<220> FEATURE:
<221> NAME/KEY: misc_feature
<222> LOCATION: (1)..(1302)
<223> OTHER INFORMATION: ORF8

<400> SEQUENCE: 29
atgcaacagc tcctcctcat cgcagtgcgc aacctgggca cccacaagcg ccgtacgctt     60
ctgctgggcg cgccatcgc cggtgtcacg gccctgctcg tcatcctcat gggcctgtcc    120
aacggcatga aggacacgat gctccggtcc gccaccacgc tggtgaccgg gcacgtcaac    180
gtggctggct tctacaaggt gacggccggc cagtctgcgc ccgtggtgac ctcctacccc    240
aagctgctcg agcagctgcg caaggaagtc cccgagctgg acttctccgt ccagcgcacg    300
cgcggctggg tcaagttggt gagcgagtct ggctccgtgc agacgggaat cggcggcatc    360
gacgtagcgg ccgagactgg catccgcaag gtgctgcagt tgcgggaggg tcggttggaa    420
gacctggcgc aacccaatac cctcctcctc ttcgacgagc aggcgaagcg gctcgaggtc    480
aaggtgggtg acagcgtcac cctctccgcg tccaccatgc gcgggatcag caacaccgtg    540
gacgtacgtg tggtggccat cgccgccaac gtgggcatgc tgagttcctt caacgtcttg    600
gtgcccaacg ccaccctgcg cgccctctac cagctgcgcg aggactccac cggcgccctc    660
atgctccacc tcaaggacat gagcgccatc cccagcgtgc aggcgcgcct ctacaagcgt    720
ctgcccgagt tgggttatca ggtgctggag catgacccc gggccttctt catgaagttc     780
cagaccgtca accgcgaggc ctggacgggg cagaagctgg acatcaccaa ctgggaggac    840
gagatctcct tcatcaagtg gaccgtgtcg gcgatggacg ccctcaccgg cgtcctcatc    900
ttcgtgctgc tcatcatcat cgcggtgggc atcatgaaca cctgtggat cgccatccgc    960 gagcgcaccc gggaaatcgg cacccctgcg gccatcggca tgcagcgctg gtacgtgctg   1020
gtgatgttcc tcctggaggc gctcgtgctc ggactgctcg gcaccacggt gggcgccctc   1080
gtgggcatgg gcgtgtgcct gctcatcaac gccgtggacc cctccgtgcc cgtgcccgtc   1140
cagctcttca tcctctccga caagctccac ctcatcgtga agcccggatc ggtgatgaga   1200
gccatcgcgt tcatcacgct gtgcaccacc ttcatctcgc tcattccctc tttcctcgcc   1260
gcgcggatga agcccatcac ggcgatgcac cacatcgggt ga                      1302

<210> SEQ ID NO 30
```

<211> LENGTH: 2106
<212> TYPE: DNA
<213> ORGANISM: Cystobacter velatus
<220> FEATURE:
<221> NAME/KEY: misc_feature
<222> LOCATION: (1)..(2106)
<223> OTHER INFORMATION: ORF9

<400> SEQUENCE: 30

```
atgggccaac tcaagctcct gctccaagtg gccctgcgca acttgttcgt gagcaggatc      60
aacctcctca tcggaggcat catcttcttc ggcaccgtgc tggtggtggt gggcggctcc     120
ctcgtcgaca gcgtggacga ggcgatgagc cgcagcatta cggcagcgt cgccggccac     180
ctccaggtgt actcggccca ctccaaggac gagctctcgc tcttcgggca gatgggccgc     240
gaaccggacc tgagcgcgct ggatgacttc tcgcgcatca agcaactggt acagcagcac     300
cccaacgtga agacggtggt gcccatgggc accggcgcca cgttcatcaa ctcgggaaac     360
accatcgacc tgaccttggc gcgcctgcgc gacctctaca agaaagcagc acagggcgac     420
acacccgaac tccgcgggca gatccacagc ctccaggcgc atgtgcgtca catcatcacc     480
ttgctcgagg aggatatgaa gcggcgcagg gaaatcatcg acgacaagac cacggacccc     540
gcggacgcgg aggccatggc ccgcgcccgt tccgaggcct tctgggcgga cttcgacgag     600
aagccattcg actcgctcga gttcctggag aaccgcatcg ccccgtatat gacggacggg     660
gacatgttgt ccctgcgcta tgtaggcacc gacctggtca acttccagaa gaccttcgac     720
cgcatgcgca tcgtggaggg cacgccggtg cccccggggc accgcggcat gatgctctcc     780
aagttcacct acgagaacga cttcaagctg aagacgcgc accggttgga tctcatcaag     840
gaggcgcgtg ataccaacca caagaccatc gcgatggatc cgcaactcca gcgctgggtg     900
aaggagaacc agacccagac gcgggagatc ctcttccagc tcgacgacct caagacgaag     960
caggccgtgg agcggctcca gcgcgtgctg ggcagccagg agacggacct gggcaagcta    1020
ctgcccgcct tcttcaccat ggatgacgcc aacttgaca cgcgctacca gcagttctac    1080
tccgagctgg cgacgctgct cgacctgtac cgcatccgca tcggggacga cctcaccatc    1140
accgcattct cgcgcaccgg ctatgtgcag agcgtgaacg tgaagatcta cggcacctac    1200
cagttcgacg ggctggagaa gtccgcggtc gccggagccc tcaacctgct ggacctgatg    1260
tccttccgcg agctgtacgg ctatctcacc gctgagaaga aggccgagct cgcgggcctg    1320
cagaaggcca gcggggtgca gcaggtgaag cgcgaggacg ccgagacggc gctctttggc    1380
gagcagggca cgcgcctcgct ggtggccgag gggaccgccg ccagatcga cgaggacaag    1440
caactcgacg ggctcgccca gaagctgcac cgcgaggagc tcgcctcccg ggtgtacacg    1500
cagcaggaaa tcgaaagcgg cgtggtgctc agcaccgcgg ttctgctgaa gcatccggag    1560
aagctggagc agaccctggc cgagctgcgg aaatcggcgg acgacgcgaa actacccttg    1620
cggatcatct cctggcagaa ggcctccggc acgatcggcc agttcgtcct ggtcgccaag    1680
ctggtgctct acttcgccgt cttcatcatc ttcgtggtgg cgctcgtcat catcaacaac    1740
gcgatgatga tggccacgct gcagcgggtg cgcgaggtgg caccctgcg ggccatcggc    1800
gcgcagcgct cgttcgtgct gagcatggtg ctggtgaaa cggtggtgct ggggctcgtc    1860
ttcggcgtgc tgggagccgc catgggaggt gccatcatga acatgctcgg ccacgtgggc    1920
atcccgccg caacgaggc gctctacttc ttcttctcgg gaccccgcct cttccccagt    1980
ctccacctgt caaacctcgt ggcggccttc gtcatcgtgc tcgtggtgtc cgccctctcc    2040
accttctacc ccgcgtacct cgcgacccgg gtctcgcctc tccaggcgat gcagacggac    2100
```

<210> SEQ ID NO 31
<211> LENGTH: 762
<212> TYPE: DNA
<213> ORGANISM: Cystobacter velatus
<220> FEATURE:
<221> NAME/KEY: misc_feature
<222> LOCATION: (1)..(762)
<223> OTHER INFORMATION: ORF10

<400> SEQUENCE: 31

```
atgagccagg tcactgccct ccccggcagc acccagccga tcgtctccct caccgaggtt      60
accaagacgt actccctggg taaggtgcag gtgcccgcac tccgaggcgt gacgctagag     120
gtgtacccgg gagagttcat ctccatcgcc ggcccatcgg gcagtggcaa gacgacggcg     180
ctcaatctca tcggctgcgt ggacacggcc tcctcgggcg tggtgagcgt ggatggccag     240
gacaccaaga agctcaccga gcggcagctc acccacttgc ggctgcacac catcggcttc     300
atcttccaga gcttcaacct cgtctcggtg ctcagcgtct tccagaacgt agagttcccc     360
ctgctgctgc agcgcaagct caacgcctcc gagcgccgca cgcgcgtgat gacgctgctg     420
gagcaggtgg gcctggagaa gcacgccaaa caccgcccca atgagctgtc tggaggccag     480
cgccagcgcg tggccgtggc gcgcgctctc gtcaccggc  ccaagctggt gctcgccgac     540
gagcccaccg ccaacctcga ctccgtcacc ggccagaaca tcatcgacct gatgaaggag     600
ctcaaccgca aggagggcac caccttcatc ttctccaccc acgacgccaa ggtgatgacc     660
cacgccaacg ccgtggtgcg cctggcggac gggaagatcc tcgaccgcat cacgccggcc     720
gaggcccaga aggtcatggc cgtgagcgag ggggccact aa                         762
```

<210> SEQ ID NO 32
<211> LENGTH: 1194
<212> TYPE: DNA
<213> ORGANISM: Cystobacter velatus
<220> FEATURE:
<221> NAME/KEY: misc_feature
<222> LOCATION: (1)..(1194)
<223> OTHER INFORMATION: ORF11

<400> SEQUENCE: 32

```
atgccgcaga agttcgtggg gaagtggaag ggcgggcggg tcaagctcgt cgatggtcgg      60
aaggtgtggc tcctcgagaa gatggtctcc ggggcccggt tctcggtctc cttggcggtc     120
tccaacgagg aggacgcgct ggccgagctg gccctgttcc ggcgcgaccg ggacgcctac     180
ctggccaagg tgaaggccga caggtcggag gaagtccagg catccactgt agccggggca     240
gttcctctgt cgggggatgt ggggcctcgg ctcgatgccg attctgtccg ggagttcctc     300
cgacacttga cccagcgggg gcgaacggag ggttaccggc gggacgcccg aacctacctg     360
tcgcaatggg ccgaggttct ggccggaagg gacctgagta ccgtcagcct cctcgagttg     420
cgccgcgccc tgagccaatg gcccacggcc aggaagatgc ggatcatcac gctcaagagc     480
ttcttctcgt ggctgaggga agaggatcgc ctcaaggctg ctgaagaccc cacgttgtcc     540
ctcaaggtgc cgcccgcgt  cgcggagaag gggagacggc caaggggta  ttcgatggcc     600
caagtggaga agctctacgc ggccatcggc tcccagacgg tgagggacgt gctgtgtctg     660
cgggccaaga ccggcatgca cgactcggag atcgcccgcc tggcatcggg caaggggaa      720
ctgcgcgtcg tcaatgaccc ctccggcatc gccggtactg cgcggttt ct gcacaagaac    780
```

```
ggccgcgttc acatcctcag tctggatgcc caggcccttg ctgccgcgca gcggctccag    840
gttcggggca gggcgcccat caggaacacc gtccgggagt ccatcgggta tgcgtcggcg    900
cgcattgggc agtcgcccat ccatcccagc gagctccgcc acagcttcac cacctgggcc    960
acgaatgagg gccaggtcgt gagggcaacc cggggcggag tgccactcga tgtcgttgcc   1020
tcggttcttg gccatcagtc cacacgggcg accaagaagt tctatgacgg gaccgaaatt   1080
cccccgatga tcaccgtccc gctcaagctg catcatccac aggacccagc ggtgatgcag   1140
ctgaggcgta actgctcgcc ggaccccgtc gtgacgagag aggcagaggc gtga         1194
```

<210> SEQ ID NO 33
<211> LENGTH: 375
<212> TYPE: DNA
<213> ORGANISM: Cystobacter velatus
<220> FEATURE:
<221> NAME/KEY: misc_feature
<222> LOCATION: (1)..(375)
<223> OTHER INFORMATION: ORF12

<400> SEQUENCE: 33

```
gtgctcctcg cattccctc cggcctcctg tcgctggcgc tcctgtccac taccaccgaa     60
atctctgcgg ctcttcccgt ggacgagtgc gagtcggcga gctgcgcat cgagctgccc    120 gctacgccag ggggaaagcc acccgtggtg tgtctcggtc caggtctgcc cattcatttc    180
cgcttcgact ccgcgctcca acagaagtcc ctgaggattc aggatcgggg ctggttcgag    240
gattgggctt tgggccagca gacgctcgta ctgactcctc acgacaacct ggtggctggg    300
aagcgatctg aagtggaggt gtgcttcgcg gatggtgccg ccccggcgtg cgcttccttc    360
gtgctccggc gctga                                                     375
```

<210> SEQ ID NO 34
<211> LENGTH: 339
<212> TYPE: DNA
<213> ORGANISM: Cystobacter velatus
<220> FEATURE:
<221> NAME/KEY: misc_feature
<222> LOCATION: (1)..(339)
<223> OTHER INFORMATION: ORF13

<400> SEQUENCE: 34

```
atgcacacga aggtgccctc cgtcttcgag gcaacgcccg agtctctcag tgacgtggac     60
taccagttct ggcatgagga cttcccgagg gtgttcgagc ggcagcacat cgacgcgcac    120
gcggtgcccg ccattggcgc gtacttgggc gaggtgctgg tgcgtaacct gggcggcaag    180 tggataccctc gccagaaact cgacgaggcc caggtgctcg tcggcaaccg tgtgtggttg    240
ccgtttgcgc gggctcacca ctacatgcgc tcgtgcgaat cgttgctgga ctactccctc    300
acccagctct accgcgtggc cgagcggtac cggggttga                           339
```

<210> SEQ ID NO 35
<211> LENGTH: 915
<212> TYPE: DNA
<213> ORGANISM: Cystobacter velatus
<220> FEATURE:
<221> NAME/KEY: misc_feature
<222> LOCATION: (1)..(915)
<223> OTHER INFORMATION: ORF 14

<400> SEQUENCE: 35

```
atgaaggtgc tggggcttgg tgacgtgaag tcggaggaca gtctccggct cacttttgag     60
ggtgcgcttg atccgcaggc tgcgcttgag aaagttctcg agccattttt ccaggcgctg    120
```

```
gaggaatatg caggcgattg gatgccggaa gtcgtcagtg gcaggcggcg actcaaatac    180
tcccgagcca atatctggaa ggctctggag gagcggcgcg atgaacgaag cacagacacc    240
tggctctacc gcacacagcg gccgacactg gagatgtcgc tgcatctctg gtttccgccg    300
cttccgcccg ctttggacgt aatgactacg gtgcaaccgc tcacccgctt cgcggagaag    360
gagcgctgcc gccaattcgt agaaatggta cgcacctggg cctcttgcta cccggtcact    420
cacgccgcag cccacagcgt ggctgacagg gcgttggcag gtgcgcccga ttttggacgc    480
gatgcgcgga ccgcacggag agacgggttc gacagaatct acgagatctt ctggctcaac    540
gtcttcggcc ccaagttggt ggaagccgtg ggccgcgagc gcatgctgtc cacgccagct    600
caccgggtgg aggaactgcc caatggctcc atcctcctgg tgacgtggcc caccgctgcg    660
gacttcgcgg cgccgaggc acggcacgca caggcgcgcg cgcacgttca cctccggccg    720
gacctccgct tcgacacggt gctgcgaacc ctgcacgagc gtagcgccgc gctcgctccc    780
gttgagccct gcttccaccc ggatgtagcg ccactcctct ctcacgtggt ggatagcgtc    840
gccatccgga tgtggaaaac ctggagcgcg ctaacgagca ttacagaact ctggctgagc    900
acctcgtggc gctga                                                    915
```

```
<210> SEQ ID NO 36
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: CysL KO For

<400> SEQUENCE: 36
tgattgattg atcggcgcga ttcggcctct gg                                  32

<210> SEQ ID NO 37
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: CysL KO Rev

<400> SEQUENCE: 37
tcaatcaatc atcgggtcgc ggtctcaggc tc                                  32

<210> SEQ ID NO 38
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(37)
<223> OTHER INFORMATION: CysK KO For

<400> SEQUENCE: 38
tgattgattg aaaaacagtc ggaggagttt cttgtcc                             37

<210> SEQ ID NO 39
```

<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)
<223> OTHER INFORMATION: CysK KO Rev

<400> SEQUENCE: 39
tcaatcaatc aactcccagt gccctcagcc tc                                  32

<210> SEQ ID NO 40
<211> LENGTH: 70
<212> TYPE: PRT
<213> ORGANISM: Cystobacter velatus
<220> FEATURE:
<221> NAME/KEY: MISC_FEATURE
<222> LOCATION: (1)..(70)
<223> OTHER INFORMATION: CysA

<400> SEQUENCE: 40

Met Ser Met Asn Gly Asp Glu Ala Glu Tyr Val Val Leu Ile Asn Gly
1               5                   10                  15

Glu Glu Gln Tyr Ser Leu Trp Pro Val His Arg Glu Ile Pro Gly Gly
            20                  25                  30

Trp Lys Thr Val Gly Pro Lys Gly Ser Lys Glu Thr Cys Gln Ser Tyr
        35                  40                  45

Ile Gln Glu Val Trp Thr Asp Met Arg Pro Lys Ser Leu Arg Glu Ala
    50                  55                  60

Leu Thr Arg Ser Asn Cys
65                  70

<210> SEQ ID NO 41
<211> LENGTH: 317
<212> TYPE: PRT
<213> ORGANISM: Cystobacter velatus
<220> FEATURE:
<221> NAME/KEY: MISC_FEATURE
<222> LOCATION: (1)..(317)
<223> OTHER INFORMATION: CysB

<400> SEQUENCE: 41

Met Ser Thr Pro Ala Ala Gly Ala Lys Pro Ser Tyr Leu Ala Gly Ile
1               5                   10                  15

Glu Thr Val Met Val Glu Pro Glu Leu Glu Glu Val Arg Tyr Leu Thr
            20                  25                  30

Val Glu Ser Gly Asp Gly Arg Gln Ser Thr Leu Tyr Glu Phe Gly Pro
        35                  40                  45

Lys Asp Ala Glu Lys Val Val Leu Pro Pro Tyr Gly Val Thr Phe
    50                  55                  60

Leu Leu Val Ala Arg Leu Ala Arg Leu Leu Ser Gln Arg Phe His Val
65                  70                  75                  80

Leu Ile Trp Glu Ser Arg Gly Cys Pro Asp Ser Ala Ile Pro Val Tyr
            85                  90                  95

Asp Thr Asp Leu Gly Leu Ala Asp Gln Ser Arg His Phe Ser Glu Val
            100                 105                 110

Leu Lys Gln Gln Gly Phe Glu Ala Phe His Phe Val Gly Trp Cys Gln
        115                 120                 125

Ala Ala Gln Leu Ala Val His Ala Thr Ala Ser Gly Gln Val Lys Pro
    130                 135                 140

```
Arg Thr Met Ser Trp Ile Ala Pro Ala Gly Leu Gly Tyr Ser Leu Val
145                 150                 155                 160

Lys Ser Glu Phe Asp Arg Cys Ala Leu Pro Ile Tyr Leu Glu Ile Glu
                165                 170                 175

Lys His Gly Leu Leu His Ala Glu Lys Leu Gly Arg Leu Leu Asn Lys
            180                 185                 190

Tyr Asn Gly Val Pro Ala Thr Ala Gln Asn Ala Ala Glu Lys Leu Thr
            195                 200                 205

Met Arg His Leu Ala Asp Pro Arg Met Thr Tyr Val Phe Ser Arg Tyr
210                 215                 220

Met Lys Ala Tyr Glu Asp Asn Arg Leu Leu Ala Lys Gln Phe Val Ser
225                 230                 235                 240

Thr Ala Leu Asp Ser Val Pro Thr Leu Ala Ile His Cys Arg Asp Asp
                245                 250                 255

Thr Tyr Ser His Phe Ser Glu Ser Val Gln Leu Ser Lys Leu His Pro
            260                 265                 270

Ser Leu Glu Leu Arg Leu Leu Gly Lys Gly His Leu Gln Ile Phe
            275                 280                 285

Asn Asp Pro Ala Thr Leu Ala Glu Tyr Val Leu Gly Phe Ile Asp Thr
290                 295                 300

Arg Ala Ser Gln Ala Ala Ala Pro Ala Val Ala Gly Ala
305                 310                 315
```

<210> SEQ ID NO 42
<211> LENGTH: 459
<212> TYPE: PRT
<213> ORGANISM: Cystobacter velatus
<220> FEATURE:
<221> NAME/KEY: MISC_FEATURE
<222> LOCATION: (1)..(459)
<223> OTHER INFORMATION: CysC

<400> SEQUENCE: 42

```
Met Ile Leu Pro Asn Asn Ile Gly Leu Asp Glu Arg Thr Gln Leu Ala
1               5                   10                  15

Arg Gln Ile Ser Ser Tyr Gln Lys Lys Phe His Val Trp Trp Arg Glu
                20                  25                  30

Arg Gly Pro Thr Glu Phe Leu Asp Arg Gln Met Arg Leu Arg Thr Pro
            35                  40                  45

Thr Gly Ala Val Ser Gly Val Asp Trp Ala Glu Tyr Lys Thr Met Arg
    50                  55                  60

Pro Asp Glu Tyr Arg Trp Gly Leu Phe Met Val Pro Met Asp Gln Asp
65                  70                  75                  80

Glu Ile Ala Phe Gly Asp His Arg Gly Lys Lys Ala Trp Glu Glu Val
                85                  90                  95

Pro Ser Glu Tyr Arg Thr Leu Leu Gln His Ile Cys Val Gln Ala
            100                 105                 110

Asp Val Glu Asn Ala Ala Val Glu Gln Ser Arg Leu Leu Thr Gln Met
            115                 120                 125

Ala Pro Ser Asn Pro Asp Leu Glu Asn Val Phe Gln Phe Phe Leu Glu
130                 135                 140

Glu Gly Arg His Thr Trp Ala Met Val His Leu Leu Ala His Phe
145                 150                 155                 160

Gly Glu Asp Gly Val Val Glu Ala Glu Ala Leu Leu Glu Arg Leu Ser
                165                 170                 175
```

```
Gly Asp Pro Arg Asn Pro Arg Leu Leu Glu Ala Phe Asn Tyr Pro Thr
            180                 185                 190

Glu Asp Trp Leu Ser His Phe Met Trp Cys Leu Leu Ala Asp Arg Val
        195                 200                 205

Gly Lys Tyr Gln Ile His Ala Val Thr Glu Ala Ser Phe Ala Pro Leu
    210                 215                 220

Ala Arg Ala Ala Lys Phe Met Met Phe Glu Glu Pro Leu His Ile Ala
225                 230                 235                 240

Met Gly Ala Val Gly Leu Glu Arg Val Leu Ala Arg Thr Ala Glu Val
                245                 250                 255

Thr Leu Arg Glu Gly Thr Phe Asp Thr Phe His Ala Gly Ala Ile Pro
            260                 265                 270

Phe Pro Val Val Gln Lys Tyr Leu Asn Tyr Trp Ala Pro Lys Val Tyr
        275                 280                 285

Asp Leu Phe Gly Asn Asp Gly Ser Glu Arg Ser Asn Glu Leu Phe Arg
    290                 295                 300

Ala Gly Leu Arg Arg Pro Arg Asn Phe Val Gly Ser Glu Ser Gln Ile
305                 310                 315                 320

Val Arg Ile Asp Glu Arg Met Gly Asp Gly Leu Thr Val Val Glu Val
                325                 330                 335

Glu Gly Glu Trp Ala Ile Asn Ala Ile Met Arg Arg Gln Phe Ile Ala
            340                 345                 350

Glu Val Gln Thr Leu Ile Asp Arg Trp Asn Ala Ser Leu Arg Ala Leu
        355                 360                 365

Gly Val Asp Phe Gln Leu Tyr Leu Pro His Gly Arg Phe Ser Arg Thr
    370                 375                 380

Tyr Gly Pro Cys Ala Gly Leu Pro Phe Asp Val Asp Gly Lys Leu Leu
385                 390                 395                 400

Pro Arg Gly Thr Glu Ala Lys Leu Ala Glu Tyr Phe Pro Thr Pro Arg
                405                 410                 415

Glu Leu Ala Asn Val Arg Ser Leu Met Gln Arg Glu Leu Ala Pro Gly
            420                 425                 430

Gln Tyr Ser Ser Trp Ile Ala Pro Ser Ala Thr Arg Leu Ser Ala Leu
        435                 440                 445

Val Gln Gly Arg Asn Thr Pro Lys Glu His Glu
    450                 455

<210> SEQ ID NO 43
<211> LENGTH: 732
<212> TYPE: PRT
<213> ORGANISM: Cystobacter velatus
<220> FEATURE:
<221> NAME/KEY: MISC_FEATURE
<222> LOCATION: (1)..(732)
<223> OTHER INFORMATION: CysD

<400> SEQUENCE: 43

Met Arg Cys Leu Ile Ile Asp Asn Tyr Asp Ser Phe Thr Trp Asn Leu
1               5                   10                  15

Ala Asp Tyr Val Ala Gln Thr Phe Gly Ser Glu Pro Leu Val Val Arg
            20                  25                  30

Asn Asp Gln His Thr Trp Gln Glu Ile Lys Ala Leu Gly Ser Phe Gly
        35                  40                  45

Cys Ile Leu Val Ser Pro Gly Pro Gly Ser Val Thr Asn Pro Lys Asp
    50                  55                  60

Phe Asn Val Ser Arg Asp Ala Leu Glu Gln Asp Glu Phe Pro Val Phe
```

-continued

```
            65                  70                  75                  80
Gly Val Cys Leu Gly His Gln Gly Leu Ala Tyr Ile Tyr Gly Gly Glu
                85                  90                  95

Ile Thr His Ala Pro Val Pro Phe His Gly Arg Thr Ser Thr Ile Tyr
            100                 105                 110

His Asp Gly Thr Gly Val Phe Gln Gly Leu Pro Pro Ser Phe Asp Ala
            115                 120                 125

Val Arg Tyr His Ser Leu Val Arg Pro Glu Ser Leu Pro Ala Asn
    130                 135                 140

Leu Val Val Thr Ala Arg Thr Glu Cys Gly Leu Ile Met Gly Leu Arg
145                 150                 155                 160

His Val Ser Arg Pro Lys Trp Gly Val Gln Phe His Pro Glu Ser Ile
                165                 170                 175

Leu Thr Ala His Gly Leu Gln Leu Ile Ser Asn Phe Arg Asp Glu Ala
            180                 185                 190

Tyr Arg Tyr Ala Gly Lys Glu Val Pro Ser Arg Arg Pro His Ser Thr
            195                 200                 205

Ala Gly Asn Gly Val Gly Ala Gly Ala Ala Arg Arg Asp Pro Ser Ala
    210                 215                 220

Arg Arg Thr Pro Glu Arg Arg Glu Leu Gln Thr Phe Thr Arg Arg
225                 230                 235                 240

Leu Ala Thr Ser Leu Glu Ala Glu Thr Val Phe Leu Gly Leu Tyr Ala
                245                 250                 255

Gly Arg Glu His Cys Phe Trp Leu Asp Ser Gln Ser Val Arg Glu Gly
            260                 265                 270

Ile Ser Arg Phe Ser Phe Met Gly Cys Val Pro Glu Gly Ser Leu Leu
        275                 280                 285

Thr Tyr Gly Ala Ala Glu Ala Ser Glu Gly Ala Glu Arg Tyr
            290                 295                 300

Leu Ala Ala Leu Glu Arg Ala Leu Glu Ser Arg Ile Val Val Arg Pro
305                 310                 315                 320

Val Asp Gly Leu Pro Phe Glu Phe His Gly Gly Tyr Ile Gly Phe Met
                325                 330                 335

Thr Tyr Glu Met Lys Glu Ala Phe Gly Ala Ala Thr His Lys Asn
            340                 345                 350

Thr Ile Pro Asp Ala Leu Trp Met His Val Lys Arg Phe Leu Ala Phe
        355                 360                 365

Asp His Ser Thr Arg Glu Val Trp Leu Val Ala Ile Ala Glu Leu Glu
    370                 375                 380

Glu Ser Ala Ser Val Leu Ala Trp Met Asp Glu Thr Ala Asp Ala Leu
385                 390                 395                 400

Lys Ser Leu Pro Arg Gly Thr Arg Ser Pro Gln Ser Leu Gly Leu Lys
                405                 410                 415

Ser Ile Ser Val Ser Met Asp Cys Gly Arg Asp Asp Tyr Phe Ala Ala
            420                 425                 430

Ile Glu Arg Cys Lys Glu Lys Ile Val Asp Gly Glu Ser Tyr Glu Val
        435                 440                 445

Cys Leu Thr Asn Gly Phe Ser Phe Asp Leu Lys Leu Asp Pro Val Glu
    450                 455                 460

Leu Tyr Val Thr Met Arg Arg Gly Asn Pro Ala Pro Phe Gly Ala Phe
465                 470                 475                 480

Ile Lys Thr Gly Lys Thr Cys Val Leu Ser Thr Ser Pro Glu Arg Phe
                485                 490                 495
```

```
Leu Lys Val Asp Glu Asp Gly Thr Val Gln Ala Lys Pro Ile Lys Gly
            500                 505                 510

Thr Cys Ala Arg Ser Asp Asp Pro Ala Thr Asp Ser Thr Asn Ala Ala
            515                 520                 525

Arg Leu Ala Ala Ser Glu Lys Asp Arg Ala Glu Asn Leu Met Ile Val
            530                 535                 540

Asp Leu Met Arg Asn Asp Leu Gly Arg Val Ser Val Pro Gly Ser Val
545                 550                 555                 560

His Val Ser Asn Leu Met Asp Ile Glu Ser Phe Lys Thr Val His Gln
            565                 570                 575

Met Val Ser Thr Val Glu Ser Thr Leu Thr Pro Glu Cys Ser Leu Val
            580                 585                 590

Asp Leu Leu Arg Ala Val Phe Pro Gly Gly Ser Ile Thr Gly Ala Pro
            595                 600                 605

Lys Ile Arg Thr Met Glu Ile Ile Asp Arg Leu Glu Lys Ser Pro Arg
            610                 615                 620

Gly Ile Tyr Cys Gly Thr Ile Gly Tyr Leu Gly Tyr Asn Arg Ile Ala
625                 630                 635                 640

Asp Leu Asn Ile Ala Ile Arg Thr Leu Ser Tyr Asp Gly Thr Leu Val
            645                 650                 655

Lys Phe Gly Ala Gly Gly Ala Ile Thr Tyr Leu Ser Gln Pro Glu Gly
            660                 665                 670

Glu Phe Gln Glu Ile Leu Leu Lys Ala Glu Ser Ile Leu Arg Pro Ile
            675                 680                 685

Trp Gln Tyr Ile Asn Gly Ala Gly Ala Pro Phe Glu Pro Gln Leu Arg
            690                 695                 700

Asp Arg Val Leu Cys Leu Glu Glu Lys Pro Arg Arg Val Ile Arg Gly
705                 710                 715                 720

His Gly Ser Ala Ile Asp Ala Val Glu Pro Ser Ala
                    725                 730

<210> SEQ ID NO 44
<211> LENGTH: 243
<212> TYPE: PRT
<213> ORGANISM: Cystobacter velatus
<220> FEATURE:
<221> NAME/KEY: MISC_FEATURE
<222> LOCATION: (1)..(243)
<223> OTHER INFORMATION: CysE

<400> SEQUENCE: 44

Met Ile Ala Phe Asn Pro Gln Ala Arg Pro Arg Leu Arg Leu Phe Cys
1               5                   10                  15

Phe Pro Tyr Ala Gly Gly Asp Ala Asn Ile Phe Arg Asp Trp Ala Ala
            20                  25                  30

Ala Met Pro Glu Gly Val Glu Val Leu Gly Val Gln Tyr Pro Gly Arg
            35                  40                  45

Gly Thr Asn Leu Ala Leu Pro Pro Ile Ser Asp Cys Asp Glu Met Ala
            50                  55                  60

Ser Gln Leu Leu Ala Val Met Thr Pro Leu Leu Gly Ile Asn Phe Ala
65                  70                  75                  80

Phe Phe Gly His Ser Asn Gly Ala Leu Ile Ser Phe Glu Val Ala Arg
            85                  90                  95

Arg Leu His Asp Glu Leu Lys Gly Arg Met Arg His Phe Leu Ser
            100                 105                 110
```

```
Ala Lys Ser Ala Pro His Tyr Pro Asn Asn Arg Ser Lys Ile Ser Gly
            115                 120                 125

Leu Asn Asp Glu Asp Phe Leu Arg Ala Ile Arg Lys Met Gly Gly Thr
    130                 135                 140

Pro Gln Glu Val Leu Asp Asp Ala Arg Leu Met Gln Ile Leu Leu Pro
145                 150                 155                 160

Arg Leu Arg Ala Asp Phe Ala Leu Gly Glu Thr Tyr Val Phe Arg Pro
                165                 170                 175

Gly Pro Thr Leu Thr Cys Asp Val Ser Ile Leu Arg Gly Glu Ser Asp
                180                 185                 190

His Leu Val Asp Gly Glu Phe Val Gln Arg Trp Ser Glu Leu Thr Thr
            195                 200                 205

Gly Gly Ala Ser Gln Tyr Ala Ile Asp Gly Gly His Phe Phe Leu Asn
    210                 215                 220

Ser His Lys Ser Gln Val Val Ala Leu Val Arg Ala Ala Leu Leu Glu
225                 230                 235                 240

Cys Val Leu

<210> SEQ ID NO 45
<211> LENGTH: 345
<212> TYPE: PRT
<213> ORGANISM: Cystobacter velatus
<220> FEATURE:
<221> NAME/KEY: MISC_FEATURE
<222> LOCATION: (1)..(345)
<223> OTHER INFORMATION: CysF

<400> SEQUENCE: 45

Met Thr Ala Gln Asn Gln Ala Ser Ala Phe Ser Phe Asp Leu Phe Tyr
1               5                   10                  15

Thr Thr Val Asn Ala Tyr Tyr Arg Thr Ala Ala Val Lys Ala Ala Ile
            20                  25                  30

Glu Leu Gly Val Phe Asp Val Val Gly Glu Lys Gly Lys Thr Leu Ala
        35                  40                  45

Glu Ile Ala Lys Ala Cys Asn Ala Ser Pro Arg Gly Ile Arg Ile Leu
    50                  55                  60

Cys Arg Phe Leu Val Ser Ile Gly Phe Leu Lys Asn Ala Gly Glu Leu
65                  70                  75                  80

Phe Phe Leu Thr Arg Glu Met Ala Leu Phe Leu Asp Lys Lys Ser Pro
                85                  90                  95

Gly Tyr Leu Gly Gly Ser Ile Asp Phe Leu Leu Ser Pro Tyr Ile Met
                100                 105                 110

Asp Gly Phe Lys Asp Leu Ala Ser Val Val Arg Thr Gly Glu Leu Thr
            115                 120                 125

Leu Pro Glu Lys Gly Val Val Ala Pro Asp His Pro Gln Trp Val Thr
    130                 135                 140

Phe Ala Arg Ala Met Ala Pro Met Met Ser Leu Pro Ser Leu Leu Leu
145                 150                 155                 160

Ala Glu Leu Ala Asp Arg Gln Ala Asn Gln Pro Leu Lys Val Leu Asp
                165                 170                 175

Val Ala Ala Gly His Gly Leu Phe Gly Leu Ala Ile Ala Gln Arg Asn
                180                 185                 190

Pro Lys Ala His Val Thr Phe Leu Asp Trp Glu Asn Val Leu Gln Val
            195                 200                 205

Ala Arg Glu Asn Ala Thr Lys Ala Gly Val Leu Asp Arg Val Glu Phe
    210                 215                 220
```

```
Arg Pro Gly Asp Ala Phe Ser Val Asp Phe Gly Lys Glu Leu Asp Val
225                 230                 235                 240

Ile Leu Leu Thr Asn Phe Leu His His Phe Asp Glu Ala Gly Cys Glu
                245                 250                 255

Lys Ile Leu Lys Lys Ala His Ala Ala Leu Lys Glu Gly Gly Arg Val
            260                 265                 270

Leu Thr Phe Glu Phe Ile Ala Asn Glu Asp Arg Thr Ser Pro Pro Leu
        275                 280                 285

Ala Ala Thr Phe Ser Met Met Met Leu Gly Thr Thr Pro Gly Gly Glu
    290                 295                 300

Thr Tyr Ala Tyr Ser Asp Leu Glu Arg Met Phe Lys Asn Thr Gly Tyr
305                 310                 315                 320

Asp Gln Val Glu Leu Lys Ala Ile Pro Pro Ala Met Glu Lys Val Val
                325                 330                 335

Val Ser Ile Lys Gly Lys Ala Gln Leu
            340                 345

<210> SEQ ID NO 46
<211> LENGTH: 1992
<212> TYPE: PRT
<213> ORGANISM: Cystobacter velatus
<220> FEATURE:
<221> NAME/KEY: MISC_FEATURE
<222> LOCATION: (1)..(1992)
<223> OTHER INFORMATION: CysG

<400> SEQUENCE: 46

Met Ala Thr Lys Leu Ser Asp Phe Ala Leu Leu Asp Ser Glu Asp Ala
1               5                   10                  15

Asn Val Ile Ser Arg Ser Asn Glu Thr Gly Ile Ser Leu Asp Leu Ser
            20                  25                  30

Lys Ser Val Val Asp Leu Phe Asn Leu Gln Val Glu Arg Ala Pro Asp
        35                  40                  45

Ala Thr Ala Cys Leu Gly Arg Gln Gly Arg Leu Thr Tyr Gly Glu Leu
    50                  55                  60

Asn Arg Arg Thr Asn Gln Leu Ala His His Leu Ile Ala Arg Gly Val
65                  70                  75                  80

Gly Pro Asp Val Pro Val Gly Val Leu Phe Glu Arg Ser Ala Glu Gln
                85                  90                  95

Leu Ile Ala Ile Leu Gly Val Leu Lys Ala Gly Gly Cys Tyr Val Pro
            100                 105                 110

Leu Asp Pro Gln Tyr Pro Ala Asp Tyr Met Gln Gln Val Leu Thr Asp
        115                 120                 125

Ala Arg Pro Arg Met Val Val Ser Ser Arg Ala Leu Gly Glu Arg Leu
    130                 135                 140

Arg Ser Gly Glu Glu Gln Ile Val Tyr Leu Asp Asp Glu Gln Leu Leu
145                 150                 155                 160

Ala Arg Glu Thr Arg Asp Pro Pro Val Lys Val Leu Pro Glu Gln Leu
                165                 170                 175

Ala Tyr Val Met Tyr Thr Ser Gly Ser Ser Gly Val Pro Lys Gly Val
            180                 185                 190

Met Val Pro His Arg Gln Ile Leu Asn Trp Leu His Ala Leu Leu Ala
        195                 200                 205

Arg Val Pro Phe Gly Glu Asn Glu Val Val Ala Gln Lys Thr Ser Thr
    210                 215                 220
```

-continued

Ser Phe Ala Ile Ser Val Lys Glu Leu Phe Ala Gly Leu Val Ala Gly
225                 230                 235                 240

Val Pro Gln Val Phe Ile Asp Asp Ala Thr Val Arg Asp Val Ala Ser
                245                 250                 255

Phe Val Arg Glu Leu Glu Gln Trp Arg Val Thr Arg Leu Tyr Thr Phe
            260                 265                 270

Pro Ser Gln Leu Ala Ala Ile Leu Ser Ser Val Asn Gly Ala Tyr Glu
        275                 280                 285

Arg Leu Arg Ser Leu Arg His Leu Tyr Ile Ser Ile Glu Pro Cys Pro
    290                 295                 300

Thr Glu Leu Leu Ala Lys Leu Arg Ala Ala Met Pro Trp Val Thr Pro
305                 310                 315                 320

Trp Tyr Ile Tyr Gly Cys Thr Glu Ile Asn Asp Val Thr Tyr Cys Asp
                325                 330                 335

Pro Gly Asp Gln Ala Gly Asn Thr Gly Phe Val Pro Ile Gly Arg Pro
                340                 345                 350

Ile Arg Asn Thr Arg Val Phe Val Leu Asp Glu Glu Leu Arg Met Val
            355                 360                 365

Pro Val Gly Ala Met Gly Glu Met Tyr Val Glu Ser Leu Ser Thr Ala
    370                 375                 380

Arg Gly Tyr Trp Gly Leu Pro Glu Leu Thr Ala Glu Arg Phe Ile Ala
385                 390                 395                 400

Asn Pro His Ala Glu Asp Gly Ser Arg Leu Tyr Lys Thr Gly Asp Leu
                405                 410                 415

Ala Arg Tyr Leu Pro Asp Gly Ser Leu Glu Phe Leu Gly Arg Arg Asp
                420                 425                 430

Tyr Glu Val Lys Ile Arg Gly Tyr Arg Val Asp Val Arg Gln Val Glu
            435                 440                 445

Lys Val Leu Gly Ala His Pro Asp Ile Leu Glu Val Ala Val Val Gly
    450                 455                 460

Trp Pro Leu Gly Gly Ala Asn Pro Gln Leu Val Ala Tyr Val Val Pro
465                 470                 475                 480

Arg Ala Lys Gly Ala Ala Pro Ile Gln Glu Ile Arg Asp Tyr Leu Ser
                485                 490                 495

Ala Ser Leu Pro Ala Tyr Met Val Pro Thr Ile Phe Gln Val Leu Ala
                500                 505                 510

Ala Leu Pro Arg Leu Pro Asn Asp Lys Val Asp Arg Leu Ser Leu Pro
            515                 520                 525

Asp Pro Lys Val Glu Glu Gln Thr Glu Gly Tyr Val Ala Pro Arg Thr
    530                 535                 540

Glu Thr Glu Lys Val Leu Ala Glu Ile Trp Ser Asp Val Leu Ser Gln
545                 550                 555                 560

Gly Arg Ala Pro Leu Thr Val Gly Ala Thr His Asn Phe Phe Glu Leu
                565                 570                 575

Gly Gly His Ser Leu Leu Ala Ala Gln Met Phe Ser Arg Ile Arg Gln
                580                 585                 590

Lys Phe Asp Leu Glu Leu Pro Ile Asn Thr Leu Phe Glu Thr Pro Val
            595                 600                 605

Leu Glu Gly Phe Ala Ser Val Asp Ala Ala Leu Ala Glu Arg Asn
    610                 615                 620

Gly Pro Ala Gln Arg Leu Ile Ser Met Thr Asp Arg Gly Gln Ala Leu
625                 630                 635                 640

Pro Leu Ser His Val Gln Glu Arg Leu Trp Phe Val His Glu His Met

```
                    645                 650                 655
Val Glu Gln Arg Ser Ser Tyr Asn Val Ala Phe Ala Cys His Met Arg
                660                 665                 670

Gly Lys Gly Leu Ser Met Pro Ala Leu Arg Ala Ala Ile Asn Gly Leu
                675                 680                 685

Val Ala Arg His Glu Thr Leu Arg Thr Thr Phe Val Val Ser Glu Gly
                690                 695                 700

Gly Gly Asp Pro Val Gln Arg Ile Ala Asp Ser Leu Trp Ile Glu Val
705                 710                 715                 720

Pro Leu Tyr Glu Val Asp Ala Ser Glu Val Pro Ala Arg Met Ala Ala
                725                 730                 735

His Ala Gly His Val Phe Asp Leu Ala Lys Gly Pro Leu Leu Lys Thr
                740                 745                 750

Ser Val Leu Arg Val Thr Pro Asp His His Val Phe Leu Met Asn Met
                755                 760                 765

His His Ile Ile Cys Asp Gly Trp Ser Ile Asp Ile Leu Leu Arg Asp
                770                 775                 780

Leu Tyr Glu Phe Tyr Lys Ala Ala Glu Thr Gly Ser Gln Pro Asn Leu
785                 790                 795                 800

Pro Val Leu Pro Ile Gln Tyr Ala Asp Tyr Ser Val Trp Gln Arg Gln
                805                 810                 815

Gln Asp Leu Ser Ser His Leu Asp Tyr Trp Lys Lys Thr Leu Glu Gly
                820                 825                 830

Tyr Gln Glu Gly Leu Ser Leu Pro Tyr Asp Phe Ala Arg Pro Ser Asn
                835                 840                 845

Arg Thr Trp Arg Ala Ala Ser Val Arg His Gln Tyr Pro Ala Glu Leu
                850                 855                 860

Ala Thr Arg Leu Ser Glu Val Ser Lys Ser His Gln Ala Thr Val Phe
865                 870                 875                 880

Met Thr Leu Met Ala Ser Thr Ala Ile Val Leu Asn Arg Tyr Thr Gly
                885                 890                 895

Arg Asp Asp Leu Cys Val Gly Ala Thr Val Ala Gly Arg Asp His Phe
                900                 905                 910

Glu Leu Glu Asn Leu Ile Gly Phe Phe Val Asn Ile Leu Ala Ile Arg
                915                 920                 925

Leu Asp Leu Ser Gly Asn Pro Thr Ala Glu Thr Val Leu Gln Arg Ala
                930                 935                 940

Arg Ala Gln Val Leu Glu Gly Met Lys His Arg Asp Leu Pro Phe Glu
945                 950                 955                 960

His Ile Leu Ala Ala Leu Gln Lys Gln Arg Asp Ser Ser Gln Ile Pro
                965                 970                 975

Leu Val Pro Val Met Val Arg His Gln Asn Phe Pro Thr Val Thr Ser
                980                 985                 990

Gln Glu Gln Gly Leu Asp Leu Gly Ile Gly Glu Ile Glu Phe Gly Glu
                995                 1000                1005

Arg Thr Thr Pro Asn Glu Leu Asp Ile Gln Phe Ile Gly Glu Gly
                1010                1015                1020

Ser Thr Leu Glu Val Val Val Glu Tyr Ala Lys Asp Leu Phe Ser
                1025                1030                1035

Glu Arg Thr Ile Gln Arg Leu Ile Thr His Leu Gln Gln Val Leu
                1040                1045                1050

Gln Thr Leu Val Asp Lys Pro Asp Cys Arg Leu Thr Asp Phe Pro
                1055                1060                1065
```

-continued

Leu Val Ala Gly Asp Ala Leu Gln Gly Val Ser Gly Ser Gly
1070                1075                1080

Gly Ala Thr Lys Thr Gly Lys Leu Asp Val Ser Lys Ser Pro Val
1085                1090                1095

Glu Leu Phe Asn Glu Arg Val Glu Ala Ser Pro Asp Ala Val Ala
1100                1105                1110

Cys Met Gly Ala Asp Gly Ser Leu Thr Tyr Arg Glu Leu Asp Arg
1115                1120                1125

Arg Ala Asn Gln Val Ala Arg His Leu Met Gly Arg Gly Val Gly
1130                1135                1140

Arg Glu Thr Arg Val Gly Leu Trp Phe Glu Arg Ser Pro Asp Leu
1145                1150                1155

Leu Val Ala Leu Leu Gly Ile Leu Lys Ala Gly Gly Cys Phe Val
1160                1165                1170

Pro Leu Asp Pro Ser Tyr Pro Gln Glu Tyr Ile Asn Asn Ile Val
1175                1180                1185

Ala Asp Ala Gln Pro Leu Leu Val Met Ser Ser Arg Ala Leu Gly
1190                1195                1200

Ser Arg Leu Ser Leu Glu Ala Gly Arg Leu Val Tyr Leu Asp Asp
1205                1210                1215

Ala Leu Ala Ala Ser Thr Asp Ala Ser Asp Pro Gln Val Arg Ile
1220                1225                1230

Asp Pro Glu Gln Leu Ile Tyr Val Met Tyr Thr Ser Gly Ser Thr
1235                1240                1245

Gly Leu Pro Lys Gly Val Leu Val Pro His Arg Gln Ile Leu Asn
1250                1255                1260

Trp Leu Tyr Pro Leu Trp Ala Met Val Pro Phe Gly Gln Asp Glu
1265                1270                1275

Val Val Ala Gln Lys Thr Ser Thr Ala Phe Ala Val Ser Met Lys
1280                1285                1290

Glu Leu Phe Thr Gly Leu Leu Ala Gly Val Pro Gln Val Phe Ile
1295                1300                1305

Asp Gly Thr Val Val Lys Asp Ala Ala Ala Phe Val Leu His Leu
1310                1315                1320

Glu Arg Trp Arg Val Thr Arg Leu Tyr Thr Leu Pro Ser His Leu
1325                1330                1335

Asp Ala Ile Leu Ser His Val Asp Gly Ala Ala Glu Arg Leu Arg
1340                1345                1350

Ser Leu Arg His Val Ile Leu Ala Gly Glu Pro Cys Pro Val Glu
1355                1360                1365

Leu Met Glu Lys Leu Arg Glu Thr Leu Pro Ser Cys Thr Ala Trp
1370                1375                1380

Phe Asn Tyr Gly Cys Thr Glu Val Asn Asp Ile Ser Tyr Cys Val
1385                1390                1395

Pro Asn Glu Gln Phe His Ser Ser Gly Phe Val Pro Ile Gly Arg
1400                1405                1410

Pro Ile Gln Tyr Thr Arg Ala Leu Val Leu Asp Asp Glu Leu Arg
1415                1420                1425

Thr Val Pro Val Gly Ile Met Gly Glu Ile Tyr Val Glu Ser Pro
1430                1435                1440

Gly Thr Ala Arg Gly Tyr Trp Arg Gln Pro Asp Leu Thr Ala Glu
1445                1450                1455

```
Arg Phe Ile Pro Asn Pro Phe Gly Glu Pro Gly Ser Arg Leu Tyr
1460             1465                 1470

Arg Thr Gly Asp Met Ala Arg Cys Leu Glu Asp Gly Ser Leu Glu
1475             1480                 1485

Phe Leu Gly Arg Arg Asp Tyr Glu Val Lys Ile Arg Gly His Arg
1490             1495                 1500

Val Asp Val Arg Gln Val Glu Lys Ile Leu Ala Ser His Pro Glu
1505             1510                 1515

Val Leu Glu Ser Ala Val Leu Gly Trp Pro Arg Gly Ala Lys Asn
1520             1525                 1530

Pro Gln Leu Leu Ala Tyr Ala Thr Lys Pro Gly Arg Pro Leu
1535             1540                 1545

Ser Thr Glu Asn Val Arg Glu Tyr Leu Ser Ala Arg Leu Pro Thr
1550             1555                 1560

Tyr Met Val Pro Thr Leu Tyr Gln Phe Leu Pro Ala Leu Pro Arg
1565             1570                 1575

Leu Pro Asn Gly Lys Leu Asp Arg Phe Gly Leu Pro Asp His Lys
1580             1585                 1590

Lys Val Glu Val Gly Gly Val Tyr Val Ala Pro Gln Thr Pro Thr
1595             1600                 1605

Glu Lys Val Leu Ala Gly Leu Trp Ala Glu Cys Leu Lys Gln Gly
1610             1615                 1620

Asp Met Pro Ala Pro Gln Val Gly Arg Leu His Asn Phe Phe Asp
1625             1630                 1635

Leu Gly Gly His Ser Leu Leu Ala Asn Arg Val Leu Met Gln Val
1640             1645                 1650

Gln Arg His Phe Gly Val Ser Leu Gly Ile Ser Ala Leu Phe Gly
1655             1660                 1665

Ser Pro Val Leu Asn Asp Phe Ala Ala Ala Ile Asp Lys Ala Leu
1670             1675                 1680

Gly Thr Glu Glu Pro Gly Glu Gly Ser Ser Asp Ala Arg Glu
1685             1690                 1695

Val Ala Ala Lys Asp Thr Ser Val Leu Val Pro Leu Ser Thr His
1700             1705                 1710

Gly Thr Leu Pro Ser Leu Phe Cys Val His Pro Val Gly Gly Gln
1715             1720                 1725

Val His Ala Tyr Arg Glu Leu Ala Gln Ala Met Glu Lys His Ala
1730             1735                 1740

Ser Met Tyr Ala Leu Gln Ser Glu Gly Ala Arg Glu Phe Asp Thr
1745             1750                 1755

Ile Glu Thr Leu Ala Arg Phe Tyr Ala Asp Ala Ile Arg Gly Ala
1760             1765                 1770

Gln Pro Asp Gly Ser Tyr Arg Leu Leu Gly Trp Ser Ser Gly Gly
1775             1780                 1785

Leu Ile Thr Leu Ala Ile Ala Arg Glu Leu Glu His Gln Gly Cys
1790             1795                 1800

Ala Val Glu Tyr Val Gly Leu Val Asp Ser Lys Pro Ile Pro Arg
1805             1810                 1815

Leu Ala Gly Glu Arg Gly Trp Ala Ser Leu Ile Ala Ala Thr Asn
1820             1825                 1830

Ile Leu Gly Ala Met Arg Gly Arg Gly Phe Ser Val Ala Glu Val
1835             1840                 1845

Asp Ala Ala Gly Lys Ile Leu Glu Ser Arg Gly Trp Thr Glu Glu
```

```
                      1850                1855                1860

Ser Phe Asp Ser Glu Gly His Ala Ala Leu Glu Leu Ala Arg
    1865                1870                1875

His Phe Gly Ile Thr Val Ala Gln Glu Ser Ser Glu Tyr Leu Leu
    1880                1885                1890

Ala Arg Phe Lys Thr Thr Lys Tyr Tyr Leu Ser Leu Phe Ala Gly
    1895                1900                1905

Phe Lys Pro Ala Ala Leu Gly Pro Glu Thr Tyr Leu Tyr Glu Ala
    1910                1915                1920

Ser Glu Arg Val Gly Ala Thr Ser Asn Asp Asp Thr Gly Glu Trp
    1925                1930                1935

Gly Asp Ala Leu Asp Arg Lys Ala Leu Arg Ala Asn Ile Val Gln
    1940                1945                1950

Val Pro Gly Asn His Tyr Thr Val Leu Gln Gly Glu Asn Val Leu
    1955                1960                1965

Gln Leu Ala Gly Arg Ile Ala Glu Ala Leu Ser Ala Ile Asp Asn
    1970                1975                1980

Ser Val Val Thr Arg Thr Arg Ala Ser
    1985                1990

<210> SEQ ID NO 47
<211> LENGTH: 975
<212> TYPE: PRT
<213> ORGANISM: Cystobacter velatus
<220> FEATURE:
<221> NAME/KEY: MISC_FEATURE
<222> LOCATION: (1)..(975)
<223> OTHER INFORMATION: CysH

<400> SEQUENCE: 47

Met Asp Asn Arg Glu Ile Ala Pro Thr Gln Ser Ala Arg Thr Arg Asp
1               5                   10                  15

Ala Tyr Thr Ala Val Pro Pro Ala Lys Ala Glu Tyr Pro Ser Asp Val
                20                  25                  30

Cys Val His Gln Leu Phe Glu Leu Gln Ala Asp Arg Ile Pro Asp Ala
            35                  40                  45

Val Ala Ala Arg Ala Gly Asn Glu Ser Leu Thr Tyr Arg Glu Leu Asn
        50                  55                  60

Phe Arg Ala Asn Gln Leu Ala Arg Tyr Leu Val Ala Lys Gly Val Val
65                  70                  75                  80

Pro Arg Gly Ser Val Ala Val Leu Met Asn Arg Thr Pro Ala Cys Leu
                85                  90                  95

Val Ser Leu Leu Ala Ile Ile Lys Ala Gly Ala Ala Tyr Val Pro Val
            100                 105                 110

Asp Ala Gly Leu Pro Ala Lys Arg Val Asp Tyr Ile Leu Thr Asp Ser
        115                 120                 125

Gly Ala Thr Cys Val Leu Thr Asp Arg Glu Thr Arg Ser Leu Leu Asp
    130                 135                 140

Glu Pro Arg Ser Ala Ser Thr Leu Val Ile Asp Val Asp Asp Pro Ser
145                 150                 155                 160

Ile Tyr Ser Gly Glu Thr Ser Asn Leu Gly Leu Ala Val Asp Pro Glu
                165                 170                 175

Gln Gln Val Tyr Cys Ile Tyr Thr Ser Gly Thr Gly Leu Pro Lys
            180                 185                 190

Gly Val Met Val Gln His Arg Ala Leu Met Asn Tyr Val Trp Trp Ala
        195                 200                 205
```

```
Lys Lys Gln Tyr Val Thr Asp Ala Val Glu Ser Phe Ala Leu Tyr Ser
    210                 215                 220

Ser Leu Ser Phe Asp Leu Thr Val Thr Ser Ile Phe Val Pro Leu Ile
225                 230                 235                 240

Ser Gly Arg Cys Ile Asp Val Tyr Pro Asp Leu Gly Glu Asp Val Pro
                245                 250                 255

Val Ile Asn Arg Val Leu Glu Asp Asn Lys Val Asp Val Val Lys Leu
            260                 265                 270

Thr Pro Ala His Leu Ala Leu Leu Arg Asn Thr Asp Leu Ser Gln Ser
        275                 280                 285

Arg Leu Lys Val Leu Ile Leu Gly Gly Glu Asp Leu Arg Ala Glu Thr
290                 295                 300

Ala Gly Asp Val His Lys Arg Leu Asp Gly Arg Ala Val Ile Tyr Asn
305                 310                 315                 320

Glu Tyr Gly Pro Thr Glu Thr Val Val Gly Cys Met Ile His Arg Tyr
                325                 330                 335

Asp Pro Ala Val Asp Leu His Gly Ser Val Pro Ile Gly Val Gly Ile
            340                 345                 350

Asp Asn Met Arg Ile Tyr Leu Leu Asp Asp Arg Arg Pro Val Lys
        355                 360                 365

Pro Gly Glu Val Gly Glu Ile Tyr Ile Gly Gly Asp Gly Val Thr Leu
370                 375                 380

Gly Tyr Lys Asp Lys Pro Gln Val Thr Ala Asp His Phe Ile Ser Asn
385                 390                 395                 400

Pro Phe Val Glu Gly Glu Arg Leu Tyr Ala Ser Gly Asp Leu Gly Arg
                405                 410                 415

Val Asn Glu Arg Gly Ala Leu Val Phe Leu Gly Arg Lys Asp Leu Gln
            420                 425                 430

Ile Lys Leu Arg Gly Tyr Arg Ile Glu Leu Gly Glu Ile Glu Ser Ala
        435                 440                 445

Leu Leu Ser Tyr Pro Gly Ile Lys Glu Cys Ile Val Asp Ser Thr Lys
450                 455                 460

Thr Ala Gln Ser Gln Ala Ala Ala Gln Leu Thr Tyr Cys Thr Lys Cys
465                 470                 475                 480

Gly Leu Ala Ser Ser Phe Pro Asn Thr Thr Tyr Ser Ala Glu Gly Val
                485                 490                 495

Cys Asn His Cys Glu Ala Phe Asp Lys Tyr Arg Ser Val Val Asp Asp
            500                 505                 510

Tyr Phe Ser Thr Met Asp Glu Leu Gln Ser Ile Val Thr Glu Met Lys
        515                 520                 525

Ser Ile His Asn Ser Lys Tyr Asp Cys Ile Val Ala Leu Ser Gly Gly
530                 535                 540

Lys Asp Ser Thr Tyr Ala Leu Cys Arg Met Ile Glu Thr Gly Ala Arg
545                 550                 555                 560

Val Leu Ala Phe Thr Leu Asp Asn Gly Tyr Ile Ser Glu Glu Ala Lys
                565                 570                 575

Gln Asn Ile Asn Arg Val Val Ala Arg Leu Gly Val Asp His Arg Tyr
            580                 585                 590

Leu Ser Thr Gly His Met Lys Glu Ile Phe Val Asp Ser Leu Lys Arg
        595                 600                 605

His Ser Asn Val Cys Asn Gly Cys Phe Lys Thr Ile Tyr Thr Phe Ala
610                 615                 620
```

```
Ile Asn Leu Ala Gln Glu Val Gly Val Lys His Val Val Met Gly Leu
625                 630                 635                 640

Ser Lys Gly Gln Leu Phe Glu Thr Arg Leu Ser Ala Leu Phe Arg Thr
            645                 650                 655

Ser Thr Phe Asp Asn Ala Ala Phe Glu Lys Ser Leu Val Asp Ala Arg
        660                 665                 670

Lys Ile Tyr His Arg Ile Asp Asp Ala Val Ser Arg Leu Leu Asp Thr
            675                 680                 685

Thr Cys Val Lys Asn Asp Lys Val Ile Glu Asn Ile Arg Phe Val Asp
        690                 695                 700

Phe Tyr Arg Tyr Cys His Ala Ser Arg Gln Glu Met Tyr Asp Tyr Ile
705                 710                 715                 720

Gln Glu Arg Val Gly Trp Ala Arg Pro Ile Asp Thr Gly Arg Ser Thr
            725                 730                 735

Asn Cys Leu Leu Asn Asp Val Gly Ile Tyr Val His Asn Lys Glu Arg
        740                 745                 750

Arg Tyr His Asn Tyr Ser Leu Pro Tyr Ser Trp Asp Val Arg Met Gly
            755                 760                 765

His Ile Ser Arg Glu Glu Ala Met Arg Glu Leu Asp Asp Ser Ala Asp
        770                 775                 780

Ile Asp Val Glu Arg Val Glu Gly Ile Ile Lys Asp Leu Gly Tyr Glu
785                 790                 795                 800

Leu Asn Asp Gln Val Val Gly Ser Ala Glu Ala Gln Leu Val Ala Tyr
            805                 810                 815

Tyr Val Ser Ala Glu Glu Phe Pro Ala Ser Asp Leu Arg Gln Phe Leu
        820                 825                 830

Ser Glu Ile Leu Pro Glu Tyr Met Val Pro Arg Ser Phe Val Gln Leu
            835                 840                 845

Asp Ser Ile Pro Leu Thr Pro Asn Gly Lys Val Asn Arg Gln Ala Leu
        850                 855                 860

Pro Lys Pro Asp Leu Leu Arg Lys Ala Gly Thr Asp Gly Gln Ala Ala
865                 870                 875                 880

Pro Arg Thr Pro Val Glu Lys Gln Leu Ala Glu Leu Trp Lys Glu Val
            885                 890                 895

Leu Gln Val Asp Ser Val Gly Ile His Asp Asn Phe Phe Glu Met Gly
        900                 905                 910

Gly His Ser Leu Pro Ala Leu Met Leu Tyr Lys Ile Asp Ser Gln
            915                 920                 925

Phe His Lys Thr Ile Ser Ile Gln Glu Phe Ser Lys Val Pro Thr Ile
930                 935                 940

Ser Ala Leu Ala Ala His Leu Gly Ser Asp Thr Glu Ala Val Pro Pro
945                 950                 955                 960

Gly Leu Gly Glu Val Val Asp Gln Ser Ala Pro Ala Tyr Arg Gly
            965                 970                 975

<210> SEQ ID NO 48
<211> LENGTH: 272
<212> TYPE: PRT
<213> ORGANISM: Cystobacter velatus
<220> FEATURE:
<221> NAME/KEY: MISC_FEATURE
<222> LOCATION: (1)..(272)
<223> OTHER INFORMATION: CysI

<400> SEQUENCE: 48

Val Arg Phe Val Thr Val Asn Gly Glu Asp Ser Ala Val Cys Ser Val
```

```
                1               5                      10                     15
            Leu Asp Arg Gly Leu Gln Phe Gly Asp Gly Leu Phe Glu Thr Met Leu
                           20                     25                     30

Cys Val Gly Gly Ala Pro Val Asp Phe Pro Glu His Trp Ala Arg Leu
                           35                     40                     45

Asp Glu Gly Cys Arg Arg Leu Gly Ile Glu Cys Pro Asp Ile Arg Arg
                50                         55                     60

Glu Val Thr Ala Ala Ile Ala Arg Trp Gly Ala Pro Arg Ala Val Ala
            65                         70                     75                     80

Lys Leu Val Val Thr Arg Gly Ser Thr Glu Arg Gly Tyr Arg Cys Ala
                               85                     90                     95

Pro Ser Val Arg Pro Asn Trp Ile Leu Thr Ile Thr Asp Ala Pro Lys
                           100                    105                    110

Tyr Pro Leu Ala His Glu Asp Arg Gly Val Ala Val Lys Leu Cys Arg
                           115                    120                    125

Thr Leu Val Ser Leu Asp Asp Pro Gln Leu Ala Gly Leu Lys His Leu
                    130                        135                    140

Asn Arg Leu Pro Gln Val Leu Ala Arg Arg Glu Trp Asp Asp Glu Tyr
            145                        150                    155                    160

His Asp Gly Leu Leu Thr Asp His Gly His Leu Val Glu Gly Cys
                               165                    170                    175

Thr Ser Asn Leu Phe Leu Val Ala Asp Gly Ala Leu Arg Thr Pro Asp
                           180                    185                    190

Leu Thr Ala Cys Gly Val Arg Gly Ile Val Arg Gln Lys Val Leu Asp
                           195                    200                    205

His Ser Lys Ala Ile Gly Ile Arg Cys Glu Val Thr Thr Leu Lys Leu
                    210                        215                    220

Arg Asp Leu Glu His Ala Asp Glu Val Phe Leu Thr Asn Ser Val Tyr
            225                        230                    235                    240

Gly Ile Val Pro Val Gly Ser Val Asp Gly Met Arg Tyr Arg Ile Gly
                           245                    250                    255

Pro Thr Thr Ala Arg Leu Leu Lys Asp Leu Cys Gln Gly Val Tyr Phe
                           260                    265                    270

<210> SEQ ID NO 49
<211> LENGTH: 327
<212> TYPE: PRT
<213> ORGANISM: Cystobacter velatus
<220> FEATURE:
<221> NAME/KEY: MISC_FEATURE
<222> LOCATION: (1)..(327)
<223> OTHER INFORMATION: CysJ

<400> SEQUENCE: 49

Met Thr Gly Asn Leu Asp Ser Ala Ala Trp Pro Val Ile Ile Thr Pro
            1               5                      10                     15

Gly Gln Gln Pro Ala Ala Leu Glu Asp Trp Val Ser Ala Asn Arg Asp
                           20                     25                     30

Gly Leu Glu Arg Gln Leu Thr Glu Cys Lys Ala Ile Leu Phe Arg Gly
                           35                     40                     45

Phe Arg Ser Arg Asn Gly Phe Glu Ser Ile Ala Asn Ser Phe Asp
                50                         55                     60

Arg Arg Leu Asn Tyr Thr Tyr Arg Ser Thr Pro Arg Thr Asp Leu Gly
            65                         70                     75                     80

Gln Asn Leu Tyr Thr Ala Thr Glu Tyr Pro Lys Gln Leu Ser Ile Pro
                               85                     90                     95
```

-continued

```
Gln His Cys Glu Asn Ala Tyr Gln Arg Asp Trp Pro Met Lys Leu Leu
                100                 105                 110

Phe His Cys Val Glu Pro Ala Ser Lys Gly Gly Arg Thr Pro Leu Ala
            115                 120                 125

Asp Met Thr Lys Val Thr Ala Met Ile Pro Ala Glu Ile Lys Glu Glu
        130                 135                 140

Phe Ala Arg Lys Lys Val Gly Tyr Val Arg Asn Tyr Arg Ala Gly Val
145                 150                 155                 160

Asp Leu Pro Trp Glu Glu Val Phe Gly Thr Ser Asn Lys Ala Glu Val
                165                 170                 175

Glu Lys Phe Cys Val Glu Asn Gly Ile Glu Tyr His Trp Thr Glu Gly
            180                 185                 190

Gly Leu Lys Thr Ile Gln Val Cys Gln Ala Phe Ala Ser His Pro Leu
        195                 200                 205

Thr Gly Glu Thr Ile Trp Phe Asn Gln Ala His Leu Phe His Leu Ser
    210                 215                 220

Ala Leu Asp Pro Ala Ser Gln Lys Met Met Leu Ser Phe Phe Gly Glu
225                 230                 235                 240

Gly Gly Leu Pro Arg Asn Ser Tyr Phe Gly Asp Gly Ser Ala Ile Gly
                245                 250                 255

Ser Asp Val Leu Asp Gln Ile Arg Ser Ala Tyr Glu Arg Asn Lys Val
            260                 265                 270

Ser Phe Glu Trp Gln Lys Asp Asp Val Leu Leu Ile Asp Asn Met Leu
        275                 280                 285

Val Ser His Gly Arg Asp Pro Phe Glu Gly Ser Arg Arg Val Leu Val
    290                 295                 300

Cys Met Ala Glu Pro Tyr Ser Glu Val Gln Arg Arg Gly Phe Ala Gly
305                 310                 315                 320

Ala Thr Asn Ser Gly Arg Ser
                325

<210> SEQ ID NO 50
<211> LENGTH: 4545
<212> TYPE: PRT
<213> ORGANISM: Cystobacter velatus
<220> FEATURE:
<221> NAME/KEY: MISC_FEATURE
<222> LOCATION: (1)..(4140)
<223> OTHER INFORMATION: CysK
<220> FEATURE:
<221> NAME/KEY: MISC_FEATURE
<222> LOCATION: (1)..(4545)
<223> OTHER INFORMATION: CysK

<400> SEQUENCE: 50

Met Leu Leu Glu Gly Glu Leu Glu Gly Tyr Glu Asp Gly Leu Glu Leu
1               5                   10                  15

Pro Tyr Asp Phe Pro Arg Thr Ser Asn Arg Ala Trp Arg Ala Ala Thr
            20                  25                  30

Phe Gln His Ser Tyr Pro Pro Glu Leu Ala Arg Lys Val Ala Glu Leu
        35                  40                  45

Ser Arg Glu Gln Gln Ser Thr Leu Phe Met Ser Leu Val Ala Ser Leu
    50                  55                  60

Ala Val Val Leu Asn Arg Tyr Thr Gly Arg Glu Asp Val Cys Ile Gly
65                  70                  75                  80

Thr Thr Val Ala Gly Arg Ala Gln Val Gly Ala Leu Gly Asp Leu Ser
                85                  90                  95
```

```
Gly Ser Thr Val Asp Ile Leu Pro Leu Arg Leu Asp Leu Ser Gly Ala
            100                 105                 110

Pro Ser Leu His Glu Val Leu Arg Arg Thr Lys Ala Val Val Leu Glu
            115                 120                 125

Gly Phe Glu His Glu Ala Leu Pro Cys Gln Ile Pro Leu Val Pro Val
            130                 135                 140

Val Val Arg His Gln Asn Phe Pro Met Ala Arg Leu Glu Gly Trp Ser
145                 150                 155                 160

Glu Gly Val Glu Leu Lys Lys Phe Glu Leu Ala Gly Glu Arg Thr Thr
                165                 170                 175

Ala Ser Glu Gln Asp Trp Gln Phe Phe Gly Asp Gly Ser Ser Leu Glu
            180                 185                 190

Leu Ser Leu Glu Tyr Ala Ala Glu Leu Phe Ser Glu Lys Thr Val Lys
            195                 200                 205

Arg Met Val Glu His His Gln Arg Val Leu Glu Ala Leu Val Glu Gly
            210                 215                 220

Leu Glu Glu Val Arg Leu His Glu Val Arg Leu Leu Thr Glu Glu Glu
225                 230                 235                 240

Glu Gly Leu His Gly Arg Leu Asn Asp Thr Ala Arg Glu Leu Glu Glu
                245                 250                 255

Arg Trp Ser Leu Ala Glu Thr Phe Glu Arg Gln Val Arg Glu Thr Pro
            260                 265                 270

Glu Ala Val Ala Cys Val Gly Val Glu Val Ala Thr Gly Gly His Ser
            275                 280                 285

Arg Pro Thr Tyr Arg Gln Leu Thr Tyr Arg Gln Leu Asn Ala Arg Ala
            290                 295                 300

Asn Gln Val Ala Arg Arg Leu Arg Ala Leu Gly Val Gly Ala Glu Thr
305                 310                 315                 320

Arg Val Ala Val Leu Ser Asp Arg Ser Pro Glu Leu Leu Val Ala Met
                325                 330                 335

Leu Ala Ile Phe Lys Ala Gly Gly Cys Tyr Val Pro Val Asp Pro Gln
            340                 345                 350

Tyr Pro Gly Ser Tyr Ile Glu Gln Ile Leu Glu Asp Ala Ala Pro Gln
            355                 360                 365

Val Val Leu Gly Lys Arg Gly Arg Ala Asp Gly Val Arg Val Asp Val
            370                 375                 380

Trp Leu Glu Leu Asp Gly Ala Gln Arg Leu Thr Asp Glu Ala Leu Ala
385                 390                 395                 400

Ala Gln Glu Glu Gly Glu Leu Glu Gly Ala Glu Arg Pro Glu Ser Gln
                405                 410                 415

Gln Leu Ala Cys Leu Met Tyr Thr Ser Gly Ser Thr Gly Arg Pro Lys
            420                 425                 430

Gly Val Met Val Pro Tyr Ser Gln Leu His Asn Trp Leu Glu Ala Gly
            435                 440                 445

Lys Glu Arg Ser Pro Leu Glu Arg Gly Glu Val Met Leu Gln Lys Thr
            450                 455                 460

Ala Ile Ala Phe Ala Val Ser Val Lys Glu Leu Leu Ser Gly Leu Leu
465                 470                 475                 480

Ala Gly Val Ala Gln Val Met Val Pro Glu Thr Leu Val Lys Asp Ser
                485                 490                 495

Val Ala Leu Ala Gln Glu Ile Glu Arg Trp Arg Val Thr Arg Ile His
            500                 505                 510
```

```
Leu Val Pro Ser His Leu Gly Ala Leu Leu Glu Gly Ala Gly Glu Glu
            515                 520                 525

Ala Lys Gly Leu Arg Ser Leu Lys Tyr Val Ile Thr Ala Gly Glu Ala
530                 535                 540

Leu Ala Gln Gly Val Arg Glu Glu Ala Arg Arg Lys Leu Pro Gly Ala
545                 550                 555                 560

Gln Leu Trp Asn Asn Tyr Gly Cys Thr Glu Leu Asn Asp Val Thr Tyr
                565                 570                 575

His Pro Ala Ser Glu Gly Gly Asp Thr Val Phe Val Pro Ile Gly
            580                 585                 590

Arg Pro Ile Ala Asn Thr Arg Val Tyr Val Leu Asp Glu Gln Leu Arg
            595                 600                 605

Arg Val Pro Val Gly Val Met Gly Glu Leu Tyr Val Asp Ser Val Gly
            610                 615                 620

Met Ala Arg Gly Tyr Trp Gly Gln Pro Ala Leu Thr Ala Glu Arg Phe
625                 630                 635                 640

Ile Ala Asn Pro Tyr Ala Ser Gln Pro Gly Ala Arg Leu Tyr Arg Thr
                645                 650                 655

Gly Asp Met Val Arg Val Leu Ala Asp Gly Ser Leu Glu Tyr Leu Gly
            660                 665                 670

Arg Arg Asp Tyr Glu Ile Lys Val Arg Gly His Arg Val Asp Val Arg
675                 680                 685

Gln Val Glu Lys Val Ala Asn Ala His Pro Ala Ile Arg Gln Ala Val
            690                 695                 700

Val Ser Gly Trp Pro Leu Gly Ser Ser Asn Ala Gln Leu Val Ala Tyr
705                 710                 715                 720

Leu Val Pro Gln Ala Gly Ala Thr Val Gly Pro Arg Gln Val Arg Asp
                725                 730                 735

Tyr Leu Ala Glu Ser Leu Pro Ala Tyr Met Val Pro Thr Leu Tyr Thr
            740                 745                 750

Val Leu Glu Glu Leu Pro Arg Leu Pro Asn Gly Lys Leu Asp Arg Leu
            755                 760                 765

Ser Leu Pro Glu Pro Asp Leu Ser Ser Arg Glu Glu Tyr Val Ala
770                 775                 780

Pro His Gly Glu Val Glu Arg Lys Leu Ala Glu Ile Phe Gly Asn Leu
785                 790                 795                 800

Leu Gly Leu Glu His Val Gly Val His Asp Asn Phe Phe Ser Leu Gly
                805                 810                 815

Gly His Ser Leu Leu Ala Ala Gln Leu Ile Ser Arg Ile Arg Ala Thr
            820                 825                 830

Phe Arg Val Glu Val Ala Met Ala Thr Val Phe Glu Ser Pro Thr Val
            835                 840                 845

Glu Pro Leu Ala Arg His Ile Glu Glu Lys Leu Lys Asp Glu Ser Arg
850                 855                 860

Val Gln Leu Ser Asn Val Val Pro Val Glu Arg Thr Gln Glu Ile Pro
865                 870                 875                 880

Leu Ser Tyr Leu Gln Glu Arg Leu Trp Phe Val His Glu His Met Lys
                885                 890                 895

Glu Gln Arg Thr Ser Tyr Asn Ile Thr Trp Thr Leu His Phe Ala Gly
            900                 905                 910

Lys Gly Phe Ser Val Glu Ala Leu Arg Thr Ala Phe Asp Glu Leu Val
            915                 920                 925

Ala Arg His Glu Thr Leu Arg Thr Trp Phe Gln Val Gly Glu Gly Thr
```

-continued

```
            930                935             940
Glu Gln Ala Val Gln Val Ile Gly Glu Pro Trp Ser Met Glu Leu Pro
945                 950             955                 960
Leu Arg Glu Val Ala Gly Thr Glu Val Thr Ala Ala Ile Asn Glu Met
                965             970             975
Ser Arg Gln Val Phe Asp Leu Arg Ala Gly Arg Leu Leu Thr Ala Ala
            980             985             990
Val Leu Arg Val Ala Glu Asp Glu His Ile Leu Val Ser Asn Ile His
        995             1000            1005
His Ile Ile Thr Asp Gly Trp Ser Phe Gly Val Met Leu Arg Glu
    1010            1015            1020
Leu Arg Glu Leu Tyr Glu Ala Ala Val Arg Gly Lys Arg Ala Glu
    1025            1030            1035
Leu Pro Pro Leu Thr Val Gln Tyr Gly Asp Tyr Ala Val Trp Gln
    1040            1045            1050
Arg Lys Gln Asp Leu Ser Glu His Leu Ala Tyr Trp Lys Gly Lys
    1055            1060            1065
Val Glu Glu Tyr Glu Asp Gly Leu Glu Leu Pro Tyr Asp Phe Pro
    1070            1075            1080
Arg Thr Ser Asn Arg Ala Trp Arg Ala Ala Thr Phe Gln Tyr Ser
    1085            1090            1095
Tyr Pro Pro Glu Leu Ala Arg Lys Val Ala Glu Leu Ser Arg Glu
    1100            1105            1110
Gln Gln Ser Thr Leu Phe Met Ser Leu Val Ala Ser Leu Ala Val
    1115            1120            1125
Val Leu Asn Arg Tyr Thr Gly Arg Gln Asp Val Cys Ile Gly Thr
    1130            1135            1140
Thr Val Ala Gly Arg Ala Gln Val Glu Leu Glu Ser Leu Ile Gly
    1145            1150            1155
Phe Phe Ile Asn Ile Leu Pro Leu Arg Leu Asp Leu Ser Gly Ala
    1160            1165            1170
Pro Ser Leu His Glu Val Leu Arg Arg Thr Lys Ala Val Val Leu
    1175            1180            1185
Glu Gly Phe Glu His Gln Glu Leu Pro Phe Glu His Leu Leu Lys
    1190            1195            1200
Ala Leu Arg Arg Gln Arg Asp Ser Ser Gln Ile Pro Leu Val Pro
    1205            1210            1215
Val Val Val Arg His Gln Asn Phe Pro Met Ala Arg Leu Glu Gly
    1220            1225            1230
Trp Ser Glu Gly Val Glu Leu Lys Lys Phe Glu Leu Ala Gly Glu
    1235            1240            1245
Arg Thr Thr Ala Ser Glu Gln Asp Trp Gln Phe Phe Gly Asp Gly
    1250            1255            1260
Ser Ser Leu Glu Leu Ser Leu Glu Tyr Ala Ala Glu Leu Phe Ser
    1265            1270            1275
Glu Lys Thr Val Arg Arg Met Val Glu His Gln Arg Val Leu
    1280            1285            1290
Glu Ala Leu Val Glu Gly Leu Glu Glu Gly Leu His Glu Val Arg
    1295            1300            1305
Leu Leu Thr Glu Glu Glu Gly Leu His Gly Arg Leu Asn Asp
    1310            1315            1320
Thr Ala Arg Glu Leu Glu Glu Arg Trp Ser Leu Ala Glu Thr Phe
    1325            1330            1335
```

-continued

```
Glu Arg Gln Val Arg Glu Thr Pro Glu Ala Val Ala Cys Val Gly
    1340            1345            1350

Val Glu Val Ala Thr Gly Gly His Ser Arg Pro Thr Tyr Arg Gln
    1355            1360            1365

Leu Thr Tyr Arg Gln Leu Asn Ala Arg Ala Asn Gln Val Ala Arg
    1370            1375            1380

Arg Leu Arg Ala Leu Gly Val Gly Ala Glu Thr Arg Val Ala Val
    1385            1390            1395

Leu Ser Asp Arg Ser Pro Glu Leu Leu Val Ala Met Leu Ala Ile
    1400            1405            1410

Phe Lys Ala Gly Gly Cys Tyr Val Pro Val Asp Pro Gln Tyr Pro
    1415            1420            1425

Gly His Tyr Ile Glu Gln Ile Leu Glu Asp Ala Ala Pro Gln Val
    1430            1435            1440

Val Leu Gly Lys Arg Gly Arg Ala Asp Gly Val Arg Val Asp Val
    1445            1450            1455

Trp Leu Glu Leu Asp Gly Ala Gln Arg Leu Thr Asp Glu Ala Leu
    1460            1465            1470

Ala Ala Gln Glu Glu Gly Glu Leu Glu Gly Ala Glu Arg Pro Glu
    1475            1480            1485

Ser Gln Gln Leu Ala Cys Leu Met Tyr Thr Ser Gly Ser Thr Gly
    1490            1495            1500

Arg Pro Lys Gly Val Met Val Pro Tyr Ser Gln Leu His Asn Trp
    1505            1510            1515

Leu Glu Ala Gly Lys Glu Arg Ser Pro Leu Glu Arg Gly Glu Val
    1520            1525            1530

Met Leu Gln Lys Thr Ala Ile Ala Phe Ala Val Ser Val Lys Glu
    1535            1540            1545

Leu Leu Ser Gly Leu Leu Ala Gly Val Ala Gln Val Met Val Pro
    1550            1555            1560

Glu Thr Leu Val Lys Asp Ser Val Ala Leu Ala Gln Glu Ile Glu
    1565            1570            1575

Arg Trp Arg Val Thr Arg Ile His Leu Val Pro Ser His Leu Gly
    1580            1585            1590

Ala Leu Leu Glu Gly Ala Gly Glu Glu Ala Lys Gly Leu Arg Ser
    1595            1600            1605

Leu Lys Tyr Val Ile Thr Ala Gly Glu Ala Leu Ala Gln Gly Val
    1610            1615            1620

Arg Glu Glu Ala Arg Arg Lys Leu Pro Gly Ala Gln Leu Trp Asn
    1625            1630            1635

Asn Tyr Gly Cys Thr Glu Leu Asn Asp Val Thr Tyr His Pro Ala
    1640            1645            1650

Ser Glu Gly Gly Gly Asp Thr Val Phe Val Pro Ile Gly Arg Pro
    1655            1660            1665

Ile Ala Asn Thr Arg Val Tyr Val Leu Asp Glu Gln Leu Arg Arg
    1670            1675            1680

Val Pro Val Gly Val Met Gly Glu Leu Tyr Val Asp Ser Val Gly
    1685            1690            1695

Met Ala Arg Gly Tyr Trp Gly Gln Pro Ala Leu Thr Ala Glu Arg
    1700            1705            1710

Phe Ile Ala Asn Pro Tyr Ala Ser Gln Pro Gly Ala Arg Leu Tyr
    1715            1720            1725
```

| | | | | | | | | | | | |
|---|---|---|---|---|---|---|---|---|---|---|---|
|Arg|Thr|Gly|Asp|Met|Val|Arg|Val|Leu|Ala|Asp|Gly|Ser|Leu|Glu|
| |1730| | | |1735| | | |1740| | | | | |

Arg Thr Gly Asp Met Val Arg Val Leu Ala Asp Gly Ser Leu Glu
    1730            1735            1740

Tyr Leu Gly Arg Arg Asp Tyr Glu Ile Lys Val Arg Gly His Arg
    1745            1750            1755

Val Asp Val Arg Gln Val Glu Lys Val Ala Asn Ala His Pro Ala
    1760            1765            1770

Ile Arg Gln Ala Val Val Ser Gly Trp Pro Leu Gly Ser Ser Asn
    1775            1780            1785

Ala Gln Leu Val Ala Tyr Leu Val Pro Gln Ala Gly Ala Thr Val
    1790            1795            1800

Gly Pro Arg Gln Val Arg Asp Tyr Leu Ala Glu Ser Leu Pro Ala
    1805            1810            1815

Tyr Met Val Pro Thr Leu Tyr Thr Val Leu Glu Glu Leu Pro Arg
    1820            1825            1830

Leu Pro Asn Gly Lys Leu Asp Arg Leu Ser Leu Pro Glu Pro Asp
    1835            1840            1845

Leu Ser Ser Arg Glu Glu Tyr Val Ala Pro His Gly Glu Val
    1850            1855            1860

Glu Arg Lys Leu Ala Glu Ile Phe Gly Asn Leu Leu Gly Leu Glu
    1865            1870            1875

His Val Gly Val His Asp Asn Phe Phe Ser Leu Gly Gly His Ser
    1880            1885            1890

Leu Leu Ala Ala Gln Val Val Ser Arg Ile Gly Lys Glu Leu Gly
    1895            1900            1905

Thr Gln Ile Ser Ile Ala Asp Leu Phe Gln Arg Pro Thr Ile Glu
    1910            1915            1920

Gln Leu Cys Glu Leu Ile Gly Gly Leu Asp Asp Gln Thr Gln Arg
    1925            1930            1935

Glu Leu Ala Leu Ala Pro Ser Gly Asn Thr Glu Ala Val Leu Ser
    1940            1945            1950

Phe Ala Gln Glu Arg Met Trp Phe Leu His Asn Phe Val Lys Gly
    1955            1960            1965

Met Pro Tyr Asn Thr Pro Gly Leu Asp His Leu Thr Gly Glu Leu
    1970            1975            1980

Asp Val Ala Ala Leu Glu Lys Ala Ile Arg Ala Val Ile Arg Arg
    1985            1990            1995

His Glu Pro Leu Arg Thr Asn Phe Val Glu Lys Asp Gly Val Leu
    2000            2005            2010

Ser Gln Leu Val Gly Thr Glu Glu Arg Phe Arg Leu Thr Val Thr
    2015            2020            2025

Pro Ile Arg Asp Glu Ser Glu Val Ala Arg Leu Met Glu Ala Val
    2030            2035            2040

Ile Gln Thr Pro Val Asp Leu Glu Arg Glu Leu Met Ile Arg Ala
    2045            2050            2055

Tyr Leu Tyr Arg Val Asp Pro Arg Asn His Tyr Leu Phe Thr Thr
    2060            2065            2070

Ile His His Ile Ala Phe Asp Gly Trp Ser Thr Ser Ile Phe Tyr
    2075            2080            2085

Arg Glu Leu Ala Ala Tyr Tyr Ala Ala Phe Leu Arg Arg Glu Asp
    2090            2095            2100

Ser Pro Leu Pro Ala Leu Glu Ile Ser Tyr Gln Asp Tyr Ala Arg
    2105            2110            2115

Trp Glu Arg Ala His Phe Gln Asp Glu Val Leu Ala Glu Lys Leu

```
                    2120                2125                    2130
Arg Tyr Trp Arg Gln Arg Leu Ser Gly Ala Arg Pro Leu Val Leu
    2135                2140                    2145

Pro Thr Thr Tyr His Arg Pro Pro Ile Gln Ser Phe Ala Gly Ala
    2150                2155                    2160

Val Val Asn Phe Glu Ile Asp Arg Ser Ile Thr Glu Arg Leu Lys
    2165                2170                    2175

Thr Leu Phe Ala Glu Ser Gly Thr Thr Met Tyr Met Val Leu Leu
    2180                2185                    2190

Gly Ala Phe Ser Val Val Leu Gln Arg Tyr Ser Gly Gln Asp Asp
    2195                2200                    2205

Ile Cys Ile Gly Ser Pro Val Ala Asn Arg Gly His Ile Gln Thr
    2210                2215                    2220

Glu Gly Leu Ile Gly Leu Phe Val Asn Thr Leu Val Met Arg Val
    2225                2230                    2235

Asp Ala Ala Gly Asn Pro Arg Phe Ile Asp Leu Leu Ala Arg Ile
    2240                2245                    2250

Gln Arg Thr Ala Ile Asp Ala Tyr Ala Asn Gln Glu Val Pro Phe
    2255                2260                    2265

Glu Lys Ile Val Asp Asp Leu Gln Val Ala Arg Asp Thr Ala Arg
    2270                2275                    2280

Ser Pro Leu Val Gln Val Ile Leu Asn Phe His Asn Thr Pro Pro
    2285                2290                    2295

Gln Ser Glu Leu Glu Leu Gln Gly Val Thr Leu Thr Arg Met Pro
    2300                2305                    2310

Val His Asn Gly Thr Ala Lys Phe Glu Leu Ser Ile Asp Val Ala
    2315                2320                    2325

Glu Thr Ser Ala Gly Leu Thr Gly Phe Val Glu Tyr Ala Thr Asp
    2330                2335                    2340

Leu Phe Ser Glu Asn Phe Ile Arg Arg Met Ile Gly His Leu Glu
    2345                2350                    2355

Val Val Leu Asp Ala Val Gly Arg Asp Pro Arg Ala Pro Ile His
    2360                2365                    2370

Glu Leu Pro Leu Leu Thr Arg Gln Asp Gln Leu Asp Leu Leu Ser
    2375                2380                    2385

Arg Ser Gly His Thr Ala Pro Ala Val Glu His Val Glu Leu Ile
    2390                2395                    2400

Pro His Thr Phe Glu Arg Arg Val Gln Glu Ser Pro Gln Ala Ile
    2405                2410                    2415

Ala Leu Val Cys Gly Asp Glu Arg Val Thr Tyr Ser Ala Leu Asn
    2420                2425                    2430

Arg Arg Ala Ser Gln Ile Ala Arg Arg Leu Arg Ala Ala Gly Ile
    2435                2440                    2445

Gly Pro Asp Thr Leu Val Gly Leu Cys Ala Gly Arg Ser Ile Glu
    2450                2455                    2460

Leu Val Cys Gly Val Leu Gly Ile Leu Lys Ala Gly Gly Ala Tyr
    2465                2470                    2475

Val Pro Ile Asp Pro Thr Ser Ser Pro Glu Val Ile Tyr Asp Val
    2480                2485                    2490

Leu Tyr Glu Ser Lys Val Arg His Leu Leu Thr Glu Ser Arg Leu
    2495                2500                    2505

Val Gly Gly Leu Pro Val Asp Asp Gln Glu Ile Leu Leu Leu Asp
    2510                2515                    2520
```

-continued

Thr Pro Ala Asp Gly Glu Gly Asp Lys Ala Val Ala Asp Arg Glu
2525                2530                2535

Glu Pro Pro Asp Leu Gly Glu Val Ser Leu Thr Pro Glu Cys Leu
2540                2545                2550

Ala Tyr Val Asn Phe Thr Ser Asp Ser Gly Gly Ala Pro Arg Gly
2555                2560                2565

Ile Ala Val Arg His Gly Ala Leu Ala Arg Arg Met Ala Ala Gly
2570                2575                2580

His Ala Gln Tyr Leu Ala Asn Ser Ala Val Arg Phe Leu Leu Lys
2585                2590                2595

Ala Pro Leu Thr Phe Asp Leu Ala Val Ala Glu Leu Phe Gln Trp
2600                2605                2610

Ile Val Ser Gly Gly Ser Leu Ser Ile Leu Asp Pro Asn Ala Asp
2615                2620                2625

Arg Asp Ala Ser Ala Phe Leu Ala Gln Val Arg Arg Asp Ser Ile
2630                2635                2640

Gly Val Leu Tyr Cys Val Pro Ser Glu Leu Ser Thr Leu Val Ser
2645                2650                2655

His Leu Glu Arg Glu Arg Glu Arg Val His Glu Leu Asn Thr Leu
2660                2665                2670

Arg Phe Ile Phe Cys Gly Gly Asp Thr Leu Ala Val Thr Val Val
2675                2680                2685

Glu Arg Leu Gly Val Leu Val Arg Ala Gly Gln Leu Pro Leu Arg
2690                2695                2700

Leu Val Asn Val Tyr Gly Thr Lys Glu Thr Gly Ile Gly Ala Gly
2705                2710                2715

Cys Phe Glu Cys Ala Leu Asp Ala Asn Asp Pro Ser Ala Glu Leu
2720                2725                2730

Pro Pro Gly Arg Leu Ser His Glu Arg Met Pro Ile Gly Gly Pro
2735                2740                2745

Ala Gln Asn Leu Trp Phe Tyr Val Val Gln Pro Asn Gly Gly Leu
2750                2755                2760

Ala Pro Leu Gly Ile Pro Gly Glu Leu Tyr Val Gly Gly Ala Gln
2765                2770                2775

Leu Ala Asp Ala Arg Phe Gly Asp Glu Pro Thr Ala Thr His Pro
2780                2785                2790

Gly Phe Val Pro Asn Pro Phe Arg Ser Gly Ala Glu Lys Asp Trp
2795                2800                2805

Leu Tyr Lys Thr Gly Asp Leu Val Arg Trp Leu Pro Gln Gly Pro
2810                2815                2820

Leu Glu Leu Val Ser Ala Ala Arg Glu Arg Asp Gly Gly Gly Asp
2825                2830                2835

His Arg Leu Asp Arg Gly Phe Ile Glu Ala Arg Met Arg Arg Val
2840                2845                2850

Ala Ile Val Arg Asp Ala Val Val Ala Tyr Val Pro Asp Arg Gln
2855                2860                2865

Asp Arg Ala Arg Leu Val Ala Tyr Val Val Leu Lys Glu Ser Pro
2870                2875                2880

Ala Ala Asp Val Glu Pro Arg Glu Gly Arg Glu Thr Leu Lys Ala
2885                2890                2895

Arg Ile Ser Ala Glu Leu Gly Ser Thr Leu Pro Glu Tyr Met Leu
2900                2905                2910

```
Pro Ala Ala Tyr Val Phe Met Asp Ser Leu Pro Leu Thr Ala Tyr
    2915                2920                2925

Gly Arg Ile Asp Arg Lys Ala Leu Pro Glu Pro Glu Asp Asp Arg
    2930                2935                2940

His Gly Gly Ser Ala Ile Ala Tyr Val Ala Pro Arg Gly Pro Thr
    2945                2950                2955

Glu Lys Ala Leu Ala His Ile Trp Gln Gln Val Leu Lys Arg Pro
    2960                2965                2970

Gln Val Gly Leu Arg Asp Asn Phe Phe Glu Leu Gly Gly His Ser
    2975                2980                2985

Val Ala Ala Ile Gln Leu Val Ser Val Ser Arg Lys His Leu Glu
    2990                2995                3000

Val Glu Val Pro Leu Ser Leu Ile Phe Glu Ser Pro Val Leu Glu
    3005                3010                3015

Ala Met Ala Arg Gly Ile Glu Ala Leu Gln Gln Gln Gly Arg Ser
    3020                3025                3030

Gly Ala Val Ser Ser Ile His Arg Val Glu Arg Thr Gly Pro Leu
    3035                3040                3045

Pro Leu Ala Tyr Val Gln Glu Arg Leu Trp Phe Val His Glu His
    3050                3055                3060

Met Lys Glu Gln Arg Thr Ser Tyr Asn Ile Thr Trp Thr Leu His
    3065                3070                3075

Phe Ala Gly Lys Gly Phe Ser Val Glu Ala Leu Arg Thr Ala Phe
    3080                3085                3090

Asp Glu Leu Val Ala Arg His Glu Thr Leu Arg Thr Trp Phe Gln
    3095                3100                3105

Val Gly Glu Gly Thr Glu Gln Ala Val Gln Val Ile Gly Glu Pro
    3110                3115                3120

Trp Ser Met Glu Leu Pro Leu Arg Glu Val Ala Gly Thr Glu Val
    3125                3130                3135

Thr Ala Ala Ile Asn Glu Met Ser Arg Gln Val Phe Asp Leu Arg
    3140                3145                3150

Ala Gly Arg Leu Leu Thr Ala Ala Val Leu Arg Val Ala Glu Asp
    3155                3160                3165

Glu His Ile Leu Val Ser Asn Ile His His Ile Thr Asp Gly
    3170                3175                3180

Trp Ser Phe Gly Val Met Leu Arg Glu Leu Arg Glu Leu Tyr Glu
    3185                3190                3195

Ala Ala Val Arg Gly Glu Arg Ala Glu Leu Pro Pro Leu Thr Val
    3200                3205                3210

Gln Tyr Gly Asp Tyr Ala Val Trp Gln Arg Lys Gln Asp Leu Ser
    3215                3220                3225

Glu His Leu Ala Tyr Trp Lys Gly Lys Val Glu Gly Asp Glu Asp
    3230                3235                3240

Gly Leu Glu Leu Pro Tyr Asp Phe Pro Arg Thr Ser Asn Arg Ala
    3245                3250                3255

Trp Arg Ala Ala Thr Phe Gln Tyr Ser Tyr His Pro Glu Leu Ala
    3260                3265                3270

Arg Lys Val Ala Glu Leu Ser Arg Glu Gln Gln Ser Thr Leu Phe
    3275                3280                3285

Met Ser Leu Val Ala Ser Leu Ala Val Val Leu Asn Arg Tyr Thr
    3290                3295                3300

Gly Arg Glu Asp Leu Cys Ile Gly Thr Val Ala Gly Arg Ala
```

-continued

Gln Val Glu Leu Glu Ser Leu Ile Gly Phe Phe Ile Asn Ile Leu
3305            3310                3315
                3320                3325            3330

Pro Leu Arg Leu Asp Leu Ser Gly Ala Pro Ser Leu His Glu Val
3335            3340                3345

Leu Arg Arg Thr Lys Val Val Leu Glu Gly Phe Glu His Gln
3350            3355                3360

Glu Leu Pro Phe Glu His Leu Leu Lys Ala Leu Arg Arg Gln Arg
3365            3370                3375

Asp Ser Ser Gln Ile Pro Leu Val Pro Val Val Arg His Gln
3380            3385                3390

Asn Phe Pro Met Ala Arg Leu Glu Gly Trp Ser Glu Gly Val Glu
3395            3400                3405

Leu Lys Lys Phe Glu Leu Ala Gly Glu Arg Thr Thr Ala Ser Glu
3410            3415                3420

Gln Asp Trp Gln Phe Phe Gly Asp Gly Ser Ser Leu Glu Leu Ser
3425            3430                3435

Leu Glu Tyr Ala Ala Glu Leu Phe Ser Glu Lys Thr Val Arg Arg
3440            3445                3450

Met Val Glu His His Gln Arg Val Leu Glu Ala Leu Val Glu Gly
3455            3460                3465

Leu Glu Glu Gly Leu His Glu Val Arg Leu Leu Thr Glu Glu Glu
3470            3475                3480

Glu Gly Leu His Gly Arg Leu Asn Asp Thr Ala Arg Glu Leu Glu
3485            3490                3495

Glu Arg Trp Ser Leu Ala Glu Thr Phe Glu Arg Gln Val Arg Glu
3500            3505                3510

Thr Pro Glu Ala Val Ala Cys Val Gly Val Glu Val Ala Thr Gly
3515            3520                3525

Gly His Ser Arg Pro Thr Tyr Arg Gln Leu Thr Tyr Arg Gln Leu
3530            3535                3540

Asn Ala Arg Ala Asn Gln Val Ala Arg Arg Leu Arg Ala Leu Gly
3545            3550                3555

Val Gly Ala Glu Thr Arg Val Ala Val Leu Ser Asp Arg Ser Pro
3560            3565                3570

Glu Leu Leu Val Ala Met Leu Ala Ile Phe Lys Ala Gly Gly Cys
3575            3580                3585

Tyr Val Pro Val Asp Pro Gln Tyr Pro Gly Ser Tyr Ile Glu Gln
3590            3595                3600

Ile Leu Glu Asp Ala Ala Pro Gln Val Val Leu Gly Lys Arg Gly
3605            3610                3615

Arg Ala Asp Gly Val Arg Val Asp Val Trp Leu Glu Leu Asp Gly
3620            3625                3630

Ala Gln Arg Leu Thr Asp Glu Ala Leu Ala Ala Gln Glu Glu Gly
3635            3640                3645

Glu Leu Glu Gly Ala Glu Arg Pro Glu Ser Gln Gln Leu Ala Cys
3650            3655                3660

Leu Met Tyr Thr Ser Gly Ser Thr Gly Arg Pro Lys Gly Val Met
3665            3670                3675

Val Pro Tyr Ser Gln Leu His Asn Trp Leu Glu Ala Gly Lys Glu
3680            3685                3690

Arg Ser Pro Leu Glu Arg Gly Glu Val Met Leu Gln Lys Thr Ala
3695            3700                3705

-continued

```
Ile Ala Phe Ala Val Ser Val Lys Glu Leu Leu Ser Gly Leu Leu
3710            3715                3720

Ala Gly Val Ala Gln Val Met Val Pro Glu Thr Leu Val Lys Asp
3725            3730                3735

Ser Val Ala Leu Ala Gln Glu Ile Glu Arg Trp Arg Val Thr Arg
3740            3745                3750

Ile His Leu Val Pro Ser His Leu Gly Ala Leu Leu Glu Gly Ala
3755            3760                3765

Gly Glu Glu Ala Lys Gly Leu Arg Ser Leu Lys Tyr Val Ile Thr
3770            3775                3780

Ala Gly Glu Ala Leu Ala Gln Gly Val Arg Glu Glu Ala Arg Arg
3785            3790                3795

Lys Leu Pro Gly Ala Gln Leu Trp Asn Asn Tyr Gly Cys Thr Glu
3800            3805                3810

Leu Asn Asp Val Thr Tyr His Pro Ala Ser Glu Gly Gly Gly Asp
3815            3820                3825

Thr Val Phe Val Pro Ile Gly Arg Pro Ile Ala Asn Thr Arg Val
3830            3835                3840

Tyr Val Leu Asp Glu Gln Leu Arg Arg Val Pro Val Gly Val Met
3845            3850                3855

Gly Glu Leu Tyr Val Asp Ser Val Gly Met Ala Arg Gly Tyr Trp
3860            3865                3870

Gly Gln Pro Ala Leu Thr Ala Glu Arg Phe Ile Ala Asn Pro Tyr
3875            3880                3885

Ala Ser Gln Pro Gly Ala Arg Leu Tyr Arg Thr Gly Asp Met Val
3890            3895                3900

Arg Val Leu Ala Asp Gly Ser Leu Glu Tyr Leu Gly Arg Arg Asp
3905            3910                3915

Tyr Glu Ile Lys Val Arg Gly His Arg Val Asp Val Arg Gln Val
3920            3925                3930

Glu Lys Val Ala Asn Ala His Pro Ala Ile Arg Gln Ala Val Val
3935            3940                3945

Ser Gly Trp Pro Leu Gly Ser Ser Asn Ala Gln Leu Val Ala Tyr
3950            3955                3960

Leu Val Pro Gln Ala Gly Ala Thr Val Gly Pro Arg Gln Val Arg
3965            3970                3975

Asp Tyr Leu Ala Glu Ser Leu Pro Ala Tyr Met Val Pro Thr Leu
3980            3985                3990

Tyr Thr Val Leu Glu Glu Leu Pro Arg Leu Pro Asn Gly Lys Leu
3995            4000                4005

Asp Arg Leu Ser Leu Pro Glu Pro Asp Leu Ser Ser Ser Arg Glu
4010            4015                4020

Glu Tyr Val Ala Pro His Gly Glu Val Glu Arg Lys Leu Ala Glu
4025            4030                4035

Ile Phe Gly Asn Leu Leu Gly Leu Glu His Val Gly Val His Asp
4040            4045                4050

Asn Phe Phe Asn Leu Gly Gly His Ser Leu Leu Ala Ser Gln Leu
4055            4060                4065

Ile Ser Arg Ile Arg Ala Thr Phe Arg Val Glu Val Ala Met Ala
4070            4075                4080

Thr Val Phe Glu Ser Pro Thr Val Glu Pro Leu Ala Arg His Ile
4085            4090                4095
```

-continued

| | | | | | | | | | | | | |
|---|---|---|---|---|---|---|---|---|---|---|---|---|
| Glu | Glu | Lys | Leu | Lys | Asp | Glu | Ser | Arg | Val | Gln | Leu | Ser | Asn | Val |
| | 4100 | | | | | 4105 | | | | | 4110 | | | |
| Val | Pro | Val | Glu | Arg | Thr | Gln | Glu | Leu | Pro | Leu | Ser | Tyr | Leu | Gln |
| | 4115 | | | | | 4120 | | | | | 4125 | | | |
| Glu | Arg | Leu | Trp | Phe | Val | His | Glu | His | Met | Lys | Glu | Gln | Arg | Thr |
| | 4130 | | | | | 4135 | | | | | 4140 | | | |
| Ser | Tyr | Asn | Gly | Thr | Ile | Gly | Leu | Arg | Leu | Arg | Gly | Pro | Leu | Ser |
| | 4145 | | | | | 4150 | | | | | 4155 | | | |
| Ile | Pro | Ala | Leu | Arg | Ala | Thr | Phe | His | Asp | Leu | Val | Ala | Arg | His |
| | 4160 | | | | | 4165 | | | | | 4170 | | | |
| Glu | Ser | Leu | Arg | Thr | Val | Phe | Arg | Val | Pro | Glu | Gly | Arg | Thr | Thr |
| | 4175 | | | | | 4180 | | | | | 4185 | | | |
| Pro | Val | Gln | Val | Ile | Leu | Asp | Ser | Met | Asp | Leu | Asp | Ile | Pro | Val |
| | 4190 | | | | | 4195 | | | | | 4200 | | | |
| Arg | Asp | Ala | Thr | Glu | Ala | Asp | Ile | Ile | Pro | Gly | Met | Asp | Glu | Leu |
| | 4205 | | | | | 4210 | | | | | 4215 | | | |
| Ala | Gly | His | Ile | Tyr | Asp | Met | Glu | Lys | Gly | Pro | Leu | Phe | Met | Val |
| | 4220 | | | | | 4225 | | | | | 4230 | | | |
| Arg | Leu | Leu | Arg | Leu | Ala | Glu | Asp | Ser | His | Val | Leu | Leu | Met | Gly |
| | 4235 | | | | | 4240 | | | | | 4245 | | | |
| Met | His | His | Ile | Val | Tyr | Asp | Ala | Trp | Ser | Gln | Phe | Asn | Val | Met |
| | 4250 | | | | | 4255 | | | | | 4260 | | | |
| Ser | Arg | Asp | Ile | Asn | Leu | Leu | Tyr | Ser | Ala | His | Val | Thr | Gly | Ile |
| | 4265 | | | | | 4270 | | | | | 4275 | | | |
| Glu | Ala | Arg | Leu | Pro | Ala | Leu | Pro | Ile | Gln | Tyr | Ala | Asp | Phe | Ser |
| | 4280 | | | | | 4285 | | | | | 4290 | | | |
| Val | Trp | Gln | Arg | Gln | Gln | Asp | Phe | Arg | His | His | Leu | Asp | Tyr | Trp |
| | 4295 | | | | | 4300 | | | | | 4305 | | | |
| Lys | Ser | Thr | Leu | Gly | Asp | Tyr | Arg | Asp | Asp | Leu | Glu | Leu | Pro | Tyr |
| | 4310 | | | | | 4315 | | | | | 4320 | | | |
| Asp | Tyr | Pro | Arg | Pro | Ser | Arg | Thr | Trp | His | Ala | Thr | Arg | Phe |
| | 4325 | | | | | 4330 | | | | | 4335 | | | |
| Thr | Phe | Arg | Tyr | Pro | Asp | Ala | Leu | Ala | Arg | Ala | Phe | Ala | Arg | Phe |
| | 4340 | | | | | 4345 | | | | | 4350 | | | |
| Asn | Gln | Ser | His | Gln | Ser | Thr | Leu | Phe | Met | Gly | Leu | Leu | Thr | Ser |
| | 4355 | | | | | 4360 | | | | | 4365 | | | |
| Phe | Ala | Ile | Val | Leu | Arg | His | Tyr | Thr | Gly | Arg | Asn | Asp | Ile | Cys |
| | 4370 | | | | | 4375 | | | | | 4380 | | | |
| Ile | Gly | Thr | Thr | Thr | Ala | Gly | Arg | Ala | Gln | Leu | Glu | Leu | Glu | Asn |
| | 4385 | | | | | 4390 | | | | | 4395 | | | |
| Leu | Val | Gly | Phe | Phe | Ile | Asn | Ile | Leu | Pro | Leu | Arg | Ile | Asn | Leu |
| | 4400 | | | | | 4405 | | | | | 4410 | | | |
| Ala | Gly | Asp | Pro | Asp | Ile | Ser | Glu | Leu | Met | Asn | Arg | Ala | Lys | Lys |
| | 4415 | | | | | 4420 | | | | | 4425 | | | |
| Ser | Val | Leu | Gly | Ala | Phe | Glu | His | Gln | Ala | Leu | Pro | Phe | Glu | Arg |
| | 4430 | | | | | 4435 | | | | | 4440 | | | |
| Leu | Leu | Ser | Ala | Leu | Asn | Lys | Gln | Arg | Asp | Ser | Ser | His | Ile | Pro |
| | 4445 | | | | | 4450 | | | | | 4455 | | | |
| Leu | Val | Pro | Val | Met | Leu | Arg | His | Gln | Asn | Phe | Pro | Thr | Ala | Met |
| | 4460 | | | | | 4465 | | | | | 4470 | | | |
| Thr | Gly | Lys | Trp | Ala | Asp | Gly | Val | Asp | Met | Glu | Val | Ile | Glu | Arg |
| | 4475 | | | | | 4480 | | | | | 4485 | | | |
| Asp | Glu | Arg | Thr | Thr | Pro | Asn | Glu | Leu | Asp | Leu | Gln | Phe | Phe | Gly |

-continued

```
                   4490                4495               4500

Asp Asp Thr Tyr Leu His Ala Val Val Glu Phe Pro Ala Gln Leu
    4505                4510               4515

Phe Ser Glu Val Thr Val Arg Arg Leu Met Gln Arg His Gln Lys
    4520                4525               4530

Val Ile Glu Phe Met Cys Ala Thr Leu Gly Ala Arg
    4535                4540               4545

<210> SEQ ID NO 51
<211> LENGTH: 1023
<212> TYPE: PRT
<213> ORGANISM: Cystobacter velatus
<220> FEATURE:
<221> NAME/KEY: MISC_FEATURE
<222> LOCATION: (1)..(1023)
<223> OTHER INFORMATION: CysL

<400> SEQUENCE: 51

Val Asn Val Leu Ala Arg His Ser Thr Gly Ser His Asp Glu Pro Val
1               5                   10                  15

Ala Gly Asp Val Glu Leu Arg Val Gly Gly Pro Gly Val Pro Asp Ala
            20                  25                  30

His Ser Ser Glu Ser Val Glu Val Leu Ala Arg Trp Leu Arg Thr Ala
        35                  40                  45

Glu Glu Lys Tyr Pro Gly Val Met Gly Pro Ile Arg Gln Glu Gly Pro
    50                  55                  60

Trp Phe Ala Ile Pro Leu Thr Cys Pro Arg Gly Ala Arg Ser Ala Arg
65                  70                  75                  80

Phe Gly Leu Trp Leu Gly Leu Asp Arg Gln Gly Gln Leu Leu His
                85                  90                  95

Met Val Ala Ser Tyr Leu Ala Ala Val His His Val Leu Val Ser Val
            100                 105                 110

Arg Glu Pro Ser Ala Asn Val Leu Glu Val Leu Val Ser Asp Ser Thr
        115                 120                 125

Thr Pro Ser Gly Leu Asn Arg Phe Leu Asn Gly Leu Asp Ser Val Leu
    130                 135                 140

Glu Ile Leu Ala His Gly Arg Ser Asp Leu Leu Leu Gln His Leu Thr
145                 150                 155                 160

Gly Arg Leu Pro Pro Asp Glu Met Pro Phe Val Glu Asp Arg Glu Glu
                165                 170                 175

Arg Glu Glu His Pro Ala Thr Asp Val Glu Ala Asp Ala Val Val Ser
            180                 185                 190

Val Leu Phe Gln Pro Val Asp Phe Pro Ser Leu Ala Arg Leu Asp Ala
        195                 200                 205

Ser Leu Leu Ala Tyr Asp Asp Glu Asp Ala Gly Ala Val Gly Arg Val
    210                 215                 220

Leu Gly Glu Leu Leu Gln Pro Phe Leu Leu Asp Ser Ala Arg Met Thr
225                 230                 235                 240

Val Gly Arg Lys Ala Val Arg Val Asp His Ile Cys Leu Pro Gly Leu
                245                 250                 255

Leu Arg Ala Asp Ser Arg Ala Ala Glu Glu Ser Val Leu Ala Pro Ala
            260                 265                 270

Leu Arg Leu Ala Thr Lys Pro Gly Arg His Phe Val Ala Leu Cys Arg
        275                 280                 285

Asn Thr Ala Leu Arg Leu Gly Asp Arg Leu Pro His Leu Leu Ala Gln
    290                 295                 300
```

```
Gly Pro Leu Cys Asp Gly Ala Ser Thr Ala Leu Leu Leu Gln Arg
305                 310                 315                 320

Val Leu Asp Thr Leu Ile Gly Ser Gly Gly Leu Lys Asp His Arg Leu
            325                 330                 335

Thr Leu Glu Leu Val Gly Ala Asp Pro Arg Thr Glu Ala Ala Phe Arg
        340                 345                 350

Ala Arg Thr Pro Trp Leu Val Ala Glu Arg Ala Ala Ser Ala Ala Ser
            355                 360                 365

Thr Asp Ala Pro Arg Val Asp Val Val Leu Phe Pro Ala Ala Arg
370                 375                 380

Pro Ser Ala Leu Glu Leu Arg Pro Asp Ser Val Val Ile Asp Leu Phe
385                 390                 395                 400

Gly Thr Trp Ser Leu Arg Pro Arg Pro Glu Val Leu Ala Lys Asn Ile
                405                 410                 415

Val Tyr Val Arg Gly Ala Ser Val Arg Leu Ala Gly Glu Ala Val Val
            420                 425                 430

Ser Thr Pro Ser Phe Ala Pro Asp Arg Val Glu Pro Ala Leu Leu Glu
            435                 440                 445

Ala Leu Leu Arg Glu Leu Asp Ala Glu Ala Ser Ser Asp Gly Leu Ala
450                 455                 460

His Glu His Arg Leu Glu Ile Gly Gly Ile Arg Gly Phe Trp Gly Glu
465                 470                 475                 480

Ile Arg Arg Ala Glu Trp Asp Ala Phe His Ser Arg Arg Gly Glu
                485                 490                 495

Leu Ala Arg Phe Gln Val Ser Gly Gln Val Thr Ala Ala Asn Pro Gly
                500                 505                 510

Leu Ala Ser Leu Pro Asp Gly Ala Thr Asn Ile Cys Glu Tyr Ile Phe
            515                 520                 525

Arg Glu Ala His Leu Arg Ser Gly Ser Cys Leu Val Asp Pro Gln Ser
530                 535                 540

Gly Gln Ser Ala Thr Tyr Ala Glu Leu Arg Arg Leu Ala Ala Ala Tyr
545                 550                 555                 560

Ala Arg Arg Phe Arg Ala Leu Gly Leu Arg Gln Gly Asp Val Val Ala
                565                 570                 575

Leu Ala Ala Pro Asp Gly Ile Ser Ser Val Ala Val Met Leu Gly Cys
            580                 585                 590

Phe Leu Gly Gly Trp Val Phe Ala Pro Leu Asn His Thr Ala Ser Ala
                595                 600                 605

Val Asn Phe Glu Ala Met Leu Ser Ser Ala Ser Pro Arg Leu Val Leu
            610                 615                 620

His Ala Ala Ser Thr Val Ala Arg His Leu Pro Val Leu Ser Thr Arg
625                 630                 635                 640

Arg Cys Ala Glu Leu Ala Ser Phe Leu Pro Pro Asp Ala Leu Asp Gly
                645                 650                 655

Val Glu Gly Asp Val Thr Pro Leu Pro Val Ser Pro Glu Ala Pro Ala
            660                 665                 670

Val Met Leu Phe Thr Ser Gly Ser Thr Gly Gly Pro Lys Ala Val Thr
            675                 680                 685

His Thr His Ala Asp Phe Ile Thr Cys Ser Arg Asn Tyr Ala Pro Tyr
            690                 695                 700

Val Val Glu Leu Arg Pro Asp Asp Arg Val Tyr Thr Pro Ser Pro Thr
705                 710                 715                 720
```

```
Phe Phe Ala Tyr Gly Leu Asn Asn Leu Leu Leu Ser Leu Ser Ala Gly
                725                 730                 735

Ala Thr His Val Ile Ser Val Pro Arg Asn Gly Gly Met Gly Val Ala
            740                 745                 750

Glu Ile Leu Ala Arg Asn Glu Val Thr Val Leu Phe Ala Val Pro Ala
        755                 760                 765

Val Tyr Lys Leu Ile Ile Ser Lys Asn Asp Arg Gly Leu Arg Leu Pro
    770                 775                 780

Lys Leu Arg Leu Cys Ile Ser Ala Gly Glu Lys Leu Pro Leu Lys Leu
785                 790                 795                 800

Tyr Arg Glu Ala Arg Ser Phe Phe Ser Val Asn Val Leu Asp Gly Ile
                805                 810                 815

Gly Cys Thr Glu Ala Ile Ser Thr Phe Ile Ser Asn Arg Glu Ser Tyr
            820                 825                 830

Val Ala Pro Gly Cys Thr Gly Val Val Pro Gly Phe Glu Val Lys
        835                 840                 845

Leu Val Asn Pro Arg Gly Glu Leu Cys Arg Val Gly Glu Val Gly Val
    850                 855                 860

Leu Trp Val Arg Gly Gly Ala Leu Thr Arg Gly Tyr Val Asn Ala Pro
865                 870                 875                 880

Asp Leu Thr Glu Lys His Phe Val Asp Gly Trp Phe Asn Thr Gln Asp
                885                 890                 895

Met Phe Phe Met Asp Ala Glu Tyr Arg Leu Tyr Asn Val Gly Arg Ala
            900                 905                 910

Gly Ser Val Ile Lys Ile Asn Ser Cys Trp Phe Ser Pro Glu Met Met
        915                 920                 925

Glu Ser Val Leu Gln Ser His Pro Ala Val Lys Glu Cys Ala Val Cys
    930                 935                 940

Val Val Ile Asp Asp Tyr Gly Leu Pro Arg Pro Lys Ala Phe Ile Val
945                 950                 955                 960

Thr Gly Glu His Glu Arg Ser Glu Pro Glu Leu Glu His Leu Trp Ala
                965                 970                 975

Glu Leu Arg Val Leu Ser Lys Glu Lys Leu Gly Lys Asp His Tyr Pro
            980                 985                 990

His Leu Phe Ala Thr Ile Lys Thr  Leu Pro Arg Thr Ser  Ser Gly Lys
        995                 1000                1005

Leu Met  Arg Ser Glu Leu Ala  Lys Leu Leu Thr Ser  Gly Pro Pro
    1010                1015                1020
```

<210> SEQ ID NO 52
<211> LENGTH: 38
<212> TYPE: PRT
<213> ORGANISM: Cystobacter velatus
<220> FEATURE:
<221> NAME/KEY: MISC_FEATURE
<222> LOCATION: (1)..(38)
<223> OTHER INFORMATION: CysM

<400> SEQUENCE: 52

```
Met Asn Pro Lys Phe Leu Gly Gly Leu Gly Ala Gly Val Cys Ile Ala
1               5                   10                  15

Ser Leu Phe Gln Thr Val Met Arg Thr Val Pro Leu Lys Asp Ala Gly
                20                  25                  30

Ser Gly Asp Arg Ala Cys
            35
```

-continued

```
<210> SEQ ID NO 53
<211> LENGTH: 357
<212> TYPE: PRT
<213> ORGANISM: Cystobacter velatus
<220> FEATURE:
<221> NAME/KEY: MISC_FEATURE
<222> LOCATION: (1)..(357)
<223> OTHER INFORMATION: CysN

<400> SEQUENCE: 53

Met Ser Thr Arg Thr Lys Asn Phe Asn Val Met Gly Ile Asp Trp Met
1               5                   10                  15

Pro Ser Ser Ala Glu Phe Lys Arg Arg Val Pro Arg Thr Gln Arg Ala
            20                  25                  30

Ala Glu Ala Val Leu Ala Gly Arg Arg Cys Leu Met Asp Ile Leu Asp
        35                  40                  45

Arg Gly Asp Pro Arg Leu Phe Val Ile Val Gly Pro Cys Ser Ile His
    50                  55                  60

Asp Pro Val Ala Gly Leu Asp Tyr Ala Lys Arg Leu Arg Lys Leu Ala
65                  70                  75                  80

Asp Glu Val Arg Glu Thr Leu Phe Val Val Met Arg Val Tyr Phe Glu
                85                  90                  95

Lys Pro Arg Thr Thr Gly Trp Lys Gly Phe Ile Asn Asp Pro Arg
            100                 105                 110

Met Asp Gly Ser Phe His Ile Glu Glu Gly Met Glu Arg Gly Arg Arg
        115                 120                 125

Phe Leu Leu Asp Val Ala Glu Glu Gly Leu Pro Ala Ala Thr Glu Ala
130                 135                 140

Leu Asp Pro Ile Ala Ser Gln Tyr Tyr Gly Asp Leu Ile Ser Trp Thr
145                 150                 155                 160

Ala Ile Gly Ala Arg Thr Ala Glu Ser Gln Thr His Arg Glu Met Ala
                165                 170                 175

Ser Gly Leu Ser Thr Pro Val Gly Phe Lys Asn Gly Thr Asp Gly Ser
            180                 185                 190

Leu Asp Ala Ala Val Asn Gly Ile Ile Ser Ala Ser His Pro His Ser
        195                 200                 205

Phe Leu Gly Val Ser Glu Asn Gly Ala Cys Ala Ile Ile Arg Thr Arg
    210                 215                 220

Gly Asn Thr Tyr Gly His Leu Val Leu Arg Gly Gly Gly Arg Pro
225                 230                 235                 240

Asn Tyr Asp Ala Val Ser Val Ala Leu Ala Glu Lys Ala Leu Ala Lys
                245                 250                 255

Ala Arg Leu Pro Thr Asn Ile Val Val Asp Cys Ser His Ala Asn Ser
            260                 265                 270

Trp Lys Asn Pro Glu Leu Gln Pro Leu Val Met Arg Asp Val Val His
        275                 280                 285

Gln Ile Arg Glu Gly Asn Arg Ser Val Val Gly Leu Met Ile Glu Ser
    290                 295                 300

Phe Ile Glu Ala Gly Asn Gln Pro Ile Pro Ala Asp Leu Ser Gln Leu
305                 310                 315                 320

Arg Tyr Gly Cys Ser Val Thr Asp Ala Cys Val Asp Trp Lys Thr Thr
                325                 330                 335

Glu Lys Met Leu Tyr Ser Ala His Glu Glu Leu Leu His Ile Leu Pro
            340                 345                 350

Arg Ser Lys Val Ala
        355
```

<210> SEQ ID NO 54
<211> LENGTH: 203
<212> TYPE: PRT
<213> ORGANISM: Cystobacter velatus
<220> FEATURE:
<221> NAME/KEY: MISC_FEATURE
<222> LOCATION: (1)..(203)
<223> OTHER INFORMATION: CysO

<400> SEQUENCE: 54

Met Pro Ala Arg Ser Thr Pro Ser Leu Glu Ser Gly Asp Phe Phe Ala
1               5                   10                  15

Asp Val Thr Phe Ser Asp Leu Ser Ile Glu Ser Ala Asp Leu Ser Gly
            20                  25                  30

Lys Glu Phe Glu Arg Cys Thr Phe Arg Arg Cys Lys Leu Pro Glu Ser
        35                  40                  45

Arg Trp Val Arg Ser Arg Leu Glu Asp Cys Val Phe Glu Gly Cys Asp
    50                  55                  60

Leu Leu Arg Met Val Pro Glu Lys Leu Ala Leu Arg Ser Val Thr Phe
65                  70                  75                  80

Lys Asp Thr Arg Leu Met Gly Val Asp Trp Ser Gly Leu Gly Thr Met
                85                  90                  95

Pro Asp Val Gln Phe Glu Gln Cys Asp Leu Arg Tyr Ser Ser Phe Leu
            100                 105                 110

Lys Leu Asn Leu Arg Lys Thr Arg Phe Val Gly Cys Ser Ala Arg Glu
        115                 120                 125

Ala Asn Phe Ile Asp Val Asp Leu Ala Glu Ser Asp Phe Thr Gly Thr
    130                 135                 140

Asp Met Pro Gly Cys Thr Met Gln Gly Cys Val Leu Thr Lys Thr Asn
145                 150                 155                 160

Phe Ala Arg Ser Thr Asn Phe Ile Phe Asp Pro Lys Ala Asn Gln Val
                165                 170                 175

Lys Gly Thr Arg Val Gly Val Glu Thr Ala Val Ala Leu Ala Gln Ala
            180                 185                 190

Leu Gly Met Val Val Asp Gly Tyr Gln Thr Pro
        195                 200

<210> SEQ ID NO 55
<211> LENGTH: 233
<212> TYPE: PRT
<213> ORGANISM: Cystobacter velatus
<220> FEATURE:
<221> NAME/KEY: MISC_FEATURE
<222> LOCATION: (1)..(233)
<223> OTHER INFORMATION: CysP

<400> SEQUENCE: 55

Met Lys Arg Phe Phe Lys Leu Gln Leu Arg Thr Thr Asn Val Pro Ala
1               5                   10                  15

Ala Arg Ala Phe Tyr Thr Ala Leu Phe Gly Glu Gly Ala Ala Asn Ala
            20                  25                  30

Asp Ile Val Pro Leu Pro Glu Gln Ala Ile Arg Gly Ala Pro Ala
        35                  40                  45

His Trp Leu Gly Tyr Val Gly Val Glu Asp Val Asp Glu Ala Val Arg
    50                  55                  60

Ser Phe Val Gly Arg Gly Ala Thr Gln Leu Gly Pro Thr His Pro Thr
65                  70                  75                  80

```
Asn Asp Gly Gly Arg Val Ala Ile Leu Arg Asp Pro Gly Gly Ala Thr
                85                  90                  95

Phe Ala Val Ala Thr Ala Pro Ala Thr Thr Arg Ala Leu Gln Pro Glu
            100                 105                 110

Val Val Trp Gln Gln Leu Tyr Ala Ala Asn Val Gln Gln Thr Ala Ala
        115                 120                 125

Ser Tyr Cys Asp Leu Phe Gly Trp Arg Leu Ser Asp Arg Arg Asp Leu
    130                 135                 140

Gly Ala Leu Gly Val His Gln Glu Phe Thr Trp Arg Ser Asp Glu Pro
145                 150                 155                 160

Ser Ala Gly Ser Val Val Asp Val Ala Gly Leu Lys Gly Val His Ser
                165                 170                 175

His Trp Leu Phe His Phe Arg Val Ala Ala Leu Asp Pro Ala Met Glu
            180                 185                 190

Val Val Arg Lys Ala Gly Gly Val Val Ile Gly Pro Met Glu Leu Pro
        195                 200                 205

Asn Gly Asp Arg Ile Ala Val Cys Glu Asp Pro Gln Arg Ala Ala Phe
    210                 215                 220

Ala Leu Arg Glu Ser Ser His Gly Arg
225                 230

<210> SEQ ID NO 56
<211> LENGTH: 264
<212> TYPE: PRT
<213> ORGANISM: Cystobacter velatus
<220> FEATURE:
<221> NAME/KEY: MISC_FEATURE
<222> LOCATION: (1)..(264)
<223> OTHER INFORMATION: CysQ

<400> SEQUENCE: 56

Met Gln Glu Ile Gly Gln Thr Ala Leu Trp Val Ala Gly Met Arg Ala
1               5                   10                  15

Leu Glu Thr Glu Arg Ser Asn Pro Leu Phe Arg Asp Pro Phe Ala Arg
            20                  25                  30

Arg Leu Ala Gly Asp Thr Leu Val Glu Glu Leu Arg Arg Arg Asn Ala
        35                  40                  45

Gly Glu Gly Ala Met Pro Pro Ala Ile Glu Val Arg Thr Arg Trp Leu
    50                  55                  60

Asp Asp Gln Ile Thr Leu Gly Leu Gly Arg Gly Ile Arg Gln Ile Val
65                  70                  75                  80

Ile Leu Ala Ala Gly Met Asp Ala Arg Ala Tyr Arg Leu Ala Trp Pro
                85                  90                  95

Gly Asp Thr Arg Leu Phe Glu Leu Asp His Asp Ala Val Leu Gln Asp
            100                 105                 110

Lys Glu Ala Lys Leu Thr Gly Val Ala Pro Lys Cys Glu Arg His Ala
        115                 120                 125

Val Ser Val Asp Leu Ala Asp Asp Trp Pro Ala Ala Leu Lys Lys Ser
    130                 135                 140

Gly Phe Asp Pro Gly Val Pro Thr Leu Trp Leu Ile Glu Gly Leu Leu
145                 150                 155                 160

Val Tyr Leu Thr Glu Ala Gln Val Thr Leu Leu Met Ala Arg Val Asn
                165                 170                 175

Ala Leu Ser Val Pro Glu Ser Ile Val Leu Ile Asp Val Val Gly Arg
            180                 185                 190

Ser Ile Leu Asp Ser Ser Arg Val Lys Leu Met His Asp Leu Ala Arg
```

195                 200                 205

Gln Phe Gly Thr Asp Glu Pro Glu Val Ile Leu Arg Pro Ile Gly Trp
    210                 215                 220

Asp Pro His Val Tyr Thr Ala Ala Ile Gly Lys Gln Leu Gly Arg
225                 230                 235                 240

Trp Pro Phe Pro Val Ala Pro Arg Gly Thr Pro Gly Val Pro Gln Gly
                245                 250                 255

Tyr Leu Val His Gly Val Lys Arg
        260

<210> SEQ ID NO 57
<211> LENGTH: 333
<212> TYPE: PRT
<213> ORGANISM: Cystobacter velatus
<220> FEATURE:
<221> NAME/KEY: MISC_FEATURE
<222> LOCATION: (1)..(333)
<223> OTHER INFORMATION: CysR

<400> SEQUENCE: 57

Val Asn Gly Thr Thr Gly Lys Thr Gly Leu Val Ala Glu Arg Ser Gly
1               5                   10                  15

Ala Ile Ser Pro Arg Asp Tyr Lys Ser Lys Glu Leu Val Trp Asp Ser
                20                  25                  30

Leu Ala Ala Thr Arg Ser Lys Pro Arg Arg Val Leu Pro Glu Gly Asp
            35                  40                  45

Val Val Gly His Leu Tyr Pro Pro Ala Lys Ala Leu Leu Thr His
        50                  55                  60

Pro Leu Met Lys Asn Leu Pro Pro Glu Thr Leu Arg Leu Phe Phe Ile
65                  70                  75                  80

His Ser Ala Tyr Lys Phe Met Gly Asp Ile Ala Ile Phe Glu Thr Glu
                85                  90                  95

Thr Val Asn Glu Val Ala Met Lys Ile Ala Asn Gly His Thr Pro Ile
                100                 105                 110

Thr Phe Pro Asp Asp Ile Arg His Asp Ala Leu Thr Val Ile Ile Asp
            115                 120                 125

Glu Ala Tyr His Ala Tyr Val Ala Arg Asp Phe Met Arg Gln Ile Glu
    130                 135                 140

Gln Arg Thr Gly Val Lys Pro Leu Pro Leu Gly Thr Glu Thr Asp Leu
145                 150                 155                 160

Ser Arg Ala Met Ala Phe Gly Lys His Arg Leu Pro Glu Thr Leu His
                165                 170                 175

Gly Leu Trp Glu Ile Ile Ala Val Cys Ile Gly Glu Asn Thr Leu Thr
            180                 185                 190

Lys Asp Leu Leu Asn Leu Thr Gly Glu Lys Ser Phe Asn Glu Val Leu
        195                 200                 205

His Gln Val Met Glu Asp His Val Arg Asp Glu Gly Arg His Ala Val
    210                 215                 220

Leu Phe Met Asn Val Leu Lys Leu Val Trp Ser Glu Met Glu Glu Ser
225                 230                 235                 240

Ala Arg Leu Ala Ile Gly Gln Leu Leu Pro Glu Phe Ile Arg Glu Tyr
                245                 250                 255

Leu Ser Pro Lys Met Met Ala Glu Tyr Glu Arg Val Val Leu Glu Gln
            260                 265                 270

Leu Gly Leu Ala Ala Glu His Ile Glu Arg Ile Leu Ser Glu Thr Tyr
    275                 280                 285

```
Ser Glu Pro Pro Leu Glu Asp Phe Arg Ala Arg Tyr Pro Leu Ser Gly
    290                 295                 300

Tyr Leu Val Tyr Val Leu Met Gln Cys Asp Val Leu Ser His Ala Pro
305                 310                 315                 320

Thr Arg Glu Ala Phe Arg Arg Phe Lys Leu Leu Ala His
                325                 330

<210> SEQ ID NO 58
<211> LENGTH: 642
<212> TYPE: PRT
<213> ORGANISM: Cystobacter velatus
<220> FEATURE:
<221> NAME/KEY: MISC_FEATURE
<222> LOCATION: (1)..(642)
<223> OTHER INFORMATION: CysS

<400> SEQUENCE: 58

Met Ala Asn Gln Arg Val Ala Phe Ile Glu Leu Thr Val Phe Ser Gly
1               5                   10                  15

Val Tyr Pro Leu Ala Ser Gly Tyr Met Arg Gly Val Ala Glu Gln Asn
                20                  25                  30

Pro Leu Ile Arg Glu Ser Cys Ser Phe Glu Ile His Ser Ile Cys Ile
            35                  40                  45

Asn Asp Asp Arg Phe Glu Asp Lys Leu Asn Lys Ile Asp Ala Asp Val
50                  55                  60

Tyr Ala Ile Ser Cys Tyr Val Trp Asn Met Gly Phe Val Lys Arg Trp
65                  70                  75                  80

Leu Pro Thr Leu Thr Ala Arg Lys Pro Asn Ala His Ile Ile Leu Gly
                85                  90                  95

Gly Pro Gln Val Met Asn His Gly Ala Gln Tyr Leu Asp Pro Gly Asn
            100                 105                 110

Glu Arg Val Val Leu Cys Asn Gly Glu Gly Glu Tyr Thr Phe Ala Asn
        115                 120                 125

Tyr Leu Ala Glu Leu Cys Ser Pro Gln Pro Asp Leu Gly Lys Val Lys
130                 135                 140

Gly Leu Ser Phe Tyr Arg Asn Gly Glu Leu Ile Thr Thr Glu Pro Gln
145                 150                 155                 160

Ala Arg Ile Gln Asp Leu Asn Thr Val Pro Ser Pro Tyr Leu Glu Gly
                165                 170                 175

Tyr Phe Asp Ser Glu Lys Tyr Val Trp Ala Pro Leu Glu Thr Asn Arg
            180                 185                 190

Gly Cys Pro Tyr Gln Cys Thr Tyr Cys Phe Trp Gly Ala Ala Thr Asn
        195                 200                 205

Ser Arg Val Phe Lys Ser Asp Met Asp Arg Val Lys Ala Glu Ile Thr
210                 215                 220

Trp Leu Ser Gln His Arg Ala Phe Tyr Ile Phe Ile Thr Asp Ala Asn
225                 230                 235                 240

Phe Gly Met Leu Thr Arg Asp Ile Glu Ile Ala Gln His Ile Ala Glu
                245                 250                 255

Cys Lys Arg Lys Tyr Gly Tyr Pro Leu Thr Ile Trp Leu Ser Ala Ala
            260                 265                 270

Lys Asn Ser Pro Asp Arg Val Thr Gln Ile Thr Arg Ile Leu Ser Gln
        275                 280                 285

Glu Gly Leu Ile Ser Thr Gln Pro Val Ser Leu Gln Thr Met Asp Ala
290                 295                 300
```

Asn Thr Leu Lys Ser Val Lys Arg Gly Asn Ile Lys Glu Ser Ala Tyr
305                 310                 315                 320

Leu Ser Leu Gln Glu Glu Leu His Arg Ser Lys Leu Ser Phe Val
            325                 330                 335

Glu Met Ile Trp Pro Leu Pro Gly Glu Thr Leu Glu Thr Phe Arg Glu
            340                 345                 350

Gly Ile Gly Lys Leu Cys Ser Tyr Asp Ala Asp Ala Ile Leu Ile His
            355                 360                 365

His Leu Leu Leu Ile Asn Asn Val Pro Met Asn Ser Gln Arg Glu Glu
            370                 375                 380

Phe Lys Leu Glu Val Ser Asn Asp Glu Asp Pro Asn Ser Glu Ala Gln
385                 390                 395                 400

Val Val Val Ala Thr Lys Asp Val Thr Arg Glu Glu Tyr Lys Glu Gly
            405                 410                 415

Val Arg Phe Gly Tyr His Leu Thr Ser Leu Tyr Ser Leu Arg Ala Leu
            420                 425                 430

Arg Phe Val Gly Arg Tyr Leu Asp Lys Gln Gly Arg Leu Ala Phe Lys
            435                 440                 445

Asp Leu Ile Ser Ser Phe Ser Glu Tyr Cys Lys Arg Asn Pro Asp His
450                 455                 460

Pro Tyr Thr Gln Tyr Ile Thr Ser Val Ile Asp Gly Thr Ser Gln Ser
465                 470                 475                 480

Lys Phe Ser Ala Asn Gly Gly Ile Phe His Val Thr Leu His Glu Phe
            485                 490                 495

Arg Arg Glu Phe Asp Gln Leu Leu Phe Gly Phe Ile Gln Thr Leu Gly
            500                 505                 510

Met Met Asn Asp Glu Leu Leu Glu Phe Leu Phe Glu Met Asp Leu Leu
            515                 520                 525

Asn Arg Pro His Val Tyr Ser Asn Thr Pro Ile Asn Asn Gly Glu Gly
            530                 535                 540

Leu Leu Lys His Val Thr Val Val Ser Lys Glu Lys Asp Ala Ile Val
545                 550                 555                 560

Leu Arg Val Pro Glu Lys Tyr Ala Gln Leu Thr Ser Glu Leu Leu Gly
            565                 570                 575

Leu Glu Gly Ala Pro Ser Thr Ser Leu Arg Val Lys Tyr Arg Gly Thr
            580                 585                 590

Gln Met Pro Phe Met Ala Asn Lys Pro Tyr Glu Asp Asn Leu Ser Tyr
            595                 600                 605

Cys Glu Ala Lys Leu His Lys Met Gly Ser Ile Leu Pro Val Trp Glu
610                 615                 620

Ser Ala Val Pro Ser Arg Thr Pro Val Arg Arg Pro Gln Val Ala Val
625                 630                 635                 640

Ala Gly

<210> SEQ ID NO 59
<211> LENGTH: 1267
<212> TYPE: PRT
<213> ORGANISM: Cystobacter velatus
<220> FEATURE:
<221> NAME/KEY: MISC_FEATURE
<222> LOCATION: (1)..(1267)
<223> OTHER INFORMATION: CysT

<400> SEQUENCE: 59

Met His Arg Val Lys Pro Leu Ile Gly Pro Val Leu Ser Ala Leu Leu
1               5                   10                  15

```
Leu Cys Ala Leu Pro Ala Arg Ala Gln Ile Ala Ala Ala His Val Tyr
         20                  25                  30

His Asn His Met Pro Asn Phe Trp Ala Tyr Tyr Asp Leu Gly Gln Tyr
         35                  40                  45

Ala Ser Thr Pro Thr Gly Gly Pro Ile Arg Tyr Met Tyr Asp Ala Gln
 50                  55                  60

Val Ile Asn Leu Lys Lys Asn Pro Pro Ser Asn Tyr Thr Tyr Tyr Leu
 65                  70                  75                  80

Pro Ser Gly Ala Pro Met Pro His Asp Asp Leu Val Thr Tyr Tyr Ser
             85                  90                  95

His Asn Ala Lys Thr Gly Ala Tyr Leu Tyr Trp Pro Pro Ser Val Ala
             100                 105                 110

Ser Asp Met Lys Thr Asn Ala Pro Thr Gly Gln Val His Val Thr Met
             115                 120                 125

Ser Gly Ala Val Val Asn Asn Val Gln Asp Leu Val Thr Leu Lys Asn
 130                 135                 140

Val Pro Gly Tyr Asp Asn Pro Asn Trp Gly Ala Ser Trp Lys Asp Arg
145                 150                 155                 160

Tyr Ser Ala Leu Leu Thr Pro Ala Gly Asn Arg Thr Leu Asp Leu Ile
             165                 170                 175

His Phe Thr Gly His His Ser Met Gly Pro Leu Val Gly Pro Asp Tyr
             180                 185                 190

Phe Leu Lys Asp Leu Ile Tyr Gln Ser Ala Thr Leu Ala Gln Pro Tyr
             195                 200                 205

Phe Leu Gly Gly Ser Phe Gln Ser Ser Lys Gly Phe Phe Pro Thr Glu
             210                 215                 220

Leu Gly Phe Ser Glu Arg Leu Ile Pro Thr Leu Ser Lys Leu Gly Val
225                 230                 235                 240

Gln Trp Ala Val Ile Gly Asp Asn His Phe Ser Arg Thr Leu Lys Asp
                 245                 250                 255

Tyr Pro Tyr Leu Asn Asp Pro Gly Ser Asp Thr Leu Val Ser Pro Pro
             260                 265                 270

Asn Arg Ala Asp Leu Gln Asn Thr Ser Ser Val Gly Ser Trp Val Ser
             275                 280                 285

Ala Gln Met Ala His Glu Gln Gln Val Ile Lys Asn Lys Tyr Pro Phe
290                 295                 300

Ala Ser Thr Pro His Trp Val Arg Tyr Val Asp Pro Ala Thr Gly Ala
305                 310                 315                 320

Glu Ser Arg Val Val Gly Ile Pro Val Asn Gln Asn Gly Ser Trp Leu
                 325                 330                 335

Glu Gly Trp Glu Gly Glu Ala Thr Val Asp Val Val Asn Leu Lys Ser
             340                 345                 350

Phe Glu Gly Leu Val Pro Gln Arg Gln Phe Phe Val Ile Ala His Asp
             355                 360                 365

Gly Asp Asn Ser Ser Gly Arg Ala Gly Ser Asp Ser Thr Trp Tyr Asn
             370                 375                 380

Gly Arg Ser Val Thr Cys Ala Asn Gly Val Gln Cys Val Gly Ile Ser
385                 390                 395                 400

Glu Tyr Leu Val His His Thr Pro Ala Ser Thr Asp Val Val His Val
                 405                 410                 415

Gln Asp Gly Ser Trp Val Asp Thr Arg Asp Ser Ser Ser Asp Pro Gln
             420                 425                 430
```

```
Trp His His Trp Lys Leu Pro Phe Gly Ile Trp Lys Gly Gln Phe Pro
            435                 440                 445

Ala Phe Asn Ala Ala Thr Gly Leu Asn Leu Ser Pro Lys Thr Asn Leu
450                 455                 460

Ser Gly Val Gln Glu Gly Met Thr Val Ser Leu Glu His Gly Trp His
465                 470                 475                 480

Tyr Leu Glu Arg Asn Phe Ala Leu Leu Gln Ala Ala Leu Asn Tyr Ala
                485                 490                 495

Lys Thr Ala Glu Gln Ile Trp Leu Asp Ala His Pro Asn His Trp Ser
            500                 505                 510

Pro Thr Thr Ala Ile Asp Lys Gln Ile Thr His Thr Gly Asn Gln Leu
        515                 520                 525

Asn Pro Trp Met Met Ser Phe Pro Val Lys Gly Asp Val Asn Asn Asp
    530                 535                 540

Trp Ala Gly Gly Ala Asn Pro Ala Glu Leu Ala Trp Tyr Phe Leu Leu
545                 550                 555                 560

Pro Ala Met Asp Ser Gly Phe Gly Tyr Tyr Asp Glu Asn Gln Asp Asp
                565                 570                 575

Asn Val Lys Pro Thr Leu Ser Phe Asn Gln Ser Leu Tyr Phe Ser Lys
            580                 585                 590

Pro Tyr Val Gln Gln Arg Ile Ala Gln Asp Lys Thr Gly Pro Ser Val
        595                 600                 605

Trp Trp Ala Gln Arg Trp Pro Tyr Asn Pro Gly Ser Ala Asn Thr Asp
    610                 615                 620

Lys Ser Glu Gly Trp Thr Leu His Phe Phe Asn Asn His Phe Ala Leu
625                 630                 635                 640

Tyr Thr Tyr Ala Tyr Asp Ala Ser Gly Ile Ser Ser Ile Lys Ala Arg
                645                 650                 655

Val Arg Val His Thr His Lys Ser Ile Asp Pro Leu Asp Asn Thr His
            660                 665                 670

Lys Val Tyr Asp Pro Ala Ala Arg Lys Ala Ala Gly Val Pro Asn Ile
        675                 680                 685

Asp Pro Ala Arg Val Gly Ala Trp Val Asp Tyr Pro Leu Thr Arg Arg
    690                 695                 700

Asp Leu Lys Pro Val Met Asn Gly Val Ser Trp Gln Pro Ala Tyr Leu
705                 710                 715                 720

Pro Val Met Ala Lys Val Pro Ala Gln Glu Ile Gly Asp Leu Tyr Tyr
                725                 730                 735

Val Tyr Leu Gly Asn Tyr Arg Asp Gln Leu Leu Asp Tyr Tyr Ile Glu
            740                 745                 750

Ala Thr Asp Ser Arg Gly Asn Ile Thr Arg Gly Glu Ile Gln Ser Val
        755                 760                 765

Tyr Val Gly Ser Gly Arg Tyr Asn Leu Val Gly Gly Lys Tyr Ile Glu
    770                 775                 780

Asp Pro Asn Gly Thr Val Gln Gly Thr His Pro Phe Leu Val Val Asp
785                 790                 795                 800

Thr Thr Ala Pro Ser Val Pro Ser Gly Leu Thr Ala Lys Ala Lys Thr
                805                 810                 815

Asp Arg Ser Val Thr Leu Ser Trp Ser Ala Ala Ser Asp Asn Val Ala
            820                 825                 830

Val Ser Gly Tyr Asp Val Phe Arg Asp Gly Thr Gln Val Gly Ser Ser
        835                 840                 845

Thr Ser Thr Ala Tyr Thr Asp Ser Gly Leu Ser Pro Ser Thr Gln Tyr
```

-continued

```
            850                 855                 860
Ser Tyr Thr Val Arg Ala Arg Asp Ala Ala Gly Asn Ala Ser Ala Gln
865                 870                 875                 880

Ser Thr Ala Leu Ser Val Ala Thr Leu Thr Pro Asp Thr Thr Pro Pro
                    885                 890                 895

Ser Val Pro Ser Gly Leu Thr Ala Ser Gly Thr Thr Ser Ser Ser Val
                900                 905                 910

Ala Leu Ala Trp Thr Ala Ser Thr Asp Asn Tyr Gly Val Ala Asn Tyr
                    915                 920                 925

Glu Val Leu Arg Asn Gly Thr Gln Val Ala Ser Val Thr Gly Thr Thr
                930                 935                 940

Tyr Ser Asp Thr Gly Leu Ser Pro Ser Thr Thr Tyr Ser Tyr Thr Val
945                 950                 955                 960

Arg Ala Arg Asp Ala Ala Gly Asn Val Ser Ser Pro Ser Thr Ala Leu
                    965                 970                 975

Ser Val Thr Thr Gln Thr Gly Asn Ser Ala Thr Val Tyr Tyr Phe Asn
                    980                 985                 990

Asn Asn Phe Ala Leu Lys Tyr Ile His Phe Arg Ile Gly Gly Gly Thr
            995                 1000                1005

Trp Thr Thr Val Pro Gly Asn Val Met Ala Thr Ser Glu Val Pro
        1010                1015                1020

Gly Tyr Ala Lys Tyr Thr Val Asn Leu Gly Ala Ala Thr Gln Leu
        1025                1030                1035

Glu Cys Val Phe Asn Asp Gly Lys Gly Thr Trp Asp Asn Asn Lys
        1040                1045                1050

Gly Asn Asn Tyr Leu Leu Pro Ala Gly Thr Ser Thr Val Lys Asp
        1055                1060                1065

Gly Val Val Ser Ser Gly Ala Pro Ala Leu Asp Thr Thr Ala Pro
        1070                1075                1080

Ser Val Pro Ser Gly Leu Thr Ala Ala Ser Lys Thr Ser Ser Ser
        1085                1090                1095

Val Ser Leu Ser Trp Ser Ala Ser Thr Asp Ala Ser Gly Ile Ala
        1100                1105                1110

Gly Tyr Asp Val Tyr Arg Asp Gly Ser Leu Val Gly Ser Pro Val
        1115                1120                1125

Ser Thr Ser Tyr Thr Asp Ser Asp Leu Ser Ala Gly Thr Thr Tyr
        1130                1135                1140

Arg Tyr Thr Val Arg Ala Arg Asp Thr Ala Gly Asn Ala Ser Ala
        1145                1150                1155

Gln Ser Thr Ala Leu Ser Val Thr Thr Ser Thr Ser Ser Ala Thr
        1160                1165                1170

Ser Val Thr Phe Asn Val Thr Ala Ser Thr Val Val Gly Gln Asn
        1175                1180                1185

Val Tyr Leu Val Gly Asn His Ala Ala Leu Gly Asn Trp Asn Thr
        1190                1195                1200

Gly Ala Ala Ile Leu Leu Ser Pro Ala Ser Tyr Pro Lys Trp Ser
        1205                1210                1215

Val Thr Leu Ser Leu Pro Gly Ser Thr Ala Leu Glu Tyr Lys Tyr
        1220                1225                1230

Ile Lys Lys Asp Gly Ser Gly Asn Val Thr Trp Glu Ser Gly Ala
        1235                1240                1245

Asn Arg Ser Thr Thr Ile Pro Ala Ser Gly Thr Ala Thr Leu Asn
        1250                1255                1260
```

Asp Thr Trp Lys
    1265

<210> SEQ ID NO 60
<211> LENGTH: 276
<212> TYPE: PRT
<213> ORGANISM: Cystobacter velatus
<220> FEATURE:
<221> NAME/KEY: MISC_FEATURE
<222> LOCATION: (1)..(276)
<223> OTHER INFORMATION: ORF1

<400> SEQUENCE: 60

Val Pro His Pro Ser Glu Gln Ser Ala Pro Ser Gly Leu Arg Ala Arg
1               5                   10                  15

Leu His Glu Ile Ile Phe Glu Ser Asp Thr Pro Ala Gly Arg Ala Phe
            20                  25                  30

Asp Val Ala Leu Leu Trp Ala Ile Val Leu Ser Val Leu Ala Val Met
        35                  40                  45

Leu Glu Ser Val Glu Ser Ile Ser Val Gln His Gly Gln Thr Ile Arg
    50                  55                  60

Val Leu Glu Trp Cys Phe Thr Gly Leu Phe Thr Leu Glu Tyr Val Leu
65                  70                  75                  80

Arg Leu Leu Ser Val Lys Arg Pro Leu Arg Tyr Ala Leu Ser Phe Phe
                85                  90                  95

Gly Leu Val Asp Leu Leu Ala Ile Leu Pro Ser Val Leu Ser Leu Met
            100                 105                 110

Leu Pro Gly Met Gln Ser Leu Leu Val Val Arg Val Phe Arg Leu Leu
        115                 120                 125

Arg Val Phe Arg Val Leu Lys Leu Ala Ser Phe Leu Gly Glu Ala Asp
    130                 135                 140

Val Leu Leu Thr Ala Leu Arg Ala Ser Arg Arg Lys Ile Ile Val Phe
145                 150                 155                 160

Leu Gly Ala Val Leu Ser Thr Val Val Ile Met Gly Ala Val Met Tyr
                165                 170                 175

Met Val Glu Gly Arg Ala Asn Gly Phe Asp Ser Ile Pro Arg Gly Met
            180                 185                 190

Tyr Trp Ala Ile Val Thr Met Thr Thr Val Gly Tyr Gly Asp Leu Ser
        195                 200                 205

Pro Lys Thr Val Pro Gly Gln Phe Ile Ala Ser Val Leu Met Ile Met
    210                 215                 220

Gly Tyr Gly Ile Leu Ala Val Pro Thr Gly Ile Val Ser Val Glu Leu
225                 230                 235                 240

Ala Gln Ala Thr Arg Gln His Ala Ile Asp Pro Arg Ala Cys Pro Gly
                245                 250                 255

Cys Gly Leu Gln Gly His Asp Leu Asp Ala His His Cys Lys His Cys
            260                 265                 270

Gly Thr Ala Leu
        275

<210> SEQ ID NO 61
<211> LENGTH: 78
<212> TYPE: PRT
<213> ORGANISM: Cystobacter velatus
<220> FEATURE:
<221> NAME/KEY: MISC_FEATURE
<222> LOCATION: (1)..(78)
<223> OTHER INFORMATION: ORF2

-continued

```
<400> SEQUENCE: 61

Met Ala Gln Asp Gln Asp Arg Glu Lys Leu His Ser Asp Ala Asp Lys
1               5                   10                  15

Glu Arg Leu His Pro Lys Val Asp Ser Gly Asp Val Ser Gly Arg Gly
            20                  25                  30

Arg Glu Arg Arg Pro Asp Glu Glu Tyr Pro Lys Gln Arg Asn Ala Gly
        35                  40                  45

Glu Phe Gly Thr His Gly Gly Pro Asn Lys Gly Lys Glu Asp Arg
    50                  55                  60

Arg Gln Leu His Ala Pro Gly Ser Ser Lys Ala Gly Ser Gln
65                  70                  75

<210> SEQ ID NO 62
<211> LENGTH: 162
<212> TYPE: PRT
<213> ORGANISM: Cystobacter velatus
<220> FEATURE:
<221> NAME/KEY: MISC_FEATURE
<222> LOCATION: (1)..(162)
<223> OTHER INFORMATION: ORF3

<400> SEQUENCE: 62

Met Gly Arg Thr Tyr Ser Phe Glu Pro Phe Leu Ser Gln Gln Pro Ala
1               5                   10                  15

Gln Thr Tyr Lys Gly Ser Gly Pro Arg Leu Gly Asn Glu Glu His Lys
            20                  25                  30

Ile Ala Leu Thr Lys Glu Glu Lys Ala Ala Leu Pro Asp Thr Pro
        35                  40                  45

Thr Gly Tyr Gly Gln Ala His Ala Glu Thr Val Lys Arg Tyr Arg Ala
    50                  55                  60

Arg Ala Glu Lys Lys Arg Thr Glu Pro Lys Thr Pro Ala Thr Arg Ala
65                  70                  75                  80

Lys Lys Ala Ala Pro Lys Ala Lys Pro Thr Arg Lys Val Ala Thr Gln
                85                  90                  95

Glu Ala Thr Ala Lys Ala Pro Thr Arg Gln Ala Arg Glu Glu Thr Glu
            100                 105                 110

Pro Lys Ala Pro Ala Arg Lys Lys Leu Ser Ala Thr Gly Leu Val Gly
        115                 120                 125

Ser Ile Gly Arg Lys Val Val Thr Arg Ala Ala Val Ala Ala Lys Lys
    130                 135                 140

Thr Val Ala Arg Ala Val Lys Thr Ala Ala Arg Lys Ser Ala Lys
145                 150                 155                 160

Lys Arg

<210> SEQ ID NO 63
<211> LENGTH: 87
<212> TYPE: PRT
<213> ORGANISM: Cystobacter velatus
<220> FEATURE:
<221> NAME/KEY: MISC_FEATURE
<222> LOCATION: (1)..(87)
<223> OTHER INFORMATION: ORF4

<400> SEQUENCE: 63

Met Ser Pro Ala Arg Arg Lys Glu Ser Lys Gln His Glu Val Gly Ser
1               5                   10                  15

Ala Thr His Ala Arg Arg Val Ile Val Ala Thr Asp Gly Arg Gly Trp
            20                  25                  30
```

```
Tyr Val Arg Phe Glu Gly Asn Arg Gln Leu Gly Arg Tyr Ser Asn Val
            35                  40                  45

Thr Gln Ala Ile His Gly Arg Arg Leu Ala Arg Gln His Lys Pro
    50                  55                  60

Ala Gly Leu Val Val Arg Tyr Leu Asp Gly Glu Glu Glu Ser Trp
65                  70                  75                  80

Tyr Gly Asp Arg Glu Ala Pro
                85

<210> SEQ ID NO 64
<211> LENGTH: 149
<212> TYPE: PRT
<213> ORGANISM: Cystobacter velatus
<220> FEATURE:
<221> NAME/KEY: MISC_FEATURE
<222> LOCATION: (1)..(149)
<223> OTHER INFORMATION: ORF5

<400> SEQUENCE: 64

Met Lys His Ile Lys Ala Val Val Gly Ala Leu Ser Ala Ala Leu
1               5                   10                  15

Leu Phe Gly Val Gly Cys Gln Thr Thr Gly Ala Gly Asn Gln Gly
            20                  25                  30

Thr Gly Gly Ser Asp Thr Ser Gln Gly Gly Thr Met Thr Gly Ser Glu
        35                  40                  45

Thr Thr Gly Thr Gly Thr Thr Gly Gly Thr Thr Glu Gly Gly Asp Thr
    50                  55                  60

Thr Gly Gly Gly Thr Gly Gly Thr Gly Ala Gly Asp Ile Asp Gly Ser
65                  70                  75                  80

Ser Ser Gly Ser Thr Gly Ser Gly Ser Asp Val Gly Gly Ser Gly Gly
                85                  90                  95

Ser Gly Val Ser Ser Glu Pro Gly Gly Phe Ser Pro Asp Ala Ser Gly
            100                 105                 110

Val Asp Ser Asp Leu Gly Gly Ser Gly Thr Gly Ser Asp Val Asp Gly
        115                 120                 125

Ser Gly Ser Thr Asp Ser Ser Gly Asn Met Ser Gly Thr Gly Ser Glu
    130                 135                 140

Asp Asp Thr Ser Arg
145

<210> SEQ ID NO 65
<211> LENGTH: 525
<212> TYPE: PRT
<213> ORGANISM: Cystobacter velatus
<220> FEATURE:
<221> NAME/KEY: MISC_FEATURE
<222> LOCATION: (1)..(525)
<223> OTHER INFORMATION: ORF6

<400> SEQUENCE: 65

Met Ser Thr Arg Thr Ser Leu Ala Leu Ala Ala Ser Leu Ala Ala Leu
1               5                   10                  15

Pro Ala Leu Ala Gln Glu Arg Pro Ser Glu Gly Asp Leu Phe Gly Gly
            20                  25                  30

Asp Thr Pro Glu Thr Lys Pro Ala Pro Ala Asp Ala Pro Arg Pro Asp
        35                  40                  45

Glu Ser Ser Leu Phe Gly Asp Thr Pro Ala Ser Thr Pro Ala Ala Gln
    50                  55                  60
```

```
Ser Ala Ala Ala Thr Ala Pro Asp Lys Pro Ser Ala Thr Pro Gln
 65                  70                  75                  80

Asp Arg Asp Ala Gln Ala Leu Gly Gly Pro Ser Ala Thr Asn Ala Phe
                 85                  90                  95

Asp Thr Glu Glu Ala Val Glu Asp Pro Leu Lys Ile Gly Gly Arg Phe
            100                 105                 110

Tyr Leu Arg Ala Tyr Ser Gln Ala Asn Glu Gly Val Ser Phe Ser Asn
        115                 120                 125

Thr Thr Phe Ser Ala Pro Met Leu Val Asp Gly Tyr Phe Asp Ala Arg
    130                 135                 140

Pro Thr Glu Arg Leu Arg Gly Phe Val Leu Gly Arg Leu Thr Phe Asp
145                 150                 155                 160

Pro Thr Arg Lys Ala Gly Ser Leu Gly Ile Val Pro Thr Ser Thr Ser
                165                 170                 175

Thr Ser Asn Val Ala Ala Asp Pro Val Val Leu Leu Asp Gln Ala Trp
            180                 185                 190

Leu Arg Phe Asp Leu Asp His Lys Leu Phe Ile Thr Val Gly Lys Gln
        195                 200                 205

His Val Lys Trp Gly Thr Ser Arg Phe Trp Asn Pro Thr Asp Phe Leu
    210                 215                 220

Ser Pro Gln Arg Arg Asp Pro Leu Ala Leu Leu Asp Thr Arg Thr Gly
225                 230                 235                 240

Ala Thr Met Leu Lys Met His Met Pro Trp Glu Ala Lys Gly Trp Asn
                245                 250                 255

Phe Tyr Val Leu Gly Leu Leu Asp Asn Ala Gly Pro Ala Asn Thr Leu
            260                 265                 270

Gly Arg Val Gly Gly Ala Ala Arg Ala Glu Val Val Leu Gly His Thr
        275                 280                 285

Glu Leu Gly Val Asp Ala Val Leu Gln His Gly Arg Lys Pro Arg Phe
    290                 295                 300

Gly Leu Asp Leu Ser Ser Gly Leu Gly Pro Ile Asp Ile Tyr Gly Glu
305                 310                 315                 320

Leu Ala Leu Lys Lys Gly Ser Asp Ala Pro Met Phe Arg Met Pro Gln
                325                 330                 335

Gly Val Ser Leu Gly Asp Leu Leu Gly Gln Phe Gln Gly Asn Gly Gly
            340                 345                 350

Met Pro Pro Asp Leu Gly Ala Leu Pro Ile Glu Ala Tyr Tyr Pro Glu
        355                 360                 365

Gly Tyr Thr Pro Gln Val Ser Gly Gly Ala Thr Trp Thr Phe Ala Tyr
    370                 375                 380

Ser Glu Ser Asp Thr Ala Thr Val Gly Val Glu Tyr Phe Tyr Asn Ser
385                 390                 395                 400

Met Gly Tyr Pro Gly Ser Leu Ala Tyr Pro Tyr Leu Ile Leu Gln Gly
                405                 410                 415

Gln Tyr Gln Pro Phe Tyr Leu Gly Arg His Tyr Ala Ala Val Tyr Ala
            420                 425                 430

Phe Leu Ser Gly Pro Gly Ser Trp Asp Asn Thr Asn Phe Ile Leu Ser
        435                 440                 445

Asn Leu Gly Asn Leu Ser Asp Arg Ser Phe Ile Thr Arg Leu Asp Val
    450                 455                 460

Thr His Arg Ala Leu Arg Tyr Leu Ser Ile Glu Ala Phe Ile Ala Ala
465                 470                 475                 480

Asn Tyr Gly Gln Arg Gly Gly Glu Phe Arg Phe Ala Leu Asn Leu Pro
```

```
                    485                 490                 495
Ala Leu Arg Met Gly Glu Gln Val Thr Pro Pro Ile Ala Val Ala Pro
                500                 505                 510

Pro Thr Ile Gln Ala Gly Val Gly Leu Arg Ile Asp Leu
            515                 520                 525

<210> SEQ ID NO 66
<211> LENGTH: 261
<212> TYPE: PRT
<213> ORGANISM: Cystobacter velatus
<220> FEATURE:
<221> NAME/KEY: MISC_FEATURE
<222> LOCATION: (1)..(261)
<223> OTHER INFORMATION: ORF7

<400> SEQUENCE: 66

Met Thr Leu Arg Asn Leu Leu Gly Ala Leu Phe Ala Ala Leu Leu Leu
1               5                   10                  15

Ala Ala Pro Thr Ala Arg Ala Asp Leu Thr Asp Pro Ala Glu Ile Lys
            20                  25                  30

Lys Leu Leu Glu Thr Leu Asp Asn Arg Gln Arg Asn Gly Gly Asp Tyr
        35                  40                  45

Lys Ser Leu Val Tyr Ile Glu Gln Lys Lys Asp Lys Thr Asp Val
    50                  55                  60

Val Arg Glu Ala Val Val Tyr Arg Arg Asp Glu Lys Asp Gln Leu Met
65                  70                  75                  80

Ile Leu Met Thr Lys Pro Lys Gly Glu Ala Gly Lys Gly Tyr Leu Arg
                85                  90                  95

Leu Asp Lys Asn Leu Trp Ser Tyr Asp Pro Asn Thr Gly Lys Trp Asp
            100                 105                 110

Arg Arg Thr Glu Arg Glu Arg Ile Ala Gly Thr Asp Ser Arg Arg Ala
        115                 120                 125

Asp Phe Asp Glu Ser Arg Leu Ala Glu Glu Leu Asp Gly Lys Phe Glu
    130                 135                 140

Gly Glu Glu Lys Leu Gly Lys Phe Thr Thr Trp Lys Leu Val Leu Thr
145                 150                 155                 160

Ala Lys Pro Asn Val Asp Val Ala Tyr Pro Val Val His Leu Trp Val
                165                 170                 175

Glu Lys Asp Thr Asn Asn Ile Leu Lys Arg Gln Glu Phe Ala Leu Ser
            180                 185                 190

Gly Arg Leu Met Arg Thr Ser Tyr Phe Pro Lys Trp Met Lys Leu Phe
        195                 200                 205

Ser Glu Ser Lys Lys Ala Asp Val Trp Tyr Pro Gln Glu Met Arg Phe
    210                 215                 220

Tyr Asp Glu Val Glu Lys Thr Asn Ser Thr Val Ile Val Val Lys Ser
225                 230                 235                 240

Val Asp Leu Arg Ser Leu Glu Glu Asn Ile Phe Thr Lys Ala Trp Phe
                245                 250                 255

Glu Ser Lys Ser Arg
            260

<210> SEQ ID NO 67
<211> LENGTH: 433
<212> TYPE: PRT
<213> ORGANISM: Cystobacter velatus
<220> FEATURE:
<221> NAME/KEY: MISC_FEATURE
<222> LOCATION: (1)..(433)
```

<223> OTHER INFORMATION: ORF8

<400> SEQUENCE: 67

```
Met Gln Gln Leu Leu Leu Ile Ala Val Arg Asn Leu Gly Thr His Lys
1               5                   10                  15

Arg Arg Thr Leu Leu Leu Gly Gly Ala Ile Ala Gly Val Thr Ala Leu
            20                  25                  30

Leu Val Ile Leu Met Gly Leu Ser Asn Gly Met Lys Asp Thr Met Leu
        35                  40                  45

Arg Ser Ala Thr Thr Leu Val Thr Gly His Val Asn Val Ala Gly Phe
    50                  55                  60

Tyr Lys Val Thr Ala Gly Gln Ser Ala Pro Val Val Thr Ser Tyr Pro
65                  70                  75                  80

Lys Leu Leu Glu Gln Leu Arg Lys Glu Val Pro Glu Leu Asp Phe Ser
                85                  90                  95

Val Gln Arg Thr Arg Gly Trp Val Lys Leu Val Ser Glu Ser Gly Ser
            100                 105                 110

Val Gln Thr Gly Ile Gly Gly Ile Asp Val Ala Ala Glu Thr Gly Ile
        115                 120                 125

Arg Lys Val Leu Gln Leu Arg Glu Gly Arg Leu Glu Asp Leu Ala Gln
    130                 135                 140

Pro Asn Thr Leu Leu Leu Phe Asp Glu Gln Ala Lys Arg Leu Glu Val
145                 150                 155                 160

Lys Val Gly Asp Ser Val Thr Leu Ser Ala Ser Thr Met Arg Gly Ile
                165                 170                 175

Ser Asn Thr Val Asp Val Arg Val Val Ala Ile Ala Ala Asn Val Gly
            180                 185                 190

Met Leu Ser Ser Phe Asn Val Leu Val Pro Asn Ala Thr Leu Arg Ala
        195                 200                 205

Leu Tyr Gln Leu Arg Glu Asp Ser Thr Gly Ala Leu Met Leu His Leu
    210                 215                 220

Lys Asp Met Ser Ala Ile Pro Ser Val Gln Ala Arg Leu Tyr Lys Arg
225                 230                 235                 240

Leu Pro Glu Leu Gly Tyr Gln Val Leu Glu His Asp Pro Arg Ala Phe
                245                 250                 255

Phe Met Lys Phe Gln Thr Val Asn Arg Glu Ala Trp Thr Gly Gln Lys
            260                 265                 270

Leu Asp Ile Thr Asn Trp Glu Asp Glu Ile Ser Phe Ile Lys Trp Thr
        275                 280                 285

Val Ser Ala Met Asp Ala Leu Thr Gly Val Leu Ile Phe Val Leu Leu
    290                 295                 300

Ile Ile Ile Ala Val Gly Ile Met Asn Thr Leu Trp Ile Ala Ile Arg
305                 310                 315                 320

Glu Arg Thr Arg Glu Ile Gly Thr Leu Arg Ala Ile Gly Met Gln Arg
                325                 330                 335

Trp Tyr Val Leu Val Met Phe Leu Leu Glu Ala Leu Val Leu Gly Leu
            340                 345                 350

Leu Gly Thr Thr Val Gly Ala Leu Val Gly Met Gly Val Cys Leu Leu
        355                 360                 365

Ile Asn Ala Val Asp Pro Ser Val Pro Val Gln Leu Phe Ile
    370                 375                 380

Leu Ser Asp Lys Leu His Leu Ile Val Lys Pro Gly Ser Val Met Arg
385                 390                 395                 400
```

```
Ala Ile Ala Phe Ile Thr Leu Cys Thr Thr Phe Ile Ser Leu Ile Pro
                405                 410                 415

Ser Phe Leu Ala Ala Arg Met Lys Pro Ile Thr Ala Met His His Ile
            420                 425                 430

Gly

<210> SEQ ID NO 68
<211> LENGTH: 701
<212> TYPE: PRT
<213> ORGANISM: Cystobacter velatus
<220> FEATURE:
<221> NAME/KEY: MISC_FEATURE
<222> LOCATION: (1)..(701)
<223> OTHER INFORMATION: ORF9

<400> SEQUENCE: 68

Met Gly Gln Leu Lys Leu Leu Gln Val Ala Leu Arg Asn Leu Phe
1               5                   10                  15

Val Ser Arg Ile Asn Leu Leu Ile Gly Gly Ile Ile Phe Phe Gly Thr
            20                  25                  30

Val Leu Val Val Val Gly Gly Ser Leu Val Asp Ser Val Asp Glu Ala
        35                  40                  45

Met Ser Arg Ser Ile Ile Gly Ser Val Ala Gly His Leu Gln Val Tyr
    50                  55                  60

Ser Ala His Ser Lys Asp Glu Leu Ser Leu Phe Gly Gln Met Gly Arg
65                  70                  75                  80

Glu Pro Asp Leu Ser Ala Leu Asp Asp Phe Ser Arg Ile Lys Gln Leu
                85                  90                  95

Val Gln Gln His Pro Asn Val Lys Thr Val Pro Met Gly Thr Gly
            100                 105                 110

Ala Thr Phe Ile Asn Ser Gly Asn Thr Ile Asp Leu Thr Leu Ala Arg
            115                 120                 125

Leu Arg Asp Leu Tyr Lys Lys Ala Ala Gln Gly Asp Thr Pro Glu Leu
        130                 135                 140

Arg Gly Gln Ile His Ser Leu Gln Ala His Val Arg His Ile Ile Thr
145                 150                 155                 160

Leu Leu Glu Glu Asp Met Lys Arg Arg Arg Glu Ile Ile Asp Asp Lys
                165                 170                 175

Thr Thr Asp Pro Ala Asp Ala Glu Ala Met Ala Arg Ala Arg Ser Glu
            180                 185                 190

Ala Phe Trp Ala Asp Phe Asp Glu Lys Pro Phe Asp Ser Leu Glu Phe
        195                 200                 205

Leu Glu Asn Arg Ile Ala Pro Tyr Met Thr Asp Gly Asp Met Leu Ser
    210                 215                 220

Leu Arg Tyr Val Gly Thr Asp Leu Val Asn Phe Gln Lys Thr Phe Asp
225                 230                 235                 240

Arg Met Arg Ile Val Glu Gly Thr Pro Val Pro Pro Gly His Arg Gly
                245                 250                 255

Met Met Leu Ser Lys Phe Thr Tyr Glu Asn Asp Phe Lys Leu Lys Thr
            260                 265                 270

Ala His Arg Leu Asp Leu Ile Lys Glu Ala Arg Asp Thr Asn His Lys
        275                 280                 285

Thr Ile Ala Met Asp Pro Gln Leu Gln Arg Trp Val Lys Glu Asn Gln
    290                 295                 300

Thr Gln Thr Arg Glu Ile Leu Phe Gln Leu Asp Asp Leu Lys Thr Lys
305                 310                 315                 320
```

Gln Ala Val Glu Arg Leu Gln Arg Val Leu Gly Ser Gln Glu Thr Asp
            325                 330                 335

Leu Gly Lys Leu Leu Pro Ala Phe Phe Thr Met Asp Asp Ala Asn Phe
            340                 345                 350

Asp Thr Arg Tyr Gln Gln Phe Tyr Ser Glu Leu Ala Thr Leu Leu Asp
            355                 360                 365

Leu Tyr Arg Ile Arg Ile Gly Asp Asp Leu Thr Ile Thr Ala Phe Ser
    370                 375                 380

Arg Thr Gly Tyr Val Gln Ser Val Asn Val Lys Ile Tyr Gly Thr Tyr
385                 390                 395                 400

Gln Phe Asp Gly Leu Glu Lys Ser Ala Val Ala Gly Ala Leu Asn Leu
            405                 410                 415

Leu Asp Leu Met Ser Phe Arg Glu Leu Tyr Gly Tyr Leu Thr Ala Glu
            420                 425                 430

Lys Lys Ala Glu Leu Ala Gly Leu Gln Lys Ala Ser Gly Val Gln Gln
            435                 440                 445

Val Lys Arg Glu Asp Ala Glu Thr Ala Leu Phe Gly Glu Gln Gly Ser
    450                 455                 460

Ala Ser Leu Val Ala Glu Gly Thr Ala Gly Gln Ile Asp Glu Asp Lys
465                 470                 475                 480

Gln Leu Asp Gly Leu Ala Gln Lys Leu His Arg Glu Glu Leu Ala Ser
            485                 490                 495

Arg Val Tyr Thr Gln Gln Glu Ile Glu Ser Gly Val Val Leu Ser Thr
            500                 505                 510

Ala Val Leu Leu Lys His Pro Glu Lys Leu Glu Gln Thr Leu Ala Glu
            515                 520                 525

Leu Arg Lys Ser Ala Asp Asp Ala Lys Leu Pro Leu Arg Ile Ile Ser
    530                 535                 540

Trp Gln Lys Ala Ser Gly Thr Ile Gly Gln Phe Val Leu Val Ala Lys
545                 550                 555                 560

Leu Val Leu Tyr Phe Ala Val Phe Ile Ile Phe Val Ala Leu Val
            565                 570                 575

Ile Ile Asn Asn Ala Met Met Met Ala Thr Leu Gln Arg Val Arg Glu
            580                 585                 590

Val Gly Thr Leu Arg Ala Ile Gly Ala Gln Arg Ser Phe Val Leu Ser
    595                 600                 605

Met Val Leu Val Glu Thr Val Val Leu Gly Leu Val Phe Gly Val Leu
610                 615                 620

Gly Ala Ala Met Gly Gly Ala Ile Met Asn Met Leu Gly His Val Gly
625                 630                 635                 640

Ile Pro Ala Gly Asn Glu Ala Leu Tyr Phe Phe Ser Gly Pro Arg
            645                 650                 655

Leu Phe Pro Ser Leu His Leu Ser Asn Leu Val Ala Ala Phe Val Ile
            660                 665                 670

Val Leu Val Ser Ala Leu Ser Thr Phe Tyr Pro Ala Tyr Leu Ala
            675                 680                 685

Thr Arg Val Ser Pro Leu Gln Ala Met Gln Thr Asp Glu
690                 695                 700

<210> SEQ ID NO 69
<211> LENGTH: 253
<212> TYPE: PRT
<213> ORGANISM: Cystobacter velatus
<220> FEATURE:

-continued

```
<221> NAME/KEY: MISC_FEATURE
<222> LOCATION: (1)..(253)
<223> OTHER INFORMATION: ORF10

<400> SEQUENCE: 69

Met Ser Gln Val Thr Ala Leu Pro Gly Ser Thr Gln Pro Ile Val Ser
1               5                   10                  15

Leu Thr Glu Val Thr Lys Thr Tyr Ser Leu Gly Lys Val Gln Val Pro
            20                  25                  30

Ala Leu Arg Gly Val Thr Leu Glu Val Tyr Pro Gly Glu Phe Ile Ser
        35                  40                  45

Ile Ala Gly Pro Ser Gly Ser Gly Lys Thr Thr Ala Leu Asn Leu Ile
    50                  55                  60

Gly Cys Val Asp Thr Ala Ser Ser Gly Val Val Ser Val Asp Gly Gln
65                  70                  75                  80

Asp Thr Lys Lys Leu Thr Glu Arg Gln Leu Thr His Leu Arg Leu His
                85                  90                  95

Thr Ile Gly Phe Ile Phe Gln Ser Phe Asn Leu Val Ser Val Leu Ser
            100                 105                 110

Val Phe Gln Asn Val Glu Phe Pro Leu Leu Leu Gln Arg Lys Leu Asn
        115                 120                 125

Ala Ser Glu Arg Arg Thr Arg Val Met Thr Leu Leu Glu Gln Val Gly
    130                 135                 140

Leu Glu Lys His Ala Lys His Arg Pro Asn Glu Leu Ser Gly Gly Gln
145                 150                 155                 160

Arg Gln Arg Val Ala Val Ala Arg Ala Leu Val Thr Arg Pro Lys Leu
                165                 170                 175

Val Leu Ala Asp Glu Pro Thr Ala Asn Leu Asp Ser Val Thr Gly Gln
            180                 185                 190

Asn Ile Ile Asp Leu Met Lys Glu Leu Asn Arg Lys Glu Gly Thr Thr
        195                 200                 205

Phe Ile Phe Ser Thr His Asp Ala Lys Val Met Thr His Ala Asn Ala
    210                 215                 220

Val Val Arg Leu Ala Asp Gly Lys Ile Leu Asp Arg Ile Thr Pro Ala
225                 230                 235                 240

Glu Ala Gln Lys Val Met Ala Val Ser Glu Gly Gly His
                245                 250

<210> SEQ ID NO 70
<211> LENGTH: 397
<212> TYPE: PRT
<213> ORGANISM: Cystobacter velatus
<220> FEATURE:
<221> NAME/KEY: MISC_FEATURE
<222> LOCATION: (1)..(397)
<223> OTHER INFORMATION: ORF11

<400> SEQUENCE: 70

Met Pro Gln Lys Phe Val Gly Lys Trp Lys Gly Arg Val Lys Leu
1               5                   10                  15

Val Asp Gly Arg Lys Val Trp Leu Leu Glu Lys Met Val Ser Gly Ala
            20                  25                  30

Arg Phe Ser Val Ser Leu Ala Val Ser Asn Glu Glu Asp Ala Leu Ala
        35                  40                  45

Glu Leu Ala Leu Phe Arg Arg Asp Arg Asp Ala Tyr Leu Ala Lys Val
    50                  55                  60

Lys Ala Asp Arg Ser Glu Glu Val Gln Ala Ser Thr Val Ala Gly Ala
```

```
                65                  70                  75                  80
Val Pro Leu Ser Gly Asp Val Gly Pro Arg Leu Asp Ala Asp Ser Val
                    85                  90                  95

Arg Glu Phe Leu Arg His Leu Thr Gln Arg Gly Arg Thr Glu Gly Tyr
                100                 105                 110

Arg Arg Asp Ala Arg Thr Tyr Leu Ser Gln Trp Ala Glu Val Leu Ala
                115                 120                 125

Gly Arg Asp Leu Ser Thr Val Ser Leu Leu Glu Leu Arg Arg Ala Leu
                130                 135                 140

Ser Gln Trp Pro Thr Ala Arg Lys Met Arg Ile Ile Thr Leu Lys Ser
145                 150                 155                 160

Phe Phe Ser Trp Leu Arg Glu Glu Asp Arg Leu Lys Ala Ala Glu Asp
                165                 170                 175

Pro Thr Leu Ser Leu Lys Val Pro Pro Ala Val Ala Glu Lys Gly Arg
                180                 185                 190

Arg Ala Lys Gly Tyr Ser Met Ala Gln Val Glu Lys Leu Tyr Ala Ala
                195                 200                 205

Ile Gly Ser Gln Thr Val Arg Asp Val Leu Cys Leu Arg Ala Lys Thr
                210                 215                 220

Gly Met His Asp Ser Glu Ile Ala Arg Leu Ala Ser Gly Lys Gly Glu
225                 230                 235                 240

Leu Arg Val Val Asn Asp Pro Ser Gly Ile Ala Gly Thr Ala Arg Phe
                245                 250                 255

Leu His Lys Asn Gly Arg Val His Ile Leu Ser Leu Asp Ala Gln Ala
                260                 265                 270

Leu Ala Ala Ala Gln Arg Leu Gln Val Arg Gly Arg Ala Pro Ile Arg
                275                 280                 285

Asn Thr Val Arg Glu Ser Ile Gly Tyr Ala Ser Ala Arg Ile Gly Gln
                290                 295                 300

Ser Pro Ile His Pro Ser Glu Leu Arg His Ser Phe Thr Thr Trp Ala
305                 310                 315                 320

Thr Asn Glu Gly Gln Val Val Arg Ala Thr Arg Gly Val Pro Leu
                325                 330                 335

Asp Val Val Ala Ser Val Leu Gly His Gln Ser Thr Arg Ala Thr Lys
                340                 345                 350

Lys Phe Tyr Asp Gly Thr Glu Ile Pro Pro Met Ile Thr Val Pro Leu
                355                 360                 365

Lys Leu His His Pro Gln Asp Pro Ala Val Met Gln Leu Arg Arg Asn
                370                 375                 380

Cys Ser Pro Asp Pro Val Val Thr Arg Glu Ala Glu Ala
385                 390                 395

<210> SEQ ID NO 71
<211> LENGTH: 124
<212> TYPE: PRT
<213> ORGANISM: Cystobacter velatus
<220> FEATURE:
<221> NAME/KEY: MISC_FEATURE
<222> LOCATION: (1)..(124)
<223> OTHER INFORMATION: ORF12

<400> SEQUENCE: 71

Val Leu Leu Ala Phe Pro Ser Gly Leu Leu Ser Leu Ala Leu Leu Ser
1               5                   10                  15

Thr Thr Thr Glu Ile Ser Ala Ala Leu Pro Val Asp Glu Cys Glu Ser
                20                  25                  30
```

```
Ala Ser Leu Arg Ile Glu Leu Pro Ala Thr Pro Gly Gly Lys Pro Pro
        35                  40                  45

Val Val Cys Leu Gly Pro Gly Leu Pro Ile His Phe Arg Phe Asp Ser
 50                  55                  60

Ala Leu Gln Gln Lys Ser Leu Arg Ile Gln Asp Arg Gly Trp Phe Glu
 65                  70                  75                  80

Asp Trp Ala Leu Gly Gln Gln Thr Leu Val Leu Thr Pro His Asp Asn
                 85                  90                  95

Leu Val Ala Gly Lys Arg Ser Glu Val Glu Val Cys Phe Ala Asp Gly
                100                 105                 110

Ala Ala Pro Ala Cys Ala Ser Phe Val Leu Arg Arg
                115                 120

<210> SEQ ID NO 72
<211> LENGTH: 112
<212> TYPE: PRT
<213> ORGANISM: Cystobacter velatus
<220> FEATURE:
<221> NAME/KEY: MISC_FEATURE
<222> LOCATION: (1)..(112)
<223> OTHER INFORMATION: ORF13

<400> SEQUENCE: 72

Met His Thr Lys Val Pro Ser Val Phe Glu Ala Thr Pro Glu Ser Leu
 1               5                  10                  15

Ser Asp Val Asp Tyr Gln Phe Trp His Glu Asp Phe Pro Arg Val Phe
                20                  25                  30

Glu Arg Gln His Ile Asp Ala His Ala Val Pro Ala Ile Gly Ala Tyr
             35                  40                  45

Leu Gly Glu Val Leu Val Arg Asn Leu Gly Gly Lys Trp Ile Pro Arg
         50                  55                  60

Gln Lys Leu Asp Glu Ala Gln Val Leu Val Gly Asn Arg Val Trp Leu
 65                  70                  75                  80

Pro Phe Ala Arg Ala His His Tyr Met Arg Ser Cys Glu Ser Leu Leu
                 85                  90                  95

Asp Tyr Ser Leu Thr Gln Leu Tyr Arg Val Ala Glu Arg Tyr Arg Gly
                100                 105                 110

<210> SEQ ID NO 73
<211> LENGTH: 304
<212> TYPE: PRT
<213> ORGANISM: Cystobacter velatus
<220> FEATURE:
<221> NAME/KEY: MISC_FEATURE
<222> LOCATION: (1)..(304)
<223> OTHER INFORMATION: ORF 14

<400> SEQUENCE: 73

Met Lys Val Leu Gly Leu Gly Asp Val Lys Ser Glu Asp Ser Leu Arg
 1               5                  10                  15

Leu Thr Phe Glu Gly Ala Leu Asp Pro Gln Ala Ala Leu Glu Lys Val
                20                  25                  30

Leu Glu Pro Phe Phe Gln Ala Leu Glu Glu Tyr Ala Gly Asp Trp Met
             35                  40                  45

Pro Glu Val Val Ser Gly Arg Arg Leu Lys Tyr Ser Arg Ala Asn
         50                  55                  60

Ile Trp Lys Ala Leu Glu Glu Arg Arg Asp Glu Arg Ser Thr Asp Thr
 65                  70                  75                  80
```

-continued

```
Trp Leu Tyr Arg Thr Gln Arg Pro Thr Leu Glu Met Ser Leu His Leu
            85              90                  95

Trp Phe Pro Pro Leu Pro Pro Ala Leu Asp Val Met Thr Thr Val Gln
            100             105                 110

Pro Leu Thr Arg Phe Ala Glu Lys Glu Arg Cys Arg Gln Phe Val Glu
            115             120                 125

Met Val Arg Thr Trp Ala Ser Cys Tyr Pro Val Thr His Ala Ala Ala
    130             135                 140

His Ser Val Ala Asp Arg Ala Leu Ala Gly Ala Pro Asp Phe Gly Arg
145             150              155                 160

Asp Ala Arg Thr Ala Arg Arg Asp Gly Phe Asp Arg Ile Tyr Glu Ile
            165             170                 175

Phe Trp Leu Asn Val Phe Gly Pro Lys Leu Val Glu Ala Val Gly Arg
            180             185                 190

Glu Arg Met Leu Ser Thr Pro Ala His Arg Val Glu Glu Leu Pro Asn
            195             200                 205

Gly Ser Ile Leu Leu Val Thr Trp Pro Thr Ala Ala Asp Phe Ala Gly
    210             215                 220

Ala Glu Ala Arg His Ala Gln Ala Arg Ala His Val His Leu Arg Pro
225             230             235                 240

Asp Leu Arg Phe Asp Thr Val Leu Arg Thr Leu His Glu Arg Ser Ala
            245             250                 255

Ala Leu Ala Pro Val Glu Pro Cys Phe His Pro Asp Val Ala Pro Leu
            260             265                 270

Leu Ser His Val Val Asp Ser Val Ala Ile Arg Met Trp Lys Thr Trp
    275             280                 285

Ser Ala Leu Thr Ser Ile Thr Glu Leu Trp Leu Ser Thr Ser Trp Arg
    290             295                 300
```

CYSTOBACTAMIDES

RELATED APPLICATIONS

This application is a continuation application of U.S. patent application Ser. No. 14/904,654, filed on Jan. 12, 2016 and is a national stage application, filed under 35 U.S.C. § 371, of International Application No. PCT/EP2014/001925, filed on Jul. 14, 2014, and claims priority to European Patent Application No. 13003539.7, filed on Jul. 12, 2013, both of which, including their contents, are incorporated herein by reference in their entireties.

Cystobactamides are novel natural products that have been isolated from myxobacterium *Cystobacter velatus* (MCy8071; internal name: *Cystobacter ferrugineus*). Cystobactamides exhibit a good antibiotic activity, especially against selected Gram-negative bacteria, such as *E. coli, P. aeruginosa*, and *A. baumannii*, as well as a broad spectrum activity against Gram-positive bacteria.

The present invention provides compounds of formula (I)

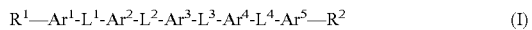

$$R^1—Ar^1-L^1-Ar^2-L^2-Ar^3-L^3-Ar^4-L^4-Ar^5—R^2 \quad (I)$$

wherein $Ar^1$ is an optionally substituted phenylene group or an optionally substituted heteroarylene group having 5 or 6 ring atoms including 1, 2, 3 or 4 heteroatoms selected from oxygen, sulphur and nitrogen;

$Ar^2$ is an optionally substituted phenylene group or an optionally substituted heteroarylene group having 5 or 6 ring atoms including 1, 2, 3 or 4 heteroatoms selected from oxygen, sulphur and nitrogen;

$Ar^3$ is an optionally substituted phenylene group or an optionally substituted heteroarylene group having 5 or 6 ring atoms including 1, 2, 3 or 4 heteroatoms selected from oxygen, sulphur and nitrogen;

$Ar^4$ is absent or an optionally substituted phenylene group or an optionally substituted heteroarylene group having 5 or 6 ring atoms including 1, 2, 3 or 4 heteroatoms selected from oxygen, sulphur and nitrogen;

$Ar^5$ is absent or an optionally substituted phenylene group or an optionally substituted heteroarylene group having 5 or 6 ring atoms including 1, 2, 3 or 4 heteroatoms selected from oxygen, sulphur and nitrogen;

$L^1$ is a bond, an oxygen atom, a sulphur atom or a group of formula NH, CONH, NHCO, COO, OCO, CONR$^3$, NR$^3$CO, OCONH, NHCOO, NHCONH, OCONR$^3$, NR$^3$COO, NR$^3$CONR$^4$, NR$^3$, —CNR$^3$—, —CO—, —SO—, —SO$_2$—, —SO$_2$NH—, —NHSO$_2$—, —SO$_2$NR$^3$—, —NR$^3$SO$_2$—, —COCH$_2$—, —CH$_2$CO—, —COCR$^3$R$^4$—, —CR$^3$R$^4$CO—, —NHCSNH—, —NR$^3$CSNR$^4$, —CH=CH—, —CR$^3$=CR$^4$—, or a heteroarylene group having 5 or 6 ring atoms including 1, 2, or 3 heteroatoms selected from oxygen, sulphur and nitrogen, or a heteroalkylene group;

$L^2$ is a bond, an oxygen atom, a sulphur atom or a group of formula NH, CONH, NHCO, COO, OCO, CONR$^3$, NR$^3$CO, OCONH, NHCOO, NHCONH, OCONR$^3$, NR$^3$COO, NR$^3$CONR$^4$, NR$^3$, —CNR$^3$—, —CO—, —SO—, —SO$_2$—, —SO$_2$NH—, —NHSO$_2$—, —SO$_2$NR$^3$—, —NR$^3$SO$_2$—, —COCH$_2$—, —CH$_2$CO—, —COCR$^3$R$^4$—, —CR$^3$R$^4$CO—, —NHCSNH—, —NR$^3$CSNR$^4$, —CH=CH—, —CR$^3$=CR$^4$—, or a heteroarylene group having 5 or 6 ring atoms including 1, 2, or 3 heteroatoms selected from oxygen, sulphur and nitrogen, or a heteroalkylene group;

$L^3$ is absent or a bond, an oxygen atom, a sulphur atom or a group of formula NH, CONH, NHCO, COO, OCO, CONR$^3$, NR$^3$CO, OCONH, NHCOO, NHCONH, OCONR$^3$, NR$^3$COO, NR$^3$CONR$^4$, NR$^3$, —CNR$^3$—, —CO—, —SO—, —SO$_2$—, —SO$_2$NH—, —NHSO$_2$—, —SO$_2$NR$^3$—, —NR$^3$SO$_2$—, —COCH$_2$—, —CH$_2$CO—, —COCR$^3$R$^4$—, —CR$^3$R$^4$CO—, —NHCSNH—, —NR$^3$CSNR$^4$, —CH=CH—, —CR$^3$=CR$^4$—, or a heteroarylene group having 5 or 6 ring atoms including 1, 2, or 3 heteroatoms selected from oxygen, sulphur and nitrogen, or a heteroalkylene group;

$L^4$ is absent or a bond, an oxygen atom, a sulphur atom or a group of formula NH, CONH, NHCO, COO, OCO, CONR$^3$, NR$^3$CO, OCONH, NHCOO, NHCONH, OCONR$^3$, NR$^3$COO, NR$^3$CONR$^4$, NR$^3$, —CNR$^3$—, —CO—, —SO—, —SO$_2$—, —SO$_2$NH—, —NHSO$_2$—, —SO$_2$NR$^3$—, —NR$^3$SO$_2$—, —COCH$_2$—, —CH$_2$CO—, —COCR$^3$R$^4$—, —CR$^3$R$^4$CO—, —NHCSNH—, —NR$^3$CSNR$^4$, —CH=CH—, —CR$^3$=CR$^4$—, or a heteroarylene group having 5 or 6 ring atoms including 1, 2, or 3 heteroatoms selected from oxygen, sulphur and nitrogen, or a heteroalkylene group;

$R^1$ is a hydrogen atom, a halogen atom, a hydroxy group, an amino group, a thiol group, a nitro group, a group of formula —COOH, —SO$_2$NH$_2$, —CONH$_2$, —NO$_2$ or —ON, an alkyl, an alkenyl, an alkynyl, a heteroalkyl, a cycloalkyl, a heterocycloalkyl, an alkylcycloalkyl, a heteroalkylcycloalkyl, an aryl, a heteroaryl, an aralkyl or a heteroaralkyl group;

$R^2$ is a hydrogen atom, a halogen atom, a hydroxy group, an amino group, a thiol group, a nitro group, a group of formula —COOH, —SO$_2$NH$_2$, —CONH$_2$, —NO$_2$ or —CN, an alkyl, an alkenyl, an alkynyl, a heteroalkyl, a cycloalkyl, a heterocycloalkyl, an alkylcycloalkyl, a heteroalkylcycloalkyl, an aryl, a heteroaryl, an aralkyl or a heteroaralkyl group;

the groups $R^3$ are independently from each other a hydrogen atom or a C$_{1-6}$ alkyl group; and the groups $R^4$ are independently from each other a hydrogen atom or a C$_{1-6}$ alkyl group;

or a pharmaceutically acceptable salt, solvate or hydrate or a pharmaceutically acceptable formulation thereof.

The expression alkyl refers to a saturated, straight-chain or branched hydrocarbon group that contains from 1 to 20 carbon atoms, preferably from 1 to 15 carbon atoms, especially from 1 to 10 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 15 carbon atoms, especially from 2 to 10 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1 to 8; especially preferably 1, 2, 3 or 4) carbon atoms have been replaced by an oxygen, nitrogen, phosphorus, boron, selenium, silicon or sulfur atom (preferably by an oxygen, sulfur or nitrogen atom) or by a SO or a SO$_2$ group. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 8 heteroatoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Especially preferably, the expression heteroalkyl refers to an alkyl group as defined above (straight-chain or branched) in which one or more (preferably 1 to 6; especially preferably 1, 2, 3 or 4) carbon atoms have been replaced by an oxygen, sulfur or nitrogen atom; this group preferably contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen); this group may preferably be substituted by one or more (preferably 1 to 6; especially preferably 1, 2, 3 or 4) fluorine, chlorine, bromine or iodine atoms or OH, =O, SH, =S, $NH_2$, =NH, $N_3$, CN or $NO_2$ groups.

The expression heteroalkylene group refers to a divalent heteroalkyl group.

Examples of heteroalkyl groups are groups of formulae: $R^a$—O—$Y^a$—, $R^a$—S—$Y^a$—, $R^a$—SO—$Y^a$—, $R^a$—$SO_2$—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, —$SO_2Me$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcyclo-alkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenyl-heterocycloalkyl, alkynylheterocycloalkyl, heteroalkylcycloalkyl, heteroalkylhetero-cycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (especially 1 or 2 rings), each containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (especially 1 or 2 rings), each containing from 5 or 6 to 9 or 10 ring carbon atoms and one or two alkyl, alkenyl and/or alkynyl groups containing 1 or 2 to 6 carbon atoms and/or one or two heteroalkyl groups containing 1 to 6 carbon atoms and 1, 2 or 3 heteroatoms selected from O, S and N and/or one or two cycloalkyl groups each containing 5 or 6 ring carbon atoms and/or one or two heterocycloalkyl groups, each containing 5 or 6 ring atoms comprising 1, 2, 3 or 4 oxygen, sulfur or nitrogen atoms.

Examples are arylheteroalkyl, arylheterocycloalkyl, arylheterocycloalkenyl, arylalkyl-heterocycloalkyl, arylalkenyl-heterocycloalkyl, arylalkynylheterocycloalkyl, arylalkyl-heterocycloalkenyl, heteroarylalkyl, heteroarylalkenyl, heteroarylalkynyl, heteroaryl-heteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocyclo-alkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxy-phenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, $=$O, SH, $=$S, $NH_2$, $=$NH, $N_3$ or $NO_2$ groups.

The expression "optionally substituted" especially refers to groups that are optionally substituted by fluorine, chlorine, bromine or iodine atoms or by OH, $=$O, SH, $=$S, $NH_2$, $=$NH, $N_3$ or $NO_2$ groups. This expression refers furthermore to groups that may be substituted by one, two, three or more unsubstituted $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Especially preferably at group $Ar^1$, $Ar^2$, $Ar^3$, $Ar^4$ and $Ar^5$, the expression "optionally substituted" refers to groups that are optionally substituted by one, two or three groups independently selected from halogen atoms, hydroxy groups, groups of formula —O-alkyl (e.g. —O—$C_{1-6}$ alkyl such as —OMe, —OEt, —O-nPr, —O-iPr, —O-nBu, —O-iBu or —O-tBu), —$NH_2$, —$NR^{5a}R^{6a}$ (wherein $R^{5a}$ and $R^{6a}$ independently from each other are a hydrogen atom or an alkyl group such as a $C_{1-6}$ alkyl group), —$SO_2NH_2$, —$CONH_2$, —CN, -alkyl (e.g. —$C_{1-6}$ alkyl, —$CF_3$), —SH, —S-alkyl (e.g. —S—$C_{1-6}$ alkyl).

Most preferably at group $Ar^1$, $Ar^2$, $Ar^3$, $Ar^4$ and $Ar^5$, the expression "optionally substituted" refers to groups that are optionally substituted by one, two or three groups independently selected from F, Cl, hydroxy groups, groups of formula —O—$C_{1-6}$ alkyl (especially —O—$C_{1-4}$ alkyl such as —OMe, —OEt, —O-nPr, —O-iPr, —O-nBu, —O-iBu or —O-tBu), and —$C_{1-6}$ alkyl (e.g. —$C_{1-4}$ alkyl such as —$CH_3$ or —$CF_3$).

Especially preferably at group $Ar^6$, the expression "optionally substituted" refers to groups that are optionally substituted by one, two or three groups independently selected from halogen atoms, hydroxy groups, groups of formula —O-alkyl (e.g. —O—$C_{1-6}$ alkyl such as —OMe, —OEt, —O-nPr, —O-iPr, —O-nBu, —O-iBu or —O-tBu), —$NH_2$, —$NR^{5a}R^{6a}$ (wherein $R^{5a}$ and $R^{6a}$ independently from each other are a hydrogen atom or an alkyl group such as a $C_{1-6}$ alkyl group), —$SO_2NH_2$, —$CONH_2$, —CN, -alkyl (e.g. —$C_{1-6}$ alkyl, —$CF_3$), —SH, —S-alkyl (e.g. —S—$C_{1-6}$ alkyl) and $NO_2$.

Most preferably at group $Ar^6$, the expression "optionally substituted" refers to groups that are optionally substituted by one, two or three groups independently selected from F, Cl, hydroxy groups, —$NH_2$, —$NO_2$, groups of formula —O—$C_{1-6}$ alkyl (especially —O—$C_{1-4}$ alkyl such as —OMe, —OEt, —O-nPr, —O-iPr, —O-nBu, —O-iBu or —O-tBu), and —$C_{1-6}$ alkyl (e.g. —$C_{1-4}$ alkyl such as —$CH_3$ or —$CF_3$).

The term halogen refers to F, Cl, Br or I.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may independently of each other optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Owing to their substitution, compounds of formula (I) may contain one or more centers of chirality. The present invention therefore includes both all pure enantiomers and all pure diastereoisomers and also mixtures thereof in any mixing ratio. The present invention moreover also includes all cis/trans-isomers of the compounds of the general formula (I) and also mixtures thereof. The present invention moreover includes all tautomeric forms of the compounds of formula (I).

Preferably, when $Ar^4$ is absent, also $L^3$ is absent.

Further preferably, when $Ar^5$ is absent, also $L^4$ is absent.

Preferably, $Ar^1$ is an optionally substituted 1,4-phenylene group or an optionally substituted 1,3-heteroarylene group having 5 ring atoms including 1, 2, or 3 heteroatoms selected from oxygen, sulphur and nitrogen.

Further preferably, $Ar^1$ is an optionally substituted 1,4-phenylene group.

Preferably, $Ar^2$ is an optionally substituted 1,4-phenylene group or an optionally substituted 1,3-heteroarylene group having 5 ring atoms including 1, 2, or 3 heteroatoms selected from oxygen, sulphur and nitrogen.

Further preferably, $Ar^2$ is an optionally substituted 1,4-phenylene group.

Preferably, $Ar^3$ is an optionally substituted 1,4-phenylene group or an optionally substituted 1,3-heteroarylene group having 5 ring atoms including 1, 2, or 3 heteroatoms selected from oxygen, sulphur and nitrogen.

Further preferably, $Ar^3$ is an optionally substituted 1,4-phenylene group.

Preferably, $Ar^4$ is an optionally substituted 1,4-phenylene group or an optionally substituted 1,3-heteroarylene group having 5 ring atoms including 1, 2, or 3 heteroatoms selected from oxygen, sulphur and nitrogen.

Further preferably, $Ar^4$ is an optionally substituted 1,4-phenylene group.

Preferably, $Ar^5$ is an optionally substituted 1,4-phenylene group or an optionally substituted 1,3-heteroarylene group having 5 ring atoms including 1, 2, or 3 heteroatoms selected from oxygen, sulphur and nitrogen.

Further preferably, $Ar^5$ is an optionally substituted 1,4-phenylene group.

Further preferably, $Ar^4$ is absent.

Further preferably, $Ar^5$ is absent.

The term 1,3-heteroarylene group having 5 ring atoms including 1, 2, or 3 heteroatoms selected from oxygen, sulphur and nitrogen especially preferably refers to one of the following groups:

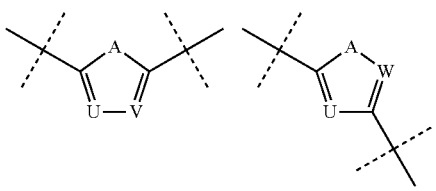

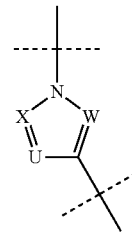

wherein A is O, S or NH; U is N or CH; V is N or CH; W is N or CH; and X is N or CH.

Further preferably, $L^1$ is a group of formula —CONH—, —NHCO—, —SO$_2$NH—, —NHSO$_2$—, —CH═CH—, —CR$^3$═CR$^4$— or an optionally substituted heteroarylene group having 5 ring atoms including 1, 2, or 3 heteroatoms selected from oxygen, sulphur and nitrogen, wherein $R^3$ and $R^4$ are independently from each other a $C_{1-6}$ alkyl group.

Further preferably, $L^2$ is a group of formula —CONH—, —NHCO—, —SO$_2$NH—, —NHSO$_2$—, —CH═CH—, —CR$^3$═CR$^4$— or an optionally substituted heteroarylene group having 5 ring atoms including 1, 2, or 3 heteroatoms selected from oxygen, sulphur and nitrogen, wherein $R^3$ and $R^4$ are independently from each other a $C_{1-6}$ alkyl group.

Further preferably, $L^3$ is absent or a group of formula —CONH—, —NHCO—, —SO$_2$NH—, —NHSO$_2$—, —CH═CH—, —CR$^3$═CR$^4$— or an optionally substituted heteroarylene group having 5 ring atoms including 1, 2, or 3 heteroatoms selected from oxygen, sulphur and nitrogen, wherein $R^3$ and $R^4$ are independently from each other a $C_{1-6}$ alkyl group.

Further preferably, $L^4$ is absent or a group of formula —CONH—, —NHCO—, —SO$_2$NH—, —NHSO$_2$—, —CH═CH—, —CR$^3$═CR$^4$— or an optionally substituted heteroarylene group having 5 ring atoms including 1, 2, or 3 heteroatoms selected from oxygen, sulphur and nitrogen, wherein $R^3$ and $R^4$ are independently from each other a $C_{1-6}$ alkyl group.

Further preferably, $L^1$ is NHCO (wherein the nitrogen atom is bound to $Ar^1$) or a group of the following formula:

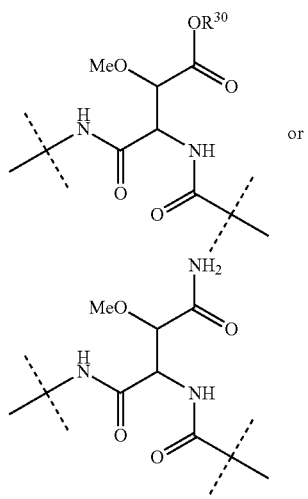

(wherein the NH group is bound to $Ar^1$), wherein $R^{30}$ is a hydrogen atom or a $C_{1-3}$ alkyl group.

Especially preferably, $L^1$ is NHCO (wherein the nitrogen atom is bound to $Ar^1$).

Moreover preferably, $L^2$ is NHCO (wherein the nitrogen atom is bound to $Ar^2$) or a group of the following formula:

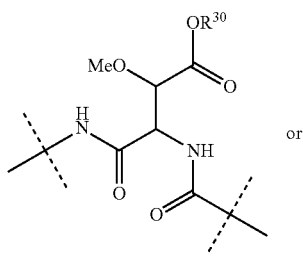

or

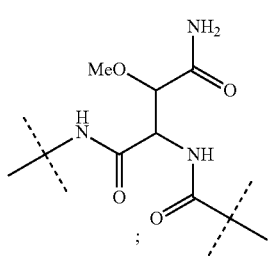

;

(wherein the NH group is bound to $Ar^2$), wherein $R^{30}$ is a hydrogen atom or a $C_{1-3}$ alkyl group.

Especially preferably, $L^2$ is NHCO (wherein the nitrogen atom is bound to $Ar^1$).

Further preferably, $L^3$ is absent or a group of the following formula:

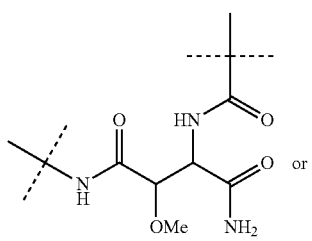

or

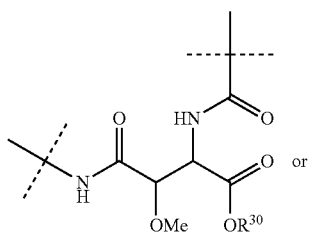

or

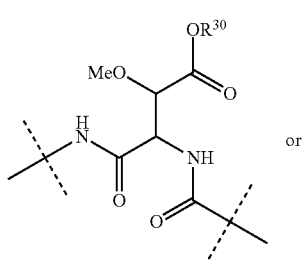

or

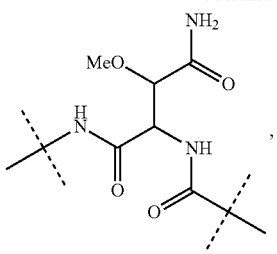

, (wherein the NH group is bound to $Ar^3$), wherein $R^{30}$ is a hydrogen atom or a $C_{1-3}$ alkyl group.

Further preferably, $L^4$ is absent or NHCO (wherein the nitrogen atom is bound to $Ar^4$).

Moreover preferably, $R^{30}$ is a hydrogen atom.

Further preferably, $R^1$ is a hydrogen atom, a halogen atom or a group of formula —OH, —$NH_2$, —COOH, —$SO_2NH_2$, —$CONH_2$, —$NO_2$, —CN, -alkyl (e.g. —$CF_3$), —O-alkyl, —O—CO-alkyl, —NH-alkyl, —NH—CO-alkyl, or an optionally substituted heteroaryl group having 5 ring atoms including 1, 2, 3 or 4 heteroatoms selected from oxygen, sulphur and nitrogen, or an optionally substituted heterocycloalkyl group having 5 ring atoms including 1, 2, 3 or 4 heteroatoms selected from oxygen, sulphur and nitrogen.

Moreover preferably, $R^2$ is a hydrogen atom, a halogen atom or a group of formula —OH, —$NH_2$, —COOH, —$SO_2NH_2$, —$CONH_2$, —$NO_2$, —CN, -alkyl (e.g. —$CF_3$), —O-alkyl, —O—CO-alkyl, —NH-alkyl, —NH—CO-alkyl, or an optionally substituted heteroaryl group having 5 ring atoms including 1, 2, 3 or 4 heteroatoms selected from oxygen, sulphur and nitrogen, or an optionally substituted heterocycloalkyl group having 5 ring atoms including 1, 2, 3 or 4 heteroatoms selected from oxygen, sulphur and nitrogen.

Preferred examples of optionally substituted heteroaryl groups having 5 ring atoms including 1, 2, 3 or 4 heteroatoms selected from oxygen, sulphur and nitrogen and of optionally substituted heterocycloalkyl groups having 5 ring atoms including 1, 2, 3 or 4 heteroatoms selected from oxygen, sulphur and nitrogen as groups $R^1$ and $R^2$ are isosteres of carboxylic acid such as groups of the following formulas:

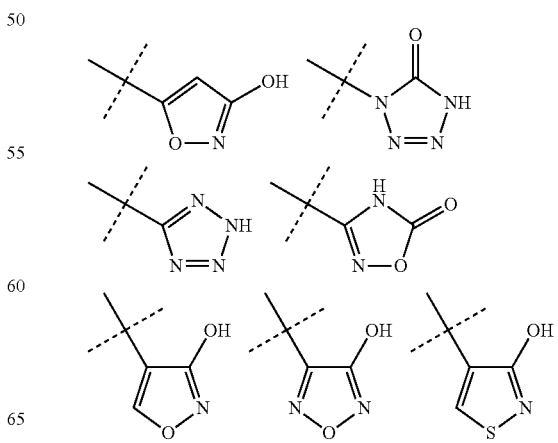

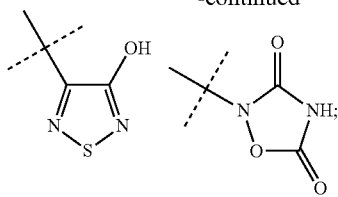

all these groups may optionally be further substituted.

Especially preferably, $R^1$ is a group of formula —$NH_2$, —$NO_2$, $COOR^{11}$, or —$CONR^{12}R^{13}$; wherein $R^1$, $R^{12}$ and $R^{13}$ are independently a hydrogen atom or a $C_{1-6}$ alkyl group; moreover preferably, $R^1$ is a group of formula —COOH.

Further especially preferably, $R^2$ is a group of formula —$NH_2$, —$NO_2$, $COOR^{11a}$, or —$CONR^{12a}R^{13a}$; wherein $R^{11a}$, $R^{12a}$ and $R^{13a}$ are independently a hydrogen atom or a $C_{1-6}$ alkyl group; moreover preferably, $R^2$ is a group of formula —$NH_2$ or —$NO_2$.

Further especially preferably, $R^1$ is a heteroaryl group having 5 ring atoms including 1, 2, 3 or 4 heteroatoms selected from oxygen, sulphur and nitrogen, and which is substituted by a hydroxy group.

Further especially preferably, $R^2$ is a heteroaryl group having 5 ring atoms including 1, 2, 3 or 4 heteroatoms selected from oxygen, sulphur and nitrogen, and which is substituted by a hydroxy group.

Especially preferred are compounds of formula (I)

$$R^1—Ar^1-L^1-Ar^2-L^2-Ar^3-L^3Ar^4-L^4-Ar^5—R^2 \quad (I)$$

wherein $Ar^1$ is an optionally substituted 1,4-phenylene group;
$Ar^2$ is an optionally substituted 1,4-phenylene group;
$Ar^3$ is an optionally substituted 1,4-phenylene group;
$Ar^4$ is absent or an optionally substituted 1,4-phenylene group;
$Ar^5$ is absent or an optionally substituted 1,4-phenylene group;
$L^1$ is a group of formula —CONH—, —NHCO—, —$SO_2NH$— or —$NHSO_2$— or a group of the following formula:

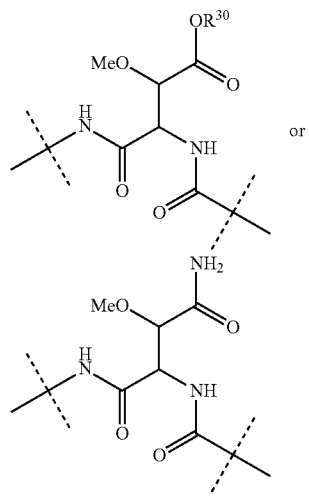

(wherein the NH group is bound to $Ar^1$);

$L^2$ is a group of formula —CONH—, —NHCO—, —$SO_2NH$— or —$NHSO_2$—;

$L^3$ is absent or a group of formula —CONH—, —NHCO—, —$SO_2NH$— or —$NHSO_2$— or a group of the following formula:

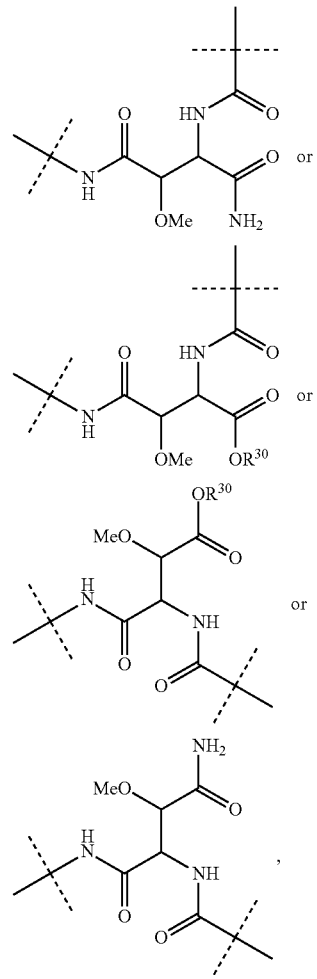

(wherein the NH group is bound to $Ar^3$);

$L^4$ is absent or a group of formula —CONH—, —NHCO—, —$SO_2NH$— or —$NHSO_2$—;

$R^{30}$ is a hydrogen atom or a $C_{1-3}$ alkyl group (especially preferably, a hydrogen atom);

$R^1$ is a group of formula —$NH_2$, —$NO_2$, $COOR^{11}$, or —$CONR^{12}R^{13}$; wherein $R^{11}$, $R^{12}$ and $R^{13}$ are independently a hydrogen atom or a $C_{1-6}$ alkyl group (especially preferably, $R^1$ is a group of formula —COOH); and $R^2$ is a group of formula —$NH_2$, —$NO_2$, $COOR^{11}$a, or —$CONR^{12a}R^{13a}$; wherein $R^{11a}$, $R^{12a}$ and $R^{13a}$ are independently a hydrogen atom or a $C_{1-6}$ alkyl group (especially preferably, $R^2$ is a group of formula —$NH_2$ or —$NO_2$);

or a pharmaceutically acceptable salt, solvate or hydrate or a pharmaceutically acceptable formulation thereof.

Therein, preferably, L is a group of formula —CONH—, —NHCO—, —$SO_2NH$— or —$NHSO_2$—, and $L^3$ is absent or a group of the following formula:

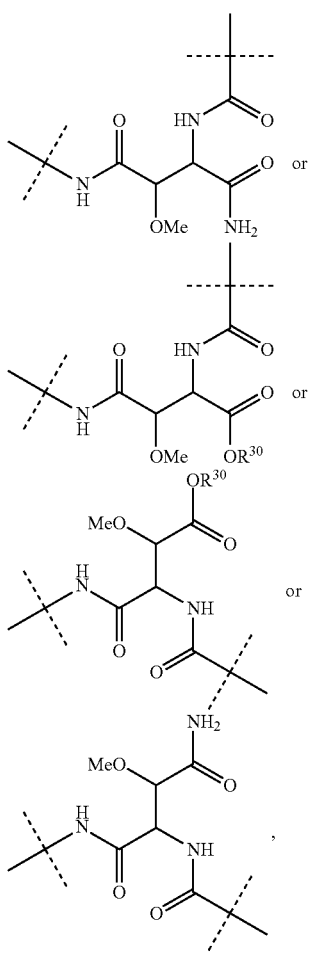

(wherein the NH group is bound to Ar³).
Further preferred are compounds of formula (II)

wherein Ar¹, Ar², Ar³, L¹, L², R¹ and R² are as defined above.

Moreover preferred are compounds of formula (III)

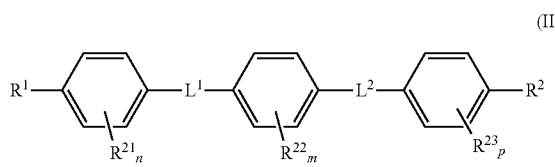

wherein
n is 0, 1, 2, 3 or 4;
m is 0, 1, 2, 3 or 4;
p is 0, 1, 2, 3 or 4;
group(s) $R^{21}$ are independently selected from halogen atoms, hydroxy groups, groups of formula —O-alkyl (e.g. —O—$C_{1-6}$ alkyl such as —OMe, —OEt, —O-nPr, —O-iPr, —O-nBu, —O-iBu or —O-tBu), —$NH_2$, —$NR^{5a}R^{6a}$ (wherein $R^{5a}$ and $R^{6a}$ independently from each other are a hydrogen atom or an alkyl group such as a $C_{1-6}$ alkyl group), —$SO_2NH_2$, —$CONH_2$, —CN, -alkyl (e.g. —$C_{1-6}$ alkyl, —$CF_3$), —SH, —S-alkyl (e.g. —S—$C_{1-6}$ alkyl); group(s) $R^{22}$ are independently selected from halogen atoms, hydroxy groups, groups of formula —O-alkyl (e.g. —O—$C_{1-6}$ alkyl such as —OMe, —OEt, —O-nPr, —O-iPr, —O-nBu, —O-iBu or —O-tBu), —$NH_2$, —$NR^{5a}R^{6a}$ (wherein $R^{5a}$ and $R^{6a}$ independently from each other are a hydrogen atom or an alkyl group such as a $C_{1-6}$ alkyl group), —$SO_2NH_2$, —$CONH_2$, —CN, -alkyl (e.g. —$C_{1-6}$ alkyl, —$CF_3$), —SH, —S-alkyl (e.g. —S—$C_{1-6}$ alkyl); group(s) $R^{23}$ are independently selected from halogen atoms, hydroxy groups, groups of formula —O-alkyl (e.g. —O—$C_{1-6}$ alkyl such as —OMe, —OEt, —O-nPr, —O-iPr, —O-nBu, —O-iBu or —O-tBu), —$NH_2$, —$NR^{5a}R^{6a}$ (wherein $R^{5a}$ and $R^{6a}$ independently from each other are a hydrogen atom or an alkyl group such as a $C_{1-6}$ alkyl group), —$SO_2NH_2$, —$CONH_2$, —CN, -alkyl (e.g. —$C_{1-6}$ alkyl, —$CF_3$), —SH, —S-alkyl (e.g. —S—$C_{1-6}$ alkyl); and $R^1$, $R^2$, $L^1$ and $L^2$ are as defined above.

Further preferred are compounds of formula (IV)

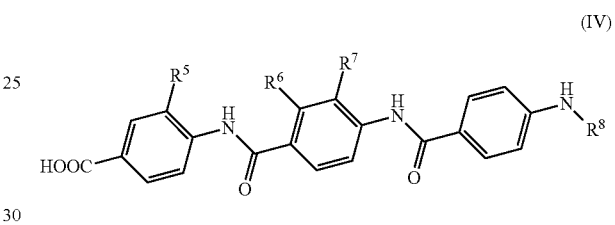

wherein $R^5$ is a group of formula —O—$C_{1-6}$ alkyl;

$R^6$ is a hydroxy group;

$R^7$ is a group of formula —O—$C_{1-6}$ alkyl; and $R^8$ is a hydrogen atom, an alkyl, an alkenyl, an alkynyl, a heteroalkyl, a cycloalkyl, a heterocycloalkyl, an alkylcycloalkyl, a heteroalkylcycloalkyl, an aryl, a heteroaryl, an aralkyl or a heteroaralkyl group.

Preferably, $R^8$ is a hydrogen atom or a group of the following formula:

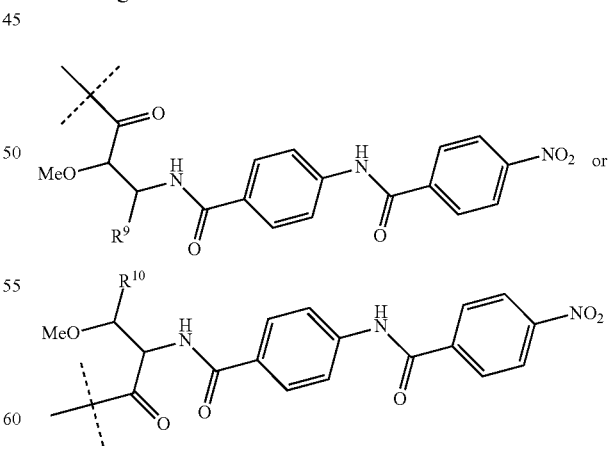

wherein $R^9$ is COOH or $CONH_2$ and $R^{10}$ is COOH or $CONH_2$.

Moreover preferably, $R^5$ is a group of formula —O—$C_{1-4}$ alkyl and $R^7$ is a group of formula —O—$C_{1-4}$ alkyl.

Further preferred are compounds of formula (V)

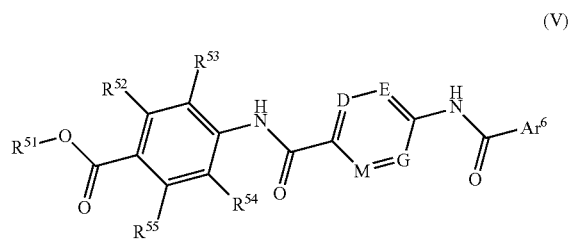

wherein
$R^{51}$ is a hydrogen atom, or a $C_{1-6}$ alkyl group;
$R^{52}$ is a hydrogen atom, F, Cl, a hydroxy group, a $C_{1-6}$ alkyl group or a group of formula —O—$C_{1-6}$ alkyl;
$R^{53}$ is a hydrogen atom, F, Cl, a hydroxy group, a $C_{1-6}$ alkyl group or a group of formula —O—$C_{1-6}$ alkyl;
$R^{54}$ is a hydrogen atom, F, Cl, a hydroxy group, a $C_{1-6}$ alkyl group or a group of formula —O—$C_{1-6}$ alkyl;
$R^{55}$ is a hydrogen atom, F, Cl, a hydroxy group, a $C_{1-6}$ alkyl group or a group of formula —O—$C_{1-6}$ alkyl;
D is N or $CR^{56}$;
E is N or $CR^{57}$;
G is N or $CR^{58}$;
M is N or $CR^{59}$;
$R^{56}$ is a hydrogen atom, F, Cl, a hydroxy group, a $C_{1-6}$ alkyl group or a group of formula —O—$C_{1-6}$ alkyl;
$R^{57}$ is a hydrogen atom, F, Cl, a hydroxy group, a $C_{1-6}$ alkyl group or a group of formula —O—$C_{1-6}$ alkyl;
$R^{58}$ is a hydrogen atom, F, Cl, a hydroxy group, a $C_{1-6}$ alkyl group or a group of formula —O—$C_{1-6}$ alkyl;
$R^{59}$ is a hydrogen atom, F, Cl, a hydroxy group, a $C_{1-6}$ alkyl group or a group of formula —O—$C_{1-6}$ alkyl; and
$Ar^6$ is an optionally substituted (by one, two or more substituents such as e.g. $R^2$, $R^8$ or $NHR^8$) phenyl group or an optionally substituted (by one, two or more substituents such as e.g. $R^2$, $R^8$ or $NHR^8$) heteroaryl group having 5 or 6 ring atoms including 1, 2, 3 or 4 heteroatoms selected from oxygen, sulphur and nitrogen;
or a pharmaceutically acceptable salt, solvate or hydrate or a pharmaceutically acceptable formulation thereof.

Especially preferred are compounds of Formula (V) wherein:
$R^5$ is a hydrogen atom, or a $C_{1-4}$ alkyl group;
$R^{52}$ is a hydrogen atom, F, Cl, a hydroxy group, a $C_{1-4}$ alkyl group or a group of formula —O—$C_{1-4}$ alkyl;
$R^{53}$ is a hydrogen atom, F, Cl, a hydroxy group, a $C_{1-4}$ alkyl group or a group of formula —O—$C_{1-4}$ alkyl;
$R^{54}$ is a hydrogen atom, F, Cl, a hydroxy group, a $C_{1-4}$ alkyl group or a group of formula —O—$C_{1-4}$ alkyl;
$R^{55}$ is a hydrogen atom, F, Cl, a hydroxy group, a $C_{1-4}$ alkyl group or a group of formula —O—$C_{1-4}$ alkyl;
D is N or $CR^{56}$;
E is N or $CR^{57}$;
G is N or $CR^{58}$;
M is N or $CR^{59}$;
$R^{56}$ is a hydrogen atom, F, Cl, a hydroxy group, a $C_{1-4}$ alkyl group or a group of formula —O—$C_{1-4}$ alkyl;
$R^{57}$ is a hydrogen atom, F, Cl, a hydroxy group, a $C_{1-4}$ alkyl group or a group of formula —O—$C_{1-4}$ alkyl;
$R^{58}$ is a hydrogen atom, F, Cl, a hydroxy group, a $C_{1-4}$ alkyl group or a group of formula —O—$C_{1-4}$ alkyl; and
$R^{59}$ is a hydrogen atom, F, Cl, a hydroxy group, a $C_{1-6}$ alkyl group or a group of formula —O—$C_{1-4}$ alkyl.

Especially preferably, only one or two (especially only one) of D, E, G and M is/are N.

Further preferred are compounds of formula (VI)

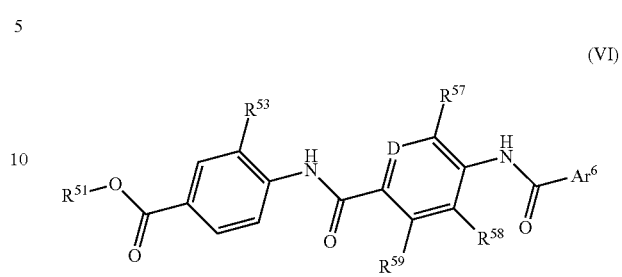

wherein
$R^{51}$ is a hydrogen atom, or a $C_{1-6}$ alkyl group;
$R^{53}$ is F, Cl, a hydroxy group, a $C_{1-6}$ alkyl group or a group of formula —O—$C_{1-6}$ alkyl (especially preferably a group of formula —O—$C_{1-6}$ alkyl);
D is N or $CR^{56}$;
$R^{56}$ is a hydrogen atom, F, Cl, a hydroxy group, a $C_{1-6}$ alkyl group or a group of formula —O—$C_{1-6}$ alkyl;
$R^{57}$ is a hydrogen atom, F, Cl, a hydroxy group, a $C_{1-6}$ alkyl group or a group of formula —O—$C_{1-6}$ alkyl;
$R^{58}$ is a hydrogen atom, F, Cl, a hydroxy group, a $C_{1-6}$ alkyl group or a group of formula —O—$C_{1-6}$ alkyl;
$R^{59}$ is a hydrogen atom, F, Cl, a hydroxy group, a $C_{1-6}$ alkyl group or a group of formula —O—$C_{1-6}$ alkyl; and
$Ar^6$ is an optionally substituted (by one, two or more substituents such as e.g. $R^2$, $R^8$ or $NHR^8$) phenyl group or an optionally substituted (by one, two or more substituents such as e.g. $R^2$, $R^8$ or $NHR^8$) heteroaryl group having 5 or 6 ring atoms including 1, 2, 3 or 4 heteroatoms selected from oxygen, sulphur and nitrogen;
or a pharmaceutically acceptable salt, solvate or hydrate or a pharmaceutically acceptable formulation thereof.

Especially preferred are compounds of Formula (VI) wherein:
$R^{51}$ is a hydrogen atom, or a $C_{1-4}$ alkyl group;
$R^{53}$ is F, Cl, a hydroxy group, a $C_{1-4}$ alkyl group or a group of formula —O—$C_{1-4}$ alkyl (especially preferably a group of formula —O—$C_{1-4}$ alkyl);
D is N or $CR^{56}$;
$R^{56}$ is a hydrogen atom, F, Cl, a hydroxy group, a $C_{1-4}$ alkyl group or a group of formula —O—$C_{1-4}$ alkyl;
$R^{57}$ is a hydrogen atom, F, Cl, a hydroxy group, a $C_{1-4}$ alkyl group or a group of formula —O—$C_{1-4}$ alkyl;
$R^{58}$ is a hydrogen atom, F, Cl, a hydroxy group, a $C_{1-4}$ alkyl group or a group of formula —O—$C_{1-4}$ alkyl; and
$R^{59}$ is a hydrogen atom, F, Cl, a hydroxy group, a $C_{1-4}$ alkyl group or a group of formula —O—$C_{1-4}$ alkyl.

Further preferred are compounds of formula (VII)

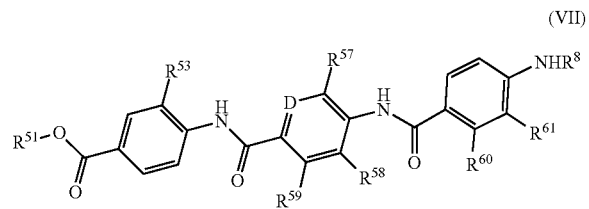

wherein $R^{51}$ is a hydrogen atom, or a $C_{1-6}$ alkyl group;

$R^{53}$ is F, Cl, a hydroxy group, a $C_{1-6}$ alkyl group or a group of formula —O—$C_{1-6}$ alkyl (especially preferably a group of formula —O—$C_{1-6}$ alkyl);

D is N or $CR^{56}$;

$R^{56}$ is a hydrogen atom, F, Cl, a hydroxy group, a $C_{1-6}$ alkyl group or a group of formula —O—$C_{1-6}$ alkyl;

$R^{57}$ is a hydrogen atom, F, Cl, a hydroxy group, a $C_{1-6}$ alkyl group or a group of formula —O—$C_{1-6}$ alkyl;

$R^{58}$ is a hydrogen atom, F, Cl, a hydroxy group, a $C_{1-6}$ alkyl group or a group of formula —O—$C_{1-6}$ alkyl;

$R^{59}$ is a hydrogen atom, F, Cl, a hydroxy group, a $C_{1-6}$ alkyl group or a group of formula —O—$C_{1-6}$ alkyl;

$R^{60}$ is a hydrogen atom, F, Cl, a hydroxy group, a $C_{1-6}$ alkyl group or a group of formula —O—$C_{1-6}$ alkyl;

$R^{61}$ is a hydrogen atom, F, Cl, a hydroxy group, a $C_{1-6}$ alkyl group or a group of formula —O—$C_{1-6}$ alkyl; and $R^8$ is a hydrogen atom, an alkyl, an alkenyl, an alkynyl, a heteroalkyl, a cycloalkyl, a heterocycloalkyl, an alkylcycloalkyl, a heteroalkylcycloalkyl, an aryl, a heteroaryl, an aralkyl or a heteroaralkyl group.

or a pharmaceutically acceptable salt, solvate or hydrate or a pharmaceutically acceptable formulation thereof.

Especially preferred are compounds of Formula (VII) wherein:

$R^{51}$ is a hydrogen atom, or a $C_{1-4}$ alkyl group;

$R^{53}$ is F, Cl, a hydroxy group, a $C_{1-4}$ alkyl group or a group of formula —O—$C_{1-4}$ alkyl (especially preferably a group of formula —O—$C_{1-4}$ alkyl);

D is N or $CR^{56}$;

$R^{56}$ is a hydrogen atom, F, Cl, a hydroxy group, a $C_{1-4}$ alkyl group or a group of formula —O—$C_{1-4}$ alkyl;

$R^{57}$ is a hydrogen atom, F, Cl, a hydroxy group, a $C_{1-4}$ alkyl group or a group of formula —O—$C_{1-4}$ alkyl;

$R^{58}$ is a hydrogen atom, F, Cl, a hydroxy group, a $C_{1-4}$ alkyl group or a group of formula —O—$C_{1-4}$ alkyl;

$R^{59}$ is a hydrogen atom, F, Cl, a hydroxy group, a $C_{1-4}$ alkyl group or a group of formula —O—$C_{1-4}$ alkyl;

$R^{60}$ is a hydrogen atom, F, Cl, a hydroxy group, a $C_{1-4}$ alkyl group or a group of formula —O—$C_{1-4}$ alkyl; and $R^{61}$ is a hydrogen atom, F, Cl, a hydroxy group, a $C_{1-4}$ alkyl group or a group of formula —O—$C_{1-4}$ alkyl.

Preferably, $R^8$ is a hydrogen atom or a group of the following formula:

wherein $R^9$ is COOH or $CONH_2$ and $R^{10}$ is COOH or $CONH_2$.

Especially preferred are the following compounds:

Cystobactamide A (1)

Cystobactamide B (2)

Cystobactamide C (3)

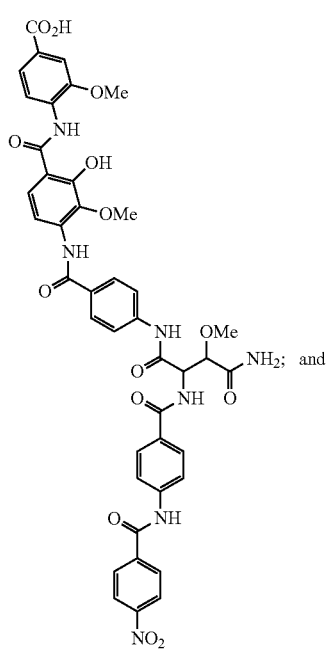
Cystobactamide D (4)
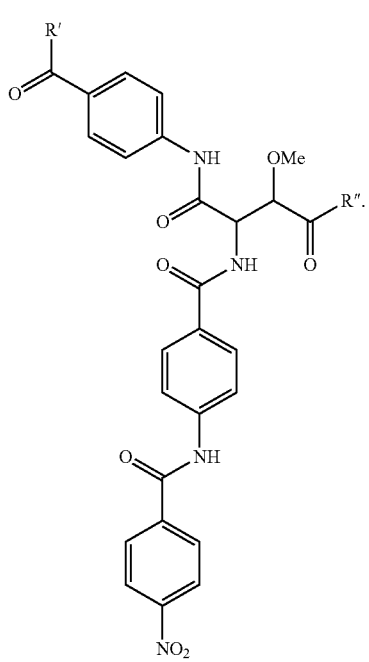
Cystobactamide E (5)
(R' is NH$_2$ or OH and R" is NH$_2$ or OH)
Moreover especially preferred are the following compounds:
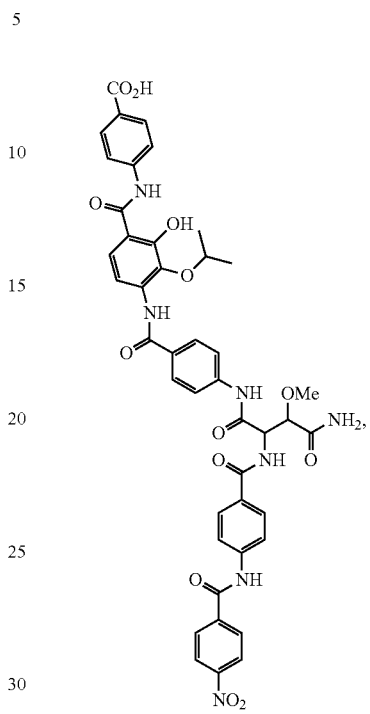
Cystobactamide F (6)
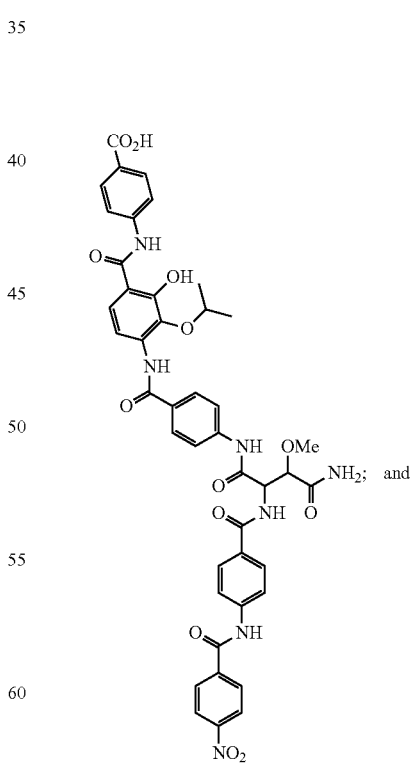
Cystobactamide G (7)

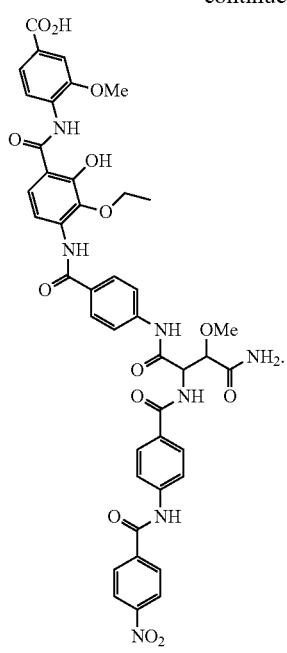
Cystobactamide H (8)
Moreover preferred are the following compounds:
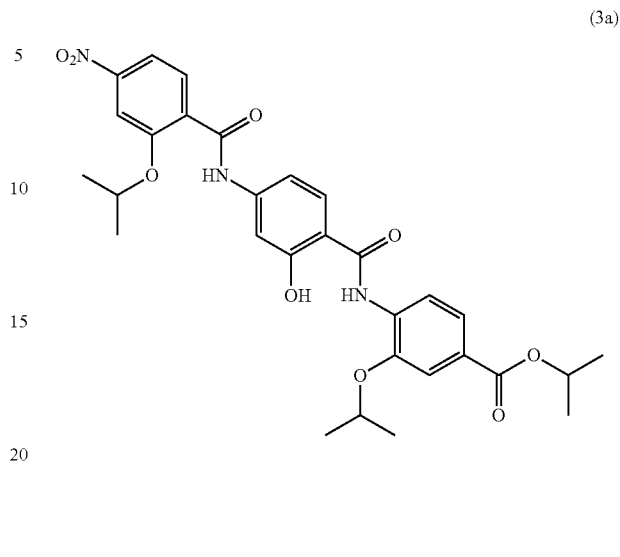
(1a)
(3a)
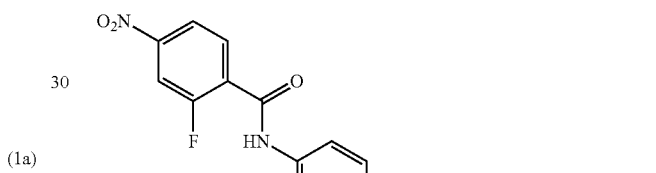
(4a)
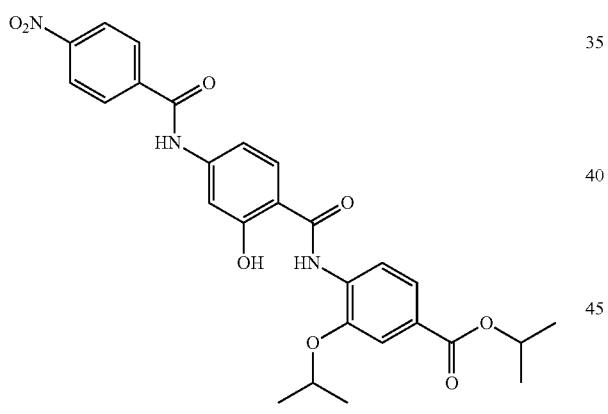
(2a)
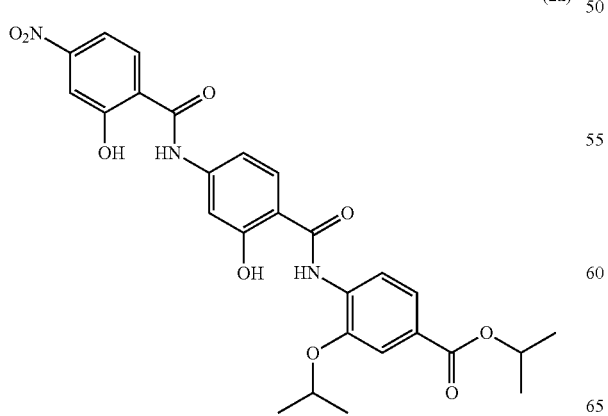
(5a)

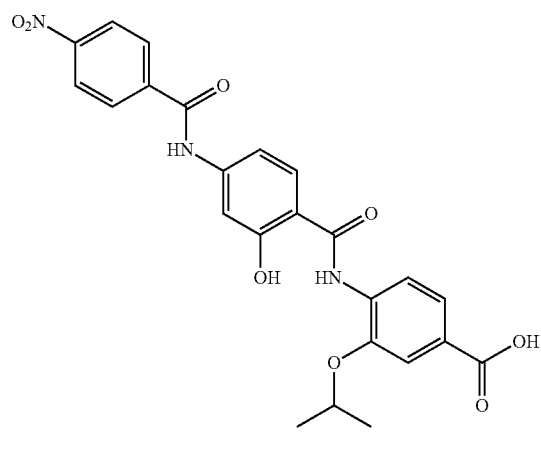
(6a)
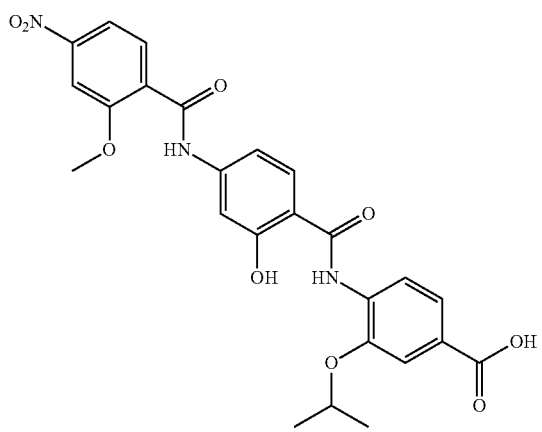
(9a)
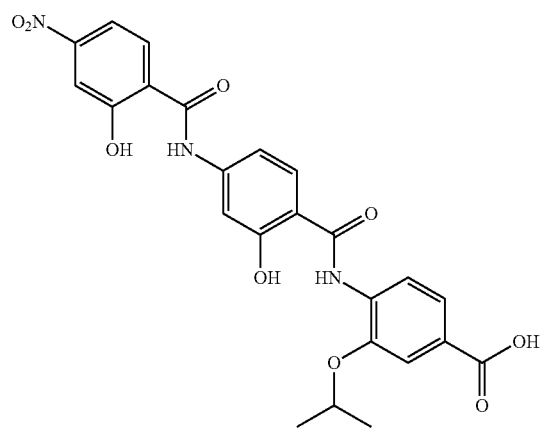
(7a)
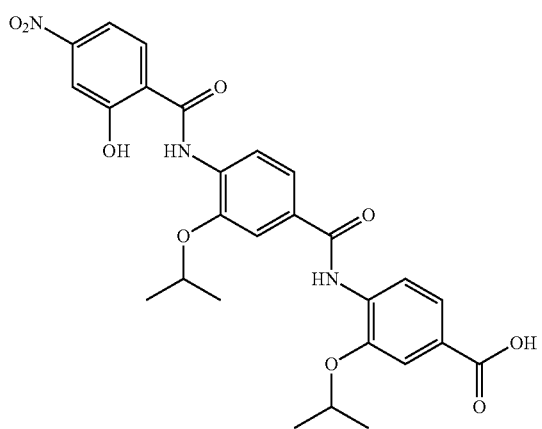
(10a)
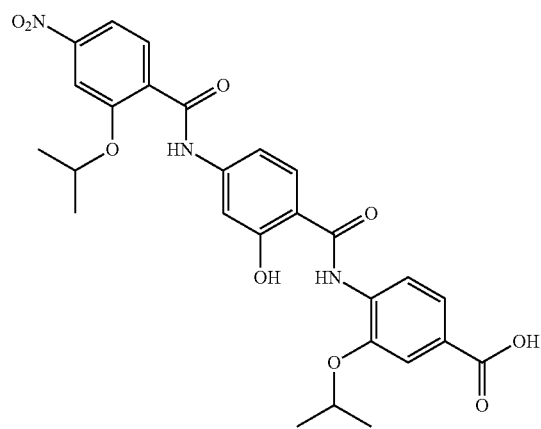
(8a)
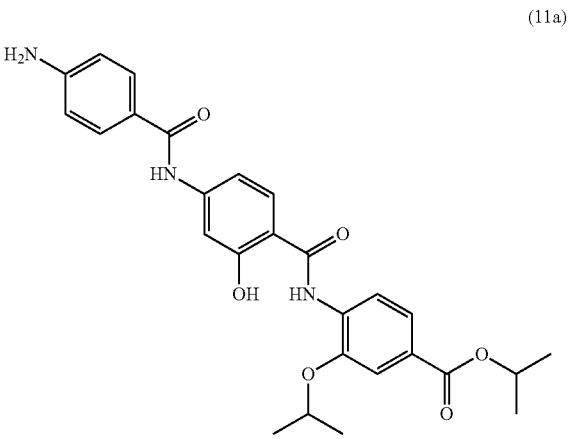
(11a)

(12a)
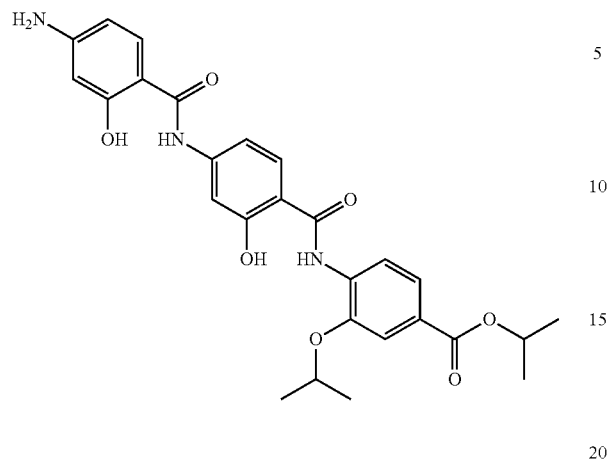
(15a)
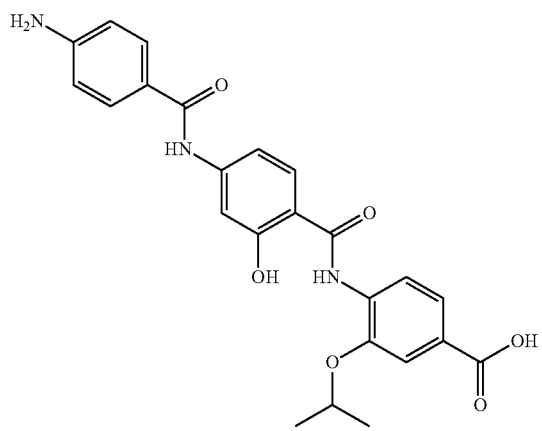
(13a)
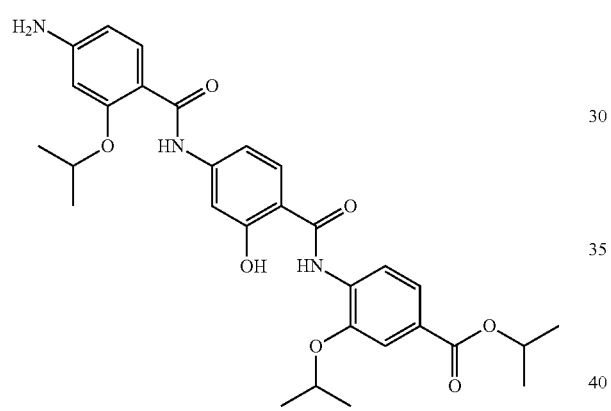
(16a)
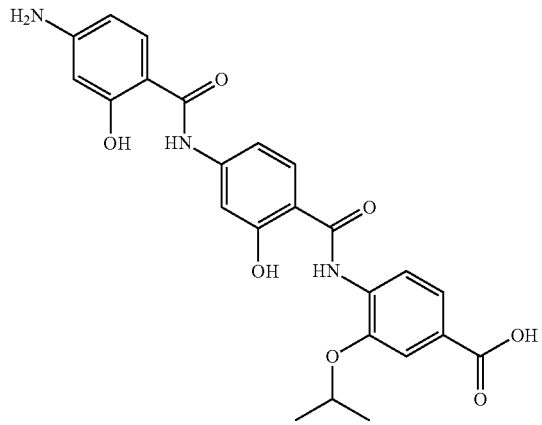
(14a)
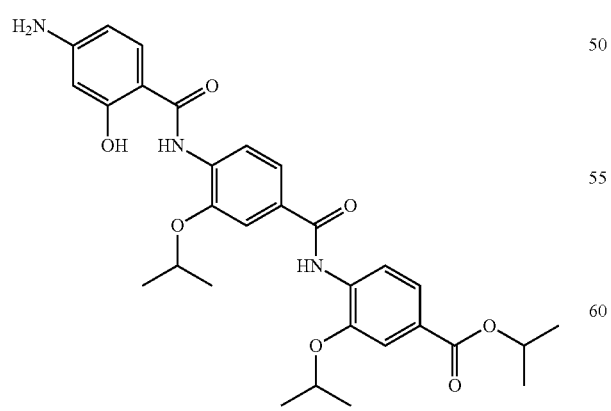
(17a)
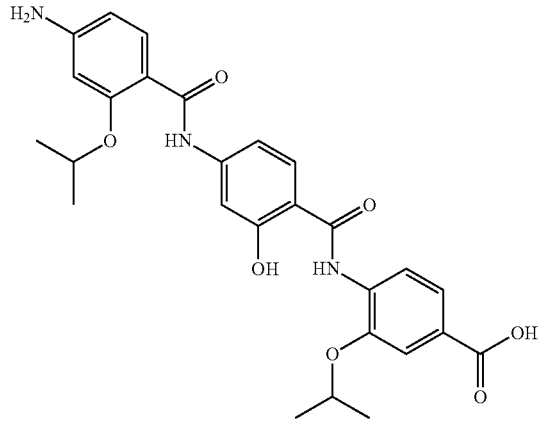

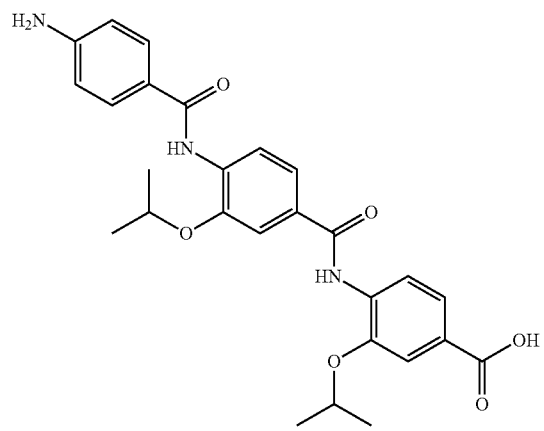
(18a)
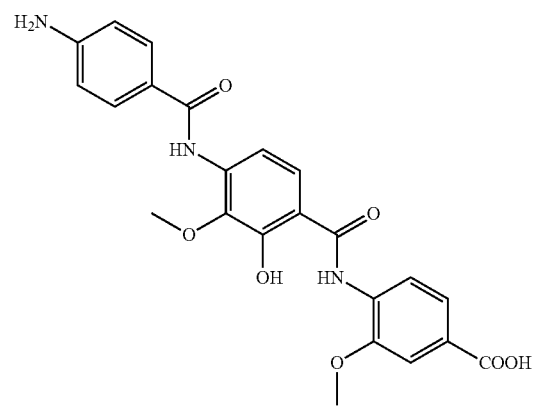
(21a)
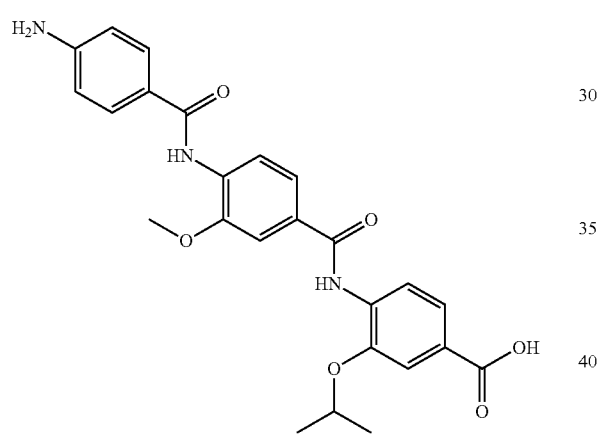
(19a)
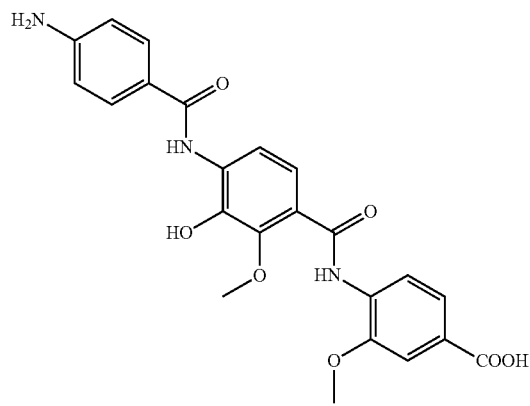
(22a)
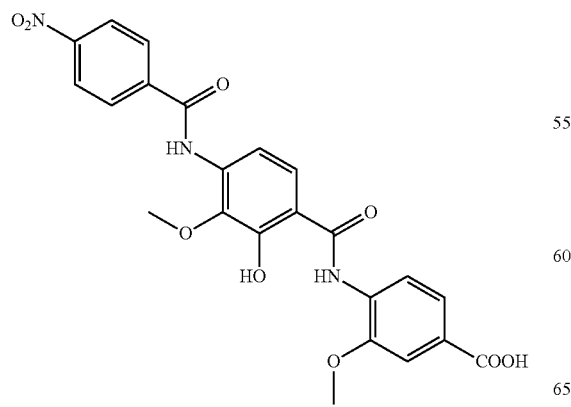
(20a)
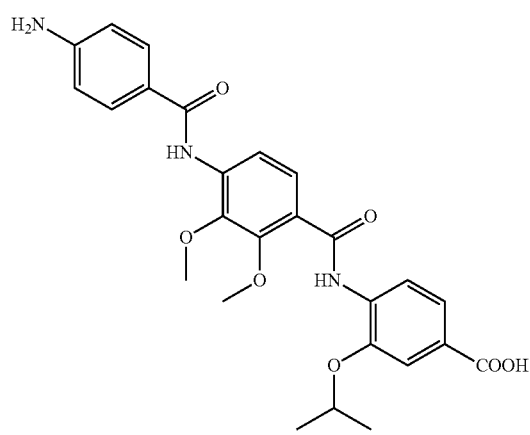
(23a)

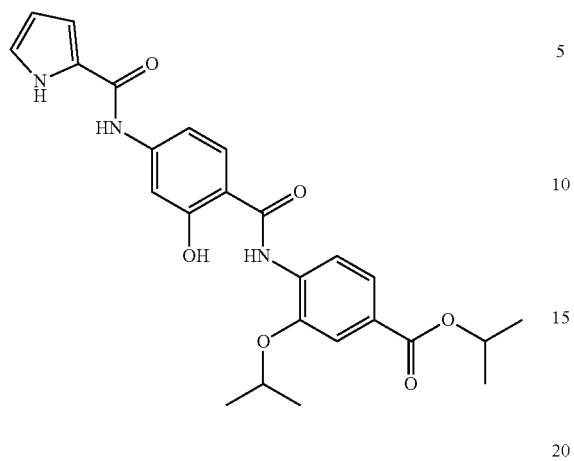
(24a)
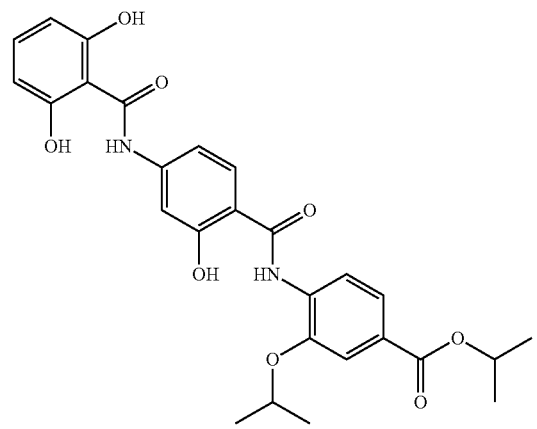
(27a)
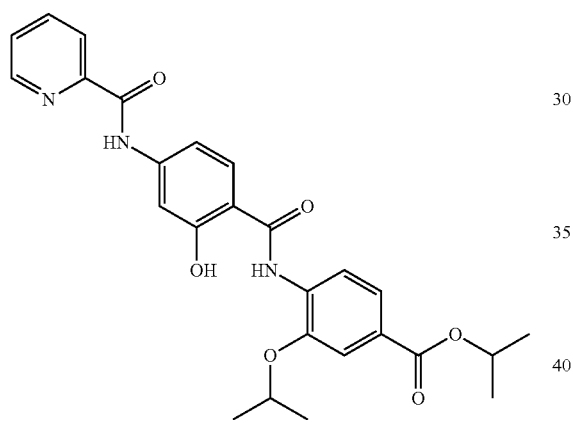
(25a)
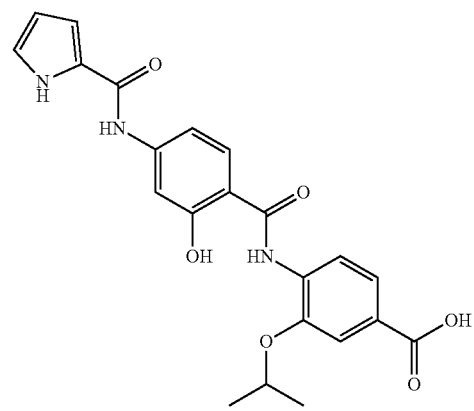
(28a)
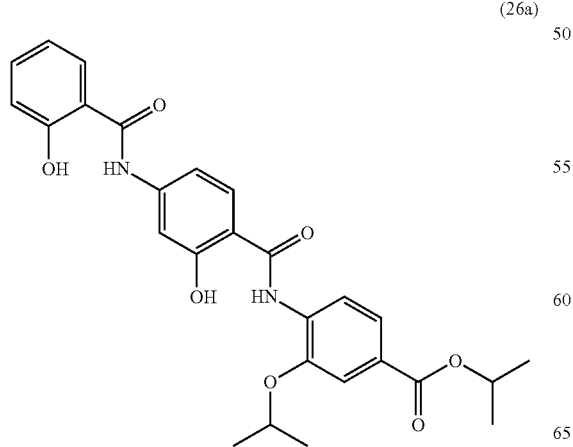
(26a)
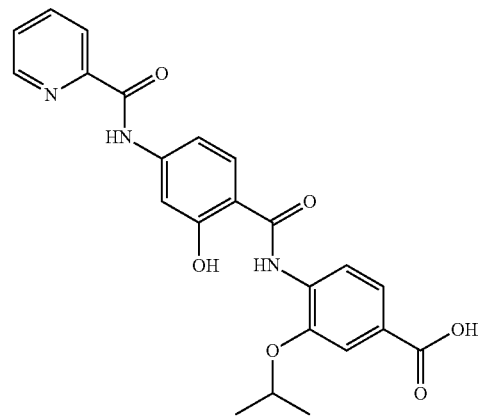
(29a)

(30a)

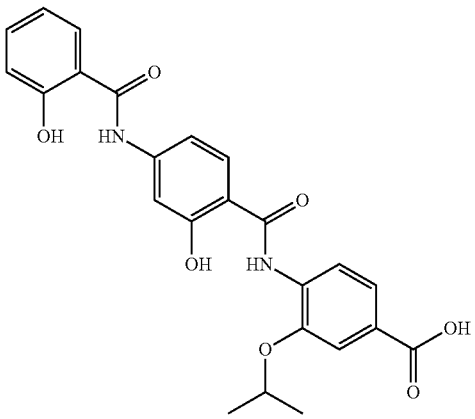

(31a)

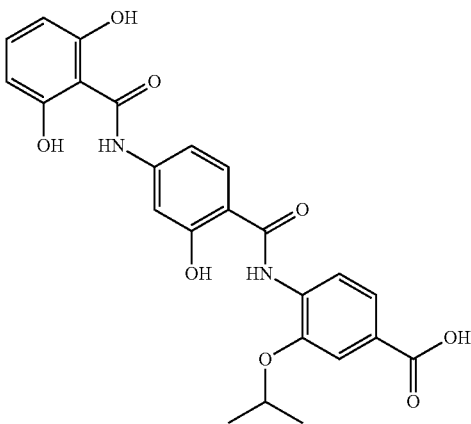

(32a)

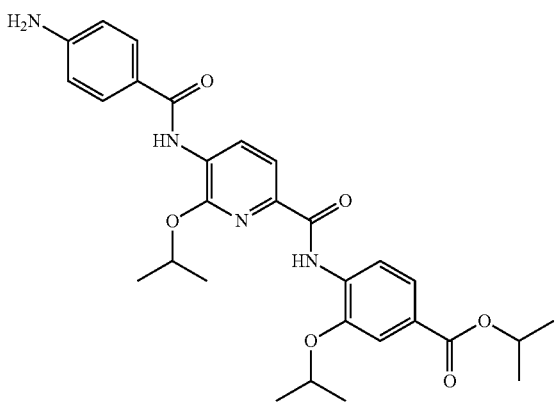

(33a)

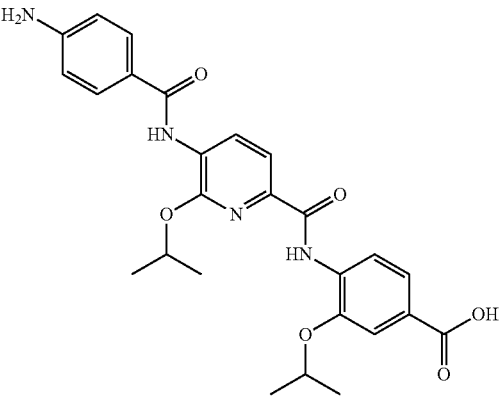

The present invention further provides pharmaceutical compositions comprising one or more compounds described herein or a pharmaceutically acceptable salt, solvate or hydrate thereof, optionally in combination with one or more carrier substances and/or one or more adjuvants.

The present invention furthermore provides compounds or pharmaceutical compositions as described herein for use in the treatment and/or prophylaxis of bacterial infections, especially caused by *E. coli, P. aeruginosa, A. baumannii*, other Gram-negative bacteria, and Gram-positive bacteria.

Moreover preferably, the present invention provides compounds for use in the treatment and/or prophylaxis of bacterial infections, especially caused by *Pseudomonas aeruginosa* and other Gram-negative bacteria.

It is a further object of the present invention to provide a compound as described herein or a pharmaceutical composition as defined herein for the preparation of a medicament for the treatment and/or prophylaxis of bacterial infections, especially caused by selected Gram-negative bacteria and Gram-positive bacteria.

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein.

The compounds described herein may be solvated, especially hydrated. The hydratization/hydration may occur during the process of production or as a consequence of the hygroscopic nature of the initially water free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

The pharmaceutical compositions according to the present invention comprise at least one compound described herein and, optionally, one or more carrier substances and/or adjuvants.

As mentioned above, therapeutically useful agents that contain compounds described herein, their solvates, salts or formulations are also comprised in the scope of the present invention. In general, the compounds described herein will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, and polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The compounds of the present invention can be prepared by fermentation (e.g. by fermentation of strain MCy8071 DSM27004) or by chemical synthesis applying procedures known to a person skilled in the art.

For example the compounds of the present invention can be prepared according to the following procedures:

Starting from the respective optionally substituted building blocks (e.g. $Ar^1$, $Ar^2$, $Ar^3$, $Ar^4$ and $Ar^5$), these building blocks can be linked to each other using acid chlorides or coupling reagents which are known to a person skilled in the art, e.g. according to the following reaction scheme:

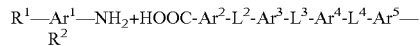

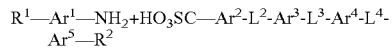

If $L^1$, $L^2$, $L^3$ and/or $L^4$ is a group of formula —CH=CH— (or another olefine group), the respective optionally substituted building blocks (e.g. $Ar^1$, $Ar^2$, $Ar^3$, $Ar^4$ and $Ar^5$) can be linked to each other using a Wittig or a Horner reaction, e.g. according to the following reaction scheme:

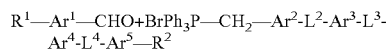

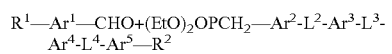

If $L^1$, $L^2$, $L^3$ and/or $L^4$ is a heterocycloalkyl or a heteroaryl group, the respective optionally substituted building blocks (e.g. $Ar^1$, $Ar^2$, $Ar^3$, $Ar^4$ and $Ar^5$) can be linked to each other applying similar reaction conditions.

Figure 12:
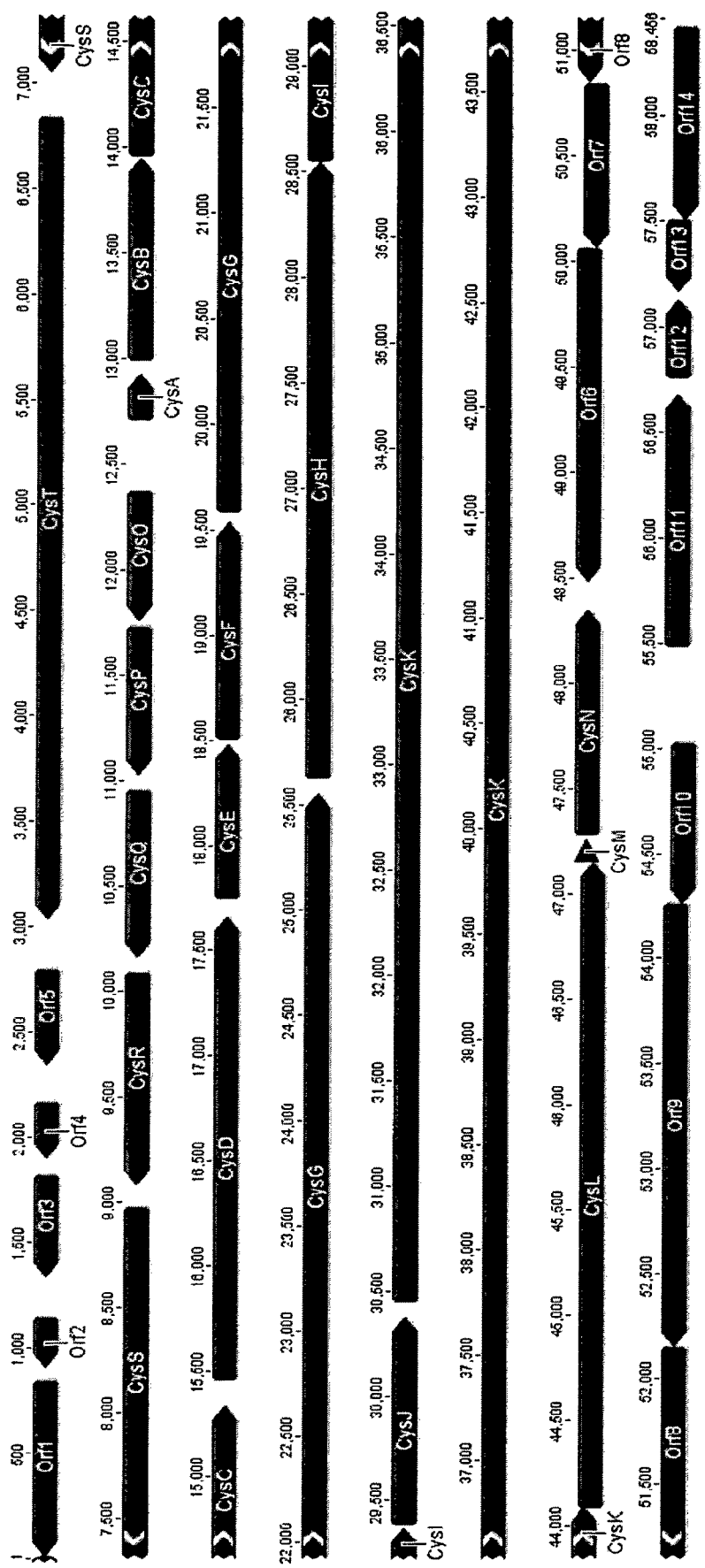

Identification of the Cystobactamide Biosynthesis Gene Cluster:

The genome of the cystobactamid producer has been sequenced by shotgun-sequencing. As the main building block of the cystobactamides is the non-proteinogenic amino acid p-aminobenzoic acid (PABA), p-aminobenzoic acid synthase (query, NP_415614) was used as query for the identification of a putative cystobactamide biosynthetic cluster in the genome of Cbv34. Importantly, a p-aminobenzoic acid synthase homologue could be identified (CysD, FIG. 12 and table A), which is forming an operon with non-ribosomal peptide synthases (CysG, H and K) in the context of an in silico predicted ~48 kb large NRPS cluster (FIG. 12, assignment: table A). The genes in this NRPS cluster have been analysed by pfam, NCBI BLAST and phyre2. Aside the p-aminobenzoic acid synthase homologue, two further PABA biosynthetic enzymes can be found in the cluster: an aminodeoxychorismate lyase (CysI) and a 3-deoxy-d-arabino-heptulosonate-7-phosphate (DAHP) synthase (CysN). DAHP synthase (CysN) is a key enzyme for the production of shikimate and chorismate. In the main trunk of the shikimate pathway, D-erythrose 4-phosphate and phosphoenolpyruvate (DAHP synthase) are converted via shikimate to chorismate. CysI and CysD allow the direct biosynthesis of PABA from chorismate. Furthermore, the cluster contains a p-aminobenzoic acid N-oxygenase homologue (CysR).

FIG. 12 shows the cystobactamide biosynthetic cluster of the invention.

A recombinant biosynthesis cluster capable of synthesizing a cystobactamide selected from the group consisting of cystobactamide A, B, C, D, E, F, G and H, wherein the cluster comprises all of the polypeptides, or a functional variant thereof, according to SEQ ID NOs. 40 to 73.

The term "functional variant" as used herein denotes a polypeptide having a sequence that is at least 85%, 90%, 95% or 99% identical to a polypeptide sequence described herein. A "functional variant" of a polypeptide may retain amino acids residues recognized as conserved for the polypeptide in nature, and/or may have non-conserved amino acid residues. Amino acids can be, relative to the native polypeptide, substituted (different), inserted, or deleted, but the variant has generally similar (enzymatic) activity or function as compared to a polypeptide described herein. A "functional variant" may be found in nature or be an engineered mutant (recombinant) thereof.

The term "identity" refers to a property of sequences that measures their similarity or relationship. Identity is measured by dividing the number of identical residues by the total number of residues and multiplying the product by 100.

The terms "protein", "polypeptide", "peptide" as used herein define an organic compound made of two or more amino acid residues arranged in a linear chain, wherein the individual amino acids in the organic compound are linked by peptide bonds, i.e. an amide bond formed between adjacent amino acid residues. By convention, the primary structure of a protein is reported starting from the amino-terminal (N) end to the carboxyl-terminal (C) end.

As used herein, "comprising", "including", "containing", "characterized by", and grammatical equivalents thereof are inclusive or open-ended terms that do not exclude additional, unrecited elements or method steps. "Comprising", etc. is to be interpreted as including the more restrictive term "consisting of".

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

Preferably, the NRPS enzyme of the invention is a not naturally occurring NRPS. The NRPS of the invention may also be a hybrid NRPS comprising modules, domains, and/or portions thereof, or functional variants thereof, from two or more NRPSs or from one or more polyketide synthase(s) (PKSs).

The cystobactamide biosynthesis cluster of the invention preferably includes the elements of Table A.

TABLE A

Cystobactamide gene cluster of the invention. Gene and NRPS domain annotation with the gene cluster sequence corresponding to SEQ ID NO. 1.

| | location within the gene cluster sequence (bp) | | | | | NRPS | | | | | |
|---|---|---|---|---|---|---|---|---|---|---|---|
| | | | | | | | location within the gene cluster sequence (bp) | | location within the protein sequence (aa) | | |
| Name | Min. | Max. | direction | Length | aa | Domains | length | Min. | Max. | length | Min. | Max. |
| Orf1 | 15 | 845 | reverse | 831 | 276 | | | | | | | |
| Orf2 | 912 | 1148 | reverse | 237 | 78 | | | | | | | |
| Orf3 | 1339 | 1827 | reverse | 489 | 162 | | | | | | | |
| Orf4 | 1907 | 2170 | reverse | 264 | 87 | | | | | | | |
| Orf5 | 2347 | 2796 | reverse | 450 | 149 | | | | | | | |
| CysT | 3035 | 6838 | reverse | 3804 | 1267 | | | | | | | |
| CysS | 7049 | 8977 | reverse | 1929 | 642 | | | | | | | |
| CysR | 9086 | 10087 | reverse | 1002 | 333 | | | | | | | |
| CysQ | 10162 | 10956 | reverse | 795 | 264 | | | | | | | |
| CysP | 11029 | 11730 | reverse | 702 | 233 | | | | | | | |
| CysO | 11764 | 12375 | reverse | 612 | 203 | | | | | | | |
| CysA | 12715 | 12927 | forward | 213 | 70 | | | | | | | |
| CysB | 12996 | 13949 | forward | 954 | 317 | | | | | | | |
| CysC | 13959 | 15338 | forward | 138 | 45 | | | | | | | |
| CysD | 15464 | 17662 | forward | 2199 | 732 | | | | | | | |
| CysE | 17749 | 18480 | forward | 732 | 243 | | | | | | | |
| CysF | 18503 | 19540 | forward | 1038 | 345 | | | | | | | |
| CysG | 19580 | 25558 | forward | 5979 | 1992 | AMP-binding domain | 1451 | 19694 | 21145 | 483 | 39 | 521 |
| | | | | | | PCP domain | 209 | 21221 | 21430 | 69 | 548 | 616 |
| | | | | | | Condensation_LCL domain | 893 | 21485 | 22378 | 297 | 636 | 932 |
| | | | | | | AMP-binding domain | 1451 | 22880 | 24331 | 483 | 1101 | 1583 |
| | | | | | | PCP domain | 215 | 24404 | 24619 | 71 | 1609 | 1679 |
| | | | | | | Thioesterase domain | 788 | 24728 | 25516 | 262 | 1717 | 1978 |
| CysH | 25626 | 28553 | forward | 2928 | 975 | AMP-binding domain | 1199 | 25737 | 26936 | 399 | 38 | 436 |
| | | | | | | novel domain type | 332 | 27231 | 27563 | 110 | 536 | 645 |
| | | | | | | AMP binding domain C-terminus | 170 | 28032 | 28202 | 56 | 803 | 858 |
| | | | | | | PCP domain | 197 | 28284 | 28481 | 65 | 887 | 951 |
| CysI | 28555 | 29373 | forward | 819 | 272 | | | | | | | |
| CysJ | 29392 | 30375 | forward | 984 | 327 | | | | | | | |
| CysK | 30450 | 44087 | forward | 13638 | 4545 | Condensation_LCL domain | 323 | 30459 | 30782 | 107 | 4 | 110 |
| | | | | | | AMP-binding domain | 1505 | 31239 | 32744 | 501 | 264 | 764 |
| | | | | | | PCP domain | 197 | 32820 | 33017 | 65 | 791 | 855 |
| | | | | | | Condensation_LCL domain | 893 | 33072 | 33965 | 297 | 875 | 1171 |

TABLE A-continued

Cystobactamide gene cluster of the invention. Gene and NRPS domain annotation with the gene cluster sequence corresponding to SEQ ID NO. 1.

| | location within the gene cluster sequence (bp) | | | | | | NRPS | | | | | |
|---|---|---|---|---|---|---|---|---|---|---|---|---|
| | | | | | | | | location within the gene cluster sequence (bp) | | location within the protein sequence (aa) | | |
| Name | Min. | Max. | direction | Length | aa | Domains | length | Min. | Max. | length | Min. | Max. |
| | | | | | | AMP-binding domain | 1505 | 34461 | 35966 | 501 | 1338 | 1838 |
| | | | | | | PCP domain | 197 | 36042 | 36239 | 65 | 1865 | 1929 |
| | | | | | | Condensation_LCL domain | 890 | 36285 | 37175 | 296 | 1946 | 2241 |
| | | | | | | AMP-binding domain | 1574 | 37668 | 39242 | 524 | 2407 | 2930 |
| | | | | | | PCP domain | 359 | 39165 | 39524 | 119 | 2906 | 3024 |
| | | | | | | Condensation_LCL domain | 893 | 39579 | 40472 | 297 | 3044 | 3340 |
| | | | | | | AMP-binding domain | 1505 | 40968 | 42473 | 501 | 3507 | 4007 |
| | | | | | | PCP domain | 197 | 42549 | 42746 | 65 | 4034 | 4098 |
| | | | | | | Condensation_LCL domain | 896 | 42801 | 43697 | 298 | 4118 | 4415 |
| CysL | 44084 | 47155 | forward | 3072 | 1023 | AMP-binding domain | 1445 | 45665 | 47110 | 481 | 528 | 1008 |
| CysM | 47152 | 47268 | forward | 117 | 38 | | | | | | | |
| CysN | 47280 | 48353 | forward | 1074 | 357 | | | | | | | |
| Orf6 | 48490 | 50067 | reverse | 1578 | 525 | | | | | | | |
| Orf7 | 50064 | 50849 | reverse | 786 | 261 | | | | | | | |
| Orf8 | 50855 | 52156 | reverse | 1302 | 433 | | | | | | | |
| Orf9 | 52161 | 54266 | reverse | 2106 | 701 | | | | | | | |
| Orf10 | 54266 | 55027 | reverse | 762 | 253 | | | | | | | |
| Orf11 | 55486 | 56679 | forward | 1194 | 397 | | | | | | | |
| Orf12 | 56760 | 57134 | forward | 375 | 124 | | | | | | | |
| Orf13 | 57166 | 57504 | reverse | 339 | 112 | | | | | | | |
| Orf14 | 57504 | 58418 | reverse | 915 | 304 | | | | | | | |

The present invention also provides isolated, synthetic or recombinant nucleic acids that encode NRPSs of the invention. Said nucleic acids include nucleic acids that include a portion or all of a NRPS of the invention, nucleic acids that further include regulatory sequences, such as promoter and translation initiation and termination sequences, and can further include sequences that facilitate stable maintenance in a host cell, i.e., sequences that provide the function of an origin of replication or facilitate integration into host cell chromosomal or other DNA by homologous recombination. These NRPSs may be used as research tools or as modules in recombinant NRPS or PKS clusters.

Preferably, the invention relates to an isolated, synthetic or recombinant nucleic acid comprising:
(i) a sequence encoding a cystobactamide biosynthesis cluster, wherein the sequence has a sequence identity to the full-length sequence of SEQ ID NO. 1 from at least 85%, 90%, 95%, 96%, 97%, 98%, 98.5%, 99%, or 99.5% to 100%;
(ii) a sequence encoding a NRPS, wherein the sequence has a sequence identity to the full-length sequence of any of SEQ ID NOs. 8, 9, 12 or 13 from at least 85%, 90%, 95%, 96%, 97%, 98%, 98.5%, 99%, or 99.5% to 100%;
(iii) a sequence completely complementary to the full length sequence of any nucleic acid sequence of (i) or (ii); or
(iv) a sequence encoding a polypeptide according to any of SEQ ID NOs. 46, 47, 50 or 51.

The phrases "nucleic acid" or "nucleic acid sequence" as used herein refer to an oligonucleotide, nucleotide, poly-nucleotide, or to a fragment of any of these, to DNA of genomic or synthetic origin which may be single-stranded or double-stranded and may represent a sense or antisense strand, natural or synthetic in origin. "Oligonucleotide" includes either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated. A "coding sequence" of or a "nucleotide sequence encoding" a particular polypeptide or protein, is a nucleic acid sequence which is transcribed and translated into a polypeptide or protein when placed under the control of appropriate regulatory sequences. The nucleic acids used to practice this invention may be isolated from a variety of sources, genetically engineered, amplified, and/or expressed/generated recombinantly. Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993). A nucleic acid encoding a polypeptide of the invention is assembled in appropriate phase with a leader sequence capable of directing secretion of the translated polypeptide or fragment thereof.

The term "isolated" as used herein means that the material, e.g., a nucleic acid, a polypeptide, a vector, a cell, is removed from its original environment, e.g., the natural environment if it is naturally occurring. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

The term "synthetic" as used herein means that the material, e.g. a nucleic acid, has been synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22: 1859.

The term "recombinant" means that the nucleic acid is adjacent to a "backbone" nucleic acid to which it is not adjacent in its natural environment. Backbone molecules according to the invention include nucleic acids such as cloning and expression vectors, self-replicating nucleic acids, viruses, integrating nucleic acids and other vectors or nucleic acids used to maintain or manipulate a nucleic acid insert of interest. Recombinant polypeptides of the invention, generated from these nucleic acids can be individually isolated or cloned and tested for a desired activity. Any recombinant expression system can be used, including bacterial, mammalian, yeast, insect or plant cell expression systems.

Also provided is a vector comprising at least one nucleic acid according to the invention. The vector may be a cloning vector, an expression vector or an artificial chromosome.

As used herein, the term "vector" refers to a nucleic acid molecule capable of transporting another nucleic acid to which it has been linked. Vectors, including cloning and expression vectors, comprise a nucleic acid of the invention or a functional equivalent thereof. Nucleoc acids of the invention can be incorporated into a recombinant replicable vector, for example a cloning or expression vector. The vector may be used to replicate the nucleic acid in a compatible host cell. Thus, the invention also provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below. The vector into which the expression cassette or nucleic acid of the invention is inserted may be any vector which may conveniently be subjected to recombinant DNA procedures, and the choice of the vector will often depend on the host cell into which it is to be introduced. A variety of cloning and expression vectors for use with prokaryotic and eukaryotic hosts are described by Sambrook, et al, Molecular Cloning: A Laboratory Manual, 2nd Ed., Cold Spring Harbor, N.Y., (1989).

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication, and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, nucleic acids of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operationally linked to the nucleic acid sequence to be expressed.

Within a vector, such as an expression vector, "operationally linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operationally linked" refers to a juxtaposition wherein the components described are in a relationship permitting them to function in their intended manner. A regulatory sequence such as a promoter, enhancer or other expression regulation signal "operationally linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

The term "regulatory sequence" or "control sequence" is intended to include promoters, operators, enhancers, attenuators and other expression control elements (e.g., polyadenylation signal). Such regulatory sequences are described, for example, in Goeddel; Gene Expression Technology: Methods in Enzymology 185, Academic Press, San Diego, Calif. (1990).

The term regulatory or control sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operationally linked to each other in a consecutive order from the 5'-end to 3'-end relative to the coding strand of the sequence encoding the polypeptide of the invention: (i) a promoter sequence capable of directing transcription of the nucleotide sequence encoding the polypeptide in the given host cell; (ii) optionally, a signal sequence capable of directing secretion of the polypeptide from the given host cell into a culture medium; (iii) optionally, a sequence encoding for a C-terminal, N-terminal or internal epitope tag sequence or a combination of the aforementioned allowing purification, detection or labeling of the polypeptide; (iv) a nucleic acid sequence of the invention encoding a polypeptide of the invention; and preferably also (v) a transcription termination region (terminator) capable of terminating transcription downstream of the nucleotide sequence encoding the polypeptide. Particular named bacterial promoters include lad, lacZ, T3, T7, SP6, K1F, tac, tet, gpt, lambda $P_R$, $P_L$ and trp. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. Downstream of the nucleotide sequence according to the invention there may be a 3' untranslated region containing one or more transcription termination sites (e.g. a terminator). The origin of the terminator is less critical. The terminator can, for example, be native to the DNA sequence encoding the polypeptide. Preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG (or TUG or GUG in prokaryotes) at the beginning and a termination codon appropriately positioned at the end of the polypeptide to be translated.

Enhanced expression of a polynucleotide of the invention may also be achieved by the selection of heterologous regulatory regions, e.g. promoter, secretion leader and/or terminator regions, which may serve to increase expression and, if desired, secretion levels of the protein of interest from the expression host and/or to provide for the inducible control of the expression of a polypeptide of the invention. It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein.

The vectors, such as recombinant expression vectors, of the invention can be designed for expression of a portion or all of a NRPS of the invention in prokaryotic or eukaryotic cells. For example, a portion or all of a NRPS of the invention can be expressed in bacterial cells such as E. coli, Bacillus strains, insect cells (using baculovirus expression vectors), filamentous fungi, yeast cells or mammalian cells. Suitable host cells are discussed further in Goeddel, Gene Expression Technology: Methods in Enzymology 185, Academic Press, San Diego, Calif. (1990). Representative examples of appropriate hosts are described hereafter. Appropriate culture media and conditions for the above-described host cells are known in the art.

As set out above, the term "control sequences" or "regulatory sequences" is defined herein to include at least any component which may be necessary and/or advantageous for the expression of a polypeptide. Any control sequence may be native or foreign to the nucleic acid sequence of the invention encoding a polypeptide. Such control sequences may include, but are not limited to, a promoter, a leader, optimal translation initiation sequences (as described in Kozak, 1991, J. Biol. Chem. 266:19867-19870), a secretion signal sequence, a pro-peptide sequence, a polyadenylation sequence, a transcription terminator. At a minimum, the control sequences typically include a promoter, and transcriptional and translational stop signals. A stably transformed microorganism is one that has had one or more DNA fragments introduced such that the introduced molecules are maintained, replicated and segregated in a growing culture. Stable transformation may be due to multiple or single chromosomal integration(s) or by (an) extrachromosomal element(s) such as (a) plasmid vector(s). A plasmid vector is capable of directing the expression of polypeptides encoded by particular DNA fragments. Expression may be constitutive or regulated by inducible (or repressible) promoters that enable high levels of transcription of functionally associated DNA fragments encoding specific polypeptides.

Expression vectors of the invention may also include a selectable marker gene to allow for the selection of bacterial strains that have been transformed, e.g., genes which render the bacteria resistant to drugs such as chloramphenicol, erythromycin, kanamycin, neomycin, tetracycline, as well as ampicillin and other penicillin derivatives like carbenicillin. Selectable markers can also include biosynthetic genes, such as those in the histidine, tryptophan and leucine biosynthetic pathways.

The appropriate polynucleotide sequence may be inserted into the vector by a variety of procedures. In general, the polynucleotide sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al, Molecular Cloning: A Laboratory Manual 2nd Ed., Cold Spring Harbor Laboratory Press (1989). The polynucleotide sequence may also be cloned using homologous recombination techniques including in vitro as well as in vivo recombination. Such procedures and others are deemed to be within the scope of those skilled in the art. The vector may be, for example, in the form of a plasmid, a viral particle, or a phage. Other vectors include chromosomal, nonchromosomal and synthetic polynucleotide sequences, derivatives of SV40; bacterial plasmids, phage DNA, baculovirus, yeast plasmids, vectors derived from combinations of plasmids and bacteriophage DNA, viral DNA such as vaccinia, adenovirus, fowl pox virus and pseudorabies.

The invention also provides an engineered or recombinant host cell, i.e. a transformed cell comprising a nucleic acid sequence of the invention as a heterologous or non-native polynucleotide, e.g. a sequence encoding the cystobactamide biosynthesis cluster or a NRPS of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells.

Preferred mammalian cells include e.g. Chinese hamster ovary (CHO) cells, COS cells, 293 cells, PerC6 cells, hybridomas, Bowes melanoma or any mouse or any human cell line. Exemplary insect cells include any species of *Spodoptera* or *Drosophila*, including *Drosophila* S2 and *Spodoptera* Sf-9. Exemplary fungal cells include any species of *Aspergillus*. Preferred yeast cell include, e.g. a cell from a *Candida, Hansenula, Kluyveromyces, Pichia, Saccharomyces, Schizosaccharomyces*, or *Yarrowia* strain. More preferably from *Kluyveromyces lactis, S. cerevisiae, Hansenula polymorpha, Yarrowia lipolytica*, or *Pichia pastoris*.

According to the invention, the host cell may be a prokaryotic cell. Preferably, the prokaryotic host cell is a bacterial cell. The term "bacterial cell" includes both Gram-negative and Gram-positive as well as archaeal microorganisms. Suitable bacteria may be selected from e.g. *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobacter crescentus* CB 15, *Methylobacterium extorquens, Rhodobacter sphaeroides, Pseudomonas putida, Paracoccus zeaxanthinifaciens, Paracoccus denitrificans, E. coli, C. glutamicum, Staphylococcus carnosus, Streptomyces lividans, Sinorhizobium melioti* and *Rhizobium radiobacter*. The selection of an appropriate host is within the abilities of those skilled in the art.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)). The nucleic acids or vectors of the invention may be introduced into the cells for screening, thus, the nucleic acids enter the cells in a manner suitable for subsequent expression of the nucleic acid. The method of introduction is largely dictated by the targeted cell type.

Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the nucleic acids of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof. Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps. The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue. Cell-free translation systems can also be employed to produce a polypeptide of the invention. Cell-free translation systems can use mRNAs transcribed from a DNA construct comprising a promoter operationally linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

Host cells containing the polynucleotides of interest, e.g., nucleic acids of the invention, can be cultured in conventional nutrient media modified as appropriate for activating promoters, selecting transformants or amplifying genes. The culture conditions such as temperature, pH and the like, are those previously used with the host cell selected for expression and will be apparent to the ordinarily skilled artisan. The clones which are identified as having the specified enzyme activity may then be sequenced to identify the polynucleotide sequence encoding a portion or all of a NRPS of the invention.

Recombinant DNA can be introduced into the host cell by any means, including, but not limited to, plasmids, cosmids, phages, yeast artificial chromosomes or other vectors that mediate transfer of genetic elements into a host cell. These vectors can include an origin of replication, along with cis-acting control elements that control replication of the vector and the genetic elements carried by the vector. Selectable markers can be present on the vector to aid in the identification of host cells into which genetic elements have been introduced. Means for introducing genetic elements into a host cell (e.g. cloning) are well known to the skilled artisan. Other cloning methods include, but are not limited to, direct integration of the genetic material into the chromosome. This can occur by a variety of means, including cloning the genetic elements described herein on non-replicating plasmids flanked by homologous DNA sequences of the host chromosome; upon transforming said recombinant plasmid into a host the genetic elements can be introduced into the chromosome by DNA recombination. Such recombinant strains can be recovered if the integrating DNA fragments contain a selectable marker, such as antibiotic resistance. Alternatively, the genetic elements can be directly introduced into the chromosome of a host cell without use of a non-replicating plasmid. This can be done by synthetically producing DNA fragments of the genetic elements in accordance to the present invention that also contain homologous DNA sequences of the host chromosome. Again if these synthetic DNA fragments also contain a selectable marker, the genetic elements can be inserted into the host chromosome.

The cystobactamide biosynthesis cluster or a NRPS of the invention may be favorably expressed in any of the above host cells. Thus, the present invention provides a wide variety of host cells comprising one or more of the isolated, synthetic or recombinant nucleic acids and/or NRPSs of the present invention. The host cell, when cultured under suitable conditions, is capable of producing a cystobactamide selected from the group consisting of cystobactamide A, B, C, D, E, F, G and H that it otherwise does not produce, or produces at a lower level, in the absence of a nucleic acid of the invention.

The invention also relates to an isolated, synthetic or recombinant polypeptide having an amino acid sequence according to any of SEQ ID NOs. 40 to 73, or an amino acid sequence encoded by a nucleic acid of the invention.

The present invention further provides a method for the preparation of a cystobactamide selected from the group consisting of cystobactamide A, B, C, D, E, F, G and H, said method generally comprising: providing a host cell of the present invention, and culturing said host cell in a suitable culture medium under suitable conditions such that at least one cystobactamide selected from the group consisting of cystobactamide A, B, C, D, E, F, G and His produced. The method may further comprise a step of isolating a cystobactamide selected from the group consisting of cystobactamide A, B, C, D, E, F, G and H, i.e. separating and retaining the compound from the culture broth. The isolation step may be carried out using affinity chromatography, anion exchange chromatography, or reversed phase chromatography.

EXAMPLES

Conditions of Production
Strain for Production

The strain *Cystobacter velatus* MCy8071 belongs to the order Myxococcales (Myxobacteria), suborder Cystobacterineae, family Cystobacteraceae, genus *Cystobacter*. The comparison of the partial 16S rRNA gene sequences with sequences of a public database (BLAST, Basic Local Alignment Search Tool provided by NCBI, National Center for Biotechnology Information) revealed 100% similarity to *Cystobacter velatus* strain DSM 14718.

MCy8071 was isolated at the Helmholtz Centre for Infection Research (HZI, formerly GBF) from a Chinese soil sample collected in 1982. The strain was deposited at the German Collection of Microorganisms in Braunschweig (DSM) in March 2013 under the designation DSM 27004.
Cultivation The strain MCy8071 grows well on yeast-agar (VY/2: 0.5% *Saccharomyces cerevisiae*, 0.14% $CaCl_2 \times 2$ $H_2O$, 0.5 µg vitamine $B_{12}$/l, 1.5% agar, pH 7.4), CY-agar (casitone 0.3%, yeast extract 0.1%, $CaCl_2 \times 2$ $H_2O$ 0.1%, agar 1.5%, pH 7.2) and P-agar (peptone Marcor 0.2%, starch 0.8%, single cell protein probione 0.4%, yeast extract 0.2%, $CaCl_2 \times 2$ $H_2O$ 0.1%, $MgSO_4$ 0.1%, Fe-EDTA 8 mg/l, 1.5% agar, pH 7.5). The working culture was nurtured in liquid medium CY/H (50% CY-medium+50 mM Hepes, 50% H-medium: soy flour 0.2%, glucose 0.8%, starch 0.2%, yeast extract 0.2%, $CaCl_2 \times 2$ $H_2O$ 0.1%, $MgSO_4$ 0.1%, Fe-EDTA 8 mg/l, Hepes 50 mM pH 7.4). Liquid cultures were shaken at 180 rpm at 30° C. For conservation aliquots a 2 ml of a three days old culture were stored at −80° C. Reactivation, even after several years, is no problem on the above mentioned agar plates or in 20 ml CY/H-medium (in 100 ml Erlenmeyer flasks with plugs and aluminium-cap). After one-two days the 20 ml cultures can be upscaled to 100 ml.
Morphological Description After two days in liquid medium CY/H the rod-shaped cells of strain MCy8071 have a length of 9.0-14.5 µm and width of 0.8-1.0 µm. On the above mentioned agar-plates swarming is circular. On VY/2-agar the swarm is thin and transparent. Yeast degradation is visible on VY/2-agar. On CY-agar the culture looks transparent-orange. On P-agar cell mass production is distinctive and swarming behaviour is reduced. The colony colour is orange-brown. Starch in P-agar is degraded.

MCy8071 is resistant against the following antibiotics: ampicillin, gentamycin, hygromycin, polymycin, bacitracin, spectinomycin, neomycin, and fusidinic acid. Weak growth is possible with cephalosporin and kasugamycin and no growth is possible with thiostrepton, trimethoprin, kanamycin, and oxytetracycline (final concentration of all antibiotics was adjusted to 50 µg $ml^{-1}$).
Production of Cystobactamides A, B, C, D, E, F, G and H The strain produces in complex media. He prefers nitrogen containing nutrients like single cell protein (Probion) and products of protein decomposition like peptone, tryptone, yeast extract, soy flour and meat extract. Here the production is better with several of the mentioned protein-mixtures compared to a single one.

Cystobactamides are produced within the logarithmical to the stationary phase of growth. After two days in 100 liter fermentation (medium E) the amount of products did not increase anymore.

Cystobactamides are delivered to the medium and bind to XAD-adsorber resin. XAD is sieved by a metal sieve and eluted in acetone. Different production temperatures were tested (21° C., 30° C., 37° C. and 42° C.) whereby at 42° C. no production was possible. The optimal temperature was at 30° C. with maximal aeration.

Fermentation of MCy8071 was conducted in a 150 liter fermenter with 100 liter medium E (skimmed milk 0.4%, soy flour 0.4%, yeast extract 0.2%, starch 1.0%, $MgSO_4$ 0.1%, Fe-EDTA 8 mg/l, glycerine 0.5%; pH 7.4) and in a 100 liter fermenter with 70 liter medium M (soy-peptone 1.0%, maltose 1.0%, $CaCl_2 \times 2$ $H_2O$ 0.1%, $MgSO_4$ 0.1%, Fe-EDTA 8 mg/l; pH 7.2) for four days at 30° C. The pH was regulated with potassium hydroxide (2.5%) and sulfuric acid between 7.2 and 7.4. The stirrer speed was 100-400 rpm, aerated with 0.05 vvm compressed air. The dissolved oxygen content within the fermentation broth was regulated by the stirrer speed to $pO_2$ 40%. To bind cystobactamides 1% adsorber resin was added to the fermentation broth. The fermenter was inoculated with 5 liter of a three days old pre-culture (E or M-medium, respectively). The production during the fermentation process was checked by HPLC-MS-analyses and serial dilution test of the methanol extract against *Escherichia coli*. The strain produces Cystobactamides A, B, C, D, E, F, G and H.
Knock-Out Experiments To confirm that the cystobactamide biosynthesis gene cluster is responsible for the production of the cystobactamides, a knock-out (KO) experiment was carried out, where CysK (NRPS) and CysL (benzoyl-CoA ligase) was knocked out, respectively. Specifically, PCR products of 1000 bp fragments of CysK and CysL genes were produced from MCy8071 genomic DNA using Taq polymerase. The primers were designed to add 3 stop codons on the extremities of the PCR products.

```
CysL KO For
TGATTGATTGATCGGCGCGATTCGGCCTCTGG

CysL KO Rev
TCAATCAATCATCGGGTCGCGGTCTCAGGCTC

CysK KO For
TGATTGATTGAAAAACAGTCGGAGGAGTTTCTTGTCC

CysK KO Rev
TCAATCAATCAACTCCCAGTGCCCTCAGCCTC
```

The PCR products were gel purified using the Nucleospin® Gel and PCR Clean-up kit from Macherey-Nagel and cloned into a pCR2.1-TOPO vector. The construct was integrated via heat shock into chemically competent E. coli HS996 and the selection was done on kanamycin-supplemented LB agar plates. Single colonies were screened for correct constructs via alkaline lysis plasmid preparation and restriction digest by EcoRI. The constructs were then sequenced to ensure the sequence homology.

A correct construct for each KO was transformed into non-methylating chemically competent E. coli SCS110. Plasmids were prepared using the GeneJET Plasmid Miniprep kit from Thermo scientific and integrated into MCy8071 via electroporation. Selection of transformed clones was done on kanamycin-supplemented CTT agar plates. KO mutants and wild type cultures were grown in parallel in the presence of an adsorber resin (XAD-16) and samples of crude extracts of the cultures were analysed.

The results showed that in the KO mutants there was a complete absence of cystobactamide production indicating that CysK and CysL are essential for the production of the cystobactamides. Furthermore, the result indicates the essential nature of the cystobactamide biosynthesis gene cluster for the production of the cystobactamides.

Structural Analysis:

HRESI(+)MS analysis of cystobactamide A (1) returned a pseudomolecular formula ion (M+H)$^+$ consistent with the molecular formula $C_{46}H_{45}N_7O_{14}$, requiring twenty eight double bond equivalents (DBE). The $^{13}$C NMR (DMSO-d$_6$) data revealed seven ester/amide carbonyls ($\delta_C$ 163.7 to 169.6) and a further 30 sp$^2$ resonances ($\delta_C$ 114.2 to 150.8), accounting for 22 DBE. Consideration of the 1D and 2D NMR data (Table 1) revealed a set of five aromatic spin systems, three of which were attributed to para-substituted, 1,3,4-trisubstituted and 1,2,3,4-tetrasubstituted benzene rings. A set of HMBC correlations from the aromatic signals H-6,6' ($\delta_H$ 7.96) and the NH ($\delta_H$ 8.92) to the amide carbonyl C-4 ($\delta_C$ 166.5); NH ($\delta_H$ 10.82) to C-7/7' ($\delta_C$ 119.8) and to the second amide carbonyl C-10 ($\delta_C$ 164.6); H-12/12 ($\delta_H$ 8.20) to C-10 established the connectivity of two of the para-substituted aromatic ring systems (FIG. 1). Further examination of the $^1$H and COSY NMR data established the connectivity of the amide NH ($\delta_H$ 8.92) across to the methines H-2 ($\delta_H$ 4.96) and H-1 ($\delta_H$ 4.70). The downfield characteristic of H-1 ($\delta_C$ 79.4) suggested substitution by an oxygen, which was confirmed from a HMBC correlation from H-1 to 1-OMe ($\delta_H$ 3.53, $\delta_C$ 59.6). Also observed were HMBC correlations from H-1 and H-2 to an ester/amide carbonyl ($\delta_C$ 169.6) leading to the construction of subunit A (FIG. 1).

For the 1,3,4 trisubstituted benzene ring HMBC correlations were observed from H-17 ($\delta_H$ 7.58) to an ester/amide carbonyl C-15 ($\delta_C$ 167.3), an oxy quaternary carbon C-18 ($\delta_C$ 146.8), C-19 ($\delta_C$ 133.6) and C-21 ($\delta_C$ 122.9). The isolated spin system for the 1,2,3,4 tetrasubstituted benzene ring showed HMBC correlations from i) H-25 ($\delta_H$ 7.82, d, 8.7) to an ester/amide carbonyl C-23 ($\delta_C$ 163.7), C-27 ($\delta_C$ 136.2) and a quaternary oxy carbon C-29 ($\delta_C$ 150.8); ii) H-26 ($\delta_H$ 7.42) to C-24 ($\delta_C$ 117.3) and C-28 ($\delta_C$ 139.5) along with the phenolic hydroxyl ($\delta_H$ 11.25) showing correlations to C-24 and C-28) The tri and tetra-substituted benzene rings were attached para to each other by HMBC correlations from the amide NH ($\delta_H$ 10.98) to C-20 ($\delta_C$ 119.8) C-18 ($\delta_C$ 146.7) and C-23 ($\delta_C$ 163.7) (FIG. 1). The last of the para-substituted aromatic spin system H-33/33' ($\delta_H$ 8.11, d, 8.3) and H-34/34' ($\delta_H$ 7.44, d, 8.3) showed attachment to the 1,2,3-trisubstituted benzene ring by HMBC correlations of the amide NH ($\delta_H$ 9.88) and H-33/33' to the amide carbonyl C-31 ($\delta_C$ 164.3). Additional interpretation of the COSY data revealed two sets of isopropoxy residues (H$_3$-39 ($\delta_H$ 1.38)-H-38 ($\delta_H$ 4.76)-H-40 ($\delta_H$ 1.38)) and (H$_3$-42 ($\delta_H$ 1.25)-H-41 ($\delta_H$ 4.30)-H$_3$-43 ($\delta_H$ 1.25). The two isopropoxy residues were confirmed to be attached to the oxy quaternary carbons C-18 ($\delta_C$ 146.7) and C-28 ($\delta_C$ 139.5) based on ROESY correlations from H-38/H-39 to H-17/NH and H-42/43 to NH/29-OH/H-33/33' (FIG. 1). A link between subunit A and B was not established, however based on structural similarity to cystobactamide B, the point of attachment of subunits A and B were inferred. Having accounted for majority of the resonances, $N_2O_3H_2$ and 1DBE were left to account for. The UV spectrum of the compound showed a $\lambda_{max}$ of 301 and 320 nm which suggested a conjugated system which was only possible to have been generated by the attachment of a nitro functionality para- to the aromatic system on subunit A. The remaining MF was adjusted to generate a carboxylic acid residue (C-15) on the 1,2,3-substituted aromatic ring in subunit B generating the 4-amino-3-isopropoxybenzoic acid moiety leading to the construction of the planar structure of cystobactamide A.

HRESI(+)MS analysis of cystobactamide B (2) returned a pseudomolecular formula ion (M+H)$^+$ consistent with the molecular formula $C_{46}H_{44}N_6O_{15}$, requiring twenty eight double bond equivalents (DBE). The NMR data (Table 2) of 2 was highly similar to (1) with now the NH ($\delta_H$ 10.19) and the oxymethine H-1 ($\delta_H$ 4.32) seeing the carbonyl C-37 ($\delta_C$ 168.6) confirming the point of attachment of subunits A and B. In addition to this the only change was that the carbonyl amide was now adjusted to a carboxylic acid which was later proven by generation of cystobactamide B dimethyl ester.

HRESI(+)MS analysis of cystobactamide C (3) returned a pseudomolecular formula ion (M+H)$^+$ consistent with the molecular formula $C_{27}H_{29}N_3O_7$, requiring 15 (DBE). The $^1$H NMR data for cystobactamide C showed aromatic signals which were reminiscent of cystobactamide A and B, however it lacked aromatic resonances for two sets of para-substituted aromatic units. The COSY data revealed the existing two sets of isopropoxy residues along with one set of para-substituted aromatic ring system. Interpretation of the 1D and 2D NMR data (Table 3, FIG. 2) identified cystobactamide C (3) bearing resemblance to the eastern part of cystobactamide A and B, consisting of 3-isopropoxybenzoic acid, 2-hydroxy-3-isopropoxybenzamide and a para-aminobenzamide unit.

TABLE 1

NMR (700 MHz, DMSO-$d_6$) data for cystobactamide A (1)

| pos | $\delta_H$, mult (J in Hz) | $\delta_C$* | COSY | HMBC | ROESY |
|---|---|---|---|---|---|
| 1 | 4.70, d (6.9) | 79.4 | 2 | 2, 1-OMe, $CO_2NH_2$ | 1-OMe, 3 |
| 2 | 4.96, dd (8.2, 6.9) | 55.6 | 1, 3 | 1, $CO_2NH_2$, 4 | 1-OMe, 3, 34 |
| 3 | 8.92, d (8.2) |  | 2 | 4 | 1, 2, 6' |
| 4 |  | 166.5 |  |  |  |
| 5 |  | 128.6 |  |  |  |
| 6, 6' | 7.96, d (8.6) | 128.9 | 7, 7' | 4, 6, 6', 8 | 3 |
| 7, 7' | 7.91, d (8.6) | 119.8 | 6, 6' | 5, 7, 7' | 9 |
| 8 |  | 142.2 |  |  |  |
| 9 | 10.82, s |  |  | 7, 7', 10 | 7', 12' |
| 10 |  | 164.6 |  |  |  |
| 11 |  | 140.4 |  |  |  |
| 12, 12' | 8.20, d (8.6) | 129.5 | 13, 13' | 12, 12', 10, 14 | 9 |
| 13, 13' | 8.39, d (8.6) | 123.8 | 12, 12' | 11, 13, 13', 14 |  |
| 14 |  | 149.6 |  |  |  |
| 15 |  | 167.3 |  |  |  |
| 16 |  | 126.2 |  |  |  |
| 17 | 7.58, s | 114.2 |  | 15, 18, 19, 21, | 38, 40 |
| 18 |  | 146.7 |  |  |  |
| 19 |  | 133.6 |  |  |  |
| 20 | 8.50, d (8.2) | 119.8 | 21 | 16, 18 | 21 |
| 21 | 7.60, d (8.2) | 122.9 | 20 | 15, 17 | 20 |
| 22 | 10.98, s |  |  | 18, 20, 23 | 25, 39 |
| 23 |  | 163.7 |  |  |  |
| 24 |  | 117.3 |  |  |  |
| 25 | 7.82, d (8.7) | 125.2 | 26 | 23, 24, 29 | 22 |
| 26 | 7.42$^a$ | 116.3 | 25 | 27, 28 | 30 |
| 27 |  | 136.2 |  |  |  |
| 28 |  | 139.5 |  |  |  |
| 29 |  | 150.8 |  |  |  |
| 30 | 9.88, s |  |  | 26, 27, 31 | 33, 41, 42, 43 |
| 31 |  | 164.3 |  |  |  |
| 32 |  | 134.0 |  |  |  |
| 33, 33' | 8.11, d (8.3) | 129.5 | 34, 34' | 31, 33, 33', 35 | 30, 41, 42, 43 |
| 34, 34' | 7.44$^a$ | 125.6 | 33, 33' | 34, 34', 32 | 1-OMe, 2 |
| 35 |  | 137.3 |  |  |  |
| 36 | 11.53, s |  |  |  |  |
| 37 |  | NO |  |  |  |
| 1-OMe | 3.53, s | 59.6 |  | 1 | 1, 2 |
| 38 | 4.76, spt (6.0) | 72.1 | 39, 40 |  | 17 |
| 39 | 1.38, d (6.0) | 22.1 | 38 | 38, 40 | 22 |
| 40 | 1.38, d (6.0) | 22.1 | 38 | 38, 39 | 17 |
| 41 | 4.30, spt (6.0) | 76.0 | 42, 43 |  | 30, 42, 43 |
| 42 | 1.25, d (6.0) | 22.4 | 41 | 41, 43 | 30, 33' |
| 43 | 1.25, d (6.0) | 22.4 | 41 | 41. 42 | 30, 33' |
| $CO_2NH_2$ |  | 169.6 |  |  |  |
| 29-OH | 11.25, s |  |  | 27, 28 |  |

$^a$Overlapping signals,
*Assignments supported by HSQC and HMBC experiments.

TABLE 2

NMR (700 MHz, DMSO-$d_6$) data for cystobactamide B (2)

| pos | $\delta_H$, mult (J in Hz) | $\delta_C$ | COSY | HMBC | ROESY |
|---|---|---|---|---|---|
| 1 | 4.31, m$^a$ | 82.0 | 2 | 2, 37, $CO_2H$, 1-OMe, $CO_2H$ | 2, 3, 36, 1-OMe |
| 2 | 5.07, dd (8.1, 5.6) | 54.4 | 1, 3 |  | 1, 1-OMe, 3, 36 |
| 3 | 8.50$^b$ |  | 2 | 4 | 1, 2, 6' |
| 4 |  | 166.0 |  |  |  |
| 5 |  | 129.3 |  |  |  |
| 6, 6' | 7.90, m$^c$ | 128.6 | 7, 7' | 6, 6', 8 |  |
| 7, 7' | 7.90, m$^c$ | 119.8 | 6, 6' | 7, 7' | 9 |
| 8 |  | 141.7 |  |  |  |
| 9 | 10.79, s |  |  | 7, 7', 10 | 7', 12' |
| 10 |  | 164.5 |  |  |  |
| 11 |  | 140.5 |  |  |  |
| 12, 12' | 8.20, d (8.3) | 129.6 | 13, 13' | 12, 12', 14, 10 | 9 |

TABLE 2-continued

NMR (700 MHz, DMSO-$d_6$) data for cystobactamide B (2)

| pos | $\delta_H$, mult (J in Hz) | $\delta_C$ | COSY | HMBC | ROESY |
|---|---|---|---|---|---|
| 13, 13' | 8.38, d (8.3) | 123.8 | 12, 12' | 11, 14, 13, 13' | |
| 14 | | 149.6 | | | |
| 15 | | 167.2 | | | |
| 16 | | 125.9 | | | |
| 17 | 7.58, s | 114.2 | | 15, 18, 19, 21, | 38, 40 |
| 18 | | 146.6 | | | |
| 19 | | 133.5 | | | |
| 20 | 8.50[b], d (8.4) | 119.9 | 21 | 16, 18 | 21 |
| 21 | 7.59, d (8.4) | 123.0 | 20 | 15, 17 | |
| 22 | 10.98, s | | | 20 | 25, 39 |
| 23 | | 163.9 | | | |
| 24 | | 116.8 | | | |
| 25 | 7.81, d (8.7) | 125.2 | 26 | 23, 29 | 22 |
| 26 | 7.52, d (8.7) | 115.6 | 25 | 27, 28 | 30 |
| 27 | | 138.8 | | | |
| 28 | | NO | | | |
| 29 | | 150.7 | | | |
| 30 | 9.62, s | | | 31 | 33, 33', 26, 41, 43 |
| 31 | | 164.5 | | | |
| 32 | | 129.3 | | | |
| 33, 33' | 7.97, d (8.4) | 128.6 | 34, 34' | 31, 33, 33' | 30, 41, 42, 43 |
| 34, 34' | 7.90, m[c] | 119.8 | 33, 33' | 34, 34', 32 | 1-OMe |
| 35 | | 141.7 | | | |
| 36 | 10.20, s | | | 34, 37 | 1, 2, 1-OMe |
| 37 | | 168.6 | | | |
| 1-OMe | 3.49, s | 59.3 | | 1 | 1, 2, 34, 36 |
| 38 | 4.75, spt (6.0) | 72.1 | 39, 40 | | 17 |
| 39 | 1.38, d (6.0) | 22.1 | 38 | 38, 40 | 22 |
| 40 | 1.38, d (6.0) | 22.1 | 38 | 38, 39 | 17 |
| 41 | 4.30, m[a] | 76.1 | 42, 43 | | 30, 42, 43 |
| 42 | 1.25, d (6.0) | 22.4 | 41 | 41, 43 | OH |
| 43 | 1.25, d (6.0) | 22.4 | 41 | 41. 42 | OH, 30, 33' |
| $CO_2H$ | | 170.7 | | | |
| OH | 11.22, s | | | 28, 29 | |

TABLE 3

NMR (500 MHz, DMSO-$d_6$) data for cystobactamide C (3)

| pos | $\delta_H$, mult (J in Hz) | $\delta_C$* | COSY | HMBC |
|---|---|---|---|---|
| 1 | | 167.3 | | |
| 2 | | 126.1 | | |
| 3 | 7.57, s | 114.1 | | 1, 5 |
| 4 | | 146.8 | | |
| 5 | | 133.6 | | |
| 6 | 8.49, d (8.4) | 120.0 | 7 | 2, 4 |
| 7 | 7.58, d (8.4) | 123.0 | 6 | 1, 3, 5 |
| 8 | 10.95, s | | | 6 |
| 9 | | 164.0 | | |
| 10 | | 116.0 | | |
| 11 | | 150.5 | | |
| 12 | | 137.5 | | |
| 13 | | NO | | |
| 14 | 7.65, d (8.7) | 114.5 | 15 | 10, 12 |
| 15 | 7.78, d (8.7) | 125.3 | 14 | 9, 11 |
| 16 | 9.12, s | | | 14, 17 |
| 17 | | 164.7 | | |
| 18 | | 120.4 | | |
| 19/19' | 7.69, d (8.8) | 129.4 | 20/20' | 19/19', 21, 17 |
| 20/20' | 6.62, d (8.8) | 113.2 | 19/19' | 18, 20/20' |
| 21 | | 152.8 | | |
| 22 | 4.75, m | 72.0 | 23/24 | |
| 23/24 | 1.37, d (6.0) | 22.1 | 22 | 23/24 |
| 25 | 4.33, m | 75.8 | 26/27 | |
| 26/27 | 1.28, d (6.1) | 22.5 | 25 | 26/27 |
| OH | 11.23, s | | 25 | 10 |

NO—Not Observed,
*Assignments supported by HSQC and HMBC experiments

HRESI (+)MS analysis of cystobactamide D (4) revealed a pseudomolecular ion ([M+H]$^+$) indicative of a molecular formula ($C_{42}H_{37}O_{14}N_7$) requiring twenty eight double bond equivalents. Interpretation of the NMR (DMSO-$d_6$) data (Table 4) revealed magnetically equivalent aromatic protons H-12'/12 ($\delta_H$ 8.17, d, 8.0) and H-13/13' ($\delta_H$ 8.36, d, 8.0) accounting for the first para-substituted benzene ring. Further interpretation of the $^1$H-$^1$H COSY data revealed the presence of two additional para-substituted benzene rings, (H-35/35') ($\delta_H$ 7.80, d, 8.1) and H-36/36' ($\delta_H$ 7.94, d, 8.1); the second set of aromatics were heavily overlapped (H-6/6') and (H-7/7' ($\delta_H$ 7.88). Diagnostic HMBC correlations of the aromatic protons (H-12/12') to an amide carbonyl C-10 ($\delta_C$ 165.1) along with the exchangable (NH) ($\delta_H$ 10.82) coupled to C-10, C-7/7' established the connectivity of the two para-substituted aromatic rings (FIG. 3), which was further corraborated by ROESY correlations between NH/H-12 and NH/H-7. The COSY data revealed an additional spin system from an oxymethine H-1 ($\delta_H$ 4.08, d, 8.0) through an α-proton H-2 ($\delta_H$ 4.91, dd, 8.0, 7.7) to an exchangable proton (NH) ($\delta_H$ 8.47). HMBC correlations from (i) H-2 to three amide carbonyls C-4 ($\delta_C$ 166.4), C-15 ($\delta_C$ 171.8) and C-32 ($\delta_C$ 169.2), (ii) NH ($\delta_H$ 8.48) to C-4, (iii) NH ($\delta_H$ 10.54) to C-35/35' ($\delta_C$ 119.5), (iv) H-6/6' to C-4 further extended the partial structure of cystobactamide D (4). Consideration of the 1-D and 2-D NMR data revealed an additional 1,3,4-trisubstituted and a 1,2,3,4-tetrasubstituted benzene ring. HMBC correlations were observed from the aromatic protons H-27 ($\delta_H$ 7.55) and H-29 ($\delta_H$ 7.60) to the carbonyl C-31 ($\delta_C$ 167.8) and the quaternary carbon C-25 ($\delta_C$ 133.0), while H-30 ($\delta_H$ 8.47, d, 7.0) and a methoxy signal ($\delta_H$ 3.96) were coupled to an oxygen bearing carbon C-26 ($\delta_C$ 149.1), hence revealing a 4-amino-3-methoxybenzoic acid moiety, which was later confirmed by esterification. Moreover, HMBC correlations were observed from the exchangeable proton (NH) ($\delta_H$ 7.46) to the oxygen bearing carbons C-1 ($\delta_C$ 80.8), C-18 ($\delta_C$ 141.0) and the aromatic carbon C-22 ($\delta_C$ 116.2), while H-22 ($\delta_H$ 7.48, d, 8.8) and the methoxy showed couplings to C-18 and H-21 ($\delta_H$ 7.77, d, 8.8) coupled to an amide carbonyl C-23 ($\delta_C$ 164.8). The presence of a hydroxyl functionality ortho to the methoxy was later confirmed by esterification (4a) (FIG. 4), revealing the presence of a 4-amino-2-hydroxy-3-methoxybenzamide.

The attachment of the 4-amino-3-methoxybenzoic acid and 4-amin0-2-hydroxy-3-methoxybenzamide substituents were confirmed by ROESY and HMBC correlations from the exchangeable NH's observed from the cystobactamide D dimethyl ester (4a). The missing substituents were to be assigned at C-14 ($\delta_C$ 150.0) and the carbonyl C-38. The $\lambda_{max}$ (320 nm) and the downfield chemical shift of C-14 was suggestive of a nitro substituent at C-14 and the primary amine attached to the carbonyl C-38, generating the planar structure of 4.

TABLE 4

NMR (700 MHz, DMSO-$d_6$) data for cystobactamide D (4)

| pos | $\delta_H$, mult (J in Hz) | $\delta_C$ | COSY | ROESY | HMBC |
|---|---|---|---|---|---|
| 1 | 4.08, d (8.0) | 80.7 | 2 | | 32 |
| 2 | 4.91, dd (8.0, 7.7) | 56.4 | 1, 3 | 33 | 1, 4, 15, 32 |
| 3 | 8.47[a] | | 2 | | 4 |
| 4 | | 166.4 | | | |
| 5 | | 129.5 | | | |
| 6/6' | 7.91, m[b] | 129.0 | 7/7' | | 4, 8, 6/6' |
| 7/7' | 7.91, m[b] | 120.4 | 6/6' | | 5, 7/7' |
| 8 | | 142.4 | | | |
| 9 | 10.82, s | | | 12/12', 7/7' | 7, 10 |
| 10 | | 165.1 | | | |
| 11 | | 140.9 | | | |
| 12/12' | 8.17, d (8.0) | 129.9 | 13/13' | 9 | 10, 12/12', 14 |
| 13/13' | 8.36, d (8.0) | 124.3 | 12/12' | 9 | 11, 13/13', 14 |
| 14 | | 150.0 | | | |
| 15 | | 171.8 | | | |
| 16 | NO | | | | |
| 17 | | 129.5 | | | |
| 18 | | 141.0 | | | |
| 19 | NO | | | | |
| 20 | | 116.5 | | | |
| 21 | 7.77, d (8.8) | 125.8 | 22 | | 23 |
| 22 | 7.48, d (8.8) | 115.3 | 21 | | 18, 20 |
| 23 | | 164.8 | | | |
| 24 | NO | | | | |
| 25 | | 133.0 | | | |
| 26 | | 149.1 | | | |
| 27 | 7.55, s | 111.7 | | | 25, 26, 31 |
| 28 | | 126.3 | | | |
| 29 | 7.60[c], d (7.0) | 123.3 | 30 | | 25, 27, 31 |
| 30 | 8.47[a], d, (7.0) | 120.1 | 29 | | 26, 28 |
| 31 | | 167.8 | | | |
| 32 | | 169.2 | | | |
| 33 | 10.54, s | | | 2, 35/35' | |
| 34 | | 142.7 | | | |
| 35/35' | 7.80, d, (8.1) | 119.5 | 36/36' | 33 | 35/35', 37 |
| 36/36' | 7.94, d, (8.1) | 129.3 | 35/35' | | 34, 36/36', 38 |
| 37 | | 129.4 | | | |
| 38 | | 165.5 | | | |
| 1-OMe | 3.30, s | 58.4 | | | 1 |
| 18-OMe | 3.76, s | 61.0 | | | 18 |
| 26-OMe | 3.95, s | 56.8 | | | 26 |

[a,b,c]overlapping signals,
$^{13}$C shifts obtained from 2D HSQC and HMBC experiments.
NO—not observed

TABLE 5

NMR (700 MHz, DMSO-$d_6$) data for cystobactamide D dimethyl ester (4a)

| pos | $\delta_H$, mult (J in Hz) | $\delta_C$ | COSY | ROESY | HMBC |
|---|---|---|---|---|---|
| 1 | 4.10[a] | 80.4 | 2 | 3 | 2 |
| 2 | 4.92, dd (8.0, 7.8) | 56.1 | 1, 3 | 3, 33 | 1, 32 |
| 3 | 8.50, d (7.8) | | 2 | 1, 2, 6/6' | |
| 4 | | 165.6 | | | |
| 5 | | 129.4 | | | |

TABLE 5-continued

NMR (700 MHz, DMSO-d6) data for cystobactamide D dimethyl ester (4a)

| pos | $\delta_H$, mult (J in Hz) | $\delta_C$ | COSY | ROESY | HMBC |
|---|---|---|---|---|---|
| 6/6' | 7.91, m[b] | 128.8 | 7/7' | 3 | 4, 8 |
| 7/7' | 7.91, m[b] | 120.1 | 6/6' | | |
| 8 | | 142.0 | | | |
| 9 | 10.82, s | | | 12/12', 7/7' | 7/7' |
| 10 | | 164.8 | | | |
| 11 | | 140.8 | | | |
| 12/12' | 8.21, d (8.7) | 129.7 | 13/13' | 9, 13/13' | 10, 12/12', 14 |
| 13/13' | 8.39, d (8.7) | 124.0 | 12/12' | 12/12' | 11, 13/13', 14 |
| 14 | | 149.9 | | | |
| 15 | | NO | | | |
| 16 | 9.65, s | | | 18-OMe, 36/36' | 38 |
| 17 | | 129.5 | | | |
| 18 | | 144.7 | | | |
| 19 | | 152.1 | | | |
| 20 | | 121.8 | | | |
| 21 | 7.88, d (8.8) | 126.1 | 22 | | 19, 23 |
| 22 | 7.95, d (8.8) | 118.9 | 21 | | 18, 20 |
| 23 | | 162.6 | | | |
| 24 | 10.94, s | | | 19-OMe | 30 |
| 25 | | 132.8 | | | |
| 26 | | 148.3 | | | |
| 27 | 7.60, s | 111.2 | | 26-OMe | 25, 29, 31 |
| 28 | | 124.9 | | | |
| 29 | 7.67, d (8.6) | 123.2 | 30 | 30 | 27 |
| 30 | 8.61, d (8.6) | 119.1 | 29 | 29 | |
| 31 | | 166.4 | | | |
| 32 | | 169.2 | | | |
| 33 | 10.59, s | | | 2, 35/35' | |
| 34 | | 142.8 | | | |
| 35/35' | 7.83, d, (8.1) | 119.2 | 36/36' | 33 | 35/35', 37 |
| 36/36' | 7.97, d, (8.1) | 129.1 | 35/35' | 16 | 34, 36/36', 37, 38 |
| 37 | | 129.3 | | | |
| 38 | | 165.5 | | | |
| 1-OMe | 3.31 | 58.1 | | | |
| 18-OMe | 3.91, s | 61.2 | | 16 | 18 |
| 19-OMe | 4.10[a], s | 62.0 | | 24 | 19 |
| 26-OMe | 4.05 | 56.7 | | 27 | |
| CO2Me | 3.86, s | 52.4 | | | 31 |

[a,b] overlapping signals,
$^{13}$C shifts obtained from 2D HSQC and HMBC experiments.
NO—not observed HRESI (+)MS analysis of cystobactamide E (5) revealed a pseudomolecular ion ([M+H]+) indicative of a molecular formula ($C_{26}H_{23}O_9N_5$) requiring eighteen double bond equivalents. The 1H NMR spectrum was similar to cystobactamide D with the principle difference being the absence of signals reminiscent for the 4-amino-3-methoxybenzoic acid and 4-amino-2-hydroxy-3-methoxybenzamide moieties. Detailed analysis of the 1-D and 2-D NMR data (Table 6) lead to the planar structure of cystobactamide E (5).

TABLE 6

NMR (700 MHz, DMSO-d6) data for cystobactamide E (5)

| pos | $\delta_H$, mult (J in Hz) | $\delta_C$ | COSY | ROESY | HMBC |
|---|---|---|---|---|---|
| 1 | 4.08, d (8.2) | 80.2 | 2 | | 1-OMe, 2 |
| 2 | 4.90, dd (8.2, 7.7) | 56.1 | 1, 3 | 17 | 1, 4, 15, 16 |
| 3 | 8.50, d (7.7) | | 2 | 6/6' | 4 |
| 4 | | 165.5 | | | |
| 5 | | 129.2 | | | |
| 6/6' | 7.91, m[a] | 128.6 | 7/7' | 3 | 4, 6/6', 8 |
| 7/7' | 7.91, m[a] | 120.0 | 6/6' | 9 | 5, 7/7' |
| 8 | | 142.0 | | | |
| 9 | 10.82, s | | | 7/7', 12/12' | 7/7', 10 |
| 10 | | 164.6 | | | |
| 11 | | 140.5 | | | |
| 12/12' | 8.21, d (8.4) | 129.6 | 13/13' | 9 | 10, 12/12', 14 |
| 13/13' | 8.38, d (8.4) | 123.9 | 12/12' | | 11, 13/13', 14 |
| 14 | | 149.9 | | | |
| 15 | | 171.2 | | | |
| 16 | | 168.9 | | | |
| 17 | 10.54, s | | | 2, 19/19', 20/20' | 16, 19/19' |
| 18 | | 142.8 | | | |
| 19/19' | 7.77, d (8.2) | 119.0 | 20/20' | 17 | 19/19', 21 |
| 20/20' | 7.90, m[a] | 130.6 | 19/19' | 17 | 18, 20/20', 22 |
| 21 | | 125.6 | | | |
| 22 | | 167.2 | | | |
| 1-OMe | 3.29 | 58.1 | | | 1 |

[a] overlapping signals,
$^{13}$C shifts obtained from 2D HSQC and HMBC experiments HRESI(+)MS analysis of cystobactamide F (6) returned a pseudomolecular ion (M+H)+ consistent with the molecular Formula $C_{43}H_{39}N_7O_{13}$, requiring 28 DBE. Interpretation of the NMR (DMSO-$d_6$) data (Table 7) revealed three sets of magnetically equivalent aromatic protons which could be connected via COSY (6/6' and 7/7', 12/12' and 13/13', 33/33' and 34/34') and additionally in contrast to all other cysto-bactamides a set of magnetically equivalent aromatic protons (26/26' and 27/27') which could be also connected via COSY. These four sets accounted for four para-substituted benzene rings in the molecule instead of three as found in all other cystobactamides. Only one 1,2,3,4-tetrasubstituted benzene ring could be detected where HMBC correlations of the aromatic proton H-22 ($d_H$ 7.22) could be observed to the carbon C-18 ($d_C$ 137.1) and C-20 ($d_H$ 114.0) and from the aromatic proton H-21 ($d_H$ 7.51) to C-23 ($d_C$ 167.3). Protons H-21 and H-22 could be connected via COSY correlations. Since carbons C-17, C-19 and C-22 were not observable, the HR-MS/MS mass of all peptide-fragments has been established and revealed the presence of 7 carbons, 11 protons, one nitrogen and three oxygen in the respective fragment, confirming the presence of a 1,2,3,4 substituted para-amino benzene moiety on this position (see FIG. 1). HMBC data further confirmed the connection of H-37 ($d_H$ 4.93) to C-18 ($d_C$ 137.1). HMBC and COSY data confirmed an identical linker between the two aromatic parts of the molecule as found in cystobactamide D. HMBC correlations from the exchangeable protons H-9 ($d_H$ 10.82) to C-10 ($d_C$ 163.9) and C-7/7' ($d_C$ 119.4), H-3 ($d_H$ 8.49) to C-4 ($d_C$ 165.1), H-31 ($d_H$ 10.56) to C-30 ($d_C$ 168.3) and C-32 ($d_C$ 141.5) and H-16 ($d_H$ 8.91) to C-36 ($d_C$ 163.1) and C-18 ($d_C$ 137.1) and COSY correlations from H-2 ($d_H$ 4.92) to the exchangeable proton H-3 ($d_H$ 8.49) as well as HRMS fragment data established the serial connectivity of all fragments. The location of the nitro-group and the presence of the free amide group in the linker between the aromatic chains was established using HR-MS/MS fragments to generate the sum-formula of the respective fragments.

TABLE 7

NMR (700 MHz, DMSO-$d_6$) data for cystobactamide F (6)

| pos | $\delta_H$, mult (J in Hz) | $\delta_C$* | COSY | ROESY | HMBC |
|---|---|---|---|---|---|
| 1 | 4.10, d (8.08) | 79.7 | 2 | 1-OMe, 3 | 1-OMe, 2, 15, 30 |
| 2 | 4.92, dd (4.10, 4.10) | 55.9 | 1, 3 | 31 | 1, 4, 15, 30 |
| 3 | 8.49, d (8.14) | | 2 | 1 | 1, 2, 4 |
| 4 | | 165.1 | | | |
| 5 | | 128.7 | | | |
| 6/6' | 7.91, m$^a$ | 128.1 | 7/7' | | 4, 6/6', 8 |
| 7/7' | 7.91, m$^a$ | 119.4 | 6/6' | 9 | 5, 7/7' |
| 8 | | 141.6 | | | |
| 9 | 10.82, s | | | 7/7', 12/12' | 7/7', 8, 10 |
| 10 | | 163.9 | | | |
| 11 | | 140 | | | |
| 12/12' | 8.21, d (8.71) | 129.1 | 13/13' | 9 | 10, 12/12', 14 |
| 13/13' | 8.39, d (8.71) | 123.3 | 12/12' | | 11, 13/13' |
| 14 | | 149 | | | |
| 15 | | 170.6 | | | |
| 16 | 8.91, s | | | 34/34', 38/38' | 18, 36 |
| 17 | | NO | | | |
| 18 | | 137.1 | | | |
| 19 | | NO | | | |
| 20 | | 114.9 | | | |
| 21 | 7.51, d (9.02) | 127.5 | 22 | | 23 |
| 22 | 7.22, d (9.02) | NO | 21 | | 18, 20 |
| 23 | | 167.3 | | | |
| 24 | 15 very broad s | | | | |
| 25 | | 144.5 | | | |
| 26/26' | 7.78, d (8.57) | 118.4 | 27/27' | | 26/26', 28 |
| 27/27' | 7.86, m$^a$ | 130.1 | 26/26' | | 25, 27/27', 29 |
| 28 | | 123.4 | | | |
| 29 | | 167.3 | | | |
| 30 | | 168.3 | | | |
| 31 | 10.56, s | | | 2, 33/33' | 30, 33/33' |
| 32 | | 141.5 | | | |
| 33/33' | 7.83, m$^a$ | 118.9 | 34/34' | | 33/33', 35 |
| 34/34' | 7.87, m$^a$ | 127.5 | 33/33' | 16 | 32, 34/34', 36 |
| 35 | | 129.2 | | | |
| 36 | | 163.1 | | | |
| 37 | 4.93, m$^a$ | 71 | 38/38' | | 18 |
| 38/38' | 1.21, d (6.18) | 22.4 | 37 | 16 | 37 |
| 1-OMe | 3.31, s | 57.4 | | 1 | 1 |

$^a$Overlapping signals,
NO = Not Observed,
*Assignments supported by HSQC and HMBC experiments.

HRESI(+)MS analysis of cystobactamide G (7) returned a pseudomolecular ion (M+H)$^+$ consistent with the molecular Formula $C_{44}H_{41}N_7O_{14}$, requiring 28 DBE. Due to overlapping aromatic signals in DMSO-$d_6$ the NMR data acquired in Methanol-$d_4$ was used to establish the partial structures of the aromatic and the linker fragment (Table 8). The para-substituted benzene rings could be established via COSY, HSQC and HMBC correlations. The configuration of the 1,3,4-trisubstituted benzene ring (4-amino-3methoxy-benzamide) and the methoxy-substituent (1-OMe, ($d_C$ 55.2, $d_H$ 3.50) was established via HSQC, COSY and HMBC correlations. Since not all signals on the 1,2,3,4-substituted benzene moiety could be detected in methanol-$d_4$ the NMR data measured in DMSO-$d_6$ was interpreted to establish a 4-amino-3-isopropoxy-2-hydroxy-benzamide and an identical linker between the aromatic parts as identified in cystobactamide D. The connection between C-39 ($d_C$ 74.4) and the carbons C-40/40' ($d_C$ 22.7) was established by COSY correlations of H-39 ($d_H$ 4.82) and H-40/40' ($d_H$ 1.31) and the connectivity between the 1,2,3,4-substituted benzene ring and H-39 ($d_H$ 4.82) was established via HMBC correlations of h-39 to C-18 ($d_C$ 137.3 in DMSO-$d_6$). The configuration of this benzene moiety was further confirmed with HMBC correlations in DMSO-$d_6$ of H-22 ($d_H$ 7.04) to C-18 ($d_C$ 137.3) and C-20 ($d_C$ 116.1) and HMBC correlations of H-21 ($d_H$ 7.45) to C-23 ($d_C$ 165.4) as well as COSY correlations from H-21 to H-22. The overall sequence, the location of the nitro-group and the presence of the free amide group in the linker between the aromatic chains was established using HR-MS/MS fragments to generate the sum-formula of the respective fragments.

TABLE 8

NMR (700 MHz, Methanol-$d_4$) data for cystobactamide G (7), including (700 MHz, DMSO-$d_6$) data for pos. 17-23 and 39-40/40'.

| pos | $δ_H$, mult (J in Hz) | $δ_C$* | COSY | ROESY | HMBC |
|---|---|---|---|---|---|
| 1 | 4.17, d (7.45) | 82.1 | 2 | | 1-OMe, 2, 15, 32 |
| 2 | 5.08, d (7.37) | 57.2 | 1 | | 1, 4, 15, 32 |
| 3 | NO | | | | |
| 4 | | 168.9 | | | |
| 5 | | 130.5 | | | |
| 6/6' | 7.93, m$^a$ | 129.4 | 7/7' | | 4, 6/6', 8 |
| 7/7' | 7.89, d (8.83) | 121.1 | 6/6' | | 5, 7/7' |
| 8 | | 142.9 | | | |
| 9 | NO | | | | |
| 10 | | 166.5 | | | |
| 11 | | 141.6 | | | |
| 12/12' | 8.16, d (8.77) | 129.9 | 13/13' | | 10, 12/12', 14 |
| 13/13' | 8.38, d (8.74) | 124.5 | 12/12' | | 11, 13/13' |
| 14 | | 150.9 | | | |
| 15 | | 174.4 | | | |
| 16 | NO | | | | |
| 17 | | 139.4 | | | |
| 18 | NO | NO | | | |
| 19 | | NO | | | |
| 20 | | NO | | | |
| 21 | 7.74, d (8.83) | 125.4 | 22 | | 23, 17 |
| 22 | 7.51, broad d | NO | | | |
| 23 | | 168.7 | | | |
| 24 | NO | | | | |
| 25 | | 133.5 | | | |
| 26 | | 149.9 | | | |
| 27 | 7.67, S | 112.7 | | | 25, 26, 28. 29, 31 |
| 28 | | 131.8 | | | |
| 29 | 7.61, d (8.22) | 129.9 | 30 | | 27, 30, 31 |
| 30 | 8.45, broad d | 120.5 | 29 | | |
| 31 | | 174.8 | | | |
| 32 | | 169.5 | | | |
| 33 | NO | | | | |
| 34 | | 142.8 | | | |
| 35/35' | 7.83, d (8.64) | 120.8 | 36/36' | | 35/35', 37 |
| 36/36' | 7.93, m$^a$ | 128.9 | 35/35' | | 34, 36/36', 38 |
| 37 | | 131.2 | | | |
| 38 | | 166.4 | | | |
| 39 | 4.82, water peak | 74.4 | 40/40' | | 40 |
| 40/40' | 1.31, d (6.13) | 22.7 | 39 | | 39 |
| 1-Ome | 3.50, s | 55.2 | | | 1 |
| 26-Ome | 4.02, s | 55.9 | | | 26 |
| 17 | | NO | | | |
| 18 | | 137.3 | | | |
| 19 | | NO | | | |
| 20 | | 116.1 | | | |
| 21 | 7.45, d (8.83) | 123.9 | 22 | | 23 |
| 22 | 7.04, d (8.66) | 99.7 | 21 | | 18, 20 |
| 23 | | 165.4 | | | |
| 39 | 5.05, m | 69.7 | 40/40' | | 18, 40/40' |
| 40/40' | 1.17, d (5.98) | 22.5 | 39 | | 39 |

$^a$Overlapping signals,
NO = Not Observed,
*Assignments supported by HSQC and HMBC experiments.

HRESI(+)MS analysis of cystobactamide H (8) returned a pseudomolecular ion (M+H)$^+$ consistent with the molecular Formula $C_{43}H_{39}N_7O_{14}$, requiring 28 DBE. The linker configuration between the aromatic chains was found to be identical as the one found in cystobactamide D. interpretation of HSQC, HMBC and COSY data acquired in DMSO-$d_6$ revealed three para-substituted benzene units as found in cystobactamide A, B, D, F and G. Further interpretation of the COSY, HSGC and HMBC data revealed a identical 1,3,4-trisubstituted benzene moiety which showed HMBC correlations to a methoxy group as found in all other cystobactamides except cystobactamide F (confirmed by HMBC correlation of 1-OMe ($d_H$ 3.27) to C-26 ($d_C$ 147.4)). Analysis of the NMR data revealed—in accordance with the other cystobactamides—a 1,2,3,4-substituted benzene moiety. Significant change came from the establishment of a ethoxy unit via COSY correlation of methylene protons H-39 ($d_H$ 4.17) to methyl group H-40 ($d_H$ 1.27) and the HMBC correlations of methylene group H-39 ($d_H$ 4.17) to C-18 ($d_C$ 139.5) expanding thereby the substitution pattern of the 4-amino-2-hydroxy-3-X-benzamide moiety to X=methoxy, isoproropoxy or ethoxy on position 3. The sequential sequence of cystobactamide H was established by HMBC correlations of the exchangeable protons H-9 ($d_H$ 10.93) to C-10 ($d_C$ 163.9) and C-7/7' ($d_C$ 119.6), H-33 ($d_H$ 10.85) to C-32 ($d_C$ 168.7) and C-35/35' ($d_C$ 118.8), H-16 ($d_H$ 8.91) to C-38 ($d_C$ 163.1), C-18 ($d_C$ 139.5) and C-22 ($d_C$ 100.4) and H-24 ($d_H$ 14.71) to C-20 ($d_C$ 116.1), C-25 ($d_C$ 131.0), C-26 ($d_C$ 147.4) and C-30 ($d_C$ 118.5) and H-2 ($d_H$ 4.85) to C-4 ($d_C$ 165.5) as well as HR-MS2 fragmentation-data which also enabled the localisation of the nitro-group and the establishment of the free amide group in the linker moiety.

TABLE 9

NMR (700 MHz, DMSO-$d_6$) data for cystobactamide H (8)

| pos | $δ_H$, mult (J in Hz) | $δ_C$* | COSY | ROESY | HMBC |
|---|---|---|---|---|---|
| 1 | 4.22, d (8.60) | 79.8 | 2 | 3, 33 | 2, 32, 1-OMe |
| 2 | 4.85, dd (8.42, 8.42) | 56.3 | 1, 3 | 3, 33 | 1, 4, 15, 32 |

TABLE 9-continued

NMR (700 MHz, DMSO-d$_6$) data for cystobactamide H (8)

| pos | $\delta_H$, mult (J in Hz) | $\delta_C$* | COSY | ROESY | HMBC |
|---|---|---|---|---|---|
| 3 | 9.02 s | | 2 | | |
| 4 | | 165.5 | | | |
| 5 | | 128.8 | | | |
| 6/6' | 7.93 m$^a$ | 128.3 | 7/7' | | 4, 6/6', 8 |
| 7/7' | 7.91 m$^a$ | 119.6 | 6/6' | | 5, 7/7' |
| 8 | | 141.7 | | | |
| 9 | 10.93 s | | | 7/7', 12/12' | |
| 10 | | 163.9 | | | |
| 11 | | 140.3 | | | |
| 12/12' | 8.22, d (8.72) | 129.4 | 13/13' | | 10, 12/12', 14 |
| 13/13' | 8.38, d (8.72) | 123.5 | 12/12' | | 11, 13/13' |
| 14 | | 149.2 | | | |
| 15 | | 170.7 | | | |
| 16 | 8.91 s | | | 22, 39, 40 | 18, 22, 38 |
| 17 | | NO | | | |
| 18 | | 139.5 | | | |
| 19 | | NO | | | |
| 20 | | 116.1 | | | |
| 21 | 7.45, d (8.63) | 124.1 | 22 | | 18, 23 |
| 22 | 6.95, d (8.66) | 100.4 | 21 | 16 | 18 |
| 23 | | 165.8 | | | |
| 24 | 14.71 s | | | 26-OMe, 39 | 23, 25, 26, 30 |
| 25 | | 131.0 | | | |
| 26 | | 147.4 | | | |
| 27 | 7.46, s | 111.1 | | | 25, 26, 29, 28, 31 |
| 28 | | 133.9 | | | |
| 29 | 7.38, m$^a$ | 121.3 | 30 | | 27, 28, 30 |
| 30 | 8.44, d (8.29) | 118.5 | 29 | | 25, 26, 28, |
| 31 | | 169.9 | | | |
| 32 | | 168.7 | | | |
| 33 | 10.85 s | | | 1, 2, 35/35' | 35/35' |
| 34 | | 141.9 | | | |
| 35/35' | 7.85, m$^a$ | 118.8 | 36/36' | | 37 |
| 36/36' | 7.85, m$^a$ | 127.7 | 35/35' | | 34, 38 |
| 37 | | 129.5 | | | |
| 38 | | 163.1 | | | |
| 39 | 4.17, q (7.03) | 65.4 | 40 | | 18, 40 |
| 40 | 1.27, t (7.07) | 15.7 | 39 | | 39 |
| 1-Ome | 3.27, s | 57.4 | | | 1 |
| 26-Ome | 3.84, s | 55.2 | | | 26 |

$^a$Overlapping signals,
NO = Not Observed,
*Assignments supported by HSQC and HMBC experiments.

FIGURES

FIG. 1: Key 2D NMR correlations (700 MHz, DMSO-d$_6$) for cystobactamide A (1)

Figure 2:
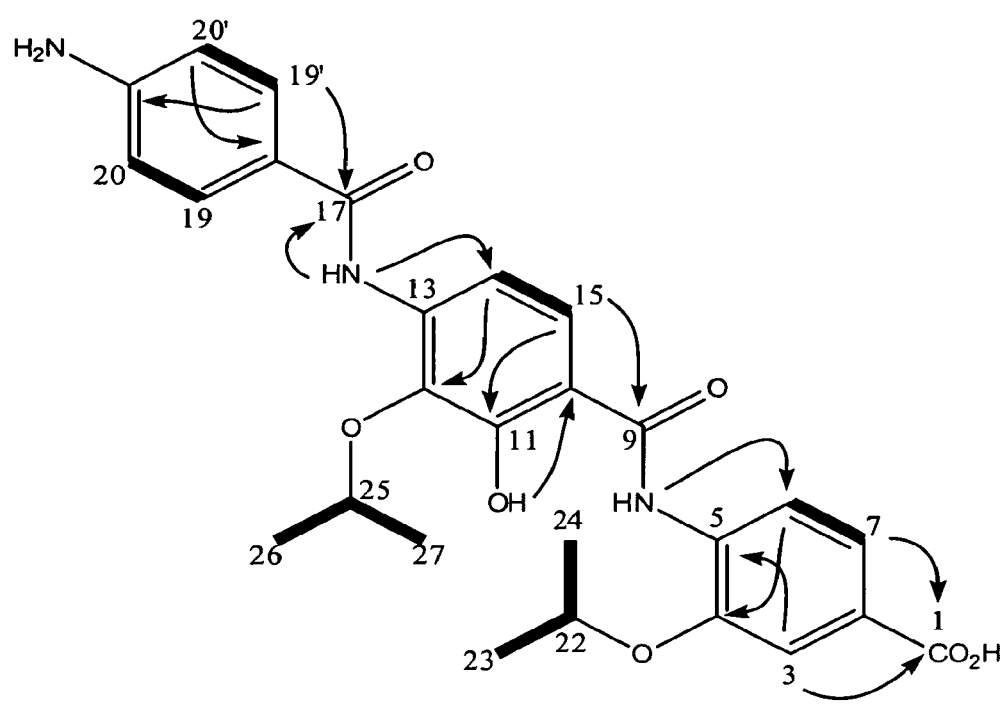

FIG. 2: Key 2D NMR correlations (500 MHz, DMSO-d$_6$) for cystobactamide C (3)

Figure 3:
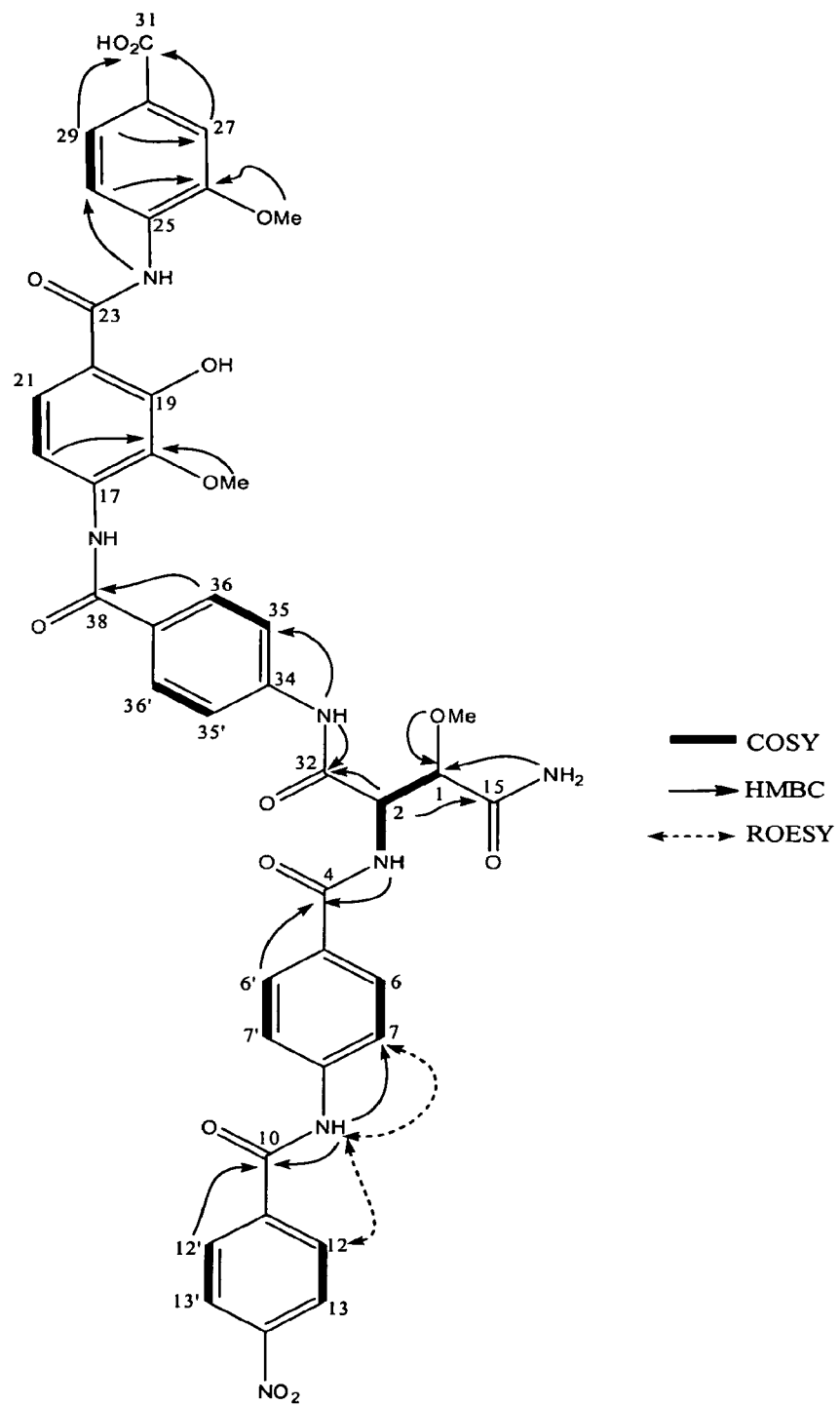

FIG. 3: Key 2D NMR correlations (700 MHz, DMSO-d$_6$) for cystobactamide D (4)

Figure 4:
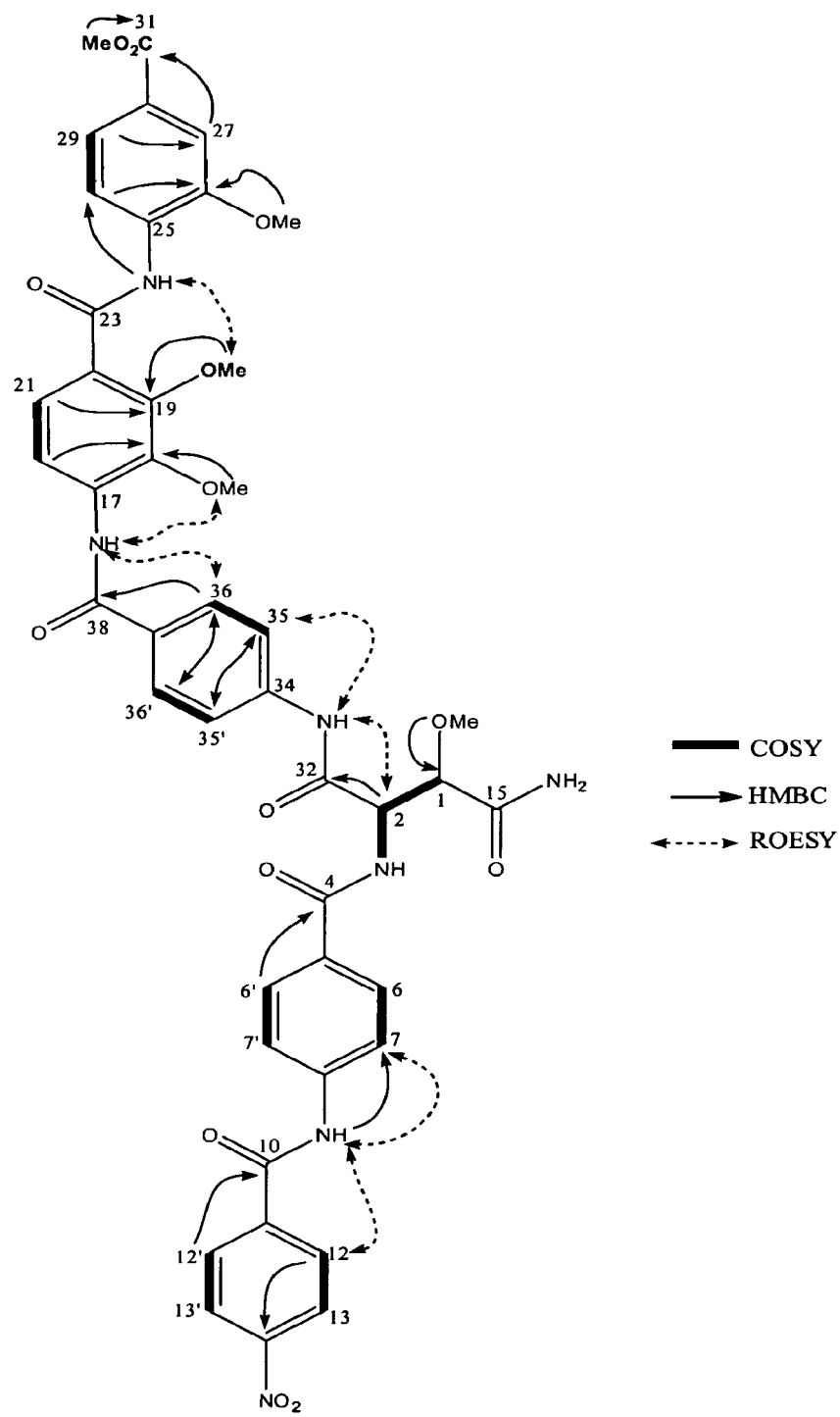

FIG. 4: Key 2D NMR correlations of cystobactamide D dimethyl ester (4a)

Figure 5:
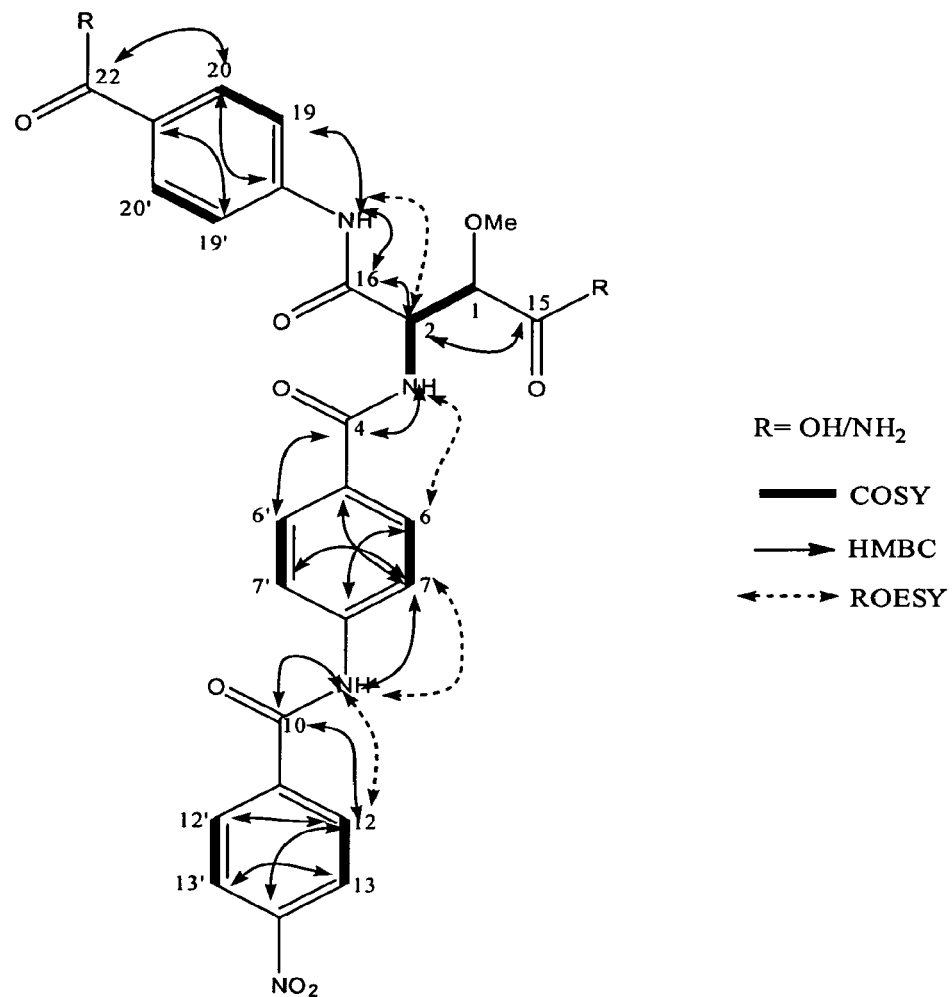

FIG. 5: Key 2D NMR correlations of cystobactamide E (5)

Figure 6:
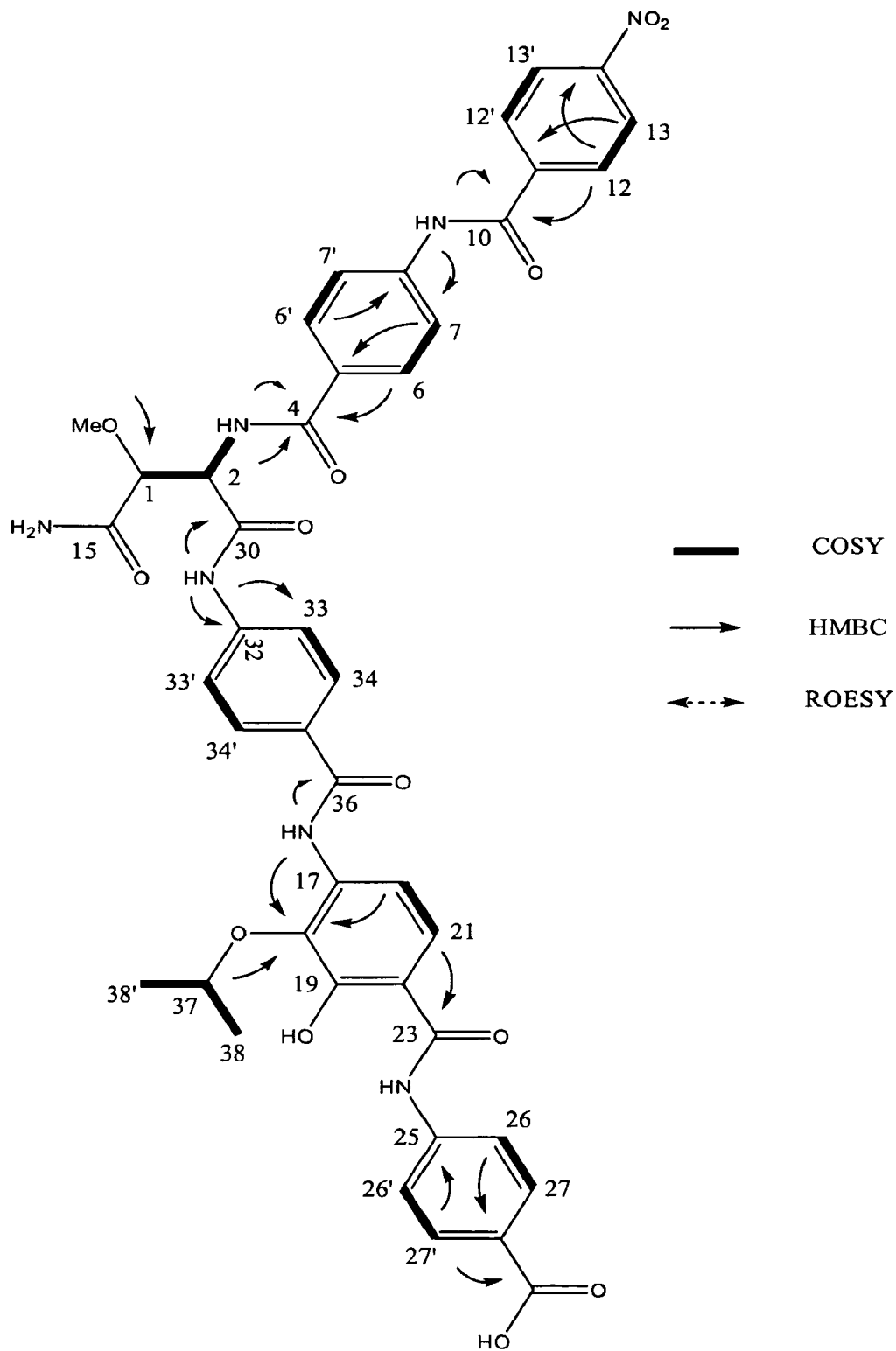

FIG. 6: Key 2D NMR correlations (700 MHz, DMSO-d$_6$) of cystobactamide F (6)

Figure 7:
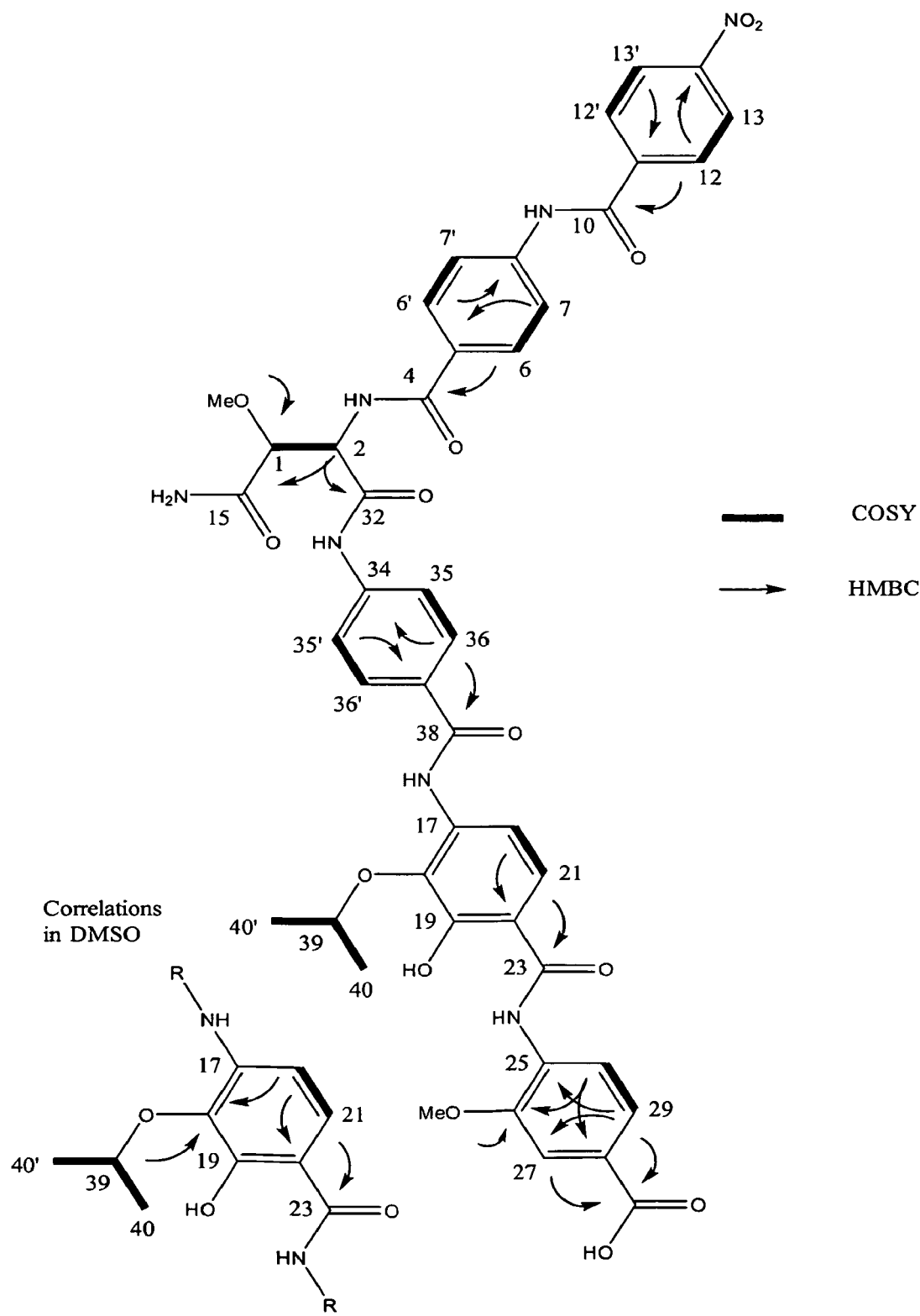

FIG. 7: Key 2D NMR correlations (700 MHz, MeOH-d$_4$) of cystobactamide G (7)

Figure 8:
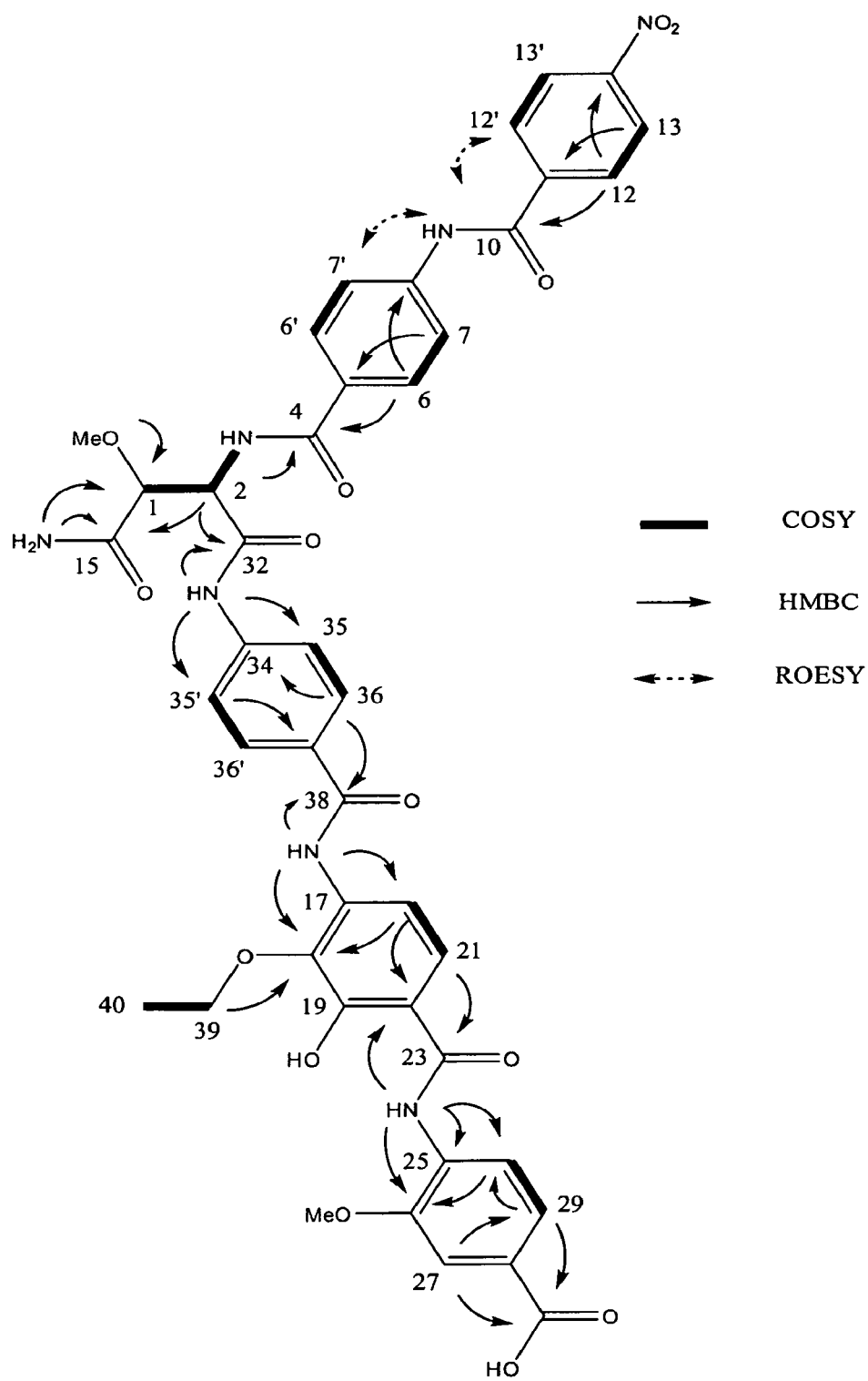

FIG. 8: Key 2D NMR correlations (700 MHz, DMSO-d$_6$) of cystobactamide H (8)

BIOLOGICAL EVALUATION OF CYSTOBACTAMIDES

As summarized in Tables 10a/b, cystobactamides were evaluated against several microorganisms and cell lines. All derivatives demonstrated a potent inhibitory effect on various E. coli strains, including a nalidixic acid resistant (NAL$^R$) isolate. Overall potency (average MIC values) of the tested derivatives increased in the following order: CysA1, CysC<CysB<CysA, CysG<CysF. Importantly, the pathogenic Gram-negative strains A. baumannii and P. aeruginosa were also inhibited by the most active derivatives, CysA, CysB, CysG, and CysF, in the low μg/ml range, which is in terms of MIC values only by one order of magnitude higher than for the reference drug ciprofloxacin.

Average MIC values on Gram-positive bacteria, such as E. faecalis, S. aureus, and S. pneumonia were partly in the sub-μg/ml range and the average potency of CysA and CysB exceeded that of ciprofloxacin.

Furthermore, it was shown that cystobactamides do not inhibit the growth of yeast and mammalian cells, respectively. Thus, the cystobactamides did not cause apparent cytotoxicity.

Susceptibility of Mutant E. coli Strains to Cystobactamides

Quinolones are a widely used class of antibiotics that target the type II topoisomerases, DNA gyrase and topoisomerase IV. Resistance to quinolones is thereby often mediated by mutations in chromosomal genes that lead to alterations in the drug targets. In GyrA the quinolone-resistance determining region (QRDR) is located between amino acids 67 and 106, whereas amino acids 83 (Ser) and 87 (Asp) are most often involved.[1,2] In analogous regions of ParC, the secondary target of quinolones, changes of amino acid 80 (Ser) are found to confer quinolone resistance. [3,4]

Cystobactamides were screened using a panel of *E. coli* strains with typical mutations in gyrA and parC genes (Table 11). With ciprofloxacin the MIC values increase approximately by factor 30 for the single-step gyrA mutations (strain MI and WT-3.2). However, a combination of both gyrA mutations (strain WT-3) results already in nearly clinical resistance (1 mg/L). A parC mutation (strain WT-4 M2.1) leads to a two-fold increase of the MIC of ciprofloxacin. However, MIC values for cystobactamides did not or only marginally increase for gyrA and parC mutant *E. coli* strains, which suggests that cystobactamides might interfere with amino acids 87 and 83 of GyrA and amino acid 80 of ParC to a lower extent than observed for ciprofloxacin.

High-level quinolone resistance often results from a combination of several target site mutations and altered efflux mechanisms. The in vitro selected mutant WT III (marR Δ74 bp) does not produce functional MarR, which acts as a repressor of marA expression. This, in turn, leads to overproduction of MarA and AcrAB and overexpression of the AcrAB efflux pump is associated with the MAR (multiple antibiotic resistance) phenotype.[5] *E. coli* strain WT III was less susceptible to ciprofloxacin treatment by a factor of ca. 4 (cp. *E. coli* WT). In comparison, MIC values of cystobactamides B, F, and G were still in the µg/ml range. Notably, the MIC of CysF on strain *E. coli* WT III only increased by factor 2 compared to wildtype *E. coli* DSM-1116, whereas the MIC of ciprofloxacin increased by ca. factor 10.

TABLE 10a

Antimicrobial activity of cystobactamides (Cys).

| Test organism | CysA | CysA1 | CysB | CysC |
|---|---|---|---|---|
| | | MIC [µg/ml] | | |
| *Acinetobacter baumannii* DSM-30008 | 7.4 | 58.9 | 3.7 | 32.5 |
| *Burkholderia cenocepacia* DSM-16553 | >59 | >59 | >59 | >65 |
| *Chromobacterium violaceum* DSM-30191 | >59 | >59 | 14.7 | 16.3 |
| *Escherichia coli* DSM-1116 | 0.9 | 14.7 | 1.8 | 16.3 |
| *Escherichia coli* DSM-12242 (NAL[R]) | 0.9 | 29.4 | 3.7 | 8.1 |
| *Escherichia coli* DSM-26863 (tolC3) | 0.5 | 7.4 | 1.8 | 4.1 |
| *Escherichia coli* ATCC35218 | 0.9 | 14.7 | 1.8 | 16.3 |
| *Escherichia coli* ATCC25922 | 0.5 | 7.4 | 0.9 | 8.1 |
| *Enterobacter aerogenes* DSM-30053 | >59 | >59 | >59 | >33 |
| *Klebsiella pneumoniae* DSM-30104 | >59 | >59 | >59 | 65 |
| *Pseudomonas aeruginosa* PA14 | >59 | 58.9 | 14.7 | 65 |
| *Pseudomonas aeruginosa* ATCC27853 | >59 | 58.9 | 14.7 | 65 |
| *Mycobacterium smegmatis* mc²155 ATCC700084 | >59 | >59 | >59 | >65 |
| *Bacillus subtilis* DSM-10 | 0.12 | 1.8 | 0.46 | 2.0 |
| *Enterococcus faecalis* ATCC29212 | 0.06 | 3.7 | 0.23 | 4.1 |
| *Micrococcus luteus* DSM-1790 | 0.06 | 7.4 | 0.23 | 4.1 |
| *Staphylococcus aureus* ATCC29213 | 0.12 | 14.7 | 0.12 | 8.1 |
| *Streptococcus pneumoniae* DSM-20566 | 0.23 | 14.7 | 0.46 | 8.1 |
| *Candida albicans* DSM-1665 | >59 | >59 | >59 | >65 |
| *Pichia anomala* DSM-6766 | >59 | >59 | >59 | >65 |

| Test organism | CysF | CysG | CIP |
|---|---|---|---|
| *Acinetobacter baumannii* DSM-30008 | — | — | 0.2 |
| *Burkholderia cenocepacia* DSM-16553 | — | — | 6.4 |
| *Chromobacterium violaceum* DSM-30191 | — | — | 0.006 |
| *Escherichia coli* DSM-1116 | 0.4 | 0.9 | 0.006 |
| *Escherichia coli* DSM-12242 (NAL[R]) | — | — | 0.05 |
| *Escherichia coli* DSM-26863 (tolC3) | 0.4 | 0.9 | ≤0.003 |
| *Escherichia coli* ATCC35218 | — | — | 0.006 |
| *Escherichia coli* ATCC25922 | — | — | ≤0.003 |
| *Enterobacter aerogenes* DSM-30053 | — | — | 0.2 |
| *Klebsiella pneumoniae* DSM-30104 | — | — | 0.025 |
| *Pseudomonas aeruginosa* PA14 | 3.4 | 7.1 | 0.1 |
| *Pseudomonas aeruginosa* ATCC27853 | — | — | 0.1 |
| *Mycobacterium smegmatis* mc²155 ATCC700084 | — | — | 0.4 |
| *Bacillus subtilis* DSM-10 | — | — | 0.1 |
| *Enterococcus faecalis* ATCC29212 | — | — | 0.8 |
| *Micrococcus luteus* DSM-1790 | — | — | 1.6 |
| *Staphylococcus aureus* ATCC29213 | — | — | 0.1 |
| *Streptococcus pneumoniae* DSM-20566 | — | — | 1.6 |
| *Candida albicans* DSM-1665 | — | — | >6.4 |
| *Pichia anomala* DSM-6766 | — | — | >6.4 |

CIP reference antibiotic ciprofloxacin
— not determined

TABLE 10b

Cytotoxicity of cystobactamides (Cys).

| Cell lines and primary cells | GI$_{50}$ [µM] | | |
|---|---|---|---|
| | CysA | CysA1 | CysB |
| CHO-K1 (Chinese hamster ovary) | 37-111 | >111 | >111 |
| HCT-116 (human colon carcinoma) | — | — | >50 |
| HUVEC (human umbilical vein endothelial cells) | — | — | >50 |

| Cell lines and primary cells | GI$_{50}$ [µM] | | |
|---|---|---|---|
| | CysC | CysF | CysG |
| CHO-K1 (Chinese hamster ovary) | ca. 111 | >111 | 37-111 |
| HCT-116 (human colon carcinoma) | — | — | — |
| HUVEC (human umbilical vein endothelial cells) | — | — | — |

— not determined

TABLE 11

Antimicrobial activity of cystobactamides (Cys) against *E. coli* mutant strains.

| Test organism [resistance mutations] | CysA | CysA1 | CysB | CysC |
|---|---|---|---|---|
| | | MIC [µg/ml] | | |
| *Escherichia coli* WT | 0.5 | 14.7 | 1.8 | 8.1 |
| *Escherichia coli* MI [gyrA (S83L)] | 3.7 | 29.4 | 3.7 | 16.3 |
| *Escherichia coli* WT-3.2 [gyrA (D87G)] | 3.7 | 29.4 | 3.7 | 32.5 |
| *Escherichia coli* WT-3 [gyrA (S83L, D87G)] | 14.7 | >59 | 7.4 | >33 |
| *Escherichia coli* WT-4 M2.1 [parC (S80I)] | 0.5 | 14.7 | 1.8 | 8.1 |
| *Escherichia coli* MI-4 [gyrA (S83L), parC (S80I)] | 0.5 | 14.7 | 1.8 | 16.3 |
| *Escherichia coli* WTIII [marRΔ74bp] | 14.7 | 58.9 | 3.7 | 65 |

| Test organism [resistance mutations] | CysF | CysG | CIP |
|---|---|---|---|
| | | MIC [µg/ml] | |
| *Escherichia coli* WT | — | — | 0.013 |
| *Escherichia coli* MI [gyrA (S83L)] | — | — | 0.4 |

TABLE 11-continued

Antimicrobial activity of cystobactamides
(Cys) against E. coli mutant strains.

| | | | |
|---|---|---|---|
| Escherichia coli WT-3.2 [gyrA (D87G)] | — | — | 0.4 |
| Escherichia coli WT-3 [gyrA (S83L, D87G)] | — | — | 0.8 |
| Escherichia coli WT-4 M2.1 [parC (S80I)] | — | — | 0.025 |
| Escherichia coli MI-4 [gyrA (S83L), parC (S80I)] | — | — | 0.4 |
| Escherichia coli WTIII [marRΔ74bp] | 0.9 | 3.6 | 0.05 |

CIP reference antibiotic ciprofloxacin
— not determined

Experimental Procedures Cell-Based Assays

Cell Lines and Primary Cells.

Human HCT-116 colon carcinoma cells (CCL-247) were obtained from the American Type Culture Collection (ATCC) and Chinese hamster ovary CHO-K1 cells (ACC-110) were obtained from the German Collection of Microorganisms and Cell Cultures (DSMZ). Both cell lines were cultured under the conditions recommended by the respective depositor. Primary HUVEC (human umbilical vein endothelial cells; single donor) were purchased from PromoCell (Heidelberg, Germany) and cultured in Endothelial Cell Growth Medium (PromoCell) containing the following supplements: 2% FCS, 0.4% ECGS, 0.1 ng/ml EGF, 1 ng/ml bFGF, 90 µg/ml heparin, 1 µg/ml hydrocortisone.

Bacterial Strains.

Bacterial wildtype strains used in susceptibility assays were either part of our strain collection or purchased from the German Collection of Microorgansims and Cell Cultures (DSMZ) or from the American Type Culture Collection (ATCC). E. coli strain WT[6] and E. coli mutants were kindly provided by Prof. Dr. P. Heisig, Pharmaceutical Biology and Microbiology, University of Hamburg.

Cytotoxicity Assay.

Cells were seeded at $6 \times 10^3$ cells per well of 96-well plates (Corning CellBind®) in complete medium (180 µl) and directly treated with cystobactamides dissolved in methanol in a serial dilution. Compound were tested in duplicate for 5 d, as well as the internal solvent control. After 5 d incubation, 5 mg/ml MTT in PBS (20 µL) was added per well and it was further incubated for 2 h at 37° C.[7] The medium was then discarded and cells were washed with PBS (100 µl) before adding 2-propanol/10N HCl (250:1, v/v; 100 µl) in order to dissolve formazan granules. The absorbance at 570 nm was measured using a microplate reader (EL808, Bio-Tek Instruments Inc.).

Susceptibility Testing.

MIC values were determined in microdilution assays. Overnight cultures were diluted in the appropriate growth medium to achieve an inoculum of $10^4$-$10^6$ cfu/mL. Yeasts were grown in Myc medium (1% phytone peptone, 1% glucose, 50 mM HEPES, pH 7.0), S. pneumonia and E. faecalis in tryptic soy broth (TSB: 1.7% peptone casein, 0.3% peptone soymeal, 0.25% glucose, 0.5% NaCl, 0.25% $K_2HPO_4$; pH 7.3); M. smegmatis in Middlebrook 7H9 medium supplemented with 10% Middlebrook ADC enrichment and 2 ml/l glycerol). All other listed bacteria were grown in Müller-Hinton broth (0.2% beef infusion solids, 1.75% casein hydrolysate, 0.15% starch, pH 7.4). Cystobactamides and reference drugs were added directly to the cultures in sterile 96-well plates as duplicates and serial dilutions were prepared. Microorganisms were grown on a microplate shaker (750 rpm, 30-37° C., 18-48 h), except S. pneumonia, which was grown at non-shaking conditions (37° C., 5% $CO_2$, 18 h). Growth inhibition was assessed by visual inspection and the MIC was defined as the lowest concentration of compound that inhibited visible growth.

Target Identification

To test the anti-gyrase activity of cystobactamides, commercial E. coli gyrase supercoiling kits (Inspiralis) were used. Cystobactamide A inhibited the E. coli gyrase (20.5 nM eq. 1 unit) showing an apparent $IC_{50}$ of 6 µM. Cystobactamide A1 inhibited the E. coli gyrase (20.5 nM eq. 1 unit) showing an apparent $IC_{50}$ of 2.5 µM. Cystobactamide D inhibited the E. coli gyrase (20.5 nM eq. 1 unit) showing an apparent $IC_{50}$ of 1 µM. Cystobactamide C inhibited the E. coli gyrase (20.5 nM eq. 1 unit) showing an apparent $IC_{50}$ of 7.7 µM. Cystobactamides thus are novel inhibitors of bacterial DNA gyrase.

$IC_{50}$ Values of Cystobactamide A-D in the Gyrase Inhibition Assay:

| Compound | $IC_{50}/\mu M$ |
|---|---|
| cystobactamide A | 6 +/− 1.4 |
| cystobactamide A1 | 2.5 +/− 0.8 |
| cystobactamide C | 7.2 +/− 0.74 |
| cystobactamide D | 0.7 +/− 0.4 |

Figure 9A:
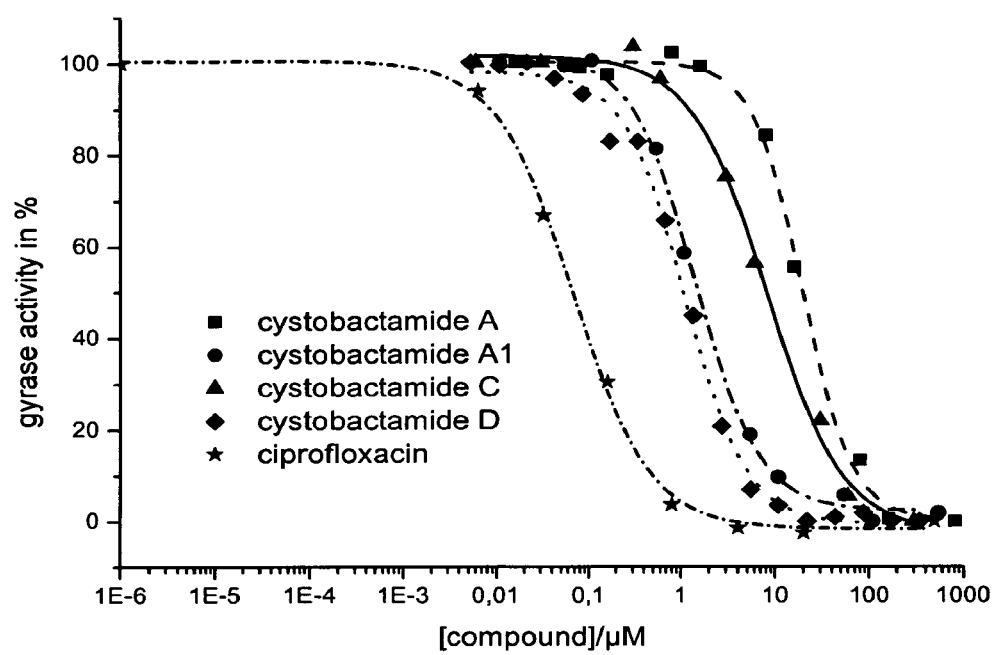

FIG. 9a show the results of the Gyrase inhibition assay. The gyrase reactions were titrated with varying concentrations of cystobactamide A, A1, C and D and resolved by agarose gel electrophoresis. For $IC_{50}$ determination the band intensity of the supercoiled plasmid was determined using Adobe Photoshop, plotted vs. [cystobactamide] and fitted using Hill's equation.

Prokaryotic DNA gyrase and topoisomerase IV share a high degree of homology and gyrase inhibitors typically show a topoisomerase IV inhibitory activity.[8] To test the influence of the cystobactamides on topoisomerase IV a commercial E. coli topoisomerase IV kit (Inspiralis) was used.

Cystobactamide A inhibited the activity of E. coli topo IV only at the highest tested concentration of 815 µM. Cystobactamide A1 inhibited E. coli topo IV showing an $IC_{50}$ value of 6.4+/−1.8 µM. Cystobactamide C inhibited the activity of E. coli topo IV only at the highest tested concentration of 300 µM. Cystobactamide D inhibited E. coli topo IV showing an $IC_{50}$ value of 10+/−3 µM.

$IC_{50}$ Values for Cystobactamide A-D in the E. coli Topoisomerase IV Inhibition Assay:

| Compound | $IC_{50}/\mu M$ |
|---|---|
| cystobactamide A | >160 |
| cystobactamide A1 | 6.4 +/− 1.8 |
| cystobactamide C | >60 |
| cystobactamide D | 10 +/− 3 |

Figure 9B:
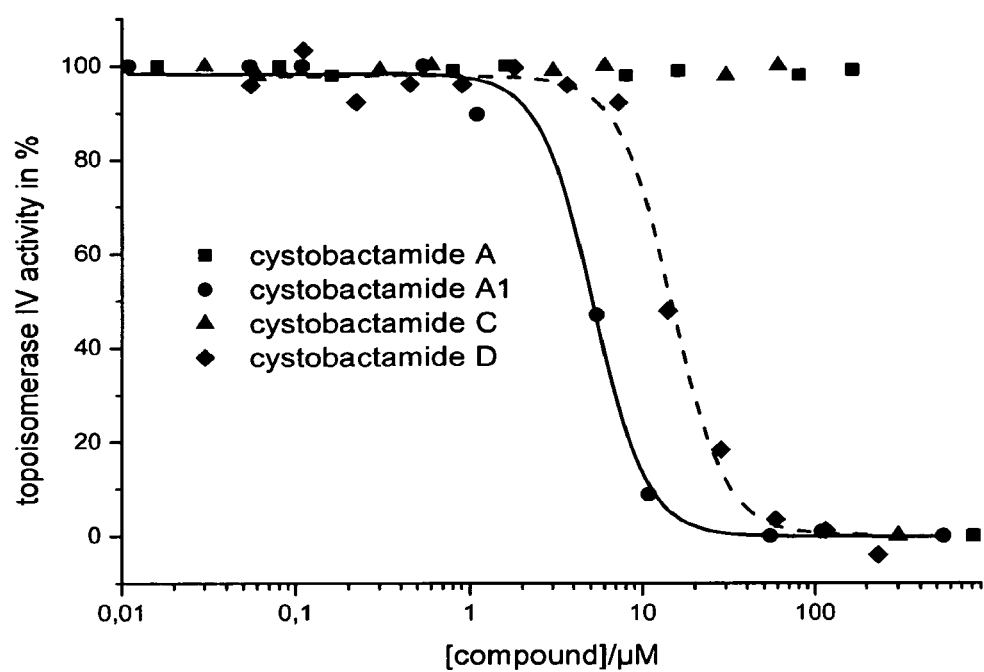

FIG. 9b shows the result of the Topoisomerase IV inhibition assay. The topo IV reactions were titrated with varying concentrations of A-D and resolved by agarose gel electrophoresis. For $IC_{50}$ determination the band intensity of the supercoiled plasmid was determined using Adobe Photoshop, plotted vs. [cystobactamide] and fitted using Hill's equation.

Prokaryotic DNA topoisomerase IV and eukaryotic topoisomerase II share a high degree of homology (type IIa topoisomerases) and inhibitors of the prokaryotic enzyme often also inhibits the eukaryotic counterpart.[8] To test the influence of the cystobactamides on eukaryotic topoisomerase IV a commercial *H. sapiens* topoisomerase II kit (Inspiralis) was used.

Cystobactamide A inhibited the activity of human topo II only at the highest tested concentration of 815 μM. Cystobactamide A1 inhibited human topo II showing an $IC_{50}$ value of 9+/−0.03 μM. Cystobactamide C inhibited the activity of human topo II only at the highest tested concentration of 300 μM. Cystobactamide D inhibited human topo II showing an $IC_{50}$ value of 41.2+/−3 μM $IC_{50}$ Values for Cystobactamide A-D in the *H. sapiens* Topoisomerase II Inhibition Assay:

| Compound | $IC_{50}$/μM |
| --- | --- |
| cystobactamide A | >160 |
| cystobactamide A1 | 9 +/− 0.03 |
| cystobactamide C | >60 |
| cystobactamide D | 41.2 +/− 3 |

Figure 9C:
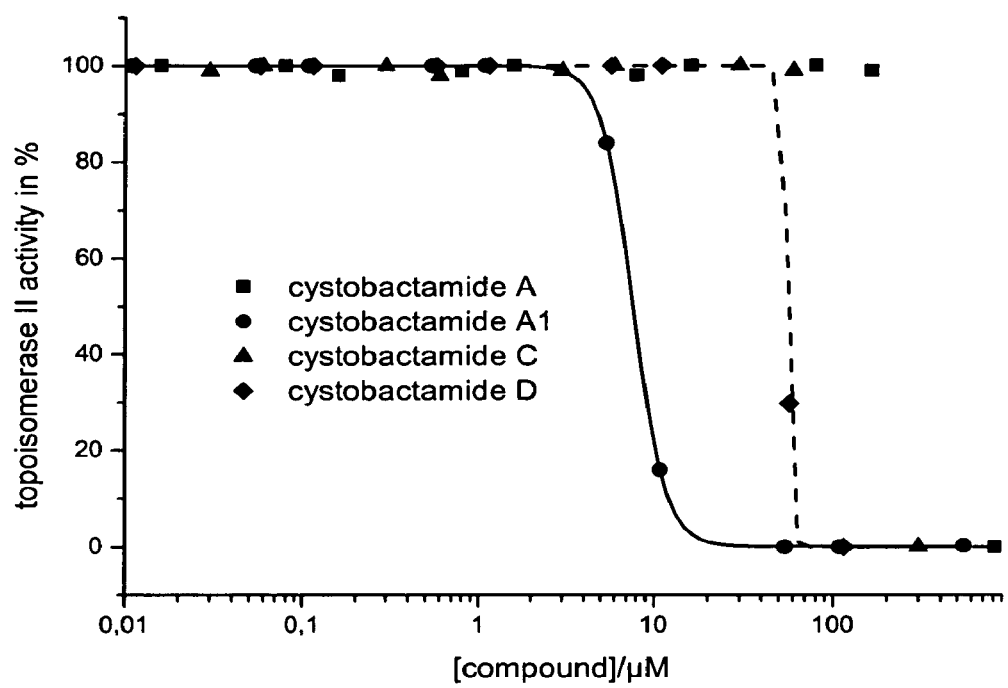

FIG. 9c shows the result of the Topoisomerase II inhibition assay. The topo II reactions were titrated with varying concentrations of A-D and resolved by agarose gel electrophoresis. For $IC_{50}$ determination the band intensity of the supercoiled plasmid was determined using Adobe Photoshop, plotted vs. [cystobactamide] and fitted using Hill's equation.

Aside the ATP-dependent type IIa topoisomerases like *E. coli* gyrase, topoIV and human topoII, the activity of cystobactamides on the ATP-independent human topoisomerase I was tested as well.

$IC_{50}$ Values for Cystobactamide A-D in the *H. sapiens* Topoisomerase I Inhibition Assay:

| Compound | $IC_{50}$/μM |
| --- | --- |
| cystobactamide A | ~10 |
| cystobactamide A1 | ~0.7 |
| cystobactamide C | ~6 |
| cystobactamide D | ~33.6 |

Figure 9D:
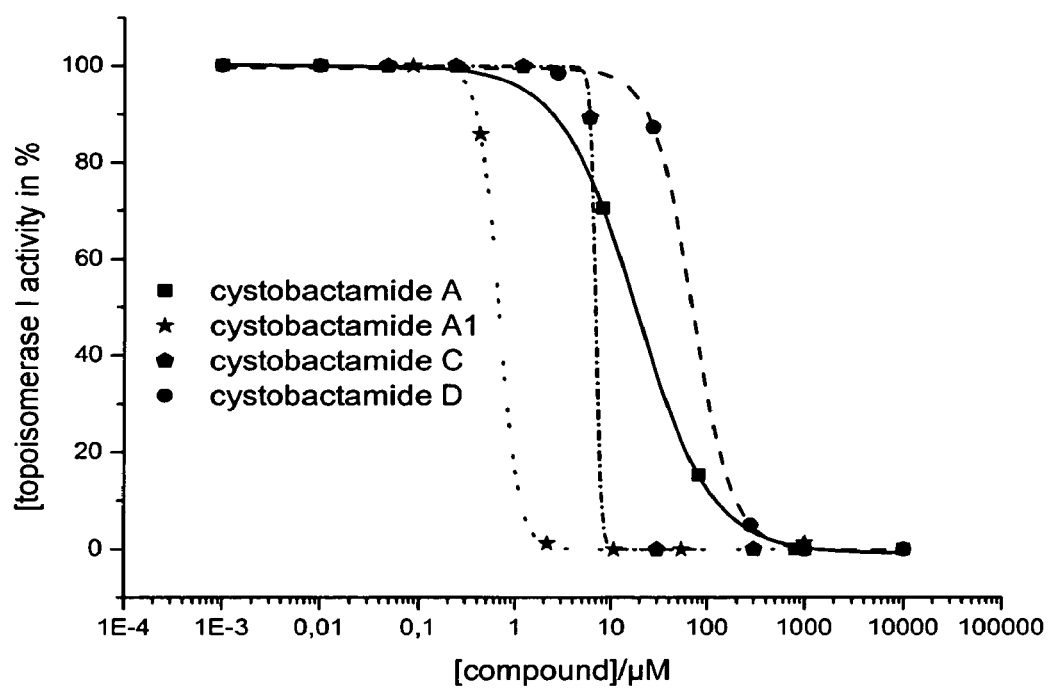

FIG. 9d shows the result of the Topoisomerase I inhibition assay. The topo I reactions were titrated with varying concentrations of A-D and resolved by agarose gel electrophoresis. For $IC_{50}$ determination the band intensity of the supercoiled plasmid was determined using Adobe Photoshop, plotted vs. [cystobactamide] and fitted using Hill's equation.

$IC_{50}$ (Gyrase) Vs. $IC_{50}$ (Topoisomerase IV) Value Comparison of Cystobactamide A-D:

| ratios | $IC_{50}$/μM | | ratios |
| --- | --- | --- | --- |
| | gyrase | Topo IV | $IC_{50}$ (topo IV)/$IC_{50}$ (gyrase) |
| cystobactamide A | 6 | ~815 | ~136 |
| cystobactamide A1 | 2.5 | 6.4 | ~2.6 |
| cystobactamide D | 0.7 | 10 | ~14 |
| cystobactamide C | 7.2 | ~300 | ~42 |

Cystobactamides A and C show a strong preference for gyrase as molecular target (40-100 fold stronger preference for gyrase). A1 and D both target gyrase and topoisomerase IV almost equally well (2.6-10 fold stronger preference for gyrase).

Generally, there are Two Described Inhibition Modes/Binding Sites for Gyrase Inhibitors:

1. Compounds like the fluoroquinolones bind to the GyrA DNA complex and avoid the religation of the nicked dsDNA (gyrase poisoning); and 2. Aminocoumarins on the other hand bind to the ATP binding pocket on GyrB (competitive inhibition).[8]

To test if cystobactamides follow any of those two inhibition modes, DNA/gyrase complex linearization assays (A) and ATP competition assays (B) were performed using cystobactamide D. (A) Here, the complex of DNA and gyrase is trapped using SDS and the gyrase is digested using proteinase K. If the gyrase/DNA complex is trapped by a gyrase inhibitor of type 1 this will lead to the formation of linearized plasmid (as the religation is inhibited). Type 2 inhibitor-bound or compound-free samples will not show the formation of linearized plasmids. The results of the assay are shown in FIG. 10a. Ciprofloxacin (a known gyrase/DNA stabilizer) and cystobactamide D show the formation of linearized plasmid after proteinase K treatment. This effect is not seen for the untreated control. Therefore, it appears likely that cystobactamides stabilize the covalent GyrA-DNA complex in a fashion comparable to the fluoroquinolones. (B) Here, standard gyrase reactions were inhibited using a constant amount of cystobactamide D and titrated with increasing amounts of ATP. If ATP and cystobactamide D would compete for binding at the ATP binding pocket on the gyrase GyrB subunit, increasing amounts of ATP would lead to the formation of supercoiled plasmid in the assay. FIG. 10b shows the assay results. Even at the highest ATP concentration of 10 mM (2000 fold cystobactamide concentration) the gyrase activity is not regained, indicating that the ATP binding pocket is not the binding site of the cystobactamides. This result is in line with the linearization assay results.

Figure 11:
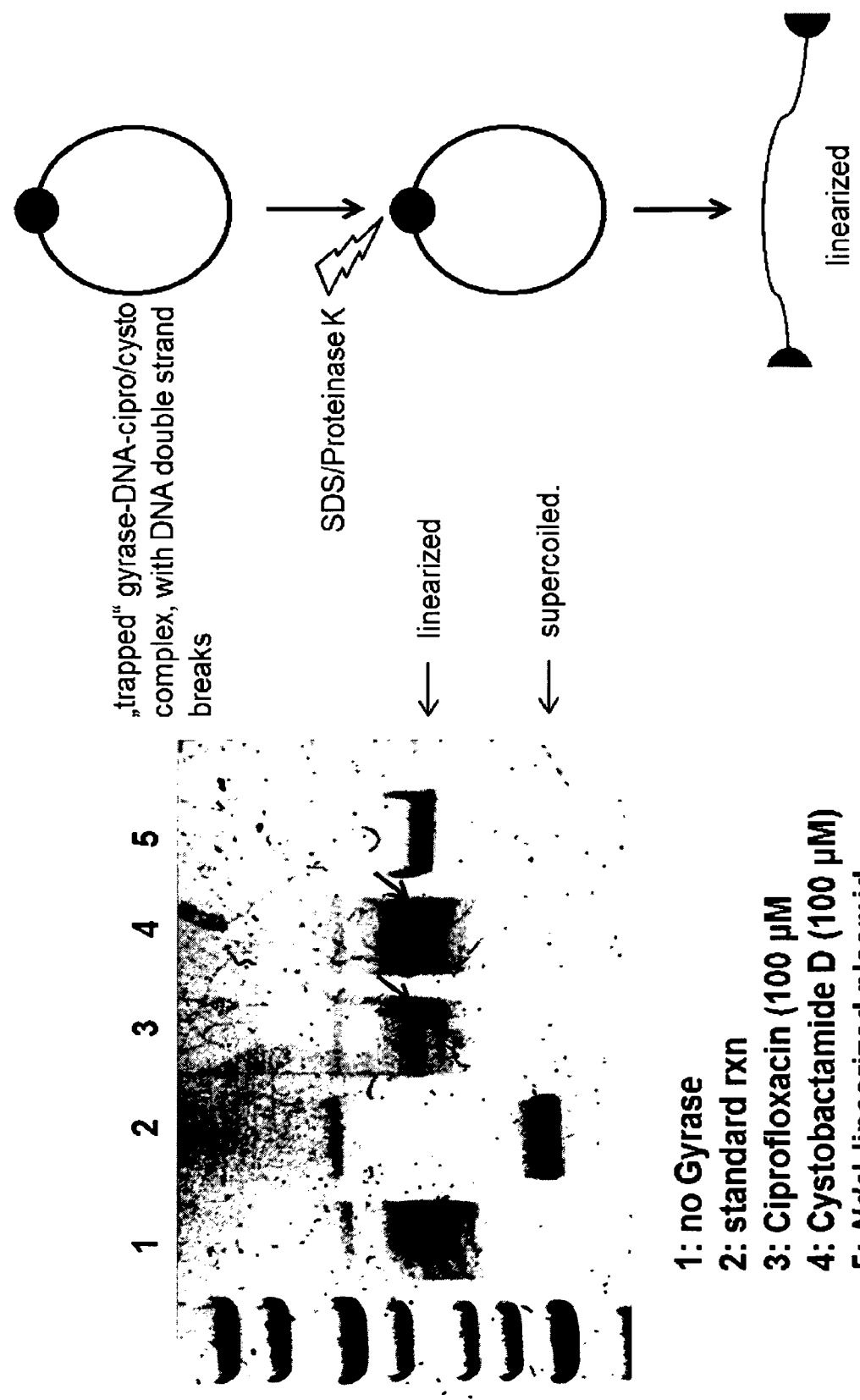

FIG. 11 shows the results of the DNA/gyrase complex linearization assay.

Experimental Procedures

Gyrase Supercoiling Assay

To test the anti-gyrase activity of cystobactamides, commercial *E. coli* gyrase supercoiling kits (Inspiralis, Norwich, UK) were used.3 For standard reactions 0.5 μg relaxed plasmid were mixed with 1 unit (~20.5 nM) *E. coli* gyrase in 1× reaction buffer (30 μl final volume, see kit manual) and incubated for 30 minutes at 37° C. The reactions were quenched by the addition of DNA gel loading buffer containing 10% (w/v) SDS. The samples were separated on 0.8% (w/v) agarose gels and DNA was visualized using Roti-GelStain (Carl Roth).

All natural products stock solutions and dilutions were prepared in 100% DMSO and added to the supercoiling reactions giving a final DMSO concentration of 5% (v/v).

Ciprofloxacin stock solutions and Dilutions were prepared in 10 mM HCl and 50% DMSO and used 1:10 in the final assay.

Following natural product concentrations were used in the assay: Cystobactamide A: 815.8 μM; 163 μM; 80 μM, 16 μM; 8 μM; 1.6 μM; 0.8 μM; 0.16 μM; 0.08 μM; 0.016 μM Cystobactamide A1: 543.5 μM; 108.7 μM; 54 μM; 10.8 μM; 5.4 μM; 1.087 μM; 0.54 μM; 0.108 μM; 0.054 μM; 0.0108 μM Cystobactamide C: 300 µM; 60 µM; 30 µM; 6 µM; 3 µM; 0.6 µM; 0.3 µM; 0.06 µM; 0.03 µM; 0.006 µM Cystobactamide D: 347 µM; 173.5 µM; 86.75 µM; 43.38 µM; 21.69 µM; 10.84 µM; 5.42 µM; 2.71 µM; 1.36 µM; 0.68 µM; 0.34 µM; 0.17 µM; 0.085 µM; 0.042 µM; 0.021 µM; 0.0106 µM; 0.0053 µM Control reactions were: no enzyme and a standard reaction in presence of 5% (v/v) DMSO.

All reaction samples were equilibrated for 10 minutes at room-temperature in the absence of DNA. Then the relaxed plasmid was added to start the reaction.

Proteinase K Linearization Assay

To test if cystobactamides stabilize the covalent complex between DNA gyrase and the nicked DNA substrate, proteinase K linearization assay were performed (see a). Standard gyrase supercoiling assays were run in the presence of cystobactamide D (18 µM; 1.8 µM). Control reactions contained no gyrase, no inhibitor or the known gyrase/DNA complex stabilizer ciprofloxacin (1 µM). The reactions were quenched by the addition of 1/10 volume of 10% SDS. To linearize the nicked DNA-gyrase complexes, 50 µg/ml proteinase K were added to the reactions and incubated for 30 minutes at 37° C. The samples were separated on 0.8% (w/v) agarose gels and DNA was visualized using Roti-GelStain (Carl Roth). To detect linearized plasmid bands the relaxed plasmid was digested by the single-cutting restriction enzyme NdeI.

Gyrase Supercoiling Assay with Varying ATP Concentrations

To test if cystobactamides compete with ATP for binding to the ATP binding pocket on GyrB, standard gyrase supercoiling assays (see a) with varying ATP concentrations were performed. Standard reaction mixes (1 mM ATP) were supplemented with ATP (0.5M ATP stock solution, ATP was purchased from Sigma-Aldrich) to final ATP concentrations of 2.5; 5 and 10 mM. All reactions were performed in triplicates.

Topoisomerase IV Relaxation Assay

To test the anti-topoisomerase IV activity of cystobactamides, commercial E. coli topoisomerase IV relaxing kits (Inspiralis, Norwich, UK) were used.4 For standard reactions 0.5 µg supercoiled plasmid were mixed with 1 unit (~20.5 nM) E. coli topoisomerase IV in 1× reaction buffer (see kit manual) and incubated for 30 minutes at 37° C. The reactions were quenched by the addition of DNA gel loading buffer containing 10% (w/v) SDS. The samples were separated on 0.8% (w/v) agarose gels and DNA was visualized using Roti-GelStain (Carl Roth).

Following Natural Product Concentrations were Used in the Assay:

Cystobactamide A: 815.8 µM; 163 µM; 80 µM, 16 µM; 8 µM; 1.6 µM; 0.8 µM; 0.16 µM; 0.08 µM; 0.016 µM Cystobactamide A1: 543.5 µM; 108.7 µM; 54 µM; 10.8 µM; 5.4 µM; 1.087 µM; 0.54 µM; 0.108 µM; 0.054 µM; 0.0108 µM Cystobactamide C: 300 µM; 60 µM; 30 µM; 6 µM; 3 µM; 0.6 µM; 0.3 µM; 0.06 µM; 0.03 µM; 0.006 µM Cystobactamide D: 347 µM; 173.5 µM; 86.75 µM; 43.38 µM; 21.69 µM; 10.84 µM; 5.42 µM; 2.71 µM; 1.36 µM; 0.68 µM; 0.34 µM; 0.17 µM; 0.085 µM; 0.042 µM; 0.021 µM; 0.0106 µM; 0.0053 µM Control reactions were: no enzyme and a standard reaction in presence of 5% (v/v) DMSO.

All reaction samples were equilibrated for 10 minutes at room-temperature in the absence of DNA. Then the relaxed plasmid was added to start the reaction.

Topoisomerase II Relaxation Assay

To test the anti-topoisomerase II activity of cystobactamides, commercial human topoisomerase IV relaxing kits (Inspiralis, Norwich, UK) were used.4 For standard reactions 0.5 µg supercoiled plasmid were mixed with 1 unit (~20.5 nM) E. coli topoisomerase II in 1× reaction buffer (see kit manual) and incubated for 30 minutes at 37° C. The reactions were quenched by the addition of DNA gel loading buffer containing 10% (w/v) SDS. The samples were separated on 0.8% (w/v) agarose gels and DNA was visualized using Roti-GelStain (Carl Roth).

Following Natural Product Concentrations were Used in the Assay:

Cystobactamide A: 815.8 µM; 163 µM; 80 µM, 16 µM; 8 µM; 1.6 µM; 0.8 µM; 0.16 µM; 0.08 µM; 0.016 µM Cystobactamide A1: 543.5 µM; 108.7 µM; 54 µM; 10.8 µM; 5.4 µM; 1.087 µM; 0.54 µM; 0.108 µM; 0.054 µM; 0.0108 µM Cystobactamide C: 300 µM; 60 µM; 30 µM; 6 µM; 3 µM; 0.6 µM; 0.3 µM; 0.06 µM; 0.03 µM; 0.006 µM Cystobactamide D: 347 µM; 173.5 µM; 86.75 µM; 43.38 µM; 21.69 µM; 10.84 µM; 5.42 µM; 2.71 µM; 1.36 µM; 0.68 µM; 0.34 µM; 0.17 µM; 0.085 µM; 0.042 µM; 0.021 µM; 0.0106 µM; 0.0053 µM Control reactions were: no enzyme and a standard reaction in presence of 5% (v/v) DMSO. All reaction samples were equilibrated for 10 minutes at room-temperature in the absence of DNA. Then the relaxed plasmid was added to start the reaction.

Topoisomerase I Relaxation Assay

To test the anti-topoisomerase II activity of cystobactamides, commercial *H. sapiens* topoisomerase I relaxing kits (Inspiralis, Norwich, UK) were used.4 For standard reactions 0.5 µg supercoiled plasmid were mixed with 1 unit (~20.5 nM) *H. sapiens* topoisomerase I in 1× reaction buffer (see kit manual) and incubated for 30 minutes at 37° C. The reactions were quenched by the addition of DNA gel loading buffer containing 10% (w/v) SDS. The samples were separated on 0.8% (w/v) agarose gels and DNA was visualized using Roti-GelStain (Carl Roth).

Following natural product concentrations were used in the assay:

Cystobactamide A: 815 µM; 81.5 µM; 8.15 µM

Cystobactamide A1: 543 µM; 54.3 µM; 5.43 µM

Cystobactamide C: 300 µM; 30 µM; 3 µM

Cystobactamide D: 277 µM; 27.2 µM; 2.77 µM

Control reactions were: no enzyme and a standard reaction in presence of 5% (v/v) DMSO. All reaction samples were equilibrated for 10 minutes at room-temperature in the absence of DNA. Then the relaxed plasmid was added to start the reaction Quantification and Analysis To determine IC50 values, the formation of supercoiled (gyrase) or relaxed (topoisomerase I, II IV) plasmid was quantified using Adobe Photoshop (Histogram mode). Plotting of these values versus the compound concentration yielded sigmoidal shaped curves, which were fitted using Hill's equation (Origin Pro 8.5). All determined IC50 values are the averages of three independent experiments.

REFERENCES

[1] T. Gruger, J. L. Nitiss, A. Maxwell, E. L. Zechiedrich, P. Heisig, S. Seeber, Y. Pommier, D. Strumberg, *Antimicrob. Agents Chemother.* 48, 2004, 4495-4504.

[2] H. Schedletzky, B. Wiedemann, P. Heisig, *J. Antimicrob. Chemother.* 43, 1999, 31-37.

[3] A. B. Khodursky, E. L. Zechiedrich, N. R. Cozzarelli, *Proc. Natl. Acad. Sci. USA* 92, 1995, 11801-11805.

[4] A. Schulte, P. Heisig, *J. Antimicrob. Chemother.* 46, 2000, 1037-1046.

[5] D. Keeney, A. Ruzin, F. McAleese, E. Murphy, P. A. Bradford, *J. Antimicrob. Chemother.* 61, 2008, 46-53.

[6] P. Heisig, H. Schedletzky, H. Falkenstein-Paul, *Antimicrob. Agents Chemother.* 37, 1993, 669-701.

[7] T. Mosmann, *J. Immunol. Meth.* 65, 1983, 55-63.

[8] Pommier, Y.; Leo, E.; Zhang, H.; Marchand, C. *Chemistry & Biology* 2010, 17, 421.

Synthesis of Cystobactamide A and C

First, the synthesis of cystobactamide C is described which can further be elaborated to the other cystobactamides.

1.1. Cystobactamide C

The following Schemes 1 and 2 provide an overview on the synthesis of individual aromatic building blocks followed by assembling these to generate cystobactamide C.

Alternatively, step e) in Scheme 1 can be modified by using another alcohol (R'OH) instead of $^i$PrOH. If for example EtOH is used, building blocks of cystobactamide H can be prepared. The same applies for step b) in the second reaction sequence given in Scheme 1. Here, also $^i$PrOH can be exchanged by any other alcohol (R'OH). If for example MeOH is used, building blocks of cystobactamides C, G and H can be prepared. For the preparation of cystobactamide F, p-amino-benzoic acid derivatives such as p-aminobenzoic acid or corresponding N-protected aminobenzoic acid derivatives and p-nitrobenzoic acids are employed instead of building block B.

Scheme 1: Synthesis of arenes A and B followed by amide coupling.
(central aromatic moiety)

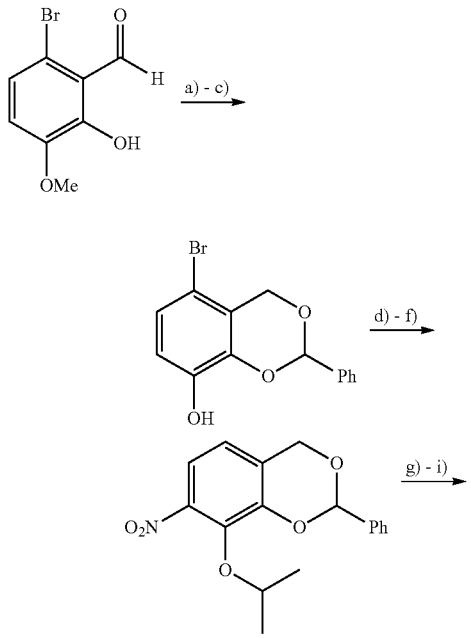

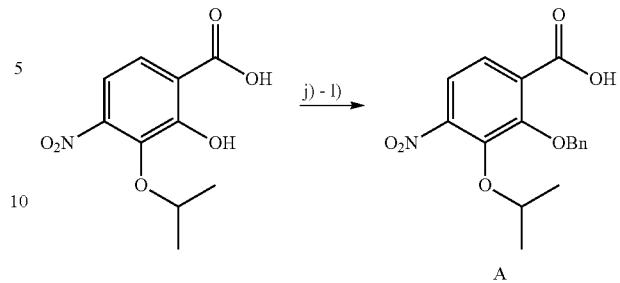

A a) BBr$_3$, CH$_2$Cl$_2$, -40° C. - rt, 17 h (95%); b) NaBH$_4$, THF, -40° C. - rt, 30 min (91%); c) PhCH(OMe)$_2$, pTSA•H$_2$O, THF, rt, 5 days (56%);
d) Ni(NO$_3$)$_2$•5H$_2$O, pTsOH•H$_2$O, acetone, rt, 2.5 h (74%); e) $^i$-PrOH, DEAD, PPh$_3$, THF, rt, 17 h (85%); f) Pd$_2$(dba)$_3$, (PhO)$_3$P, $^i$PrOH, dioxane, 80° C., 1.5 h (70%); g) Camphor-10-sulfonic acid, CH$_2$Cl$_2$/MeOH (1:2), 0° C. - rt, 17 h (90%); h) MnO$_2$, CH$_2$Cl$_2$, rt, 17 h (81%); i) 2-methyl-2-butene, NaClO$_2$/NaH$_2$PO$_4$, $^t$BuOH, rt, 17 h (75%); j) TMSCHN$_2$, MeOH/PhMe, 0° C, - rt, 30 min (57%); k) BNOH, DEAD, PPH$_3$, THF, rt, 17 h (90%); l) LiOH, THF/H$_2$O (1:1), rt, 17 h (99%).

(terminal trisubstituted aromatic moiety)

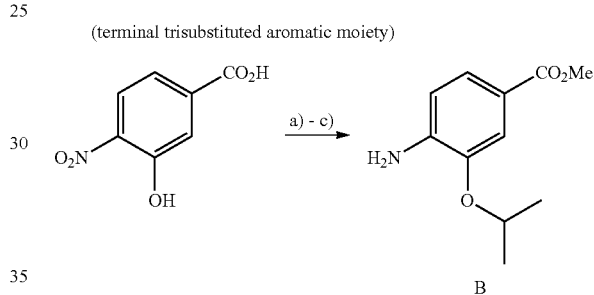

B a) TMSCHN$_2$, MeOH/PhMe, 0° C. - rt, 30 min (90%); b) $^i$PrOH, DEAD, PPH$_3$, THF, rt, 17 h (quant); c) Pd/C, MeOH, H$_2$ atm., rt, 17 h (quant).

(merging aromatic moieties A and B)

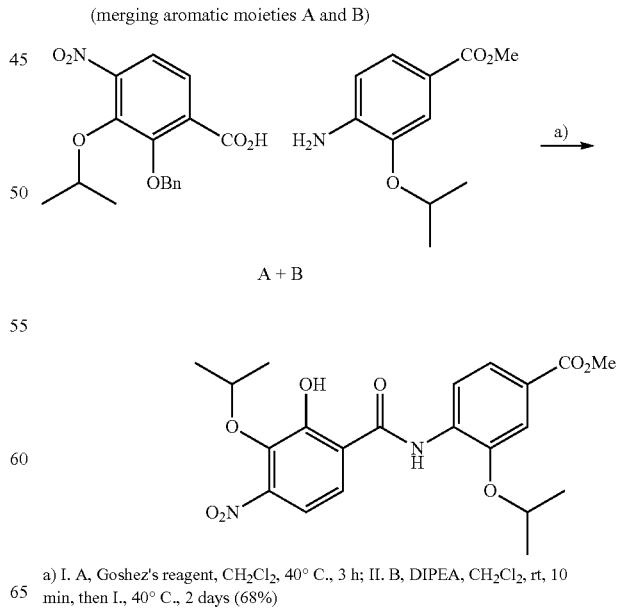

a) I. A, Goshez's reagent, CH$_2$Cl$_2$, 40° C., 3 h; II. B, DIPEA, CH$_2$Cl$_2$, rt, 10 min, then I., 40° C., 2 days (68%)

Scheme 2: Finalization of cystobactamide C synthesis.
Cystobactamide C (finalization of synthesis)

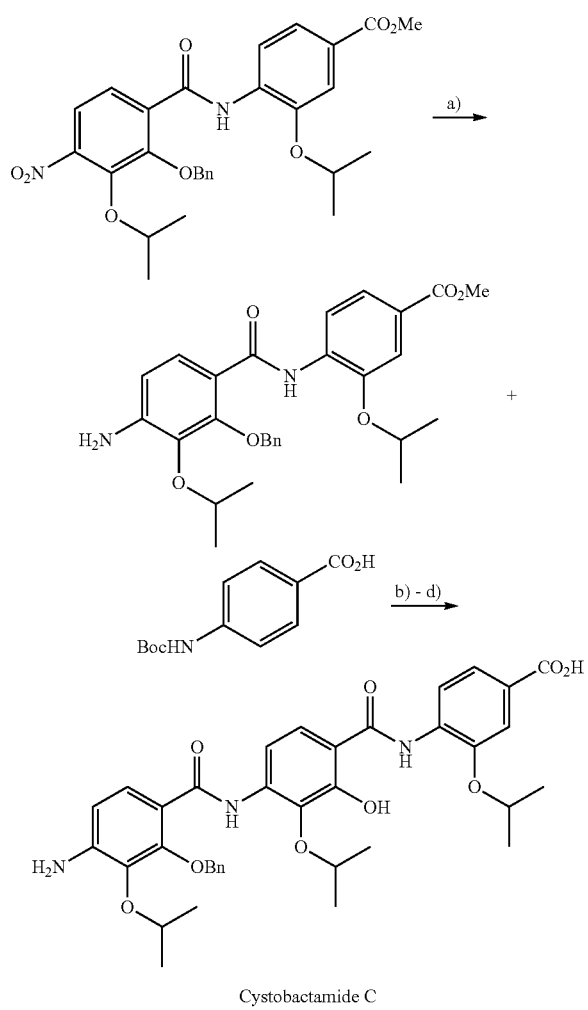

Cystobactamide C a) Pd/C, MeOH, H₂ atm, rt, 3 h (96%); b) I. 4-Boc aminobenzoic acid, Goshez's reagent, CH₂Cl₂, rt, 1 h; II..B, DIPEA, CH₂Cl₂; then I., rt, 1 day (72%); c) TFA/CH₂Cl₂ (10:1), rt,17 h (quant.); d) LiOH, THF/H₂O (1:1), rt, 17 h (99%).

1.2 Cystobactamide A

The more complex cystobactamides consist of the bis-amide that represents cystobactamide C, a bisarylamide (fragment C) and a chiral linker element. In this section fragment C and the chiral linker element are reported first which is followed by the assembling of all three elements to provide cystobactamide A.

1.2.1 Synthesis of Bisarene C.

Scheme 3: Synthesis of activated fragment C.
Fragment C

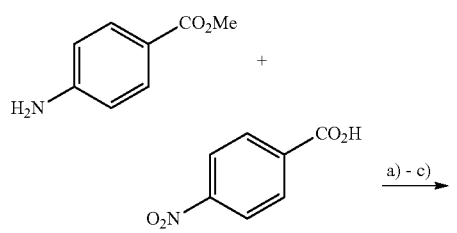

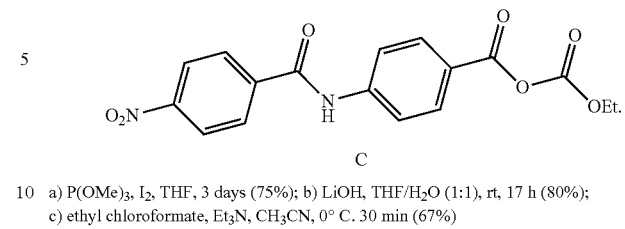

a) P(OMe)₃, I₂, THF, 3 days (75%); b) LiOH, THF/H₂O (1:1), rt, 17 h (80%); c) ethyl chloroformate, Et₃N, CH₃CN, 0° C. 30 min (67%)

1.2.2 Synthesis of the Chiral Building Block D with Bisarene C Attached

The synthesis starts from methyl cinnamate and chirality is introduced by the Sharpless asymmetric dihydroxylation. The phenyl ring serves as protecting group for the second carboxylate which is oxidatively liberated. Finally, building block C is attached to the free amino group. The corresponding enantiomeric fragment (ent)-D was prepared using AD mix α instead of AD mix β.

Scheme 4: Synthesis of carboxylic acid D starting from methylcinnamate.

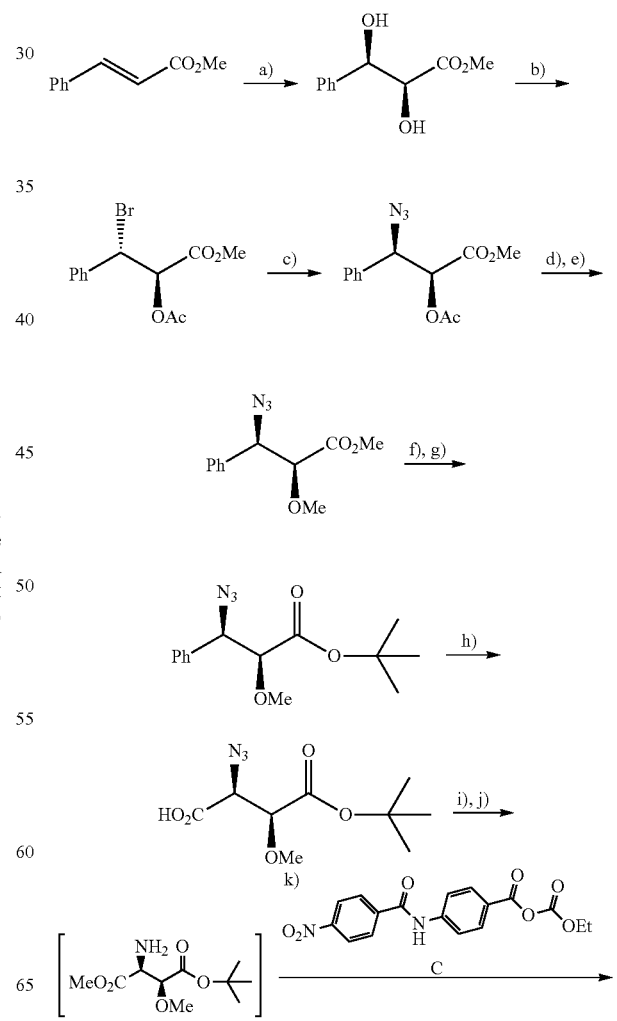

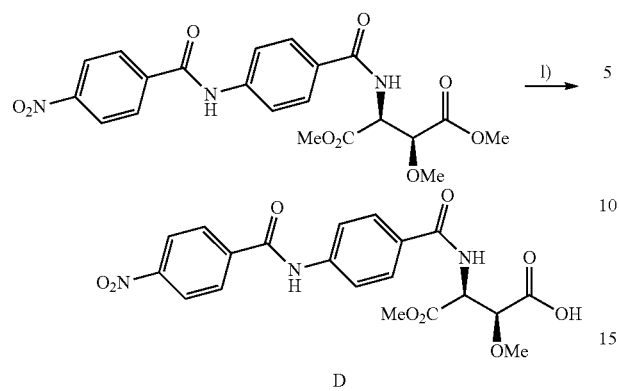
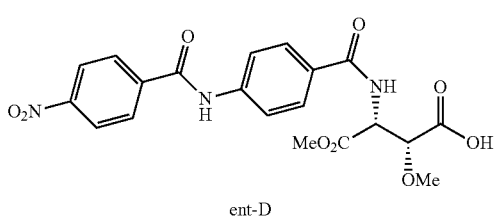

a) AD mix β, MeSO₂NH₂, tBuOH/H₂O (1:1), 0° C., 12 h, then 25° C., 12 h, (79%, ee > 99%); b) 33% HBr/HOAc, 45° C., 30 min., (71%); c) NaN₃, DMF, 25° C., then 40° C., 2 h, (89%); d) KOH, THF/H₂O; e) 2. MeI, Ag₂O, CaSO₄ (74% for two steps); h) RuCl₃H₂O, NaIO₄, CHCl₃/CH₃CN/H₂O, 70° C.; i) MeI, Ag₂O, CaSO₄; j) PH₃P, THF/H₂O, 50° C., k) DMF (16% for four steps); l) CF₃CO₂H, CH₂Cl₂, (quant).

Scheme 5: Finalization of cystobactamide A synthesis.
Cystobactamide A (finalization of synthesis)

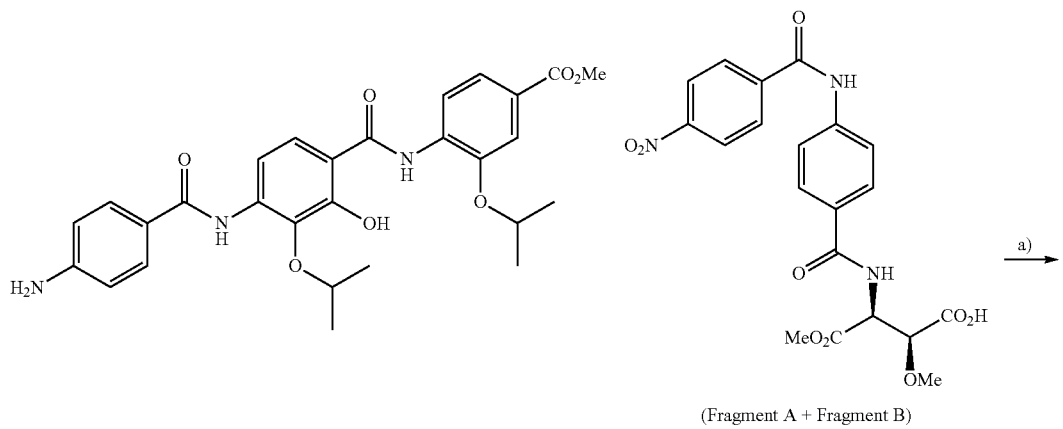

(Fragment A + Fragment B)

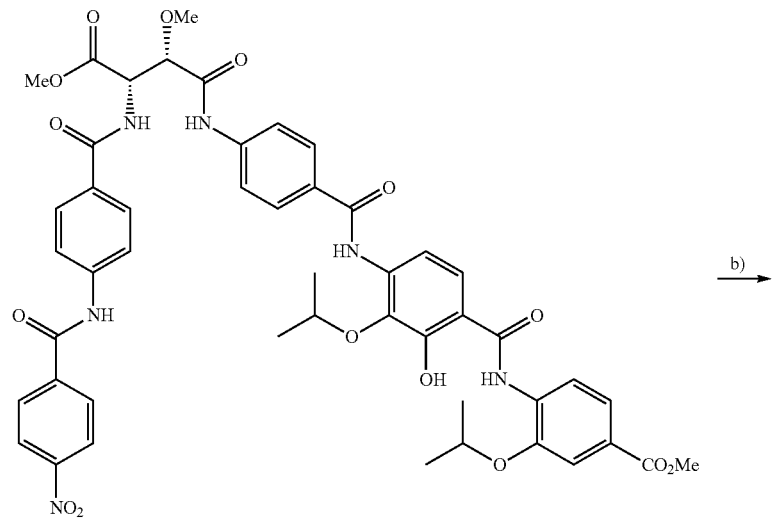

-continued

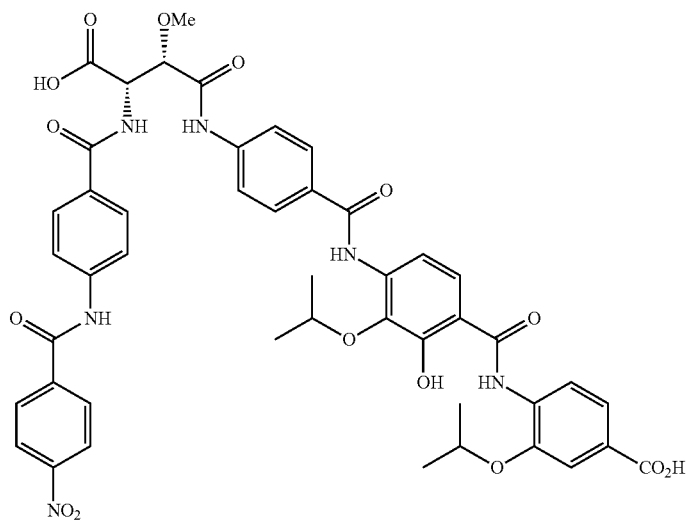

Cystobactamide A a) HOAt, EDC·HCl, DIPEA, CH$_2$Cl$_2$, rt, 17 h (75%);
b) LiOH, THF/H$_2$O(1/1), rt, (95%).

2.1 General Experimental Information

All reactions were performed in oven dried glassware under an atmosphere of nitrogen gas unless otherwise stated. $^1$H-NMR spectra were recorded at 400 MHz with a Bruker AVS-400 or at 500 MHz with a Bruker DRX-500. $^{13}$C-NMR spectra were recorded at 100 MHz with a Bruker AVS-400 and at 125 MHz with a Bruker DRX-500. Multiplicities are described using the following abbreviations: s=singlet, d=doublet, t=triplet, q=quartet, m=multiplet, b=broad. Chemical shift values of $^1$H and $^{13}$C NMR spectra are commonly reported as values in ppm relative to residual solvent signal as internal standard. The multiplicities refer to the resonances in the off-resonance decoupled spectra. These were elucidated using the distortionless enhancement by polarization transfer (DEPT) spectral editing technique, with secondary pulses at 90° and 135°. Multiplicities are reported using the following abbreviations: s=singlet (due to quaternary carbon), d=doublet (methine), t=triplet (methylene), q=quartet (methyl). Mass spectra (EI) were obtained at 70 eV with a type VG Autospec spectrometer (Micromass), with a type LCT (ESI) (Micromass) or with a type Q-TOF (Micromass) spectrometer in combination with a Waters Aquity Ultraperformance LC system. Analytical thin-layer chromatography was performed using precoated silica gel 60 F$_{254}$ plates (Merck, Darmstadt), and the spots were visualized with UV light at 254 nm or alternatively by staining with potassium permanganate, phosphomolybdic acid, 2,4-dinitrophenol or p-anisaldehyde solutions. Tetrahydrofuran (THF) was distilled under nitrogen from sodium/benzophenone. Dichloromethane (CH$_2$Cl$_2$) was dried using a Solvent Purification System (SPS). Commercially available reagents were used as supplied. Preparative high performance liquid chromatography using a Merck Hitachi LaChrom system (pump L-7150, interface D-7000, diode array detector L-7450 (λ=220-400 nm, preferred monitoring at A=230 nm)) with column (abbreviation referred to in the experimental part given in parentheses): Trentec Reprosil-Pur 120 C18 AQ 5 µm, 250×8 mm, with guard column, 40×8 mm (C18-SP). Flash column chromatography was performed on Merck silica gel 60 (230-400 mesh). Eluents used for flash chromatography were distilled prior to use. Melting points were measured using a SRS OptiMelt apparatus. Optical rotations [α] were measured on a Polarimeter 341 (Perkin Elmer) at a wavelength of 589 nm and are given in $10^{-1}$ deg cm$^2$ g$^{-1}$

2.2 Specific Procedures

4-Aminomethylbenzoate

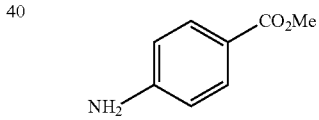

MeOH (200 mL) was provided in a flask and acetyl choride (2.6 mL, 36.5 mmol, 1 eq) was slowly added. Then 4-aminobenzoic acid (5.00 g, 36.5 mmol) was added and the solution was stirred 7 days at room temperature. The solvent was removed under reduced pressure and 4-aminomethylbenzoate (5.38 g, 35.59 mmol, quantitative) was obtained as a beige solid.

The titled compound decomposes before reaching its melting point.

ATR-IR (neat): 0̃=2828, 2015, 1724, 1612, 1558, 1508, 1430, 1316, 1280, 1181, 1109, 1072, 1022, 984, 959, 853, 786, 757, 686, 653 cm$^{-1}$.

$^1$H-NMR (400 MHz, CD$_3$OD): δ 8.19-8.13 (m, 2H), 7.53-7.48 (m, 2H), 3.93 (s, 3H) ppm.

$^{13}$C-NMR (100 MHz, CD$_3$OD): δ 167.2 137.0, 132.4, 131.7, 124.2, 53.0 ppm

HRMS (ESI): Calculated for C$_8$H$_{10}$NO$_2$ (M+H)$^+$: 152.0712, found: 152.0706.

4-(4-Nitrobenzamido)methyl benzoate

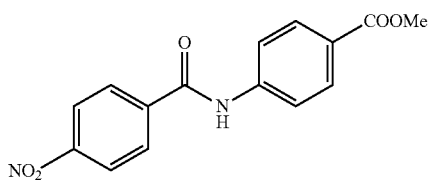 [SMILES: COC(=O)c1ccc(NC(=O)c2ccc([N+](=O)[O-])cc2)cc1]

A solution of P(OMe)$_3$ (3.5 mL, 29.8 mmol) in CH$_2$Cl$_2$ (100 mL) was cooled with an ice bath, then I$_2$ (7.56 g, 29.8 mmol) was added. After the solid iodine was completely dissolved, p-nitrobenzoic acid (5.52 g, 29.8 mmol) and Et$_3$N (4.70 mL, 33.7 mmol) were added in sequential order, and the solution was stirred for 10 minutes in a cooling bath. 4-aminomethylbenzoate (3.00 gr, 19.9 mmol) was added and the mixture was stirred for 10 minutes. After removing the cooling bath, the reaction mixture was stirred for 3 days at room temperature, then diluted with saturated aqueous NaHCO$_3$ and extracted with dichloromethane (3×). The combined, organic layer was sequentially washed with H$_2$O, 1 M HCl, H$_2$O, and brine. The combined organic layers were dried with anhydrous MgSO$_4$ and the solvent concentrated in vacuo, yielding the title compound (4.4 g, 14.65 mmol, 75%) as a beige solid. mp: 245-246° C.

$^1$H NMR (400 MHz, DMSO) δ 10.87 (s, 1H$_{NH}$), 8.39 (d, J=8.8 Hz, 2H), 8.20 (d, J=8.8 Hz, 2H), 7.99 (d, J=8.8 Hz, 2H), 7.95 (d, J=8.8 Hz, 2H), 3.84 (s, 3H$_{OMe}$) ppm.

$^{13}$C NMR (100 MHz, DMSO) δ 166.2, 164.9, 149.77, 143.6, 140.7, 130.7, 129.8, 125.3, 124.2, 120.2, 52.4 ppm.

HRMS (ESI): Calculated for C$_{15}$H$_{13}$N$_2$O$_2$Na (M+H)$^+$: 301.0824, found: 301.0828.

4-(4-Nitrobenzamido) benzoate

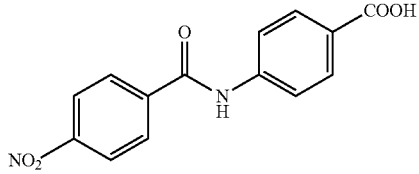 [SMILES: O=C(O)c1ccc(NC(=O)c2ccc([N+](=O)[O-])cc2)cc1]

4-(4-Nitrobenzamido)methyl benzoate (4.32 g, 14.38 mmol) was dissolved in a mixture 1/1 of THF/H$_2$O (77/77 mL). Then, solid LiOH (5.16 g, 215.66 mmol) was added and the system was stirred at room temperature for 17 hours. 1M HCl was added until pH-1 and the resulting solid was filtered and dried in vacuo. The title compound (3.3 g, 11.54 mmol, 80%) was obtained as a pale yellow solid. mp: 322-324° C.

$^1$H NMR (400 MHz, C$_6$D$_6$) δ 10.83 (s, 1H$_{CO2H}$), 8.34 (d, J=8.6 Hz, 1H), 8.29 (d, J=8.6 Hz, 1H), 8.13 (d, J=8.6 Hz, 1H), 8.06 (d, J=8.6 Hz, 1H), 7.75 (s, 1H$_{NH}$) ppm.

$^{13}$C NMR (100 MHz, C$_6$D$_6$) δ 168.2, 164.6, 162.2, 149.7, 143.9, 141.1, 131.1, 129.8, 123.5, 120.4 ppm.

HRMS (ESI): Calculated for C$_{14}$H$_9$N$_2$O$_5$(M-H)$^-$: 285.0511, found: 285.0506.

(Ethyl carbonic) 4-(4-nitrobenzamido)benzoic anhydride

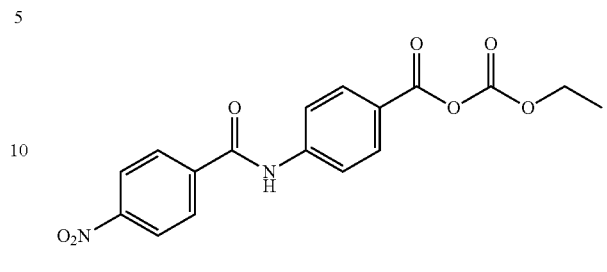

To a stirred solution of 4-aminobenzoic acid (1.5 g, 10.9 mmol) and N,N-dimethylaniline (2.0 g, 10.9 mmol) in acetone was added 4-nitrobenzoyl chloride at 0° C. Then, the reaction mixture was allowed to warm to room temperature and stirred for another hour. The resulting solid was filtered and purified by recrystallization in DMF to afford 4-(4-nitrobenzoylamino)-benzoic acid (2.75 g, 88%).

4-(4-Nitro-benzoylamino)-benzoic acid (0.6 g, 2.1 mmol) was dissolved in 14 ml CH$_3$CN. Then Et$_3$N (0.31 ml, 2.2 mmol) was added at 0° C. To this resulting solution ethyl chloroformate was added. After stirring for 30 min at 0° C., the white precipitate was filtered and washed with cold CH$_3$CN, then dried under high vacuum at room temperature to afford the title anhydride 0.5 g, 67%.

$^1$H-NMR (400 MHz, DMSO, DMSO=2.50 ppm): δ=1.33 (dd, J=7.2 Hz, 3H), 4.37 (q, J=7.2 Hz, 2H), 8.02-8.09 (m, 4H), 8.21 (d, J=8.8 Hz, 2H), 8.40 (d, J=8.8 Hz, 2H), 11.01 (s, 1H).

3-Hydroxy-4-nitromethylbenzoate

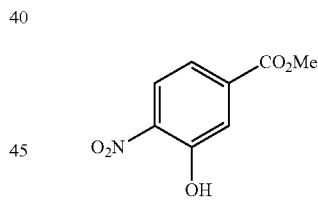

TMSCHN$_2$ (2.0 M in Et$_2$O, 13.20 mL, 26.48 mmol) was added to a solution of 3-hydroxy-2-nitrobenzoic acid (2.50 g, 13.65 mmol) in a mixture of toluene/methanol (81/36 mL) at 0° C. After stirring at 0° C. for 30 minutes, the solvent was evaporated in vacuo to give an oily residue, which was purified by flash chromatography (petroleum ether/ethyl acetate=9:1) to yield the title compound (2.43 g, 12.33 mmol, 90%) as a yellow solid.

mp: 91-92° C.

$^1$H NMR (400 MHz, CDCl$_3$) δ 10.49 (s, 1H$_{OH}$), 8.17 (d, J=8.8 Hz, 1H), 7.83 (d, J=1.8 Hz, 1H), 7.61 (dd, J=8.8, 1.8 Hz, 1H), 3.96 (s, 3H) ppm.

$^{13}$C NMR (100 MHz, CDCl$_3$) δ 165.0, 154.8, 138.1, 125.4, 121.8, 120.74, 53.1 ppm.

HRMS (ESI): Calculated for C$_8$H$_6$NO$_5$ (M-H)$^-$: 196.0246, found: 196.0249.

3-Isopropoxy-4-nitromethylbenzoate

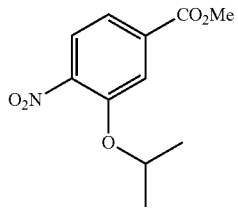 [SMILES: COC(=O)c1ccc([N+](=O)[O-])c(OC(C)C)c1]

3-Hydroxy-4-nitromethylbenzoate (2.30 g, 10.89 mmol) was dissolved in THF (100 mL). $^i$PrOH (1.10 mL, 14.16 mmol) and PPh$_3$ (3.90 g, 14.70 mmol) were added, and the mixture was stirred until all components were dissolved. DEAD (2.2 M in toluene, 14.16 mmol, 6.50 mL) was added and the mixture was stirred at room temperature 17 hours. The solvent was evaporated in vacuo to give an oily residue, which was purified by flash chromatography (petroleum ether/ethyl acetate=95:5) to yield the title compound (2.61 g, 10.91 mmol, quantitative) as a yellow oil.

$^1$H NMR (400 MHz, CDCl$_3$) δ 7.75 (d, J=8.4 Hz, 2H), 7.64 (dd, J=8.3, 1.6 Hz, 1H), 4.77 (hept, J=6.1 Hz, 1H), 3.95 (s, 3H), 1.41 (s, 3H), 1.40 (s, 3H) ppm.

$^{13}$C NMR (100 MHz, CDCl$_3$) δ 165.5, 150.9, 134.6, 125.2, 121.2, 117.1, 73.2, 52.9, 21.9 ppm.

HRMS (Qtof): Calculated for C$_5$H$_6$NO$_5$ (M+Na)$^+$: 262.0691, found: 262.0700.

3-Isopropoxy-4-aminomethylbenzoate

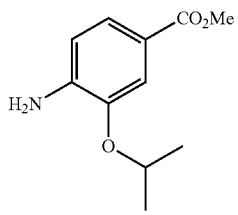

3-Isopropoxy-4-nitromethylbenzoate (2.60 g, 10.87 mmol) was dissolved in MeOH (91.0 mL) and degassed. Pd/C (10% wt., 0.58 g, 0.54 mmol) was added and vacuum was applied under cooling to remove air. The flask was flushed with H$_2$ and the suspension was stirred for 17 hours at room temperature. The catalyst was filtered over Celite®, washed with MeOH and the solvent was removed under reduced pressure. The crude product was purified by flash chromatography (petroleum ether/EtOAc=7/3). 3-Isopropoxy-4-aminomethylbenzoate was obtained (2.27 g, 10.85 mmol, quantitative) as a light orange solid.

mp: 55-57° C.

$^1$H NMR (400 MHz, CDCl$_3$) δ 7.51 (dd, J=8.2, 1.7 Hz, 1H), 7.46 (d, J=1.7 Hz, 1H), 6.66 (dd, J=8.2, 5.1 Hz, 1H), 4.63 (sept, J=5.1 Hz, 1H), 3.85 (s, 3H), 1.36 (s, 3H), 1.35 (s, 3H) ppm.

$^{13}$C NMR (100 MHz, CDCl$_3$) δ 167.5, 144.24, 142.3, 124.0, 119.5, 114.1, 113.5, 70.9, 51.8, 22.3 ppm.

HRMS (ESI): Calculated for C$_{11}$H$_{16}$NO$_3$ (M+H)$^+$: 210.1130, found: 210.1126.

6-Bromo-2,3-dihydroxybenzaldehyde

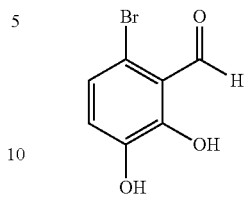

To a solution of 6-bromo-2-hydroxy-3-methoxybenzaldehyde (25.0 g, 108.2 mmol) in CH$_2$Cl$_2$ (270 mL) at −30° C. was slowly added BBr$_3$ (1 M in CH$_2$Cl$_2$, 200.0 mL, 200.0 mmol) via additional funnel over a period of 45 minutes. The solution was allowed to warm to room temperature and stirred 17 hours. H$_2$O was added and the reaction mixture was stirred for additional 30 minutes. The solution was then extracted with EtOAc (3×) and washed with H$_2$O. The combined, organic layers were dried over anhydrous MgSO$_4$, filtered and concentrated in vacuo to give the title compound (22.16 g, 102.11 mmol, 95%) as a yellow solid.

mp: 135-136° C.

$^1$H NMR (400 MHz, CDCl$_3$) δ 12.13 (d, J=0.5 Hz, 1H$_{OH}$), 10.27 (s, 1H$_{CHO}$), 7.07 (d, J=8.5 Hz, 1H), 7.02 (dd, J=8.5, 0.5 Hz, 1H), 5.67 (s, 1H$_{OH}$) ppm.

$^{13}$C NMR (100 MHz, CDCl$_3$) δ 198.4, 151.2, 145.0, 124.4, 122.0, 117.5, 116.1 ppm.

HRMS (ESI): Calculated for C$_7$H$_4$BrO$_3$ (M−H)$^-$: 214.3943, found: 214.9344.

4-Bromo-3-hydroxymethylbenzene-1,2-diol

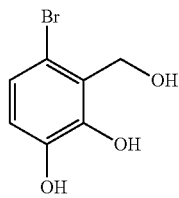 [SMILES: OCc1c(Br)ccc(O)c1O]

A solution of 6-bromo-2,3-dihydroxybenzaldehyde (22.16 g, 102.10 mmol) in THF (650 mL) at −40° C. was treated with NaBH$_4$ (3.86 g, 102.10 mmol) portion wise (3×).

The resulting mixture was stirred for 30 minutes at room temperature. A saturated aqueous solution of NH$_4$Cl was added and the mixture was stirred for another 10 minutes, before being finally treated with 1M HCl. After 10 minutes of additional stirring, the aqueous phase was extracted with EtOAc (3×). The combined, organic extracts were dried over anhydrous MgSO$_4$ and filtered. The solvent was removed under reduced pressure to yield the title compound (20.27 g, 92.53 mmol, 91%) as a colorless solid.

mp: 90-92° C.

$^1$H NMR (400 MHz, MeOD) δ 6.88 (d, J=8.5 Hz, 1H), 6.64 (d, J=8.5 Hz, 1H), 4.82 (s, 2H) ppm.

$^{13}$C NMR (100 MHz, MeOD) δ 147.1, 146.1, 126.9, 123.9, 116.6, 114.4, 61.1 ppm.

HRMS (ESI): Calculated for C$_7$H$_6$BrO$_3$ (M−H)$^-$: 216.9500, found: 216.9505.

5-Bromo-2-phenyl-4H-benzo-[1,3]-dioxin-8-ol

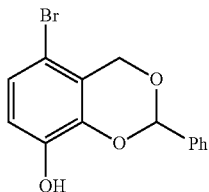 [SMILES: Oc1ccc(Br)c2c1OC(c1ccccc1)OC2]

A solution of 4-bromo-3-hydroxymethylbenzene-1,2-diol (20.27 g, 92.53 mmol) in THF (550 mL) was treated with PhCH(OMe)$_2$ (20.8 mL, 138.8 mmol) and pTSA.H$_2$O (0.19 g, 1.02 mmol). The mixture was stirred at room temperature for 5 days. CH$_2$Cl$_2$ was added and then washed successively with 5% aqueous NaHCO$_3$ and brine. The aqueous phase was extracted with EtOAc (3×). The combined, organic extracts were dried over anhydrous MgSO$_4$, filtered and the solvent was removed under reduced pressure. Purification by flash chromatography (petroleum ether/EtOAc=95/5) afforded 5-bromo-2-phenyl-4H-benzo-[1,3]-dioxin-8-ol (16.02 g, 52.16 mmol, 56%) as a colorless solid.

mp: 89-91° C.

$^1$H NMR (400 MHz, CDCl$_3$) δ 7.62-7.55 (m, 2H), 7.50-7.43 (m, 3H), 7.07 (d, J=8.6 Hz, 1H), 6.78 (d, J=8.6 Hz, 1H), 5.97 (s, 1H), 5.40 (s, 1H$_{-OH}$), 4.99 (s, 2H) ppm.

$^{13}$C NMR (100 MHz, CDCl$_3$) δ 144.0, 141.8, 136.1, 130.1, 128.8, 126.7, 124.9, 121.0, 115.0, 109.4, 100.0, 67.8 ppm.

HRMS (ESI): Calculated for C$_{14}$H$_{10}$BrO$_3$ (M−H)$^-$: 304.9813, found: 304.9813.

5-Bromo-7-nitro-2-phenyl-4H-benzo-[1,3]-dioxin-8-ol

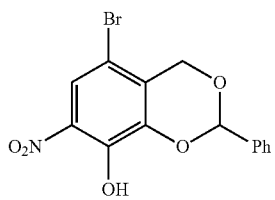 [SMILES: O=[N+]([O-])c1cc(Br)c2c(c1O)OC(c1ccccc1)OC2]

5-Bromo-2-phenyl-4H-benzo-[1,3]-dioxin-8-ol (6.00 g, 19.54 mmol; max. amount) was dissolved in acetone (250 mL). Then, Ni(NO$_3$)$_2$.5H$_2$O (5.68 g, 19.54 mmol) and pTSA.H$_2$O (3.72 g, 19.54 mmol) were added. The mixture was stirred at room temperature for 2.5 h. The reaction mixture was filtered over Celite®, washed with CH$_2$Cl$_2$ and concentrated in vacuo. Purification by flash chromatography (dry load: SiO$_2$+CH$_2$Cl$_2$; petroleum ether/ethyl acetate=9:1) yielded the title compound (5.08 g, 14.43 mmol, 74%) as a bright yellow solid.

mp: 154-156° C.

$^1$H NMR (400 MHz, CDCl$_3$) δ 10.60 (s, 1H$_{-OH}$), 7.96 (s, 1H), 7.65-7.57 (m, 2H), 7.48-7.42 (m, 3H), 6.02 (s, 1H), 4.99 (s, 2H) ppm.

$^{13}$C NMR (100 MHz, CDCl$_3$) δ 144.9, 135.5, 133.2, 130.2, 129.0, 128.9, 126.7, 119.2, 109.2, 99.9, 67.4 ppm.

HRMS (ESI): Calculated for C$_{14}$H$_9$BrNO$_5$ (M−H)$^-$: 359.9664, found: 349.9660.

5-Bromo-8-isopropoxy-7-nitro-2-phenyl-4H-benzo-[1,3]-dioxine

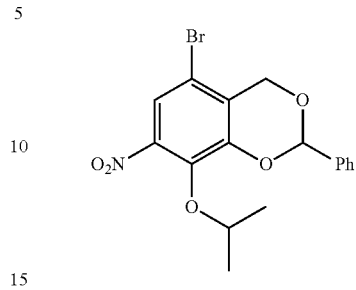

5-Bromo-7-nitro-2-phenyl-4H-benzo-[1,3]-dioxin-8-ol (13.79 g, 39.16 mmol) was dissolved in THF (429 mL). iPrOH (4.00 mL, 50.91 mmol) and PPh$_3$ (13.87 g, 52.87 mmol) were added, and the mixture was stirred until all components were dissolved. DEAD (2.2 M in toluene, 23.1 mL, 50.91 mmol) was slowly added (via syringe pump) and the mixture was stirred at room temperature 17 hours. The solvent was evaporated in vacuo to give an oily residue, which was purified by flash chromatography (petroleum ether/ethyl acetate=96:4) to yield the title compound (13.08 g, 33.18 mmol, 85%) as a colorless solid.

mp: 87-89° C.

$^1$H NMR (400 MHz, CDCl$_3$) δ 7.59 (s, 1H), 7.59-7.54 (m, 2H), 7.50-7.43 (m, 3H), 5.97 (s, 1H), 5.00 (s, 2H), 4.69 (hept, J=6.2 Hz, 1H), 1.31 (d, J=6.2 Hz, 3H), 1.28 (d, J=6.2 Hz, 3H) ppm.

$^{13}$C NMR (100 MHz, CDCl$_3$) δ 216.8, 149.0, 144.5, 139.9, 135.7, 130.1, 128.8, 126.4, 126.2, 119.8, 112.7, 99.7, 78.1, 67.6, 22.6, 22.4 ppm.

HRMS (Qtof): Calculated for C$_{14}$H$_9$BrNO$_5$ (M+Na)$^+$: 416.0110, found: 416.0101.

8-Isopropoxy-7-nitro-2-phenyl-4H-benzo-[1,3]-dioxine, 73

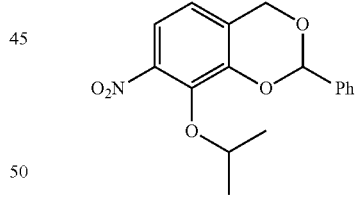

5-Bromo-8-isopropoxy-7-nitro-2-phenyl-4H-benzo-[1,3]-dioxine 72 (4.00 g, 10.15 mmol), Pd$_2$(dba)$_3$ (0.93 g, 1.01 mmol), (PhO)$_3$P (0.53 mL, 2.03 mmol), Cs$_2$CO$_3$ (4.30 g, 13.19 mmol) and $^i$PrOH (4.7 mL, 60.88 mmol) were dissolved in 1,4-dioxane (28 mL). The oil bath was preheated to 60° C. and the mixture was stirred at 80° C. for 1.5 hours. The reaction mixture was filtered through Celite® and washed with EtOAc. The combined, organic extracts were dried over anhydrous MgSO$_4$ and concentrated in vacuo. The crude material was purified by flash chromatography (petroleum ether/ethyl acetate=96:4) to yield the title compound (2.24 g, 7.10 mmol, 70%) as a pale yellow solid.

mp: 80-82° C.

$^1$H NMR (400 MHz, CDCl$_3$) δ 7.65-7.55 (m, 2H), 7.51-7.41 (m, 3H), 7.37 (d, J=8.5 Hz, 1H), 6.81 (d, J=8.5 Hz, 1H), 6.01 (s, 1H), 5.19 (d, J=15.5 Hz, 1H), 5.03 (d, J=15.5 Hz, 1H), 4.71 (hept, J=6.2 Hz, 1H), 1.32 (d, J=6.2 Hz, 3H), 1.28 (d, J=6.2 Hz, 3H) ppm.

$^{13}$C NMR (100 MHz, CDCl$_3$) δ 147.67, 144.27, 140.55, 136.26, 129.85, 128.72, 126.54, 126.34, 118.82, 116.69, 99.61, 77.71, 66.44, 22.65, 22.41 ppm.

HRMS (QTof): Calculated for C$_{17}$H$_{17}$NO$_5$Na (M+Na)$^+$: 338.1004. Found: 338.1003.

6-Hydroxymethyl-2-isopropoxy-3-nitrophenol

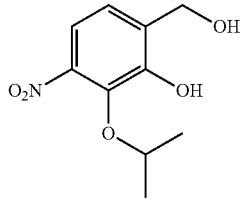 [SMILES: CC(C)Oc1c([N+](=O)[O-])ccc(CO)c1O]

To a mixture of 8-isopropoxy-7-nitro-2-phenyl-4H-benzo-[1,3]-dioxine (4.24 g, 13.43 mmol) in MeOH (102 mL) and CH$_2$Cl$_2$ (42 mL) at 0° C. was added camphor sulfonic acid (3.12 g, 13.43 mmol). The mixture was stirred at room temperature for 17 hours. The reaction mixture was quenched with Et$_3$N until pH-8, concentrated in vacuo and purified by flash chromatography (petroleum ether/ethyl acetate=7:3) to yield the title compound (2.75 g, 12.09 mmol, 90%) as a brownish solid.

mp: 39-41° C.

$^1$H NMR (400 MHz, CDCl$_3$) δ 7.46 (d, J=7.4 Hz, 1H), 7.12 (d, J=7.4 Hz, 1H), 6.61 (s, 1H$_{OH}$), 4.81 (d, J=3.5 Hz, 2H), 4.39 (hept, J=7.4 Hz, 1H), 1.36 (s, 3H), 1.35 (s, 3H) ppm.

$^{13}$C NMR (100 MHz, CDCl$_3$) δ 148.9, 138.5, 132.4, 122.1, 116.5, 79.2, 61.3, 22.5 ppm.

HRMS (ESI): Calculated for C$_{10}$H$_{12}$NO$_5$ (M−H)$^-$: 226.0715, found: 226.0717.

2-Hydroxy-3-isopropoxy-4-nitrobenzaldehyde

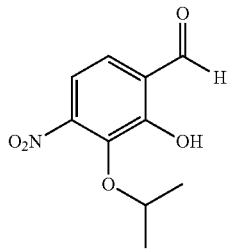 [SMILES: CC(C)Oc1c([N+](=O)[O-])ccc(C=O)c1O]

6-Hydroxymethyl-2-isopropoxy-3-nitrophenol (2.97 g, 13.05 mmol) was dissolved in CH$_2$Cl$_2$ (58 mL). Then MnO$_2$ (11.35 g, 130.53 mmol) was added and the mixture was stirred at rt 17 h. The mixture was filtered over Celite® and washed with CH$_2$Cl$_2$. The solvent was concentrated to give the title compound (2.38 g, 10.57 mmol, 81%) as a brown oil.

$^1$H NMR (400 MHz, CDCl$_3$) δ 11.44 (s, 1H$_{CHO}$), 9.97 (s, 1H$_{OH}$), 7.39 (d, J=8.4 Hz, 1H), 7.23 (d, J=8.4 Hz, 1H), 4.88 (hept, J=6.2 Hz, 1H), 1.33 (s, 3H), 1.32 (s, 3H) ppm.

$^{13}$C NMR (100 MHz, CDCl$_3$) δ 196.39, 156.53, 149.36, 139.74, 127.28, 122.57, 114.32, 77.42, 77.16, 22.51. ppm.

HRMS (ESI): Calculated for C$_{10}$H$_{10}$NO$_5$ (M−H)$^-$: 224.0559. Found: 224.0535.

2-Hydroxy-3-isopropoxy-4-nitrobenzoic acid

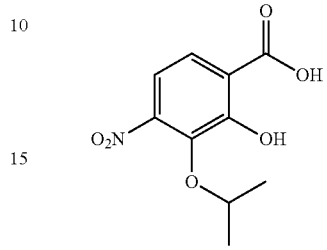

2-Hydroxy-3-isopropoxy-4-nitrobenzaldehyde (2.36 g, 10.49 mmol) was dissolved in tert-buthanol (71 mL). 2-Methyl-2-butene (2M in THF, 36.7 mL, 73.45 mmol) and a solution of NaClO$_2$ (2.85 g, 31.48 mmol) and NaH$_2$PO$_4$ (6.32 g, 47.22 mmol) in H$_2$O (51 mL) were added in sequential order. The reaction mixture was stirred at room temperature for 17 hours. 6M NaOH was added until ph-10 and the solvent was concentrated in vacuo. H$_2$O was added and the organic layer was extracted with petroleum ether (2×). The aqueous layer was acidified with 6M HCl until pH- and extracted with ethyl acetate (3×). The organic extracts were combined, dried over MgSO$_4$ and filtered. The solvent was concentrated in vacuo to yield the title compound (1.90 g, 7.87 mmol, 75%) as a dark wax.

$^1$H NMR (400 MHz, MeOD) δ 7.72 (d, J=8.7 Hz, 1H), 7.15 (d, J=8.7 Hz, 1H), 4.86-4.82 (m, 1H), 1.28 (s, 3H), 1.26 (s, 3H) ppm.

$^{13}$C NMR (100 MHz, MeOD) δ 172.7, 158.0, 140.0, 125.8, 117.4, 113.8, 77.5, 22.6 ppm.

HRMS (ESI): Calculated for C$_{10}$H$_{10}$NO$_6$ (M−H)$^-$: 240.0508, found: 240.0510.

2-Hydroxy-3-isopropoxy-4-nitro benzoate

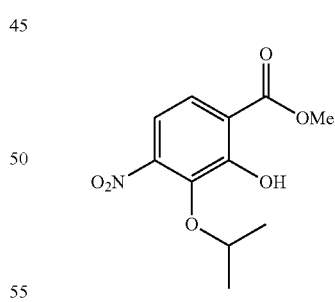

TMSCHN$_2$ (2.0 M in Et$_2$O, 0.87 mL, 1.75 mmol) was added to a solution of 2-hydroxy-3-isopropoxy-4-nitrobenzoic acid (0.32 g, 1.35 mmol) in a mixture of toluene/methanol (10.4/2 mL) at 0° C. After stirring at 0° C. for 30 minutes, the solvent was evaporated in vacuo to give an oily residue, which was purified by flash chromatography (SiO$_2$.Et$_3$N; petroleum ether/ethyl acetate=95:5) to yield the title compound (0.24 g, 0.94 mmol, 57%) as a yellow oil.

$^1$H NMR (400 MHz, CDCl$_3$) δ 11.29 (s, 1H$_{OH}$), 7.63 (d, J=8.8 Hz, 1H), 7.12 (d, J=8.8 Hz, 1H), 4.84 (hept, J=6.2 Hz, 1H), 4.00 (s, 3H), 1.32 (s, 3H), 1.31 (s, 3H) ppm.

$^{13}$C NMR (100 MHz, CDCl$_3$) δ 198.2, 188.9, 176.1, 170.0, 157.0, 149.2, 139.8, 123.9, 115.7, 113.4, 77.4, 53.2, 22.5 ppm.

HRMS (ESI): Calculated for C$_{11}$H$_{12}$NO$_6$ (M−H)$^−$: 254.0665, found: 254.0666.

2-Benzyloxy-3-isopropoxy-4-nitrobenzoate

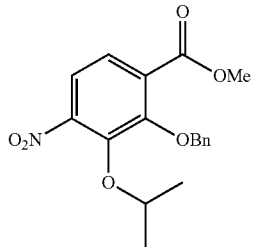 [SMILES: COC(=O)c1ccc([N+](=O)[O-])c(OC(C)C)c1OCc1ccccc1]

2-Hydroxy-3-isopropoxy-4-nitrobenzoate (0.17 g, 0.69 mmol) was dissolved in THF (7.5 mL). BnOH (92.6 µL, 0.89 mmol) and PPh$_3$ (0.24 g, 0.93 mmol) were added, and the mixture was stirred until all components are dissolved. DEAD (2.2 M in toluene, 0.41 mL, 0.89 mmol) was slowly added (via syringe pump) and the mixture was stirred at room temperature 17 hours. The solvent was evaporated in vacuo to give an oily residue, which was purified by flash chromatography (petroleum ether/ethyl acetate=95:5) to yield the title compound (0.20 g, 0.58 mmol, 85%) as a colorless oil.

$^1$H NMR (400 MHz, CDCl$_3$) δ 7.53 (d, J=8.6 Hz, 1H), 7.50 (d, J=8.6 Hz, 1H), 7.48-7.44 (m, 2H), 7.42-7.35 (m, 3H), 5.14 (s, 2H), 4.74 (hept, J=6.2 Hz, 1H), 3.86 (s, 3H), 1.28 (s, 3H), 1.26 (s, 3H) ppm.

$^{13}$C NMR (100 MHz, CDCl$_3$) δ 165.3, 153.4, 148.4, 145.7, 136.4, 130.9, 128.7, 128.7, 128.7, 125.1, 119.3, 78.2, 76.4, 52.8, 22.5 ppm.

HRMS (QTof): Calculated for C$_{18}$H$_{19}$NO$_6$Na (M+Na)$^+$: 368.1110, found: 368.1112.

2-Benzyloxy-3-isopropoxy-4-nitrobenzoic acid

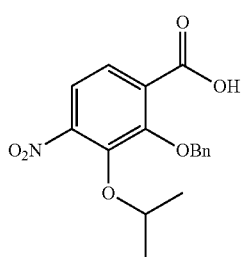 [SMILES: CC(C)Oc1c([N+](=O)[O-])ccc(C(=O)O)c1OCc1ccccc1]

2-Benzyloxy-3-isopropoxy-4-nitrobenzoate (0.23 g, 0.67 mmol) was dissolved in a mixture 1/1 of THF/H$_2$O (3.5/3.5 mL). Then, solid LiOH (0.16 g, 6.67 mmol) was added and the reaction mixture was stirred at room temperature for 17 hours. The aqueous layer was acidified with 1M HCl until pH-1 and extracted with EtOAc (3×). The organic extracts were combined, dried over anhydrous MgSO$_4$ and filtered. The solvent was concentrated in vacuo to yield the title compound (0.21 g, 0.63 mmol, 95%) as a yellow wax.

$^1$H NMR (400 MHz, CDCl$_3$) δ 7.91 (d, J=8.7 Hz, 1H), 7.58 (d, J=8.7 Hz, 1H), 7.41 (s, 5H), 5.35 (s, 2H), 4.71-4.62 (m, 1H), 1.36 (s, 3H), 1.35 (s, 3H) ppm.

$^{13}$C NMR (100 MHz, CDCl$_3$) δ 164.3, 152.8, 149.7, 144.7, 134.1, 129.8, 129.4, 129.2, 126.98, 120.0, 79.1, 77.7, 22.5 ppm.

HRMS (ESI): Calculated for C$_{17}$H$_{16}$NO$_6$ (M−H)$^−$: 330.0978, found: 330.0976.

4-(2-(Benzyloxy)-3-isopropoxy-4-nitrobenzamido)-3-isopropoxybenzoate

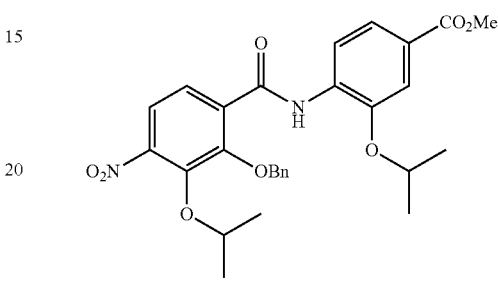

2-Benzyloxy-3-isopropoxy-4-nitrobenzoic acid (51.5 mg, 0.16 mmol) was dissolved in CH$_2$Cl$_2$ (8 mL) and preactivated with Ghosez's reagent (66.0 µL, 0.50 mmol) for 3 hours at 40° C. 3-Isopropoxy-4-aminomethylbenzoate (0.12 g, 0.55 mmol) was dissolved in CH$_2$Cl$_2$ (8 mL) and N,N-diisopropylethylamine (DIPEA) was added (0.20 mL, 1.12 mmol). The solution containing the acid chloride was then added and the reaction mixture stirred for 2 days at 40° C. The solvent was then removed and the crude product was purified by preparative HPLC (RP-18; run time 100 min; H$_2$O/MeCN=100:0→0:100; tr=80 min) providing the title compound (56.9 mg, 0.11 mmol, 68%) as a light yellow oil.

$^1$H NMR (400 MHz, CDCl$_3$) δ 10.33 (s, 1H$_{—NH}$), 8.55 (d, J=8.5 Hz, 1H), 7.85 (d, J=8.7 Hz, 1H), 7.70 (dd, J=8.5, 1.7 Hz, 1H), 7.59 (d, J=8.7 Hz, 1H), 7.57 (d, J=1.7 Hz, 1H), 7.25-7.12 (m, 5H), 5.25 (s, 2H), 4.75-4.67 (m, 1H), 4.67-4.59 (m, 1H), 3.93 (s, 3H), 1.40 (d, J=6.2 Hz, 6H), 1.28 (d, J=6.0 Hz, 6H) ppm.

$^{13}$C NMR (100 MHz, CDCl$_3$) δ 167.0, 161.4, 151.1, 147.9, 146.1, 145.2, 134.1, 132.9, 132.9, 130.0, 129.4, 128.7, 125.79, 125.6, 123.3, 120.1, 119.5, 113.3, 78.9, 77.4, 71.7, 52.3, 22.6, 22.1 ppm.

HRMS (ESI): Calculated for C$_{28}$H$_{31}$N$_2$O$_8$ (M+H)$^+$: 523.2080, found: 523.2075.

4-(4-Amino-2-hydroxy-3-isopropoxybenzamido)-3-isopropoxybenzoate

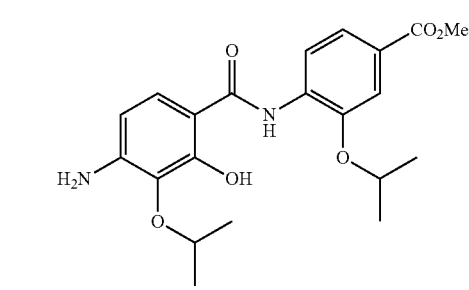 [SMILES: COC(=O)c1ccc(NC(=O)c2ccc([N+](=O)[O-])c(OC(C)C)c2OCc2ccccc2)c(OC(C)C)c1]

4-[2-(Benzyloxy)-3-isopropoxy-4-nitrobenzamido]-3-isopropoxy-benzoate (7.9 mg, 0.015 mmol) was dissolved in MeOH (0.5 mL) and degassed. Pd/C (10% wt., 2 mg, 0.0014 mmol) was added and vacuum was applied under cooling to remove air. The flask was flushed with H₂ and the suspension was stirred for 3 hours at room temperature. The catalyst was filtered off over Celite®, washed with MeOH and the solvent was removed under reduced pressure. The crude product was purified by flash chromatography (petroleum ether/ethyl acetate=7:3) and the title compound was obtained (5.8 g, 0.014 mmol, 96%) as a yellow oil.

¹H NMR (400 MHz, CDCl₃) δ 12.21 (s, 1H_OH), 8.81 (s, 1H_NH), 8.49 (d, J=8.5 Hz, 1H), 7.69 (dd, J=8.5, 1.8 Hz, 1H), 7.58 (d, J=1.7 Hz, 1H), 7.07 (d, J=8.8 Hz, 1H), 6.28 (d, J=8.7 Hz, 1H), 4.80-4.72 (m, 1H), 4.72-4.63 (m, 1H), 4.28 (s, 2H_NH2), 3.91 (s, 3H), 1.44 (d, J=6.1 Hz, 6H), 1.34 (d, J=6.2 Hz, 7H) ppm.

¹³C NMR (100 MHz, CDCl₃) δ 168.5, 166.9, 156.4, 146.5, 146.0, 132.7, 132.0, 125.1, 123.40, 121.5, 119.1, 113.4, 106.5, 106.3, 77.4, 74.4, 72.0, 52.3, 22.9, 22.4 ppm.

HRMS (ESI): Calculated for C₂₁H₂₅N₂O₆ (M−H)⁻: 401.1713, found: 401.1716.

4-(tert-butoxycarbonylamino)benzoic acid

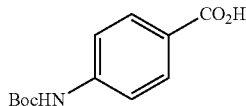

4-Aminobenzoic acid (1.00 g, 7.29 mmol) was dissolved in 1,4-dioxane (15 mL) and H₂O (7 mL). Et₃N (2.0 mL, 14.58 mmol) was added to the solution and the reaction mixture was stirred for 5 minutes at room temperature. Di-tert-butyl dicarbonate (3.18 g, 14.58 m mol) was then added to the solution in one portion and the reaction mixture was stirred for 24 hours. Following removal of the solvent in vacuo, 3M HCl was added to the residue yielding a white precipitate. The slurry was then filtered and washed with H₂O before drying in under high vacuum. Recrystallization from hot methanol yielded the titled compound as a colorless solid (1.63 g, 6.85 mmol, 94% yield).

mp: 192-194° C.

¹H NMR (400 MHz, DMSO) δ 9.73 (s, 1H_CO2H), 7.83 (d, 2H, J=8.9 Hz), 7.55 (d, 2H, J=8.9 Hz), 1.47 (s, 9H) ppm.

¹³C NMR (100 MHz, CDCl₃) δ 167.1, 152.6, 143.8, 130.4, 124.0, 117.2, 79.7, 28.1 ppm.

HRMS (ESI): Calculated for C₁₂H₁₅NnaO₄ (M+Na)⁺: 260.0893, found: 260.0897.

The spectroscopic data are in accordance with those reported in the literature (*J. Am. Chem. Soc.* 2012, 134, 7406-7413).

Methyl-4-(4-(4-(tert-butoxycarbonyl)amino)benzamido)-2-hydroxy-3-isopropxybenzamido)-3-isopropoxybenzoate

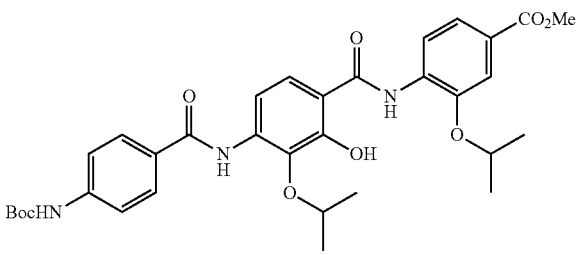 [SMILES: COC(=O)c1ccc(NC(=O)c2ccc(NC(=O)c3ccc(NC(=O)OC(C)(C)C)cc3)c(OC(C)C)c2O)c(OC(C)C)c1]

4-(Tert-butoxycarbonylamino)benzoic acid (40.0 mg, 0.17 mmol) was dissolved in CH₂Cl₂ (8.4 mL) and preactivated with Ghosez's reagent (22.5 µL, 0.17 mmol) for 2 hours at room temperature. 4-(4-Amino-2-hydroxy-3-isopropoxybenzamido)-3-isopropoxybenzoate (68.4 mg, 0.17 mmol) was dissolved in CH₂Cl₂ (8.4 mL) and N,N-diisopropylethylamine (DIPEA) was added (59.2 µL, 0.34 mmol). The solution containing the acid chloride was then added and the reaction mixture stirred for 1 day at room temperature. The solvent was then removed and the crude product was purified by preparative HPLC (RP-18; run time 100 min; H₂O/MeCN=100:0→0:100; tr=70 min) providing the title compound as a light yellow oil (47.3 mg, 0.076 mmol, 72%).

¹H NMR (400 MHz, CDCl₃) δ 7.98 (d, J=7.5 Hz, 2H), 7.78 (d, J=1.4 Hz, 1H), 7.72 (dd, J=7.5, 1.4 Hz, 1H), 7.69 (s, 1H_NH), 7.68 (d, J=7.3 Hz, 3H), 7.56 (d, J=7.5 Hz, 1H), 7.17 (d, J=7.5 Hz, 1H), 5.72 (s, 1H_NH), 5.49 (s, 1H_NH), 4.02-3.96 (m, 2H), 3.95 (d, J=3.7 Hz, 3H), 1.49 (s, 9H), 1.46 (d, J=5.6 Hz, 6H), 1.41 (d, J=5.5 Hz, 6H) ppm.

¹³C NMR (100 MHz, CDCl₃) δ 166.89, 166.67, 166.61, 158.88, 154.93, 146.90, 141.47, 135.07, 134.68, 131.70, 130.38, 130.38, 127.26, 127.17, 123.25, 121.40, 120.63, 120.63, 115.87, 114.85, 113.39, 106.06, 80.65, 75.89, 74.13, 52.08, 28.41, 28.41, 28.41, 21.80, 21.80, 21.80, 21.80 ppm.

HRMS (ESI): Calculated for C₃₃H₃₈N₃O₉ (M−H)⁻: 620.2687, found: 620.2689.

Methyl-4-(4-(4-aminobenzamido)-2-hydroxy-3-isopropxybenzamido)-3-isopropoxybenzoate

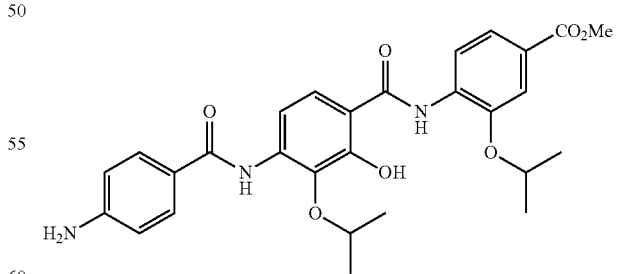

Methyl-4-(4-(4-(tert-butoxycarbonyl)amino)benzamido)-2-hydroxy-3-isopropxybenzamido)-3-isopropoxybenzoate (40.0 mg, 0.064 mmol) was dissolved in a mixture 10/1 dichloromethane/trifluoroacetic acid (1 mL) and stirred 17 hours at room temperature. The solvent was removed under reduced pressure and the residual acid was removed under high vacuum to give the titled compound (33.4 mg, 0.064 mmol, quantitative) as yellow oil.

$^1$H NMR (400 MHz, CDCl$_3$) δ 7.86 (d, J=1.4 Hz, 1H), 7.83 (s, 1H$_{-NH}$), 7.79 (dd, J=7.5, 1.4 Hz, 1H), 7.75 (d, J=7.5 Hz, 1H), 7.70 (d, J=7.5 Hz, 2H), 7.65 (d, J=7.5 Hz, 1H), 7.05 (d, J=7.5 Hz, 1H), 6.94 (s, 1H$_{-NH}$), 6.75 (d, J=7.5 Hz, 2H), 6.09 (s, 1H$_{-OH}$), 4.02-3.97 (m, 1H), 3.95-3.89 (s, 3H), 3.92 (m, 1H), 3.85 (s, 2H$_{-NH}$), 1.47 (d, J=5.7 Hz, 6H), 1.40 (d, J=5.5 Hz, 6H) ppm.

$^{13}$C NMR (100 MHz, CDCl$_3$) δ 166.89, 166.67, 166.61, 158.88, 152.59, 146.90, 135.07, 134.68, 131.70, 130.93, 130.93, 127.17, 123.25, 122.42, 121.40, 115.87, 114.85, 114.35, 114.35, 113.39, 106.06, 75.89, 74.13, 52.08, 21.80, 21.80, 21.80, 21.80 ppm.

HRMS (ESI): Calculated for C$_{28}$H$_{32}$N$_3$O$_7$ (M+H)$^+$: 522.2162, found: 522.2160.

Cystobactamide C

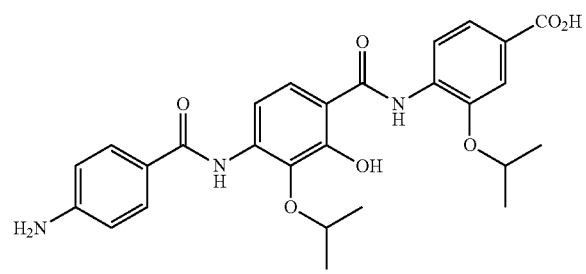 [SMILES: CC(C)Oc1cc(C(=O)O)ccc1NC(=O)c1ccc(NC(=O)c2ccc(N)cc2)c(OC(C)C)c1O]

Methyl-4-[4-(4-aminobenzamido)-2-hydroxy-3-isopropxybenzamido]-3-isopropoxybenzoate (30.0 mg, 0.058 mmol) was dissolved in a mixture 1/1 of THF/H$_2$O (0.3/0.3 mL). Then, solid LiOH (13.9 mg, 0.58 mmol) was added and the reaction mixture was stirred at room temperature for 17 hours. The aqueous layer was acidified with 1M HCl until pH- and extracted with ethyl acetate (3×). The organic extracts were combined, dried over anhydrous MgSO$_4$ and filtered. The solvent was concentrated in vacuo to yield the title compound (27.4 mg, 0.054 mmol, 93%) as a yellow oil.

$^1$H NMR (400 MHz, CDCl$_3$) δ 7.91 (d, J=1.4 Hz, 1H), 7.87 (dd, J=7.5, 1.4 Hz, 1H), 7.70 (d, J=7.5 Hz, 2H), 7.65 (d, J=7.5 Hz, 1H), 7.53 (d, J=7.5 Hz, 1H), 7.05 (d, J=7.5 Hz, 1H), 6.95 (s, 1H$_{-NH}$), 6.77 (s, 1H$_{-NH}$), 6.75 (d, J=7.5 Hz, 2H), 6.12 (s, 1H$_{-OH}$), 3.97-3.89 (m, 2H), 3.85 (s, 2H$_{-NH}$), 1.40 (d, J=5.5 Hz, 6H), 1.39 (d, J=5.5 Hz, 6H) ppm.

$^{13}$C NMR (100 MHz, CDCl$_3$) δ 167.79, 166.67, 166.61, 158.88, 152.59, 149.81, 136.38, 135.07, 134.68, 130.93, 130.93, 125.08, 123.25, 122.80, 122.42, 120.37, 114.35, 114.35, 113.76, 113.39, 106.06, 75.89, 74.13, 21.80, 21.80, 21.80, 21.80 ppm.

HRMS (ESI): Calculated for C$_{28}$H$_{32}$N$_3$O$_7$ (M+H)$^+$: 508.2006, found: 508.2008.

(2S,3R)-Methyl 2,3-dihydroxy-3-phenylpropanoate

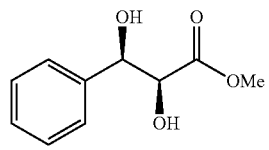 [SMILES: COC(=O)[C@@H](O)[C@H](O)c1ccccc1]

AD mix β (20.0 g) was dissolved in a mixture of tBuOH/H$_2$O (1:1; 142 mL) at 25° C. Afterwards, CH$_3$SO$_2$NH$_2$ (1.36 g, 14.3 mmol, 1.0 eq.) was added and the reaction mixture cooled to 0° C. Then, methylcinnamate (2.31 g, 14.3 mmol, 1.0 eq.) was added and the resulting mixture was vigorously stirred for 16 h at 0° C. Stirring was continued for additional 6 h at 25° C. The reaction mixture was hydrolyzed by addition of an aqueous Na$_2$SO$_3$ solution (21.4 g, 170 mmol, 12.0 eq.) and stirring was continued for additional 2.5 h. The reaction mixture was diluted with ethyl acetate and the layers were separated. The aqueous layer was extracted with EtOAc (3×). The combined organic layers were washed with H$_2$O (1×) and dried over Na$_2$SO$_4$, filtered and concentrated under reduced pressure. Purification by flash chromatography (petroleum ether/ethyl acetate=1:1) afforded the desired diol (2.21 g, 11.3 mmol, 79%) as a colorless solid. The spectroscopic data are in accordance with those reported in the literature.

R$_f$=0.38 (PE/EtOAc 1:1); m.p.=84-85° C. (lit: m.p.=80-81° C.); [α]$_D^{20}$=−9.8° (c 1.28, CHCl$_3$) {lit.: [α]$_D^{26}$=−9.80 (c 1.07, CHCl$_3$)};

$^1$H-NMR (400 MHz, CDCl$_3$, CHCl$_3$=7.26 ppm): δ=7.42-7.29 (5H, m, ArH), 5.03 (1H, dd, J=2.7, 7.2 Hz, H-3), 4.38 (1H, dd, J=2.7, 6.0 Hz, H-2), 3.82 (3H, s, H-8), 3.12 (1H, d, J=6.0 Hz, OH-□), 2.76 (1H, d, J=7.2 Hz, OH-β) ppm;

$^{13}$C-NMR (100 MHz, CDCl$_3$, CHCl$_3$=77.16 ppm): δ=173.3 (q, C-1), 140.1 (q, C-4), 128.6 (2C, t, C-6), 128.3 (t, C-7), 126.3 (2C, t, C-5), 74.8 (t, C-2), 74.6 (t, C-3), 53.1 (p, C-8) ppm; HRMS (ESI): m/z calculated for C$_{10}$H$_{12}$O$_4$Na [M+Na]$^+$: 219.0633; found 219.0633.

(2R,3S)-Methyl 2-acetoxy-3-bromo-3-phenylpropanoate (3)

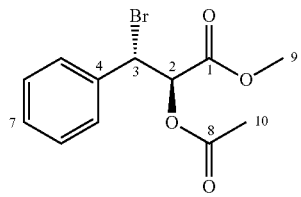 [SMILES: COC(=O)[C@@H](OC(C)=O)[C@@H](Br)c1ccccc1]

To (2S,3R)-Methyl 2,3-dihydroxy-3-phenylpropanoate (2.15 g, 10.9 mmol, 1.0 eq.) was added HBr/HOAc (33%; 16.9 mL) dropwise at 25° C. The resulting mixture was heated to 45° C. and stirred for 30 min. Then, the reaction mixture was cooled to 25° C. and poured into an ice-cooled NaHCO$_3$-solution (40 mL). The aqueous layer was extracted with Et$_2$O (3×). The combined organic layers were washed with H$_2$O (1×) and with brine. Then, the combined organic layers were dried over Na$_2$SO$_4$, filtered and concentrated under reduced pressure. Purification by flash chromatography (petroleum ether/ethyl acetate=12.5:1) gave the title compound (2.32 g, 7.71 mmol, 71%) as a colorless solid. The spectroscopic data are in accordance with those reported in the literature.

R$_f$=0.79 (PE/EtOAc 1:1); m.p.=78-82° C. (lit: m.p.=78-79° C.); [α]$_D^{20}$=+89.9° (c 1.74, CHCl$_3$) {Lit.: [α]$_D^{26}$=+100.3° (c 1.36, CHCl$_3$)};

$^1$H-NMR (400 MHz, CDCl$_3$, CHCl$_3$=7.26 ppm): δ=7.46-7.44 (2H, m, H-6), 7.36-7.30 (3H, m, H-5, H-7), 5.65 (1H, d, J=6.3 Hz, H-3), 5.35 (1H, d, J=6.3 Hz, H-2), 3.71 (3H, s, H-9), 2.11 (3H, s, H-10) ppm;

$^{13}$C-NMR (100 MHz, CDCl$_3$, CHCl$_3$=77.16 ppm): δ=169.7 (q, C-1), 167.5 (q, C-8), 136.8 (q, C-4), 129.3 (t, C-7), 128.7 (4C, t, C-5, C-6), 75.4 (t, C-3), 52.9 (p, C-9), 49.3 (t, C-2), 20.6 (p, C-10) ppm;

HRMS (ESI): m/z calculated for $C_{12}H_{13}O_4BrNa$ [M+Na]$^+$: 322.9895; found 322.9891.

(2S,3R)-Methyl 2-acetoxy-3-azido-3-phenylpropanoate

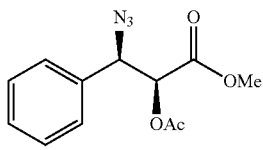 [SMILES: COC(=O)[C@@H](OC(C)=O)[C@H](N=[N+]=[N-])c1ccccc1]

(2S,3R)-Methyl 2-acetoxy-3-azido-3-phenylpropanoate (2.27 g, 7.55 mmol, 1.0 eq.) was dissolved in DMF (27.0 mL) at 25° C. Then, NaN$_3$ (1.96 g, 30.2 mmol, 4.0 eq.) was added and the resulting mixture was heated up to 40° C. for 3 h. After cooling the reaction mixture was cooled to 25° C. and EtOAc was added. The organic layer was washed with H$_2$O (2×), followed by brine (1×). The combined, organic phases were dried over Na$_2$SO$_4$, filtered and concentrated under reduced pressure. Purification by flash chromatography (petroleum ether/ethyl acetate=10:1) afforded the title compound (1.77 g, 6.71 mmol, 89%) as yellow oil. The spectroscopic data are in accordance with those reported in the literature.

$R_f$=0.24 (PE/EtOAc=10:1); $[\alpha]D_{20}$=−97.8° (c 2.3, CHCl$_3$); {lit.: $[\alpha]_D^{26}$=−104.2° (c 2.33, CHCl$_3$)};

IR: ν=2955 (w), 2103 (s, azide), 1747 (s, C=O), 1495 (w), 1454 (m), 1437 (m), 1373 (m), 1210 (s), 1099 (m), 1030 (m), 910 (m), 751 (m), 701 (s) cm$^{-1}$;

$^1$H-NMR (400 MHz, CDCl$_3$, CHCl$_3$=7.26 ppm): δ=7.42-7.33 (5H, m, ArH), 5.24 (1H, d, J=4.8 Hz, H-2), 5.07 (1H, d, J=4.8 Hz, H-3), 3.69 (3H, s, H-9), 2.14 (3H, s, H-10) ppm;

$^{13}$C-NMR (100 MHz, CDCl$_3$, CHCl$_3$=77.16 ppm): δ=169.9 (q, C-1), 168.0 (q, C-8), 134.6 (q, C-4), 129.3 (t, C-7), 129.0 (2C, t, C-6), 127.6 (2C, t, C-5), 74.9 (t, C-2), 65.4 (t, C-3), 52.8 (p, C-9), 20.5 (p, C-10) ppm;

HRMS (ESI): m/z calculated for $C_{12}H_{13}N_3O_4Na$ [M+Na]$^+$: 286.0804; found 286.0805.

(2S,3R)-Methyl 3-azido-2-methoxy-3-phenylpropanoate

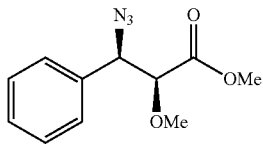 [SMILES: COC(=O)[C@@H](OC)[C@H](N=[N+]=[N-])c1ccccc1]

(2S,3R)-Methyl 2-acetoxy-3-azido-3-phenylpropanoate (2.5 g, 1.0 eq) was dissolved in 190 ml THF at 0° C. Then a solution of KOH (0.5M, 10.0 eq) was added dropwise and the reaction mixture was stirred at 0° C. for 5 h. Afterwards, aqueous 2N HCl was added to the reaction mixture and the aqueous phase was extracted with ethyl acetate. The organic phases were combined and dried over Na$_2$SO$_4$, filtered and concentrated under reduced pressure to afford the crude acid which was directly used for the next step without further purification. The crude material (0.5 g, 1.0 eq) was dissolved in 17 ml methyl iodide. Then, CaSO$_4$ (2.6 g, 8.0 eq) and Ag$_2$O (1.7 g, 3.0 eq) were added and stirring of the suspension was carried out in the dark at room temperature for 22 h. Then, the crude mixture was filtered and concentrated in vacuum to give the title compound (70% yield) which can be directly used in the next step without further purification.

$[\alpha]_D^{20}$=−143.7° (c 1.1, CHCl$_3$);

$^1$H-NMR (400 MHz, CDCl$_3$, CHCl$_3$=7.26 ppm): δ=3.44 (s, 3H), 3.61 (s, 3H), 3.94 (d, J=6.4 Hz, 1H), 4.79 (d, J=6.4 Hz, 1H), 7.35-7.36 (m, 5H);

$^{13}$C-NMR (100 MHz, CDCl$_3$, CHCl$_3$=77.0 ppm): δ=52.2, 59.1, 66.9, 84.7, 127.7, 128.7, 128.9, 135.1, 170.0;

HRMS (ESI): m/z calculated for $C_{11}H_{13}N_3O_3Na$ [M+Na]$^+$: 258.0855; found 258.0852.

(2S,3S)-tert-Butyl 3-azido-2-methoxy-3-phenylpropanoate

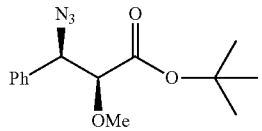 [SMILES: CO[C@H](C(=O)OC(C)(C)C)[C@H](N=[N+]=[N-])c1ccccc1]

To a stirred solution of (2S,3R)-Methyl 3-azido-2-methoxy-3-phenylpropanoate (1.2 g, 1.0 eq) in 100 ml THF was added an aqueous solution of KOH (0.5 M, 10.0 eq) dropwise. The reaction mixture was stirred for 5 h at rt and hydrolyzed by addition of 2N HCl. The aqueous phase was extracted with ethyl acetate and the combined organic phases were dried over Na$_2$SO$_4$ and concentrated under reduced pressure to give carboxylic acid (1.2 g, 98% yield) which was subjected to the next reaction without further purification. Crude acid (0.3 g, 1.0 eq) and 3.9 ml dimethylformamide di-tert-butyl acetal (3.9 ml, 12 eq) were dissolved in 8 ml toluene at room temperature. The resulting reaction mixture was heated up to 80° C. and stirred for 7 h. The solvent was removed under reduced pressure and the crude product was purified by flash column chromatography (petroleum ether/ethyl acetate=30:1) to afford the title compound (0.34 g, 89% yield).

$[\alpha]_D^{20}$=−113.3° (c 1.0, CHCl$_3$);

$^1$H-NMR (400 MHz, CDCl$_3$, CHCl$_3$=7.26 ppm): δ=1.26 (s, 9H), 3.45 (s, 3H), 3.85 (d, J=7.2 Hz, 1H), 4.70 (d, J=7.2 Hz, 1H), 7.34-7.35 (m, 5H);

$^{13}$C-NMR (100 MHz, CDCl$_3$, CHCl$_3$=77.0 ppm): δ=27.7, 58.6, 67.2, 82.3, 85.1, 128.2, 128.6, 128.9, 135.2, 168.5;

HRMS (ESI): m/z calculated for $C_{14}H_{19}O_3N_3Na$ [M+Na]$^+$: 300.1324; found 300.1332.

(2S,3S)-4-tert-Butyl 1-methyl 2-azido-3-methoxysuccinate

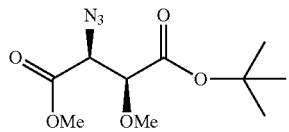 [SMILES: COC(=O)[C@@H](N=[N+]=[N-])[C@H](OC)C(=O)OC(C)(C)C]

To a stirred solution of (2S,3S)-tert-butyl 3-azido-2-methoxy-3-phenylpropanoate (310 mg, 1.0 eq) in a solvent mixture of 3 ml CHCl$_3$, 13 ml CH$_3$CN and 26 ml H$_2$O NaIO$_4$ (7.2 g, 30 eq) and RuCl₃ (0.3 eq, 69 mg) were added portionwise at room temperature. The reaction mixture was heated under refluxing conditions for 3 h. A white precipitate formed upon cooling to room temperature. The solid was filtered off and the filtrate was extracted with diethyl ether. The combined organic phases were concentrated under reduced pressure to yield the crude product. This material was dissolved in 9 ml methyl iodide. Then, CaSO₄ (1.2 g, 8.0 eq) and Ag₂O (778 mg, 3.0 eq) were added and the reaction mixture was stirred in the dark at room temperature for 22 h. After filtration the filtrate was concentrated under reduced pressure to afford the title compound in pure form so that it can directly be employed in the next step without further purification.

¹H-NMR (400 MHz, CDCl₃, CHCl₃=7.26 ppm): δ=1.51 (s, 3H), 3.48 (s, 3H), 4.15 (d, J=3.6 Hz, 1H), 4.21 (d, J=4.0 Hz, 1H);
¹³C-NMR (100 MHz, CDCl₃, CHCl₃=77.0 ppm): δ=28.1, 53.0, 59.5, 63.4, 81.2, 83.0, 167.7, 168.3.

(2S,3R)-1-tert-Butyl 4-methyl 2-methoxy-3-[4-(4-nitrobenzamido)benzamido]succinate

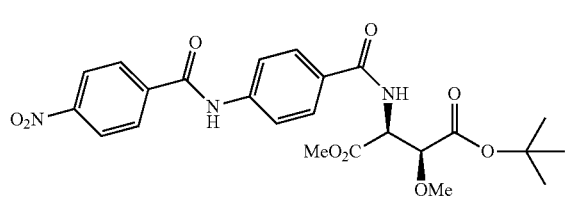 [SMILES: COC(=O)[C@@H](NC(=O)c1ccc(NC(=O)c2ccc([N+](=O)[O-])cc2)cc1)[C@H](OC)C(=O)OC(C)(C)C]

The crude mixture (2S,3S)-4-tert-butyl 1-methyl 2-azido-3-methoxysuccinate was dissolved in 12 ml THF, then 0.5 ml water and PPh₃ (881 mg, 3.0 eq) were added. The resulting reaction mixture was warmed up to 50° C. and stirring was continued for 12 hours. Then, the solvent was removed under reduced pressure to afford the crude product which was pure enough to be used directly in the next step. The crude product was dissolved in 5 ml DMF and (ethyl carbonic) 4-(4-nitrobenzamido)benzoic anhydride (481 mg, 1.2 eq) was added at room temperature. After stirring for 20 h, water was added and the aqueous solution was extracted with ethyl acetate. The combined organic phases were concentrated under reduced pressure. Purification by flash column chromatography (petroleum ether/ethyl acetate=2:1) afforded the title compound (81 mg, 16% over four steps).

[α]$_D^{20}$=−11.8 (c 1.1, CHCl₃);
¹H-NMR (400 MHz, CDCl₃, CHCl₃=7.26 ppm): δ=1.41 (s, 9H), 3.45 (s, 3H), 3.78 (s, 3H), 4.34 (d, J=2.4 Hz, 1H), 5.29 (dd, J=2.4, 9.6 Hz, 1H), 6.76 (d, J=9.6 Hz, 1H), 7.27-7.35 (m, 4H), 8.07 (d, J=8.8 Hz, 2H), 8.26 (2, J=8.8 Hz, 2H), 8.83 (s, 1H);
¹³C-NMR (100 MHz, CDCl₃, CHCl₃=77.0 ppm): δ=27.9, 52.9, 54.8, 59.1, 79.8, 83.2, 120.1, 123.8, 128.3, 128.7, 129.6, 140.3, 141.1, 149.7, 164.1, 166.9, 168.0, 169.7.
HRMS (ESI): m/z calculated for C₂₄H₂₇O₉N₃Na [M+Na]⁺: 524.1645; found 524.1647.

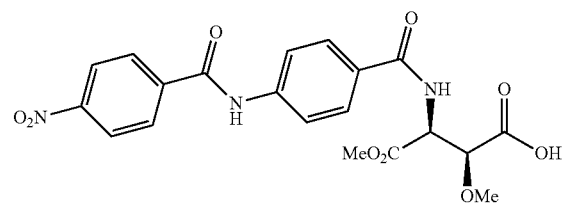 [SMILES: COC(=O)[C@@H](NC(=O)c1ccc(NC(=O)c2ccc([N+](=O)[O-])cc2)cc1)[C@H](OC)C(=O)O]

To a stirred solution of (2S,3R)-1-tert-Butyl 4-methyl 2-methoxy-3-[4-(4-nitrobenzamido)benzamido]succinate (74.3 mg, 0.15 mmol) in 2.5 ml CH₂Cl₂ was added 1.5 ml TFA at room temperature. After stirring for 5 h, the reaction mixture was added water and extracted with ethyl acetate. The combined organic phases were washed with water (three times), dried over Na₂SO₄ and concentrated under reduced pressure to give the title compound in quantitative yield (65.9 mg, quant.).

[α]$_D^{20}$=−16.4° (c 1.1, EtOAc);
¹H-NMR (400 MHz, DMSO, DMSO=2.50 ppm): δ=3.37 (s, 3H), 3.69 (s, J=3H), 4.34 (d, J=4.4 Hz, 1H), 5.09 (dd, J=4.8, 8.8 Hz, 1H), 7.89-7.90 (m, 4H), 8.21 (dd, J=2, 6.8 Hz, 1H), 8.39 (dd, J=2, 6.8 Hz, 1H), 8.55 (d, J=8.8 Hz, 1H), 10.8 (s, 1H).
¹³C-NMR (100 MHz, DMSO, DMSO=40.0 ppm): δ=52.9, 54.8, 58.7, 79.5, 120.0, 124.1, 129.0, 129.2, 129.8, 140.8, 142.2, 149.8, 164.7, 166.6, 170.2, 170.9.
HRMS (ESI): m/z calculated for C₂₀H₁₉O₉N₃Na [M+Na]⁺: 468.1019; found 468.1016.

Optical Rotation of Other Enantiomer:

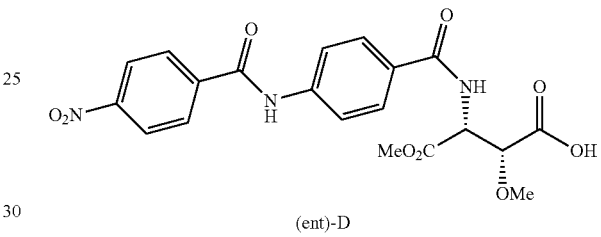

(ent)-D

[α]$_D^{20}$=+13.9° (c 1.1, EtOAc);

Methyl-4-(4-(4-((2S,3S)-2,4-di methoxy-3-(4-(4-nitrobenzamido)benzamido)-4-oxobutanamido)benzamido)-2-hydroxy-3-isopropxybenzamido)-3-isopropoxybenzoate

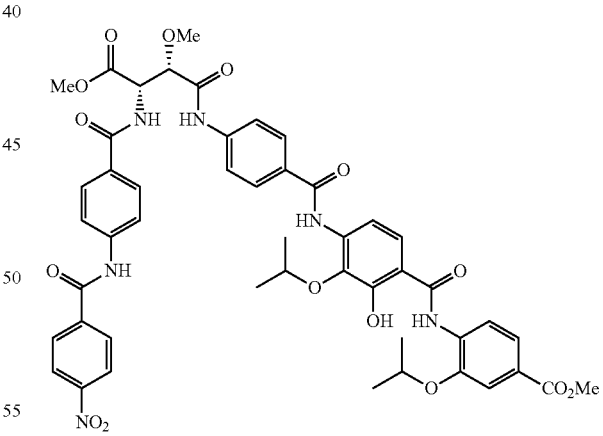

Methyl-4-[4-(4-aminobenzamido)-2-hydroxy-3-isopropxybenzamido]-3-isopropoxybenzoate (15.3 mg, 0.029 mmol) and (2S,3R)-2,4-dimethoxy-3-[4-(4-nitrobenzamido)benzamido]succinate (14.2 mg, 0.032 mmol) were dissolved in CH₂Cl₂ (3.4 mL) and cooled to 0° C. Then, HOAt (5.9 mg, 0.044 mmol), DIPEA (7.7 μL, 0.044 mmol), and EDC.HCl (6.9 mg, 0.036 mmol) were added. The mixture was stirred from 0° C. to room temperature for 17 hours. The solvent was concentrated in vacuo to give an oily residue, which was purified by flash chromatography (petroleum ether/ethyl acetate=94/6) to yield the title compound (20.1 mg, 0.021 mmol, 73%) as a colourless oil.

$^1$H NMR (400 MHz, CDCl$_3$) δ 9.07 (s, 1H$_{-OH}$), 8.37 (d, J=7.5 Hz, 2H), 8.20 (d, J=7.5 Hz, 2H), 8.11 (s, 1H$_{-NH}$), 8.02 (s, 1H$_{-NH}$), 8.01 (d, J=1.4 Hz, 2H), 7.98 (d, J=7.5 Hz, 2H), 7.90 (d, J=1.3 Hz, 1H), 7.81 (dd, J=7.5, 1.4 Hz, 1H), 7.78 (d, J=7.4 Hz, 1H), 7.69 (d, J=7.5 Hz, 1H), 7.61 (d, J=7.5 Hz, 2H), 7.55 (s, 1H), 7.54 (s, 1H$_{-NH}$), 7.53 (s, 1H), 7.41 (d, J=7.5 Hz, 1H), 5.72 (s, 1H$_{-NH}$), 5.63 (s, 1H$_{-NH}$), 5.10 (d, J=3.8 Hz, 1H), 4.76 (d, J=3.8 Hz, 1H), 4.04-3.98 (m, 2H), 3.97 (s, J=3.1 Hz, 3H), 3.74 (s, 3H), 3.32 (s, 3H), 1.47 (d, J=5.7 Hz, 6H), 1.39 (d, J=5.7 Hz, 6H) ppm.

$^{13}$C NMR (100 MHz, CDCl$_3$) δ 173.30, 168.15, 168.07, 167.77, 166.93, 166.88, 166.82, 158.83, 151.01, 146.97, 140.78, 139.42, 138.71, 134.97, 134.55, 131.57, 130.00, 130.00, 129.41, 129.41, 129.39, 129.39, 128.12, 127.53, 127.24, 124.17, 124.17, 123.28, 122.61, 122.61, 121.78, 121.78, 121.44, 115.94, 114.88, 113.30, 106.09, 78.00, 75.89, 74.13, 58.51, 56.50, 52.17, 52.08, 21.80, 21.80, 21.80, 21.80 ppm.

HRMS (ESI): Calculated for C$_{48}$H$_{47}$N$_6$O$_{15}$ (M−H)$^-$: 947.3178, found: 947.3175.

Cystobactamide A

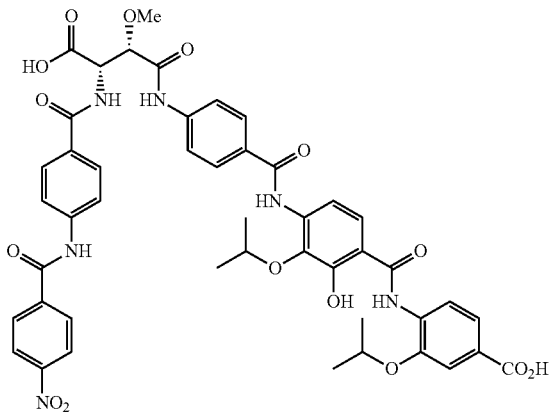 [SMILES: CO[C@H](C(=O)Nc1ccc(C(=O)Nc2ccc(C(=O)Nc3ccc(C(=O)O)cc3OC(C)C)c(O)c2OC(C)C)cc1)[C@H](NC(=O)c1ccc(NC(=O)c2ccc([N+](=O)[O-])cc2)cc1)C(=O)O]

Methyl-4-4-[4-{[4-((2S,3S)-2,4-dimethoxy-3-(4-(4-nitrobenzamido)benzamido)-4-oxobutanamido]benzamido}-2-hydroxy-3-isopropxybenzamido)-3-isopropoxybenzoate (15.2 mg, 0.016 mmol) was dissolved in a mixture 1/1 of THF/H$_2$O (0.2/0.2 mL). Then, solid LiOH (3.8 mg, 0.16 mmol) was added and the reaction mixture was stirred at room temperature for 17 hours. The aqueous layer was acidified with 1M HCl until pH~1 and extracted with ethyl acetate (3×). The organic extracts were combined, dried over MgSO$_4$ and filtered. The solvent was concentrated in vacuo to yield the title compound (13.3 mg, 0.014 mmol, 90%) as a yellow wax.

[α]$_D^{20}$=−19.1° (c 1.1, EtOAc)

$^1$H NMR (400 MHz, CDCl$_3$) δ 8.35 (d, J=7.5 Hz, 2H), 8.15 (d, J=7.5 Hz, 2H), 8.00 (d, J=1.8 Hz, 2H), 7.98 (d, J=1.8 Hz, 2H), 7.90 (d, J=1.8 Hz, 1H), 7.86 (dd, J=7.5, 1.8 Hz, 1H), 7.78 (d, J=7.5 Hz, 1H), 7.65 (s, 1H), 7.63 (d, J=7.5 Hz, 2H), 7.58 (s, 1H$_{-NH}$), 7.54 (d, J=7.5 Hz, 2H), 7.51 (s, 1H$_{-NH}$), 7.10 (s, 1H$_{-NH}$), 7.03 (d, J=7.5 Hz, 1H), 6.35 (s, 1H$_{-NH}$), 5.57 (s, 1H$_{-NH}$), 5.42 (s, 1H$_{-OH}$), 4.93 (s, 1H), 4.70 (s, 1H), 4.01 (hept, J=5.6 Hz, 1H), 3.95 (hept, J=5.6 Hz, 1H), 3.38 (s, 3H), 1.48 (s, 6H), 1.47 (s, 6H) ppm.

$^{13}$C NMR (100 MHz CDCl$_3$) δ 173.30, 169.54, 168.18, 168.07, 167.77, 166.88, 166.82, 158.83, 151.01, 149.88, 140.78, 139.42, 138.71, 136.26, 134.97, 134.55, 130.00, 130.00, 129.41, 129.41, 129.39, 129.39, 128.12, 127.53, 125.15, 124.17, 124.17, 123.28, 122.84, 122.61, 122.61, 121.78, 121.78, 120.41, 113.82, 113.30, 106.09, 77.86, 75.89, 74.13, 58.51, 54.58, 21.80, 21.80, 21.80, 21.80 ppm.

HRMS (ESI): Calculated for C$_{46}$H$_{43}$N$_6$O$_{15}$ (M−H)$^-$: 920.2865, found: 920.2866.

Synthesis of Cystobactamide C Derivatives

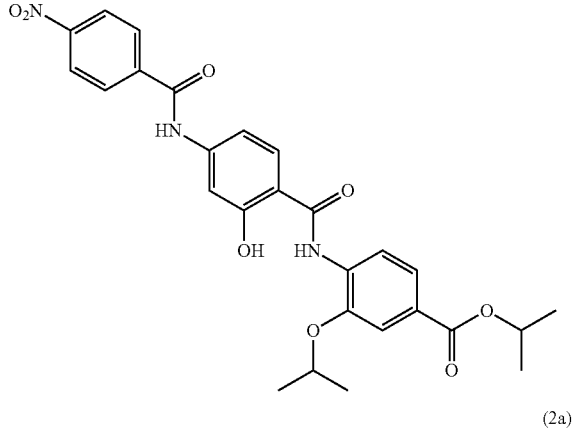

(1a)

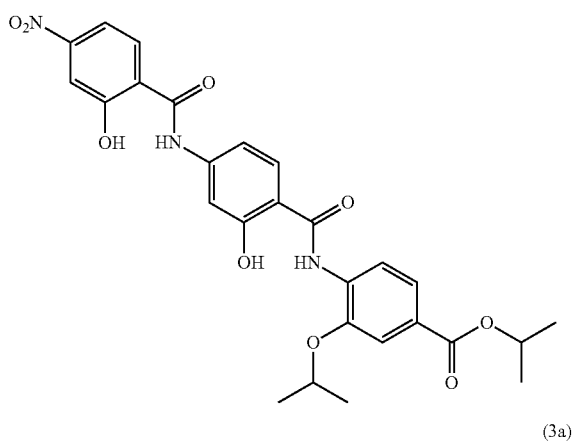

(2a)

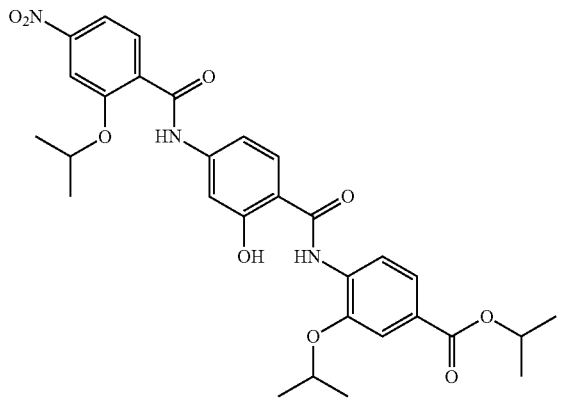

(3a)

(4a)
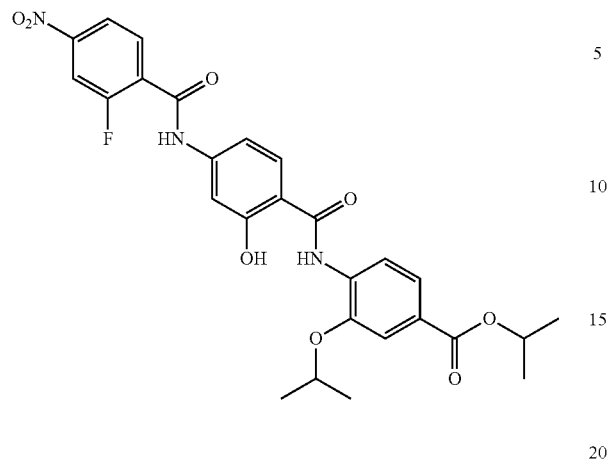
(7a)
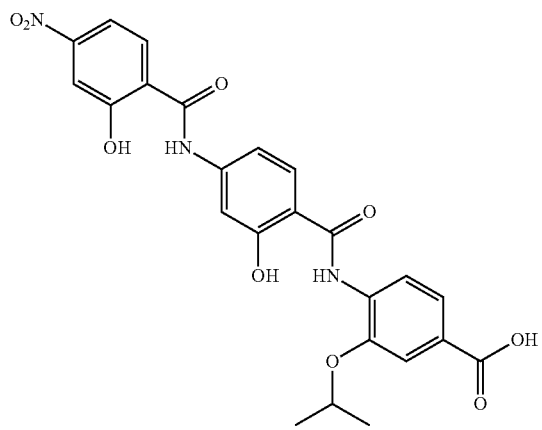
(5a)
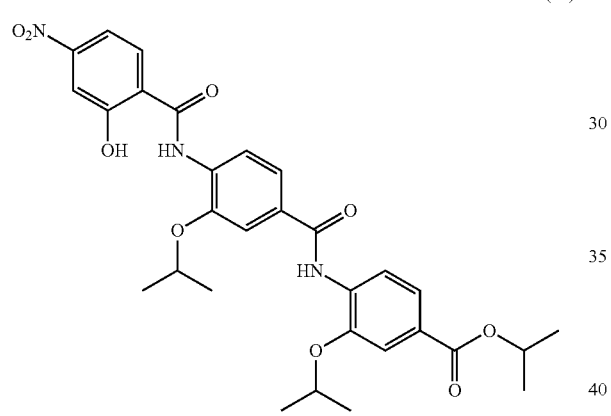
(8a)
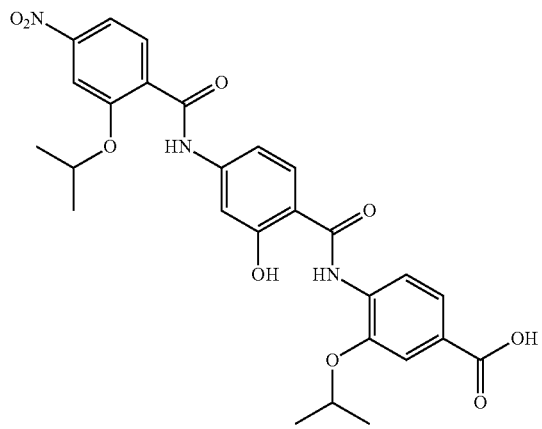
(6a)
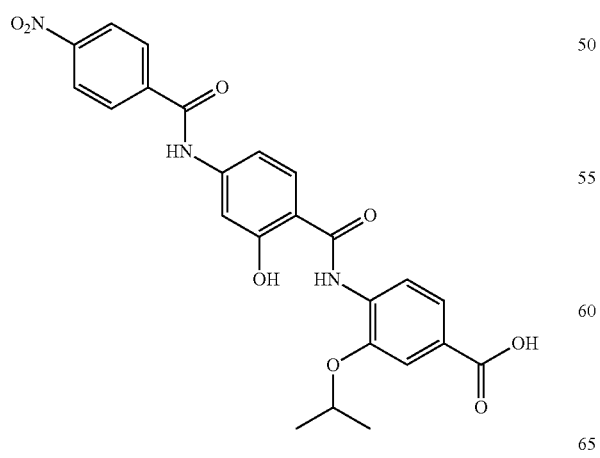
(9a)
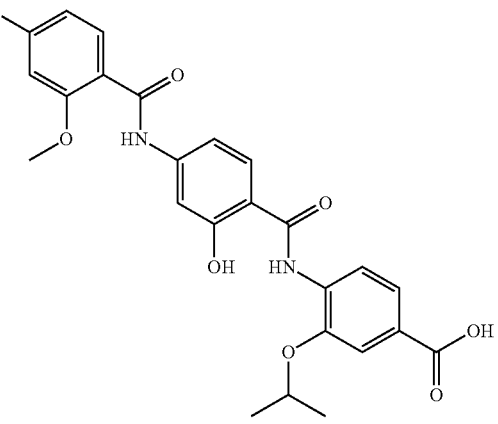

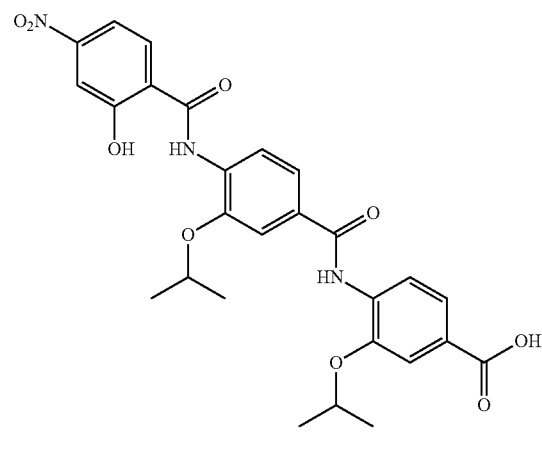
(10a)
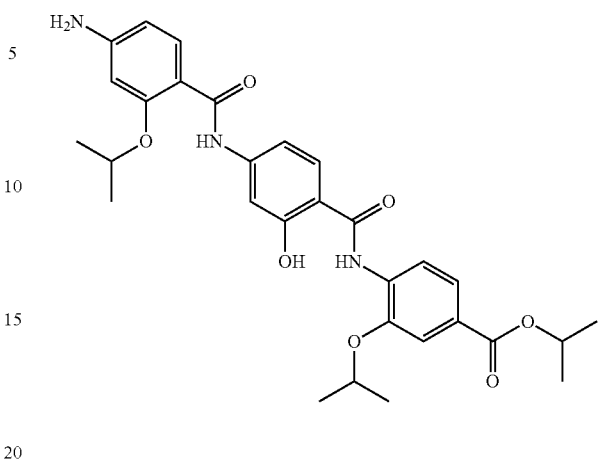
(13a)
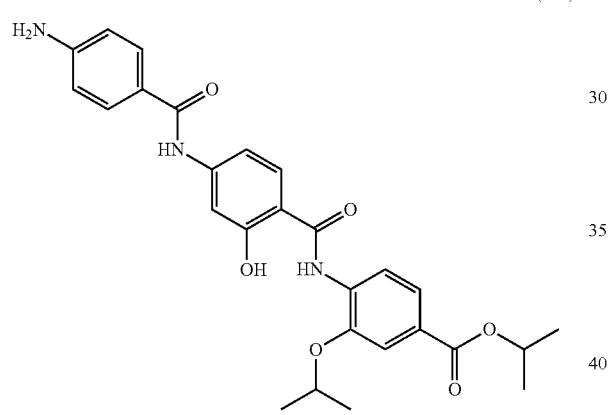
(11a)
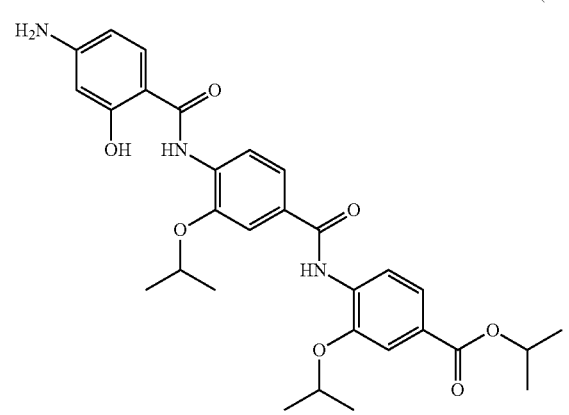
(14a)
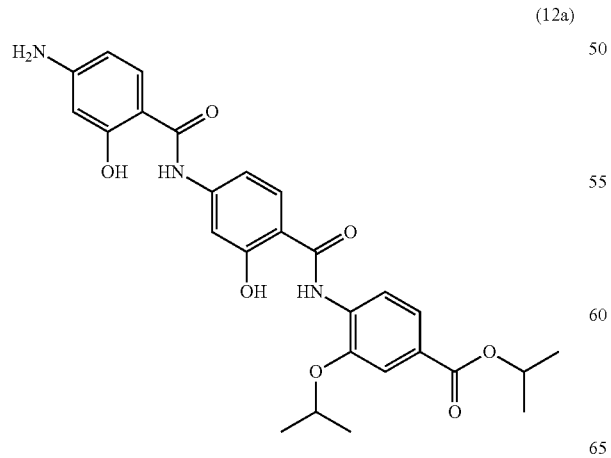
(12a)
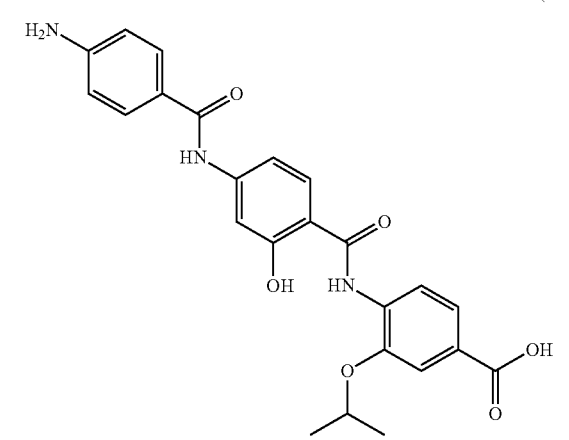
(15a)

(16a)
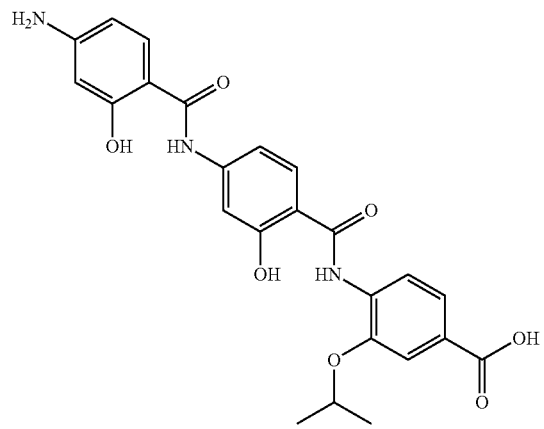
(17a)
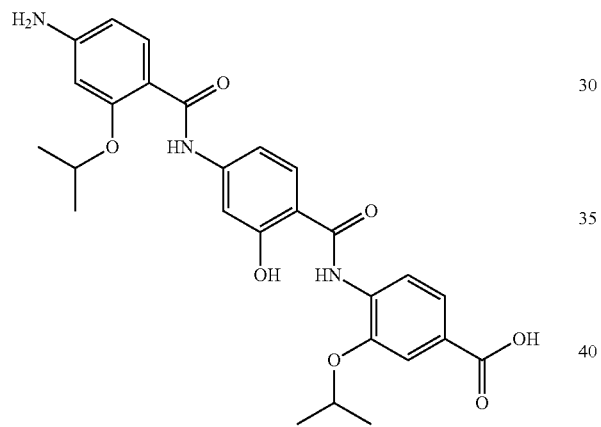
(18a)
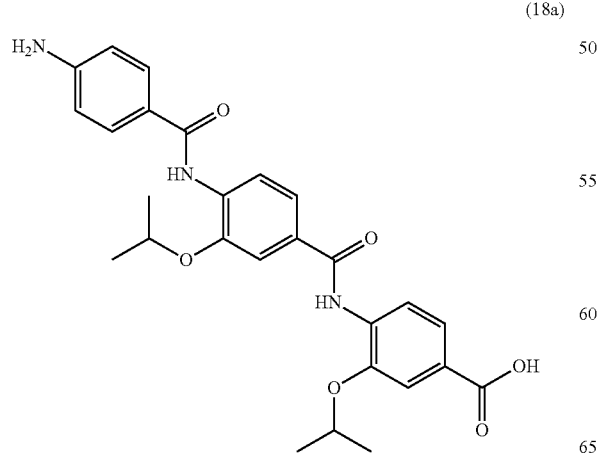
(19a)
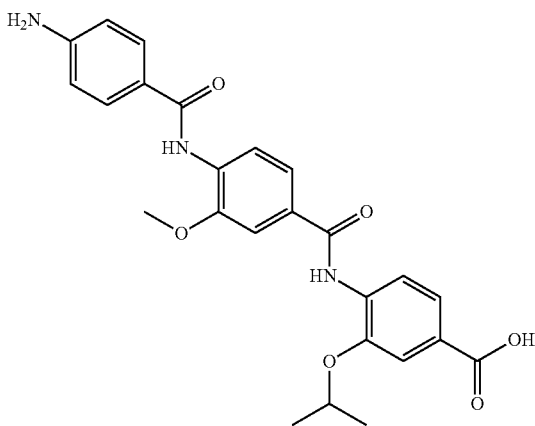
(20a)
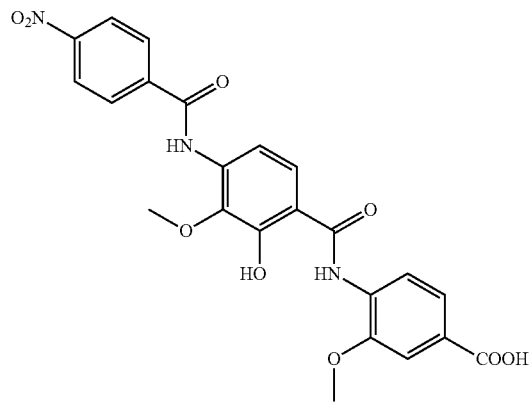
(21a)
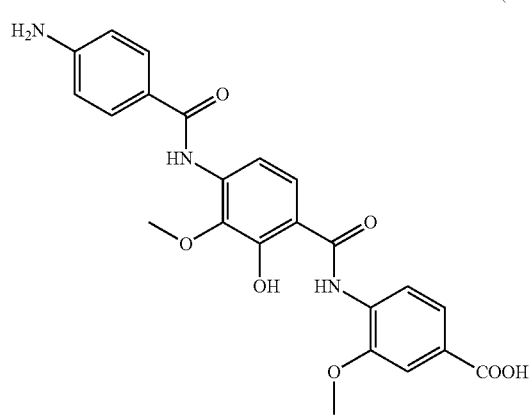

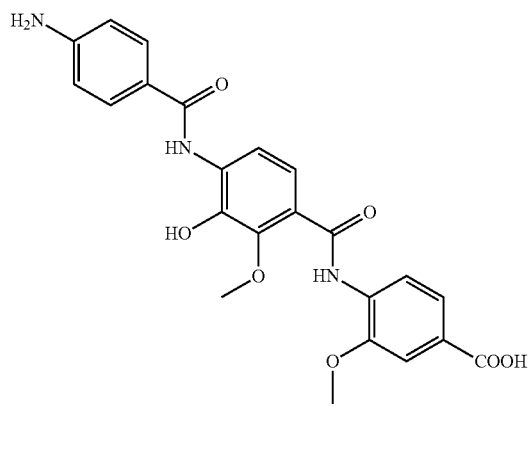
(22a)
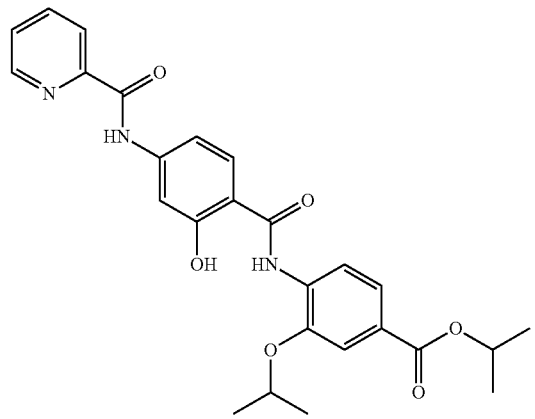
(25a)
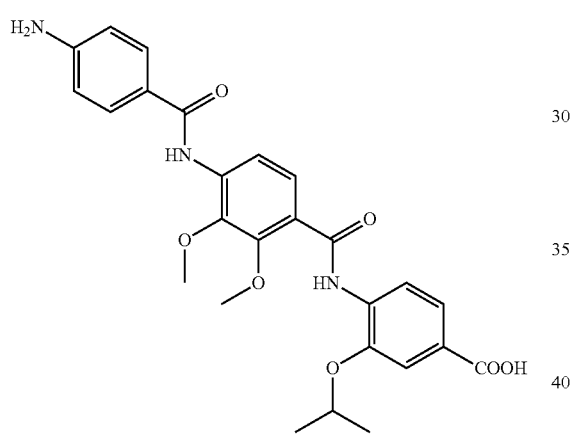
(23a)
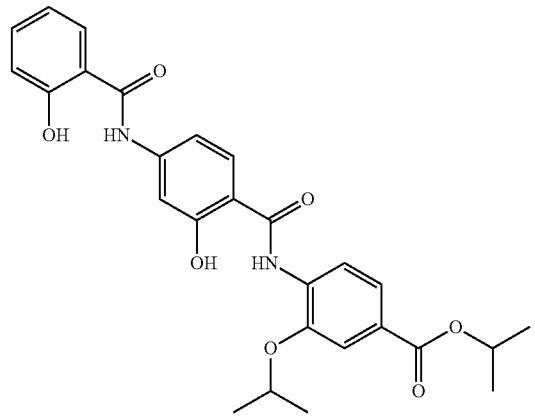
(26a)
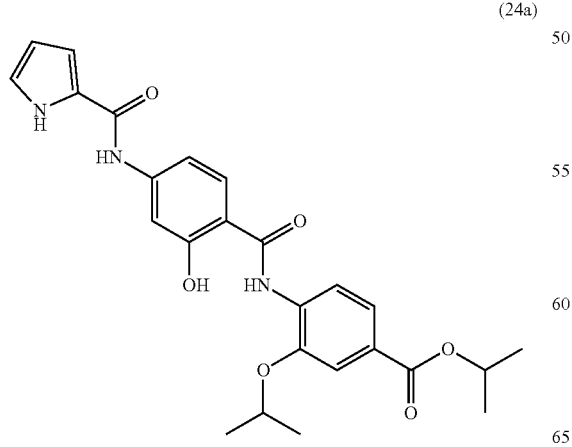
(24a)
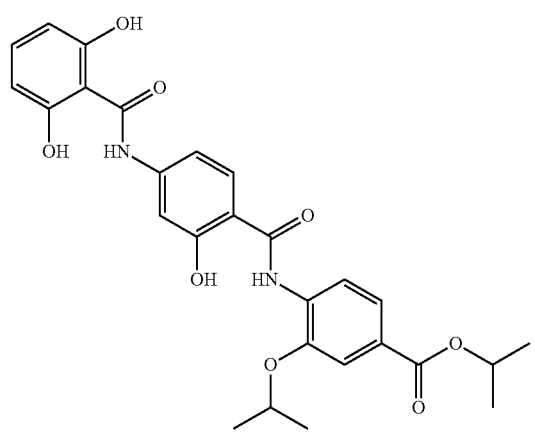
(27a)

(28a)
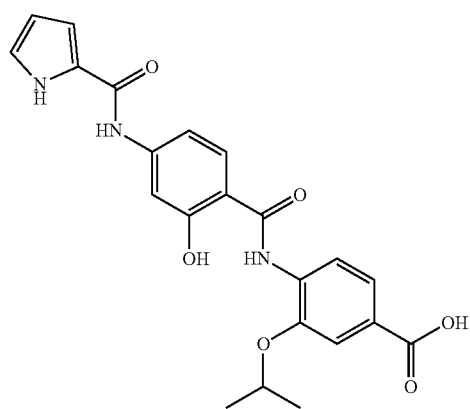
(29a)
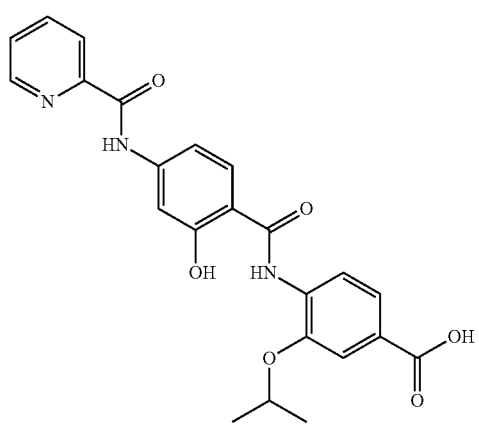
(30a)
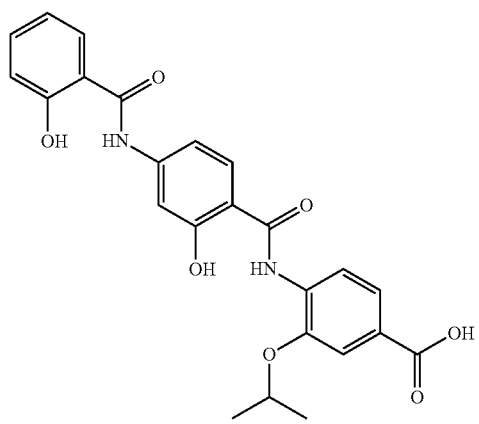
(31a)
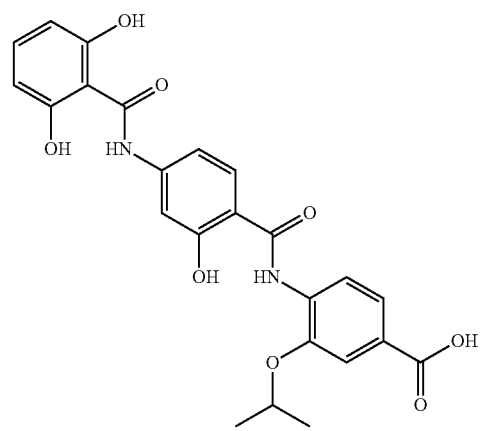
(32a)
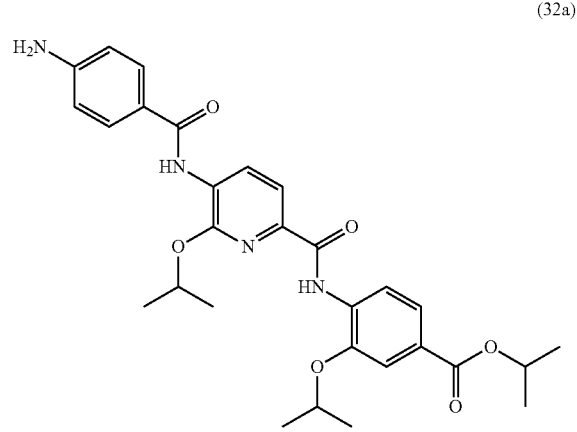
(33a)
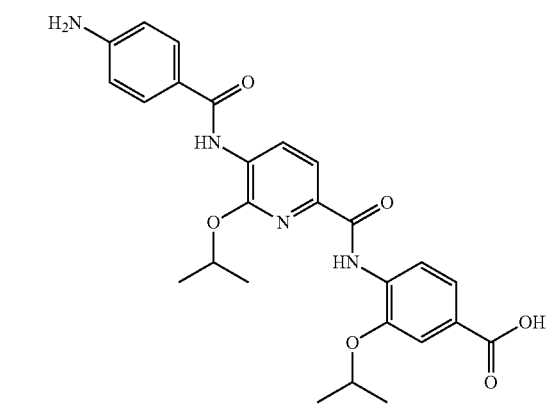
1.1. Synthesis of the Different Used Individual Rings
The preparation of the different individual rings that were used during the synthesis of the cystobactamide C derivatives is described here.
Preparation of Ring C
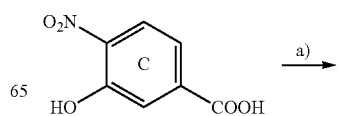

109
-continued
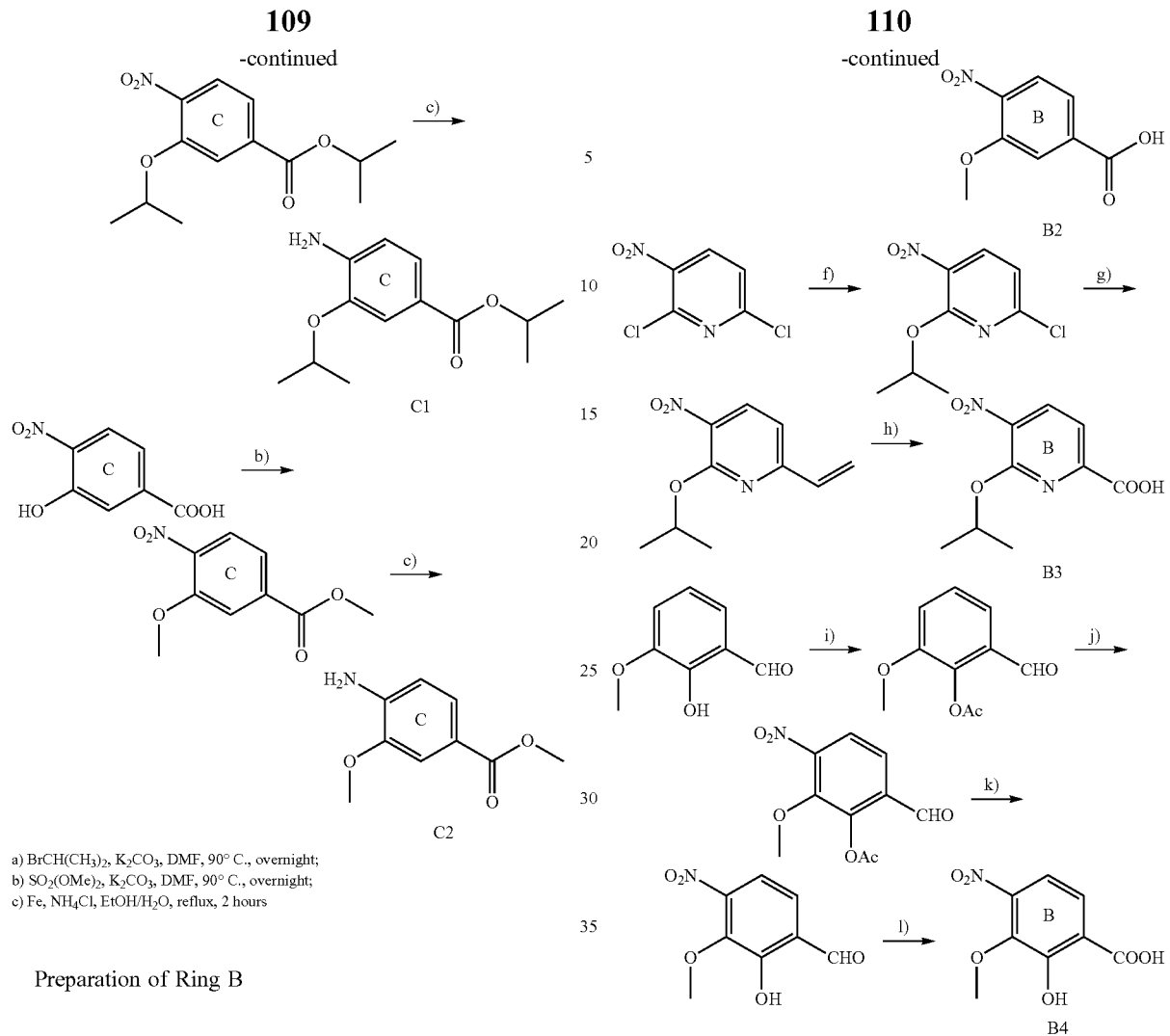
a) BrCH(CH₃)₂, K₂CO₃, DMF, 90° C., overnight;
b) SO₂(OMe)₂, K₂CO₃, DMF, 90° C., overnight;
c) Fe, NH₄Cl, EtOH/H₂O, reflux, 2 hours
Preparation of Ring B
110
-continued
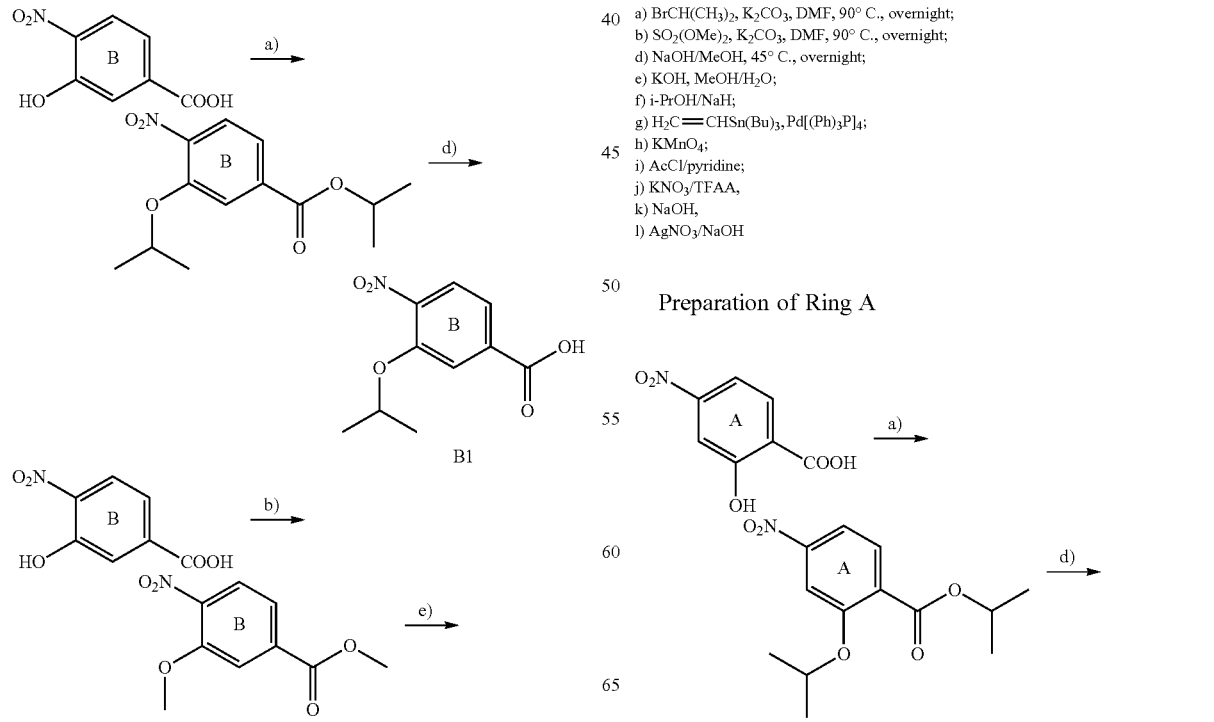
a) BrCH(CH₃)₂, K₂CO₃, DMF, 90° C., overnight;
b) SO₂(OMe)₂, K₂CO₃, DMF, 90° C., overnight;
d) NaOH/MeOH, 45° C., overnight;
e) KOH, MeOH/H₂O;
f) i-PrOH/NaH;
g) H₂C=CHSn(Bu)₃, Pd[(Ph)₃P]₄;
h) KMnO₄;
i) AcCl/pyridine;
j) KNO₃/TFAA,
k) NaOH,
l) AgNO₃/NaOH
Preparation of Ring A

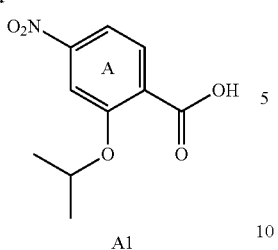
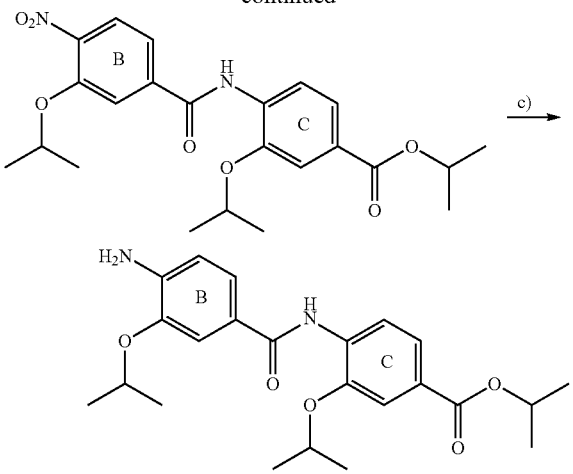
a) BrCH(CH₃)₂, K₂CO₃, DMF, 90° C., overnight;
d) NaOH/MeOH, 45° C., overnight
1.2. Coupling of Ring B and C to Give the Different Prepared BC Fragments
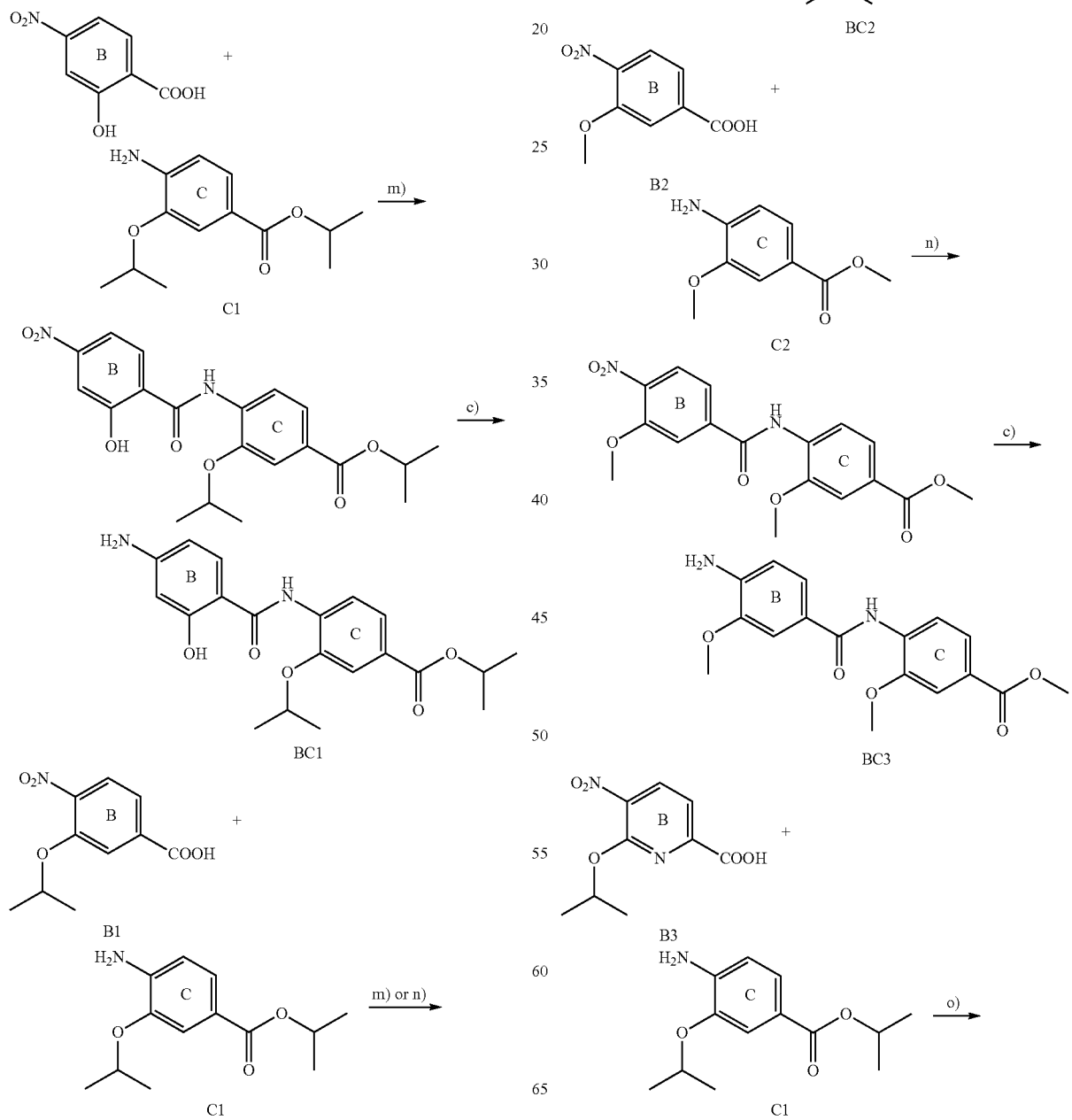

113
-continued
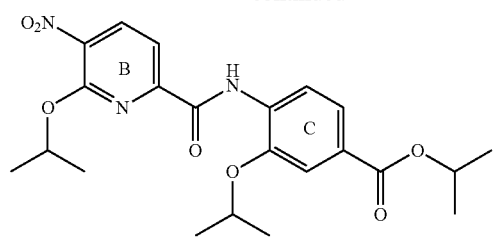
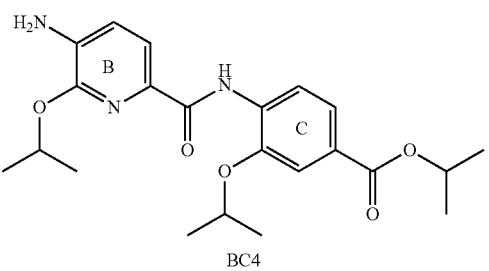
BC4
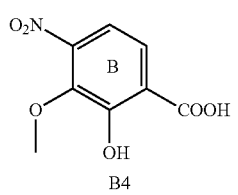
B4
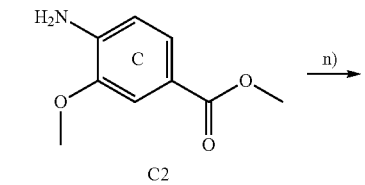
C2
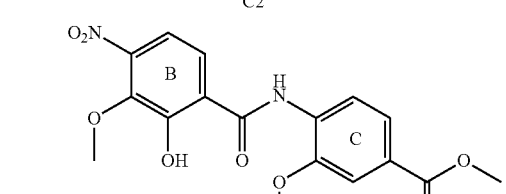
BC5
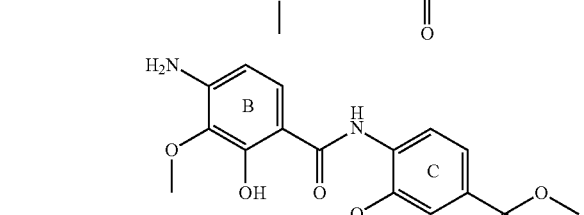
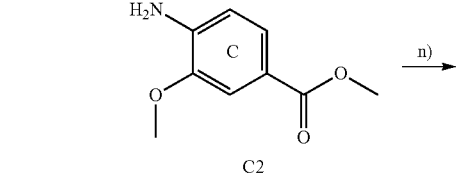
C2
114
-continued
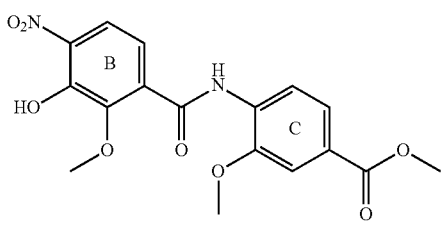
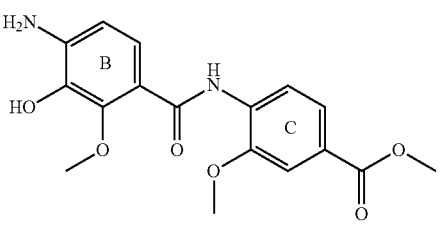
BC6
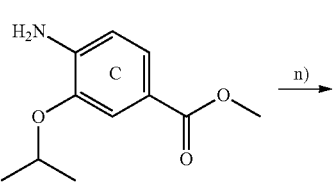
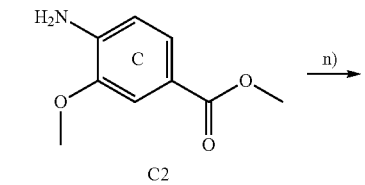
C1
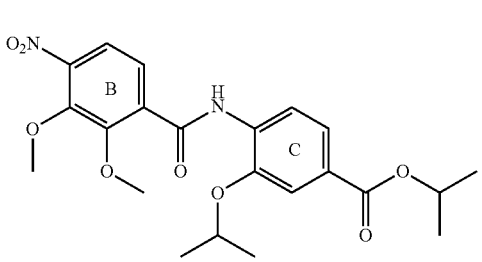
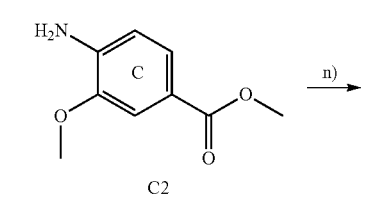
BC7
c) Fe, NH₄Cl, EtOH/H₂O, reflux, 2 hours; m) PCl₃, CH₂Cl₂, Xylene, 145° C, 2 hours; n) Cl₂PPh₃, CHCl₃; o) EDC, HOBT 1.3. Coupling of Ring a with BC Fragments
1.3.1. Coupling of Ring a with BC Fragments (BC1, BC2, BC3, BC5, BC6, BC7) to Synthesize the Cystobactamide C Derivatives (1a)-(23a)

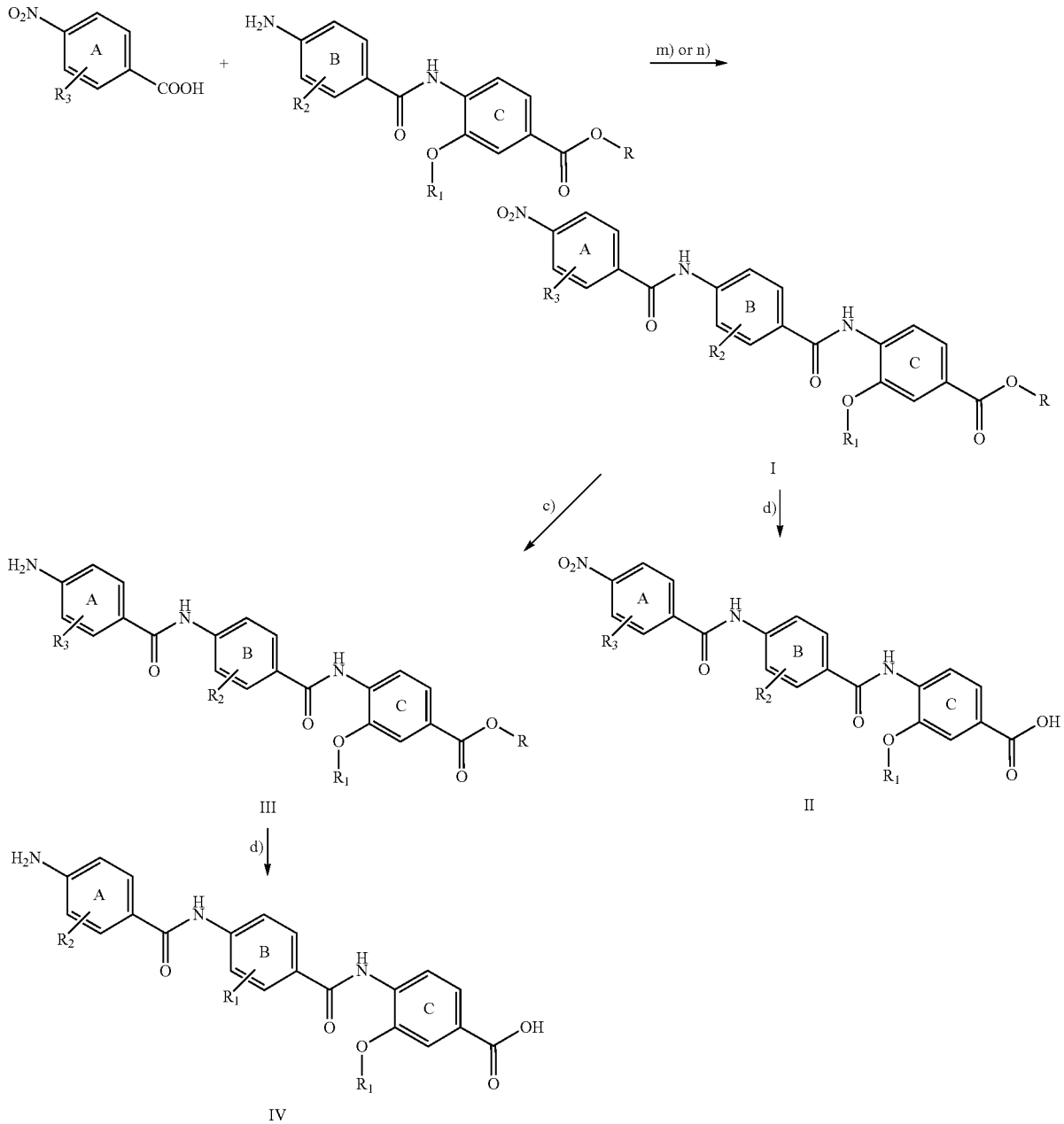

c) Fe, NH$_4$Cl, EtOH/H$_2$O, reflux, 2 hours;
d) NaOH/MeOH, 45° C., overnight;
m) PCl$_3$, CH$_2$Cl$_2$, Xylene, 145° C., 2 hours;
n) Cl$_2$PPh$_3$, CHCl$_3$

| Compound | Scaffold | R | R$_1$ | R$_2$ | R$_3$ |
|---|---|---|---|---|---|
| (1a) | I | iPr | iPr | 2-OH | H |
| (2a) | I | iPr | iPr | 2-OH | 2-OH |
| (3a) | I | iPr | iPr | 2-OH | 2-OiPr |
| (4a) | I | iPr | iPr | 2-OH | 2-F |
| (5a) | I | iPr | iPr | 3-OiPr | 2-OH |
| (6a) | II | — | iPr | 2-OH | H |

| Compound | Scaffold | R | R$_1$ | R$_2$ | R$_3$ |
|---|---|---|---|---|---|
| (7a) | II | — | iPr | 2-OH | 2-OH |
| (8a) | II | — | iPr | 2-OH | 2-OiPr |
| (9a) | II | — | iPr | 2-OH | 2-OMe |
| (10a) | II | — | iPr | 3-OiPr | 2-OH |
| (11a) | III | iPr | iPr | 2-OH | H |

-continued

| Compound | Scaffold | R | R₁ | R₂ | R₃ |
|---|---|---|---|---|---|
| (12a) | III | iPr | iPr | 2-OH | 2-OH |
| (13a) | III | iPr | iPr | 2-OH | 2-OiPr |
| (14a) | III | iPr | iPr | 3-OiPr | 2-OH |
| (15a) | IV | — | iPr | 2-OH | H |
| (16a) | IV | — | iPr | 2-OH | 2-OH |
| (17a) | IV | — | iPr | 2-OH | 2-OiPr |
| (18a) | IV | — | iPr | 3-OiPr | H |
| (19a) | IV | — | Me | 3-OMe | H |
| (20a) | II | — | Me | 2-OH, 3OMe | H |
| (21a) | IV | — | Me | 2-OH, 3OMe | H |
| (22a) | IV | — | Me | 2-OMe, 3OH | H |
| (23a) | IV | — | iPr | 2,3-diOMe | H |

1.3.2. Coupling of Ring a with BC1 Fragment to Synthesize the Cystobactamide C Derivatives (24a)-(31a)

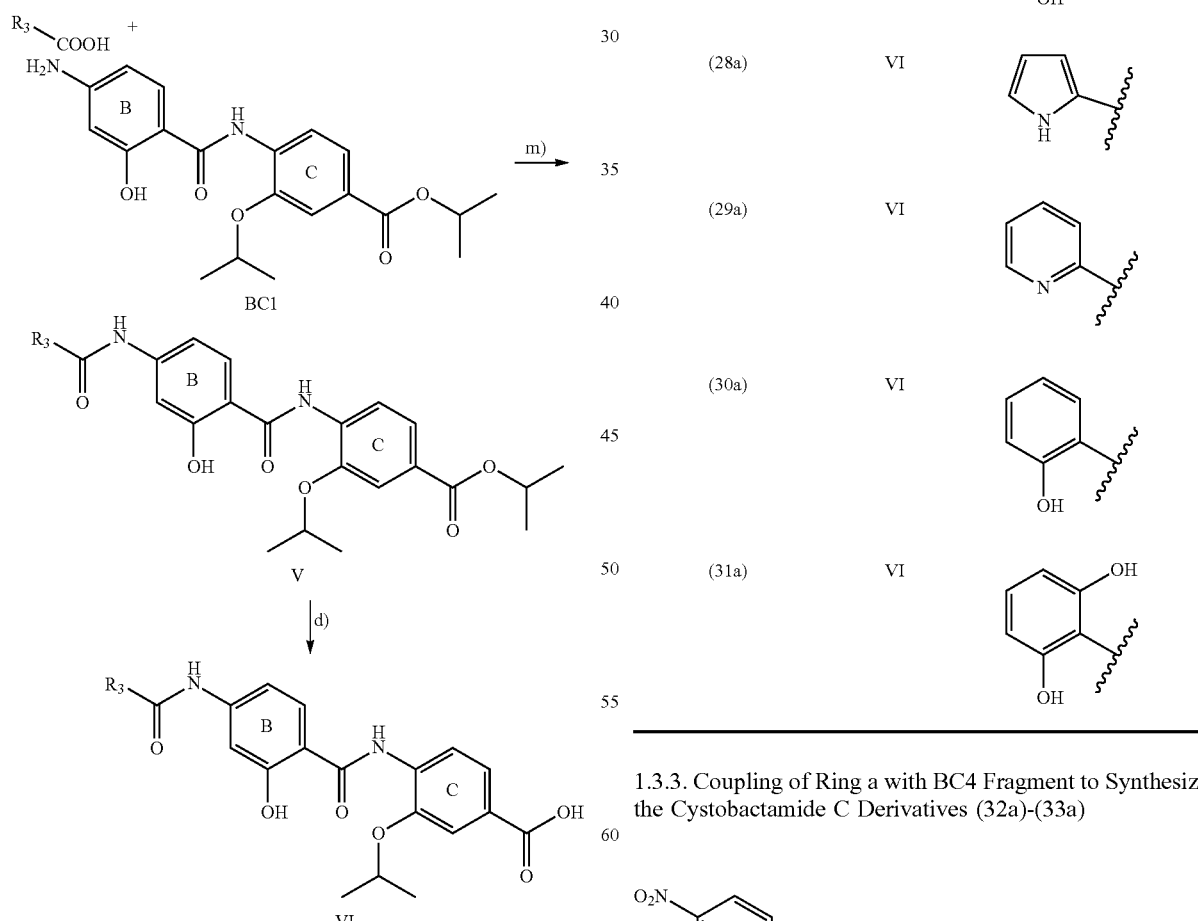

d) NaOH/MeOH, 45° C., overnight;
m) PCl₃, CH₂Cl₂, Xylene, 145° C., 2 hours

| Compound | Scaffold | R₃ |
|---|---|---|
| (24a) | V | pyrrol-2-yl (NH) |
| (25a) | V | pyridin-2-yl |
| (26a) | V | 2-hydroxyphenyl |
| (27a) | V | 2,6-dihydroxyphenyl |
| (28a) | VI | pyrrol-2-yl (NH) |
| (29a) | VI | pyridin-2-yl |
| (30a) | VI | 2-hydroxyphenyl |
| (31a) | VI | 2,6-dihydroxyphenyl |

1.3.3. Coupling of Ring a with BC4 Fragment to Synthesize the Cystobactamide C Derivatives (32a)-(33a)

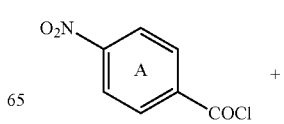

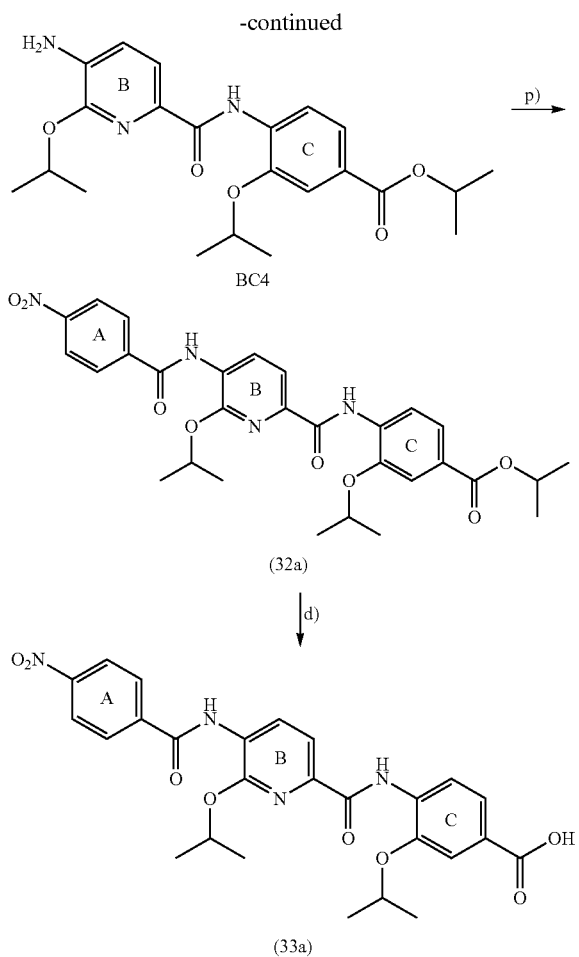

d) NaOH/MeOH, 45° C., overnight;
p) CH$_2$Cl$_2$, pyridine, rt, overnight

2. EXPERIMENTAL

2.1. General Experimental Information

Starting materials and solvents were purchased from commercial suppliers, and used without further purification. All chemical yields refer to purified compounds, and not optimized. Reaction progress was monitored using TLC Silica gel 60 F$_{254}$ aluminium sheets, and visualization was accomplished by UV at 254 nm. Flash chromatography was performed using silica gel 60 Å (40-63 μm). Preparative RP-HPLC was carried out on a Waters Corporation setup contains a 2767 sample manager, a 2545 binary gradient module, a 2998 PDA detector and a 3100 electron spray mass spectrometer. Purification was performed using a Waters XBridge column (C18, 150×19 mm, 5 μm), a binary solvent system A and B (A=water with 0.1% formic acid; B=MeCN with 0.1% formic acid) as eluent, a flow rate of 20 mL/min and a gradient of 60% to 95% B in 8 min were applied. Melting points were determined on a Stuart Scientific melting point apparatus SMP3 (Bibby Sterilin, UK), and are uncorrected.

NMR spectra were recorded either on Bruker DRX-500 ($^1$H, 500 MHz; $^{13}$C, 126 MHz), or Bruker Fourier 300 ($^1$H, 300 MHz; $^{13}$C, 75 MHz) spectrometer at 300 K. Chemical shifts are recorded as δ values in ppm units by reference to the hydrogenated residues of deuterated solvent as internal standard (CDCl$_3$: δ=7.26, 77.02; DMSO-d$_6$: δ=2.50, 39.99). Splitting patterns describe apparent multiplicities and are designated as s (singlet), br s (broad singlet), d (doublet), dd (doublet of doublet), t (triplet), q (quartet), m (multiplet). Coupling constants (J) are given in Hertz (Hz). Purity of all compounds used in biological assays was ≥95% as measured by LC/MS Finnigan Surveyor MSQ Plus (Thermo Fisher Scientific, Dreieich, Germany). The system consists of LC pump, autosampler, PDA detector, and single-quadrupole MS detector, as well as the standard software Xcalibur for operation. RP C18 Nucleodur 100-5 (125×3 mm) column (Macherey-Nagel GmbH, Dühren, Germany) was used as stationary phase, and a binary solvent system A and B (A=water with 0.1% TFA; B=MeCN with 0.1% TFA) was used as mobile phase. In a gradient run the percentage of B was increased from an initial concentration of 0% at 0 min to 100% at 15 min and kept at 100% for 5 min. The injection volume was 10 μL and flow rate was set to 800 μL/min. MS (ESI) analysis was carried out at a spray voltage of 3800 V, a capillary temperature of 350° C. and a source CID of 10 V. Spectra were acquired in positive mode from 100 to 1000 m/z and at 254 nm for UV tracing.

2.2. LC/MS Data for the Triaryl Derivatives

| Compound | LC/MS m/z (ESI+) |
| --- | --- |
| (1a) | 521.99 [M + H]$^+$ |
| (2a) | 537.87 [M + H]$^+$ |
| (3a) | 579.90 [M + H]$^+$ |
| (4a) | 540.07 [M + H]$^+$ |
| (5a) | 580.11 [M + H]$^+$ |
| (6a) | 479.98 [M + H]$^+$ |
| (7a) | 496.02 [M + H]$^+$ |
| (8a) | 537.99 [M + H]$^+$ |
| (9a) | 509.98 [M + H]$^+$ |
| (10a) | 538.11 [M + H]$^+$ |
| (11a) | 492.02 [M + H]$^+$ |
| (12a) | 508.01 [M + H]$^+$ |
| (13a) | 550.02 [M + H]$^+$ |
| (14a) | 550.13 [M + H]$^+$ |
| (15a) | 449.87 [M + H]$^+$ |
| (16a) | 465.93 [M + H]$^+$ |
| (17a) | 508.07 [M + H]$^+$ |
| (18a) | 492 [M + H]$^+$ |
| (19a) | 435 [M]$^+$ |
| (20a) | 482 [M + H]$^+$ |
| (21a) | 452 [M + H]$^+$ |
| (22a) | 452 [M + H]$^+$ |
| (23a) | 494 [M + H]$^+$ |
| (24a) | 466.20 [M + H]$^+$ |
| (25a) | 478.07 [M + H]$^+$ |
| (26a) | 493.17 [M + H]$^+$ |
| (27a) | 509.12 [M + H]$^+$ |
| (28a) | 423.53 [M + H]$^+$ |
| (29a) | 436.13 [M + H]$^+$ |
| (30a) | 451.10 [M + H]$^+$ |
| (31a) | 467.11 [M + H]$^+$ |
| (32a) | 535 [M + H]+ |
| (33a) | 493 [M + H]+ |

2.3 General Synthetic Procedures:

a) A mixture of the acid (25 mmol), isopropyl bromide (52 mmol) and potassium carbonate (52 mmol) in 100 ml DMF were heated overnight at 90° C. Excess DMF was then removed under reduced pressure and the remaining residue was partitioned between water and ethyl acetate. The organic layer was dried over sodium sulphate and the excess solvent was then removed under reduced pressure to give the pure product.

c) To a stirred solution of the nitro derivative (10 mmol) in EtOH (60 mL), iron powder (2.80 g, 50 mmol) was added at 55° C. followed by NH$_4$Cl (266 mg, 5 mmol) solution in water (30 mL). The reaction was refluxed for 1-2 h, then iron was filtered while hot and the filtrate was concentrated under vacuum till dryness. The residue was diluted with water (30 mL) and basified by NaHCO$_3$ (saturated aqueous solution) to pH 7-8. The mixture was extracted with EtOAc. The combined organic extract was washed with brine, dried (MgSO$_4$), and the solvent was removed by vacuum distillation. The obtained crude material was triturated with n-hexane, and collected by filtration.

d) Ester hydrolysis was done according to the following reported procedure.[1] The ester (0.1 mmol), sodium hydroxide 1M (3 mL) and anhydrous methanol were heated overnight at 45° C. On cooling, the reaction mixture was acidified to pH 1 (3 mL, hydrochloric acid 1 M) and extracted with dichloromethane (3×150 mL). The organic was dried over sodium sulphate and the solvent removed under reduced pressure to leave give the pure product.

m) Amide formation was done according to the following reported procedure.[2] A boiling solution of the acid (1 mmol) and the amine (1 mmol) in xylenes 2.5 ml was treated with a 2M solution of PCl$_3$ in CH$_2$Cl$_2$ (0.4 mmol). After 2 hours the excess solvent was evaporated and the residue was purified using column chromatography.

n) To a stirred solution of the acid (2 mmol), amine (2.4 mmol) in anhydrous CHCl$_3$ (50 mL) under a nitrogen atmosphere, dichlorotriphenylphosphorane (3.0 g, 9 mmol) was added. The reaction was heated at 80° C. for 5 h. Solvent was removed by vacuum distillation. The residue was then purified using flash chromatography.

2.4 Specific Synthetic Procedures:

Methyl 3-methoxy-4-nitrobenzoate

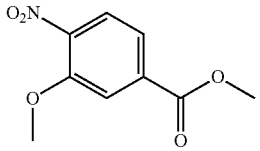

To a stirred mixture of 3-hydroxy-4-nitrobenzoic acid (9.16 g, 50 mmol) and K$_2$CO$_3$ (15.2 g, 110 mmol) in DMF (150 mL), dimethyl sulfate (25.2 g, 200 mmol) was added portion wise then the reaction was stirred at 90° C. overnight. After cooling the mixture was poured on to ice cooled water (400 mL), the precipitate was filtered, washed with cold water then n-hexane.

Yield 95% (pale yellow solid), m/z (ESI+) 212 [M+H]$^+$.

3-Methoxy-4-nitrobenzoic acid

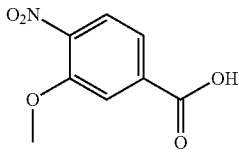

To a stirred solution of methyl 3-methoxy-4-nitrobenzoate (2.11 g, 10 mmol) in MeOH (30 mL), KOH (1.68 g, 30 mmol) in water (30 mL) was added. The reaction was refluxed for 2 h then MeOH was evaporated by vacuum distillation. The residue was diluted with water (20 mL). The solution was cooled in an ice bath and acidified by KHSO$_4$ (saturated aqueous solution) to pH 3-4. The precipitated solid was collected by filtration, washed with cold water then n-hexane.

Yield 96% (off-white solid), m/z (ESI+) 198 [M+H]$^+$.

6-Chloro-2-isopropoxy-3-nitropyridine

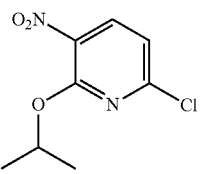

To a stirred solution of 2,6-dichloro-3-nitropyridine (3.86 g, 20 mmol) in toluene (30 mL), isopropanol (1.44 g, 24 mmol) was added. The mixture was stirred at 0° C. for 15 min. then NaH (50-60% in mineral oil, 1.22 g, 28 mmol) was added portion wise under a nitrogen atmosphere, and the reaction was allowed to stir at room temperature overnight. The reaction was quenched with brine, then diluted with water and extracted with EtOAc. The combined organic extract was washed with brine, dried (MgSO$_4$), and the solvent was removed by vacuum distillation. The residue was dissolved in toluene and purified using flash chromatography (SiO$_2$, n-hexane-EtOAc=5:1).

Yield 70% (yellowish white crystals), m/z (ESI+) 217 [M+H]$^+$.

2-Isopropoxy-3-nitro-6-vinylpyridine

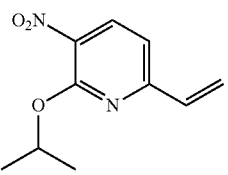

To a stirred solution of 6-chloro-2-isopropoxy-3-nitropyridine (650 mg, 3 mmol), and tributyl(vinyl)tin (1.0 g, 3.15 mmol) in toluene (20 mL) under a nitrogen atmosphere, tetrakis(triphenylphosphine) palladium(0) (180 mg, 5% eq.) was added. The reaction was refluxed overnight. Brine was added, and the reaction was extracted with EtOAc. The combined organic extract was washed with brine, dried (MgSO$_4$), and the solvent was removed by vacuum distillation. The crude product was used directly in the next step without further purification. Yield 90% (yellow liquid), m/z (ESI+) 208 [M]$^+$.

6-Isopropoxy-5-nitropyridine-2-carboxylic acid

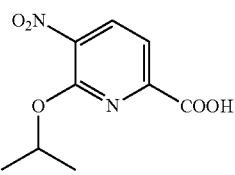 [SMILES: CC(C)Oc1nc(C(=O)O)ccc1[N+](=O)[O-]]

To a stirred solution of 2-isopropoxy-3-nitro-6-vinylpyridine (625 mg, 3 mmol) in acetone (10 mL), KMnO₄ (1.9 g, 12 mmol) solution in 50% aq. acetone (50 mL) was added. The reaction was stirred at room temperature for 24 h. NaOH 0.5 M (5 mL) was added, then the mixture was filtered and filtrate was concentrated under vacuum. The residue was cooled in an ice bath and carefully acidified by KHSO₄ (saturated aqueous solution) to pH 4-5, then extracted with EtOAc. The combined organic extract was washed with brine, dried (MgSO₄), and the solvent was removed by vacuum distillation. The obtained crude material was triturated with n-hexane, and collected by filtration.

Yield 75% (beige solid), m/z (ESI+) 227 [M+H]⁺.

Isopropyl 3-isopropoxy-4-{[(6-isopropoxy-5-nitropyridin-2-yl)carbonyl]amino}benzoate

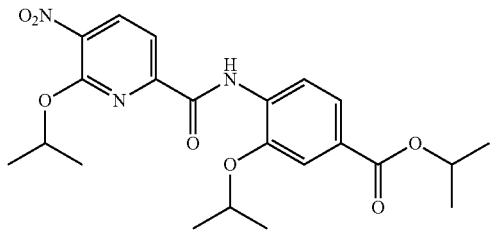 [SMILES: CC(C)OC(=O)c1ccc(NC(=O)c2ccc([N+](=O)[O-])c(OC(C)C)n2)c(OC(C)C)c1]

To a stirred solution of 6-isopropoxy-5-nitropyridine-2-carboxylic acid (226 mg, 1 mmol), and isopropyl 4-amino-3-isopropoxybenzoate (237 mg, 1 mmol) in a mixture of anhydrous CHCl₃ (50 mL) and DMF (1 mL) under a nitrogen atmosphere, HOBt (676 mg, 5 mmol) was added at 0° C. followed by EDC.HCl (958 mg, 5 mmol). The reaction was allowed to stir at 0° C. for 2 h. then at room temperature overnight.

Solvent was removed by vacuum distillation. The residue was dissolved in toluene and purified using flash chromatography (SiO₂, n-hexane-EtOAc=2:1). Yield 70% (pale yellow solid), m/z (ESI+) 446 [M+H]⁺.

2-formyl-6-methoxyphenyl acetate

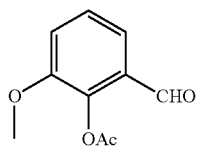

To a stirred solution of 3-methoxysalicylaldehyde (4.56 g, 30 mmol), and pyridine (2.43 mL, 30 mmol) in DCM (40 mL), acetyl chloride (2.36 g, 30 mmol) was added drop wise. The reaction was stirred at room temperature overnight then the solvent was removed by vacuum distillation. The residue was triturated in cold dil. HCl and filtered, washed with cold water then n-hexane.

Yield 94% (off-white solid), m/z (ESI+) 195 [M+H]⁺.

6-formyl-2-methoxy-3-nitrophenyl acetate

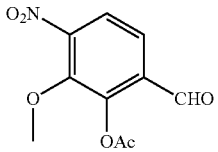 [SMILES: COc1c([N+](=O)[O-])ccc(C=O)c1OC(C)=O]

To a stirred ice-cooled suspension of 2-formyl-6-methoxyphenyl acetate (1.94 g, 10 mmol), and KNO₃ (1.01 g, 10 mmol) in CHCl₃ (15 mL), trifluoroacetic anhydride (12 mL) was added. The reaction was stirred in an ice bath for 2 h. then at room temperature overnight. The reaction was diluted very carefully with water (50 mL) and extracted with CHCl₃. The combined organic extract was dried (MgSO₄), and the solvent was removed by vacuum distillation. The residue was dissolved in toluene and purified using flash chromatography (SiO₂, n-hexane-EtOAc=3:1). Yield 45% (yellow semisolid), m/z (ESI+) 239 [M]⁺.

2-hydroxy-3-methoxy-4-nitrobenzaldehyde

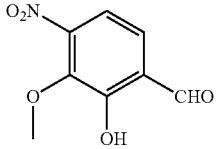

To a stirred suspension of 6-formyl-2-methoxy-3-nitrophenyl acetate (957 mg, 4 mmol) in water (30 mL), NaOH (0.8 g, 20 mmol) was added. The reaction was refluxed for 2 h then allowed to stir at room temperature overnight. The solution was cooled in an ice bath and acidified by HCl 2 M to pH 3-4. The precipitated solid was collected by filtration, washed with cold water then n-hexane.

Yield 90% (yellowish brown solid), m/z (ESI+) 197 [M]⁺.

2-hydroxy-3-methoxy-4-nitrobenzoic acid

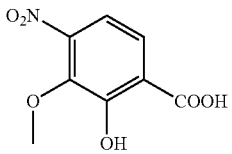

To a stirred solution of 2-hydroxy-3-methoxy-4-nitrobenzaldehyde (788 mg, 4 mmol), and NaOH (0.8 g, 20 mmol) in water (50 mL), AgNO₃ (3.4 g, 20 mmol) was added portion wise. The reaction was refluxed overnight, then allowed to cool and filtered through celite. Filtrate was cooled in an ice bath and acidified with HCl 37% to pH 3-4. The precipitated solid was collected by filtration, washed with cold water then n-hexane. Yield 65% (beige solid), m/z (ESI+) 213 [M]⁺.

125

Isopropyl 3-isopropoxy-4-[({6-isopropoxy-5-[(4-nitrobenzoyl)amino]pyridin-2-yl}carbonyl)amino]benzoate

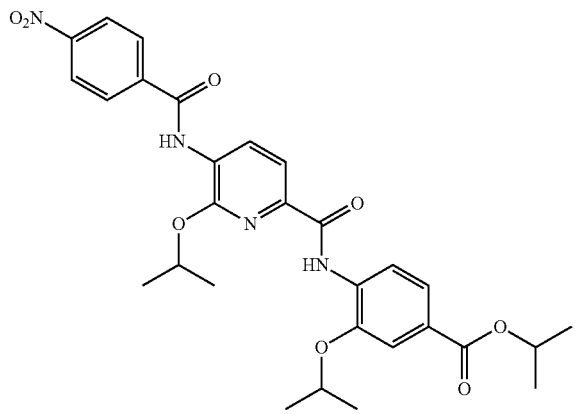 [SMILES: CC(C)OC(=O)c1ccc(NC(=O)c2ccc(NC(=O)c3ccc([N+](=O)[O-])cc3)c(OC(C)C)n2)c(OC(C)C)c1]

To a stirred solution of isopropyl 4-{[(5-amino-6-isopropoxypyridin-2-yl)carbonyl]amino}-3-isopropoxybenzoate (207 mg, 0.5 mmol), and pyridine (0.1 mL) in DCM (20 mL), 4-nitrobenzoyl chloride (185 mg, 1 mmol) was added. The reaction was stirred at room temperature overnight then the HCl 2 M (20 mL) was added. The mixture was extracted with DCM then EtOAc. The combined organic extract was dried (MgSO$_4$), and the solvent was removed by vacuum distillation. The residue was dissolved in toluene and purified using flash chromatography (SiO$_2$, n-hexane-EtOAc=1:1). Yield 80% (yellow crystals), m/z (ESI+) 565 [M+H]$^+$.

5. REFERENCES

1) Valeria Azzarito, Panchami Prabhakaran, Alice I. Bartlett, Natasha Murphy, Michaele J. Hardie, Colin A. Kilner, Thomas A. Edwards, Stuart L. Warriner, Andrew J. Wilson. *2-O-Alkylated Para-Benzamide a-Helix Mimetics: The Role of Scaffold Curvature*. Org. Biomol. Chem., 2012, 10, 6469.

2) Alina Fomovska, Richard D. Wood, Ernest Mui, Jitenter P. Dubey, Leandra R. Ferreira, Mark R. Hickman, Patricia J. Lee, Susan E. Leed, Jennifer M. Auschwitz, William J. Welsh, Caroline Sommerville, Stuart Woods, Craig Roberts, and Rima McLeod. *Salicylanilide Inhibitors of Toxoplasma gondii*. J. Med. Chem., 2012, 55 (19), pp 8375-8391.

6. ACTIVITY OF THESE COMPOUNDS

Several of these compounds were tested for their activity against an *E. coli* strain (ToIC-deficient) according to the procedures described above. Most tested compounds showed an activity (MIC) of from 1 to 320 µM.

---

The invention claimed is:

1. A method for treatment or prophylaxis of bacterial infections comprising administering a pharmaceutical composition,
wherein the pharmaceutical composition comprises a compound of formula (V)

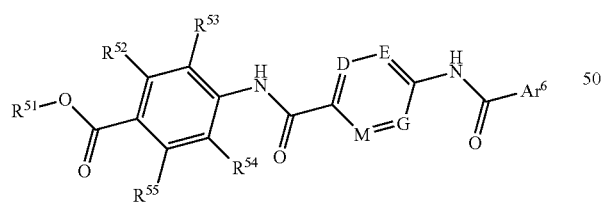

(V)

wherein $R^{51}$ is a hydrogen atom, or a $C_{1-6}$ alkyl group;
$R^{52}$ is a hydrogen atom, F, Cl, a hydroxy group, a $C_{1-6}$ alkyl group or a group of formula —O—$C_{1-6}$ alkyl;
$R^{53}$ is a hydrogen atom, F, Cl, a hydroxy group, a $C_{1-6}$ alkyl group or a group of formula —O—$C_{1-6}$ alkyl;
$R^{54}$ is a hydrogen atom, F, Cl, a hydroxy group, a $C_{1-6}$ alkyl group or a group of formula —O—$C_{1-6}$ alkyl;
$R^{55}$ is a hydrogen atom, F, Cl, a hydroxy group, a $C_{1-6}$ alkyl group or a group of formula —O—$C_{1-6}$ alkyl;
D is N or $CR^{56}$;

E is N or $CR^{57}$;
G is N or $CR^{58}$;
M is N or $CR^{59}$;
$R^{56}$ is a hydrogen atom, F, Cl, a hydroxy group, a $C_{1-6}$ alkyl group or a group of formula —O—$C_{1-6}$ alkyl;
$R^{57}$ is a hydrogen atom, F, Cl, a hydroxy group, a $C_{1-6}$ alkyl group or a group of formula —O—$C_{1-6}$ alkyl;
$R^{58}$ is a hydrogen atom, F, Cl, a hydroxy group, a $C_{1-6}$ alkyl group or a group of formula —O—$C_{1-6}$ alkyl;
$R^{59}$ is a hydrogen atom, F, Cl, a hydroxy group, a $C_{1-6}$ alkyl group or a group of formula —O—$C_{1-6}$ alkyl; and
$Ar^6$ is an optionally substituted phenyl group or an optionally substituted heteroaryl group having 5 or 6 ring atoms including 1, 2, 3 or 4 heteroatoms selected from oxygen, sulphur and nitrogen;
with the proviso that $Ar^6$ is substituted by a group of formula —$NHR^8$; wherein $R^8$ is a group of the following formula:

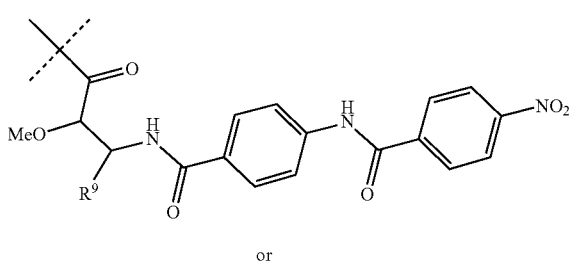

or

-continued

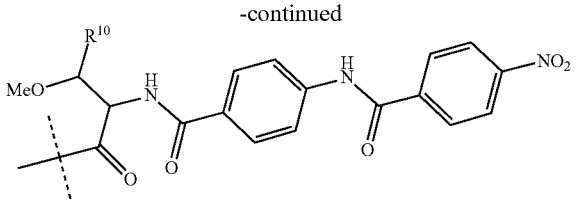

wherein R⁹ is COOH or CONH₂ and R¹⁰ is COOH or CONH₂;
or a pharmaceutically acceptable salt, or a pharmaceutically acceptable formulation thereof.

2. The method of claim 1, wherein the compound has formula (VI)

(VI)

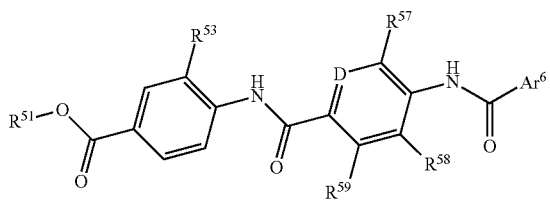

wherein
$R^{51}$ is a hydrogen atom, or a $C_{1-6}$ alkyl group;
$R^{53}$ is a hydrogen atom, F, Cl, a hydroxy group, a $C_{1-6}$ alkyl group or a group of formula —O—$C_{1-6}$ alkyl;
D is N or $CR^{56}$;
$R^{56}$ is a hydrogen atom, F, Cl, a hydroxy group, a $C_{1-6}$ alkyl group or a group of formula —O—$C_{1-6}$ alkyl;
$R^{57}$ is a hydrogen atom, F, Cl, a hydroxy group, a $C_{1-6}$ alkyl group or a group of formula —O—$C_{1-6}$ alkyl;
$R^{58}$ is a hydrogen atom, F, Cl, a hydroxy group, a $C_{1-6}$ alkyl group or a group of formula —O—$C_{1-6}$ alkyl;
$R^{59}$ is a hydrogen atom, F, Cl, a hydroxy group, a $C_{1-6}$ alkyl group or a group of formula —O—$C_{1-6}$ alkyl; and
$Ar^6$ is an optionally substituted phenyl group or an optionally substituted heteroaryl group having 5 or 6 ring atoms including 1, 2, 3 or 4 heteroatoms selected from oxygen, sulphur and nitrogen;
with the proviso that $Ar^6$ is substituted by a group of formula —$NHR^8$ wherein $R^8$ is a group of the following formula:

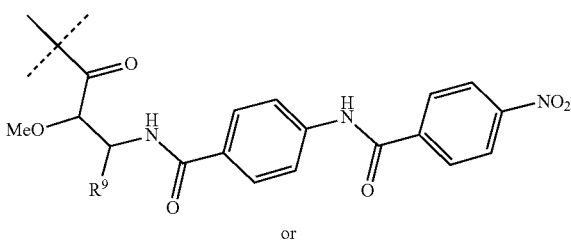

or

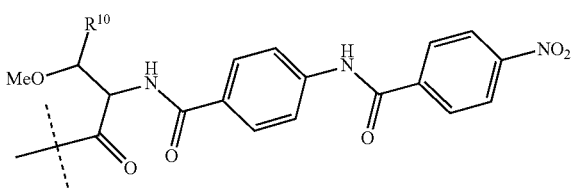

wherein R⁹ is COOH or CONH₂ and R¹⁰ is COOH or CONH₂;
or a pharmaceutically acceptable salt or a pharmaceutically acceptable formulation thereof.

3. The method of claim 1, wherein the compound is formula (VII)

(VII)

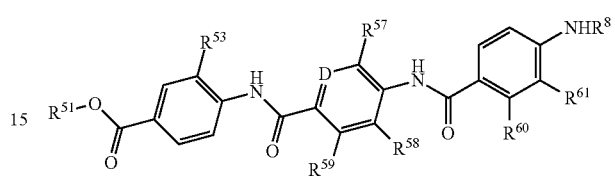

wherein
$R^{51}$ is a hydrogen atom, or a $C_{1-6}$ alkyl group;
$R^{53}$ is a hydrogen atom, F, Cl, a hydroxy group, a $C_{1-6}$ alkyl group or a group of formula —O—$C_{1-6}$ alkyl;
D is N or $CR^{56}$;
$R^{56}$ is a hydrogen atom, F, Cl, a hydroxy group, a $C_{1-6}$ alkyl group or a group of formula —O—$C_{1-6}$ alkyl;
$R^{57}$ is a hydrogen atom, F, Cl, a hydroxy group, a $C_{1-6}$ alkyl group or a group of formula —O—$C_{1-6}$ alkyl;
$R^{58}$ is a hydrogen atom, F, Cl, a hydroxy group, a $C_{1-6}$ alkyl group or a group of formula —O—$C_{1-6}$ alkyl;
$R^{59}$ is a hydrogen atom, F, Cl, a hydroxy group, a $C_{1-6}$ alkyl group or a group of formula —O—$C_{1-6}$ alkyl;
$R^{60}$ is a hydrogen atom, F, Cl, a hydroxy group, a $C_{1-6}$ alkyl group or a group of formula —O—$C_{1-6}$ alkyl;
$R^{61}$ is a hydrogen atom, F, Cl, a hydroxy group, a $C_{1-6}$ alkyl group or a group of formula —O—$C_{1-6}$ alkyl; and
$R^8$ is a group of the following formula:

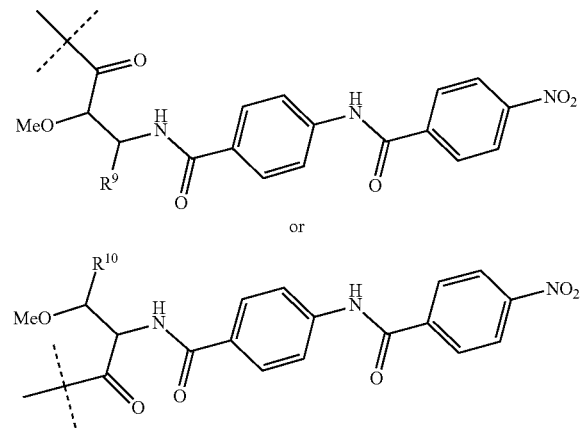

wherein R⁹ is COOH or CONH₂ and R¹⁰ is COOH or CONH₂;
or a pharmaceutically acceptable salt or a pharmaceutically acceptable formulation thereof.

4. The method of claim 1, wherein the compound is formula (IV)

(IV)

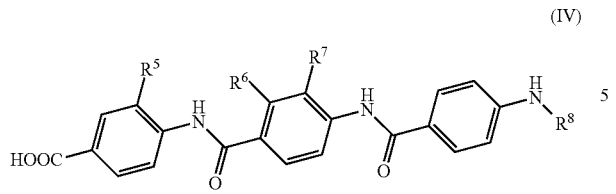

wherein $R^5$ is a hydrogen atom or a group of formula —O—$C_{1-6}$ alkyl;

$R^6$ is a hydroxy group;

$R^7$ is a hydrogen atom or a group of formula —O—$C_{1-6}$ alkyl; and $R^8$ is a group of the following formula:

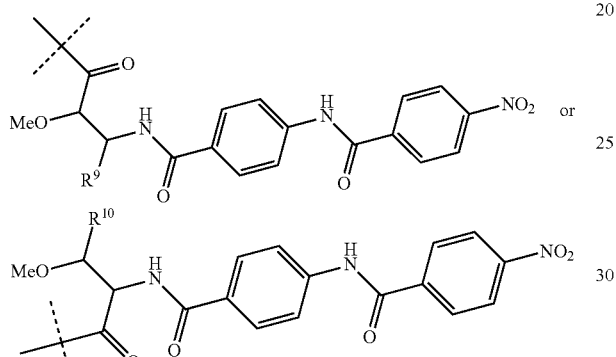

wherein $R^9$ is COOH or $CONH_2$ and $R^{10}$ is COOH or $CONH_2$;

or a pharmaceutically acceptable salt or a pharmaceutically acceptable formulation thereof.

5. The method of claim 1, wherein the pharmaceutical composition optionally comprises one or more carrier substances and/or one or more adjuvants.

6. A method for treatment or prophylaxis of bacterial infections comprising administering a pharmaceutical composition, wherein the pharmaceutical composition comprises a compound selected from:

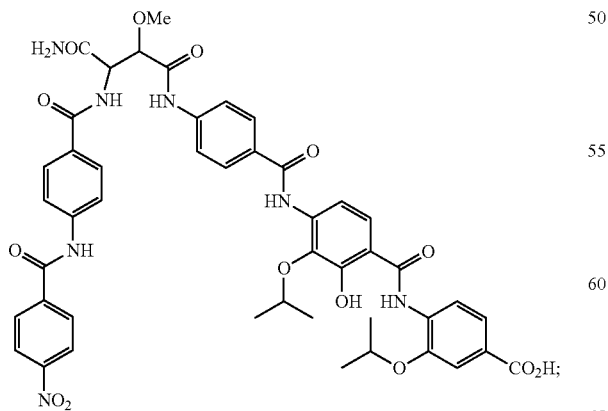

Cystobactamide A (1)

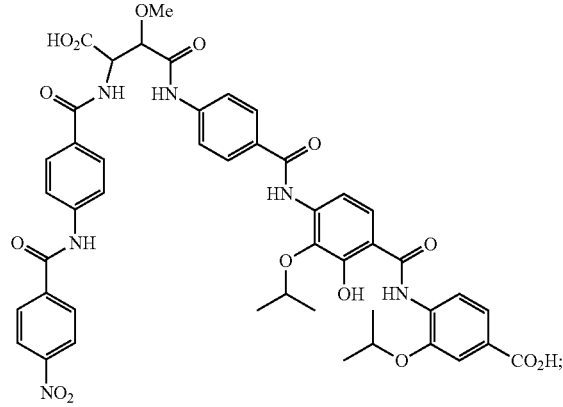

Cystobactamide B (2)

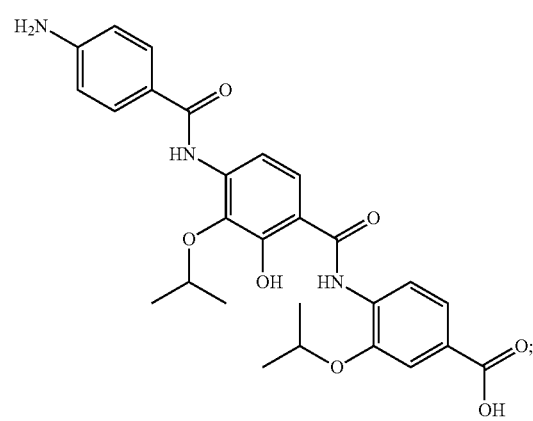

Cystobactamide C (3)

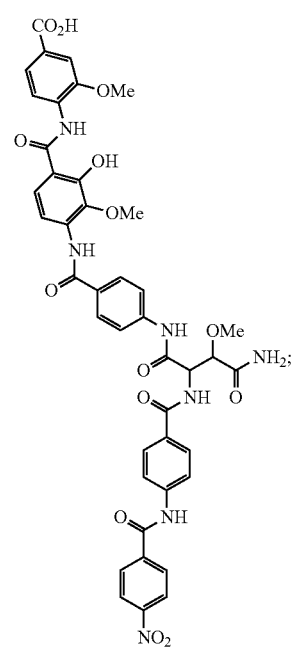

Cystobactamide D (4)

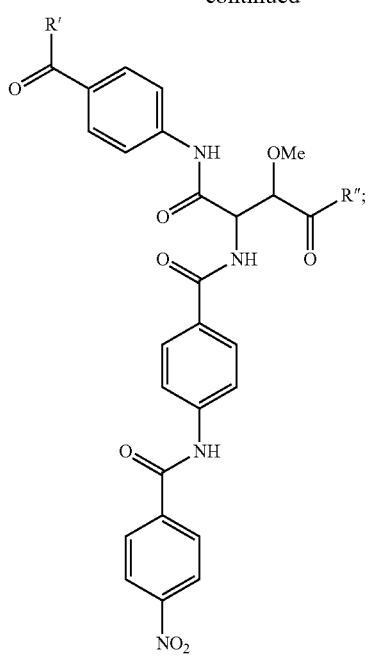
Cystobactamide E (5)
(R' is NH$_2$ or OH and R$^2$ is NH$_2$ or OH)
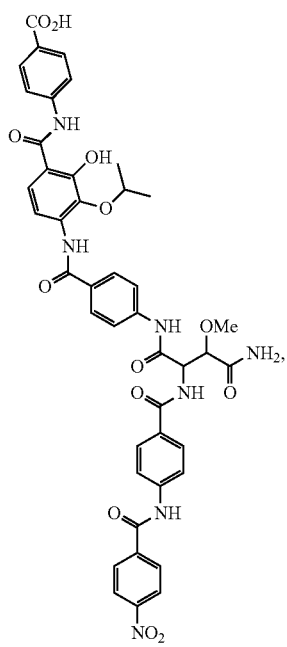
Cystobactamide F (6)
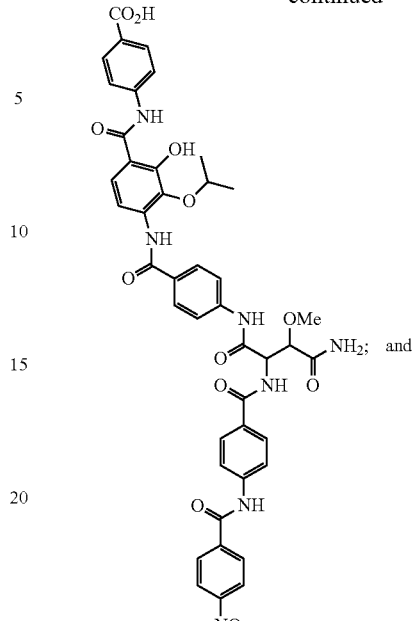
Cystobactamide G (7)
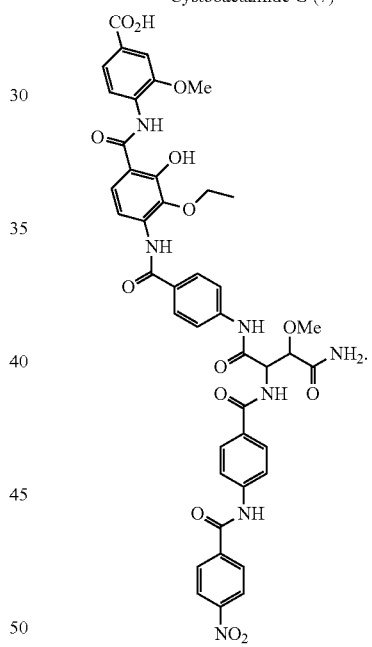
Cystobactamide H (8)
or a pharmaceutically acceptable salt or a pharmaceutically acceptable formulation thereof.
7. The method of claim 6, wherein the pharmaceutical composition optionally comprises one or more carrier substances and/or one or more adjuvants.
* * * * *

UNITED STATES PATENT AND TRADEMARK OFFICE
CERTIFICATE OF CORRECTION

PATENT NO. : 10,793,600 B2
APPLICATION NO. : 16/042753
DATED : October 6, 2020
INVENTOR(S) : Sascha Baumann et al.

It is certified that error appears in the above-identified patent and that said Letters Patent is hereby corrected as shown below:

In the Specification

Column 20, replace the structure of Cystobactamide G (7) with the following structure:

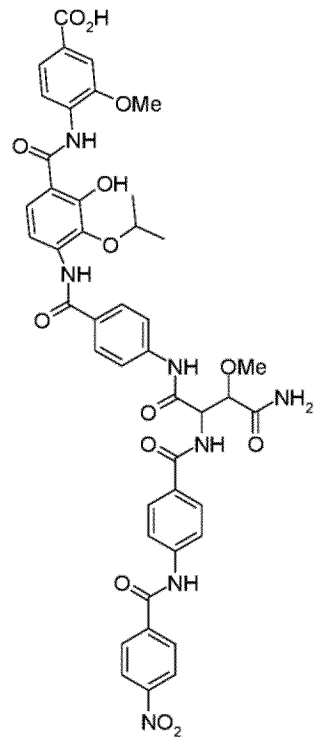

Cystobactamide G (7);

In the Claims

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

Column 342, Claim 6, replace the structure of Cystobactamide G (7) with the following structure:
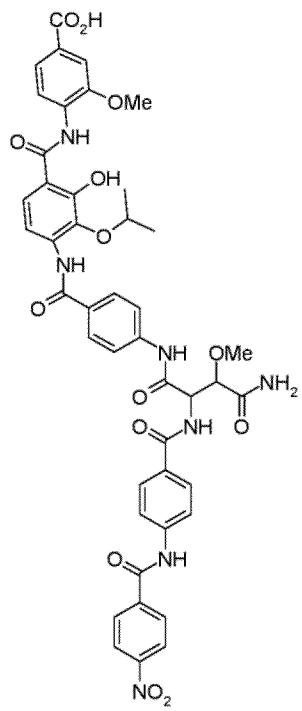
Cystobactamide G (7);